(12) United States Patent
Aggen et al.

(10) Patent No.: US 8,383,596 B2
(45) Date of Patent: Feb. 26, 2013

(54) ANTIBACTERIAL AMINOGLYCOSIDE ANALOGS

(75) Inventors: James Bradley Aggen, Burlingame, CA (US); Adam Aaron Goldblum, Berkeley, CA (US); Martin Sheringham Linsell, San Mateo, CA (US); Paola Dozzo, San Francisco, CA (US); Heinz Ernst Moser, San Mateo, CA (US); Darin James Hildebrandt, Mountain View, CA (US); Micah James Gliedt, Sunnyvale, CA (US)

(73) Assignee: Achaogen, Inc., South San Francisco, CA (US)

( * ) Notice: Subject to any disclaimer, the term of this patent is extended or adjusted under 35 U.S.C. 154(b) by 923 days.

(21) Appl. No.: 12/487,427

(22) Filed: Jun. 18, 2009

(65) Prior Publication Data
US 2010/0099661 A1    Apr. 22, 2010

Related U.S. Application Data

(63) Continuation of application No. PCT/US2008/084399, filed on Nov. 21, 2008.

(60) Provisional application No. 60/989,645, filed on Nov. 21, 2007.

(51) Int. Cl.
A01N 43/04 (2006.01)
A61K 31/70 (2006.01)
C07H 15/20 (2006.01)
C07H 15/00 (2006.01)
C07H 17/00 (2006.01)

(52) U.S. Cl. .............. 514/40; 514/27; 514/35; 514/36; 536/13.9; 536/16.8

(58) Field of Classification Search ............... None
See application file for complete search history.

(56) References Cited

U.S. PATENT DOCUMENTS

| | | | |
|---|---|---|---|
| 3,872,079 A | 3/1975 | Naito et al. | 260/210 AB |
| 3,940,382 A | 2/1976 | Umezawa et al. | 260/210 K |
| 3,997,524 A | 12/1976 | Nagabhushan | 536/17 |
| 4,000,261 A | 12/1976 | Daniels | 424/180 |
| 4,000,262 A | 12/1976 | Daniels | 424/180 |
| 4,002,742 A | 1/1977 | Wright et al. | 424/180 |
| 4,029,882 A | 6/1977 | Wright | 536/17 |
| 4,055,715 A | 10/1977 | Tomioka et al. | 536/17 |
| 4,085,208 A | 4/1978 | Mallams et al. | 424/180 |
| 4,091,202 A | 5/1978 | Umezawa et al. | 536/10 |
| 4,107,424 A | 8/1978 | Umezawa et al. | 536/10 |
| 4,117,221 A | 9/1978 | Daniels | 536/17 |
| 4,120,955 A | 10/1978 | Umezawa et al. | |
| 4,136,254 A | 1/1979 | Nagabhushan et al. | 536/10 |
| 4,166,114 A | 8/1979 | Igarashi | 424/180 |
| 4,169,141 A | 9/1979 | Topliss et al. | 424/177 |
| 4,178,437 A | 12/1979 | Thomas | 536/10 |
| 4,190,722 A | 2/1980 | Voss et al. | 536/17 R |
| 4,195,171 A | 3/1980 | Tomioka et al. | 536/17 R |
| 4,199,570 A | 4/1980 | Igarashi et al. | 424/180 |
| 4,199,572 A | 4/1980 | Schröder et al. | 424/180 |
| 4,200,628 A | 4/1980 | Igarashi et al. | 424/180 |
| 4,201,774 A | 5/1980 | Igarashi et al. | 424/180 |
| 4,212,859 A | 7/1980 | Daniels et al. | 424/180 |
| 4,214,074 A | 7/1980 | Richardson et al. | 536/10 |
| 4,224,315 A | 9/1980 | Stadler et al. | 424/180 |
| 4,230,847 A | 10/1980 | Nagabhushan et al. | 536/10 |
| 4,234,572 A | 11/1980 | Petersen et al. | 424/180 |
| 4,235,888 A | 11/1980 | Stadler | 424/180 |
| 4,248,865 A | 2/1981 | Igarashi et al. | 424/180 |
| 4,273,923 A | 6/1981 | Igarashi et al. | 536/10 |
| 4,282,350 A | 8/1981 | Wright | 536/10 |
| 4,312,859 A | 1/1982 | Petersen et al. | 424/180 |
| 4,335,114 A | 6/1982 | Voss et al. | 424/180 |
| 4,337,335 A | 6/1982 | Nagabhushan et al. | 536/13.6 |
| 4,347,354 A | 8/1982 | Cron et al. | 536/10 |
| 4,380,625 A | 4/1983 | Stadler et al. | 536/13.9 |
| 4,393,051 A | 7/1983 | Stadler et al. | 424/180 |
| 4,438,260 A | 3/1984 | Petersen et al. | 536/13.9 |
| 4,617,293 A | 10/1986 | Wahlig et al. | 514/41 |
| 5,534,408 A | 7/1996 | Green et al. | 435/5 |

(Continued)

FOREIGN PATENT DOCUMENTS

| | | |
|---|---|---|
| CA | 1 034 573 | 7/1978 |
| CA | 1 105 452 | 7/1981 |

(Continued)

OTHER PUBLICATIONS

Banker, G.S. et al, "Modern Pharmaceutics, 3ed.", Marcel Dekker, New York, 1996, p. 596.*

(Continued)

Primary Examiner — Traviss C McIntosh, III

(57) ABSTRACT

Compounds having antibacterial activity are disclosed. The compounds have the following structure (I):

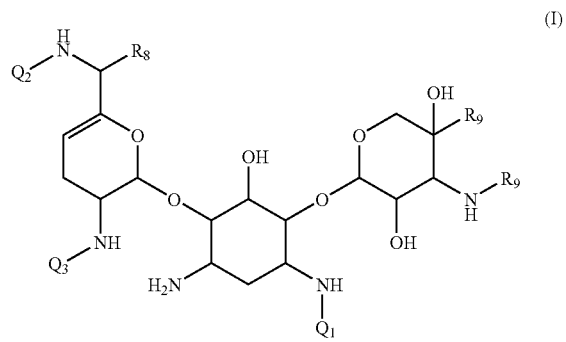

including stereoisomers, pharmaceutically acceptable salts and prodrugs thereof, wherein $Q_1$, $Q_2$, $Q_3$, $R_8$ and $R_9$ are as defined herein. Methods associated with preparation and use of such compounds, as well as pharmaceutical compositions comprising such compounds, are also disclosed.

44 Claims, No Drawings

U.S. PATENT DOCUMENTS

| | | | |
|---|---|---|---|
| 5,696,244 A | 12/1997 | Kim et al. ............... 536/13.9 |
| 5,900,406 A | 5/1999 | von Ahsen et al. ........... 514/35 |
| 5,935,776 A | 8/1999 | Green et al. ............... 435/5 |
| 6,541,456 B1 | 4/2003 | Swayze et al. |
| 6,759,523 B2 | 7/2004 | Swayze et al. |
| 6,967,242 B2 | 11/2005 | Swayze et al. |
| 7,893,039 B2 | 2/2011 | Swayze et al. |
| 7,943,749 B2 | 5/2011 | Hanessian et al. |
| 8,114,856 B2 | 2/2012 | Swayze et al. |
| 2004/0072798 A1 | 4/2004 | Naggi et al. ............... 514/58 |
| 2007/0161581 A1 | 7/2007 | Minowa et al. ............. 514/35 |
| 2008/0045468 A1 | 2/2008 | Hanessian et al. .......... 514/39 |
| 2008/0214845 A1 | 9/2008 | Migawa et al. ............. 549/415 |
| 2008/0293649 A1 | 11/2008 | Swayze et al. ............. 514/39 |
| 2008/0300199 A1 | 12/2008 | Linsell et al. .............. 514/38 |
| 2011/0245476 A1 | 10/2011 | Migawa et al. |
| 2011/0275586 A1 | 11/2011 | Aggen et al. |
| 2011/0288041 A1 | 11/2011 | Aggen et al. |
| 2012/0122809 A1 | 5/2012 | Goldblum et al. |
| 2012/0135945 A1 | 5/2012 | Dozzo et al. |
| 2012/0135946 A1 | 5/2012 | Goldblum et al. |
| 2012/0135948 A1 | 5/2012 | Goldblum et al. |
| 2012/0165282 A1 | 6/2012 | Dozzo et al. |
| 2012/0172332 A1 | 7/2012 | Aggen et al. |
| 2012/0184501 A1 | 7/2012 | Dozzo et al. |
| 2012/0196791 A1 | 8/2012 | Armstrong et al. |
| 2012/0208781 A1 | 8/2012 | Bruss et al. |
| 2012/0214759 A1 | 8/2012 | Bruss et al. |
| 2012/0214760 A1 | 8/2012 | Bruss et al. |
| 2012/0283207 A1 | 11/2012 | Maianti et al. |
| 2012/0283208 A1 | 11/2012 | Aggen et al. |
| 2012/0283209 A1 | 11/2012 | Dozzo et al. |

FOREIGN PATENT DOCUMENTS

| | | |
|---|---|---|
| CA | 1 105 454 | 7/1981 |
| CN | 1397562 A | 2/2003 |
| DE | 24 37 160 A1 | 2/1975 |
| DE | 24 40 956 A1 | 3/1975 |
| DE | 24 58 921 A1 | 6/1975 |
| DE | 25 55 405 A1 | 6/1976 |
| DE | 27 48 257 A1 | 5/1978 |
| DE | 28 18 822 A1 | 11/1978 |
| DE | 29 36 120 A1 | 3/1980 |
| DE | 3100739 A1 | 8/1982 |
| DE | 31 08 068 A1 | 9/1982 |
| DE | 34 05 326 A1 | 8/1985 |
| EP | 0 001 643 A2 | 5/1979 |
| EP | 0 002 450 A1 | 6/1979 |
| EP | 0 009 670 A1 | 4/1980 |
| EP | 0 056 575 A1 | 7/1982 |
| GB | 1 470 329 | 4/1977 |
| GB | 1 473 733 A | 5/1977 |
| GB | 1 494 129 | 12/1977 |
| GB | 1 535 215 | 12/1978 |
| GB | 2 030 141 A | 4/1980 |
| GB | 1 583 366 | 1/1981 |
| GB | 1 598 294 | 9/1981 |
| JP | 54-46770 A | 4/1979 |
| JP | 54-61151 A | 5/1979 |
| JP | 55-329 A | 1/1980 |
| JP | 55-17397 A | 6/1980 |
| JP | 56-15298 A | 2/1981 |
| JP | 1-254694 A | 10/1989 |
| SU | 623524 | 12/1975 |
| WO | WO 2005/070945 A1 | 8/2005 |
| WO | WO 2006/052930 A1 | 5/2006 |
| WO | WO 2007/028012 A2 | 3/2007 |
| WO | WO 2007/064954 A2 | 6/2007 |
| WO | WO 2008/124821 A1 | 10/2008 |
| WO | 2009/067692 A1 | 5/2009 |
| WO | WO 2010/030690 A1 | 3/2010 |
| WO | WO 2010/030704 A2 | 3/2010 |
| WO | WO 2010/042850 A1 | 4/2010 |
| WO | WO 2010/042851 A1 | 4/2010 |
| WO | WO 2010/132757 A2 | 11/2010 |
| WO | WO 2010/132759 A1 | 11/2010 |
| WO | WO 2010/132760 A1 | 11/2010 |
| WO | WO 2010/132765 A2 | 11/2010 |
| WO | WO 2010/132768 A1 | 11/2010 |
| WO | WO 2010/132770 A1 | 11/2010 |
| WO | WO 2010/132777 A2 | 11/2010 |
| WO | WO 2010/132839 | 11/2010 |
| WO | WO 2010/147836 | 12/2010 |
| WO | WO 2011/044501 A1 | 4/2011 |
| WO | WO 2011/044502 A1 | 4/2011 |
| WO | WO 2011/044503 A1 | 4/2011 |
| WO | WO 2011/044538 A1 | 4/2011 |
| WO | WO 20111044498 A1 | 4/2011 |
| WO | WO 2012/067978 A1 | 5/2012 |

OTHER PUBLICATIONS

Wolff, Manfred E. "Burger's Medicinal Chemistry, 5ed, Part I", John Wiley & Sons, 1995, pp. 975-977.*

Bassaris et al., "Once-Daily High-Dose Netilmicin—A New Short-Term Treatment Regimen for Patients with Moderate to Severe Gram-Negative Infections," *Clin. Drug Invest.* 15(3):205-216, 1998.

Bonfiglio et al., "In vitro Activity of Piperacillin/Tazobactam against 615 *Pseudomonas aeruginosa* Strains Isolated in Intensive Care Units," *Chemotherapy* 44:305-312, 1998.

Christenson et al., "In vitro activity of meropenem, imipenem, cefepime and ceftazidime against *Pseudomonas aeruginosa* isolates from cystic fibrosis patients," *Journal of Antimicrobial Chemotherapy* 45:899-901, 2000.

de Vries et al., "Prospective Randomized Study of Once-Daily versus Thrice-Daily Netilmicin Regimens in Patients with Intraabdominal Infections," *Eur. J. Clin. Microbiol. Infect. Dis.* 9(3):161-168, Mar. 1990.

Etra et al., "Sisomicin in Urinary Tract Infection. Tolerance and Efficacy Study," *Urology* 7(2):160-164, Feb. 1976.

French, G. L., "Bactericidal agents in the treatment of MRSA infections—the potential role of daptomycin," *Journal of Antimicrobial Chemotherapy* 58:1107-1117, 2006.

Grohs et al., "In Vitro Bactericidal Activities of Linezolid in Combination with Vancomycin, Gentamicin, Ciprofloxacin, Fusidic Acid, and Rifampin against *Staphylococcus aureus,*" *Antimicrobial Agents and Chemotherapy* 47(1):418-420, Jan. 2003.

Invitation to Pay Additional Fees and Partial International Search Report for PCT/US2010/034884, mailed Oct. 26, 2010, 7 pages.

International Search Report and Written Opinion for PCT/US2010/034896, mailed Sep. 6, 2010, 21 pages.

International Search Report and Written Opinion for PCT/US2010/034909, mailed Dec. 2, 2010, 31 pages.

International Search Report and Written Opinion for PCT/US2010/035006, mailed Dec. 8, 2010, 39 pages.

International Search Report and Written Opinion for PCT/US2010/038138, mailed Aug. 20, 2010, 18 pages.

Martino et al., "N-Formimidoyl-Thienamycin and Norfloxacin Against Multiple-Resistant *Pseudomonas aeruginosa* Strains. Combined In Vitro Activity and Comparison With 14 Other Antibiotics," *Drugs Exptl. Clin. Res.* 11(4):247-251, 1985.

Theuretzbacher, Ursula, "Future antibiotics scenarios: is the tide starting to turn?" *International Journal of Antimicrobial Agents* 34:15-20, 2009.

Traczewski et al., "In Vitro Activity of Doripenem against *Pseudomonas aeruginosa* and *Burkholderia cepacia* Isolates from both Cystic Fibrosis and Non-Cystic Fibrosis Patients," *Antimicrobial Agents and Chemotherapy* 50(2):819-821, Feb. 2006.

Urban et al., "Daily Dosage of Aminoglycosides," *Current Clinical Topics in Infectious Diseases* 17:236-255, 1997.

Van der Auwera et al., "Pharmacodynamic Parameters and Toxicity of Netilmicin (6 Milligrams/Kilogram/Day) Given Once Daily or in Three Divided Doses to Cancer Patients with Urinary Tract Infection," *Antimicrobial Agents and Chemotherapy* 35(4):640-647, Apr. 1991.

Widmer, Andreas F., "Ceftobiprole: A New Option for Treatment of Skin and Soft-Tissue Infections due to Methicillin-Resistant *Staphylococcus aureus,*" *Clinical Infectious Diseases* 46:656-658, Mar. 1, 2008.

Yamasaki et al., "Synthesis and Biological Activity of 1-N-[4-(Substituted)Amidino and Guanidino-2-Hydroxybutyryl]Kanamycins A and B," *The Journal of Antibiotics* 44(6):646-658, Jun. 1991.

Afonso et al., "Synthesis of 1-N-Peptidyl Derivatives of Sisomicin," *Current Chemotherapy and Infectious Disease, Proceedings of the 11th International Congress of Chemotherapy and the 19th Interscience Conference on Antimicrobial Agents and Chemotherapy* 1:405-406, 1980 (7 pages total).

Aggen et al., "Synthesis, Structure, and In Vitro Activity of the Neoglycoside Achn-490," Poster No. FI-840 presented at 49th Interscience Conference on Antimicrobial Agents and Chemotherapy (ICAAC), San Francisco, California, Sep. 12-15, 2009 (+ Abstract 085(F1) p. 185) (3 pages).

Ahsen et al., "Non-competitive Inhibition of Group I Intron RNA Self-splicing by Aminoglycoside Antibiotics," *J. Mol. Biol.* 226(4):935-941, 1992.

Alper et al., "Probing the Specificity of Aminoglycoside—Ribosomal RNA Interactions with Designed Synthetic Analogs," *J. Am. Chem. Soc.* 120(9):1965-1978, 1998.

Armstrong et al., "Surveying Aminoglycoside-Resistance Mechanisms: A Tool for the Development of Neoglycosides," Presented at 19th European Congress of Clinical Microbiology and Infectious Diseases (ECCMID), Helsinki, Finland, May 16-19, 2009 (+ Abstract P643, p. S149).

Biedenbach et al., "Ten Year Trend in Aminoglycoside Resistance from a Worldwide Collection of Gram-Negative Pathogens (1998-2007)," Poster No. 636 presented at 19th European Congress of Clinical Microbiology and Infectious Diseases (ECCMID), Helsinki, Finland, May 16-19, 2009 (+ Abstract P636, p. S147).

Chambers, H. F., *Goodman & Gilman's The Pharmcological Basis of Therapeutics*, Eleventh Edition, Brunton et al. (ed.), McGraw-Hill, Inc., New York, 2006, Chapter 45, "Aminoglycosides," pp. 1155-1171 (+ 3 cover pages).

Chow et al., "A Structural Basis for RNA-Ligand Interactions," *Chem. Rev.* 97(5):1489-1513, Jul./Aug. 1997.

Daniels et al., "Semisynthetic Aminoglycoside Antibacterials. Part 11. Solution Conformations of Semisynthetic and Naturally Occurring Aminoglycoside Antibiotics," *J Chem. Soc., Perkin Trans. 1*:2209-2227, 1981.

Doi et al., "16S Ribosomal RNA Methylation: Emerging Resistance Mechanism against Aminoglycosides," *Clinical Infectious Diseases* 45:88-94, Jul. 1, 2007.

Drusano et al., "Back to the Future: Using Aminoglycosides Again and How to Dose Them Optimally," *Clinical Infectious Diseases* 45:753-760, Sep. 15, 2007.

Hare et al., "Evaluation of New 1-N-Substituted Aminoglycosides Against Strains with Known Resistance Mechanisms," *Current Chemotherapy and Infectious Disease, Proceedings of the 11th International Congress of Chemotherapy and the 19th Interscience Conference on Antimicrobial Agents and Chemotherapy* 1:403-405, 1980 (7 pages total).

Hawkey et al., "The changing epidemiology of resistance," *Journal of Antimicrobial Chemotherapy* 64(Suppl 1):i3-i10, 2009.

Hawser et al., "In vitro susceptibilities of aerobic and facultative anaerobic Gram-negative bacilli from patients with intra-abdominal infections worldwide from 2005-2007: results from the SMART study," *International Journal of Antimicrobial Agents* 34:585-588, 2009.

Hermann, T., "Biomedicine & Diseases: Review. Aminoglycoside antibiotics: old drugs and new therapeutic approaches," *Cell. Mol. Life. Sci.* 64:1841-1852, 2007.

Jana et al., "Molecular understanding of aminoglycoside action and resistance," *Appl Microbiol Biotechnol* 70:140-150, 2006.

Jones et al., "Spectrum and activity of three contemporary fluoroquinolones tested against *Pseudomonas aeruginosa* isolates from urinary tract infections in the SENTRY Antimicrobial Surveillance Program (Europe and the Americas; 2000): More alike than different!" *Diagnostic Microbiology and Infectious Disease* 41:161-163, 2001.

Klastersky et al., "Clinical Significance of In Vitro Synergism Between Antibiotics in Gram-Negative Infections," *Antimicrobial Agents and Chemotherapy* 2(6):470-475, Dec. 1972.

Lee et al., "Selective reactions of reactive amino groups in polyamino compounds by metal-chelated or—mediated methods," *Tetrahedron* 57:4801-4815, 2001.

Miller et al., "The Most Frequent Aminoglycoside Resistance Mechanisms—Changes with Time and Geographic Area: A Reflection of Aminoglycoside Usage Patterns?" *Clinical Infectious Diseases* 24(Suppl 1):S46-62, 1997.

Miller et al., "The Most Frequently Occurring Aminoglycoside Resistance Mechanisms—Combined Results of Surveys in Eight Regions of the World," *Journal of Chemotherapy* 7(Supplement n. 2):17-30, 1995.

Moazed et al., "Interaction of antibiotics with functional sites in 16S ribosomal RNA," *Nature* 327:389-394, Jun. 4, 1987.

Nagabhushan et al., "Interaction of Vicinal and Nonvicinal Amino-Hydroxy Group Pairs in Aminoglycoside—Aminocyclitol Antibiotics with Transition Metal Cations. Selective N Protection," *Journal of the American Chemical Society* 100(16):5253-5254, Aug. 2, 1978.

Nam et al., "An Efficient and Selective 1-N-Monoethylation of Sisomicin: Process Development of Netilmicin," *Organic Process Research & Development* 6(1):78-81, 2002.

Rane et al., "Synthesis and In Vitro Microbiological Properties of the 1-N-(3-Amino-2-Hydroxypropionyl) Derivatives of Sisomicin and 5-Episisomicin," *Current Chemotherapy and Infectious Disease, Proceedings of the 11th International Congress of Chemotherapy and the 19th Interscience Conference on Antimicrobial Agents and Chemotherapy* 1:408-410, 1980 (7 pages total).

Rossi et al., "In vitro susceptibilities of aerobic and facultatively anaerobic Gram-negative bacilli isolated from patients with intra-abdominal infections worldwide: 2004 results from SMART (Study for Monitoring Antimicrobial Resistance Trends)," *Journal of Antimicrobial Chemotherapy* 58:205-210, 2006.

Rybak et al., "Combination Antimicrobial Therapy for Bacterial Infections," *Drugs* 52(3):390-405, 1996.

Shaw et al., "Molecular Genetics of Aminoglycoside Resistance Genes and Familial Relationships of the Aminoglycoside-Modifying Enzymes," *Microbiological Reviews* 57(1):138-163, Mar. 1993.

Waitz et al., "Chemotherapeutic Evaluation of 5-Episisomicin (Sch 22591), a New Semisynthetic Aminoglycoside," *Antimicrobial Agents and Chemotherapy* 13(1):41-48, Jan. 1978.

Wallis et al., "The Binding of Antibiotics to RNA," *Prog. Biophys. Molec. Biol.*, 67(2/3):141-154, 1997.

Wright, Gerard D., "Aminoglycoside-modifying enzymes," *Current Opinion in Microbiology* 2(5):499-503, Oct. 1, 1999.

Wright et al., "Selective N-Acylation of Gentamicin Antibiotics—Synthesis of 1-N-Acyl Derivatives," *The Journal of Antibiotics* 29(7):714-719, Jul. 1976.

International Search Report and Written Opinion, mailed Apr. 21, 2009, for PCT/US2008/084399, 8 pages.

Database WPI Accession No. 2003-713635 [68], retrieved Feb. 23, 2011, 1 page.

Invitation to Pay Additional Fees and, Where Applicable, Protest Fee, for International Application No. PCT/US2010/034893, mailed Mar. 2, 2011, 9 pages.

Notification of Transmittal of the International Search Report and the Written Opinion of the International Searching Authority, or the Declaration, for International Application No. PCT/US2010/034884, mailed Jan. 3, 2011, 19 pages.

European Patent Office Communication pursuant to Rules 161(1) and 162 EPC, for European Application No. 08851633.1, dated Jun. 29, 2010, 2 pages.

PCT International Search Report and Written Opinion for International Application No. PCT/US2010/034893, mailed May 3, 2011, 20 pages.

Mori et al., "Antibacterial Derivative Active Gram Positive Negative Bacteria Amino Glycoside Resistance Strain," Database WPI, AN 1980-11681C [07], Week 198007, Jan. 5, 1980, 1 page.

Adachi et al., "Synthesis and Evaluation of Aminoglycosides as Inhibitors for Rev binding to Rev Responsive Element," *Letters in Drug Design & Discovery* 3:71-75, 2006.

Alhambra et al., "In vitro susceptibility of recent antibiotic-resistant urinary pathogens to ertapenem and 12 other antibiotics," *Journal of Antimicrobial Chemotherapy* 53:1090-1094, 2004.

Andes et al., "Pharmacodynamics of the New Fluoroquinolone Gatifloxacin in Murine Thigh and Lung Infection Models," *Antimicrobial Agents and Chemotherapy* 46(6):1665-1670, Jun. 2002.

Bailey et al., "Comparison of single dose netilmicin with a five-day course of co-trimoxazole for uncomplicated urinary tract infections," *New Zealand Medical Journal* 97:262-264, 1984.

Beauchamp et al., "Pharmacologic Basis for the Treatment of Pyelonephritis," *Current Infectious Disease Reports* 1:371-378, 1999.

Benenson et al., "Carbapenem-resistant *Klebsiella pneumoniae* endocarditis in a young adult Successful treatment with gentamicin and colistin," *International Journal of Infectious Diseases* 13:e295-e298, 2009.

Bergeron, "Treatment of Pyelonephritis in Adults," *Medical Clinics of North America* 79(3):619-649, May 1995.

Biedenbach et al., "Activity of ACHN-490 Against Complicated Urinary Tract Infection (cUTI) Pathogens From the United States and Europe," ICAAC 2009, Poster # F1-843, 1 page.

Blaser et al., "Multicenter Quality Control Study of Amikacin Assay for Monitoring Once-Daily Dosing Regimens," *Therapeutic Drug Monitoring* 17:133-136, 1995.

Boxler et al., "Semisynthetic Aminoglycoside Antibacterials. Part 9. Synthesis of Novel 1- and 3-Substituted and 1- and 3-*epi*-Substituted Derivatives of Sisomicin and Gentamicin from the 1- and 3-Oxo-derivatives," *J.C.S. Perkin I:*2168-2185, 1981.

Bratu et al., "Carbapenemase-producing *Klebsiella pneumoniae* in Brooklyn, NY: molecular epidemiology and in vitro activity of polymyxin B and other agents," *Journal of Antimicrobial Chemotherapy* 56:128-132, 2005.

Brummett et al., "Ototoxicity of tobramycin, gentamicin, amikacin and sisomicion in the guinea pig," *Journal of Antimicrobial Chemotherapy* 4(Suppl. A):73-83, 1978.

Buijk et al., "Experience with a once-daily dosing program of aminoglycosides in critically ill patients," *Intensive Care Med.* 28:936-942, 2002.

Carapetis et al., "Randomized, controlled trial comparing once daily and three times daily gentamicin in children with urinary tract infections," *Pediatr. Infect. Dis. J.* 20(3):240-246, 2001.

Cass et al., "Pharmacokinetics of the Novel Neoglycoside ACHN-490 in Mouse, Rat, and Dog," ICAAC 2009, Poster # F1-846, 1 page.

Centrón et al., "Characterization of the 6'-$N$-Aminoglycoside Acetyltransferase Gene *aac(6')-Iq* from the Integron of a Natural Multiresistance Plasmid," *Antimicrobial Agents and Chemotherapy* 42(6):1506-1508, Jun. 1998.

Chanal et al., "Comparative Study of a Novel Plasmid-Mediated β-Lactamase, CAZ-2, and the CTX-1 and CAZ-1 Enzymes Conferring Resistance to Broad-Spectrum Cephalosporins," *Antimicrobial Agents and Chemotherapy* 32(11):1660-1665, Nov. 1988.

Conil et al., "Increased amikacin dosage requirements in burn patients receiving a once-daily regimen," *International Journal of Antimicrobial Agents* 28:226-230, 2006.

Credito et al., "Activity of Daptomycin Alone and in Combination with Rifampin and Gentamicin against *Staphylococcus aureus* Assessed by Time-Kill Methodology," *Antimicrobial Agents and Chemotherapy* 51(4):1504-1507, Apr. 2007.

Cunha, B.A., "Aminoglycosides in Urology," *Urology* 36(1):1-14, Jul. 1990.

Daniels et al., "Some Recent Advances in the Chemistry of Antibiotics of the Gentamicin Series," *The Japanese Journal of Antibiotics* 32(S-195) (11 pages), Dec. 1979.

Davies et al., "Semisynthetic Aminoglycoside Antibacterials. 6. Synthesis of Sisomicin, Antibiotic G-52, and Novel 6'-Substituted Analogues of Sisomicin from Aminoglycoside 66-40C," *Journal of Medicinal Chemistry* 21(2):189-193, 1978.

De Broe et al., "Influence of dosage schedule on renal cortical accumulation of amikacin and tobramycin in man," *Journal of Antimicrobial Chemotherapy* 27(Suppl. C):41-47, 1991.

Dozzo et al., "New aminoglycoside antibiotics," *Expert Opin. Ther. Patents* 20(10):1-21, 2010.

Echols et al., "Demographic, Clinical, and Treatment Parameters Influencing the Outcome of Acute Cystitis," *Clinical Infectious Diseases* 29(1):113-119, Jul. 1999.

Endimiani et al., "Presence of Plasmid-Mediated Quinolone Resistance in *Klebsiella pneumoniae* Isolates Possessing $bla_{KPC}$ in the United States," *Antimicrobial Agents and Chemotherapy* 52(7):2680-2682, Jul. 2008.

Endimiani et al., "Characterization of $bla_{KPC}$-containing *Klebsiella pneumoniae* isolates detected in different institutions in the Eastern USA," *Journal of Antimicrobial Chemotherapy* 63:427-437, 2009.

Endiamiani et al., "ACHN-490, a Neoglycoside with Potent In Vitro Activity against Multidrug-Resistant *Klebsiella pneumoniae* Isolates," *Antimicrobial Agents and Chemotherapy* 53(10):4504-4507, Oct. 2009.

Food and Drug Administration, Center for Drug Evaluation and Research (CDER), U.S. Department of Health and Human Services, *Guidance for Industry, Complicated Urinary Tract Infections and Pyelonephritis—Developing Antimicrobial Drugs for Treatment,* Draft Guidance, Jul. 1998, 11 pages.

Forge et al., "Aminoglycoside Antibiotics," *Audiol. Neurootol.* 5:3-22, 2000.

Freeman et al., "Once-daily dosing of aminoglycosides: review and recommendations for clinical practice," *Journal of Antimicrobial Chemotherapy* 39:677-686, 1997.

Gaynes et al., "Overview of Nosocomial Infections Caused by Gram-Negative Bacilli," *Clinical Infectious Diseases* 41:848-854, Sep. 15, 2005.

Georgescu et al., "Activity of ACHN-490, a Novel Neoglycoside Antibiotic, Against Contemporary Gram-Negative Clinical Isolates from Brooklyn, NY Hospitals," ICAAC 2009, Poster # F1-842, 1 page.

Giuliano et al., "The Effect of Dosing Strategy on Kidney Cortical Accumulation of Aminoglycosides in Rats," *American Journal of Kidney Diseases* 8(5):297-303, Nov. 1986.

Giuliano et al., "In Vivo Uptake Kinetics of Aminoglycosides in the Kidney Cortex of Rats," *The Journal of Pharmacology and Experimental Therapeutics* 236(2):470-475, 1986.

Goldfarb et al., "Detection of Plasmid-Mediated KPC-Producing *Klebsiella pneumoniae* in Ottawa, Canada: Evidence of Intrahospital Transmission," *Journal of Clinical Microbiology* 47(6):1920-1922, Jun. 2009.

Goossens et al., "Prevalence and antimicrobial susceptibility data for extended-spectrum β-lactamase- and AmpC-producing Enterobacteriaceae from the MYSTIC Program in Europe and the United States (1997-2004)," *Diagnostic Microbiology and Infectious Disease* 53:257-264, 2005.

Griebling, T. L., "Urinary Tract Infection in Women," in Litwin et al. (eds.), *Urologic Diseases in America,* DHHS, PHS, NIH, NIDDK, Washington, D.C.: GPO, 2007, NIH Publication 07-5512:587-619.

Guan et al., "A biochemical basis for the inherited susceptibility to aminoglycoside ototoxicity," *Human Molecular Genetics* 9(12):1787-1793, 2000.

Gülmez et al., "Carbapenem-resistant *Escherichia coli* and *Klebsiella pneumoniae* isolates from Turkey with OXA-48-like carbapenemases and outer membrane protein loss," *International Journal of Antimicrobial Agents* 31:523-526, 2008.

Hanessian et al., "Probing the functional requirements of the L-haba side-chain of amikacin—synthesis, 16S A-site rRNA binding, and antibacterial activity," *Tetrahedron* 59:995-1007, 2003.

Harrison, L. H., "Treatment of Complicated Urinary Tract Infections With Amikacin," *Urology* 10(2):110-113, Aug. 1977.

Hiraiwa et al., "Synthesis and antibacterial activity of 5-deoxy-5-episubstituted arbekacin derivatives," *Bioorganic & Medicinal Chemistry Letters* 17:3540-3543, 2007.

Hirakata et al., "Regional variation in the prevalence of extended-spectrum β-lactamase-producing clinical isolates in the Asia-Pacific region (SENTRY 1998-2002)," *Diagnostic Microbiology and Infectious Disease* 52:323-329, 2005.

Hottendorf et al., "Nonparallel Nephrotoxicity Dose-Response Curves of Aminoglycosides," *Antimicrobial Agents and Chemotherapy* 19(6):1024-1028, Jun. 1981.

Hujer et al., "Analysis of Antibiotic Resistance Genes in Multidrug-Resistant *Acinetobacter* sp. Isolates from Military and Civilian Patients Treated at the Walter Reed Army Medical Center," *Antimicrobial Agents and Chemotherapy* 50(12):4114-4123, Dec. 2006.

International Preliminary Report on Patentability, for International Application No. PCT/US2008/084399, mailed May 25, 2010, 6 pages.
International Search Report and Written Opinion, for International Application No. PCT/US2010/034886, mailed Aug. 25, 2010, 19 pages.
International Search Report and Written Opinion, for International Application No. PCT/US2010/034888, mailed Aug. 25, 2010, 21 pages.
International Search Report and Written Opinion, for International Application No. PCT/US2010/034898, mailed Oct. 8, 2010, 23 pages.
Invitation to Pay Additional Fees, and Partial International Search Report, for International Application No. PCT/US2010/034886, mailed Jul. 2, 2010, 4 pages.
Invitation to Pay Additional Fees, and Partial International Search Report, for International Application No. PCT/US2010/034888, mailed Jun. 30, 2010, 5 pages.
Invitation to Pay Additional Fees, and Partial International Search Report, for International Application No. PCT/US2010/034896, mailed Jul. 12, 2010, 6 pages.
Invitation to Pay Additional Fees, and Partial International Search Report, for International Application No. PCT/US2010/034898, mailed Aug. 4, 2010, 5 pages.
Invitation to Pay Additional Fees, and Partial International Search Report, for International Application No. PCT/US2010/034909, mailed Aug. 25, 2010, 7 pages.
Invitation to Pay Additional Fees, and Partial International Search Report, for International Application No. PCT/US2010/035006, mailed Aug. 18, 2010, 8 pages.
Johnson et al., "Urinary Tract Infections in Women: Diagnosis and Treatment," *Annals of Internal Medicine* 111:906-917, 1989.
Jones et al., "Antimicrobial Activity of ACHN-490, a Neoglycoside, Tested Against a Contemporary Collection of Clinical Isolates Including Problematic Antimicrobial-Resistant Phenotypes," ICAAC 2009, Poster # F1-846a, 1 page.
Kahlmeter et al., "Aminoglycoside toxicity—a review of clinical studies published between 1975 and 1982," *J. Antimicrob. Chemo.* 13(Suppl. A):9-22, 1984.
Kahlmeter et al., "Cross-resistance and associated resistance in 2478 *Escherichia coli* isolates from the Pan-European ECO•SENS Project surveying the antimicrobial susceptibility of pathogens from uncomplicated urinary tract infections," *J. Antimirob. Chemo.* 52(1):128-131, 2003.
Karlowsky et al., "Trends in Antimicrobial Resistance among Urinary Tract Infection Isolates of *Escherichia coli* from Female Outpatients in the United States," *Antimicrobial Agents and Chemotherapy* 46(8):2540-2545, Aug. 2002.
Karlowsky et al., "Fluoroquinolone-Resistant Urinary Isolates of *Escherichia coli* from Outpatients Are Frequently Multidrug Resistant: Results from the North American Urinary Tract Infection Collaborative Alliance-Quinolone Resistance Study," *Antimicrobial Agents and Chemotherapy* 50(6):2251-2254, Jun. 2006.
Kishi et al., "Comparative Study on Intravenous Drip Infusion of Dibekacin Once Daily and Twice Daily in Treatment of Complicated Urinary Tract Infections," *Hinyokika Kiyo* 30(1):103-120, 1984.
Kitasato et al., "Reduction of Dibekacin-Induced Nephrotoxicty in the Rat by the Formation of *N*-Alkylsulfonate Derivatives," *Drugs Exptl. Clin. Res.* 15(6/7):239-247, 1989.
Kitasato et al., "Comparative Ototoxicity of Ribostamycin, Dactimicin, Dibekacin, Kanamycin, Amikacin, Tobramycin, Gentamicin, Sisomicin and Netilmicin in the Inner Ear of Guinea Pigs," *Chemotherapy* 36:155-168, 1990.
Klevens et al., "Estimating Health Care-Associated Infections and Deaths in U.S. Hospitals, 2002," *Public Health Reports* 122:160-166, Mar.-Apr. 2007.
Kondo et al., "Synthesis of 2''-Amino-2''-Deoxyarbekacin and Its Analogs Having Potent Activity Against Methicillin-Resistant *Staphylococcus aureus*," *The Journal of Antibiotics* 47(7):821-832, Jul. 1994.
Kondo et al., "Semisynthetic aminoglycoside antibiotics: Development and enzymatic modifications," *J. Infect. Chemother.* 5:1-9, 1999.

Kotretsou et al., "Synthesis and Antimicrobial and Toxicological Studies of Amino Acid and Peptide Derivatives of Kanamycin A and Netilmicin," *J. Med. Chem.* 38:4710-4719, 1995.
Kostrub et al., "Quantitative Comparison of Aminoglycoside Nephrotoxicity in Rats for Effective Screening and Evaluation of New Derivatives, and Dosing Rationales That Minimise Toxicity," ECCMID 2009, Poster # P-1979, 1 page.
Kostrub et al., "Ototoxic Potential of ACHN-490 Compared to Gentamicin and Amikacin in the Guinea Pig," ECCMID 2010, Poster # P-1249, 1 page.
Lee et al., "Decreased Susceptibility to Polymyxin B during Treatment for Carbapenem-Resistant *Klebsiella pneumoniae* Infection," *Journal of Clinical Microbiology* 47(5): 1611-1612, May 2009.
Li et al., "Tuning the Regioselectivity of the Staudinger Reaction for the Facile Synthesis of Kanamycin and Neomycin Class Antibiotics with N-1 Modification," *Organic Letters* 7(14):3061-3064, 2005.
Li et al., "Colistin: the re-emerging antibiotic for multidrug-resistant Gram-negative bacterial infections," *Lancet Infect. Dis.* 6:589-601, Sep. 2006.
Lin et al., "Activity of ACHN-490 in Combination with Daptomycin, Ceftobiprole, or Linezolid against 47 Methicillin-resistant *Staphylococcus aureus* by Synergy Time-kill," ICAAC 2009, Poster # F1-844, 1 page.
Lin et al., "Antistaphylococcal Activity of ACHN-490 Tested Alone and in Combination With Other Agents by Time-Kill Assay," *Antimicrobial Agents and Chemotherapy* 54(5):2258-2261, 2010.
Madsen et al., "Treatment of Complicated Urinary Tract Infections, Comparative Study of Sisomicin and Gentamicin," *Urology* 9(6):635-638, Jun. 1977.
Magnet et al., "Molecular Insights into Aminoglycoside Action and Resistance," *Chem. Rev.* 105:477-497, 2005.
Maigaard et al., "Comparison of Netilmicin and Amikacin in Treatment of Complicated Urinary Tract Infections," *Antimicrobial Agents and Chemotherapy* 14(4):544-548, Oct. 1978.
Mallams et al., "Synthesis of Novel 1-*N* Aminoalkyloxycarbonyl and 1-*N* Aminoalkylcarboxamido Derivatives of Sisomicin, Gentamicin B, Gentamicin C-1a, and Kanamycin A," Current Chemotherapy and Infectious Disease: Proceedings of the 11th International Congress of Chemotherapy and the 19th Interscience Conference on Antimicrobial Agents and Chemotherapy, Boston, Massachusetts, Oct. 1-5, 1979, vol. 1, Jan. 1, 1980, pp. 406-408.
Mallams et al., "Semisynthetic Aminoglycoside Antibacterials. Part 10. Synthesis of Novel 1-*N*-Aminoalkoxycarbonyl and 1-*N*-Aminoalkylcarboxamido Derivatives of Sisomicin,Gentamicin B, Gentamicin C, and Kanamycin A," J. Chem. Soc., Perkin Trans. 1:2186-2208, 1981.
Maller et al., "Once- versus twice-daily amikacin regimen: efficacy and safety in systemic Gram-negative infections," *Journal of Antimicrobial Chemotherapy* 31:939-948, 1993.
Maltezou et al., "Outbreak of infections due to KPC-2-producing *Klebsiella pneumoniae* in a hospital in Crete (Greece)," *Journal of Infection* 58:213-219, 2009.
Marrie et al, "Clinical and laboratory study of tobramycin in the treatment of infections due to gram-negative organisms," *Canadian Medical Association Journal* 117(2):138,141-143, Jul. 23, 1977.
Mentec et al., "Piperacillin, Tazobactam, and Gentamicin Alone or Combined in an Endocarditis Model of Infection by a TEM-3-Producing Strain of *Klebsiella pneumoniae* or Its Susceptible Variant," *Antimicrobial Agents and Chemotherapy* 36(9):1883-1889, Sep. 1992.
Nagabhushan et al., "Chemical Modification of Some Gentamicins and Sisomicin at the 3''-Position," *The Journal of Antibiotics* 31(1):43-54, Jan. 1978.
Nagabhushan et al., "The Syntheses and Biological Properties of 1-*N*-(S-4-Amino-2-Hydroxybutyryl)-Gentamicin B and 1-*N*-(S-3-Amino-2-Hydroxypropionyl)-Gentamicin B," *The Journal of Antibiotics* 31(7):681-687, Jul. 1978.
National Center for Health Statistics. National Hospital Discharge Survey: 2004 Annual Summary with Detailed Diagnosis and Procedure Data. DHHS, Centers for Disease Control and Prevention, Hyattsville, MD: GPO; 2006. DHHS publication 2006-1733, 218 pages.

Nicolau et al., "Experience with a Once-Daily Aminoglycoside Program Administered to 2,184 Adult Patients," *Antimicrobial Agents and Chemotherapy* 39(3):650-655, Mar. 1995.

Nishimura et al., "A proof of the specificity of kanamycin-ribosomal RNA interaction with designed synthetic analogs and the antibacterial activity," *Bioorganic & Medicinal Chemistry Letters* 15:2159-2162, 2005.

Nordmann et al., "The real threat of *Klebsiella pneumoniae* carbapenemase-producing bacteria," *Lancet Infect. Dis.* 9:228-236, Apr. 2009.

Odds, F.C., "Synergy, antagonism, and what the chequerboard puts between them," *Journal of Antimicrobial Chemotherapy* 52:1, 2003.

O'Shea et al., "Physiochemical Properties of Antibacterial Compounds: Implications for Drug Discovery," *Journal of Medicinal Chemistry* 51(10):2871-2878, May 22, 2008.

Pavez et al., "Early Dissemination of KPC-2-Producing *Klebsiella pneumoniae* Strains in Brazil," *Antimicrobial Agents and Chemotherapy* 53(6):2702, Jun. 2009.

Peloquin et al., "Aminoglycoside Toxicity: Daily versus Thrice-Weekly Dosing for Treatment of Mycobacterial Diseases," *Clinical Infectious Diseases* 38:1538-1544, Jun. 1, 2004.

Peterson, "A review of tigecycline—the first glyclycline," *International Journal of Antimicrobial Agents* 32(S4):S215-S222, 2008.

Queenan et al., "Carbapenemases: the Versatile β-Lactamases," *Clinical Microbiology Reviews* 20(3):440-458, Jul. 2007.

Rai et al., "Novel Method for the Synthesis of 3', 4'-Dideoxygenated Pyranmycin and Kanamycin Compounds, and Studies of Their Antibacterial Activity Against Aminoglycoside-Resistant Bacteria," *Journal of Carbohydrate Chemistry* 24:131-143, 2005.

Reyes et al., "In Vivo Efficacy of the Neoglycoside ACHN-490 Against Enterobacteriaceae and MRSA," ICAAC 2009, Poster # F1-845, 1 page.

Rodriguez-Baño et al., "Clinical significance of extended-spectrum β-lactamases," *Expert Rev. Anti Infect. Ther.* 6(5):671-683, 2008.

*The Sanford Guide to Antimicrobial Therapy*, 37th Edition, Gilbert et al. (eds.), Antimicrobial Therapy: Sperryville, VA, 2007, p. 93.

Santucci et al., "Gentamicin for the Practicing Urologist: Review of Efficacy, Single Daily Dosing and "Switch" Therapy," *The Journal of Urology* 163:1076-1084, Apr. 2000.

Selimoglu, E., "Aminoglycoside-Induced Ototoxicity," *Current Pharmaceutical Design* 13:119-126, 2007.

Sepulchre et al., "The Chemical Ionisation Mass Spectrometry of Aminocyclitol-Aminogylcoside Antibiotics," *Nouveau Journal de Chimie* 2(4):405-409, Jul. 1978.

Singh et al., "Microwave-Assisted Synthesis of Substituted Tetrahydropyrans Catalyzed by $ZrCl_4$ and Its Application in the Asymmetric Synthesis of exo- and endo-brevicomin," *J. Org. Chem.* 74:5758-5761, 2009.

Stamm, W. E., "Urinary Tract Infections and Pyelonephritis," in Braunwald et al. (eds.), *Harrison's 15th Edition Principles of Internal Medicine*, McGraw-Hill, New York, 2001, pp. 1620-1626.

Streicher et al., "Synthesis and Structure/Activity Relationships of New Guanidino Derivatives of Aminoglycoside Antibiotics," Drugs Exptl. Clin. Res. IX(8/9):591-598, 1983.

Talan et al., "Prevalence and Risk Factor Analysis of Trimethoprim-Sulfamethoxazole- and Fluoroquinolone-Resistant *Escherichia coli* Infection among Emergency Department Patients with Pyelonephritis," *Clinical Infectious Diseases* 47:1150-1158, 2008.

Tanabe et al., "Aminoglycoside Antibiotics: Synthesis of Nebramine, Tobramycin and 4"-Epi-Tobramycin," *Tetrahedron Letters* 41:3607-3610, 1977.

Van Schepdael et al., "New Derivatives of Kanamycin B Obtained by Modifications and Substitutions in Position 6". 1. Synthesis and Microbiological Evaluation," *J. Med. Chem.* 34:1468-1475, 1991.

Van Schepdael et al., "New Derivatives of Kanamycin B Obtained by Combined Modifications in Positions 1 and 6". Synthesis, Microbiological Properties, and in Vitro and Computer-Aided Toxicological Evaluation," *J. Med. Chem.* 34:1483-1492, 1991.

Verpooten et al., "Once-daily dosing decreases renal accumulation of gentamicin and netilmicin," *Clin. Pharmacol. Ther.* 45:22-27, 1989.

Wachino et al., "Novel Plasmid-Mediated 16S rRNA $m^1$ A1408 Methyltransferase, NpmA, Found in a Clinically Isolated *Escherichia coli* Strain Resistant to Structurally Diverse Aminoglycosides," *Antimicrobial Agents and Chemotherapy* 51(12):4401-4409, Dec. 2007.

Wang et al., "Design, Chemical Synthesis, and Antibacterial Activity of Kanamycin and Neomycin Class Aminoglycoside Antibiotics," in Dev P. Arya (ed.),*Aminoglycoside Antibiotics, From Chemical Biology to Drug Discovery*, Wiley-Interscience, 2007, pp. 141-180.

Warren et al., "Guidelines From the Infectious Diseases Society of America: Guidelines for Antimicrobial Treatment of Uncomplicated Acute Bacterial Cystitis and Acute Pyelonephritis in Women," *Clinical Infectious Diseases* 29:745-758, 1999.

Woodford et al., "Arrival of *Klebsiella pneumoniae* producing KPC carbapenemase in the United Kingdom," *Journal of Antimicrobial Chemotherapy* 62:1261-1264, 2008.

Yamane et al., "Antimicrobial susceptibilities of organisms isolated from patients with complicated urinary tract infections in 2004 and 2005," *Japanese Journal of Chemotherapy* 55(6):473-478, Nov. 2007 (with English Abstract).

International Preliminary Report on Patentability, for International Application No. PCT/US2010/038138, mailed Jan. 5, 2012, 11 pages.

International Preliminary Report on Patentability, for International Application No. PCT/US2010/035006, mailed Nov. 24, 2011, 26 pages.

International Preliminary Report on Patentability, for International Application No. PCT/US2010/034898, mailed Nov. 24, 2011, 13 pages.

International Preliminary Report on Patentability, for International Application No. PCT/US2010/034909, mailed Nov. 24, 2011. 17 pages.

International Preliminary Report on Patentability, for International Application No. PCT/US2010/034896, mailed Nov. 24, 2011, 14 pages.

International Preliminary Report on Patentability, for International Application No. PCT/US2010/034893, mailed Nov. 24, 2011, 14 pages.

International Preliminary Report on Patentability, for International Application No. PCT/US2010/034888, mailed Nov. 24, 2011, 15 pages.

International Preliminary Report on Patentability, for International Application No. PCT/US2010/034886, mailed Nov. 24, 2011, 15 pages.

International Preliminary Report on Patentability, for International Application No. PCT/US2010/034884, mailed Nov. 24, 2011, 12 pages.

Kotretsou et al., "Synthesis of Amino Acid and Peptide Derivatives of Aminoglycosides Targeted Against Resistance of Bacteria," Topics in Molecular Organization and Engineering 11:277-280, 1994.

Office Action for U.S. Appl. No. 13/295,227, dated Nov. 7, 2012 (8 pages).

Office Action for U.S. Appl. No. 13/295,247, dated Aug. 29, 2012 (8 pages).

Office Action for U.S. Appl. No. 13/295,238, dated Aug. 28, 2012 (8 pages).

Office Action for U.S. Appl. No. 13/295,233, dated Aug. 28, 2012 (8 pages).

Office Action for U.S. Appl. No. 13/295,231, dated Sep. 13, 2012 (7 pages).

Restriction Requirement for U.S. Appl. No. 13/327,377, dated Aug. 30, 2012 (9 pages).

* cited by examiner

ANTIBACTERIAL AMINOGLYCOSIDE ANALOGS

CROSS-REFERENCE TO RELATED APPLICATIONS

This application is a continuation of International PCT Application No. PCT/US2008/084399, filed Nov. 21, 2008, now pending, which claims the benefit under 35 U.S.C. §119 (e) of U.S. Provisional Patent Application No. 60/989,645, filed Nov. 21, 2007, which applications are incorporated herein by reference in their entireties.

BACKGROUND

1. Field

The present invention is directed to novel aminoglycoside compounds, more specifically, novel sisomicin derivatives, and methods for their preparation and use as therapeutic or prophylactic agents.

2. Description of the Related Art

A particular interest in modern drug discovery is the development of novel low molecular weight orally-bioavailable drugs that work by binding to RNA. RNA, which serves as a messenger between DNA and proteins, was thought to be an entirely flexible molecule without significant structural complexity. Recent studies have revealed a surprising intricacy in RNA structure. RNA has a structural complexity rivaling proteins, rather than simple motifs like DNA. Genome sequencing reveals both the sequences of the proteins and the mRNAs that encode them. Since proteins are synthesized using an RNA template, such proteins can be inhibited by preventing their production in the first place by interfering with the translation of the mRNA. Since both proteins and the RNAs are potential drug targeting sites, the number of targets revealed from genome sequencing efforts is effectively doubled. These observations unlock a new world of opportunities for the pharmaceutical industry to target RNA with small molecules.

Classical drug discovery has focused on proteins as targets for intervention. Proteins can be extremely difficult to isolate and purify in the appropriate form for use in assays for drug screening. Many proteins require post-translational modifications that occur only in specific cell types under specific conditions. Proteins fold into globular domains with hydrophobic cores and hydrophilic and charged groups on the surface. Multiple subunits frequently form complexes, which may be required for a valid drug screen. Membrane proteins usually need to be embedded in a membrane to retain their proper shape. The smallest practical unit of a protein that can be used in drug screening is a globular domain. The notion of removing a single alpha helix or turn of a beta sheet and using it in a drug screen is not practical, since only the intact protein may have the appropriate 3-dimensional shape for drug binding. Preparation of biologically active proteins for screening is a major limitation in classical high throughput screening. Quite often the limiting reagent in high throughput screening efforts is a biologically active form of a protein which can also be quite expensive.

For screening to discover compounds that bind RNA targets, the classic approaches used for proteins can be superceded with new approaches. All RNAs are essentially equivalent in their solubility, ease of synthesis or use in assays. The physical properties of RNAs are independent of the protein they encode. They may be readily prepared in large quantity through either chemical or enzymatic synthesis and are not extensively modified in vivo. With RNA, the smallest practical unit for drug binding is the functional subdomain. A functional subdomain in RNA is a fragment that, when removed from the larger RNA and studied in isolation, retains its biologically relevant shape and protein or RNA-binding properties. The size and composition of RNA functional subdomains make them accessible by enzymatic or chemical synthesis. The structural biology community has developed significant experience in identification of functional RNA subdomains in order to facilitate structural studies by techniques such as NMR spectroscopy. For example, small analogs of the decoding region of 16S rRNA (the A-site) have been identified as containing only the essential region, and have been shown to bind antibiotics in the same fashion as the intact ribosome.

The binding sites on RNA are hydrophilic and relatively open as compared to proteins. The potential for small molecule recognition based on shape is enhanced by the deformability of RNA. The binding of molecules to specific RNA targets can be determined by global conformation and the distribution of charged, aromatic, and hydrogen bonding groups off of a relatively rigid scaffold. Properly placed positive charges are believed to be important, since long-range electrostatic interactions can be used to steer molecules into a binding pocket with the proper orientation. In structures where nucleobases are exposed, stacking interactions with aromatic functional groups may contribute to the binding interaction. The major groove of RNA provides many sites for specific hydrogen bonding with a ligand. These include the aromatic N7 nitrogen atoms of adenosine and guanosine, the O4 and O6 oxygen atoms of uridine and guanosine, and the amines of adenosine and cytidine. The rich structural and sequence diversity of RNA suggests to us that ligands can be created with high affinity and specificity for their target.

Although our understanding of RNA structure and folding, as well as the modes in which RNA is recognized by other ligands, is far from being comprehensive, significant progress has been made in the last decade (see, e.g., Chow, C. S.; Bogdan, F. M., Chem. Rev., 1997, 97, 1489 and Wallis, M. G.; Schroeder, R., Prog. Biophys. Molec. Biol. 1997, 67, 141). Despite the central role RNA plays in the replication of bacteria, drugs that target these pivotal RNA sites of these pathogens are scarce. The increasing problem of bacterial resistance to antibiotics makes the search for novel RNA binders of crucial importance.

Certain small molecules can bind and block essential functions of RNA. Examples of such molecules include the aminoglycoside antibiotics and drugs such as erythromycin which binds to bacterial rRNA and releases peptidyl-tRNA and mRNA. Aminoglycoside antibiotics have long been known to bind RNA. They exert their antibacterial effects by binding to specific target sites in the bacterial ribosome. For the structurally related antibiotics neamine, ribostamycin, neomycin B, and paromomycin, the binding site has been localized to the A-site of the prokaryotic 16S ribosomal decoding region RNA (see Moazed, D.; Noller, H. F., Nature, 1987, 327, 389). Binding of aminoglycosides to this RNA target interferes with the fidelity of mRNA translation and results in miscoding and truncation, leading ultimately to bacterial cell death (see Alper, P. B.; Hendrix, M.; Sears, P.; Wong, C., J. Am. Chem. Soc., 1998, 120, 1965).

There is a need in the art for new chemical entities that work against bacteria with broad-spectrum activity. Perhaps the biggest challenge in discovering RNA-binding antibacterial drugs is identifying vital structures common to bacteria that can be disabled by small molecule drug binding. A challenge in targeting RNA with small molecules is to develop a chemical strategy which recognizes specific shapes of RNA.

There are three sets of data that provide hints on how to do this: natural protein interactions with RNA, natural product antibiotics that bind RNA, and man-made RNAs (aptamers) that bind proteins and other molecules. Each data set, however, provides different insights to the problem.

Several classes of drugs obtained from natural sources have been shown to work by binding to RNA or RNA/protein complexes. These include three different structural classes of antibiotics: thiostreptone, the aminoglycoside family and the macrolide family of antibiotics. These examples provide powerful clues to how small molecules and targets might be selected. Nature has selected RNA targets in the ribosome, one of the most ancient and conserved targets in bacteria. Since antibacterial drugs are desired to be potent and have broad-spectrum activity, these ancient processes, fundamental to all bacterial life, represent attractive targets. The closer we get to ancient conserved functions the more likely we are to find broadly conserved RNA shapes. It is important to also consider the shape of the equivalent structure in humans, since bacteria were unlikely to have considered the therapeutic index of their RNAs while evolving them.

A large number of natural antibiotics exist, these include the aminoglycosides, such as, kirromycin, neomycin, paromomycin, thiostrepton, and many others. They are very potent, bactericidal compounds that bind RNA of the small ribosomal subunit. The bactericidal action is mediated by binding to the bacterial RNA in a fashion that leads to misreading of the genetic code. Misreading of the code during translation of integral membrane proteins is thought to produce abnormal proteins that compromise the barrier properties of the bacterial membrane.

Antibiotics are chemical substances produced by various species of microorganisms (bacteria, fungi, actinomycetes) that suppress the growth of other microorganisms and may eventually destroy them. However, common usage often extends the term antibiotics to include synthetic antibacterial agents, such as the sulfonamides, and quinolines, that are not products of microbes. The number of antibiotics that have been identified now extends into the hundreds, and many of these have been developed to the stage where they are of value in the therapy of infectious diseases. Antibiotics differ markedly in physical, chemical, and pharmacological properties, antibacterial spectra, and mechanisms of action. In recent years, knowledge of molecular mechanisms of bacterial, fungal, and viral replication has greatly facilitated rational development of compounds that can interfere with the life cycles of these microorganisms.

At least 30% of all hospitalized patients now receive one or more courses of therapy with antibiotics, and millions of potentially fatal infections have been cured. At the same time, these pharmaceutical agents have become among the most misused of those available to the practicing physician. One result of widespread use of antimicrobial agents has been the emergence of antibiotic-resistant pathogens, which in turn has created an ever-increasing need for new drugs. Many of these agents have also contributed significantly to the rising costs of medical care.

When the antimicrobial activity of a new agent is first tested, a pattern of sensitivity and resistance is usually defined. Unfortunately, this spectrum of activity can subsequently change to a remarkable degree, because microorganisms have evolved the array of ingenious alterations discussed above that allow them to survive in the presence of antibiotics. The mechanism of drug resistance varies from microorganism to microorganism and from drug to drug.

The development of resistance to antibiotics usually involves a stable genetic change, inheritable from generation to generation. Any of the mechanisms that result in alteration of bacterial genetic composition can operate. While mutation is frequently the cause, resistance to antimicrobial agents may be acquired through transfer of genetic material from one bacterium to another by transduction, transformation or conjugation.

For the foregoing reasons, while progress has been made in this field, there is a need for new chemical entities that possess antibacterial activity. Further, in order to accelerate the drug discovery process, new methods for synthesizing aminoglycoside antibiotics are needed to provide an array of compounds that are potentially new drugs for the treatment of bacterial infections. The present invention fulfills these needs and provides further related advantages.

BRIEF SUMMARY

In brief, the present invention is directed to novel aminoglycoside compounds, more specifically, novel sisomicin derivatives, having antibacterial activity, including stereoisomers, pharmaceutically acceptable salts and prodrugs thereof, and the use of such compounds in the treatment of bacterial infections.

In one embodiment, compounds having the following structure (I) are provided:

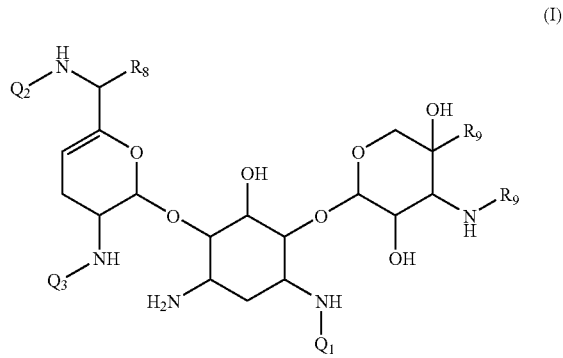

or a stereoisomer, pharmaceutically acceptable salt or prodrug thereof, wherein:

$Q_1$ is hydrogen,

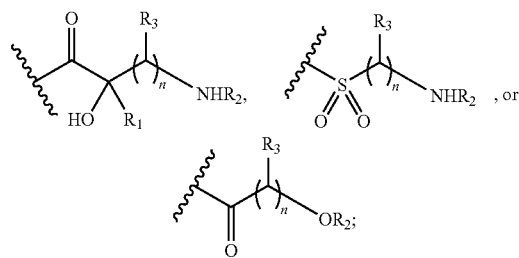

$Q_2$ is hydrogen, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —C(=NH)NR$_4$R$_5$, —(CR$_{10}$R$_{11}$)$_p$R$_{12}$,

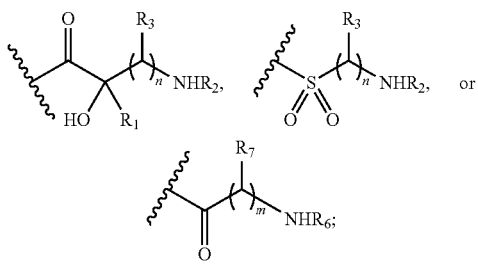

$Q_3$ is hydrogen, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —C(=NH)NR$_4$R$_5$, —(CR$_{10}$R$_{11}$)$_p$R$_{12}$,

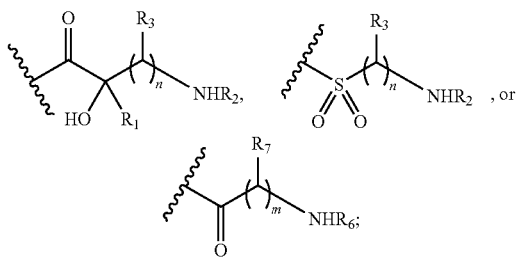

each $R_1$, $R_2$, $R_3$, $R_4$, $R_5$, $R_8$ and $R_{10}$ is, independently, hydrogen or $C_1$-$C_6$ alkyl, or $R_1$ and $R_2$ together with the atoms to which they are attached can form a heterocyclic ring having from 4 to 6 ring atoms, or $R_2$ and $R_3$ together with the atoms to which they are attached can form a heterocyclic ring having from 4 to 6 ring atoms, or $R_1$ and $R_3$ together with the atoms to which they are attached can form a carbocyclic ring having from 4 to 6 ring atoms, or $R_4$ and $R_5$ together with the atom to which they are attached can form a heterocyclic ring having from 4 to 6 ring atoms;

each $R_6$ and $R_7$ is, independently, hydrogen, hydroxyl, amino or $C_1$-$C_6$ alkyl, or $R_6$ and $R_7$ together with the atoms to which they are attached can form a heterocyclic ring having from 4 to 6 ring atoms;

each $R_9$ is, independently, hydrogen or methyl;

each $R_{11}$ is, independently, hydrogen, hydroxyl, amino or $C_1$-$C_6$ alkyl;

each $R_{12}$ is, independently, hydroxyl or amino;

each n is, independently, an integer from 0 to 4;

each m is, independently, an integer from 0 to 4; and each p is, independently, an integer from 1 to 5, and wherein (i) at least two of $Q_1$, $Q_2$ and $Q_3$ are other than hydrogen, and (ii) if $Q_1$ is hydrogen, then at least one of $Q_2$ and $Q_3$ is —C(=NH)NR$_4$R$_5$.

In another embodiment, a pharmaceutical composition is provided comprising a compound having structure (I), or a stereoisomer, pharmaceutically acceptable salt or prodrug thereof, and a pharmaceutically acceptable carrier, diluent or excipient.

In another embodiment, a method of using a compound having structure (I) in therapy is provided. In particular, the present invention provides a method of treating a bacterial infection in a mammal comprising administering to the mammal an effective amount of a compound having structure (I), or a stereoisomer, pharmaceutically acceptable salt or prodrug thereof.

These and other aspects of the invention will be apparent upon reference to the following detailed description.

DETAILED DESCRIPTION

In the following description, certain specific details are set forth in order to provide a thorough understanding of various embodiments of the invention. However, one skilled in the art will understand that the invention may be practiced without these details.

Unless the context requires otherwise, throughout the present specification and claims, the word "comprise" and variations thereof, such as, "comprises" and "comprising" are to be construed in an open, inclusive sense, that is as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in the specification and appended claims, unless specified to the contrary, the following terms have the meaning indicated.

"Amino" refers to the —NH$_2$ radical.

"Cyano" refers to the —CN radical.

"Hydroxy" or "hydroxyl" refers to the —OH radical.

"Imino" refers to the =NH substituent.

"Nitro" refers to the —NO$_2$ radical.

"Oxo" refers to the =O substituent.

"Thioxo" refers to the =S substituent.

"Alkyl" refers to a straight or branched hydrocarbon chain radical consisting solely of carbon and hydrogen atoms, which is saturated or unsaturated (i.e., contains one or more double and/or triple bonds), having from one to twelve carbon atoms ($C_1$-$C_{12}$ alkyl), preferably one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl(iso-propyl), n-butyl, n-pentyl, 1,1-dimethylethyl(t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. Unless stated otherwise specifically in the specification, an alkyl group may be optionally substituted.

"Alkylene" or "alkylene chain" refers to a straight or branched divalent hydrocarbon chain linking the rest of the molecule to a radical group, consisting solely of carbon and hydrogen, which is saturated or unsaturated (i.e., contains one or more double and/or triple bonds), and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain may be optionally substituted.

"Alkoxy" refers to a radical of the formula —OR$_a$ where R$_a$ is an alkyl radical as defined above containing one to twelve carbon atoms. Unless stated otherwise specifically in the specification, an alkoxy group may be optionally substituted.

"Alkylamino" refers to a radical of the formula —NHR$_a$ or —NR$_a$R$_a$ where each R$_a$ is, independently, an alkyl radical as defined above containing one to twelve carbon atoms. Unless stated otherwise specifically in the specification, an alkylamino group may be optionally substituted.

"Thioalkyl" refers to a radical of the formula —SR$_a$ where R$_a$ is an alkyl radical as defined above containing one to twelve carbon atoms. Unless stated otherwise specifically in the specification, a thioalkyl group may be optionally substituted.

"Aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Aralkyl" refers to a radical of the formula —R$_b$-R$_c$ where R$_b$ is an alkylene chain as defined above and R$_c$ is one or more aryl radicals as defined above, for example, benzyl, diphenylmethyl and the like. Unless stated otherwise specifically in the specification, an aralkyl group may be optionally substituted.

"Cycloalkyl" or "carbocyclic ring" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like. Unless otherwise stated specifically in the specification, a cycloalkyl group may be optionally substituted.

"Cycloalkylalkyl" refers to a radical of the formula —R$_b$R$_d$ where R$_d$ is an alkylene chain as defined above and R$_g$ is a cycloalkyl radical as defined above. Unless stated otherwise specifically in the specification, a cycloalkylalkyl group may be optionally substituted.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Heterocyclyl" or "heterocyclic ring" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, Unless stated otherwise specifically in the specification, a heterocyclyl group may be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group may be optionally substituted.

"Heterocyclylalkyl" refers to a radical of the formula —R$_b$R$_e$ where R$_b$ is an alkylene chain as defined above and R$_e$ is a heterocyclyl radical as defined above, and if the heterocyclyl is a nitrogen-containing heterocyclyl, the heterocyclyl may be attached to the alkyl radical at the nitrogen atom. Unless stated otherwise specifically in the specification, a heterocyclylalkyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl(benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group may be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group may be optionally substituted.

"Heteroarylalkyl" refers to a radical of the formula —$R_bR_f$ where $R_b$ is an alkylene chain as defined above and $R_f$ is a heteroaryl radical as defined above. Unless stated otherwise specifically in the specification, a heteroarylalkyl group may be optionally substituted.

The term "substituted" used herein means any of the above groups (i.e., alkyl, alkylene, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(=O)OR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted" also means any of the above groups in which one or more hydrogen atoms are replaced with —$C(=O)R_g$, —$C(=O)OR_g$, —$C(=O)NR_gR_h$, —$CH_2SO_2R_g$, —$CH_2SO_2NR_gR_h$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In addition, each of the foregoing substituents may also be optionally substituted with one or more of the above substituents.

"Prodrug" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)). A discussion of prodrugs is provided in Higuchi, T., et al., A.C.S. Symposium Series, Vol. 14, and in Bioreversible Carriers in Drug Design, Ed. Edward B. Roche, American Pharmaceutical Association and Pergamon Press, 1987.

The term "prodrug" is also meant to include any covalently bonded carriers, which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxyl, amino or mercapto group is bonded to any group that, when the prodrug of the compound of the invention is administered to a mammalian subject, cleaves to form a free hydroxyl, free amino or free mercapto group, respectively. Examples of prodrugs include, but are not limited to, acetate, formate and benzoate derivatives of alcohol or amide derivatives of amine functional groups in the compounds of the invention and the like.

The invention disclosed herein is also meant to encompass all pharmaceutically acceptable compounds of structure (I) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radiolabelled compounds could be useful to help determine or measure the effectiveness of the compounds, by characterizing, for example, the site or mode of action, or binding affinity to pharmacologically important site of action. Certain isotopically-labelled compounds of structure (I), for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of structure (I) can generally be prepared by conventional techniques known to those skilled in the art or by processes analogous to those described in the Preparations and Examples as set out below using an appropriate isotopically-labeled reagent in place of the non-labeled reagent previously employed.

The invention disclosed herein is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the invention includes compounds produced by a process comprising administering a compound of this invention to a mammal for a period of time sufficient to yield a metabolic product thereof Such products are typically identified by administering a radiolabelled compound of the invention in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

"Mammal" includes humans and both domestic animals such as laboratory animals and household pets (e.g., cats, dogs, swine, cattle, sheep, goats, horses, rabbits), and non-domestic animals such as wildlife and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethyl amino ethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Effective amount" or "therapeutically effective amount" refers to that amount of a compound of the invention which, when administered to a mammal, preferably a human, is sufficient to effect treatment, as defined below, of a bacterial infection in the mammal, preferably a human. The amount of a compound of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) relieving the symptoms resulting from the disease or condition, i.e., relieving pain without addressing the underlying disease or condition. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

As noted above, in one embodiment of the present invention, compounds having antibacterial activity are provided, the compounds having the following structure (I):

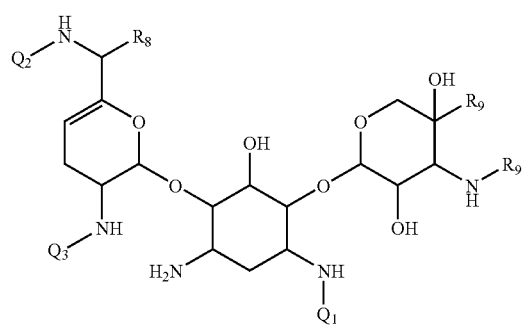

(I)

or a stereoisomer, pharmaceutically acceptable salt or prodrug thereof,
wherein:
$Q_1$ is hydrogen,

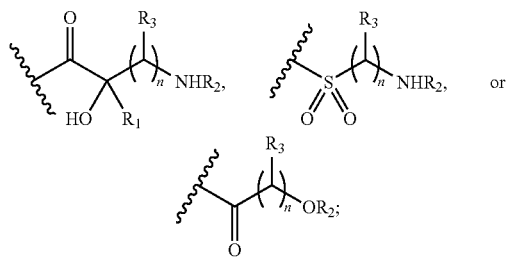

$Q_2$ is hydrogen, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —C(=NH)NR$_4$R$_5$, —(CR$_{10}$R$_{11}$)$_p$R$_{12}$,

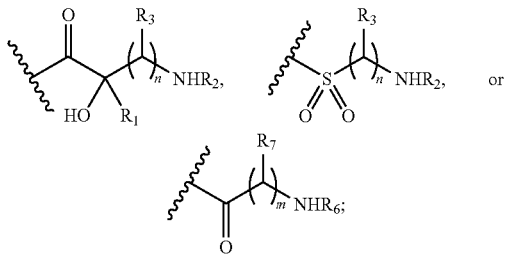

$Q_3$ is hydrogen, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —C(=NH)NR$_4$R$_5$, —(CR$_{10}$R$_{11}$)$_p$R$_{12}$,

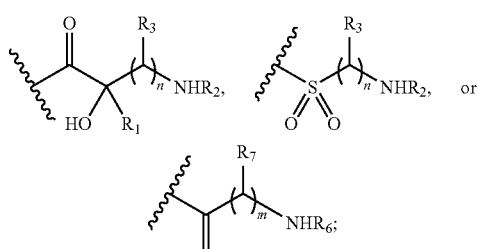

each $R_1$, $R_2$, $R_3$, $R_4$, $R_5$, $R_8$ and $R_{10}$ is, independently, hydrogen or $C_1$-$C_6$ alkyl, or $R_1$ and $R_2$ together with the atoms to which they are attached can form a heterocyclic ring having from 4 to 6 ring atoms, or $R_2$ and $R_3$ together with the atoms to which they are attached can form a heterocyclic ring having from 4 to 6 ring atoms, or $R_1$ and $R_3$ together with the atoms to which they are attached can form a carbocyclic ring having from 4 to 6 ring atoms, or $R_4$ and $R_5$ together with the atom to which they are attached can form a heterocyclic ring having from 4 to 6 ring atoms;

each $R_6$ and $R_7$ is, independently, hydrogen, hydroxyl, amino or $C_1$-$C_6$ alkyl, or $R_6$ and $R_7$ together with the atoms to which they are attached can form a heterocyclic ring having from 4 to 6 ring atoms;

each $R_9$ is, independently, hydrogen or methyl;

each $R_{11}$ is, independently, hydrogen, hydroxyl, amino or $C_1$-$C_6$ alkyl;

each $R_{12}$ is, independently, hydroxyl or amino;

each n is, independently, an integer from 0 to 4;

each m is, independently, an integer from 0 to 4; and each p is, independently, an integer from 1 to 5, and wherein (i) at least two of $Q_1$, $Q_2$ and $Q_3$ are other than hydrogen, and (ii) if $Q_1$ is hydrogen, then at least one of $Q_2$ and $Q_3$ is —C(=NH)NR$_4$R$_5$.

In further embodiments, $R_8$ is hydrogen.

In further embodiments, each $R_9$ is methyl.

In further embodiments, $Q_1$ and $Q_2$ are other than hydrogen. In certain embodiments of the foregoing, $Q_3$ is hydrogen.

In more specific embodiments of the foregoing, $Q_1$ is:

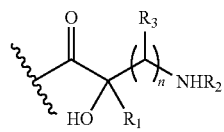

wherein: $R_1$ is hydrogen; $R_2$ is hydrogen; and each $R_3$ is hydrogen. For example, $Q_1$ may be:

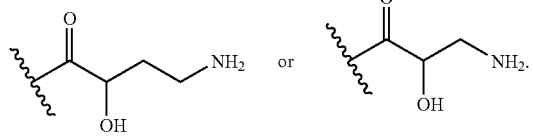

In other more specific embodiments of the foregoing, $Q_1$ is:

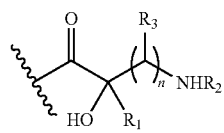

wherein: $R_1$ is hydrogen; and $R_2$ and $R_3$ together with the atoms to which they are attached form a heterocyclic ring having from 4 to 6 ring atoms. For example, $Q_1$ may be:

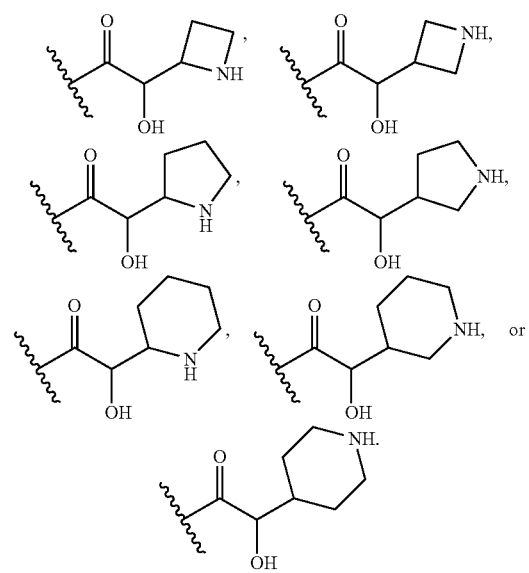

In other more specific embodiments of the foregoing, $Q_1$ is:

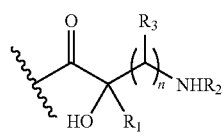

wherein: $R_3$ is hydrogen; and $R_1$ and $R_2$ together with the atoms to which they are attached form a heterocyclic ring having from 4 to 6 ring atoms. For example, $Q_1$ may be:

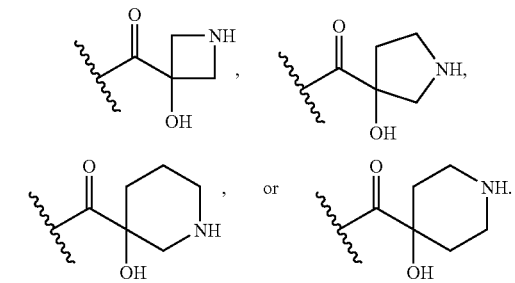

In other more specific embodiments of the foregoing, $Q_1$ is:

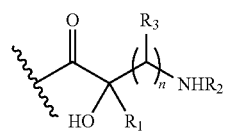

wherein: $R_2$ is hydrogen; and $R_1$ and $R_3$ together with the atoms to which they are attached form a carbocyclic ring having from 4 to 6 ring atoms. For example, $Q_1$ may be:

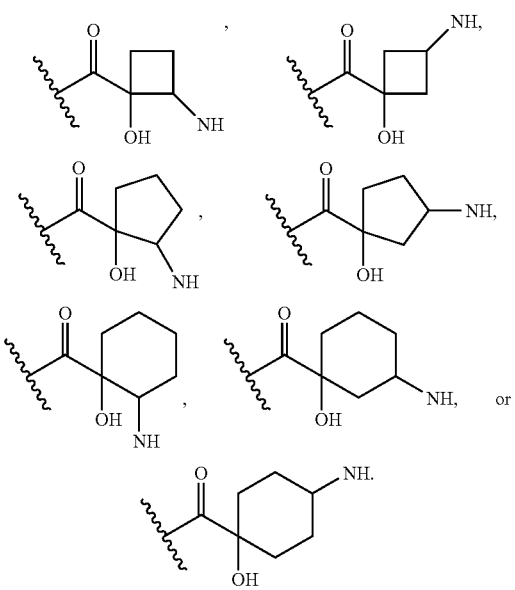

In other more specific embodiments of the foregoing, $Q_1$ is:

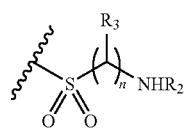

wherein: $R_2$ is hydrogen; and each $R_3$ is hydrogen.

In other more specific embodiments of the foregoing, $Q_1$ is:

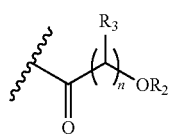

wherein: $R_2$ is hydrogen; and each $R_3$ is hydrogen.

In other more specific embodiments of the foregoing, $Q_2$ is —$(CR_{10}R_{11})_pR_{12}$. In certain embodiments, each $R_{10}$ is hydrogen. In certain embodiments, each $R_{11}$ is hydrogen.

In other more specific embodiments of the foregoing, $Q_2$ is optionally substituted cycloalkylalkyl. In certain embodiments, $Q_2$ is unsubstituted. In certain embodiments, $Q_2$ is substituted with hydroxyl or amino.

In other more specific embodiments of the foregoing, $Q_2$ is optionally substituted heterocyclylalkyl. In certain embodiments, $Q_2$ is unsubstituted. In certain embodiments, $Q_2$ is substituted with hydroxyl or amino.

In other further embodiments, $Q_1$ and $Q_3$ are other than hydrogen. In certain embodiments, $Q_2$ is hydrogen.

In more specific embodiments of the foregoing, $Q_1$ is:

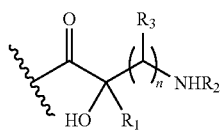

wherein: $R_1$ is hydrogen; $R_2$ is hydrogen; and each $R_3$ is hydrogen. For example, $Q_1$ may be:

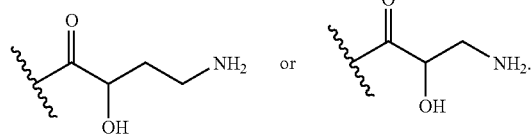

In other more specific embodiments of the foregoing, $Q_1$ is:

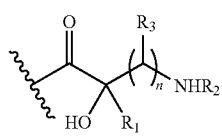

wherein:
$R_1$ is hydrogen; and
$R_2$ and $R_3$ together with the atoms to which they are attached form a heterocyclic ring having from 4 to 6 ring atoms. For example, $Q_1$ may be:

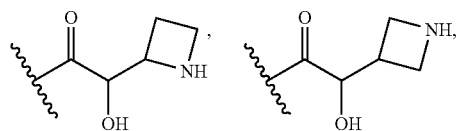

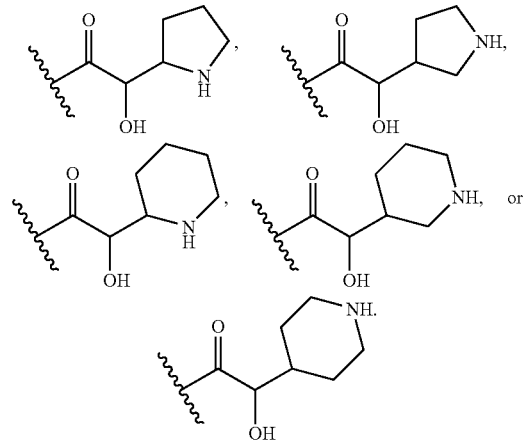

In other more specific embodiments of the foregoing, $Q_1$ is:

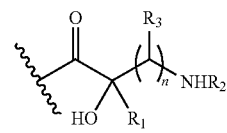

wherein: $R_3$ is hydrogen; and $R_1$ and $R_2$ together with the atoms to which they are attached form a heterocyclic ring having from 4 to 6 ring atoms. For example, $Q_1$ may be:

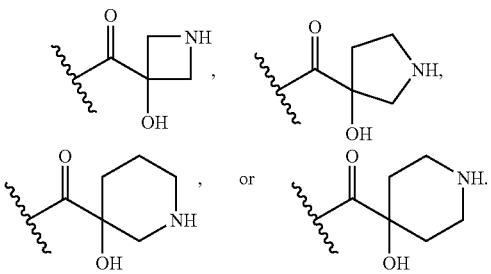

In other more specific embodiments of the foregoing, $Q_1$ is:

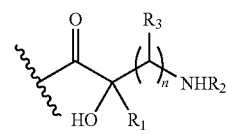

wherein: $R_2$ is hydrogen; and $R_1$ and $R_3$ together with the atoms to which they are attached form a carbocyclic ring having from 4 to 6 ring atoms. For example, $Q_1$ may be:

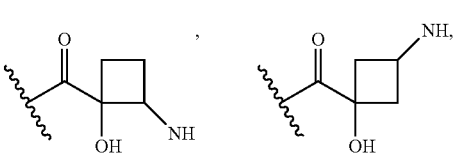

-continued

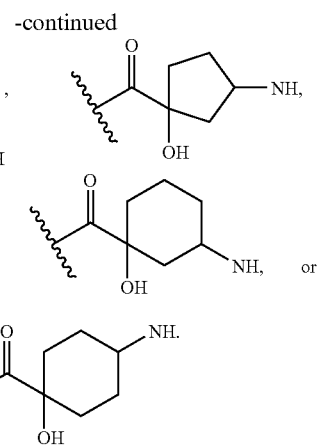

In other more specific embodiments of the foregoing, $Q_1$ is:

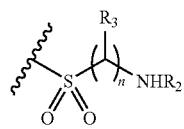

wherein: $R_2$ is hydrogen; and each $R_3$ is hydrogen.

In other more specific embodiments of the foregoing, $Q_1$ is:

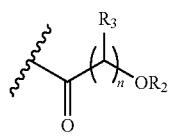

wherein: $R_2$ is hydrogen; and each $R_3$ is hydrogen.

In other more specific embodiments of the foregoing, $Q_3$ is —$(CR_{10}R_{11})_pR_{12}$. In certain embodiments, each $R_{10}$ is hydrogen. In certain embodiments, each $R_{11}$ is hydrogen.

In other more specific embodiments of the foregoing, $Q_3$ is optionally substituted cycloalkylalkyl. In certain embodiments, $Q_3$ is unsubstituted. In certain embodiments, $Q_3$ is substituted with hydroxyl or amino.

In other more specific embodiments of the foregoing, $Q_3$ is optionally substituted heterocyclylalkyl. In certain embodiments, $Q_3$ is unsubstituted. In certain embodiments, $Q_3$ is substituted with hydroxyl or amino.

In other more specific embodiments of the foregoing, $Q_3$ is optionally substituted heterocyclyl. In certain embodiments, $Q_3$ is unsubstituted. In certain embodiments, $Q_3$ is substituted with hydroxyl or amino.

In other more specific embodiments of the foregoing, $Q_3$ is —C(=NH)NH$_2$.

In other further embodiments, $Q_2$ and $Q_3$ are other than hydrogen. In certain embodiments, $Q_1$ is hydrogen.

In more specific embodiments of the foregoing, $Q_2$ is —C(=NH)NH$_2$.

In other more specific embodiments of the foregoing, $Q_3$ is —C(=NH)NH$_2$.

It is understood that any embodiment of the compounds of structure (I), as set forth above, and any specific substituent set forth herein for a $Q_1$, $Q_2$, $Q_3$, $R_1$, $R_2$, $R_3$, $R_4$, $R_5$, $R_6$, $R_7$, $R_8$, $R_9$, $R_{10}$, $R_{11}$ or $R_{12}$ group in the compounds of structure (I), as set forth above, may be independently combined with other embodiments and/or substituents of compounds of structure (I) to form embodiments of the invention not specifically set forth above. In addition, in the event that a list of substitutents is listed for any particular substituent group in a particular embodiment and/or claim, it is understood that each individual substituent may be deleted from the particular embodiment and/or claim and that the remaining list of substituents will be considered to be within the scope of the invention.

For the purposes of administration, the compounds of the present invention may be administered as a raw chemical or may be formulated as pharmaceutical compositions. Pharmaceutical compositions of the present invention comprise a compound of structure (I) and a pharmaceutically acceptable carrier, diluent or excipient. The compound of structure (I) is present in the composition in an amount which is effective to treat a particular disease or condition of interest—that is, in an amount sufficient to treat a bacterial infection, and preferably with acceptable toxicity to the patient. The antibacterial activity of compounds of structure (I) can be determined by one skilled in the art, for example, as described in the Examples below. Appropriate concentrations and dosages can be readily determined by one skilled in the art.

The compounds of the present invention possess antibacterial activity against a wide spectrum of gram positive and gram negative bacteria, as well as enterobacteria and anaerobes. Representative susceptible organisms generally include those gram positive and gram negative, aerobic and anaerobic organisms whose growth can be inhibited by the compounds of the invention such as *Staphylococcus, Lactobacillus, Streptococcus, Sarcina, Escherichia, Enterobacter, Klebsiella, Pseudomonas, Acinetobacter, Mycobacterium, Proteus, Campylobacter, Citrobacter, Nisseria, Baccillus, Bacteroides, Peptococcus, Clostridium, Salmonella, Shigella, Serratia, Haemophilus, Brucella* and other organisms.

Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see *Remington: The Science and Practice of Pharmacy,* 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

The pharmaceutical composition of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

Compounds of the invention, or pharmaceutically acceptable derivatives thereof, may also be administered simultaneously with, prior to, or after administration of one or more other therapeutic agents. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention and the other active agent can be administered to the patient together in a single oral dosage composition such as a tablet or capsule, or each agent administered in separate oral dosage formulations. Where separate dosage formulations are used, the compounds of the invention and one or more additional active agents can be administered at essentially the same time, i.e., concurrently, or at separately staggered times, i.e., sequentially; combination therapy is understood to include all these regimens.

It is understood that in the present description, combinations of substituents and/or variables of the depicted formulae are permissible only if such contributions result in stable compounds.

It will also be appreciated by those skilled in the art that in the synthetic processes described herein the functional groups of intermediate compounds may need to be protected by suitable protecting groups. Such functional groups include hydroxyl, amino, mercapto and carboxylic acid. Suitable protecting groups for hydroxyl include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although a protected derivative of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

Furthermore, all compounds of the invention which exist in free base or acid form can be converted to their pharmaceutically acceptable salts by treatment with the appropriate inorganic or organic base or acid by methods known to one skilled in the art. Salts of the compounds of the invention can be converted to their free base or acid form by standard techniques.

The following Examples illustrate various methods of making compounds of this invention, i.e., compounds of structure (I):

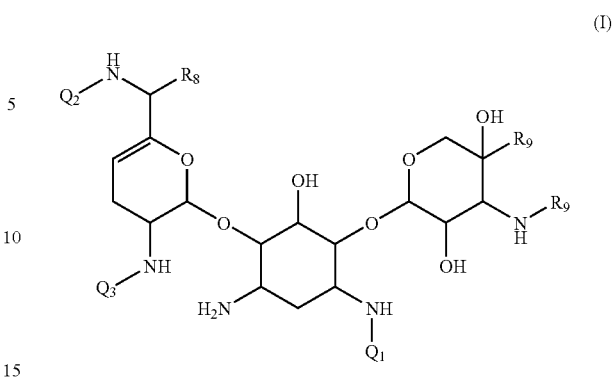

(I)

wherein $Q_1$, $Q_2$, $Q_3$, $R_8$ and $R_9$ are as defined herein. It is understood that one skilled in the art may be able to make these compounds by similar methods or by combining other methods known to one skilled in the art. It is also understood that one skilled in the art would be able to make, in a similar manner as described below, other compounds of structure (I) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, e.g., Advanced Organic Chemistry: Reactions, Mechanisms, and Structure, 5th edition (Wiley, December 2000)) or prepared as described herein.

The following examples are provided for purposes of illustration, not limitation.

EXAMPLES

General Synthetic Procedures

Procedure 1: Reductive Amination

Method A: To a stirring solution of the sisomicin derivative (0.06 mmol) in MeOH (2 mL) was added the aldehyde (0.068 mmol), silica supported cyanoborohydride (0.1 g, 1.0 mmol/g), and the reaction mixture was heated by microwave irradiation to 100° C. (100 watts power) for 15 minutes. The reaction was checked by MS for completeness, and once complete all solvent was removed by rotary evaporation. The resulting residue was dissolved in EtOAc (20 ml), and washed with 5% $NaHCO_3$ (2×5 mL), followed by brine (5 mL). The organic phase was then dried over $Na_2SO_4$, filtered and the solvent was removed by rotary evaporation.

Method B: To a solution of sisomicin derivative (0.078 mmol) in DMF (1 ml) were added 3 Å molecular sieves (15-20), followed by the aldehyde (0.15 mmol) and the reaction was shaken for 2.5 hours. The reaction was checked by MS for completeness and, if needed, more aldehyde (0.5 eq) was added. The reaction mixture was then added dropwise to a stirring solution of $NaBH_4$ (0.78 mmol) in MeOH (2 mL) at 0° C., and the reaction was stirred for 1 hour. The reaction was diluted with $H_2O$ (2 mL) and EtOAc (2 ml). The organic layer was separated and the aqueous layer was extracted with EtOAc (3×3 mL). The combined organic layers were dried over $Na_2SO_4$, filtered and concentrated to dryness.

Procedure 2: PNZ Deprotection

To a stirring solution of the PNZ protected sisomicin derivative (0.054 mmol) in EtOH (1.5 mL) and $H_2O$ (1 mL) was added 1N NaOH (0.3 mL), followed by $Na_2S_2O_4$ (0.315 mmol), and the reaction mixture was heated at 70° C. for 12 hours. The reaction progress was monitored by MS. Once complete, the reaction mixture was diluted with $H_2O$ (5 mL) and then extracted with EtOAc (2×10 mL). The combined organic layers were washed with $H_2O$ (2×5 mL), brine (5 mL), dried over $Na_2SO_4$, filtered and concentrated to dryness.
Procedure 3: Boc Deprotection (tert-Butyl Dimethyl Silyl Protecting Group is Removed Under these Conditions)

Important: Before Boc deprotection a sample must be dried well by pumping at high vacuum for 3 h.

Method A: To a stirring solution of the Boc protected sisomicin (0.054 mmol) in DCM (1 mL) were added 3 Å molecular sieves (4-6), and trifluoroacetic acid (0.6 mL). The reaction was stirred at room temperature for 1 h, and checked for completeness by MS. Upon completion the reaction mixture was diluted with ether (15 mL) to induce precipitation. The vial was centrifuged and the supernatant was decanted. The precipitate was washed with ether (2×15 ml), decanted and dried under vacuum.

Method B: To a stirring solution of Boc-protected sisomicin derivative (0.078 mmol) in DCM (1.5 mL) at 0° C. was added trifluoroacetic acid (1.5 mL). The reaction was stirred for 45 minutes, and checked for completeness by MS. Upon completion, the reaction was diluted with dichloroethane (10 ml) and concentrated to dryness. The last dilution/concentration step was repeated twice.
Procedure 4: BOP and PyBOP Coupling Method A: To a stirring solution of sisomicin derivative (0.078 mmol) in DMF (1 mL) was added the acid (0.16 mmol), followed by PyBOP (0.16 mmol) and DIPEA (0.31 mmol) and the reaction was stirred overnight. The reaction mixture was diluted with EtOAc (3 mL) and $H_2O$ (3 mL), and the aqueous layer was separated and extracted with EtOAc (3×3 mL). The combined organic layers were dried over $Na_2SO_4$, filtered and concentrated to dryness.

Method B: To a stirring solution of sisomicin derivative (0.073 mmol) in DMF (1 mL) was added the acid (0.102 mmol), DIPEA (0.43 mmol) and a solution of BOP (0.102 mmol) in DMF (1 mL) and the reaction was stirred for 4 hours, with its progress monitored by MS. The reaction mixture was diluted with water (8 mL) and was extracted with EtOAc (2×10 mL). The combined organic layers were washed with 5% aq. $NaHCO_3$ (2×3 mL) and brine (3 mL), dried over $Na_2SO_4$, filtered and concentrated to dryness.
Procedure 5: Epoxide Opening To a stirring solution of the sisomicin derivative (0.06 mmol) in MeOH (2 mL) was added the epoxide (0.07 mmol), $LiClO_4$ (0.15 mmol), and the reaction mixture was heated by microwave irradiation to 100° C. for 90 minutes. The reaction progress was monitored by MS. Upon completion, the solvent was removed by rotary evaporation. The resulting residue was dissolved in EtOAc (20 mL), washed with $H_2O$ (2×5 mL) and brine (5 mL), dried over $Na_2SO_4$, filtered and concentrated to dryness.
Procedure 6: Phthalimido Deprotection To a stirring solution of the phthalimido protected sisomicin (0.064 mmol) in EtOH (3 mL) was added hydrazine (0.32 mmol), and the reaction mixture was heated to reflux for 2 h. The reaction progress was monitored by MS. Upon cooling to room temperature, the cyclic by-product precipitated and was removed by filtration. The filtrate was concentrated to dryness to yield a residue, which was dissolved in EtOAc (20 mL), washed with 5% $NaHCO_3$ (2×5 mL) and brine (5 mL), dried over $Na_2SO_4$, filtered and concentrated to dryness.
Procedure 7: Addition of Guanidinium Group To a stirring solution of the sisomicin derivative (0.063 mmol) in DMF (1 mL) was added 1H-pyrazole-1-carboxamidine hydrochloride (0.09 mmol), followed by DIPEA (0.862 ml) and the reaction mixture was heated to 80° C. and stirred overnight. The reaction progress was monitored by MS. Upon completion, the reaction mixture was cooled to room temperature and diluted with water (3 mL). The aqueous phase was separated and extracted with EtOAc (2×5 mL), and the combined organics were washed with brine (5 mL), dried over $Na_2SO_4$, filtered and concentrated to dryness.
Procedure 8: Nosylation To a stirring solution of the sisomicin derivative (0.23 mmol) in DCM (20 mL) was added 2-nitrobenzenesulfonyl chloride (0.25 mmol), and DIPEA (0.3 mmol), and the reaction was allowed to stir for 3 h. The reaction progress was monitored by MS. Upon completion, the DCM was removed by rotary evaporation and the resulting residue was dissolved in ethyl acetate (50 mL) and washed with 5% $NaHCO_3$ (2×10 mL), and brine (10 mL). The combined organic layers were then dried over $Na_2SO_4$, filtered and concentrated to dryness.
Procedure 9: Nosyl Group Deprotection To a stirring solution of the nosyl protected sisomicin derivative (0.056 mmol) in DMF (1.5 mL) was added benzenethiol (0.224 mmol), $K_2CO_3$ (1.12 mmol) and the reaction mixture was stirred for 2 hours, with its progress monitored by MS. Upon completion, the reaction mixture was diluted with water (5 mL) and extracted with ethyl acetate (2×10 mL). The combined organic layers were washed with water (2×5 mL) and brine (5 mL), dried over $Na_2SO_4$, filtered and concentrated to dryness.
Procedure 10: PNZ Removal by Hydrogenolysis To a stirring solution of sisomicin derivative (0.41 mmol) in EtOH (60 mL) was added AcOH (0.14 mL), followed by Pd/C (30% by weight). The reaction vessel was evacuated and replenished with $H_2$ (1 atm), and the reaction mixture was stirred for 6 h. The reaction vessel was then evacuated and replenished with nitrogen. The solids were removed by filtration through a pad of Celite, and washed with MeOH (10 mL). Solvent evaporation gave the desired product.
Procedure 11: Mono Alkylation To a stirring solution of the nosyl protected sisomicin derivative (0.072 mmol) in DMF (1.5 mL) was added the halogenated alkane (0.144 mmol), $K_2CO_3$ (0.216 mmol) and the reaction mixture was heated to 80° C. with its progress monitored by MS. Upon completion, the reaction mixture was diluted with water (2 mL) and extracted with ethyl acetate (2×5 mL). The combined organic layers were washed with brine (1.5 mL), dried over $Na_2SO_4$, filtered and concentrated to dryness.
Procedure 12: Sulfonylation To a stirring solution of the sisomicin scaffold (0.067 mmol) in DCM (3 mL) was added DIPEA (0.128 mol) and the sulfonyl chloride (0.07 mmol). The reaction mixture was stirred at room temperature and its progress was monitored by MS. Once complete, the solvent was removed by rotary evaporation and the residue was dissolved in ethyl acetate (20 mL), washed with 5% $NaHCO_3$ (2×5 mL) and brine (5 mL), dried over $Na_2SO_4$, filtered and concentrated to dryness.
Procedure 13: N-Boc Protection To a stirring solution of the amine (4.64 mmol) in THF (10 mL) was added 1N NaOH (10 mL), followed by Boc-anhydride (5.57 mmol) and the reaction progress was checked by MS. Once complete, the THF was removed by rotary evaporation and water (40 mL) was added. The aqueous phase was separated and extracted with $Et_2O$ (2×30 ml). The aqueous phase was acidified to pH 3 by the addition of dilute $H_3PO_4$ and was then extracted with EtOAc (2×60 ml). The combined organic layers were washed with $H_2O$ (2×30 mL) and brine (30 mL), dried over $Na_2SO_4$, filtered and concentrated to dryness.

Procedure 14: Syntheses of Epoxides

To a stirring solution of the alkene (5.16 mmol) in chloroform (20 mL) at 0° C. was added m-chloroperbenzoic acid (8.0 mmol) and the reaction mixture was stirred for 30 minutes at 0° C. and was then allowed to warm to room temperature. The reaction progress was monitored by MS and TLC, and additional portions of m-CPBA were added as needed. Upon completion, the reaction mixture was diluted with chloroform (50 mL) and washed with 10% aq. $Na_2SO_3$ (2×30 mL), 10% aq. $NaHCO_3$ (2×50 mL) and brine (50 mL). The organic layer was dried over $Na_2SO_4$, filtered and concentrated to yield a crude product, which was purified by flash choromatography (silica gel/hexanes: ethyl acetate 0-25%).

Procedure 15: General Procedure for Synthesis of α-hydroxy Carboxylic Acids

Step #1. O-(Trimethylsilyl)cyanohydrines: A 50-mL flask equipped with a magnetic stirring bar and drying tube was charged with the ketone or aldehyde (0.010 mmol), followed by THF (50 mL), trimethylsilyl cyanide (1.39 g, 14 mmol), and zinc iodide (0.090 g, 0.28 mmol), and the reaction mixture was stirred at room temperature for 24 hr. Solvent evaporation gave a residue, which was dissolved in EtOAc (60 mL), washed with 5% aq. $NaHCO_3$ (2×30 mL), $H_2O$ (30 mL), and brine (30 mL), dried over $Na_2SO_4$, filtered and concentrated to dryness to yield a crude, which was carried through to the next step without further purification.

Step #2. Acid hydrolysis to a-hydroxy carboxylic acid: AcOH (25 ml) and conc. HCl (25 ml) were added to the unpurified material from step #1 and the reaction mixture was refluxed for 2-3 hr. The reaction mixture was then concentrated to dryness to give a white solid, which was carried through to the next step without further purification.

Step #3. Boc protection: To a stirring solution of solid from step #2 in 2 M NaOH (20 mL) and i-PrOH (20 mL) at 0° C. was added $Boc_2O$ (6.6 g, 3 mmol) in small portions, and the reaction mixture was allowed to warm to room temperature over 4 h. i-PrOH was then evaporated, and $H_2O$ (50 mL) was added, and the aqueous phase was separated and extracted with $Et_2O$ (2×30 ml). The aqueous layer was acidified to pH 3 by addition of dilute $H_3PO_4$ and was extracted with EtOAc (2×60 ml). The combined organic layers were washed with $H_2O$ (2×30 mL) and brine (30 mL), dried over $Na_2SO_4$, filtered and concentrated to yield the desired N-Boc-α-hydroxy carboxylic acids in 56-72% yield.

Aldehydes and ketones used: N-Boc-3-Pyrrolidonone, N-Boc-3-azetidinone, N-Boc-4-piperidone and N-Boc-3-azetidincarboxaldehyde.

Procedure 16: Protection of Amine by Fmoc Group

To a stirring solution of the amine (0.049 mol) in DCM (100 mL), was added DIPEA (16 mL, 0.099 mol) and the reaction mixture was cooled to 0° C. Fmoc-Cl (12.8 g, 0.049 mol) was then added portion-wise over several minutes, and the reaction was allowed to warm to room temperature for 2 hr. The organic layer was washed with water (2×50 mL) and brine (50 mL), dried over $Na_2SO_4$, filtered and concentrated to dryness to yield the Fmoc protected amine (90-95% yield).

Procedure 17: Mitsunobu Alkylation

To a stirring solution of the nosylated sisomicin derivative (0.087 mmol) in toluene (2.5 mL) was added the alcohol (0.174 mmol), triphenylphosphine (0.174 mmol) and the reaction mixture was cooled in a 4° C. refrigerator for 10 minutes. A cooled solution of DEAD (0.174 mmol in 2 mL anhydrous toluene) was then added and the reaction was allowed to shake overnight. The reaction progress was monitored by MS, and additional alcohol and triphenylphosphine were added if needed. Once complete, ethyl acetate (30 mL) was added and the organic phase was washed with 5% aq. $NaHCO_3$ (2×5 mL) and brine (5 mL), dried over $Na_2SO_4$, filtered and concentrated to dryness.

Procedure 18: Synthesis of Aldehydes via TEMPO/Bleach Oxidation

To a vigorously stirring solution of the alcohol (1.54 mmol) in DCM (4 mL) was added TEMPO (0.007 g, 0.045 mmol, 0.03 mol %) and a 2M aqueous KBr solution (75 mL, 0.15 mmol, 10 mol %) and the reaction mixture was cooled to −10° C. In a separate flask $NaHCO_3$ (0.5 g, 9.5 mmol) was dissolved in bleach (25 mL, Chlorox 6.0% NaOCl) to yield a 0.78 M buffered NaOCl solution. This freshly prepared 0.78 M NaOCl solution (2.3 mL, 1.8 mmol, 117 mol %) was added to the reaction mixture over 5 min and the reaction was stirred for an additional 30 min at 0° C. The organic phase was separated and the aqueous layer was extracted with dichloromethane (2×4 mL). The combined organic layers were washed with 10% aq. $Na_2S_2O_3$ (4 mL), sat. aq. $NaHCO_3$ (2×4 mL), brine (5 mL), dried over $Na_2SO_4$ and concentrated to dryness.

Procedure 19: Synthesis of Alcohols via Borane Reduction

To a stirring solution of the acid (1.5 mmol) in THF (5 mL) at −10° C. was slowly added 1.0 M $BH_3$-THF (2.98 mL, 2.98 mmol). The reaction mixture was stirred vigorously for an additional 3 min at −10° C., and was then allowed to warm to room temperature overnight. The reaction was quenched by the dropwise addition of a solution of $HOAc/H_2O$ (1:1 v/v, 2.0 mL). The THF was removed by rotary evaporation and sat. aq. $NaHCO_3$ (15 mL) was added. The aqueous layer was extracted with DCM (3×5 mL) and the combined organic layers were washed with sat. aq. $NaHCO_3$ (2×5 mL), brine (10 mL), dried over $Na_2SO_4$, filtered and concentrated to dryness.

Procedure 20: EDC Coupling

To a stirring solution of sisomicin derivative (0.048 mmol) in DMF (0.3 mL) and THF (0.6 mL) was added EDC (0.058 mmol), followed by HONb (0.062 mmol), and the acid (0.058 mmol) and the reaction was allowed to stir overnight. The reaction was quenched with $H_2O$ (2 mL) and EtOAc (4 mL) was added. The organic layer was washed with sat. aq. $NaHCO_3$, sat. aq. $NH_4Cl$, dried over $Na_2SO_4$, filtered and concentrated to dryness.

General Purification Procedures

Method #1: Purification by Basic Condition
Mobile Phases:
   A—Water with 10 mM $NH_4OH$
   B—Acetonitrile with 10 mM $NH_4OH$
Columns:
   A: Waters-XTerra Prep MS C18 OBD Column
     19×100 mm, 5 μm
     Gradient: 20 min at 0%, then 0-20% in 200 min at a flow of 20 ml/min
   B: Waters-XTerra Prep MS C18 OBD Column
     50×100 mm, 5 μm
     Gradient: 20 min at 0%, then 0-20% in 200 min at a flow of 20 ml/min Using the Waters-XTerra, collection was triggered by MS signal. Collected fractions were dried by lyophilization and analyzed by LC/MS/ELSD. Pure fractions were combined and analyzed by LC/MS/ELSD for final purity check. Quantitation was done by LC/MS/CLND system.

Method #2: Purification by Acidic Condition
Mobile Phases:
   A—Water with 0.1% TFA
   B—Acetonitrile with 0.1% TFA Columns:
  A: Microsorb BDS Dynamax
    21.4×250 mm, 10 μm, 100 Å
    Gradient: 0-100%, flow 25 ml/min
  B: Microsorb BDS Dynamax
    41.4×250 mm, 10 μm, 100 Å
    Gradient: 0-100%, flow 45 ml/min
Method #3: Hydrophilic Interaction Chromatography (HILIC) Purification
Buffers:
  Buffer A —3400 ml of Acetonitrile
    —600 ml of Water
    —15 ml of Acetic Acid
    —15 ml of TEA
  Buffer B —4000 ml of Water
    —100 ml of TEA
    —100 ml of Acetic Acid
Column: PolyC-PolyHydroxyethyl A
  150×21 mm, 5 um
Gradient: 20-70% 10 ml/35 min ELSD signal was used to trigger the collection. Fractions were dried by lyophilization and analyzed by LC/MS/ELSD. Pure fractions were then combined, diluted with water, and lyophilized. Dried fractions were again dissolved in water and lyophilized for a third time to ensure complete removal of TEA. Any samples showing traces of TEA went through additional drying. For delivery, purified compounds were dissolved in >10 mg/ml concentration. Final purity check was done by LC/MS/ELSD and quantitation by LC/MS/CLND.

Common Intermediates

Sisomicin

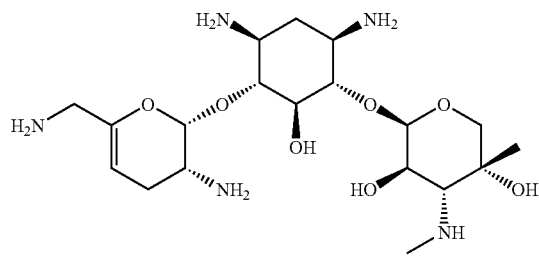 [SMILES: CN[C@@H]1[C@@H](O)[C@@H](O[C@@H]2[C@@H](O)[C@H](O[C@H]3OC(CN)=CC[C@H]3N)[C@@H](N)C[C@H]2N)OC[C@]1(C)O]

Amberlite IRA-400 (OH form) (200 g) was washed with MeOH (3×200 ml). To a stirring suspension of the washed resin in MeOH (150 mL) was added sisomicin sulfate (20.0 g, 0.029 mol) and the mixture was stirred overnight. The resin was then filtered and washed with MeOH (100 mL) and the combined organic layers were concentrated to dryness to yield the desired sisomicin (11.57 g, 0.026 mol, 89.6% yield): MS m/e [M+H]$^+$ calcd 448.3, found 448.1.

(N-Hydroxy-5-norbornene-2,3-dicarboxyl-imido)-4-nitro-benzoate

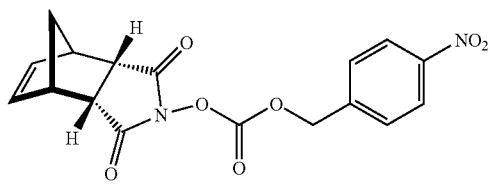

To a stirring solution of 4-nitrobenzyl chloroformate (5.0 g, 0.023 mol) in THF (90 mL) at 0° C. was added N-hydroxy-5-norbornene-2,3-dicarboximide (4.16 g, 0.023 mol), followed by the dropwise addition of a solution of Et$_3$N (3.2 mL, 0.02 mol) in THF (50 mL) and the reaction was stirred for 4 hours with gradual warming to room temperature. The reaction vessel was then placed in the freezer (−5° C.) for 1 hour to induce precipitation of triethylamine hydrochloride, which was removed by filtration. The filtrate was concentrated to dryness to yield a residue, which was vigorously stirred in MeOH (80 mL) for 1 h and then filtered to yield (N-hydroxy-5-norbornene-2,3-dicarboxyl-imido)-4-nitro-benzoate as a white solid (7.98 g, 0.022 mol, 96% yield): TLC (hexanes: EtOAc v/v 1:1) Rf=0.35.

2,5-Dioxo-pyrrolidin-1-yl-4-nitrobenzyl carbonate (PNZ-succinimide)

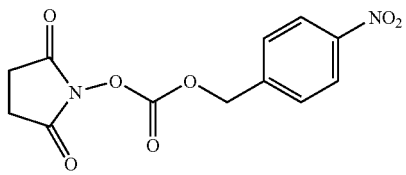 [SMILES: O=C(OCc1ccc([N+](=O)[O-])cc1)ON1C(=O)CCC1=O]

To a stirring solution of N-hydroxysuccinimide (5.35 g, 46.5 mmol) in anhydrous THF (100 mL) was added para-nitrobenzylchloroformate (10.0 g, 46.5 mmol), and the solution was cooled in an ice bath. Triethylamine (6.5 mL, 4.89 g, 46.5 mmol) was added over 10 minutes, and, after 30 minutes, the reaction mixture was allowed to warm to room temperature and stir overnight. The slurry was cooled in an ice-bath, and was filtered, followed by rinsing with ethyl acetate. The filtrate was concentrated in vacuo, and the residue was triturated with methanol. The solids were isolated by filtration to give 2,5-dioxopyrrolidin-1-yl-4-nitrobenzyl carbonate.

6'-Trifluoroacetyl-2',3-diPNZ-sisomicin

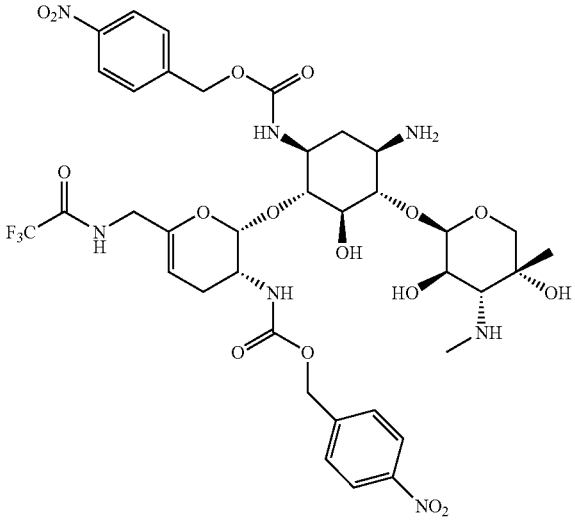 [SMILES: CN[C@@H]1[C@@H](O)[C@@H](O[C@@H]2[C@@H](O)[C@H](O[C@H]3OC(CNC(=O)C(F)(F)F)=CC[C@H]3NC(=O)OCc3ccc([N+](=O)[O-])cc3)[C@@H](NC(=O)OCc3ccc([N+](=O)[O-])cc3)C[C@H]2N)OC[C@]1(C)O]

To a stirring solution of sisomicin (30.1 g, 0.067 mol) in MeOH (700 mL) was added zinc acetate (37.07 g, 0.202 mol), followed by the slow addition of a solution of S-ethyltrifluorothioacetate (9.37 mL, 0.074 mol) in MeOH (100 mL) and the reaction was allowed to stir under N$_2$ overnight. A solution of triethylamine (37.5 mL, 0.27 mol) and PNZ-succinimide (64.2 g, 0.179 mol) in THF (1 L) was then added dropwise, and the reaction was stirred for 3 hours. Solvent evaporation gave a crude, which was dissolved in DCM (2 L) and washed with conc. NH₄OH:H₂O (3:1 v/v, 2×800 mL) and brine (800 mL), dried over MgSO₄, filtered and concentrated to dryness. The residue was dissolved in ethyl acetate (1 L) and extracted with AcOH: H₂O (1/9 v/v 1 L). The aqueous layer was washed with ethyl acetate (2×1 L), basified to pH 12 with 10N NaOH, and extracted with ethyl acetate (2×1 L). The organic layer was washed with brine (500 mL), dried over MgSO₄, filtered and concentrated to yield a residue. The crude was dissolved in ethyl acetate (500 mL), and the solution was allowed to stand overnight. The precipitated solids were removed by filtration and the remaining filtrate was concentrated to give a crude, which was purified by RP HPLC Method 2-Column B to yield the desired 6'-trifluoroacetyl-2',3-diPNZ-sisomicin (MS m/e [M+H]⁺ calcd 902.3, found 902.2.

6'-Trifluoroacetyl-2',3-diPNZ-1-acetyl-3"-Boc-sisomicin

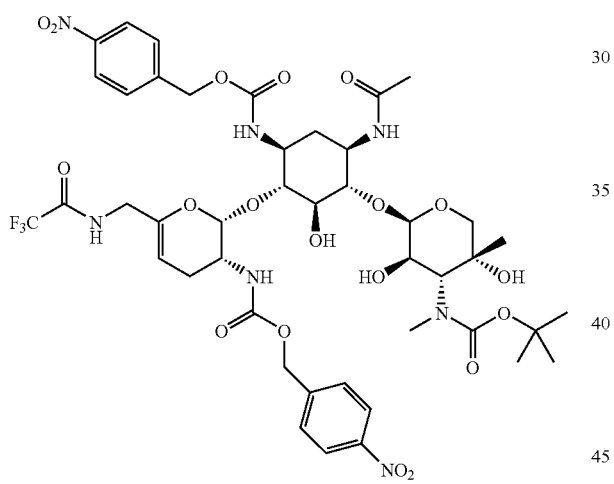

To a stirring solution of 6'-trifluoroacetyl-2',3-diPNZ-sisomicin (0.7 g, 0.77 mmol) in MeOH (7 mL) at 0° C. was slowly added acetic anhydride (0.095 mL, 1.01 mmol) and the reaction was allowed to warm to room temperature overnight. The reaction was followed by MS, which confirmed the complete formation of the intermediate 6'-trifluoroacetyl-2',3-diPNZ-1-acetyl-sisomicin (MS m/e [M+H]⁺ calcd 944.3, found 944.2, [M+Na]⁺ 966.3). The reaction mixture was then cooled to 0° C. and DIPEA (0.54 mL, 3.11 mmol) was added, followed by Boc anhydride (0.53 mL, 2.33 mmol) and the reaction was stirred for 6 hours with its progress followed by MS. The reaction was quenched with glycine (0.29 g, 3.88 mmol) and K₂CO₃ (0.54 g, 3.88 mmol), and the reaction was stirred overnight. After solvent evaporation, the residue was partitioned between H₂O (10 mL) and EtOAc (10 ml). The aqueous layer was separated and further extracted with EtOAc (3×10 mL), and the combined organic layers were dried over Na₂SO₄, filtered and concentrated to dryness to yield the desired 6'-trifluoroacetyl-2',3-diPNZ-1-acetyl-3"-Boc-sisomicin (MS m/e [M+H]⁺ calcd 1044.4, found 1044.0, [M+Na]⁺ 1066.3), which was carried through to the next step without further purification.

2',3-diPNZ-1-acetyl-3"-Boc-sisomicin

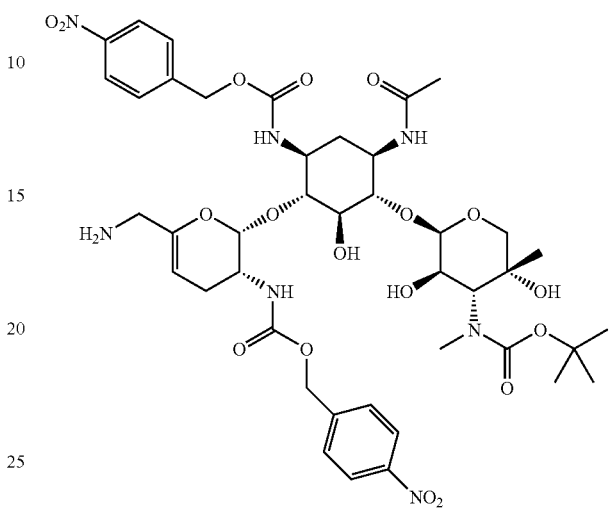

To a stirring solution of 6'-trifluoroacetyl-2',3-diPNZ-1-acetyl-3"-Boc-sisomicin (0.77 mmol) in MeOH (5 mL) was added conc. NH₄OH (8.2 mL) and the reaction was stirred overnight. Solvent evaporation gave a crude, which was purified by RP HPLC Method 2-Column B to yield the desired 2',3-diPNZ-1-acetyl-3"-Boc-sisomicin (0.35 g, 0.36 mmol, 46.7% yield, >95% purity): MS m/e [M+H]⁺ calcd 948.4, found 948.2.

N-PNZ-4-amino-2(S)-hydroxy-butyric acid

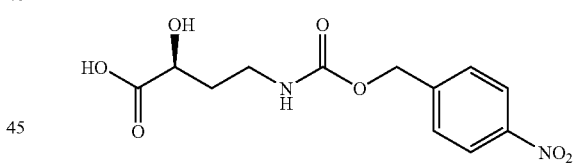

To a stirring solution of 4-amino-2(S)-hydroxybutyric acid (5.0 g, 0.041 mol) in dioxane: H₂O (200 mL, 1:1 v/v) was added K₂CO₃ (11.6 g, 0.084 mol), followed by p-nitrobenzyl chloroformate (9.23 g, 0.043 mol) and the reaction mixture was stirred overnight. The resulting precipitate was removed by filtration and the organic solvent was removed by rotary evaporation. The resulting aqueous solution was acidified to pH 1 by the addition of 1 M HCl (100 mL). Upon the addition of ethyl acetate (100 mL) to the aqueous layer, the product precipitated and was collected by filtration. The filtrate was added to a separatory funnel and the organic layer was separated. Upon addition of ethyl acetate (100 mL) to the aqueous layer, a second precipitation occurred, the product was collected by filtration and this process was repeated once more. The combined organic layers were then placed at −5° C. overnight, to induce precipitation of the product, which was collected by filtration. The desired N-PNZ-4-amino-2(S)-hydroxy-butyric acid (9.3 g, 0.031 mol, 75% yield, 90% purity) was carried through to the next step without further purification. MS m/e [M+H]⁺ calcd 299.1, found 298.9.

33
(N-Hydroxy-5-norbornene-2,3-dicarboxyl-imido)-N-PNZ-4-amino-2(S)-hydroxy-butanoate

34
(N-Hydroxy-5-norbornene-2,3-dicarboxyl-imido)-N-PNZ-4-amino-2(R)-benzoyl-butanoate

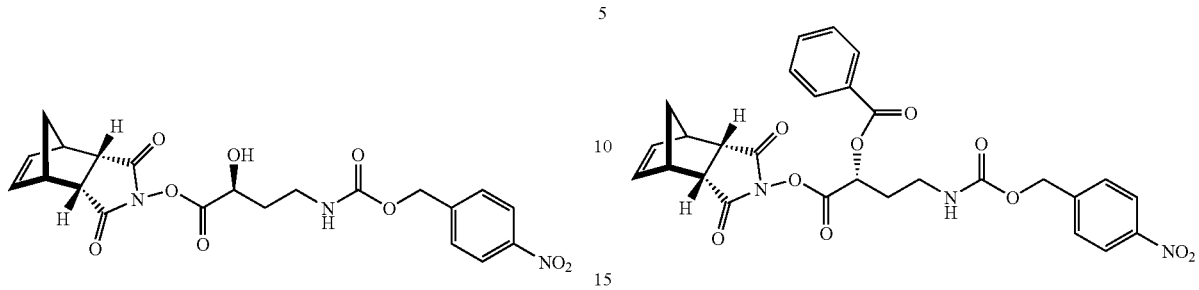

To a stirring solution of N-PNZ-4-amino-2(S)-hydroxy-butyric acid (8.95 g, 30.0 mmol) in THF (200 mL) at 0° C. was slowly added DCC (6.8 g, 33.0 mmol) and the reaction was stirred for 30 min. A solution of N-hydroxy-5-norbornene-2,3-dicarboxylic acid imide (6.45 g, 36.0 mmol) in THF (100 mL) was then added dropwise over 1 hour. The precipitated urea was removed by filtration and the remaining filtrate was concentrated to dryness. The residue was dissolved in ethyl acetate (200 mL) and washed with $H_2O$ (150 mL), dried over $MgSO_4$, filtered and concentrated to dryness. The product was recrystallized from ethyl acetate/diethyl ether to yield the desired N-hydroxy-5-norbornene-2,3-dicarboxyl-imido)-N-PNZ-4-amino-2(S)-hydroxy-butanoate (10.0 g, 21.78 mmol, 72.6% yield). MS m/e [M+H]$^+$ calcd 482.1, found 482.2.

To a stirring solution of (N-hydroxy-5-norbornene-2,3-dicarboxyl-imido)-N-PNZ-4-amino-2(S)-hydroxy-butanoate (6.4 g, 0.014 mol) in THF (65 mL) was added triphenyl phosphine (4.0 g, 0.015 mmol), followed by benzoic acid (1.9 g, 0.015 mmol) and the reaction mixture was cooled to 0° C. DIAD (3.0 mL, 0.015 mol) was then added dropwise, and the reaction mixture was stirred for an additional 50 min. Solvent evaporation gave a crude, which was purified by flash chromatography (silica gel/hexanes: ethyl acetate 20-100%) to yield the desired (N-hydroxy-5-norbornene-2,3-dicarboxyl-imido)-N-PNZ-4-amino-2(R)-benzoyl-butanoate (2.3 g, 4.08 mmol, 29.1% yield), with minor contamination with triphenyl phosphine oxide: $^1$H NMR (400 MHz, CDCl3) δ 8.17 (d, 2 H), 7.98 (d, 2 H), 7.44-7.70 (m, 5 H), 5.96-6.18 (m, 2 H), 5.41-5.55 (m, 1 H), 5.10 (s, 2 H), 3.40-3.58 (m, 2 H), 3.21-3.39 (m, 4 H), 2.10-2.22 (m, 2 H), 1.44-1.60 (m, 2 H).

6'-Trifluoroacetyl-2',3-diPNZ-1-(N-PNZ-4-amino-2(R)-O-benzoyl-butyryl)-3"-Boc-sisomicin

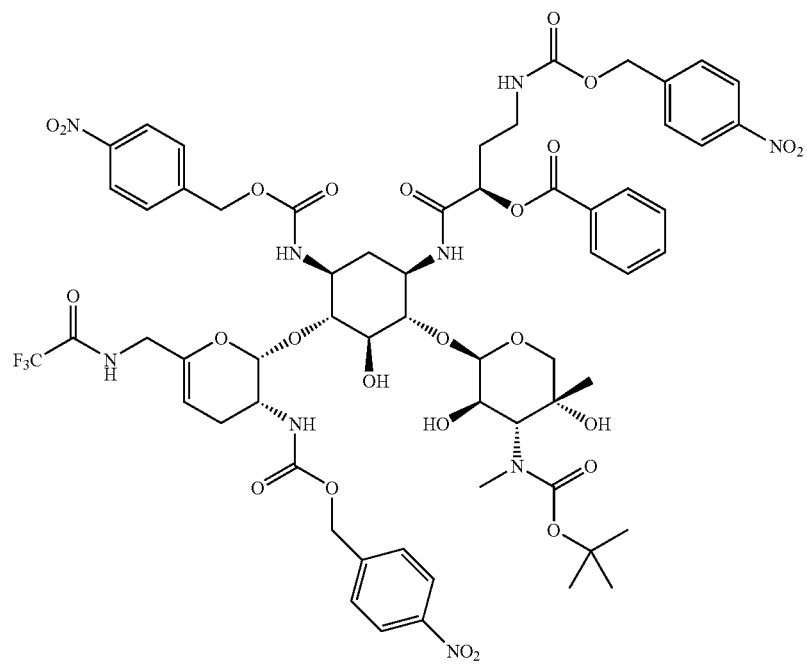 [SMILES: CN(C(=O)OC(C)(C)C)[C@@H]1[C@@H](O)[C@@H](O[C@@H]2[C@@H](O)[C@H](O[C@H]3OC(CNC(=O)C(F)(F)F)=CC[C@H]3NC(=O)OCc3ccc([N+](=O)[O-])cc3)[C@@H](NC(=O)OCc3ccc([N+](=O)[O-])cc3)C[C@H]2NC(=O)[C@@H](CCNC(=O)OCc2ccc([N+](=O)[O-])cc2)OC(=O)c2ccccc2)OC[C@]1(C)O]

To a stirring solution of 6'-trifluoroacetyl-2',3-diPNZ-sisomicin (2.5 g, 2.77 mmol) in DMF (50 mL) was added (N-hydroxy-5-norbornene-2,3-dicarboxyl-imido)-N-PNZ-4-amino-2(R)-benzoyl-butanoate (2.3 g, 4.08 mmol) and the reaction was stirred for 24 hr. DIPEA (2.5 mL, 0.014 mol) was then added, followed by Boc anhydride (2.5 mL, 0.011 mol) and the reaction mixture was stirred for an additional 2 hr. A solution of glycine (2.5 g, 0.033 mol) and K$_2$CO$_3$ (4.6 g, 0.033 mol) in H$_2$O (50 mL) was then added in portions over 5 minutes, and the reaction mixture was stirred for 1 hour. The reaction mixture was diluted with ethyl acetate (300 mL) and the aqueous layer was separated. The organic layer was washed with 1M citric acid (150 mL), sat. aq. NaHCO$_3$ (30 mL), brine (30 mL), dried over MgSO$_4$, filtered and concentrated to dryness to yield a crude, which was purified by RP HPLC Method 2-Column B to yield the desired 6'-trifluoroacetyl-2',3-diPNZ-1-(N-PNZ-4-amino-2(R)-O-benzoyl-butyryl)-3"-Boc-sisomicin (1.6 g, 1.15 mmol, 41.5% yield).

2',3-diPNZ-1-(N-PNZ-4-amino-2(R)-hydroxy-butyryl)-3"-Boc-sisomicin

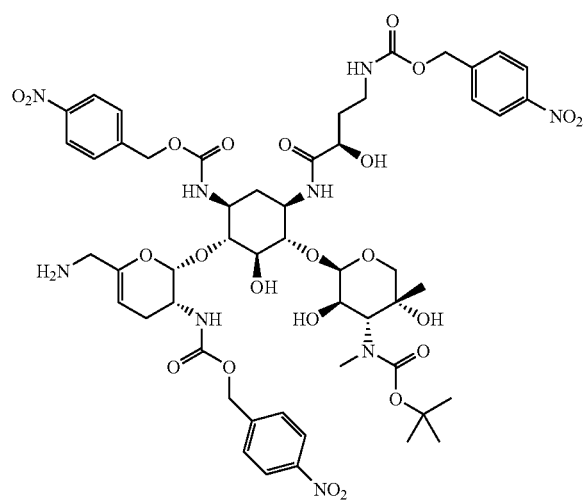 [SMILES: CN(C(=O)OC(C)(C)C)[C@@H]1[C@@H](O)[C@@H](O[C@@H]2[C@@H](O)[C@H](O[C@H]3OC(CN)=CC[C@H]3NC(=O)OCc3ccc([N+](=O)[O-])cc3)[C@@H](NC(=O)OCc3ccc([N+](=O)[O-])cc3)C[C@H]2NC(=O)[C@H](O)CCNC(=O)OCc2ccc([N+](=O)[O-])cc2)OC[C@]1(C)O]

To a stirring solution of 6'-Trifluoroacetyl-2',3-diPNZ-1-(N-PNZ-4-amino-2(R)-O-benzoyl-butyryl)-3"-Boc-sisomicin (1.6 g, 1.15 mmol) in MeOH (30 mL) was added conc. NH$_4$OH (3 mL) and the reaction was stirred for 3 days. Ethyl acetate (30 mL) was then added and the aqueous layer was separated. The organic layer was washed with 1 M NaOH (20 mL), brine (20 mL), dried over MgSO$_4$, and concentrated to dryness to yield 2',3-diPNZ-1-(N-PNZ-4-amino-2(R)-hydroxy-butyryl)-3"-Boc-sisomicin (1.4 g, MS m/e [M+H]$^+$ calcd 1186.4, found 1186.2, [M+Na]$^+$ 1208.3), which was carried throught to the next step without further purification.

(R)-Ethyl 3-azido-2-hydroxypropionate

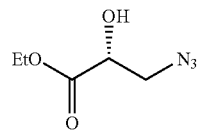

Ethyl-(2R)-2,3-epoxyproprionate (0.5 g, 4.3 mmol), ammonium chloride (0.253 g, 4.73 mmol), and sodium azide (0.336 g, 5.17 mmol) were combined in DMF (8 mL), and the mixture was heated at 75° C. for 14 hours. The reaction was cooled to room temperature, and was partitioned between water and ether/hexanes (1:1 v/v). The phases were separated, and the organic phase was washed once each with water, brine, dried over MgSO$_4$, filtered, and concentrated to an oil, which was purified by flash chromatography (silica gel/hexanes: 10% ethyl acetate) to give (R)-ethyl-3-azido-2-hydroxypropionate as a clear oil (0.47 g, 2.97 mmol, 69% yield). Rf 0.27 (hexanes: 10% EtOAc, v/v, p-anisaldehyde); MS m/e [M+Na]$^+$ calcd 182.1, found 182.0.

(R)-3-(tert-Butoxycarbonylamino)-2-hydroxypropionic acid

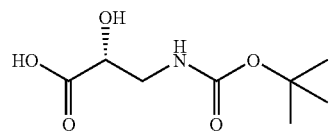

Step 1) To a stirring solution of (R)-ethyl-3-azido-2-hydroxypropionate (159 mg, 1.0 mmol) in ethanol (4 mL) was added acetic acid (0.10 mL), followed by 5% Pd/C (25 mg) after the flask had been flushed with nitrogen. The flask was fitted with a balloon of hydrogen, and stirred for 1 hour. The flask was then flushed with nitrogen, the mixture was filtered through Celite, and the pad was rinsed with ethanol (4 mL).

Step 2) To the filtrate was added 1M NaOH (3 mL), followed by Boc$_2$O (0.28 mL, 0.27 g, 1.2 mmol), and the solution was stirred at room temperature for 2 days. The solution was then partitioned between ether and water, and the phases were separated. The aqueous phase was washed twice with ether, acidified with 1M NaHSO$_4$, and extracted with ethyl acetate. The ethyl acetate phase was washed with brine, dried over MgSO$_4$, filtered, and concentrated to an oil, which solidified to give (R)-3-(tert-butoxycarbonylamino)-2-hydroxypropionic acid (117 mg, 57% yield): Rf 0.22 (CHCl$_3$: 10% IPA, 1% AcOH, ninhydrin).

6'-Trifluoroacetyl-2',3-di-PNZ-1-[(R)-3-(tert-butoxycarbonylamino)-2-hydroxy-propionyl]-sisomicin

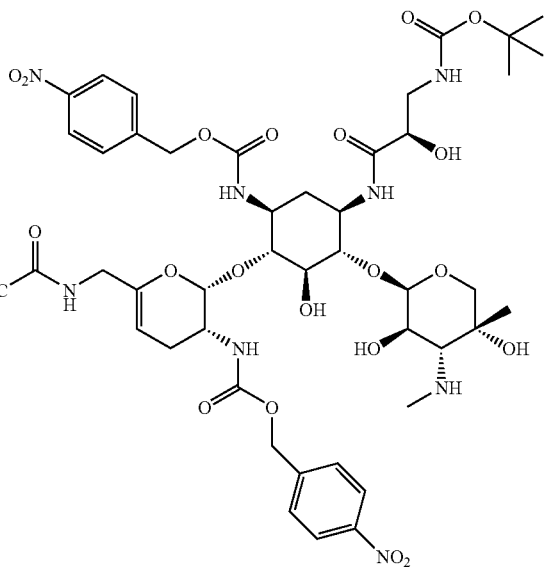

(R)-3-(tert-Butoxycarbonylamino)-2-hydroxypropionic acid (1.3 g, 6.3 mmol) and HONB (1.35 g, 7.5 mmol) were dissolved in THF (40 mL), the solution was cooled to 0° C., and EDC (1.33 g, 6.9 mmol) was added. After 20 minutes the reaction was allowed to warm to room temperature. After 6 hours, a solution of 6'-trifluoroacetyl-2',3-di-PNZ-sisomicin (5.23 g, 5.8 mmol) in DMF (25 mL) was added, and the solution was allowed to stir overnight. The reaction was concentrated to remove the THF, and was partitioned between water and ethyl acetate. The phases were separated, and the ethyl acetate phase was washed once each with water, sat. NaHCO$_3$, water, and brine. The ethyl acetate phase was then dried over Na$_2$SO$_4$, filtered, and concentrated to a residue. The residue was chromatographed by RP HPLC Method 2-Column B to give 6'-trifluoroacetyl-2',3-di-PNZ-1-[(R)-3-(tert-butoxycarbonylamino)-2-hydroxy-propionyl]-sisomicin as an off-white foam (1.64 g, 1.51 mmol, 24% yield): MS m/e [M+H]$^+$ calcd 1089.4, found 1089.2.

6'-Trifluoroacetyl-2',3-di-PNZ-1-[(R)-3-(tert-butoxycarbonylamino)-2-hydroxy-propionyl]-3''-Boc-sisomicin

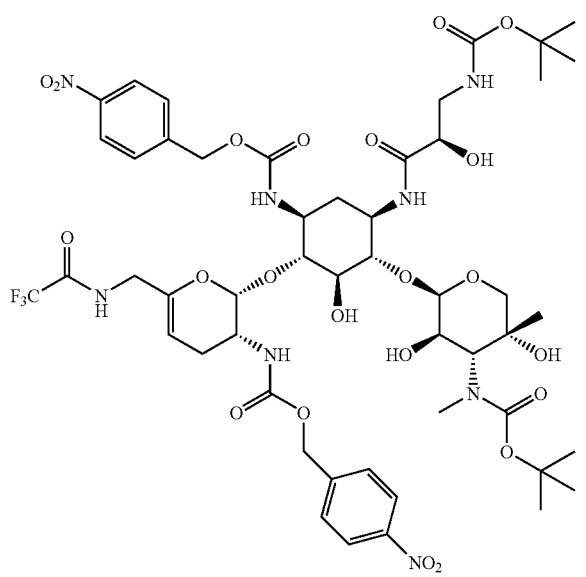 [SMILES: CN(C(=O)OC(C)(C)C)[C@@H]1[C@@H](O)[C@@H](O[C@@H]2[C@@H](O)[C@H](O[C@H]3OC(CNC(=O)C(F)(F)F)=CC[C@H]3NC(=O)OCc3ccc([N+](=O)[O-])cc3)[C@@H](NC(=O)OCc3ccc([N+](=O)[O-])cc3)C[C@H]2NC(=O)[C@H](O)CNC(=O)OC(C)(C)C)OC[C@]1(C)O]

To a stirring solution of 6'-trifluoroacetyl-2',3-diPNZ-1-[(R)-3-(tert-butoxycarbonylamino)-2-hydroxy-propionyl]-sisomicin (1.52 g, 1.39 mmol) in THF (10 mL) and methanol (5 mL) was added Boc$_2$O (0.65 mL, 0.62 g, 2.8 mmol). After three hours, glycine (312 mg, 4.17 mmol) and 0.5 M K$_2$CO$_3$ (24 mL) were added, and the reaction was stirred vigorously for one hour. The mixture was then partitioned between ethyl acetate and water, and the phases were separated. The ethyl acetate phase was washed once each with water and brine, dried over MgSO$_4$, filtered, and concentrated to dryness to give 6'-trifluoroacetyl-2',3-diPNZ-1-[(R)-3-(tert-butoxycarbonylamino)-2-hydroxy-propionyl]-3''-Boc-sisomicin as a solid that was carried through to the next step without further purification. MS m/e [M-Boc]$^+$ calcd 1089.4, found 1089.2.

2',3-diPNZ-1-[(R)-3-(tert-butoxycarbonylamino)-2-hydroxy-propionyl]-3''-Boc-sisomicin

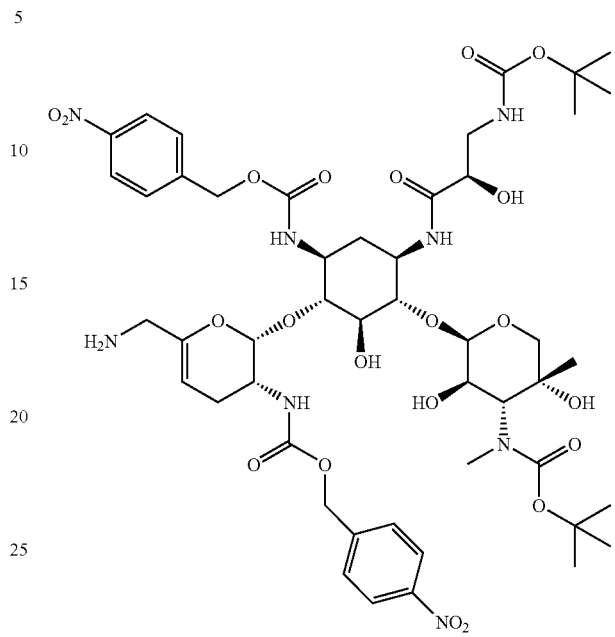

To a solution of 6'-trifluoroacetyl-2',3-diPNZ-1-[(R)-3-(tert-butoxycarbonylamino)-2-hydroxy-propionyl]-3''-Boc-sisomicin (1.39 mmol) in methanol (45 mL) was added concentrated ammonium hydroxide (45 mL, ~12M). The solution was allowed to sit at ambient temperature for 18 hours, and was then concentrated in vacuo. The residue was partitioned between ethyl acetate and water, and the phases were separated. The water phase was back-extracted once with ethyl acetate. The combined ethyl acetate phases were concentrated to give a residue, which was dissolved in a 1:1:1 v/v mixture of methanol/acetic acid/water, and was purified by RP HPLC Method 2-Column B. The pure fractions were combined, basified with 1M Na$_2$CO$_3$, and were concentrated in vacuo to remove the acetonitrile. The mixture was then extracted twice with ethyl acetate. The final ethyl acetate phases were combined, washed with brine, dried over MgSO$_4$, filtered, and concentrated to give 2',3-diPNZ-1-[(R)-3-(tert-butoxycarbonylamino)-2-hydroxy-propionyl]-3''-Boc-sisomicin (316 mg, 30% yield) as a white solid. MS m/e [M+H]$^+$ calcd 1093.4, found 1093.3.

N-Boc-3-amino-2(S)-hydroxy-propionic acid

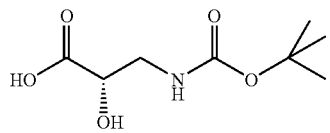

To a stirring solution of S-isoserine (4.0 g, 0.038 mol) in dioxane: H$_2$O (100 mL, 1:1 v/v) at 0° C. was added N-methylmorpholine (4.77 mL, 0.043 mol), followed by Boc$_2$O (11.28 mL, 0.049 mol) and the reaction was stirred overnight with gradual warming to room temperature. Glycine (1.0 g, 0.013 mol) was then added and the reaction was stirred for 20 min. The reaction was cooled to 0° C. and sat aq. NaHCO$_3$ (75 mL) was added. The aqueous layer was washed with ethyl acetate (2×60 mL) and then acidified to pH 1 with NaHSO$_4$. This solution was then extracted with ethyl acetate (3×70 mL) and these combined organic layers were dried over Na$_2$SO$_4$, filtered and concentrated to dryness to give the desired N-Boc-3-amino-2(S)-hydroxy-propanoic acid (6.30 g, 0.031 mmol, 81.5% yield): $^1$H NMR (400 MHz, CDCl3) δ 7.45 (bs, 1 H), 5.28 (bs, 1 H), 4.26 (m, 1 H), 3.40-3.62 (m, 2 H), 2.09 (s, 1 H), 1.42 (s, 9 H); $^{13}$C NMR (100 MHz, CDCl3) δ 174.72, 158.17, 82, 71.85, 44.28, 28.45.

6'-Trifluoroacetyl-2',3-diPNZ-1-(N-Boc-3-amino-2(S)-hydroxy-propionyl)-sisomicin

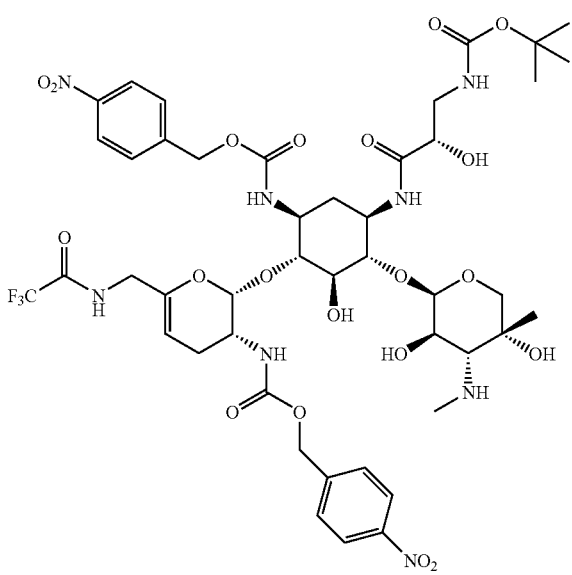 [SMILES: CN[C@@H]1[C@@H](O)[C@@H](O[C@@H]2[C@@H](O)[C@H](O[C@H]3OC(CNC(=O)C(F)(F)F)=CC[C@H]3NC(=O)OCc3ccc([N+](=O)[O-])cc3)[C@@H](NC(=O)OCc3ccc([N+](=O)[O-])cc3)C[C@H]2NC(=O)[C@@H](O)CNC(=O)OC(C)(C)C)OC[C@]1(C)O]

To a stirring solution of N-Boc-3-amino-2(S)-hydroxy-propionic acid (1.30 g, 6.34 mmol) in DMF (14 ml) was slowly added HONB (1.14 g, 6.34 mmol) and EDC (1.21 g, 6.34 mmol) and the reaction mixture was stirred for 2 hours, when MS showed complete formation of the activated ester (MS m/e [M+Na]$^+$ calcd 389.1, found 389.1). 6'-trifluoroacetyl-2',3-diPNZ-sisomicin (4.76 g, 5.28 mmol) was then added and the reaction was allowed to stir overnight. The reaction was quenched with sat. aq. NaHCO$_3$ (10 ml) and was extracted with EtOAc (5×15 mL). The combined organic layers were dried over Na$_2$SO$_4$, filtered and evaporated to dryness to yield a crude, which was purified by RP HPLC Method 2-Column B to yield the desired 6'-trifluoroacetyl-2',3-diPNZ-1-(N-Boc-3-amino-2(S)-hydroxy-propionyl)-sisomicin (1.66 g, 1.52 mmol, 29% yield, >95% purity): MS m/e [M+H]$^+$ calcd 1089.4, found 1089.2, [M+Na]$^+$ 1111.3.

6'-Trifluoroacetyl-2',3-diPNZ-1-(N-Boc-3-amino-2(S)-hydroxy-propionyl)-3"-Boc-sisomicin

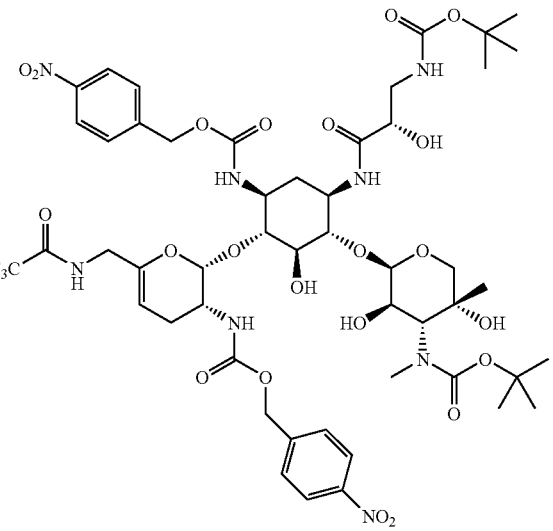

To a stirring suspension of 6'-trifluoroacetyl-2',3-diPNZ-1-(N-Boc-3-amino-2(S)-hydroxy-propionyl)-sisomicin (1.66 g, 1.52 mmol) in MeOH (20 mL) at 0° C. was added DIPEA (0.53 mL, 3.05 mmol) followed by Boc-anhydride (0.52 mL, 2.29 mmol) and the reaction was allowed to warm to room temperature. After 2 hours everything had gone into solution. The reaction was cooled to 0° and quenched with glycine (0.5 g, 6.66 mmol) and sat. aq. NaHCO$_3$. The reaction was extracted with EtOAc (3×20 mL) and the combined organic layers were dried over Na$_2$SO$_4$, filtered and evaporated to dryness to yield 6'-trifluoroacetyl-2',3-diPNZ-1-(N-Boc-3-amino-2(S)-hydroxy-propionyl)-3"-Boc-sisomicin (MS m/e [M+H]$^+$ calcd 1189.4, found 1188.8, [M+Na]$^+$ 1211.3), which was used in the next step without further purification.

2',3-diPNZ-1-(N-Boc-3-amino-2(S)-hydroxy-propionyl)-3"-Boc-sisomicin

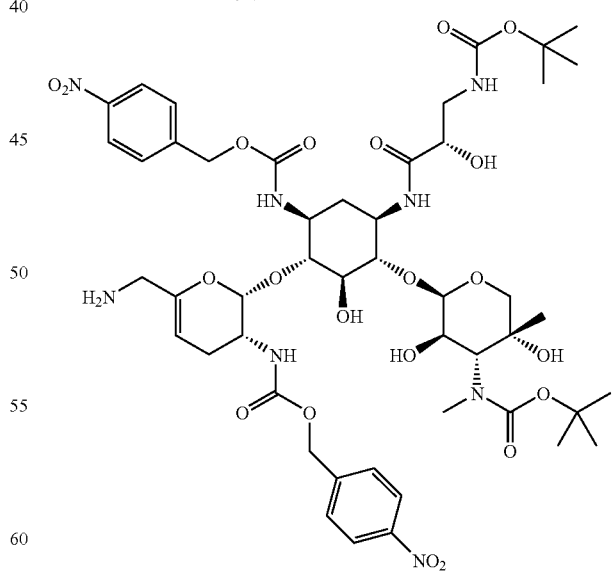

6'-Trifluoroacetyl-2',3-diPNZ-1-(N-Boc-3-amino-2(S)-hydroxy-propionyl)-3"-Boc-sisomicin (1.52 mmol) was dissolved in MeOH (12 mL) and conc. NH$_4$OH (20 mL) was added, and the reaction was stirred overnight. Solvent evaporation gave a crude, which was purified by RP HPLC Method 2-Column B to yield the desired 2',3-diPNZ-1-(N-Boc-3-amino-2(S)-hydroxy-propionyl)-3''-Boc-sisomicin (0.96 g, 0.79 mmol, 51.9% yield, >95% purity): MS m/e [M+H]$^+$ calcd 1093.4, found 1093.2, [M+Na]$^+$ 1115.3.

6'-Trifluoroacetyl-2',3-diPNZ-1-(N-PNZ-4-amino-2(S)-hydroxy-butyryl)-sisomicin

To a stirring solution of N-PNZ-4-amino-2(S)-hydroxy-butiric acid (1.47 g, 4.9 mmol) in DMF (50 ml) was slowly added HONB (0.884 g, 4.9 mmol) and EDC (0.945 g, 4.9 mmol) and the reaction mixture was stirred for 2 hours. 6'-Trifluoroacetyl-2',3-diPNZ-sisomicin (3.42 g, 3.8 mmol) was then added and the reaction was allowed to stir overnight. The reaction was quenched with sat. aq. NaHCO$_3$ (30 ml) and was extracted with EtOAc (5×50 mL). The combined organic

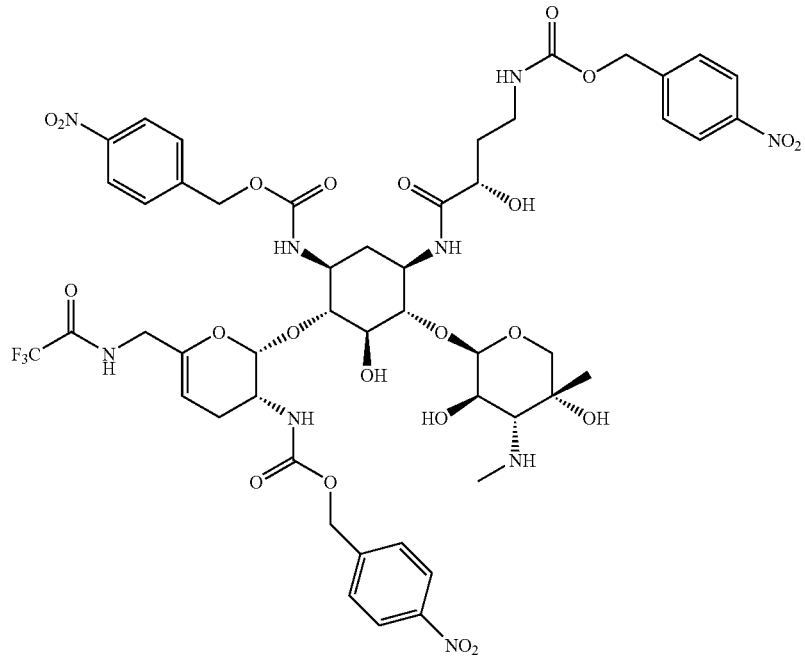 [SMILES: CN[C@@H]1[C@@H](O)[C@@H](O[C@@H]2[C@@H](O)[C@H](O[C@H]3OC(CNC(=O)C(F)(F)F)=CC[C@H]3NC(=O)OCc3ccc([N+](=O)[O-])cc3)[C@@H](NC(=O)OCc3ccc([N+](=O)[O-])cc3)C[C@H]2NC(=O)[C@@H](O)CCNC(=O)OCc2ccc([N+](=O)[O-])cc2)OC[C@]1(C)O]

layers were dried over MgSO$_4$, filtered and concentrated to yield the desired 6'-trifluoroacetyl-2',3-diPNZ-1-(N-PNZ-3-amino-2(S)-hydroxy-butyryl)-sisomicin (MS m/e [M+H]$^+$ 1182.4, found 1182.4), which was carried through to the next step without further purification.

6'-Trifluoroacetyl-2',3-diPNZ-1-(N-PNZ-4-amino-2(S)-hydroxy-butyryl)-3''-Boc-sisomicin

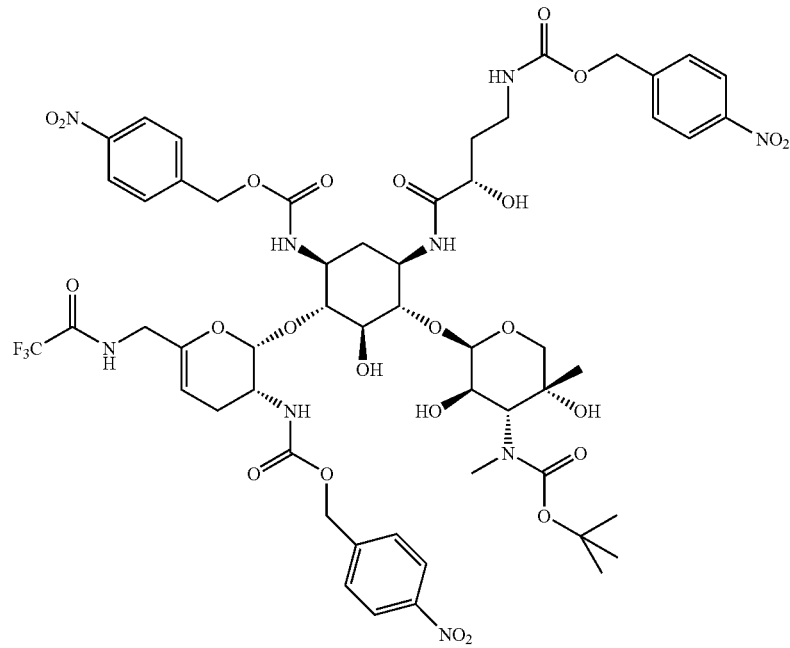 [SMILES: CN(C(=O)OC(C)(C)C)[C@@H]1[C@@H](O)[C@@H](O[C@@H]2[C@@H](O)[C@H](O[C@H]3OC(CNC(=O)C(F)(F)F)=CC[C@H]3NC(=O)OCc3ccc([N+](=O)[O-])cc3)[C@@H](NC(=O)OCc3ccc([N+](=O)[O-])cc3)C[C@H]2NC(=O)[C@@H](O)CCNC(=O)OCc2ccc([N+](=O)[O-])cc2)OC[C@]1(C)O]

To a stirring solution of 6'-trifluoroacetyl-2',3-diPNZ-1-(N-PNZ-3-amino-2(S)-hydroxy-butyryl)-sisomicin (4.9 mmol) in MeOH (50 mL) at 0° C. was added DIPEA (1.70 mL, 9.8 mmol), followed by Boc anhydride (1.6 g, 7.35 mmol) and the reaction was allowed to warm to room temperature. The reaction was then cooled to 0° C. and quenched with glycine (1.10 g, 14.7 mmol) and sat. aq. NaHCO₃. The reaction was extracted with EtOAc (3×50 mL) and the combined organic layers were dried over MgSO₄, filtered and evaporated to dryness to yield 6'-trifluoroacetyl-2',3-diPNZ-1-(N-PNZ-4-amino-2(S)-hydroxy-butyryl)-3''-Boc-sisomicin, which was used in the next step without further purification.

2',3-diPNZ-1-(N-PNZ-4-amino-2(S)-hydroxy-butyryl)-3''-Boc-sisomicin

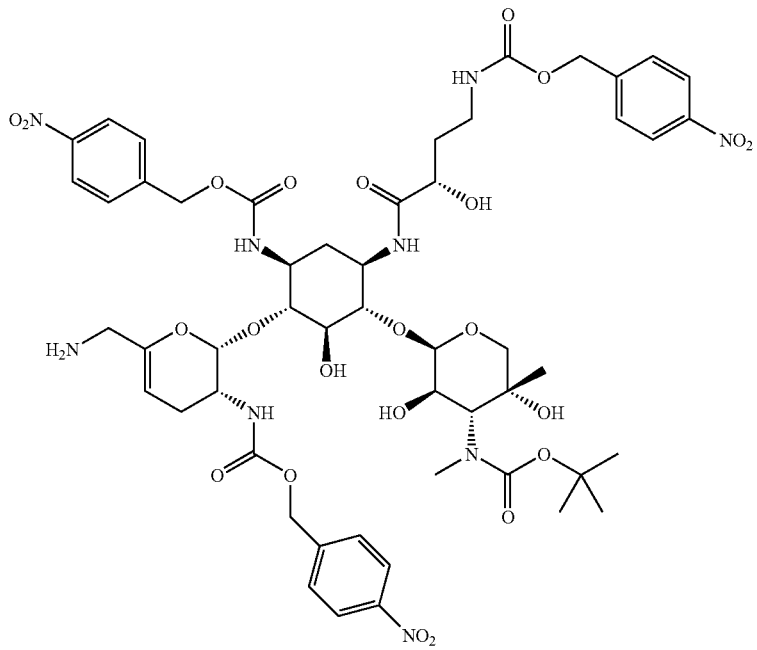 [SMILES: CN(C(=O)OC(C)(C)C)[C@@H]1[C@@H](O)[C@@H](O[C@@H]2[C@@H](O)[C@H](O[C@H]3OC(CN)=CC[C@H]3NC(=O)OCc3ccc([N+](=O)[O-])cc3)[C@@H](NC(=O)OCc3ccc([N+](=O)[O-])cc3)C[C@H]2NC(=O)[C@@H](O)CCNC(=O)OCc2ccc([N+](=O)[O-])cc2)OC[C@]1(C)O]

40

6'-Trifluoroacetyl-2',3-diPNZ-1-(N-Boc-3-amino-2(S)-hydroxy-butyryl)-3''-Boc-sisomicin (4.9 mmol) was dissolved in MeOH (30 mL) and conc. NH₄OH (50 mL) was added, and the reaction was stirred overnight. Solvent evaporation gave a crude, which was purified by RP HPLC Method 2-Column B to yield the desired product 2',3-diPNZ-1-(N-PNZ-4-amino-2(S)-hydroxy-butyryl)-3''-Boc-sisomicin. MS m/e [M+H]⁺ calcd 1186.4, found 1186.3.

6'-PNZ-sisomicin

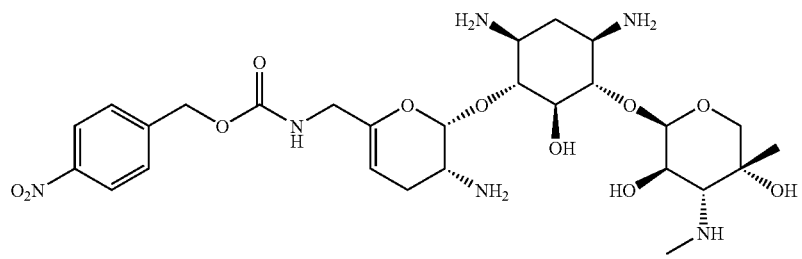 [SMILES: CN[C@@H]1[C@@H](O)[C@@H](O[C@@H]2[C@@H](O)[C@H](O[C@H]3OC(CNC(=O)OCc4ccc([N+](=O)[O-])cc4)=CC[C@H]3N)[C@@H](N)C[C@H]2N)OC[C@]1(C)O]

To a stirring solution of sisomicin (19.1 g, 42.65 mmol) in MeOH (300 mL) was added Zn(OAc)$_2$ (23.5 g, 0.128 mol) and the reaction mixture was stirred for 1 hour until all the zinc had gone into solution. A solution of (N-hydroxy-5-norbornene-2,3-dicarboxyl-imido)-4-nitro-benzoate (15.28 g, 42.65 mmol) in DCM (150 mL) was then added dropwise over 3 hours and the reaction was allowed to stir overnight. The reaction was then concentrated to dryness to yield a crude, which was slowly added to a vigorously stirring solution of 10% aq NH$_4$OH (480 mL) and DCM (180 mL). The aqueous layer was separated, washed with DCM (3×160 mL), and diluted with brine (250 mL). The aqueous layer was extracted with DCM: IPA (7:3 v/v, 4×160 mL). The combined organic layers were washed with 10% aq. NH$_4$OH: brine (7:3 v/v, 200 mL), dried over MgSO$_4$, filtered and concentrated to yield the desired 6'-PNZ-sisomicin: MS m/e [M+H]$^+$ calcd 627.3, found 627.2; CLND 95% purity.

(N-Hydroxy-5-norbornene-2,3-dicarboxyl-imido)-tert-butyl-carbonate

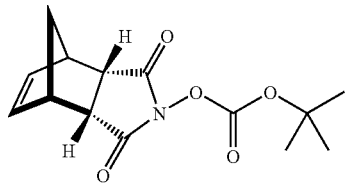 [SMILES: CC(C)(C)OC(=O)ON1C(=O)[C@@H]2[C@H]3C=CC(C3)[C@@H]2C1=O]

To a stirring solution of N-hydroxy-5-norbornene-2,3-dicarboximide (20.0 g, 0.112 mol) in THF (200 mL) at 0° C. was added triethylamine (0.65 mL, 4.8 mmol), followed by the dropwise addition of a solution of Boc$_2$O (29.23 g, 0.134 mol) in THF (30 mL) and the reaction was allowed to stir overnight with gradual warming to room temperature. A precipitate formed, which was filtered and washed with cold THF (200 mL). The crude solid was then vigorously stirred in MeOH (100 mL) for 1 hour, before being filtered, washed with MeOH (50 mL), and dried under high vacuum to yield the desired (N-hydroxy-5-norbornene-2,3-dicarboxyl-imido)-tert-butylcarbonate as a white solid (28.0 g, 0.1 mol, 89.3% yield): TLC (hexanes: ethyl acetate, 1:1 v/v) R$_f$=0.44; NMR (400 MHz, DMSO-d$_6$) δ 6.10 (bs, 2 H), 3.48 (bs, 2 H), 3.29-3.32 (m, 2 H), 1.58-1.62 (m, 1 H), 1.50-1.55 (m, 1 H), 1.47 (s, 9 H).

6'-PNZ-2',3-diBoc-sisomicin

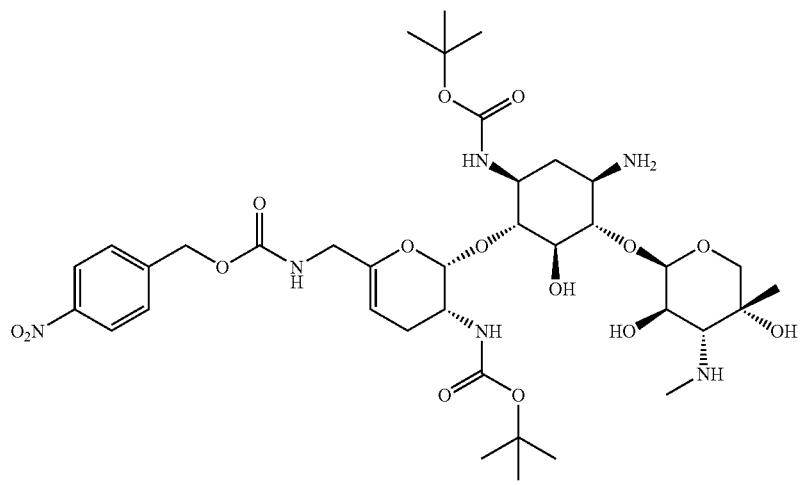 [SMILES: CN[C@@H]1[C@@H](O)[C@@H](O[C@@H]2[C@@H](O)[C@H](O[C@H]3OC(CNC(=O)OCc4ccc([N+](=O)[O-])cc4)=CC[C@H]3NC(=O)OC(C)(C)C)[C@@H](NC(=O)OC(C)(C)C)C[C@H]2N)OC[C@]1(C)O]

To a stirring solution of 6'-PNZ-sisomicin (5.86 g, 9.35 mmol) in MeOH (100 mL) was added Zn(OAc)$_2$ (5.15 g, 28.05 mmol) and the reaction mixture was stirred for 1 hour until all solids had dissolved. A solution of (N-hydroxy-5-norbornene-2,3-dicarboxyl-imido)-tert-butylcarbonate (4.96 g, 17.77 mmol) in THF (48 mL) was added dropwise over 4 hours and the reaction mixture was allowed to stir overnight. Triethylamine (2.61 ml, 18.7 mmol) was then added, followed by a solution of (N-hydroxy-5-norbornene-2,3-dicarboxyl-imido)-tert-butylcarbonate (1.31 g, 4.68 mmol) in THF (12 mL) and the reaction mixture was stirred for an additional 24 hours. The reaction was quenched by the addition of glycine (2.81 g, 37.4 mmol). The solvent was removed by rotary evaporation to yield a residue, which was dissolved in DCM (200 mL) and washed with H$_2$O: conc. NH$_4$OH (7:3 v/v, 3×50 mL). The organic layer was dried over MgSO$_4$, filtered and concentrated to dryness. The solids were dissolved in 0.1 M aq AcOH (2.0 L) and washed with ethyl acetate: diethyl ether (9:1 v/v, 4×1.0 L). The aqueous layer was then basified to pH 10 with conc. NH$_4$OH, salted and extracted with ethyl acetate (3×30 mL). The combined organic layers were dried over MgSO$_4$, filtered and concentrated to yield 6'-PNZ-2',3-di-Boc-sisomicin (4.1 g, 4.96 mmol, 53.0% yield, 92% purity): MS m/e [M+H]$^+$ calcd 827.4, found 827.2.

(N-Hydroxy-5-norbornene-2,3-dicarboxyl-imido)-9-fluorene-acetate

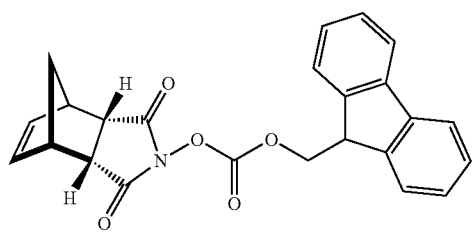 [SMILES: O=C(OCC1c2ccccc2-c2ccccc21)ON1C(=O)[C@@H]2[C@H]3C=CC(C3)[C@@H]2C1=O]

To a stirring solution of N-hydroxy-5-norbornene-2,3-dicarboximide (7.38 g, 0.041 mol) in THF (200 mL) at 0° C. was added N-methylmorpholine (4.53 mL, 0.041 mol), followed by the dropwise addition of a solution of 9-fluorenylmethyl chloroformate (10.15 g, 0.039 mol) in THF (50 mL), and the reaction was stirred overnight with gradual warming to room temperature. The flask was then cooled to 0° C. and the precipitated salts were removed by filtration. The filtrate was concentrated under vacuum to yield a waxy residue, which was precipitated from methanol to yield (N-hydroxy-5-norbornene-2,3-dicarboxyl-imido)-9-fluorene-acetate (9.9 g, 0.025 mol, 61.0% yield), which was carried through to the next step without further purification: TLC (hexanes: ethyl acetate 3:1 v/v) R$_f$=0.28.

6'-PNZ-2',3,3''-triBoc-1-Fmoc-sisomicin

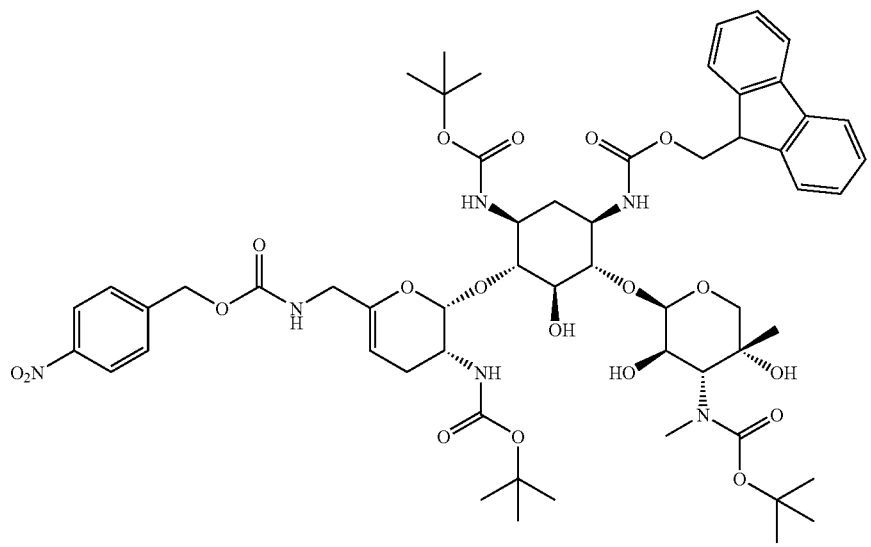 [SMILES: CN(C(=O)OC(C)(C)C)[C@@H]1[C@@H](O)[C@@H](O[C@@H]2[C@@H](O)[C@H](O[C@H]3OC(CNC(=O)OCc4ccc([N+](=O)[O-])cc4)=CC[C@H]3NC(=O)OC(C)(C)C)[C@@H](NC(=O)OC(C)(C)C)C[C@H]2NC(=O)OCC2c3ccccc3-c3ccccc32)OC[C@]1(C)O]

To a stirring solution of 6'-PNZ-2',3-diBoc-sisomicin (7.38 g, 8.93 mmol) in THF (200 mL) was added (N-hydroxy-5-norbornene-2,3-dicarboxyl-imido)-9-fluorene-acetate (2.51 g, 6.25 mmol), and the reaction was allowed to stir for 1 hour with its progress monitored by HPLC and MS (MS m/e [M+H]$^+$ calcd 1049.5, found 1049.4. Additional (N-hydroxy-5-norbornene-2,3-dicarboxyl-imido)-9-fluorene-acetate (0.05 eq) was added and the reaction was stirred for 1.5 hours. N-Methylmorpholine (0.98 ml, 8.93 mmol) was then added followed by the addition of Boc anhydride (3.94 g, 17.85 mmol), and the reaction was stirred for 3 hours. The reaction was quenched by the addition of glycine (7.51 g, 40.18 mmol) and was allowed to stir overnight. The precipitated salts were filtered and the resulting solution was concentrated to dryness to yield a residue, which was dissolved in DCM (150 mL) and washed with sat. aq. NaHCO$_3$ (3×80 mL), 1 M citric acid (3×80 mL), H$_2$O: NaHCO$_3$ (1:1 v/v, 80 mL), brine (40 mL) and dried over MgSO$_4$. Filtration and solvent evaporation gave the desired 6'-PNZ-2',3,3''-triBoc-1-Fmoc-sisomicin (MS m/e [M+Na]$^+$ calcd 1171.5, found 1171.3), which was carried through to the next step without further purification.

6'-PNZ-2',3,3''-triBoc-sisomicin

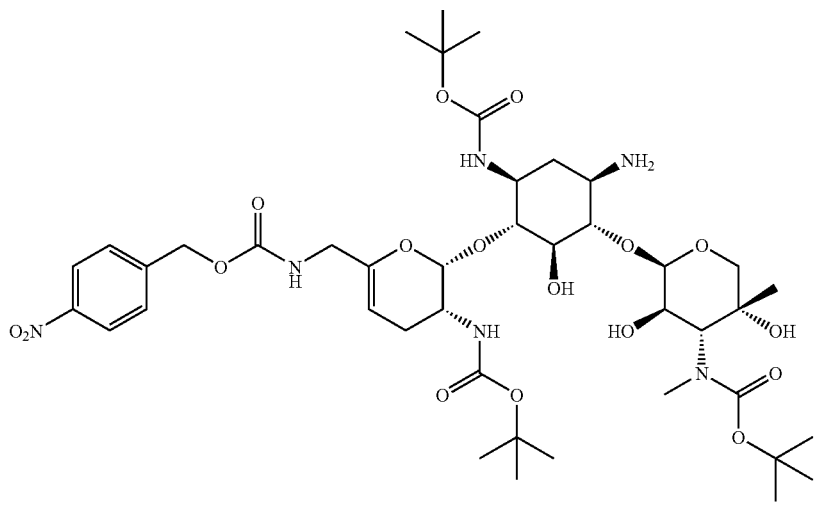 [SMILES: CN(C(=O)OC(C)(C)C)[C@@H]1[C@@H](O)[C@@H](O[C@@H]2[C@@H](O)[C@H](O[C@H]3OC(CNC(=O)OCc4ccc([N+](=O)[O-])cc4)=CC[C@H]3NC(=O)OC(C)(C)C)[C@@H](NC(=O)OC(C)(C)C)C[C@H]2N)OC[C@]1(C)O]

To a stirring solution of 6'-PNZ-2',3,3''-triBoc-1-Fmoc-sisomicin (8.93 mmol) in DCM (150 mL) was slowly added tris(2-aminoethyl)amine (13.37 mL, 89.27 mmol) and the reaction was stirred for 45 min. The reaction mixture was then washed with brine (3×100 mL), a pH 5.5 phosphate buffered solution (2×500 mL, 1×100 mL), H$_2$O (100 mL), sat. aq. NaHCO$_3$ (100 mL), and brine (100 mL). The organic phase was concentrated to yield a crude, which was purified by RP HPLC Method 2-Column B to yield the desired 6'-PNZ-2',3,3''-triBoc-sisomicin (2.77 g, 2.99 mmol, 33.5% yield, 93% purity): MS m/e [M+H]$^+$ calcd 927.4, found 927.2.

6'-PNZ-2',3,3''-triBoc-1-(N-Boc-3-amino-2(S)-hydroxy-propionyl)-sisomicin

To a stirring solution of N-Boc-3-amino-2(S)-hydroxy-propionic acid (0.93 g, 4.53 mmol) in DMF (8 ml) was slowly added HONB (0.82 g, 4.53 mmol) and EDC (0.87 g, 4.53 mmol) and the reaction mixture was stirred for 2 hours. 6'-PNZ-2',3,3''-triBoc-sisomicin (3.0 g, 3.23 mmol) was then added and the reaction was allowed to stir overnight. The reaction was quenched with H$_2$O (10 ml) and was extracted with EtOAc (5×15 mL). The combined organic layers were dried over Na$_2$SO$_4$, filtered and concentrated to dryness to give the desired 6'-PNZ-2',3,3''-triBoc-1-(N-Boc-3-amino-2(S)-hydroxy-propionyl)-sisomicin (MS m/e [M+H]$^+$ calcd 1114.5, found 1113.9, [M+Na]$^+$ 1136.3), which was carried through to the next step without further purification.

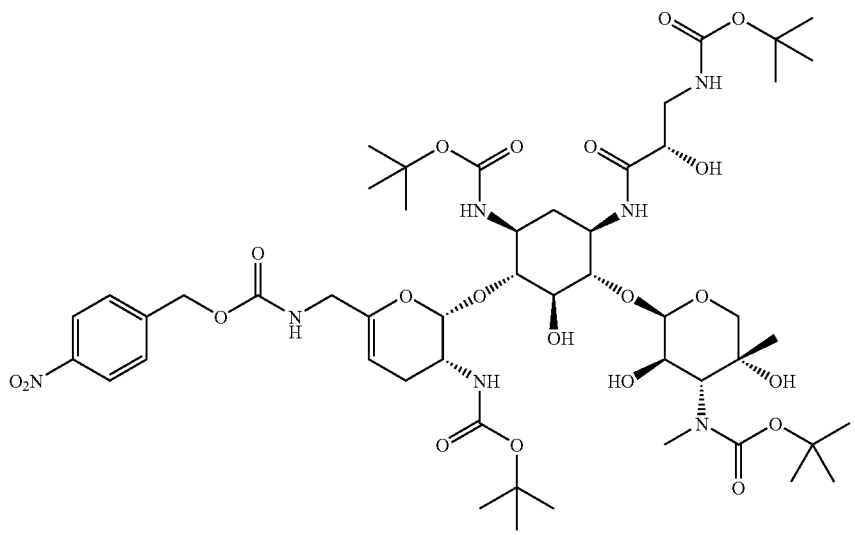 [SMILES: CN(C(=O)OC(C)(C)C)[C@@H]1[C@@H](O)[C@@H](O[C@@H]2[C@@H](O)[C@H](O[C@H]3OC(CNC(=O)OCc4ccc([N+](=O)[O-])cc4)=CC[C@H]3NC(=O)OC(C)(C)C)[C@@H](NC(=O)OC(C)(C)C)C[C@H]2NC(=O)[C@@H](O)CNC(=O)OC(C)(C)C)OC[C@]1(C)O]

2',3,3''-triBoc-1-(N-Boc-3-amino-2(S)-hydroxy-propionyl)-sisomicin

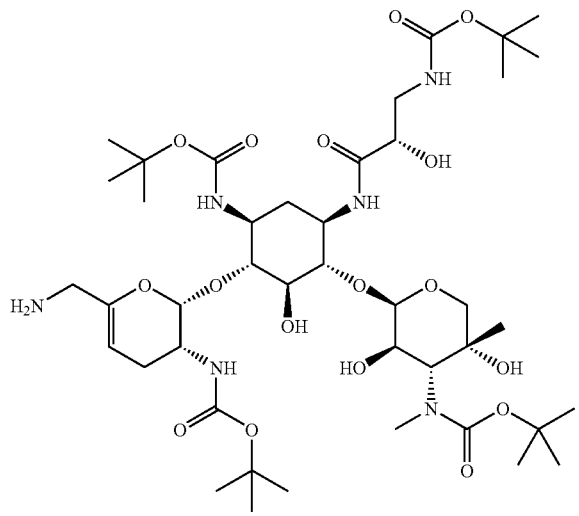 [SMILES: CN(C(=O)OC(C)(C)C)[C@@H]1[C@@H](O)[C@@H](O[C@@H]2[C@@H](O)[C@H](O[C@H]3OC(CN)=CC[C@H]3NC(=O)OC(C)(C)C)[C@@H](NC(=O)OC(C)(C)C)C[C@H]2NC(=O)[C@@H](O)CNC(=O)OC(C)(C)C)OC[C@]1(C)O]

6'-PNZ-2',3,3''-triBoc-1-(N-Boc-3-amino-2(S)-hydroxy-propionyl)-sisomicin (3.23 mmol) was submitted to Procedure 2 for PNZ removal to yield 2',3,3''-triBoc-1-(N-Boc-3-amino-2(S)-hydroxy-propionyl)-sisomicin (2.0 g, 2.14 mmol, 66.2% yield, purity >65%): MS m/e [M+H]$^+$ calcd 935.5, found 935.3, [M+Na]$^+$ 957.3

N-Boc-4-amino-2(S)-hydroxy-butyric acid

To a stirring solution of S-4-amino-2-hydroxy-butyric acid (51.98 g, 0.44 mol) in dioxane:H$_2$O (2 L, 1:1 v/v) was added K$_2$CO$_3$ (106 g, 0.91 mol) followed by a solution of Boc-anhydride (100 g, 0.46 mol) in dioxane (100 mL), and the reaction was stirred overnight. The reaction was washed with DCM (2×300 mL), and the aqueous layer was acidified to pH 2 with H$_3$PO$_4$. The aqueous layer was extracted with DCM (2×300 mL), and the combined organic layers were dried over MgSO$_4$, filtered and concentrated to dryness to yield the desired N-Boc-4-amino-2(S)-hydroxybutyric acid (48.2 g, 50% yield).

6'-PNZ-2',3,3''-triBoc-1-(N-Boc-4-amino-2(S)-hydroxy-butyryl)-sisomicin

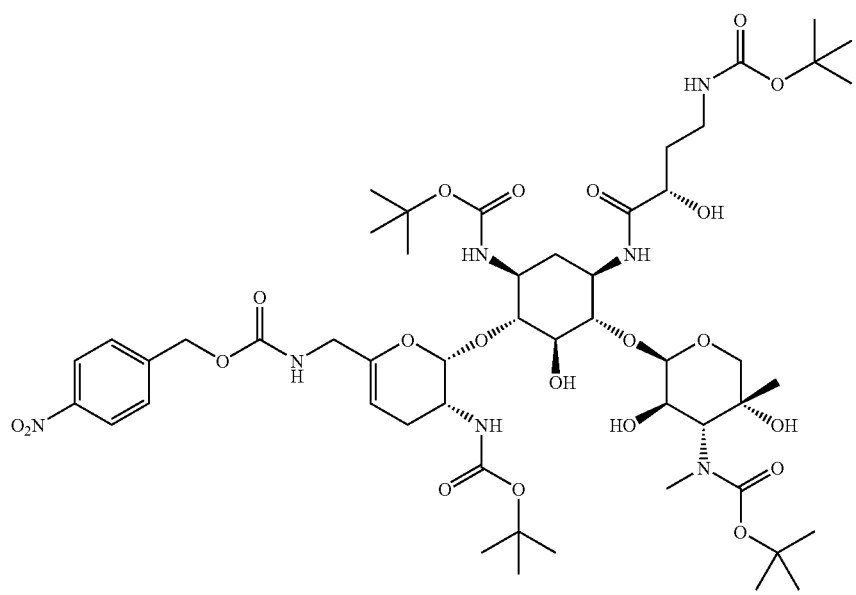 [SMILES: CN(C(=O)OC(C)(C)C)[C@@H]1[C@@H](O)[C@@H](O[C@@H]2[C@@H](O)[C@H](O[C@H]3OC(CNC(=O)OCc4ccc([N+](=O)[O-])cc4)=CC[C@H]3NC(=O)OC(C)(C)C)[C@@H](NC(=O)OC(C)(C)C)C[C@H]2NC(=O)[C@@H](O)CCNC(=O)OC(C)(C)C)OC[C@]1(C)O]

To a stirring solution of N-Boc-4-amino-2(S)-hydroxy-butyric acid (1.35 g, 6.17 mmol) in DMF (12 ml) was slowly added HONB (1.11 g, 6.17 mmol) and EDC (1.18 g, 6.17 mmol). A solution of 6'-PNZ-2',3,3''-triBoc-sisomicin (4.4 g, 4.75 mmol) in DMF (13 mL) was then slowly added, and the reaction was allowed to stir overnight. The reaction was cooled to 0° C. and quenched with sat. aq. $NaHCO_3$ (20 mL) and was extracted with EtOAc (50 mL). The combined organic layers were washed with sat. aq. $NaHCO_3$ (2×20 mL), brine (25 mL), dried over $MgSO_4$, filtered and concentrated to dryness to give the desired 6'-PNZ-2',3,3''-triBoc-1-(N-Boc-4-amino-2(S)-hydroxy-butyryl)-sisomicin (MS m/e [M+H]+ calcd 1128.5, found 1129.4), which was carried through to the next step without further purification.

2',3,3''-triBoc-1-(N-Boc-4-amino-2(S)-hydroxy-butyryl)-sisomicin

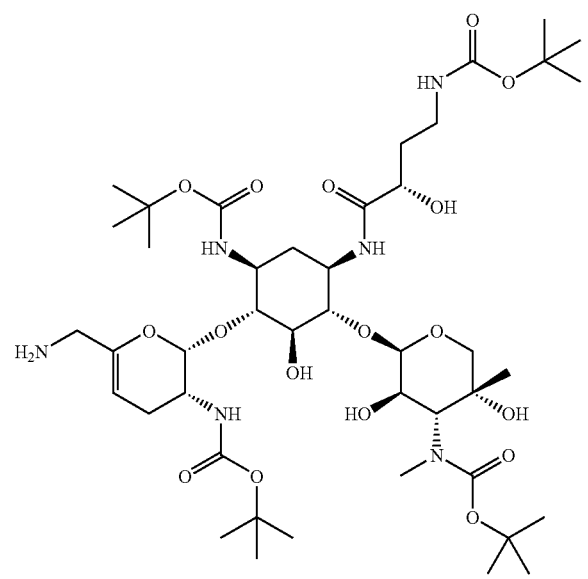 [SMILES: CN(C(=O)OC(C)(C)C)[C@@H]1[C@@H](O)[C@@H](O[C@@H]2[C@@H](O)[C@H](O[C@H]3OC(CN)=CC[C@H]3NC(=O)OC(C)(C)C)[C@@H](NC(=O)OC(C)(C)C)C[C@H]2NC(=O)[C@@H](O)CCNC(=O)OC(C)(C)C)OC[C@]1(C)O]

6'-PNZ-2',3,3''-triBoc-1-(N-Boc-4-amino-2(S)-hydroxy-butyryl)-sisomicin (4.75 mmol) was submitted to Procedure 2 for PNZ removal to yield 2',3,3''-triBoc-1-(N-Boc-4-amino-2(S)-hydroxy-butyryl)-sisomicin: MS m/e [M+H]+ calcd 949.5, found 949.1, [M+Na]+ 971.4.

6',2'-diPNZ-sisomicin

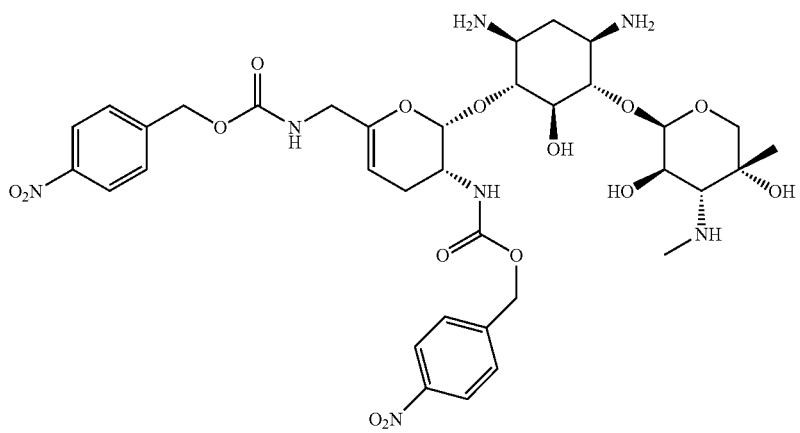 [SMILES: CN[C@@H]1[C@@H](O)[C@@H](O[C@@H]2[C@@H](O)[C@H](O[C@H]3OC(CNC(=O)OCc4ccc([N+](=O)[O-])cc4)=CC[C@H]3NC(=O)OCc3ccc([N+](=O)[O-])cc3)[C@@H](N)C[C@H]2N)OC[C@]1(C)O]

Sisomicin (12.9 g, 28.9 mmol) and Nickel (II) acetate (29 g, 115.6 mmol) were dissolved in methanol (900 ml), and the green solution was cooled in an ice-water bath. To this solution was added 2,4-dioxo-3-azabicyclo[3.2.1]oct-6-en-3-yl 4-nitrobenzyl carbonate (16.6 g, 46.2 mmol) as a solid. The mixture was allowed to slowly warm to room temperature and stir overnight. The solution was concentrated in vacuo to a green oil, and the oil was partitioned between concentrated ammonium hydroxide (~12M) and ethyl acetate. The phases were separated, and the purple aqueous phase was back-extracted once with ethyl acetate. The combined ethyl acetate phases were washed once with brine, diluted with 10% by volume with isopropanol, and extracted three times with 5% aqueous acetic acid. The combined acetic acid phases were basified with 6M NaOH to pH>11, and were then extracted twice with ethyl acetate. The final two ethyl acetate phases were combined and washed once with brine, dried over $Na_2SO_4$, filtered, and concentrated to ½ volume in vacuo. The product precipitated during the concentration, and was isolated by filtration to give 6',2'-di-PNZ-sisomicin (12.1 g, 65% yield) as a white solid. MS m/e [M+H]+ calcd 806.3, found 806.2.

6',2'-diPNZ-1,3,3''-triBoc-sisomicin

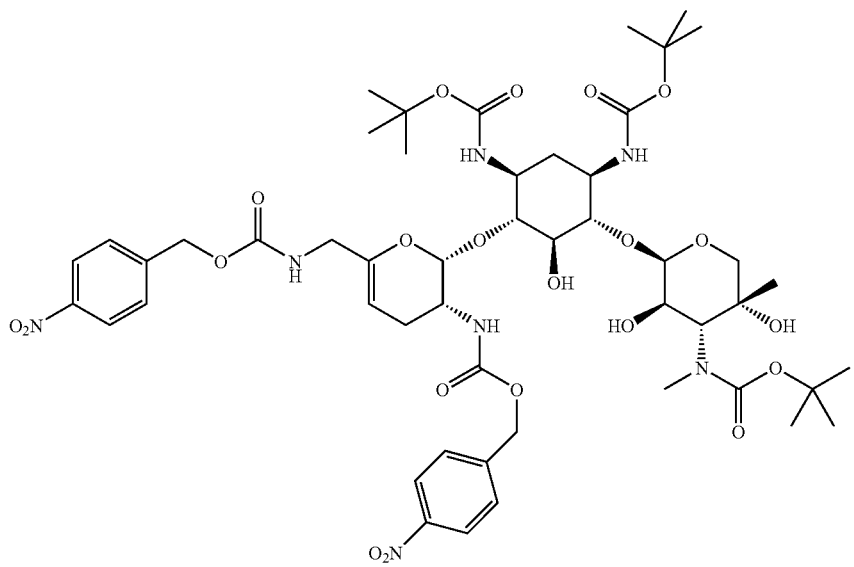 [SMILES: CN(C(=O)OC(C)(C)C)[C@@H]1[C@@H](O)[C@@H](O[C@@H]2[C@@H](O)[C@H](O[C@H]3OC(CNC(=O)OCc4ccc([N+](=O)[O-])cc4)=CC[C@H]3NC(=O)OCc3ccc([N+](=O)[O-])cc3)[C@@H](NC(=O)OC(C)(C)C)C[C@H]2NC(=O)OC(C)(C)C)OC[C@]1(C)O]

To a stirring solution of 6',2'-diPNZ-sisomicin (4.1 g, 5.09 mmol) in THF (70 mL) and methanol (70 mL) with the flask placed in a water bath, was added di-tert-butyl-dicarbonate (5.8 mL, 5.51 g, 25.5 mmol). After 2 hours, glycine (1.9 g, 25.5 mmol), water (70 mL), and 1 M sodium carbonate (15 mL) were added, and the mixture was stirred vigorously for 12 hours. The mixture was concentrated to remove the THF and methanol, and water (100 mL) was added to suspend the solids. The solids were isolated by filtration, washed with water, and dried to give 6',2'-diPNZ-1,3,3''-triBoc-sisomicin (5.41 g, 96% yield) as a white solid. Rf 0.15 (CHCl$_3$:5% IPA v/v, UV) MS m/e [M-Boc]$^+$ calcd 1006.5, found 1006.4.

1,3,3''-triBoc-sisomicin

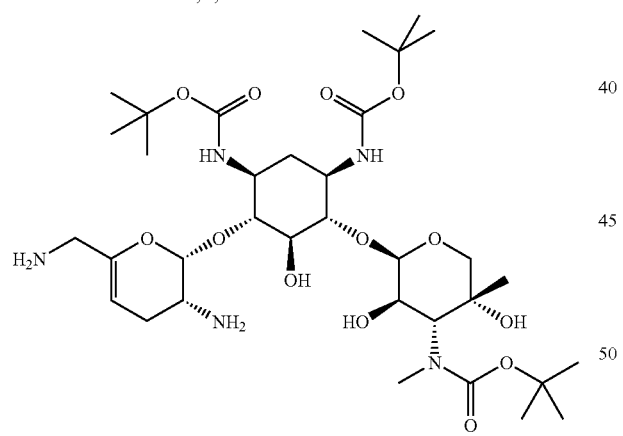

6',2'-diPNZ-1,3,3''-triBoc-sisomicin (4.84 g, 4.38 mmol) and sodium hydrosulfite (7.6 g, 44 mmol) were combined with ethanol (70 mL) and water (70 mL) in a flask. The flask was fitted with a condenser, and the mixture was heated at 60° C. for 12 hours. The mixture was then heated at 65° C. for an additional three hours, followed by cooling to room temperature. The mixture was partitioned between 0.2 M NaOH and ethyl acetate, and the phases were separated. The aqueous phase was back-extracted once with ethyl acetate. The combined organic phases were washed once with brine, dried over Na$_2$SO$_4$, filtered, and concentrated to an oil. The oil was triturated with ether, and the solids were isolated by filtration to give 6',2'-di-PNZ-1,3,3''-triBoc-sisomicin (2.71 g, 83% yield) as a white solid. Rf 0.23 (IPA: CHCl$_3$ 4:1, with 2% NH$_3$, UV, ninhydrin); MS m/e [M+H]$^+$ calcd 748.4, found 748.3.

6'-PNZ-1,3,3''-triBoc-sisomicin

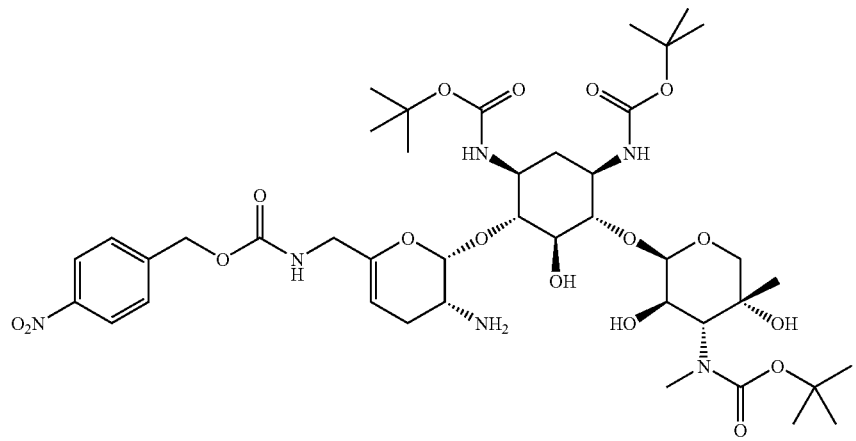 [SMILES: CN(C(=O)OC(C)(C)C)[C@@H]1[C@@H](O)[C@@H](O[C@@H]2[C@@H](O)[C@H](O[C@H]3OC(CNC(=O)OCc4ccc([N+](=O)[O-])cc4)=CC[C@H]3N)[C@@H](NC(=O)OC(C)(C)C)C[C@H]2NC(=O)OC(C)(C)C)OC[C@]1(C)O]

1,3,3''-triBoc-sisomicin (8.5 g, 11.4 mmol) was dissolved in methanol (212 mL) and cooled in an ice-water bath, and triethylamine (1.75 mL, 12.5 mmol) was added. 2,4-Dioxo-3-azabicyclo[3.2.1]oct-6-en-3-yl 4-nitrobenzyl carbonate (4.08 g, 11.4 mmol) was added as a solid. After 1 hour, the reaction was concentrated to a residue, which was partitioned between ether/ethyl acetate (1:1 v/v) and water. The phases were separated, and the organic phase was washed once with 5% aqueous acetic acid to remove the remaining starting material. The organic phase was then diluted with ⅓ volume of hexane, and was extracted three times with 5% aqueous acetic acid.

These last three aqueous phases were combined, salted to approximately 10% saturation with NaCl, and were extracted twice with ethyl acetate. These last two ethyl acetate phases were combined, washed once each with 1 M NaOH and brine, dried over $Na_2SO_4$, filtered, and concentrated. The resulting residue was triturated with ether/hexanes, and the solids were isolated by filtration to give 6'-PNZ-1,3,3''-triBoc-sisomicin (6.2 g, 61% yield) as a white solid. The unreacted starting material in the initial aqueous phase can be re-cycled by simply basifying the solution, extracting it into ethyl acetate, drying over $Na_2SO_4$, and concentrating. MS m/e $[M+H]^+$ calcd 927.4, found 927.4.

6',2'-diPNZ-3-Boc-sisomicin

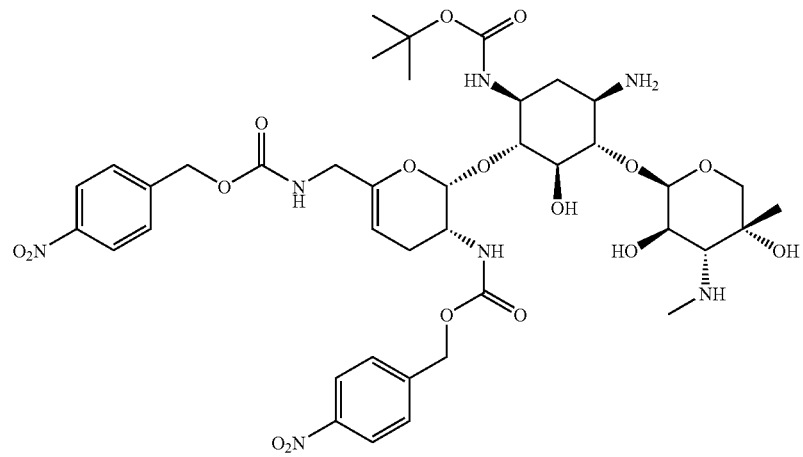 [SMILES: CN[C@@H]1[C@@H](O)[C@@H](O[C@@H]2[C@@H](O)[C@H](O[C@H]3OC(CNC(=O)OCc4ccc([N+](=O)[O-])cc4)=CC[C@H]3NC(=O)OCc3ccc([N+](=O)[O-])cc3)[C@@H](NC(=O)OC(C)(C)C)C[C@H]2N)OC[C@]1(C)O]

6',2'-diPNZ-sisomicin (5.5 g, 6.8 mmol) and Zinc acetate (4.5 g, 20.4 mmol) were dissolved in methanol (200 mL) and the solution was cooled in an ice-water bath. tert-Butyl-2,4-dioxo-3-azabicyclo[3.2.1]oct-6-en-3-yl carbonate (1.9 g, 6.8 mmol, Boc-ONb) was added, and the reaction was allowed to warm slowly to room temperature and stir overnight. tent-Butyl-2,4-dioxo-3-azabicyclo[3.2.1]oct-6-en-3-yl carbonate (500 mg, ~1.7 mmol) was added, and the solution was stirred for four hours. Another portion of tert-butyl-2,4-dioxo-3-azabicyclo[3.2.1]oct-6-en-3-yl carbonate (500 mg) was added, and the reaction was stirred for another four hours. The reaction was then concentrated to an oil, which was partitioned between concentrated ammonium hydroxide (~12 M) and ethyl acetate, and the phases were separated. The ethyl acetate phase was washed once each with conc. ammonium hydroxide and water, and was then washed twice with 5% aqueous acetic acid that was 20% saturated with NaCl. The ethyl acetate phase was then diluted with 20% by volume hexanes, and was extracted with 5% aqueous acetic acid. The final acetic acid phase was basified with 6 M NaOH to pH >11, and was extracted once with fresh ethyl acetate. The final ethyl acetate phase was washed once with brine, dried over Na$_2$SO$_4$, filtered, and concentrated to an oil. The oil was dissolved in ethyl acetate (16 mL), and was dripped into ether (200 mL) to precipitate the product. The solids were isolated by filtration and washed with ether to give 6',2'-di-PNZ-3-Boc-sisomicin (3.82 g, 62% yield) as a white solid. MS m/e [M+H]$^+$ calcd 906.4, found 906.3.

6',2'-diPNZ-3-Boc-1-(N-Boc-4-amino-2(S)-hydroxy-butyryl)-sisomicin

To a stirring solution of 6',2'-diPNZ-3-Boc-sisomicin (10.0 g, 11.0 mmol) in DMF (100 mL) was added N-Boc-4-amino-2(S)-hydroxy-butyric acid (3.15 g, 14.4 mmol) and the reaction was cooled to −40° C. and stirred for 30 min. PyBOP (6.9 g, 13.2 mmol) was then added, followed by DIPEA (7.7 mL, 40.4 mmol) and the reaction was stirred for 3 hours at −40° C. The reaction was diluted with EtOAc (200 mL), and washed with water (2×100 mL). The aqueous layer was separated and extracted with EtOAc (100 mL). The combined organic layers were dried over Na$_2$SO$_4$, filtered and concentrated to yield 6',2'-diPNZ-3-Boc-1-(N-Boc-4-amino-2(S)-hydroxy-butyryl)-sisomicin as a yellow-orange solid (HPLC 67% purity), which was carried through to the next step without further purification.

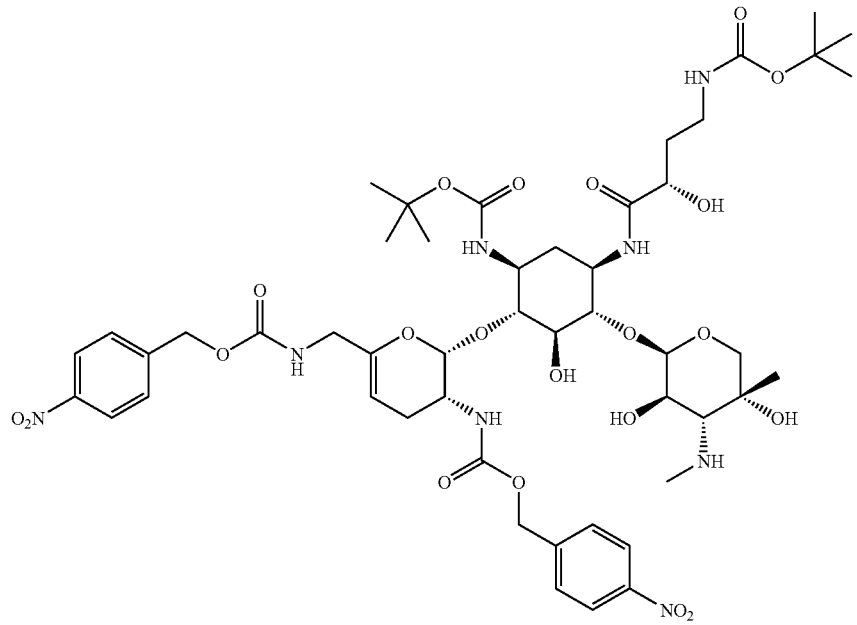 [SMILES: CN[C@@H]1[C@@H](O)[C@@H](O[C@@H]2[C@@H](O)[C@H](O[C@H]3OC(CNC(=O)OCc4ccc([N+](=O)[O-])cc4)=CC[C@H]3NC(=O)OCc3ccc([N+](=O)[O-])cc3)[C@@H](NC(=O)OC(C)(C)C)C[C@H]2NC(=O)[C@@H](O)CCNC(=O)OC(C)(C)C)OC[C@]1(C)O]

6',2'-diPNZ-3,3''-diBoc-1-(N-Boc-4-amino-2(S)-hydroxy-butyryl)-sisomicin

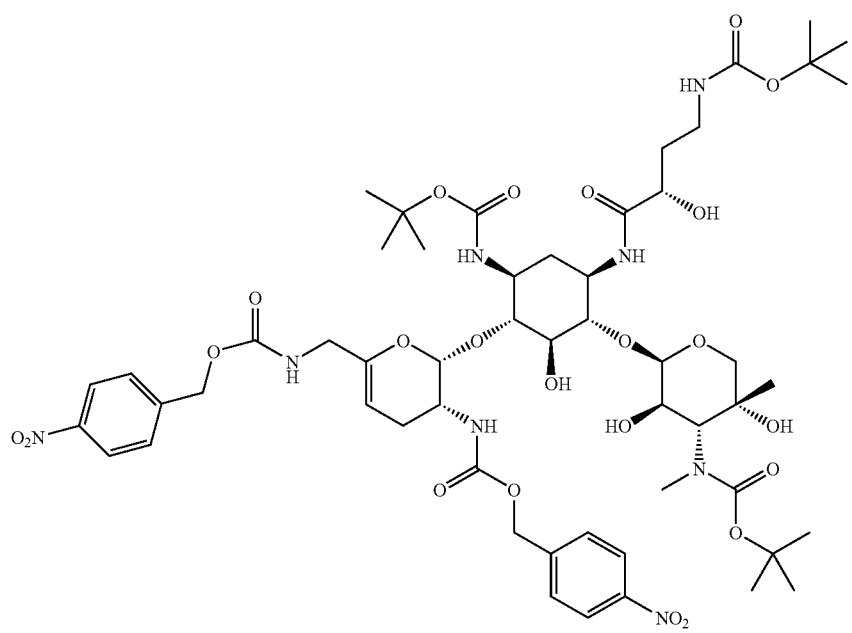 [SMILES: CN(C(=O)OC(C)(C)C)[C@@H]1[C@@H](O)[C@@H](O[C@@H]2[C@@H](O)[C@H](O[C@H]3OC(CNC(=O)OCc4ccc([N+](=O)[O-])cc4)=CC[C@H]3NC(=O)OCc3ccc([N+](=O)[O-])cc3)[C@@H](NC(=O)OC(C)(C)C)C[C@H]2NC(=O)[C@@H](O)CCNC(=O)OC(C)(C)C)OC[C@]1(C)O]

To a stirring solution of 6',2'-diPNZ-3-Boc-1-(N-Boc-4-amino-2(S)-hydroxy-butyryl)-sisomicin (11.0 mmol) in THF (100 mL) at 0° C. was added N-methyl morpholine (2.44 mL, 22.1 mmol), followed by Boc-anhydride (4.82 g, 22.1 mmol) and the reaction mixture was stirred for 18 h. The reaction mixture was concentrated to dryness to yield a crude, which was purified by flash chromatography (silica gel/dichloromethane: methanol 0-7%) to yield the desired 6',2'-diPNZ-3,3''-diBoc-1-(N-Boc-4-amino-2(S)-hydroxy-butyryl)-sisomicin (10.47 g, 9.46 mmol, 86.0% yield, anal. HPLC 85% purity): MS m/e [M+Na]+ calcd 1229.5, found 1229.4.

3,3''-diBoc-1-(N-Boc-4-amino-2(S)-hydroxy-butyryl)-sisomicin

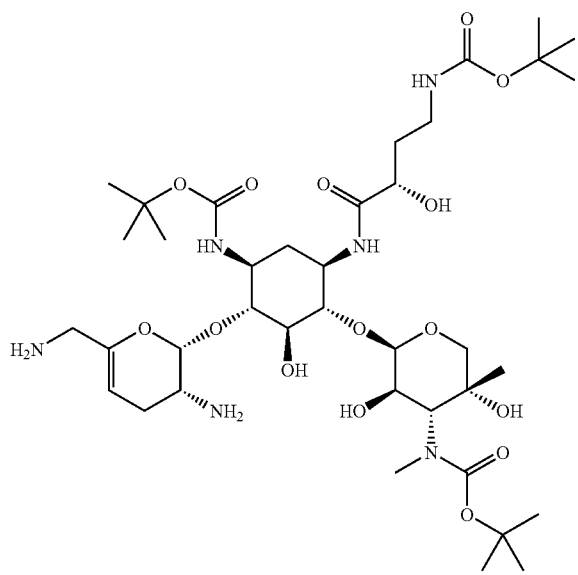 [SMILES: CN(C(=O)OC(C)(C)C)[C@@H]1[C@@H](O)[C@@H](O[C@@H]2[C@@H](O)[C@H](O[C@H]3OC(CN)=CC[C@H]3N)[C@@H](NC(=O)OC(C)(C)C)C[C@H]2NC(=O)[C@@H](O)CCNC(=O)OC(C)(C)C)OC[C@]1(C)O]

To a stirring solution of 6',2'-diPNZ-3,3''-diBoc-1-(N-Boc-4-amino-2(S)-hydroxy-butyryl)-sisomicin (10.5 g, 8.71 mmol) in EtOH (100 mL) and $H_2O$ (50 mL) was added 1 M NaOH (34.8 ml, 34.8 mmol), followed by $Na_2S_2O_4$ (12.1 g, 69.6 mmol) and the reaction mixture was heated at 70° C. for 18 hours. Upon cooling, a precipitate formed, which was removed by filtration and washed with MeOH (25 mL). Removal of the organic solvents by rotary evaporation was followed by the addition of $H_2O$ (100 mL) and acetic acid (200 mL) to obtain an acidic solution (pH~4), which was washed with EtOAc (2×100 mL). The aqueous layer was then basified to pH 12 with conc. $NH_4OH$ (20 mL), salted with NaCl (6.0 g) and extracted with EtOAc (2×200 mL). The combined organic layers were dried over $Na_2SO_4$, filtered, and concentrated to give the desired 3,3''-diBoc-1-(N-Boc-4-amino-2(S)-hydroxy-butyryl)-sisomicin (4.78 g, 5.45 mmol, 62.6% yield, MS m/e [M+H]+ calcd 849.5, found 849.3, [M+Na]+ 871.3), which was carried through to the next step without further purification.

6'-PNZ-3,3''-diBoc-1-(N-Boc-4-amino-2(S)-hydroxy-butyryl)-sisomicin

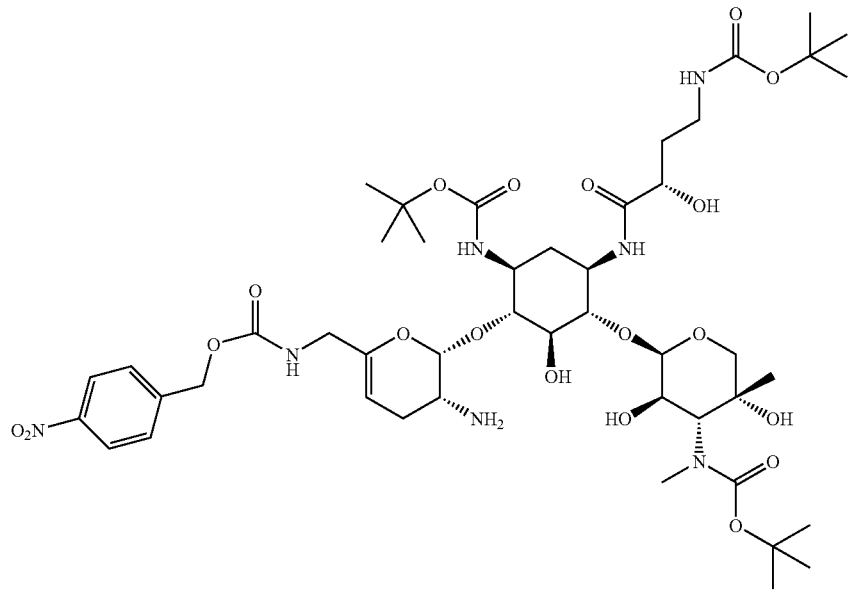 [SMILES: CN(C(=O)OC(C)(C)C)[C@@H]1[C@@H](O)[C@@H](O[C@@H]2[C@@H](O)[C@H](O[C@H]3OC(CNC(=O)OCc4ccc([N+](=O)[O-])cc4)=CC[C@H]3N)[C@@H](NC(=O)OC(C)(C)C)C[C@H]2NC(=O)[C@@H](O)CCNC(=O)OC(C)(C)C)OC[C@]1(C)O]

To a stirring solution of 3,3"-diBoc-1-(N-Boc-4-amino-2(S)-hydroxy-butyryl)-sisomicin (4.78 g, 5.45 mmol) in MeOH (75 mL) was added DIPEA (0.95 mL, 5.45 mmol), followed by (N-hydroxy-5-norbornene-2,3-dicarboxylimido)-4-nitro-benzyl carbonate (HONB-PNZ, 1.75 g, 4.90 mmol) and the reaction mixture was stirred for 1 hour. Solvent evaporation gave an oily residue, which was dissolved in EtOAc (100 mL), washed with H$_2$O (2×100 mL), and diluted with Et$_2$O (75 mL) and hexanes (50 mL). The organic layer was then extracted with 5% aq. AcOH (100 mL) and the aqueous layer was separated, salted with NaCl (3.0 g) and extracted with EtOAc (3×100 mL). The combined organic layers were dried over Na$_2$SO$_4$, filtered and concentrated to yield the desired 6'-PNZ-3,3"-diBoc-1-(N-Boc-4-amino-2(S)-hydroxy-butyryl)-sisomicin (3.08 g, 3.32 mmol, 60.9% yield; MS m/e [M+H]$^+$ calcd 1028.5, found 1028.3; HPLC 90.0% purity), which was carried through to the next step without further purification.

Example 1

6'-(2-Hydroxy-ethyl)-1-(4-amino-2(S)-hydroxy-butyryl)-sisomicin

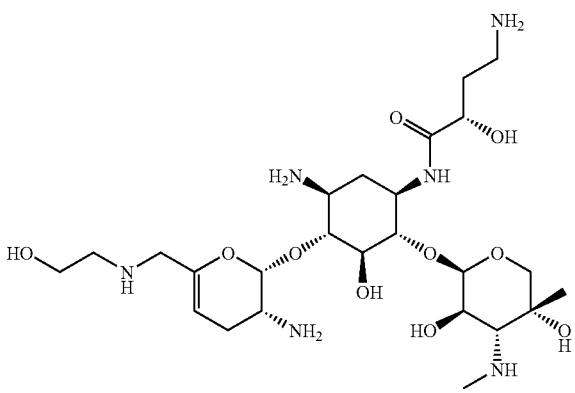

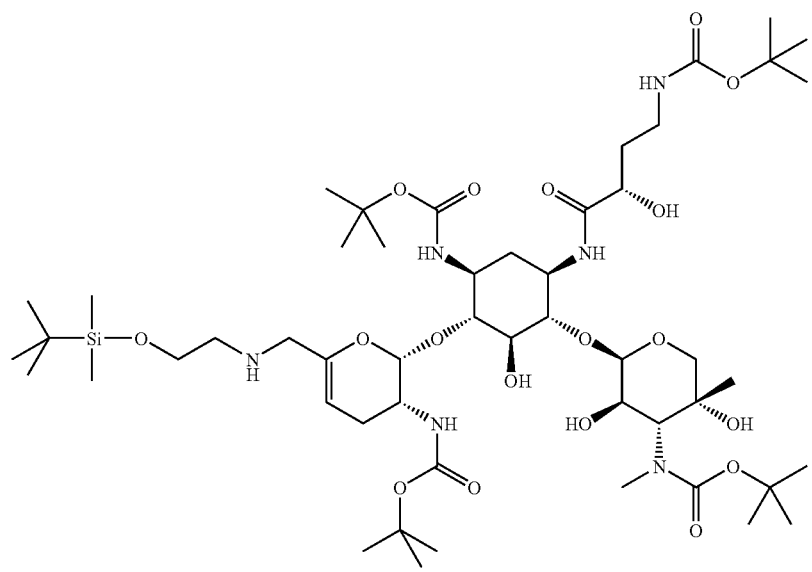 [SMILES: CN(C(=O)OC(C)(C)C)[C@@H]1[C@@H](O)[C@@H](O[C@@H]2[C@@H](O)[C@H](O[C@H]3OC(CNCCO[Si](C)(C)C(C)(C)C)=CC[C@H]3NC(=O)OC(C)(C)C)[C@@H](NC(=O)OC(C)(C)C)C[C@H]2NC(=O)[C@@H](O)CCNC(=O)OC(C)(C)C)OC[C@]1(C)O]

6'-(2-tert-Butyldimethylsililoxy-ethyl)-2',3,3"-tri-Boc-1-(N-Boc-4-amino-2(S)-hydroxy-butyryl)-sisomicin 2',3,3"-triBoc-1-(N-Boc-4-amino-2(S)-hydroxy-butyryl)-sisomicin (0.10 g, 0.105 mmol) was treated with tert-butyldimethylsilyloxy acetaldehyde following Procedure 1-Method A to yield the desired 6'-(2-tert-butyldimethylsilyloxy-ethyl)-2',3,3"-triBoc-1-(N-Boc-4-amino-2(S)-hydroxy-butyryl)-sisomicin (MS m/e [M+H]$^+$ calcd 1107.6, found 1107.4), which was carried through to the next step without further purification.

6'-(2-Hydroxy-ethyl)-1-(4-amino-2(S)-hydroxy-butyryl)-sisomicin

6'-(2-tert-butyldimethylsililoxy-ethyl)-2',3,3"-triBoc-1-(N-Boc-4-amino-2(S)-hydroxy-butyryl)-sisomicin (0.105 mmol) was submitted to Procedure 3-Method B for Boc removal to yield a crude, which was purified by RP HPLC Method 1-Column A to yield 6'-(2-hydroxy-ethyl)-1-(4-amino-2(S)-hydroxy-butyryl)-sisomicin: MS m/e [M+H]$^+$ calcd 593.3, found 593.2, [M+Na]$^+$ 615.3; CLND 97.5% purity.

Example 2

6'-(2-Hydroxy-ethyl)-1-(4-amino-2 (R)-hydroxy-butyryl)-sisomicin

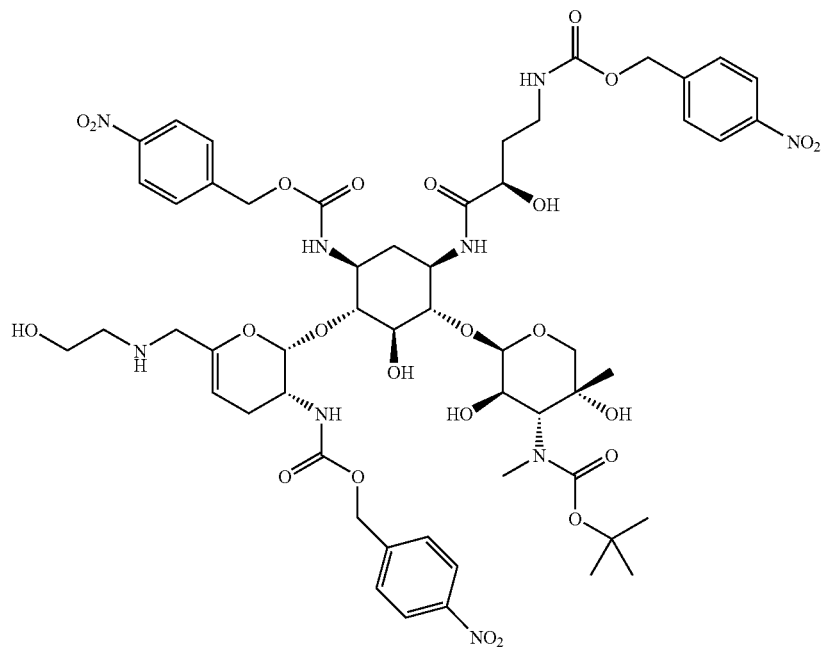 [SMILES: CN(C(=O)OC(C)(C)C)[C@@H]1[C@@H](O)[C@@H](O[C@@H]2[C@@H](O)[C@H](O[C@H]3OC(CNCCO)=CC[C@H]3NC(=O)OCc3ccc([N+](=O)[O-])cc3)[C@@H](NC(=O)OCc3ccc([N+](=O)[O-])cc3)C[C@H]2NC(=O)[C@H](O)CCNC(=O)OCc2ccc([N+](=O)[O-])cc2)OC[C@]1(C)O]

6'-(2-Hydroxy-ethyl)-2',3-diPNZ-1-(N-PNZ-4-amino-2(R)-hydroxy-butyryl)-3"-Boc-sisomicin To a stirring solution of 2',3-diPNZ-1-(N-PNZ-4-amino-2 (R)-hydroxy-butyryl)-3"-Boc-sisomicin (0.075 g, 0.063 mmol) in DMF (2 mL) was added glycolaldehyde dimer (0.015 g, 0.125 mmol) and the reaction mixture was stirred for 6 hours. A solution of NaCNBH$_3$ (0.070 g, 1.11 mmol) and AcOH (0.145 mL) in MeOH (6 mL) was then added and the reaction mixture for stirred for an additional 5 min. The reaction was diluted with EtOAc (10 mL), and was washed with H$_2$O (10 mL), dried over MgSO$_4$, filtered and concentrated to dryness to yield the desired 6'-(2-hydroxy-ethyl)-2', 3-diPNZ-1-(N-PNZ-4-amino-2(R)-hydroxy-butyryl)-3"-Boc-sisomicin (MS m/e [M+H]$^+$ calcd 1230.5, found 1230.3), which was carried through to the next step without further purification.

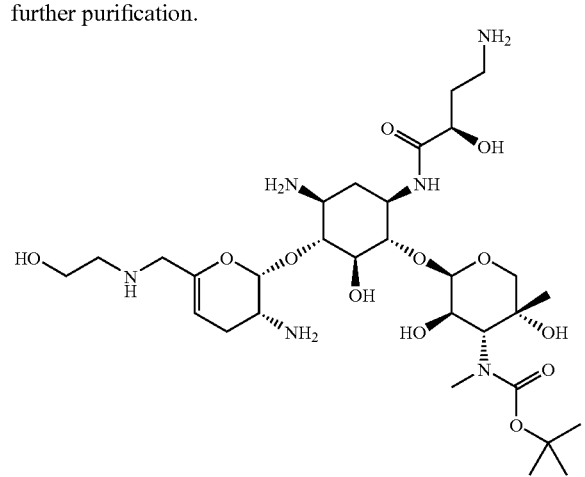

6'-(2-Hydroxy-ethyl)-1-(4-amino-2(R)-hydroxy-butyryl)-3"-Boc-sisomicin

6'-(2-Hydroxy-ethyl)-2',3-diPNZ-1-(N-PNZ-4-amino-2 (R)-hydroxy-butyryl)-3"-Boc-sisomicin (0.063 mmol) was submitted to Procedure 10 for PNZ removal to yield a crude, which was purified by Method 2-Column A to yield 6'-(2-hydroxy-ethyl)-1-(4-amino-2(R)-hydroxy-butyryl)-3"-Boc-sisomicin (0.016 g, 0.023 mmol, 36.5% yield).

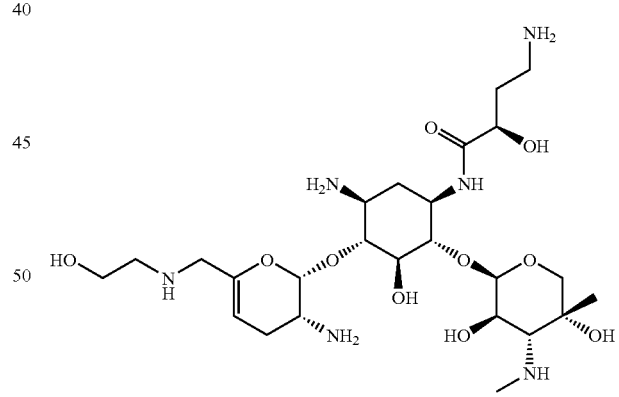

6'-(2-Hydroxy-ethyl)-1-(4-amino-2(R)-hydroxy-butyryl)-sisomicin

6'-(2-Hydroxy-ethyl)-1-(4-amino-2(R)-hydroxy-butyryl)-3"-Boc-sisomicin (0.016 g, 0.023 mmol) was treated with 90% aq. trifluoroacetic acid (0.5 mL) for 25 minutes. The reaction was quenched by the addition of H$_2$O (5 mL), and the aqueous layer was lyophilized to yield a crude, which was purified by Method 1-Column A to yield the desired 6'-(2-hydroxy-ethyl)-1-(4-amino-2(R)-hydroxy-butyryl)-sisomicin (MS m/e [M+H]$^+$ calcd 593.3, found 593.2, [M+Na]$^+$ 615.4; CLND: 98.2% purity).

Example 3

6'-(2-Hydroxy-propanol)-1-(4-amino-2(R)-hydroxy-butyryl)-sisomicin

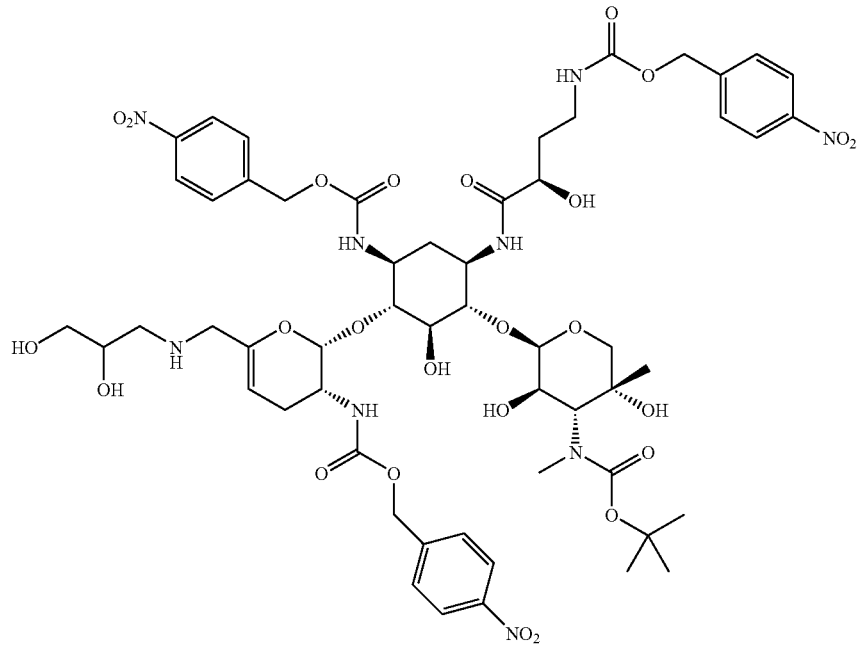 [SMILES: CN(C(=O)OC(C)(C)C)[C@@H]1[C@@H](O)[C@@H](O[C@@H]2[C@@H](O)[C@H](O[C@H]3OC(CNCC(O)CO)=CC[C@H]3NC(=O)OCc3ccc([N+](=O)[O-])cc3)[C@@H](NC(=O)OCc3ccc([N+](=O)[O-])cc3)C[C@H]2NC(=O)[C@H](O)CCNC(=O)OCc2ccc([N+](=O)[O-])cc2)OC[C@]1(C)O]

6'-(2-Hydroxy-propanol)-2',3-diPNZ-1-(N-PNZ-4-amino-2(R)-hydroxy-butyryl)-3"-Boc-sisomicin To a stirring solution of 2',3-diPNZ-1-(N-PNZ-4-amino-2 (R)-hydroxy-butyryl)-3"-Boc-sisomicin (0.075 g, 0.063 mmol) in DMF (2 mL) was added glyceraldehyde dimer (0.023 g, 0.126 mmol) and the reaction mixture was stirred for 6 hours. A solution of NaCNBH$_3$ (0.070 g, 1.11 mmol) and AcOH (0.145 mL) in MeOH (6 mL) was then added and the reaction mixture for stirred for an additional 5 min. The reaction was diluted with EtOAc (10 mL), and was washed with H$_2$O (10 mL), dried over MgSO$_4$, filtered and concentrated to dryness to yield the desired 6'-(2-hydroxy-propanol)-2',3-diPNZ-1-(N-PNZ-4-amino-2(R)-hydroxy-butyryl)-3"-Boc-sisomicin (MS m/e [M+H]$^+$ calcd 1260.5, found 1260.3), which was carried through to the next step without further purification.

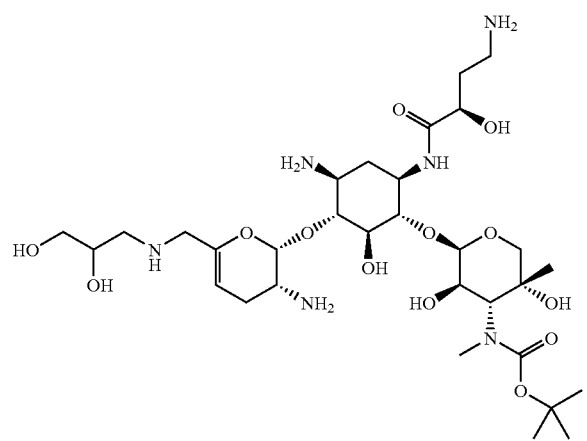 [SMILES: CN(C(=O)OC(C)(C)C)[C@@H]1[C@@H](O)[C@@H](O[C@@H]2[C@@H](O)[C@H](O[C@H]3OC(CNCC(O)CO)=CC[C@H]3N)[C@@H](N)C[C@H]2NC(=O)[C@H](O)CCN)OC[C@]1(C)O]

6'-(2-Hydroxy-propanol)-1-(4-amino-2(R)-hydroxy-butyryl)-3"-Boc-sisomicin

6'-(2-Hydroxy-propanol)-2',3-diPNZ-1-(N-PNZ-4-amino-2(R)-hydroxy-butyryl)-3"-Boc-sisomicin (0.063 mmol) was submitted to Procedure 10 for PNZ removal to yield a crude, which was purified by Method 2-Column A to yield 6'-(2-hydroxy-propanol)-1-(4-amino-2(R)-hydroxy-butyryl)-3"-Boc-sisomicin (0.016 g, 0.022 mmol, 34.9% yield): MS m/e [M+H]$^+$ calcd 723.4, found 723.3, [M+Na]$^+$ 745.4.

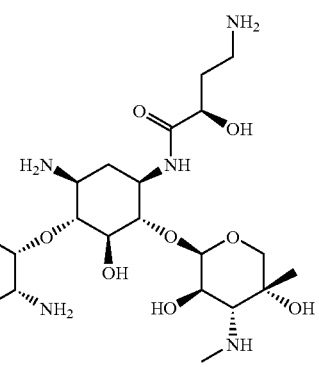

6'-(2-Hydroxy-propanol)-1-(4-amino-2(R)-hydroxy-butyryl)-sisomicin

6'-(2-Hydroxy-propanol)-1-(4-amino-2(R)-hydroxy-butyryl)-3"-Boc-sisomicin (0.016 g, 0.022 mmol) was treated with 90% aq. trifluoroacetic acid (0.5 mL) for 25 minutes. The reaction was quenched by the addition of H$_2$O (5 mL), and the aqueous layer was lyophilized to yield a crude, which was purified by Method 1-Column A to yield the desired 6'-(2-hydroxy-propanol)-1-(4-amino-2(R)-hydroxy-butyryl)-sisomicin (MS m/e [M+H]$^+$ calcd 623.3, found 623.3, [M+Na]$^+$ 645.4; CLND: 99.0% purity).

Example 4

6'-(Methyl-piperidin-4-yl)-1-(4-amino-2(R)-hydroxy-butyryl)-sisomicin

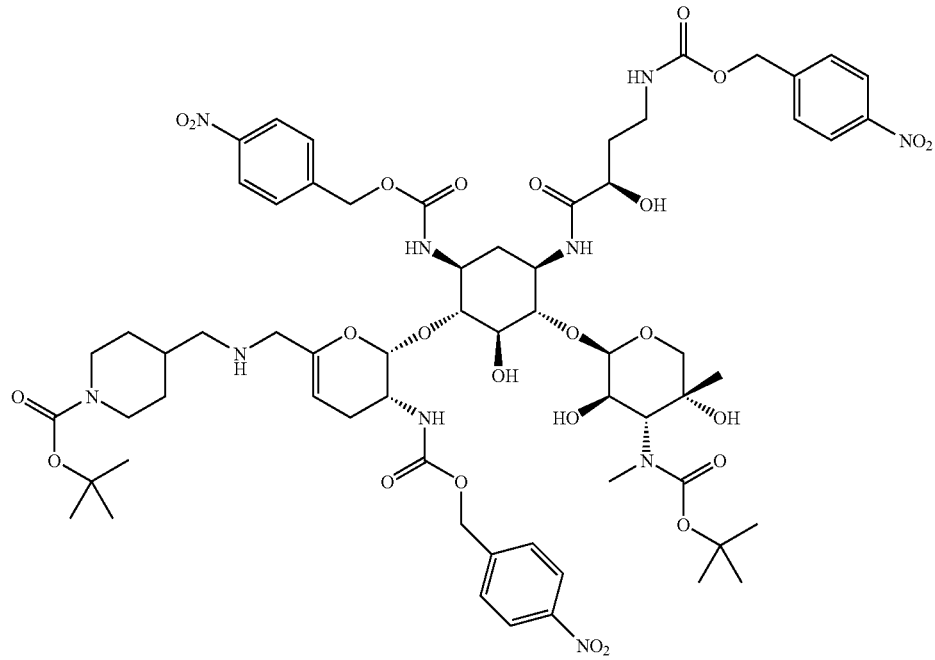

6'-(Methyl-N-Boc-piperidin-4-yl)-2',3-diPNZ-1-(N-PNZ-4-amino-2(R)-hydroxy-butyryl)-3"-Boc sisomicin To a stirring solution of 2',3-diPNZ-1-(N-PNZ-4-amino-2(R)-hydroxy-butyryl)-3"-Boc-sisomicin (0.100 g, 0.084 mmol) in DMF (2 mL) was added N-Boc-piperidine-4-carboxaldehyde (0.036 g, 0.168 mmol) and the reaction mixture was stirred for 6 hours. A solution of NaCNBH$_3$ (0.070 g, 1.11 mmol) and AcOH (0.145 mL) in MeOH (6 mL) was then added and the reaction mixture for stirred for an additional 5 min. The reaction was diluted with EtOAc (10 mL), and was washed with H$_2$O (10 mL), dried over MgSO$_4$, filtered and concentrated to dryness to yield a crude, which was purified by Method 2-Column A to yield the desired 6'-(methyl-N-Boc-piperidin-4-yl)-2',3-diPNZ-1-(N-PNZ-4-amino-2(R)-hydroxy-butyryl)-3"-Boc-sisomicin (0.037 g, 0.027 mmol, 32.1% yield): MS m/e [M+H]$^+$ calcd 1383.6, found 1383.4.

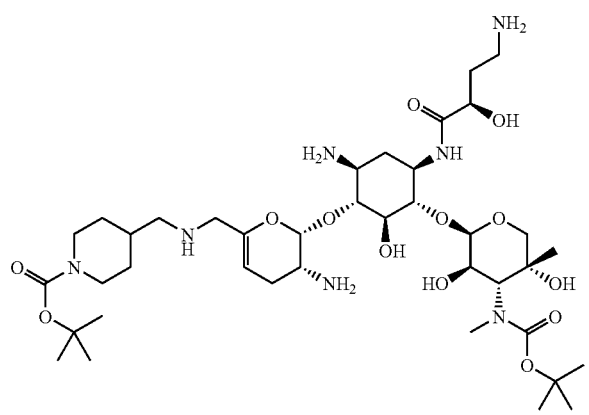 [SMILES: CN(C(=O)OC(C)(C)C)[C@@H]1[C@@H](O)[C@@H](O[C@@H]2[C@@H](O)[C@H](O[C@H]3OC(CNCC4CCN(C(=O)OC(C)(C)C)CC4)=CC[C@H]3N)[C@@H](N)C[C@H]2NC(=O)[C@H](O)CCN)OC[C@]1(C)O]

6'-(Methyl-N-Boc-piperidin-4-yl)-1-(4-amino-2(R)-hydroxy-butyryl)-3"-Boc-sisomicin 6'-(Methyl-N-Boc-piperidin-4-yl)-2',3-diPNZ-1-(N-PNZ-4-amino-2(R)-hydroxy-butyryl)-3"-Boc-sisomicin (0.037 g, 0.027 mmol) was submitted to Procedure 10 for PNZ removal to yield a crude, which was purified by Method 2-Column A to yield 6'-(methyl-N-Boc-piperidin-4-yl)-1-(4-amino-2(R)-hydroxy-butyryl)-3"-Boc-sisomicin (0.005 g, 0.006 mmol, 22.2% yield): MS m/e [M+H]$^+$ calcd 846.5, found 846.4, [M+Na]$^+$ 868.5.

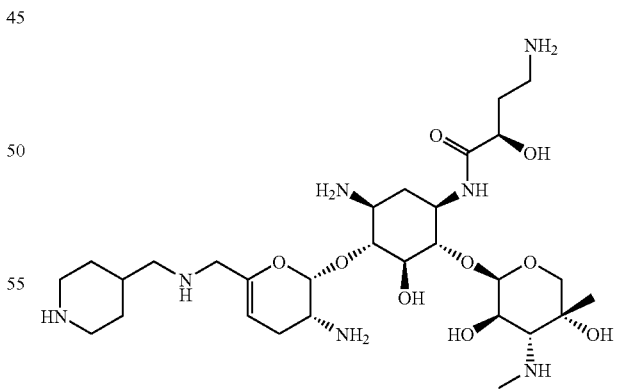

6'-(Methyl-piperidin-4-yl)-1-(4-amino-2(R)-hydroxy-butyryl)-sisomicin

6'-(Methyl-N-Boc-piperidin-4-yl)-1-(4-amino-2(R)-hydroxy-butyryl)-3"-Boc-sisomicin (0.015 g, 0.018 mmol) was treated with 90% aq. trifluoroacetic acid (0.5 mL) for 25 minutes. The reaction was quenched by the addition of H₂O (5 mL), and the aqueous layer was lyophilized to yield a crude, which was purified by Method 1-Column A to yield the desired 6'-(methyl-piperidin-4-yl)-1-(4-amino-2(R)-hydroxy-butyryl)-sisomicin (MS m/e [M+H]$^+$ calcd 646.4, found 646.3, [M+Na]$^+$ 668.4; CLND: 99.2% purity.

Example 5

6'-(Methyl-cyclopropyl)-1-(4-amino-2(R)-hydroxy-butyryl)-sisomicin

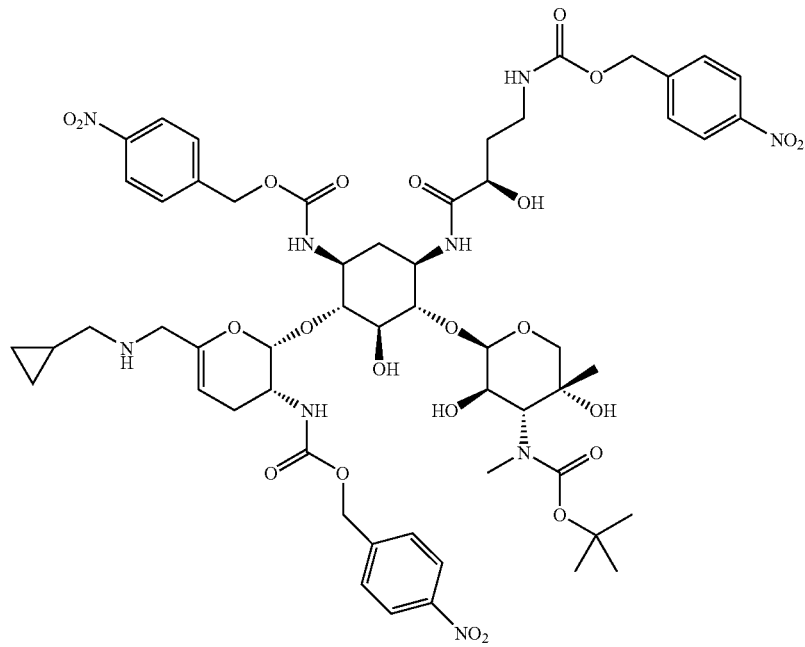 [SMILES: CN(C(=O)OC(C)(C)C)[C@@H]1[C@@H](O)[C@@H](O[C@@H]2[C@@H](O)[C@H](O[C@H]3OC(CNCC4CC4)=CC[C@H]3NC(=O)OCc3ccc([N+](=O)[O-])cc3)[C@@H](NC(=O)OCc3ccc([N+](=O)[O-])cc3)C[C@H]2NC(=O)[C@H](O)CCNC(=O)OCc2ccc([N+](=O)[O-])cc2)OC[C@]1(C)O]

6'-(Methyl-cyclopropyl)-2',3-diPNZ-1-(N-PNZ-4-amino-2(R)-hydroxy-butyryl)-3''-Boc-sisomicin To a stirring solution of 2',3-diPNZ-1-(N-PNZ-4-amino-2 (R)-hydroxy-butyryl)-3''-Boc-sisomicin (0.100 g, 0.084 mmol) in DMF (2 mL) was added cyclopropane carboxaldehyde (0.012 mL, 0.168 mmol) and the reaction mixture was stirred for 6 hours. A solution of NaCNBH₃ (0.070 g, 1.11 mmol) and AcOH (0.145 mL) in MeOH (6 mL) was then added and the reaction mixture for stirred for an additional 5 min. The reaction was diluted with EtOAc (10 mL), and was extracted with H₂O (10 mL), dried over MgSO₄, filtered and concentrated to dryness to yield the desired 6'-(methylcyclopropyl)-2',3-diPNZ-1-(N-PNZ-4-amino-2(R)-hydroxy-butyryl)-3''-Boc-sisomicin (MS m/e [M+H]$^+$ calcd 1240.5, found 1240.4), which was carried through to the next step without further purification.

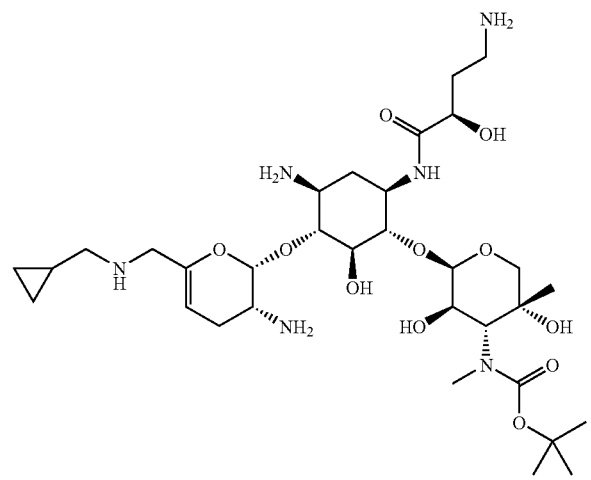 [SMILES: CN(C(=O)OC(C)(C)C)[C@@H]1[C@@H](O)[C@@H](O[C@@H]2[C@@H](O)[C@H](O[C@H]3OC(CNCC4CC4)=CC[C@H]3N)[C@@H](N)C[C@H]2NC(=O)[C@H](O)CCN)OC[C@]1(C)O]

6'-(Methyl-cyclopropyl)-1-(4-amino-2(R)-hydroxy-butyryl)-3"-Boc-sisomicin

6'-(Methyl-cyclopropyl)-2',3-diPNZ-1-(N-PNZ-4-amino-2(R)-hydroxy-butyryl)-3"-Boc-sisomicin (0.084 mmol) was submitted to Procedure 10 for PNZ removal to yield 6'-(methylcyclopropyl)-1-(4-amino-2(R)-hydroxy-butyryl)-3"-Boc-sisomicin (MS m/e [M+H]+ calcd 703.4, found 703.3, [M+Na]+ 725.4), which was carried through to the next step without further purification.

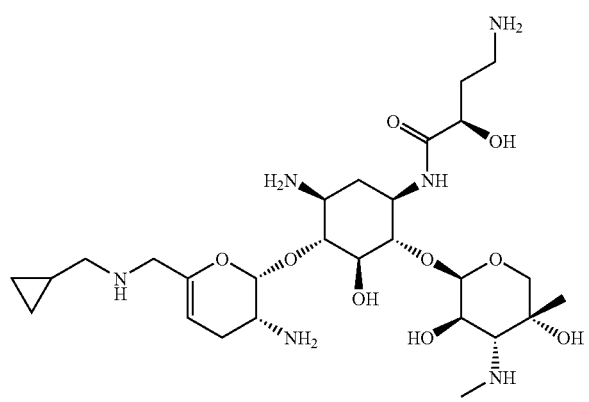 [SMILES: CN[C@@H]1[C@@H](O)[C@@H](O[C@@H]2[C@@H](O)[C@H](O[C@H]3OC(CNCC4CC4)=CC[C@H]3N)[C@@H](N)C[C@H]2NC(=O)[C@H](O)CCN)OC[C@]1(C)O]

6'-(Methyl-cyclopropyl)-1-(4-amino-2(R)-hydroxy-butyryl)-sisomicin

6'-(Methyl-cyclopropyl)-1-(4-amino-2(R)-hydroxy-butyryl)-3"-Boc-sisomicin (0.084 mmol) was treated with 90% aq. trifluoroacetic acid (0.5 mL) for 25 minutes. The reaction was quenched by the addition of H$_2$O (5 mL), and the aqueous layer was lyophilized to yield a crude, which was purified by Method 1-Column A to yield the desired 6'-(methyl-cyclopropyl)-1-(4-amino-2(R)-hydroxy-butyryl)-sisomicin (0.0014 g, 0.0023 mmol, 2.7% yield): MS m/e [M+H]+ calcd 603.4, found 603.2, [M+Na]+ 625.4; CLND: 98.3% purity

Example 6

6'-(3-Amino-propyl)-1-(4-amino-2(R)-hydroxy-butyryl)-sisomicin

N-Boc-3-amino-propanal

To a stirring solution of 3-(Boc-amino)-1-propanol (25 mL, 0.144 mol) in water saturated DCM (1.0 L) was added Dess-Martin reagent (99.2 g, 233.9 mmol) and the reaction mixture was stirred for 1 hour. The reaction was then diluted with ether (1.0 L), followed by a solution of Na$_2$S$_2$O$_3$ (250 g) in 80% NaHCO$_3$ (450 g in 1.0 L H$_2$O). The reaction was stirred vigorously for 30 minutes until two layers formed, the top layer was clear. The reaction was filtered to remove the precipitated solids and the aqueous layer was extracted with ether (1.0 L). The organic layer was washed with sat. NaHCO$_3$ (1.0 L), H$_2$O (1.0 L), and brine (1 L), dried over Na$_2$SO$_4$ and concentrated to a clear oil. The crude oil was dissolved in EtOAc: hexanes (1:1 v/v, 1.0 L) and filtered through a short silica gel column to yield the desired N-Boc-3-amino-propanal (21.7 g, 0.125 mol, 85.6% yield): $^1$H NMR (400 MHz, CDCl$_3$) δ 9.77 (s, 1 H, CHO), 4.85 (bs, 1 H, NH), 3.36-3.42 (m, 2 H, CH$_2$), 2.67 (t, 2 H, CH2), 1.39 (s, 9 H, (CH$_3$)$_3$).

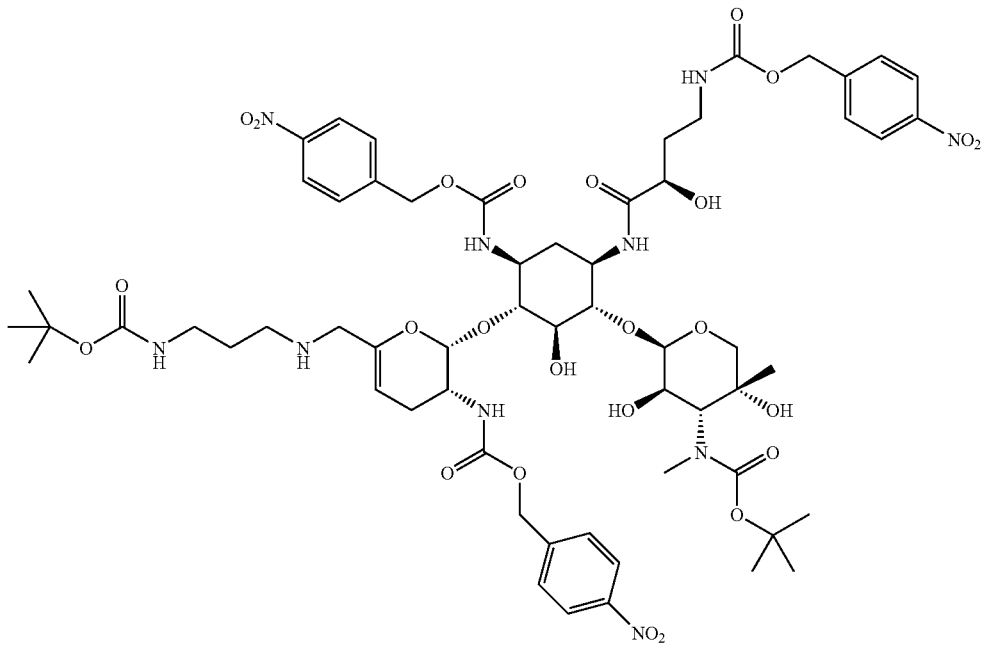 [SMILES: CN(C(=O)OC(C)(C)C)[C@@H]1[C@@H](O)[C@@H](O[C@@H]2[C@@H](O)[C@H](O[C@H]3OC(CNCCCNC(=O)OC(C)(C)C)=CC[C@H]3NC(=O)OCc3ccc([N+](=O)[O-])cc3)[C@@H](NC(=O)OCc3ccc([N+](=O)[O-])cc3)C[C@H]2NC(=O)[C@H](O)CCNC(=O)OCc2ccc([N+](=O)[O-])cc2)OC[C@]1(C)O]

6'-(N-Boc-3-amino-propyl)-2',3-diPNZ-1-(N-PNZ-4-amino-2(R)-hydroxy-butyryl)-3"-Boc-sisomicin To a stirring solution of 2',3-diPNZ-1-(N-PNZ-4-amino-2(R)-hydroxy-butyryl)-3"-Boc-sisomicin (0.150 g, 0.126 mmol) in DMF (2 mL) was added N-Boc-propionaldehyde (0.043 g, 0.252 mmol) and the reaction mixture was stirred for 6 hours. A solution of NaCNBH$_3$ (0.070 g, 1.11 mmol) and AcOH (0.145 mL) in MeOH (6 mL) was then added and the reaction mixture for stirred for an additional 5 min. The reaction was diluted with EtOAc (10 mL), and was washed with H$_2$O (10 mL), dried over MgSO$_4$, filtered and concentrated to dryness to yield the desired 6'-(N-Boc-3-amino-propyl)-2',3-diPNZ-1-(N-PNZ-4-amino-2(R)-hydroxy-butyryl)-3"-Boc-sisomicin (MS m/e [M+H]$^+$ calcd 1343.5, found 1343.4), which was carried through to the next step without further purification.

6'-(3-Amino-propyl)-1-(4-amino-2(R)-hydroxy-butyryl)-sisomicin

6'-(N-Boc-3-amino-propyl)-1-(4-amino-2(R)-hydroxy-butyryl)-3"-Boc-sisomicin (0.126 mmol) was treated with 90% aq. trifluoroacetic acid (0.5 mL) for 25 minutes. The reaction was quenched by the addition of H$_2$O (5 mL), and the aqueous layer was lyophilized to yield a crude, which was purified by Method 1-Column A to yield the desired 6'-(3-amino-propyl)-1-(4-amino-2(R)-hydroxy-butyryl)-sisomicin (MS m/e [M+H]$^+$ calcd 606.4, found 606.3; CLND: 99.4% purity).

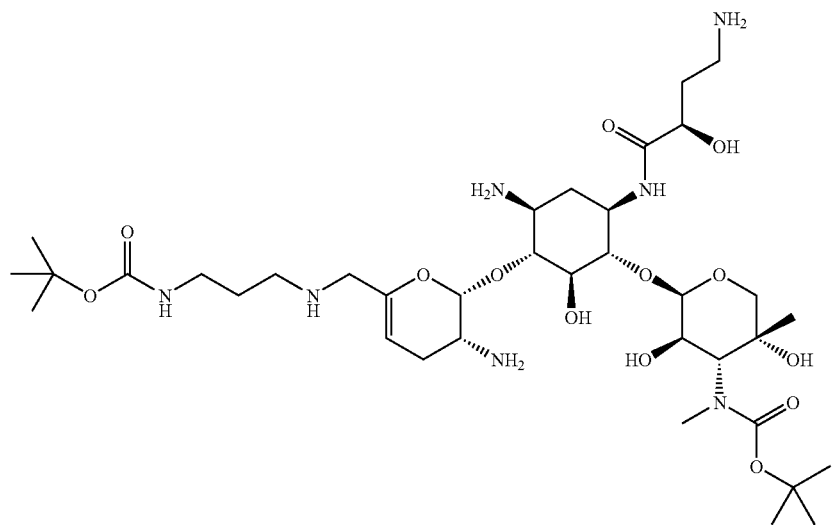 [SMILES: CN(C(=O)OC(C)(C)C)[C@@H]1[C@@H](O)[C@@H](O[C@@H]2[C@@H](O)[C@H](O[C@H]3OC(CNCCCNC(=O)OC(C)(C)C)=CC[C@H]3N)[C@@H](N)C[C@H]2NC(=O)[C@H](O)CCN)OC[C@]1(C)O]

6'-(N-Boc-3-amino-propyl)-1-(4-amino-2(R)-hydroxy-butyryl)-3"-Boc-sisomicin

6'-(N-Boc-3-amino-propyl)-2',3-diPNZ-1-(N-PNZ-4-amino-2(R)-hydroxy-butyryl)-3"-Boc-sisomicin (0.126 mmol) was submitted to Procedure 10 for PNZ removal to yield 6'-(N-Boc-3-amino-propyl)-1-(4-amino-2(R)-hydroxy-butyryl)-3"-Boc-sisomicin (MS m/e [M+H]$^+$ calcd 806.5, found 806.4, [M+Na]$^+$ 828.4), which was carried through to the next step without further purification.

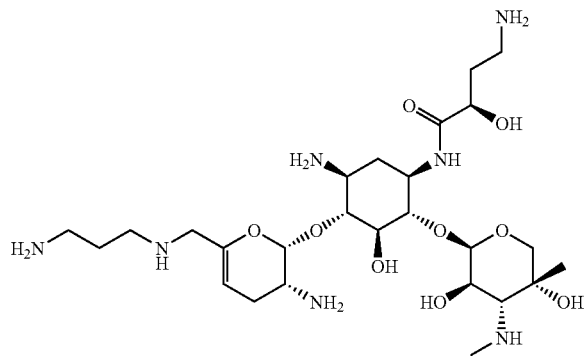 [SMILES: CN[C@@H]1[C@@H](O)[C@@H](O[C@@H]2[C@@H](O)[C@H](O[C@H]3OC(CNCCCN)=CC[C@H]3N)[C@@H](N)C[C@H]2NC(=O)[C@H](O)CCN)OC[C@]1(C)O]

Example 7

6'-Methyl-cyclopropyl-1-(3-amino-2(R)-hydroxy-propionyl)-sisomicin

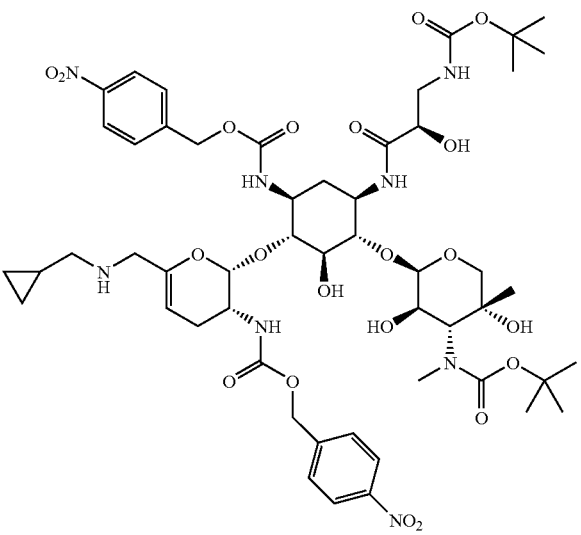 [SMILES: CN(C(=O)OC(C)(C)C)[C@@H]1[C@@H](O)[C@@H](O[C@@H]2[C@@H](O)[C@H](O[C@H]3OC(CNCC4CC4)=CC[C@H]3NC(=O)OCc3ccc([N+](=O)[O-])cc3)[C@@H](NC(=O)OCc3ccc([N+](=O)[O-])cc3)C[C@H]2NC(=O)[C@H](O)CNC(=O)OC(C)(C)C)OC[C@]1(C)O]

6'-Methyl-cyclopropyl-2',3-diPNZ-1-(N-Boc-3-amino-2(R)-hydroxy-propionyl)-3"-Boc sisomicin Treatment of 2',3-diPNZ-1-(N-Boc-3-amino-2(S)-hydroxy-propionyl)-3"-Boc-sisomicin (0.078 mmol) with cyclopropanecarboxaldehyde following Procedure 1-Method B gave the desired 6'-methylcyclopropyl-2',3-diPNZ-1-(N-Boc-3-amino-2(R)-hydroxy-propionyl)-3"-Boc sisomicin, which was carried through to the next step without further purification.

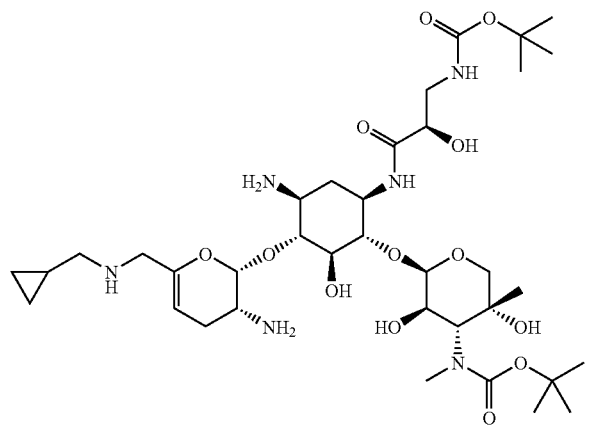 [SMILES: CN(C(=O)OC(C)(C)C)[C@@H]1[C@@H](O)[C@@H](O[C@@H]2[C@@H](O)[C@H](O[C@H]3OC(CNCC4CC4)=CC[C@H]3N)[C@@H](N)C[C@H]2NC(=O)[C@H](O)CNC(=O)OC(C)(C)C)OC[C@]1(C)O]

6'-Methyl-cyclopropyl-1-(N-Boc-3-amino-2(R)-hydroxy-propionyl)-3"-Boc sisomicin The crude 6'-methylcyclopropyl-2',3-diPNZ-1-(N-Boc-3-amino-2(R)-hydroxy-propionyl)-3"-Boc sisomicin (0.078 mmol) was submitted to Procedure 10 to yield 6'-methylcyclopropyl-1-(N-Boc-3-amino-2(S)-hydroxy-propionyl)-3"-Boc sisomicin, which was carried through to the next step without further purification.

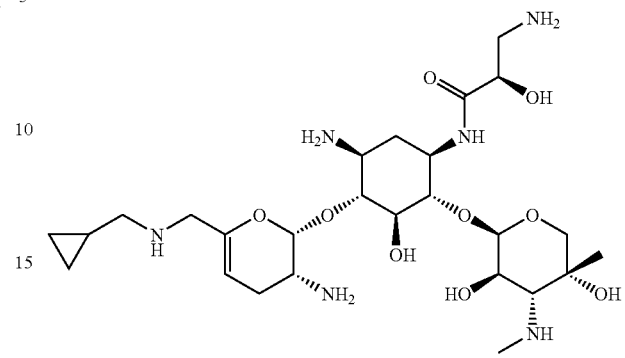

6'-Methyl-cyclopropyl-1-(3-amino-2(R)-hydroxy-propionyl)-sisomicin

6'-Methyl-cyclopropyl-1-(N-Boc-3-amino-2(R)-hydroxy-propionyl)-3"-Boc sisomicin (0.078 mmol) was submitted to Procedure 3-Method B to yield a crude, which was purified by RP HPLC Method 1-Column A to yield the desired 6'-methylcyclopropyl-1-(3-amino-2(R)-hydroxy-propionyl)-sisomicin: MS m/e [M+H]$^+$ calcd 589.3, found 589.3; CLND 99.5% purity.

Example 8

6'-Methyl-piperidinyl-1-(3-amino-2(R)-hydroxy-propionyl)-sisomicin

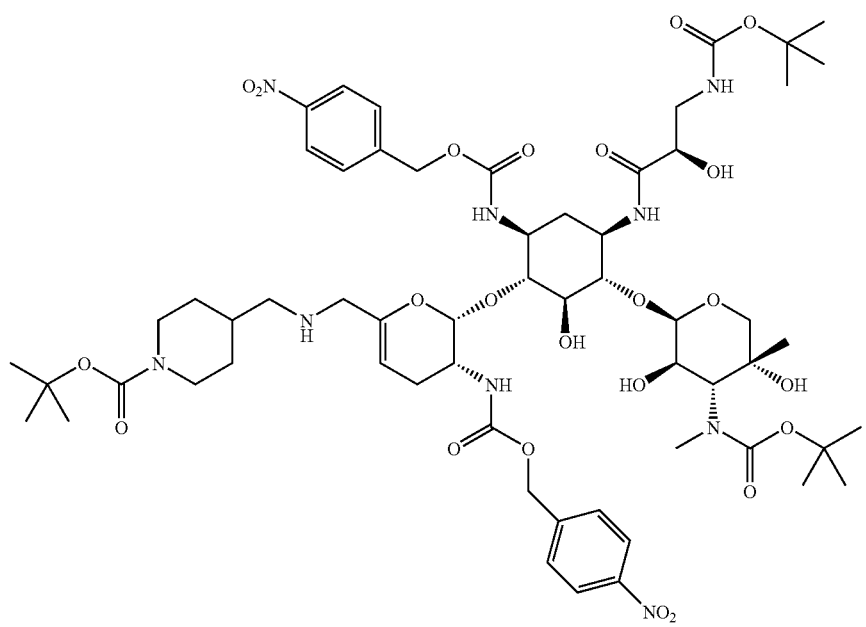 [SMILES: CN(C(=O)OC(C)(C)C)[C@@H]1[C@@H](O)[C@@H](O[C@@H]2[C@@H](O)[C@H](O[C@H]3OC(CNCC4CCN(C(=O)OC(C)(C)C)CC4)=CC[C@H]3NC(=O)OCc3ccc([N+](=O)[O-])cc3)[C@@H](NC(=O)OCc3ccc([N+](=O)[O-])cc3)C[C@H]2NC(=O)[C@H](O)CNC(=O)OC(C)(C)C)OC[C@]1(C)O]

6'-(Methyl-N-Boc-piperidinyl)-2',3-diPNZ-1-(N-Boc-3-amino-2(R)-hydroxy-propionyl)-3"-Boc sisomicin Treatment of 2',3-diPNZ-1-(N-Boc-3-amino-2(R)-hydroxy-propionyl)-3"-Boc-sisomicin (0.055 mmol) with N-Boc-piperidine-4-carboxaldehyde following Procedure 1-Method B gave the corresponding 6'-(methyl-N-Boc-piperidinyl)-2',3-diPNZ-1-(N-Boc-3-amino-2(R)-hydroxy-propionyl)-3"-Boc sisomicin, which was carried through to the next step without further purification.

6'-Methyl-piperidinyl-1-(3-amino-2(R)-hydroxy-propionyl)-sisomicin

6'-(Methyl-N-Boc-piperidinyl)-1-(N-Boc-3-amino-2(R)-hydroxy-propionyl)-3"-Boc sisomicin (0.055 mmol) was submitted to Procedure 3-Method B to yield a crude, which was purified by RP HPLC Method 1-Column A to yield the desired 6'-methylpiperidinyl-1-(3-amino-2(R)-hydroxy-propionyl)-sisomicin: MS m/e [M+H]$^+$ calcd 632.4, found 632.4; CLND 99.0% purity.

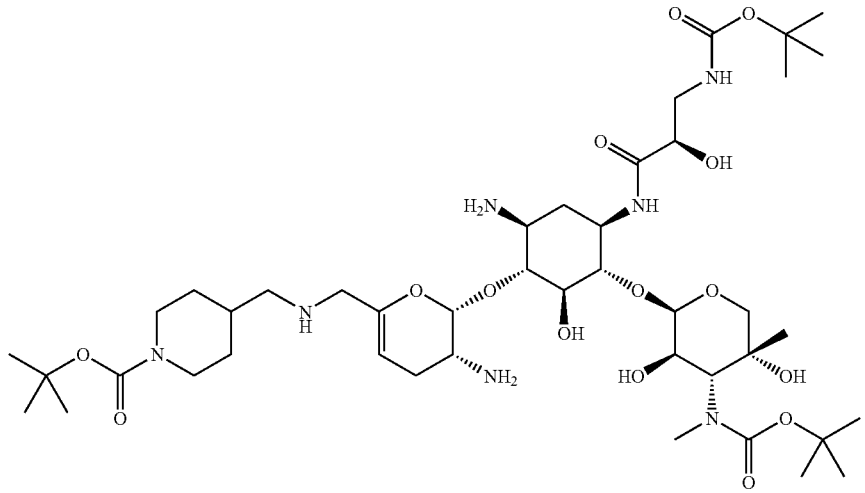 [SMILES: CN(C(=O)OC(C)(C)C)[C@@H]1[C@@H](O)[C@@H](O[C@@H]2[C@@H](O)[C@H](O[C@H]3OC(CNCC4CCN(C(=O)OC(C)(C)C)CC4)=CC[C@H]3N)[C@@H](N)C[C@H]2NC(=O)[C@H](O)CNC(=O)OC(C)(C)C)OC[C@]1(C)O]

6'-(Methyl-N-Boc-piperidinyl)-1-(N-Boc-3-amino-2(R)-hydroxy-propionyl)-3"-Boc sisomicin 6'-(Methyl-N-Boc-piperidinyl)-2',3-diPNZ-1-(N-Boc-3-amino-2(R)-hydroxy-propionyl)-3"-Boc sisomicin (0.055 mmol) was submitted to Procedure 10 for PNZ removal to yield 6'-(methyl-N-Boc-piperidinyl)-1-(N-Boc-3-amino-2(R)-hydroxy-propionyl)-3"-Boc sisomicin, which was carried through to the next step without further purification.

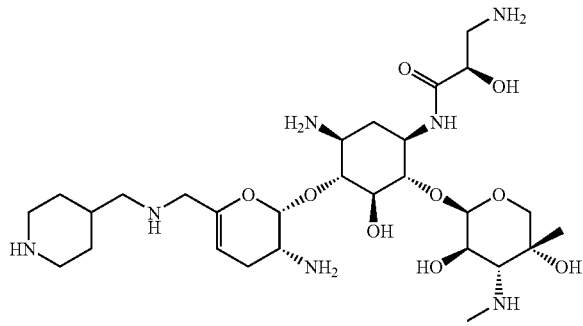 [SMILES: CN[C@@H]1[C@@H](O)[C@@H](O[C@@H]2[C@@H](O)[C@H](O[C@H]3OC(CNCC4CCNCC4)=CC[C@H]3N)[C@@H](N)C[C@H]2NC(=O)[C@H](O)CN)OC[C@]1(C)O]

Example 9

6'-(2-Hydroxy-ethyl)-1-(3-amino-2(R)-hydroxy-propionyl)-sisomicin

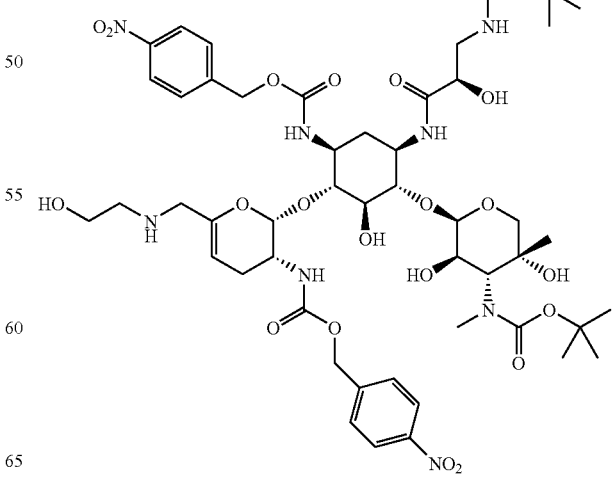

6'-(2-Hydroxy-ethyl)-2',3-diPNZ-1-(N-Boc-3-amino-2(R)-hydroxy-propionyl)-3"-Boc sisomicin Treatment of 2',3-diPNZ-1-(N-Boc-3-amino-2(S)-hydroxy-propionyl)-3"-Boc-sisomicin (0.055 mmol) with glycolaldehyde dimer and AcOH (0.005 ml) following Procedure 1-Method B gave the desired 6'-(2-hydroxy-ethyl)-2',3-diPNZ-1-(N-Boc-3-amino-2(R)-hydroxy-propionyl)-3"-Boc sisomicin, which was carried through to the next step without further purification.

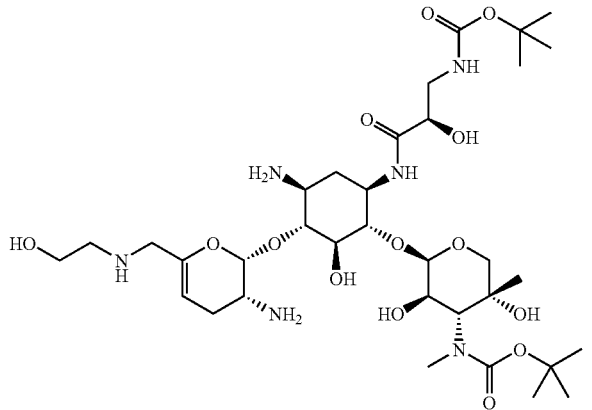 [SMILES: CN(C(=O)OC(C)(C)C)[C@@H]1[C@@H](O)[C@@H](O[C@@H]2[C@@H](O)[C@H](O[C@H]3OC(CNCCO)=CC[C@H]3N)[C@@H](N)C[C@H]2NC(=O)[C@H](O)CNC(=O)OC(C)(C)C)OC[C@]1(C)O]

6'-(2-Hydroxy-ethyl)-1-(N-Boc-3-amino-2(R)-hydroxy-propionyl)-3"-Boc sisomicin

6'-(2-Hydroxy-ethyl)-2',3-diPNZ-1-(N-Boc-3-amino-2(R)-hydroxy-propionyl)-3"-Boc sisomicin (0.055 mmol) was submitted to Procedure 10 for PNZ removal to yield 6'-(2-hydroxy-ethyl)-1-(N-Boc-3-amino-2(R)-hydroxy-propionyl)-3"-Boc sisomicin (MS m/e [M+H]$^+$ calcd 779.4, found 779.4), which was carried through to the next step without further purification.

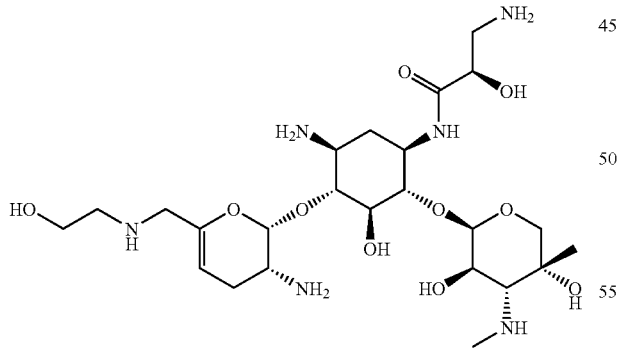

6'-(2-Hydroxy-ethyl)-1-(3-amino-2(R)-hydroxy-propionyl)-sisomicin

6'-(2-Hydroxy-ethyl)-1-(N-Boc-3-amino-2(R)-hydroxy-propionyl)-3"-Boc sisomicin (0.055 mmol) was submitted to Procedure 3-Method B to yield a crude, which was purified by RP HPLC Method 1-Column A to yield 6'-(2-hydroxy-ethyl)-1-(3-amino-2(R)-hydroxy-propionyl)-sisomicin: MS m/e [M+H]$^+$ calcd 579.3, found 579.3; CLND 99.0% purity.

Example 10

6'-(2-Hydroxy-propanol)-1-(3-amino-2(R)-hydroxy-propionyl)-sisomicin

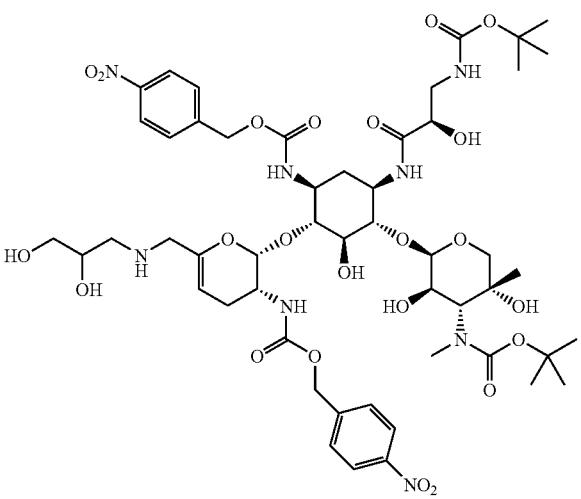 [SMILES: CN(C(=O)OC(C)(C)C)[C@@H]1[C@@H](O)[C@@H](O[C@@H]2[C@@H](O)[C@H](O[C@H]3OC(CNCC(O)CO)=CC[C@H]3NC(=O)OCc3ccc([N+](=O)[O-])cc3)[C@@H](NC(=O)OCc3ccc([N+](=O)[O-])cc3)C[C@H]2NC(=O)[C@H](O)CNC(=O)OC(C)(C)C)OC[C@]1(C)O]

6'-(2-Hydroxy-propanol)-2',3-diPNZ-1-(N-Boc-3-amino-2(R)-hydroxy-propionyl)-3"-Boc sisomicin Treatment of 2',3-diPNZ-1-(N-Boc-3-amino-2(R)-hydroxy-propionyl)-3"-Boc-sisomicin (0.078 mmol) with glyceraldehyde dimer and AcOH (0.005 ml) following Procedure 1-Method B gave the corresponding 6'-(2-hydroxy-propanol)-2',3-diPNZ-1-(N-Boc-3-amino-2(R)-hydroxy-propionyl)-3"-Boc sisomicin, which was carried through to the next step without further purification.

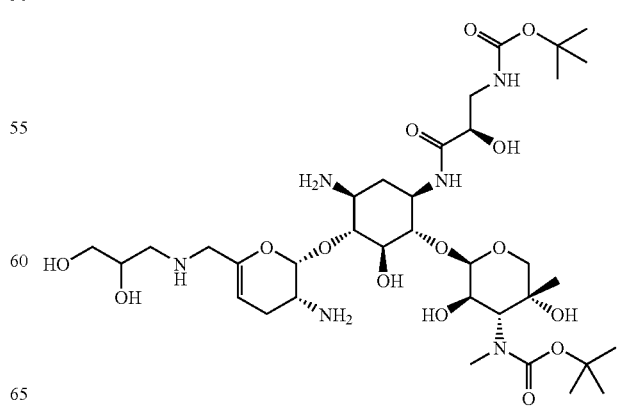

83

6'-(2-Hydroxy-propanol)-1-(3-amino-2(R)-hydroxy-propionyl)-3''-Boc sisomicin 6'-(2-Hydroxy-propanol)-2',3-diPNZ-1-(N-Boc-3-amino-2(R)-hydroxy-propionyl)-3''-Boc sisomicin (0.078 mmol) was submitted to Procedure 10 for PNZ removal to yield 6'-(2-hydroxy-propanol)-1-(N-Boc-3-amino-2(R)-hydroxy-propionyl)-3''-Boc sisomicin (MS m/e $[M+H]^+$ calcd 809.4, found 809.4), which was carried through to the next step without further purification.

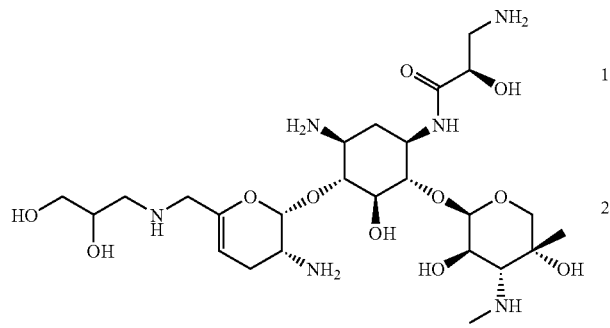

84

6'-(2-Hydroxy-propanol)-1-(3-amino-2(R)-hydroxy-propionyl)-sisomicin

6'-(2-Hydroxy-propanol)-1-(N-Boc-3-amino-2(R)-hydroxy-propionyl)-3''-Boc sisomicin (0.078 mmol) was submitted to Procedure 3-Method B to yield a crude, which was purified by RP HPLC Method 1-Column A to yield the desired 6'-(2-hydroxy-propanol)-1-(3-amino-2(R)-hydroxy-propionyl)-sisomicin: MS m/e $[M+H]^+$ calcd 609.3, found 609.2, $[M+Na]^+$ 631.2; CLND 98.2% purity.

Example 11

6'-(3-Amino-propyl)-1-(3-amino-2(R)-hydroxy-propionyl)-sisomicin

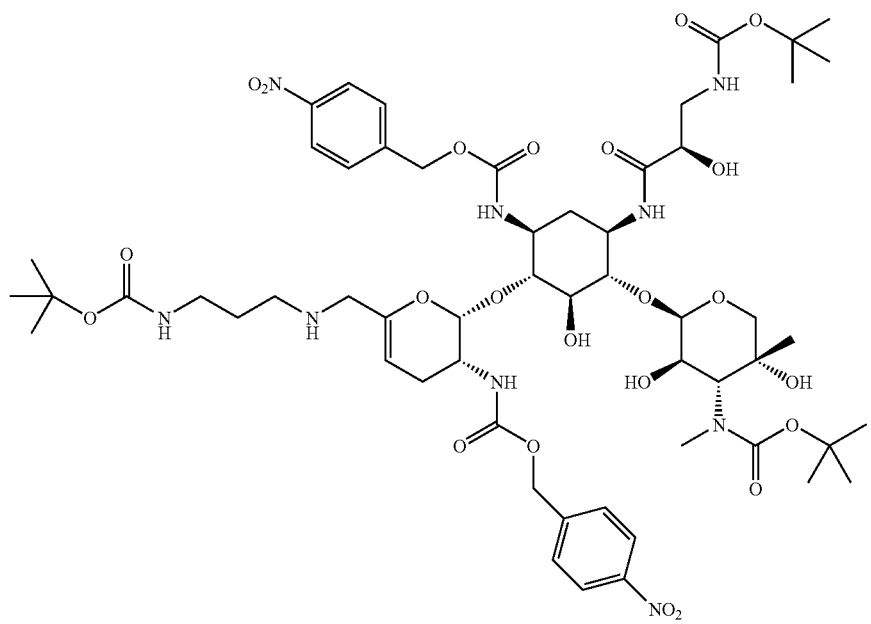

6'-(N-Boc-3-aminopropyl)-2',3-diPNZ-1-(N-Boc-3-amino-2(R)-hydroxy-propionyl)-3"-Boc sisomicin Treatment of 2',3-diPNZ-1-(N-Boc-3-amino-2(R)-hydroxy-propionyl)-3"-Boc-sisomicin (0.078 mmol) with N-Boc-3-amino-propionaldehyde following Procedure 1-Method B gave the corresponding 6'-(N-Boc-3-amino-propyl)-2',3-diPNZ-1-(N-Boc-3-amino-2(R)-hydroxy-propionyl)-3"-Boc sisomicin, which was carried through to the next step without further purification.

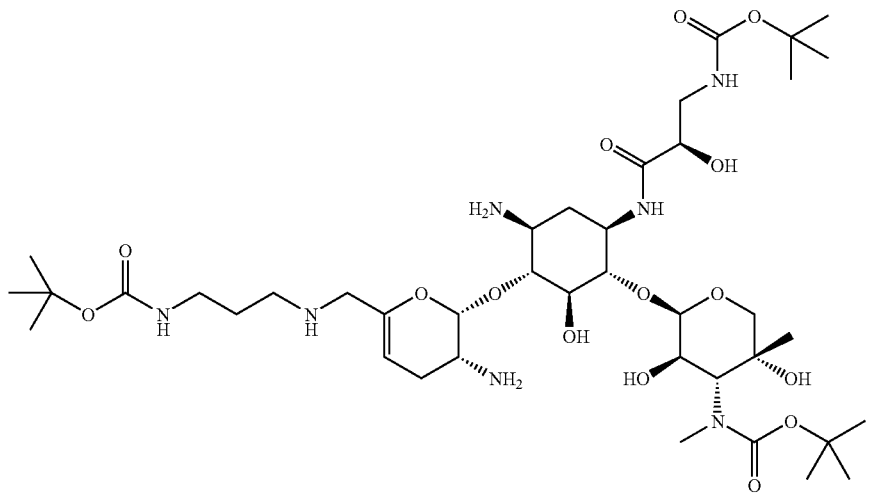 [SMILES: CN(C(=O)OC(C)(C)C)[C@@H]1[C@@H](O)[C@@H](O[C@@H]2[C@@H](O)[C@H](O[C@H]3OC(CNCCCNC(=O)OC(C)(C)C)=CC[C@H]3N)[C@@H](N)C[C@H]2NC(=O)[C@H](O)CNC(=O)OC(C)(C)C)OC[C@]1(C)O]

6'-(N-Boc-3-aminopropyl)-1-(N-Boc-3-amino-2(R)-hydroxy-propionyl)-3"-Boc sisomicin 6'-(N-Boc-3-aminopropyl)-2',3-diPNZ-1-(N-Boc-3-amino-2(R)-hydroxy-propionyl)-3"-Boc sisomicin (0.078 mmol) was submitted to Procedure 10 for PNZ removal to yield 6'-(N-Boc-3-aminopropyl)-1-(N-Boc-3-amino-2(R)-hydroxy-propionyl)-3"-Boc sisomicin (MS m/e [M+H]$^+$ calc 892.5, found 892.3), which was carried through to the next step without further purification.

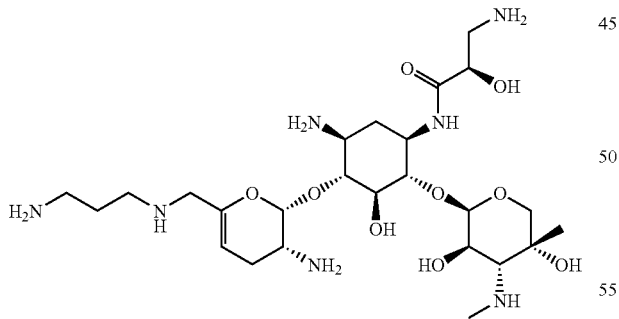

6'-(3-Amino-propyl)-1-(3-amino-2(R)-hydroxy-propionyl)-sisomicin

6'-(N-Boc-3-amino-propyl)-1-(N-Boc-3-amino-2(R)-hydroxy-propionyl)-3"-Boc sisomicin (0.078 mmol) was submitted to Procedure 3-Method B and purification by RP HPLC Method 1-Column A to yield the desired 6'-(3-amino-propyl)-1-(3-amino-2(R)-hydroxy-propionyl)-sisomicin: MS m/e [M+H]$^+$ calcd 593.4, found 593.3, [M+Na]$^+$ 614.3; CLND 92.8% purity.

Example 12

6'-(Methyl-piperidin-4-yl)-1-(4-amino-2(S)-hydroxy-butyryl)-sisomicin

6'-(Methyl-N-Boc-piperidin-4-yl)-1-(4-amino-2(S)-hydroxy-butyryl)-3"-Boc-sisomicin 6'-(Methyl-N-Boc-piperidin-4-yl)-2',3-diPNZ-1-(N-PNZ-4-amino-2(S)-hydroxy-butyryl)-3"-Boc-sisomicin  (0.17

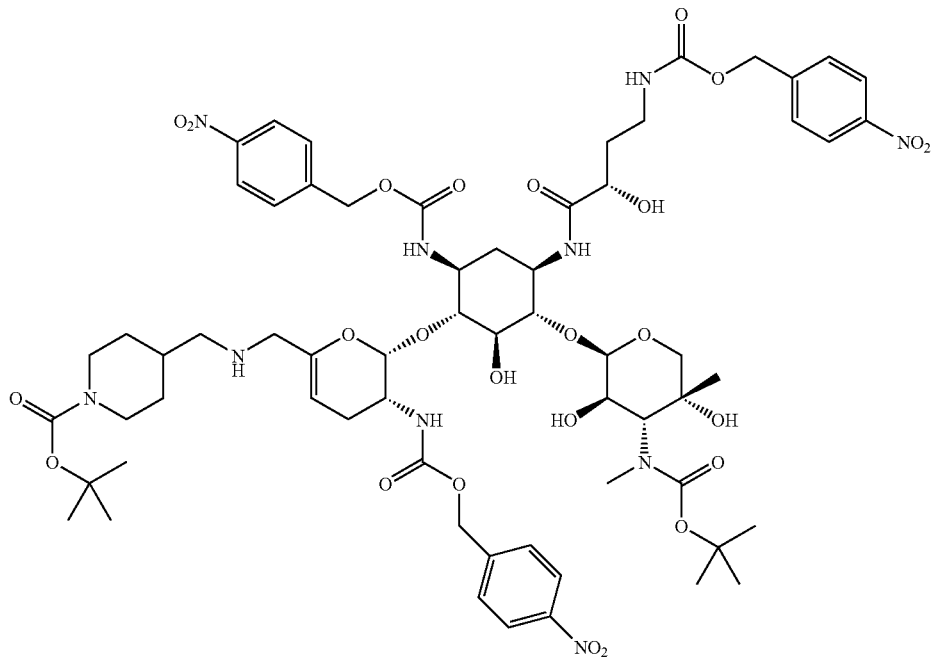 [SMILES: CN(C(=O)OC(C)(C)C)[C@@H]1[C@@H](O)[C@@H](O[C@@H]2[C@@H](O)[C@H](O[C@H]3OC(CNCC4CCN(C(=O)OC(C)(C)C)CC4)=CC[C@H]3NC(=O)OCc3ccc([N+](=O)[O-])cc3)[C@@H](NC(=O)OCc3ccc([N+](=O)[O-])cc3)C[C@H]2NC(=O)[C@@H](O)CCNC(=O)OCc2ccc([N+](=O)[O-])cc2)OC[C@]1(C)O]

6'-(Methyl-N-Boc-piperidin-4-yl)-2',3-diPNZ-1-(N-PNZ-4-amino-2(S)-hydroxy-butyryl)-3"-Boc sisomicin Treatment of 2',3-diPNZ-1-(N-Boc-4-amino-2(S)-hydroxy-butyryl)-3"-Boc-sisomicin (0.17 mmol) with N-Boc-piperidine-4-carboxaldehyde following Procedure 1-Method B gave the corresponding 6'-(methyl-N-Boc-piperidin-4-yl)-2',3-diPNZ-1-(N-PNZ-4-amino-2(S)-hydroxy-butyryl)-3"-Boc sisomicin, which was carried through to the next step without further purification.

mmol) was submitted to Procedure 10 for PNZ removal to yield 6'-(methyl-N-Boc-piperidin-4-yl)-1-(4-amino-2(S)-hydroxy-butyryl)-3"-Boc-sisomicin: MS m/e [M+H]$^+$ calcd 846.5, found 846.4.

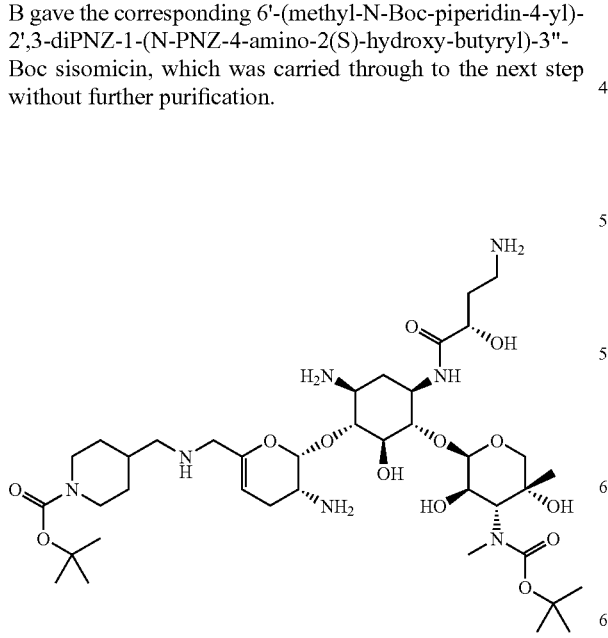

6'-(Methyl-piperidin-4-yl)-1-(4-amino-2(S)-hydroxy-butyryl)-sisomicin

6'-(Methyl-N-Boc-piperidin-4-yl)-1-(4-amino-2(S)-hydroxy-butyryl)-3"-Boc-sisomicin (0.17 mmol) was submitted to Procedure 3-Method B to yield a crude, which was purified by RP HPLC Method 1-Column A to yield the desired 6'-(methyl-piperidin-4-yl)-1-(4-amino-2(S)-hydroxy-butyryl)-sisomicin: MS m/e [M+H]⁺ calcd 646.4, found 646.3, [M+Na]⁺ 668.4; CLND 97.8% purity.

Example 13

6'-(Methyl-cyclopropyl)-1-(3-amino-2(S)-hydroxy-propionyl)-sisomicin

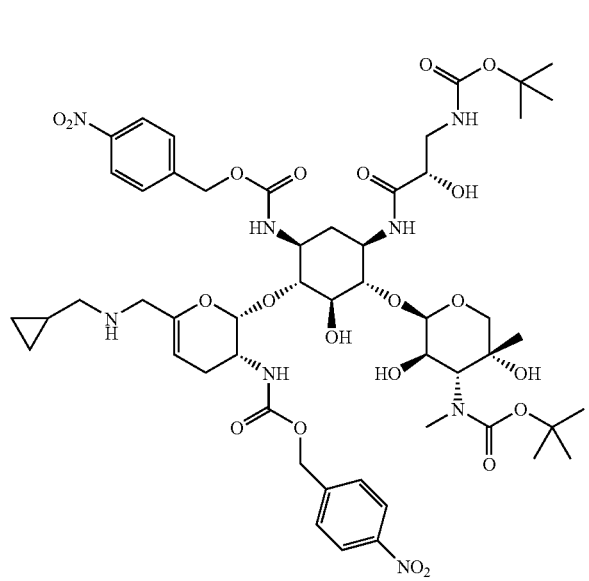 [SMILES: CN(C(=O)OC(C)(C)C)[C@@H]1[C@@H](O)[C@@H](O[C@@H]2[C@@H](O)[C@H](O[C@H]3OC(CNCC4CC4)=CC[C@H]3NC(=O)OCc3ccc([N+](=O)[O-])cc3)[C@@H](NC(=O)OCc3ccc([N+](=O)[O-])cc3)C[C@H]2NC(=O)[C@@H](O)CNC(=O)OC(C)(C)C)OC[C@]1(C)O]

6'-(Methyl-cyclopropyl)-2',3-diPNZ-1-(N-Boc-3-amino-2(S)-hydroxy-propionyl)-3''-Boc-sisomicin Treatment of 2',3-diPNZ-1-(N-Boc-3-amino-2(S)-hydroxy-propionyl)-3''-Boc-sisomicin (0.078 mmol) with cyclopropanecarboxaldehyde following Procedure 1-Method B gave the desired 6'-(methyl-cyclopropyl)-2',3-diPNZ-1-(N-Boc-3-amino-2(S)-hydroxy-propionyl)-3''-Boc-sisomicin (MS m/e [M+H]⁺ calcd 1147.5, found 1147.4), which was carried through to the next step without further purification.

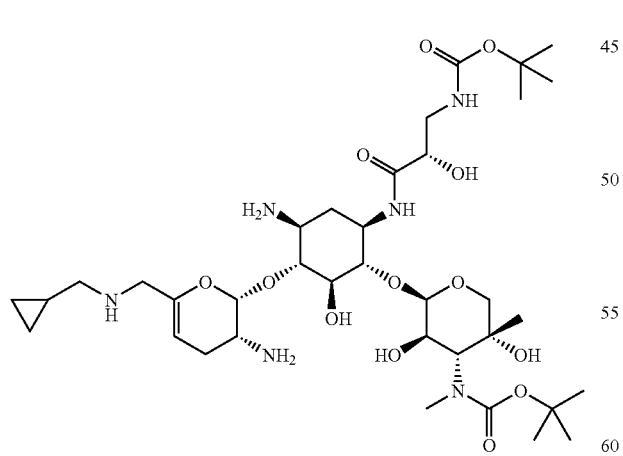

6'-(Methyl-cyclopropyl)-1-(N-Boc-3-amino-2(S)-hydroxy-propionyl)-3''-Boc-sisomicin 6'-(Methyl-cyclopropyl)-2',3-diPNZ-1-(N-Boc-3-amino-2(S)-hydroxy-propionyl)-3''-Boc-sisomicin (0.078 mmol) was submitted to Procedure 2 to yield 6'-(methyl-cyclopropyl)-1-(N-Boc-3-amino-2(S)-hydroxy-propionyl)-3''-Boc-sisomicin (MS m/e [M+H]⁺ calcd 789.4, found 789.4, [M+Na]⁺ 811.3), which was carried through to the next step without further purification.

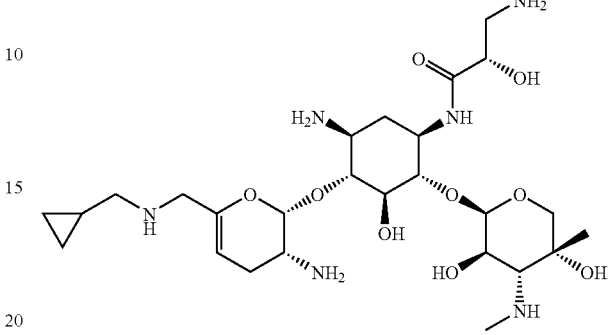

6'-(Methyl-cyclopropyl)-1-(3-amino-2(S)-hydroxy-propionyl)-sisomicin

6'-(Methyl-cyclopropyl)-1-(N-Boc-3-amino-2(S)-hydroxy-propionyl)-3''-Boc-sisomicin (0.078 mmol) was submitted to Procedure 3-Method B to yield a crude, which was purified by RP HPLC Method 1-Column A to yield the desired 6'-(methyl-cyclopropyl)-1-(3-amino-2(S)-hydroxy-propionyl)-sisomicin (0.0008 g, 0.0014 mmol, 1.8% yield): MS m/e [M+H]⁺ calcd 589.3, found 589.3, [M+Na]⁺ 611.4; CLND 98.9% purity.

Example 14

6'-(2-Hydroxy-propanol)-1-(3-amino-2(S)-hydroxy-propionyl)-sisomicin

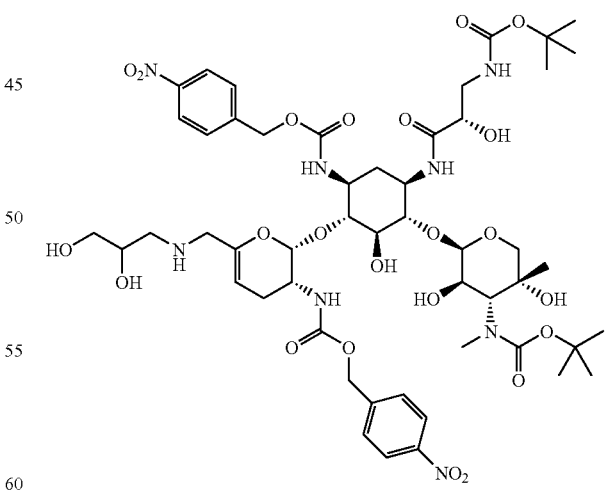

6'-(2-Hydroxy-propanol)-2',3-diPNZ-1-(N-Boc-3-amino-2(S)-hydroxy-propionyl)-3''-Boc-sisomicin Treatment of 2',3-diPNZ-1-(N-Boc-3-amino-2(S)-hydroxy-propionyl)-3''-Boc-sisomicin (0.078 mmol) with glyceraldehyde dimer and AcOH (0.005 ml) following Procedure 1-Method B gave the corresponding 6'-(2-hydroxy-propanol)-2',3-diPNZ-1-(N-Boc-3-amino-2(S)-hydroxy-propionyl)-3''-Boc-sisomicin (MS m/e [M+H]$^+$ calcd 1167.5, found 1167.3, [M+Na]$^+$ 1189.4), which was carried through to the next step without further purification.

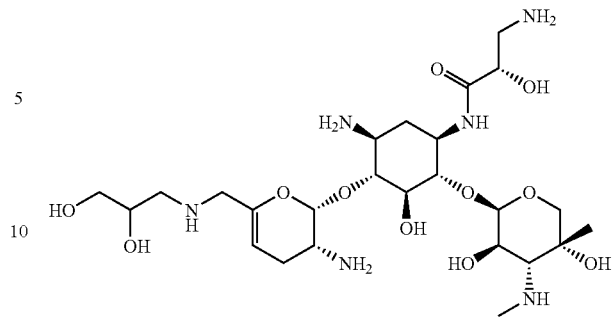

6'-(2-Hydroxy-propanol)-1-(3-amino-2(S)-hydroxy-propionyl)-sisomicin

6'-(2-Hydroxy-propanol)-1-(N-Boc-3-amino-2(S)-hydroxy-propionyl)-3''-Boc-sisomicin (0.078 mmol) was submitted to Procedure 3-Method B to yield a crude, which was purified by RP HPLC Method 1-Column A to yield the desired 6'-(2-hydroxy-propanol)-1-(3-amino-2(S)-hydroxy-propionyl)-sisomicin (0.00137 g, 0.0022 mmol, 2.8% yield): MS m/e [M+H]$^+$ calcd 609.3, found 609.3, [M+Na]$^+$ 631.4; CLND 97.9% purity.

Example 15

6'-(Methyl-piperidin-4-yl)-1-(3-amino-2(S)-hydroxy-propionyl)-sisomicin

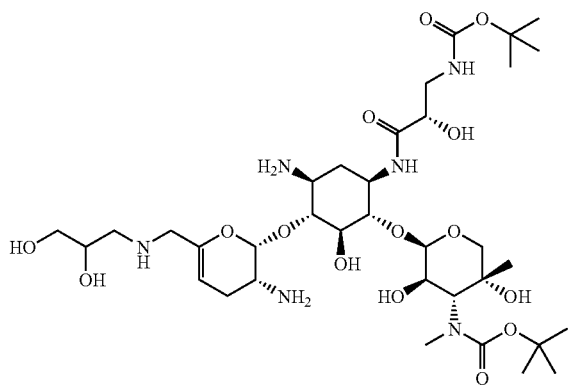 [SMILES: CN(C(=O)OC(C)(C)C)[C@@H]1[C@@H](O)[C@@H](O[C@@H]2[C@@H](O)[C@H](O[C@H]3OC(CNCC(O)CO)=CC[C@H]3N)[C@@H](N)C[C@H]2NC(=O)[C@@H](O)CNC(=O)OC(C)(C)C)OC[C@]1(C)O]

6'-(2-Hydroxy-propanol)-1-(3-amino-2(S)-hydroxy-propionyl)-3''-Boc-sisomicin

6'-(2-Hydroxy-propanol)-2',3-diPNZ-1-(N-Boc-3-amino-2(S)-hydroxy-propionyl)-3''-Boc-sisomicin (0.078 mmol) was submitted to Procedure 2 for PNZ removal to yield 6'-(2-hydroxy-propanol)-1-(N-Boc-3-amino-2(S)-hydroxy-propionyl)-3''-Boc-sisomicin (MS m/e [M+H]$^+$ calcd 809.4, found 809.3, [M+Na]$^+$ 831.3), which was carried through to the next step without further purification.

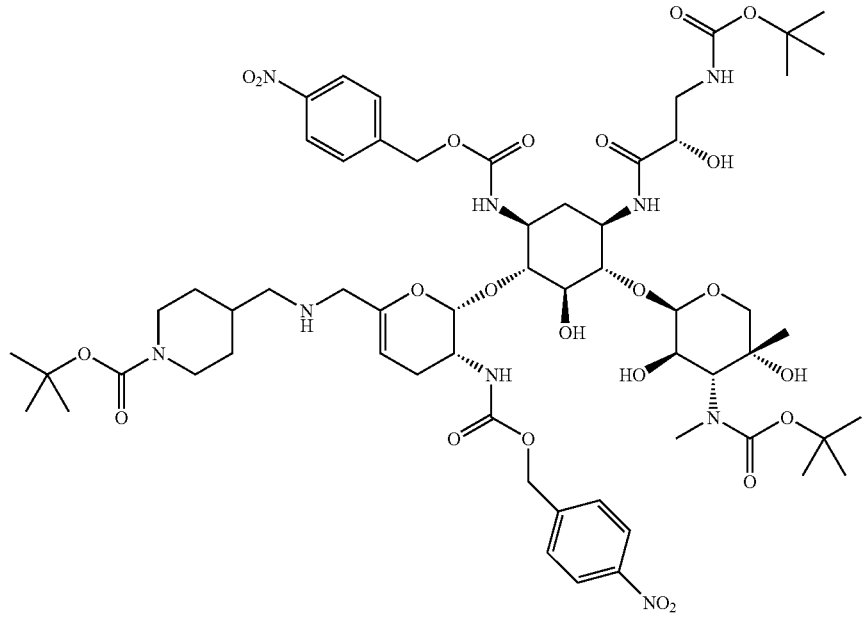 [SMILES: CN(C(=O)OC(C)(C)C)[C@@H]1[C@@H](O)[C@@H](O[C@@H]2[C@@H](O)[C@H](O[C@H]3OC(CNCC4CCN(C(=O)OC(C)(C)C)CC4)=CC[C@H]3NC(=O)OCc3ccc([N+](=O)[O-])cc3)[C@@H](NC(=O)OCc3ccc([N+](=O)[O-])cc3)C[C@H]2NC(=O)[C@@H](O)CNC(=O)OC(C)(C)C)OC[C@]1(C)O]

6'-(Methyl-N-Boc-piperidin-4-yl)-2',3-diPNZ-1-(N-Boc-3-amino-2(S)-hydroxy-propionyl)-3''-Boc-sisomicin Treatment of 2',3-diPNZ-1-(N-Boc-3-amino-2(S)-hydroxy-propionyl)-3''-Boc-sisomicin (0.082 mmol) with N-Boc-piperidine-4-carboxaldehyde following Procedure 1-Method B, followed by purification by RP HPLC Method 2-Column A gave the corresponding 6'-(methyl-N-Boc-piperidin-4-yl)-2',3-diPNZ-1-(N-Boc-3-amino-2(S)-hydroxypropionyl)-3"-Boc-sisomicin (0.021 g, 0.017 mmol, 20.7%): MS m/e [M+H]+ calcd 1290.6, found 1290.3, [M+Na]+ 1312.5).

droxy-propionyl)-sisomicin (0.003 g, 0.0047 mmol, 27.6% yield): MS m/e [M+H]+ calcd 632.4, found 632.3, [M+Na]+ 654.4; CLND 96.9% purity.

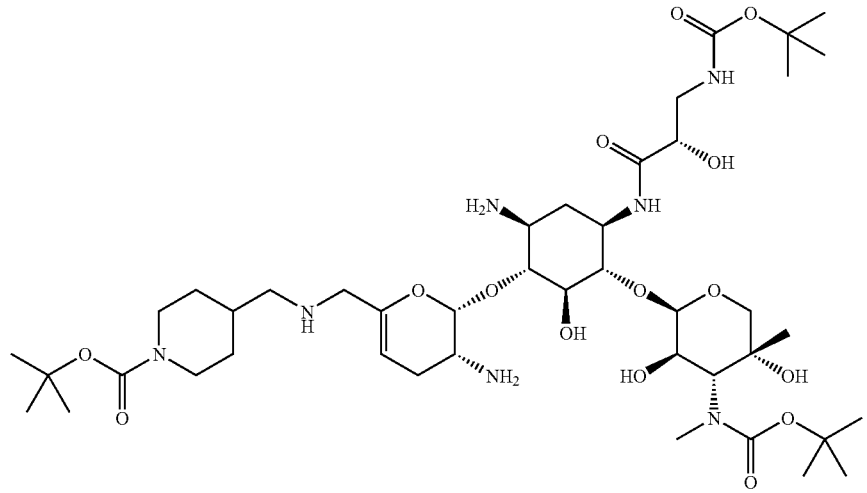 [SMILES: CN(C(=O)OC(C)(C)C)[C@@H]1[C@@H](O)[C@@H](O[C@@H]2[C@@H](O)[C@H](O[C@H]3OC(CNCC4CCN(C(=O)OC(C)(C)C)CC4)=CC[C@H]3N)[C@@H](N)C[C@H]2NC(=O)[C@@H](O)CNC(=O)OC(C)(C)C)OC[C@]1(C)O]

6'-(Methyl-N-Boc-piperidin-4-yl)-1-(N-Boc-3-amino-2(S)-hydroxy-propionyl)-3"-Boc-sisomicin 6'-(Methyl-N-Boc-piperidin-4-yl)-2',3-diPNZ-1-(N-Boc-3-amino-2(S)-hydroxy-propionyl)-3"-Boc-sisomicin (0.021 g, 0.017 mmol) was submitted to Procedure 2 for PNZ removal to yield 6'-(methyl-N-Boc-piperidin-4-yl)-1-(N-Boc-3-amino-2(S)-hydroxy-propionyl)-3"-Boc-sisomicin (MS m/e [M+H]+ calcd 932.5, found 932.4, [M+Na]+ 954.5), which was carried through to the next step without further purification.

Example 16

6'-(2-Hydroxy-ethyl)-1-(3-amino-2(S)-hydroxy-propionyl)-sisomicin

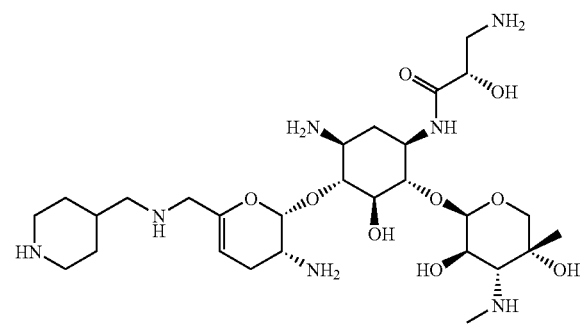 [SMILES: CN[C@@H]1[C@@H](O)[C@@H](O[C@@H]2[C@@H](O)[C@H](O[C@H]3OC(CNCC4CCNCC4)=CC[C@H]3N)[C@@H](N)C[C@H]2NC(=O)[C@@H](O)CN)OC[C@]1(C)O]

6'-(Methyl-piperidin-4-yl)-1-(3-amino-2(S)-hydroxy-propionyl)-sisomicin

6'-(Methyl-N-Boc-piperidin-4-yl)-1-(N-Boc-3-amino-2(S)-hydroxy-propionyl)-3"-Boc-sisomicin (0.017 mmol) was submitted to Procedure 3-Method B to yield a crude, which was purified by RP HPLC Method 1-Column A to yield the desired 6'-(methyl-piperidin-4-yl)-1-(3-amino-2(S)-hy-

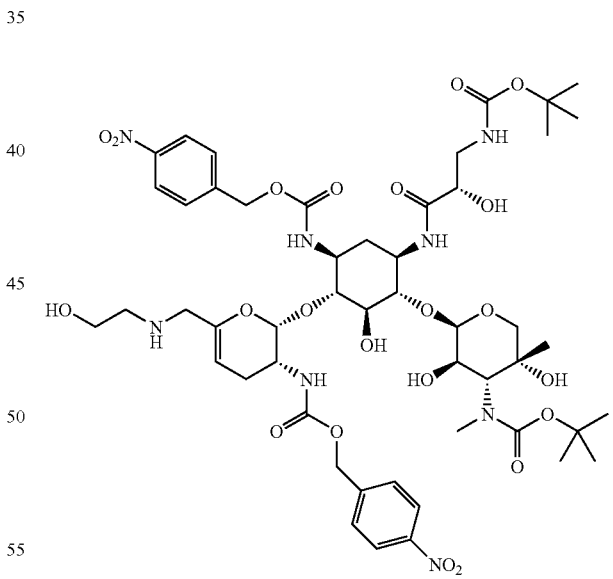

6'-(2-Hydroxy-ethyl)-2',3-diPNZ-1-(N-Boc-3-amino-2(S)-hydroxy-propionyl)-3"-Boc-sisomicin Treatment of 2',3-diPNZ-1-(N-Boc-3-amino-2(S)-hydroxy-propionyl)-3"-Boc-sisomicin (0.5 g, 0.41 mmol) with glycolaldehyde dimer and AcOH (0.005 ml) following Procedure 1-Method B gave 6'-(2-hydroxy-ethyl)-2',3-diPNZ-1-(N-Boc-3-amino-2(S)-hydroxy-propionyl)-3"-Boc-sisomicin (MS m/e [M+Na]+ calcd 1159.5, found 1159.4), which was carried through to the next step without further purification.

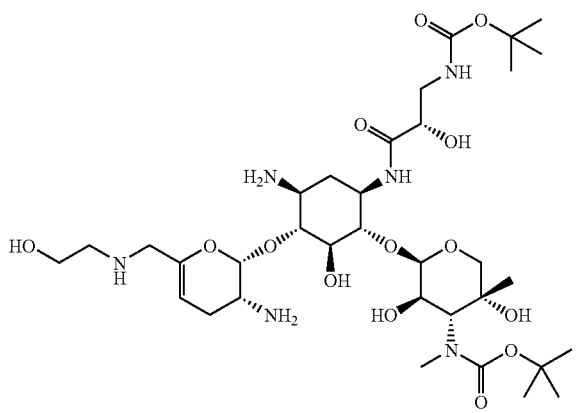 [SMILES: CN(C(=O)OC(C)(C)C)[C@@H]1[C@@H](O)[C@@H](O[C@@H]2[C@@H](O)[C@H](O[C@H]3OC(CNCCO)=CC[C@H]3N)[C@@H](N)C[C@H]2NC(=O)[C@@H](O)CNC(=O)OC(C)(C)C)OC[C@]1(C)O]

6'-(2-Hydroxy-ethyl)-1-(N-Boc-3-amino-2(S)-hydroxy-propionyl)-3''-Boc-sisomicin

The crude mixture of 6'-(2-hydroxy-ethyl)-2',3-diPNZ-1-(N-Boc-3-amino-2(S)-hydroxy-propionyl)-3''-Boc-sisomicin was submitted to Procedure 2 for PNZ removal to yield 6'-(2-hydroxy-ethyl)-1-(N-Boc-3-amino-2(S)-hydroxy-propionyl)-3''-Boc-sisomicin (MS m/e [M+H]+ calcd 779.4, found 779.3), which was carried through to the next step without further purification.

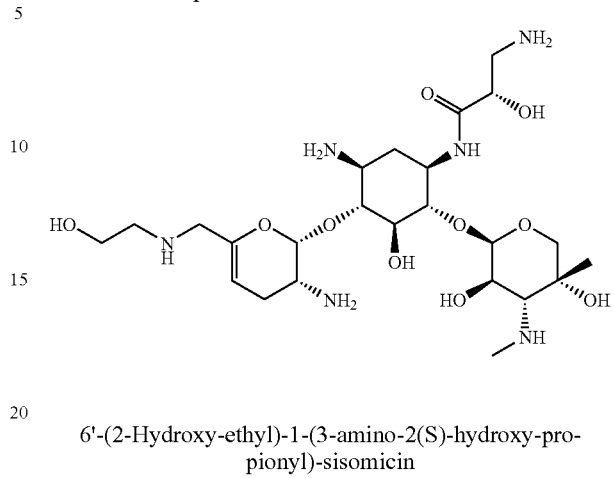

6'-(2-Hydroxy-ethyl)-1-(3-amino-2(S)-hydroxy-propionyl)-sisomicin

The crude mixture of 6'-(2-hydroxy-ethyl)-1-(N-Boc-3-amino-2(S)-hydroxy-propionyl)-3''-Boc-sisomicin was submitted to Procedure 3-Method B to yield a crude, which was purified by RP HPLC Method 1-Column A to yield: 6'-(2-hydroxy-ethyl)-1-(3-amino-2(S)-hydroxy-propionyl)-sisomicin (0.0142 g, 0.0245 mmol, 5.9% yield): MS m/e [M+H]+ calcd 579.3, found 579.2, [M+Na]+ 601.3; CLND 94.5% purity.

Example 17

6'-(3-Amino-propyl)-1-(3-amino-2(S)-hydroxy-propionyl)-sisomicin

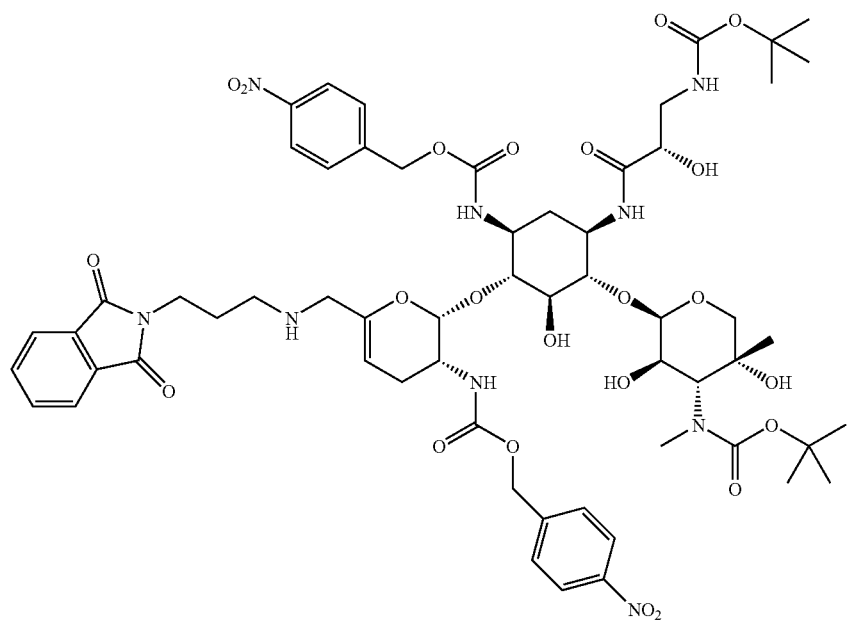 [SMILES: CN(C(=O)OC(C)(C)C)[C@@H]1[C@@H](O)[C@@H](O[C@@H]2[C@@H](O)[C@H](O[C@H]3OC(CNCCCN4C(=O)c5ccccc5C4=O)=CC[C@H]3NC(=O)OCc3ccc([N+](=O)[O-])cc3)[C@@H](NC(=O)OCc3ccc([N+](=O)[O-])cc3)C[C@H]2NC(=O)[C@@H](O)CNC(=O)OC(C)(C)C)OC[C@]1(C)O]

6'-(N-Phthalimido-3-amino-propyl)-2',3-diPNZ-1-(N-Boc-3-amino-2(S)-hydroxy-propionyl)-3"-Boc-sisomicin To a solution of 2',3-diPNZ-1-(N-Boc-3-amino-2(S)-hydroxy-propionyl)-3"-Boc-sisomicin (0.176 g, 0.15 mmol) in DMF (2 mL) was added 3-phthalimido-propionaldehyde (0.06 g, 0.29 mmol) and 3 Å Molecular Sieves (15-20), and the reaction was shaken for 2 hours. A solution of NaCNBH$_3$ (0.018 g, 0.29 mmol) in MeOH (4 mL) was then added and the reaction was stirred overnight. The reaction was diluted with EtOAc (5 mL) and the organic layer was washed with sat. aq. NaHCO$_3$ (3 mL), brine (3 mL), dried over Na$_2$SO$_4$, filtered and concentrated to yield 6'-(N-phthalimido-3-aminopropyl)-2',3-diPNZ-1-(N-Boc-3-amino-2(S)-hydroxy-propionyl)-3"-Boc-sisomicin (MS m/e [M+H]$^+$ calcd 1280.5, found 1280.3), which was carried through to the next step without further purification.

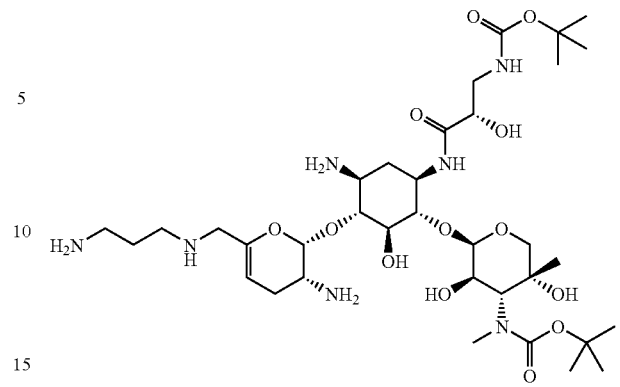

6'-(3-Amino-propyl)-1-(N-Boc-3-amino-2(S)-hydroxy-propionyl)-3"-Boc-sisomicin 6'-(3-Amino-propyl)-2',3-diPNZ-1-(N-Boc-3-amino-2(S)-hydroxy-propionyl)-3"-Boc-sisomicin (0.15 mmol) was submitted to Procedure 2 for PNZ removal to yield 6'-(3-amino-propyl)-1-(N-Boc-3-amino-2(S)-hydroxy-propionyl)-3"-Boc-sisomicin (MS m/e [M+H]$^+$ calcd 792.5, found 792.4), which was carried through to the next step without further purification.

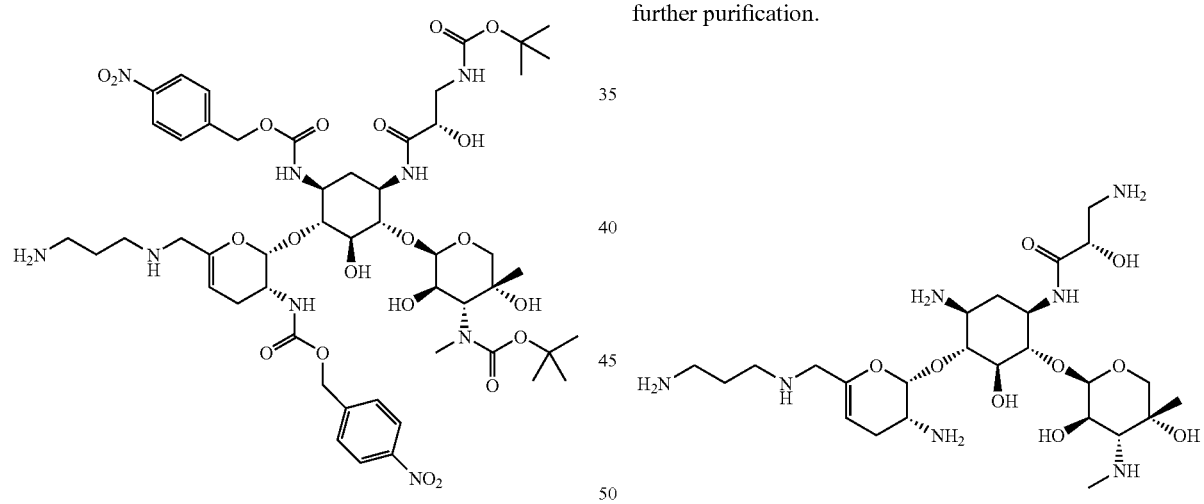

6'-(3-Amino-propyl)-2',3-diPNZ-1-(N-Boc-3-amino-2(S)-hydroxy-propionyl)-3"-Boc sisomicin 6'-(N-Phthalimido-3-amino-propyl)-2',3-diPNZ-1-(N-Boc-3-amino-2(S)-hydroxy-propionyl)-3"-Boc-sisomicin (0.15 mmol) was submitted to Procedure 6 for phthalimido removal to yield 6'-(3-amino-propyl)-2',3-diPNZ-1-(N-Boc-3-amino-2(S)-hydroxy-propionyl)-3"-Boc-sisomicin (MS m/e [M+H]$^+$ calcd 1150.5, found 1150.4), which was carried through to the next step without further purification.

6'-(3-Amino-propyl)-1-(3-amino-2(S)-hydroxy-propionyl)-sisomicin

6'-(3-Amino-propyl)-1-(N-Boc-3-amino-2(S)-hydroxy-propionyl)-3"-Boc-sisomicin (0.15 mmol) was submitted to Procedure 3-Method B to yield a crude, which was purified by RP HPLC Method 1-Column A to yield the desired 6'-(3-amino-propyl)-1-(3-amino-2(S)-hydroxy-propionyl)-sisomicin (0.0021 g, 0.0034 mmol, 2.3% yield): MS m/e [M+H]$^+$ calcd 592.4, found 592.2, [M+Na]$^+$ 614.3; CLND 91.6% purity.

Example 18

6'-(Methyl-cyclopropyl)-1-(4-amino-2(S)-hydroxy-butyryl)-sisomicin

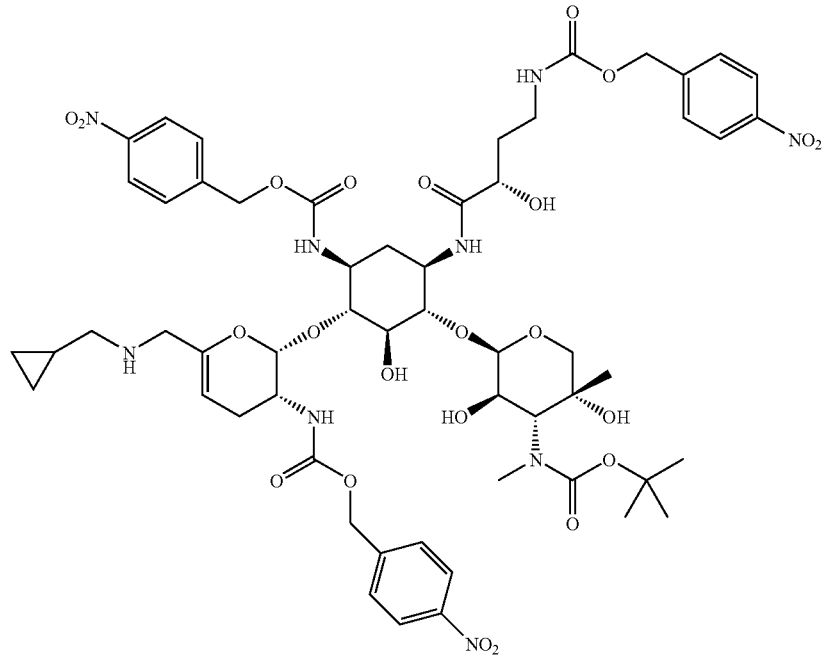 [SMILES: CN(C(=O)OC(C)(C)C)[C@@H]1[C@@H](O)[C@@H](O[C@@H]2[C@@H](O)[C@H](O[C@H]3OC(CNCC4CC4)=CC[C@H]3NC(=O)OCc3ccc([N+](=O)[O-])cc3)[C@@H](NC(=O)OCc3ccc([N+](=O)[O-])cc3)C[C@H]2NC(=O)[C@@H](O)CCNC(=O)OCc2ccc([N+](=O)[O-])cc2)OC[C@]1(C)O]

6'-(Methyl-cyclopropyl)-2',3-diPNZ-1-(N-PNZ-4-amino-2(S)-hydroxy-butyryl)-3"-Boc-sisomicin Treatment of 2',3-diPNZ-1-(N-PNZ-4-amino-2(S)-hydroxy-butyryl)-3"-Boc-sisomicin (0.084 mmol) with cyclopropanecarboxaldehyde following Procedure 1-Method B gave the desired 6'-(methyl-cyclopropyl)-2',3-diPNZ-1-(N-PNZ-4-amino-2(S)-hydroxy-butyryl)-3"-Boc-sisomicin (MS m/e [M+H]$^+$ calcd 1240.5, found 1240.4, [M+Na]$^+$ 1262.4), which was carried through to the next step without further purification.

6'-(Methyl-cyclopropyl)-1-(4-amino-2(S)-hydroxy-butyryl)-3"-Boc-sisomicin

6'-(Methyl-cyclopropyl)-2',3-diPNZ-1-(N-PNZ-4-amino-2(S)-hydroxy-butyryl)-3"-Boc-sisomicin (0.084 mmol) was submitted to Procedure 10 for PNZ removal to yield 6'-(methyl-cyclopropyl)-1-(4-amino-2(S)-hydroxy-butyryl)-3"-Boc-sisomicin (MS m/e [M+H]$^+$ calcd 703.4, found 703.3, [M+Na]$^+$ 725.4), which was carried through to the next step without further purification.

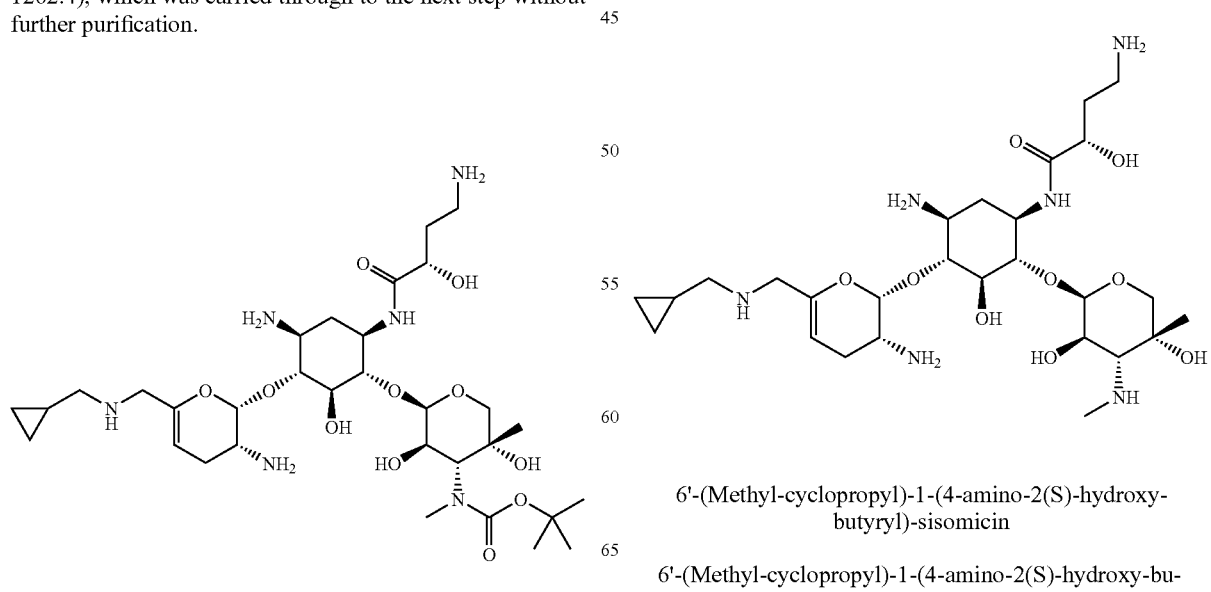

6'-(Methyl-cyclopropyl)-1-(4-amino-2(S)-hydroxy-butyryl)-sisomicin

6'-(Methyl-cyclopropyl)-1-(4-amino-2(S)-hydroxy-butyryl)-3"-Boc-sisomicin (0.084 mmol) was treated with 90% aq. trifluoroacetic acid (0.5 mL) for 25 minutes. The reaction was quenched by the addition of H$_2$O (5 mL), and the aqueous layer was lyophilized to yield a crude, which was purified by Method 1-Column A to yield the desired 6'-(methyl-cyclopropyl)-1-(4-amino-2(S)-hydroxy-butyryl)-sisomicin (MS m/e [M+H]$^+$ calcd 603.4, found 603.2, [M+Na]$^+$ 625.4; CLND 98.3% purity).

Example 19

6'-(2-Hydroxy-propanol)-2',3-diPNZ-1-(N-Boc-4-amino-2(S)-hydroxy-butyryl)-sisomicin

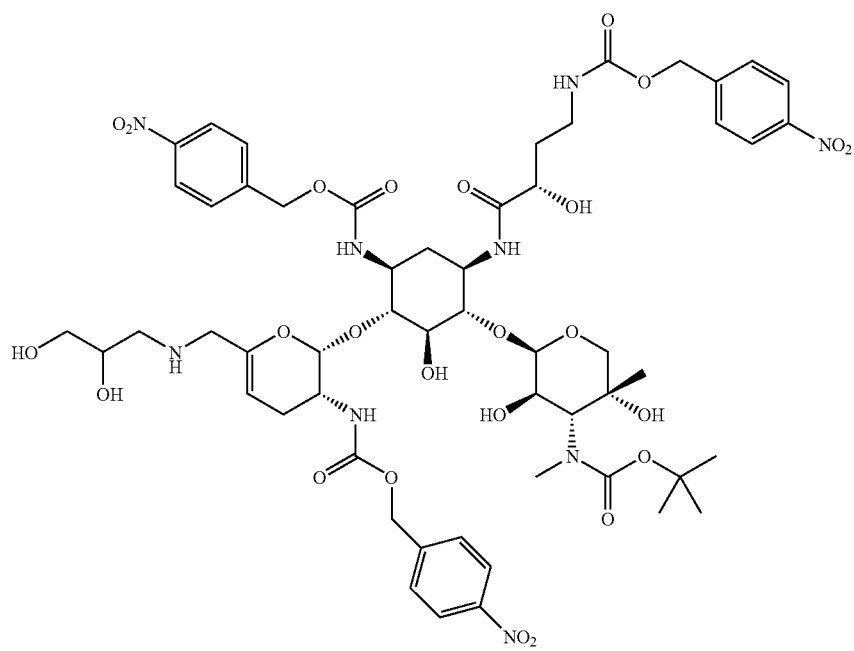 [SMILES: CN(C(=O)OC(C)(C)C)[C@@H]1[C@@H](O)[C@@H](O[C@@H]2[C@@H](O)[C@H](O[C@H]3OC(CNCC(O)CO)=CC[C@H]3NC(=O)OCc3ccc([N+](=O)[O-])cc3)[C@@H](NC(=O)OCc3ccc([N+](=O)[O-])cc3)C[C@H]2NC(=O)[C@@H](O)CCNC(=O)OCc2ccc([N+](=O)[O-])cc2)OC[C@]1(C)O]

6'-(2-Hydroxy-propanol)-2',3-diPNZ-1-(N-PNZ-4-amino-2(S)-hydroxy-butyryl)-3"-Boc-sisomicin To a stirring solution of 2',3-diPNZ-1-(N-PNZ-4-amino-2(R)-hydroxy-butyryl)-3"-Boc-sisomicin trifluoroacetic acid salt (0.110 g, 0.085 mmol) in DMF (1 mL) was added DIPEA (0.019 mL, 0.11 mmol), followed by glyceraldehyde dimer (0.032 g, 0.17 mmol) and the reaction mixture was stirred for 6 hours. A solution of NaCNBH$_3$ (0.070 g, 1.11 mmol) and AcOH (0.145 mL) in MeOH (6 mL) was then added and the reaction mixture for stirred for an additional 5 min. The reaction was diluted with EtOAc (10 mL), and was extracted with H$_2$O (10 mL), dried over MgSO$_4$, filtered and concentrated to dryness to yield the desired 6'-(2-hydroxy-propanol)-2',3-diPNZ-1-(N-PNZ-4-amino-2(S)-hydroxy-butyryl)-3"-Boc-sisomicin, which was carried through to the next step without further purification. MS m/e [M+H]$^+$ calcd 1260.5, found 1260.3.

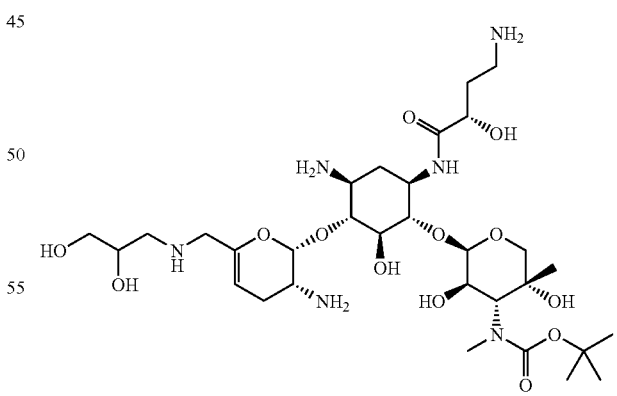

6'-(2-Hydroxy-propanol)-1-(4-amino-2(S)-hydroxy-butyryl)-3"-Boc-sisomicin

6'-(2-Hydroxy-propanol)-2',3-diPNZ-1-(N-PNZ-4-amino-2(S)-hydroxy-butyryl)-3"-Boc-sisomicin (0.085 mmol) was submitted to Procedure 10 for PNZ removal to yield a crude, which was purified by Method 2-Column A to yield 6'-(2-hydroxy-propanol)-1-(4-amino-2(S)-hydroxy-butyryl)-3''-Boc-sisomicin (0.009 g, 0.011 mmol, 13.4% yield). MS m/e [M+H]$^+$ calcd 723.4, found 723.3.

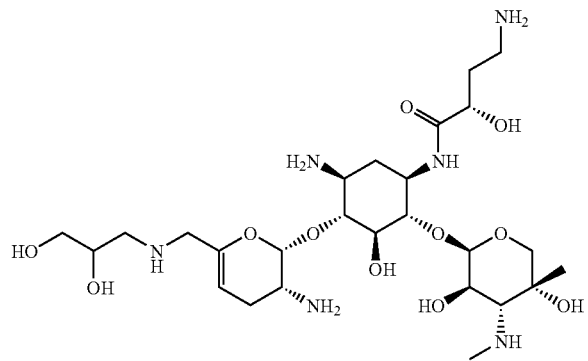 [SMILES: CN[C@@H]1[C@@H](O)[C@@H](O[C@@H]2[C@@H](O)[C@H](O[C@H]3OC(CNCC(O)CO)=CC[C@H]3N)[C@@H](N)C[C@H]2NC(=O)[C@@H](O)CCN)OC[C@]1(C)O]

6'-(2-Hydroxy-propanol)-1-(4-amino-2(S)-hydroxy-butyryl)-sisomicin

6'-(2-Hydroxy-propanol)-1-(4-amino-2(S)-hydroxy-butyryl)-3''-Boc-sisomicin (0.009 g, 0.011 mmol) was treated with 90% aq. trifluoroacetic acid (0.5 mL) for 25 minutes. The reaction was quenched by the addition of H$_2$O (5 mL), and the aqueous layer was lyophilized to yield a crude, which was purified by Method 1-Column A to yield the desired 6'-(2-hydroxy-propanol)-1-(4-amino-2(R)-hydroxy-butyryl)-sisomicin (MS m/e [M+H]$^+$ calcd 623.3, found 623.3, [M+Na]$^+$ 645.4; CLND 96.6% purity.

Example 20

6'-(3-Amino-2-hydroxy-propionyl)-1-(3-amino-2(S)-hydroxy-propionyl)-sisomicin

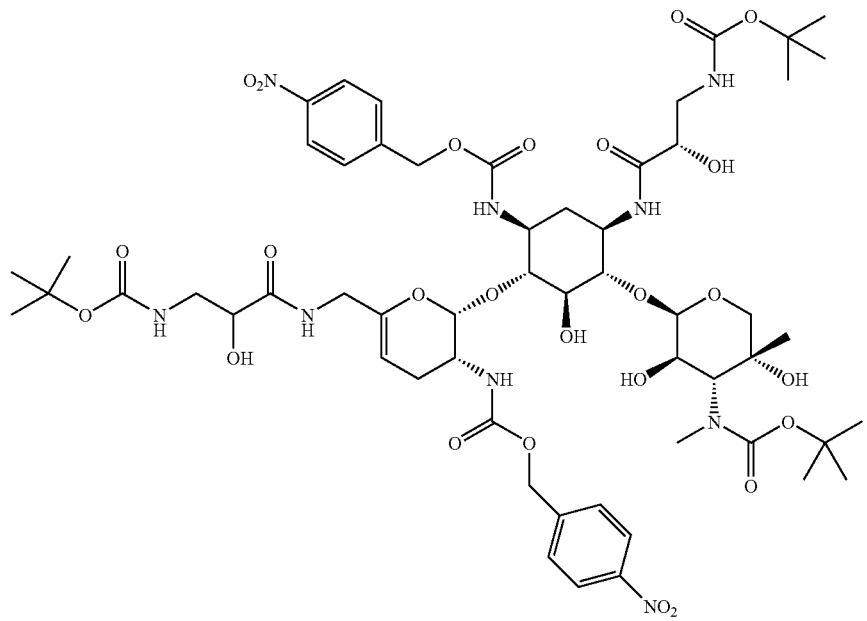 [SMILES: CN(C(=O)OC(C)(C)C)[C@@H]1[C@@H](O)[C@@H](O[C@@H]2[C@@H](O)[C@H](O[C@H]3OC(CNC(=O)C(O)CNC(=O)OC(C)(C)C)=CC[C@H]3NC(=O)OCc3ccc([N+](=O)[O-])cc3)[C@@H](NC(=O)OCc3ccc([N+](=O)[O-])cc3)C[C@H]2NC(=O)[C@@H](O)CNC(=O)OC(C)(C)C)OC[C@]1(C)O]

105

6'-(N-Boc-3-amino-2-hydroxy-propionyl)-2',3-diPNZ-1-(N-Boc-3-amino-2(S)-hydroxy-propionyl)-3''-Boc sisomicin Treatment of 2',3-diPNZ-1-(N-Boc-3-amino-2(S)-hydroxy-propionyl)-3''-Boc-sisomicin (0.078 mmol) with N-Boc-3-amino-2-hydroxy-propionic acid following Procedure 4-Method A gave the corresponding 6'-(N-Boc-3-amino-2-hydroxy-propionyl)-2',3-diPNZ-1-(N-Boc-3-amino-2(S)-hydroxy-propionyl)-3''-Boc sisomicin (MS m/e [M+Na]$^+$ calcd 1302.5, found 1302.4), which was carried through to the next step without further purification.

106

6'-(3-Amino-2-hydroxy-propionyl)-1-(3-amino-2(S)-hydroxy-propionyl)-sisomicin 6'-(N-Boc-3-amino-2-hydroxy-propionyl)-1-(N-Boc-3-amino-2(S)-hydroxy-propionyl)-3''-Boc sisomicin (0.078 mmol) was submitted to Procedure 3-Method B to yield a crude, which was purified by RP HPLC Method 1-Column A to yield the desired 6'-(3-amino-2-hydroxy-propionyl)-1-(3-amino-2(S)-hydroxy-propionyl)-sisomicin (0.0076 g, 0.012

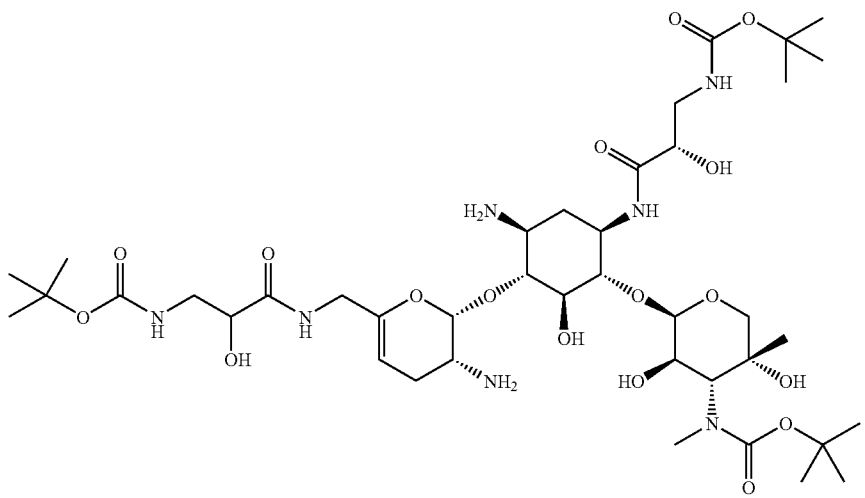 [SMILES: CN(C(=O)OC(C)(C)C)[C@@H]1[C@@H](O)[C@@H](O[C@@H]2[C@@H](O)[C@H](O[C@H]3OC(CNC(=O)C(O)CNC(=O)OC(C)(C)C)=CC[C@H]3N)[C@@H](N)C[C@H]2NC(=O)[C@@H](O)CNC(=O)OC(C)(C)C)OC[C@]1(C)O]

6'-(N-Boc-3-amino-2-hydroxy-propionyl)-1-(N-Boc-3-amino-2(S)-hydroxy-propionyl)-3''-Boc sisomicin mmol, 15.4% yield): MS m/e [M+H]$^+$ calcd 622.3, found 622.3, [M+Na]$^+$ 644.4; CLND 99.5% purity.

6'-(N-Boc-3-amino-2-hydroxy-propionyl)-2',3-diPNZ-1-(N-Boc-3-amino-2(S)-hydroxy-propionyl)-3''-Boc sisomicin (0.078 mmol) was submitted to Procedure 2 for PNZ removal to yield 6'-(N-Boc-3-amino-2-hydroxy-propionyl)-1-(N-Boc-3-amino-2(S)-hydroxy-propionyl)-3''-Boc sisomicin (MS m/e [M+H]$^+$ calcd 922.5, found 922.3, [M+Na]$^+$ 944.4), which was carried through to the next step without further purification.

Example 21

6'-(2-Hydroxy-3-propionamide)-1-(3-amino-2(S)-hydroxy-propionyl)-sisomicin

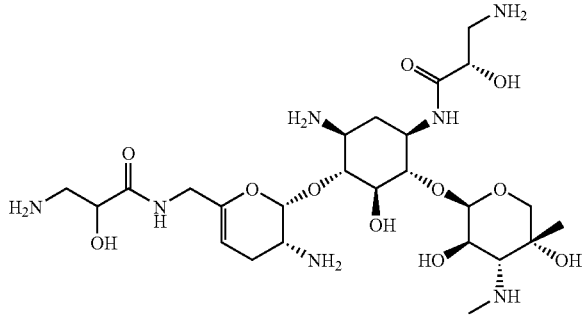 [SMILES: CN[C@@H]1[C@@H](O)[C@@H](O[C@@H]2[C@@H](O)[C@H](O[C@H]3OC(CNC(=O)C(O)CN)=CC[C@H]3N)[C@@H](N)C[C@H]2NC(=O)[C@@H](O)CN)OC[C@]1(C)O]

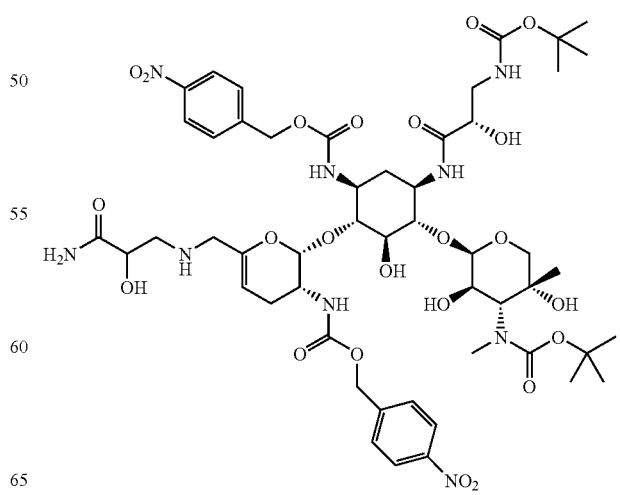

6'-(2-Hydroxy-3-propionamide)-2',3-diPNZ-1-(N-Boc-3-amino-2(S)-hydroxy-propionyl)-3"-Boc-sisomicin Treatment of 2',3-diPNZ-1-(N-Boc-3-amino-2(S)-hydroxy-propionyl)-3"-Boc-sisomicin (0.15 mmol) with glycidamide following Procedure 5 gave 6'-(2-hydroxy-3-propionamide)-2',3-diPNZ-1-(N-Boc-3-amino-2(S)-hydroxy-propionyl)-3"-Boc-sisomicin (MS m/e [M+H]$^+$ calcd 1180.5, found 1180.8), which was carried through to the next step without further purification.

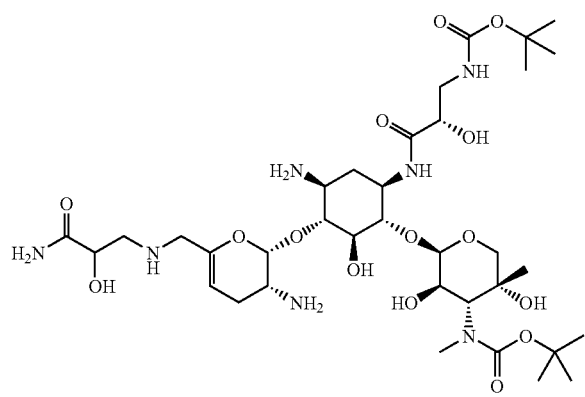 [SMILES: CN(C(=O)OC(C)(C)C)[C@@H]1[C@@H](O)[C@@H](O[C@@H]2[C@@H](O)[C@H](O[C@H]3OC(CNCC(O)C(N)=O)=CC[C@H]3N)[C@@H](N)C[C@H]2NC(=O)[C@@H](O)CNC(=O)OC(C)(C)C)OC[C@]1(C)O]

6'-(2-Hydroxy-3-propionamide)-1-(N-Boc-3-amino-2(S)-hydroxy-propionyl)-3"-Boc-sisomicin The crude mixture of 6'-(2-hydroxy-3-propionamide)-2',3-diPNZ-1-(N-Boc-3-amino-2(S)-hydroxy-propionyl)-3"-Boc-sisomicin was submitted to Procedure 2 for PNZ removal to yield 6'-(2-hydroxy-3-propionamide)-1-(N-Boc-3-amino-2-(S)-hydroxy-propionyl)-3"-Boc-sisomicin (MS m/e [M+H]$^+$ calcd 822.4, found 822.3), which was carried through to the next step without further purification.

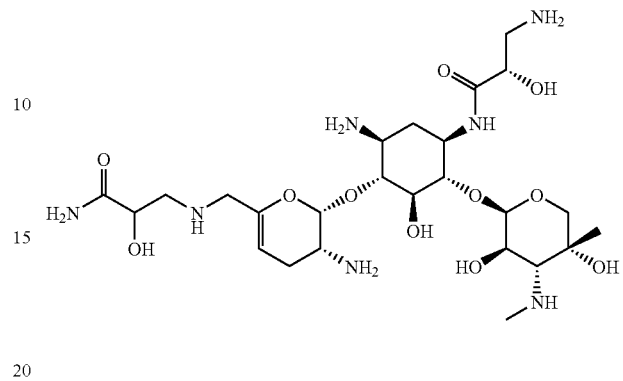

6'-(2-Hydroxy-3-propionamide)-1-(3-amino-2(S)-hydroxy-propionyl)-sisomicin

The crude mixture of 6'-(2-hydroxy-3-propionamide)-1-(N-Boc-3-amino-2(S)-hydroxy-propionyl)-3"-Boc-sisomicin was submitted to Procedure 3-Method B for Boc removal, followed by purification by RP HPLC Method 1-Column A to yield: 6'-(2-hydroxy-3-propionamide)-1-(3-amino-2(S)-hydroxy-propionyl)-sisomicin (0.0093 g, 0.015 mmol, 10% yield): MS m/e [M+H]$^+$ calcd 622.3, found 622.2, [M+Na]$^+$ 644.3; CLND 96.2% purity.

Example 22

6'-(3-Amino-2-hydroxy-propyl)-1-(3-amino-2(S)-hydroxy-propionyl)-sisomicin

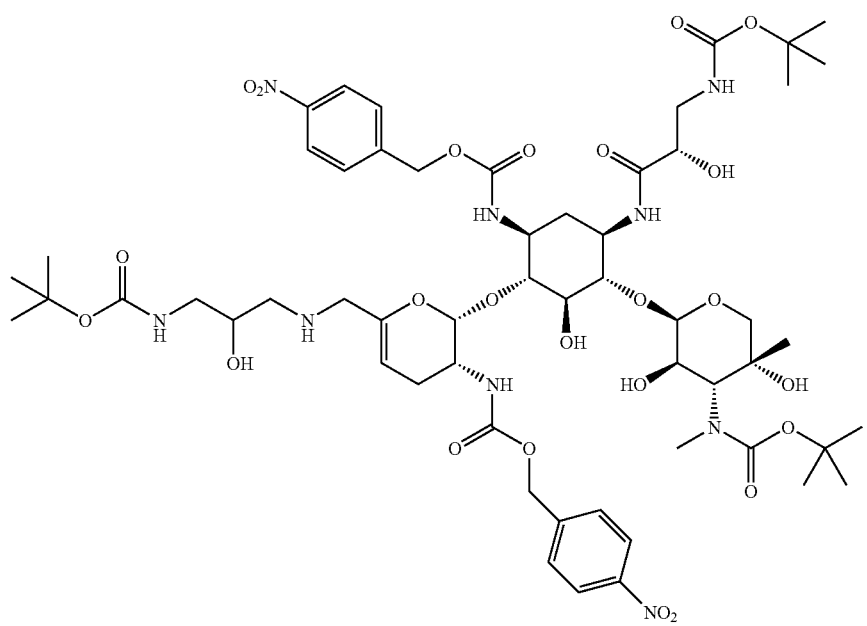 [SMILES: CN(C(=O)OC(C)(C)C)[C@@H]1[C@@H](O)[C@@H](O[C@@H]2[C@@H](O)[C@H](O[C@H]3OC(CNCC(O)CNC(=O)OC(C)(C)C)=CC[C@H]3NC(=O)OCc3ccc([N+](=O)[O-])cc3)[C@@H](NC(=O)OCc3ccc([N+](=O)[O-])cc3)C[C@H]2NC(=O)[C@@H](O)CNC(=O)OC(C)(C)C)OC[C@]1(C)O]

6'-(N-Boc-3-amino-2-hydroxy-propyl)-2',3-diPNZ-1-(N-Boc-3-amino-2(S)-hydroxy-propionyl)-3"-Boc-sisomicin Treatment of 2',3-diPNZ-1-(N-Boc-3-amino-2(S)-hydroxy-propionyl)-3"-Boc-sisomicin (0.15 mmol) with N-Boc-oxiran-2-yl-methanamine following Procedure 5 gave the corresponding 6'-(N-Boc-3-amino-2-hydroxy-propyl)-2',3-diPNZ-1-(N-Boc-3-amino-2(S)-hydroxy-propionyl)-3"-Boc-sisomicin (MS m/e [M+H]$^+$ calcd 1266.6, found 1266.7), which was carried through to the next step without further purification.

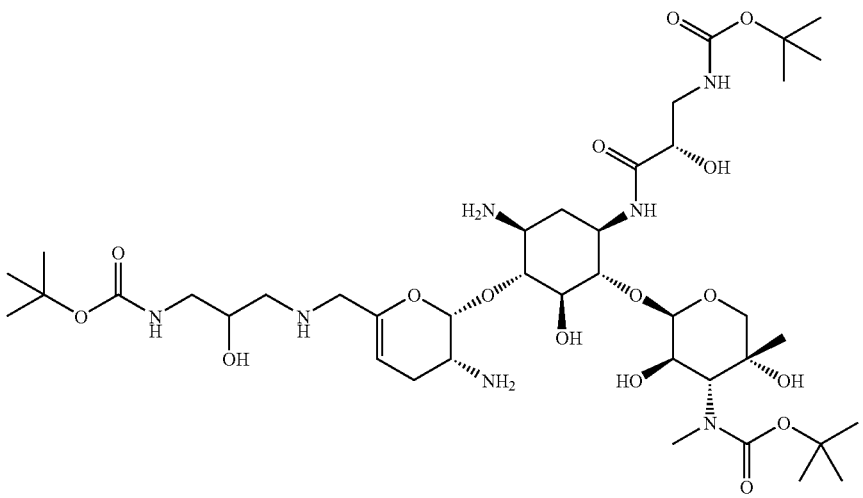 [SMILES: CN(C(=O)OC(C)(C)C)[C@@H]1[C@@H](O)[C@@H](O[C@@H]2[C@@H](O)[C@H](O[C@H]3OC(CNCC(O)CNC(=O)OC(C)(C)C)=CC[C@H]3N)[C@@H](N)C[C@H]2NC(=O)[C@@H](O)CNC(=O)OC(C)(C)C)OC[C@]1(C)O]

6'-(N-Boc-3-amino-2-hydroxy-propyl)-1-(N-Boc-3-amino-2(S)-hydroxy-propionyl)-3"-Boc-sisomicin 6'-(N-Boc-3-amino-2-hydroxy-propyl)-2',3-diPNZ-1-(N-Boc-3-amino-2(S)-hydroxy-propionyl)-3"-Boc-sisomicin (0.15 mmol) was submitted to Procedure 2 for PNZ removal to yield 6'-(N-Boc-3-amino-2-hydroxy-propyl)-1-(N-Boc-3-amino-2(S)-hydroxy-propionyl)-3"-Boc-sisomicin (MS m/e [M+H]$^+$ calcd 908.5, found 908.4), which was carried through to the next step without further purification.

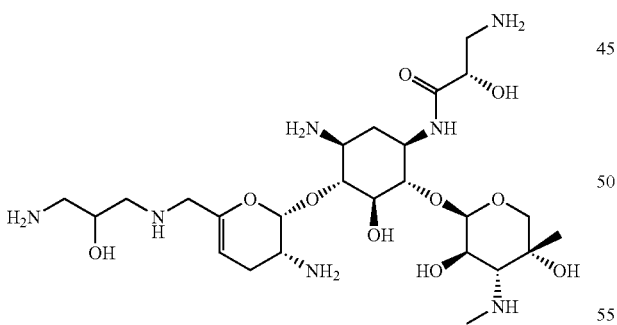

6'-(3-Amino-2-hydroxy-propyl)-1-(3-amino-2(S)-hydroxy-propionyl)-sisomicin

6'-(N-Boc-3-amino-2-hydroxy-propyl)-1-(N-Boc-3-amino-2(S)-hydroxy-propionyl)-3"-Boc-sisomicin (0.15 mmol) was submitted to Procedure 3-Method B for Boc removal, followed by purification by RP HPLC Method 1-Column A to yield 6'-(3-amino-2-hydroxy-propyl)-1-(3-amino-2(S)-hydroxy-propionyl)-sisomicin (0.0044 g, 0.0072 mmol, 4.8% yield):MS m/e [M+H]$^+$ calcd 608.3, found 608.2, [M+Na]$^+$ 630.3; CLND 91% purity.

Example 23

6'-(2-Hydroxy-propanol)-1-(2-hydroxy-acetyl)-sisomicin

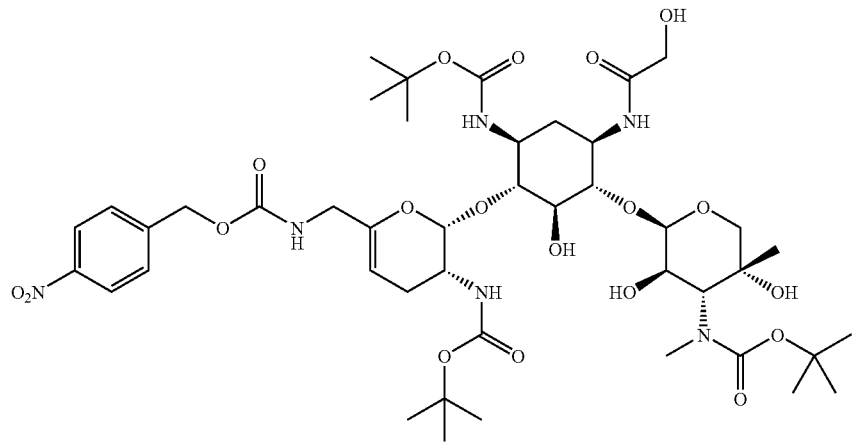 [SMILES: CN(C(=O)OC(C)(C)C)[C@@H]1[C@@H](O)[C@@H](O[C@@H]2[C@@H](O)[C@H](O[C@H]3OC(CNC(=O)OCc4ccc([N+](=O)[O-])cc4)=CC[C@H]3NC(=O)OC(C)(C)C)[C@@H](NC(=O)OC(C)(C)C)C[C@H]2NC(=O)CO)OC[C@]1(C)O]

6'-PNZ-2',3,3''-triBoc-1-(2-hydroxy-acetyl)-sisomicin

Treatment of 6'-PNZ-2',3,3''-triBoc-sisomicin (0.075 g, 0.081 mmol) with glycolic acid following Procedure 4-Method B gave the desired 6'-PNZ-2',3,3''-triBoc-1-(2-hydroxy-acetyl)-sisomicin (MS m/e [M+H]$^+$ calcd 985.5, found 985.9), which was carried through to the next step without further purification.

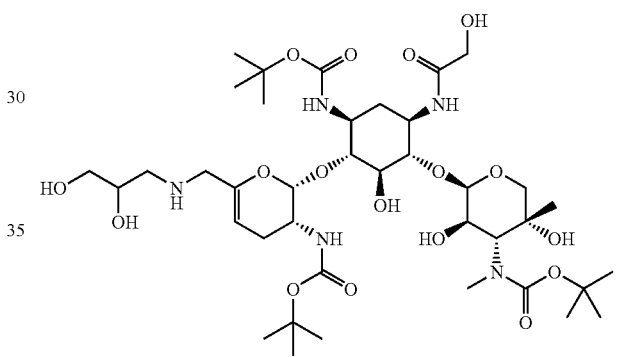

6'-(2-Hydroxy-propanol)-2',3,3''-triBoc-1-(2-hydroxy-acetyl)-sisomicin

2',3,3''-triBoc-1-(2-hydroxy-acetyl)-sisomicin (0.081 mmol) was treated with DL-glyceraldehyde following Procedure 1-Method A to yield the desired 6'-(2-hydroxy-propanol)-2',3,3''-triBoc-1-(2-hydroxy-acetyl)-sisomicin (MS m/e [M+H]$^+$ calcd 880.5, found 880.9), which was carried through to the next step without further purification.

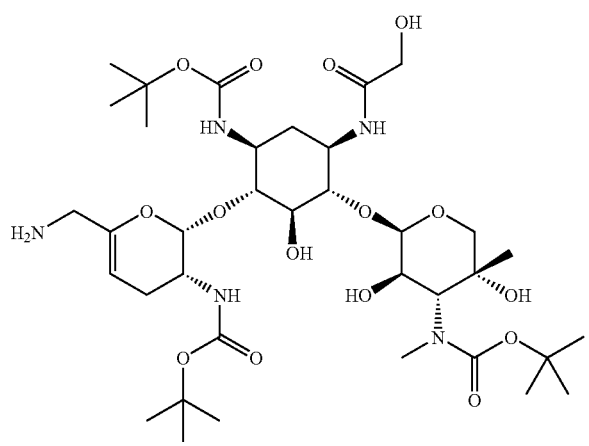 [SMILES: CN(C(=O)OC(C)(C)C)[C@@H]1[C@@H](O)[C@@H](O[C@@H]2[C@@H](O)[C@H](O[C@H]3OC(CN)=CC[C@H]3NC(=O)OC(C)(C)C)[C@@H](NC(=O)OC(C)(C)C)C[C@H]2NC(=O)CO)OC[C@]1(C)O]

2',3,3''-triBoc-1-(2-hydroxy-acetyl)-sisomicin

6'-PNZ-2',3,3''-triBoc-1-(2-hydroxy-acetyl)-sisomicin (0.081 mmol) was submitted to Procedure 2 for PNZ removal to yield 2',3,3''-triBoc-1-(2-hydroxy-acetyl)-sisomicin (MS m/e [M+H]$^+$ calcd 806.4, found 806.9), which was carried through to the next step without further purification.

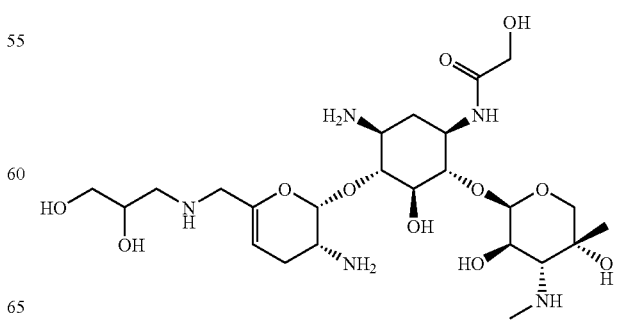

6'-(2-Hydroxy-propanol)-1-(2-hydroxy-acetyl)-sisomicin

6'-(2-hydroxy-propanol)-2',3,3''-triBoc-1-(2-hydroxy-acetyl)-sisomicin (0.081 mmol) was submitted to Procedure 3-Method A for Boc removal to yield a crude, which was purified by RP HPLC Method 3 to yield 6'-(2-hydroxy-propanol)-1-(2-hydroxy-acetyl)-sisomicin (0.0058 g, 0.010 mmol, 12.3% yield): MS m/e [M+H]$^+$ calcd 580.3, found 580.6; CLND 89.3% purity.

Example 24

6'-(3-Amino-propyl)-1-(2-hydroxy-acetyl)-sisomicin

6'-(3-Amino-propyl)-2',3,3''-triBoc-1-(2-hydroxy-acetyl)-sisomicin

6'-(N-Phthalimido-3-amino-propyl)-2',3,3''-triBoc-1-(2-hydroxy-acetyl)-sisomicin (0.081 mmol) was submitted to Procedure 6 for phthalamido deprotection to yield 6'-(3-amino-propyl)-2',3,3''-triBoc-1-(2-hydroxy-acetyl)-sisomicin (MS m/e [M+H]$^+$ calcd 863.5, found 864.1), which was carried through to the next step without further purification.

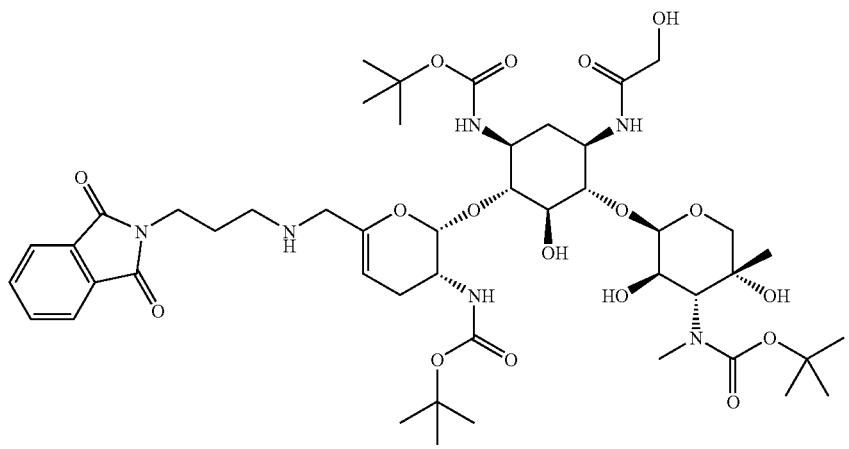 [SMILES: CN(C(=O)OC(C)(C)C)[C@@H]1[C@@H](O)[C@@H](O[C@@H]2[C@@H](O)[C@H](O[C@H]3OC(CNCCCN4C(=O)c5ccccc5C4=O)=CC[C@H]3NC(=O)OC(C)(C)C)[C@@H](NC(=O)OC(C)(C)C)C[C@H]2NC(=O)CO)OC[C@]1(C)O]

6'-(N-Phthalimido-3-amino-propyl)-2',3,3''-triBoc-1-(2-hydroxy-acetyl)-sisomicin 2',3,3''-triBoc-1-(2-hydroxy-acetyl)-sisomicin (0.081 mmol) was treated with N-phthalimido-propionaldehyde following Procedure 1-Method A to yield the desired 6'-(N-phthalimido-3-amino-propyl)-2',3,3''-triBoc-1-(2-hydroxy-acetyl)-sisomicin (MS m/e [M+H]$^+$ calcd 993.5, found 993.9), which was carried through to the next step without further purification.

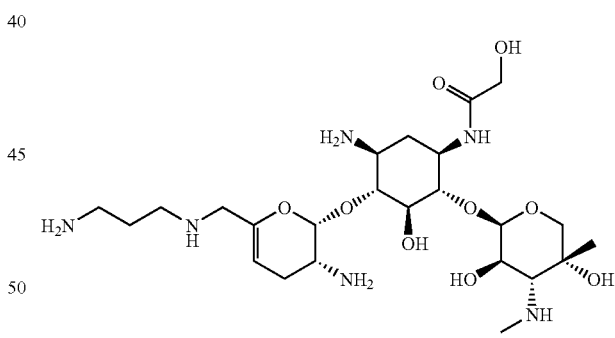

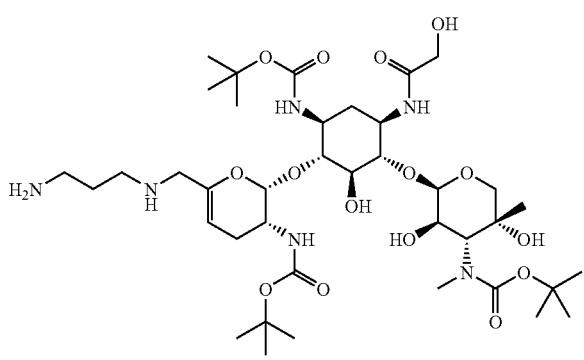 [SMILES: CN(C(=O)OC(C)(C)C)[C@@H]1[C@@H](O)[C@@H](O[C@@H]2[C@@H](O)[C@H](O[C@H]3OC(CNCCCN)=CC[C@H]3NC(=O)OC(C)(C)C)[C@@H](NC(=O)OC(C)(C)C)C[C@H]2NC(=O)CO)OC[C@]1(C)O]

6'-(3-Amino-propyl)-1-(2-hydroxy-acetyl)-sisomicin

6'-(3-Amino-propyl)-2',3,3''-triBoc-1-(2-hydroxy-acetyl)-sisomicin (0.081 mmol) was submitted to Procedure 3-Method A for Boc removal to yield a crude, which was purified by RP HPLC Method 3 to yield 6'-(3-amino-propyl)-1-(2-hydroxy-acetyl)-sisomicin (0.0035 g, 0.0062 mmol, 7.6% yield): MS m/e [M+H]$^+$ calcd 563.3, found 563.2; CLND 88.9% purity.

Example 25

6'-(2-Hydroxy-ethyl)-1-(2-hydroxy-acetyl)-sisomicin

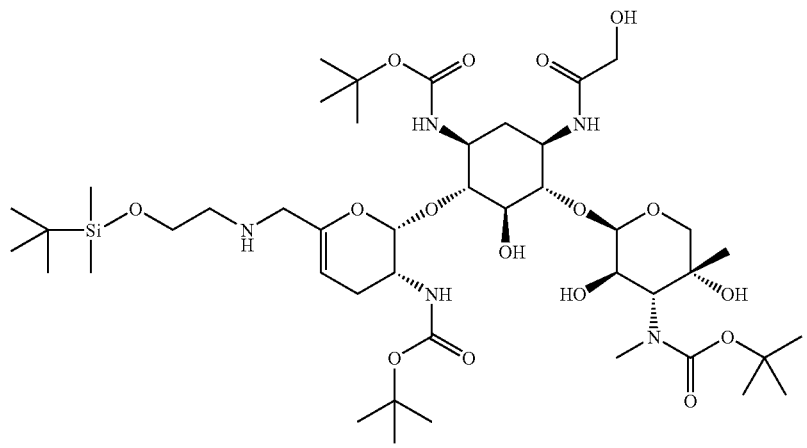 [SMILES: CN(C(=O)OC(C)(C)C)[C@@H]1[C@@H](O)[C@@H](O[C@@H]2[C@@H](O)[C@H](O[C@H]3OC(CNCCO[Si](C)(C)C(C)(C)C)=CC[C@H]3NC(=O)OC(C)(C)C)[C@@H](NC(=O)OC(C)(C)C)C[C@H]2NC(=O)CO)OC[C@]1(C)O]

6'-(2-tert-Butyldimethylsilyloxy-ethyl)-2',3,3"-tri-Boc-1-(2-hydroxy-acetyl)-sisomicin 2',3,3"-triBoc-1-(2-hydroxy-acetyl)-sisomicin (0.081 mmol) was treated with tert-butyl-dimethylsilyloxy-acetaldehyde following Procedure 1-Method A to yield the desired 6'-(2-tert-butyldimethylsilyloxy-ethyl)-2',3,3"-triBoc-1-(2-hydroxy-acetyl)-sisomicin (MS m/e [M+H]$^+$ calcd 964.6, found 964.9), which was carried through to the next step without further purification

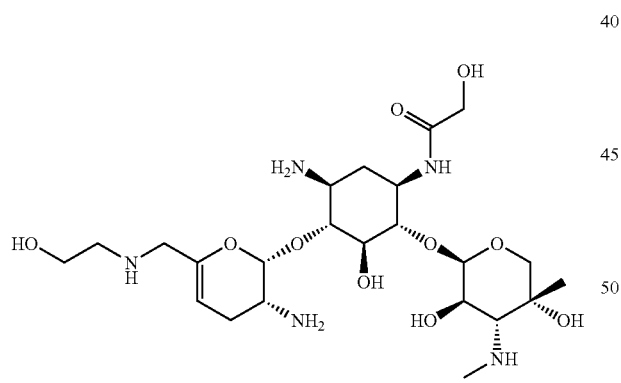

6'-(2-Hydroxy-ethyl)-1-(2-hydroxy-acetyl)-sisomicin

6'-(2-tert-butyldimethylsilyloxy-ethyl)-2',3,3"-triBoc-1-(2-hydroxy-acetyl)-sisomicin (0.081 mmol)) was submitted to Procedure 3-Method A for Boc and TBS removal to yield a crude, which was purified by RP HPLC Method 3 to yield 6'-(2-hydroxy-ethyl)-1-(2-hydroxy-acetyl)-sisomicin (0.0152 g, 0.028 mmol, 34.6% yield): MS m/e [M+H]$^+$ calcd 550.3, found 550.5; CLND 90.7% purity.

Example 26

6'-(3-Amino-propyl)-1-(2-amino-ethylsulfonamide)-sisomicin

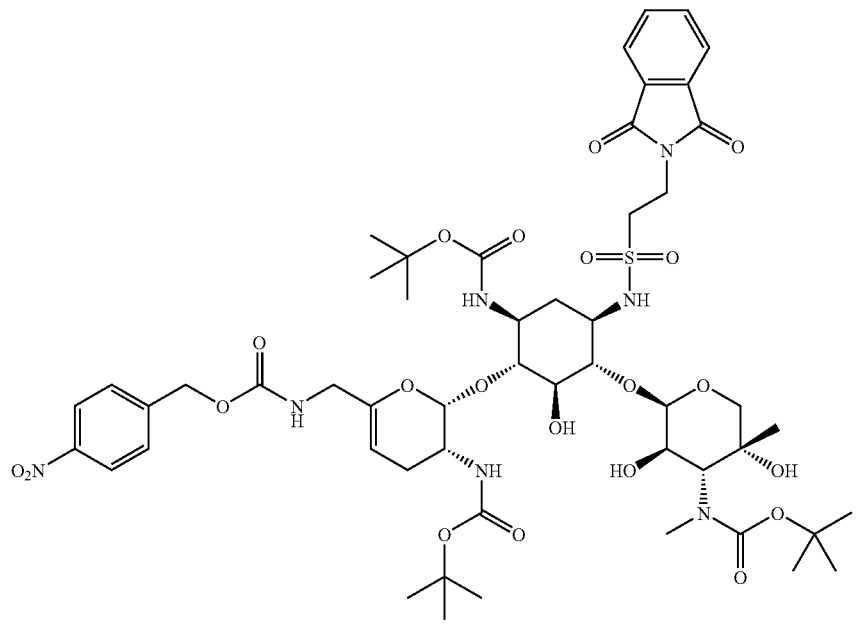 [SMILES: CN(C(=O)OC(C)(C)C)[C@@H]1[C@@H](O)[C@@H](O[C@@H]2[C@@H](O)[C@H](O[C@H]3OC(CNC(=O)OCc4ccc([N+](=O)[O-])cc4)=CC[C@H]3NC(=O)OC(C)(C)C)[C@@H](NC(=O)OC(C)(C)C)C[C@H]2NS(=O)(=O)CCN2C(=O)c3ccccc3C2=O)OC[C@]1(C)O]

6'-PNZ-2',3,3"-triBoc-1-(N-phthalimido-2-amino-ethylsulfonamide)-sisomicin

Treatment of 6'-PNZ-2',3,3"-triBoc-sisomicin (0.075 g, 0.081 mmol) with N-phthalimido-ethanesulfonyl chloride following Procedure 12 gave the desired 6'-PNZ-2',3,3"-triBoc-1-(N-phthalimido-2-amino-ethylsulfonamide)-sisomicin (MS m/e [M+H]$^+$ calcd 1164.5, found 1164.6), which was carried through to the next step without further purification.

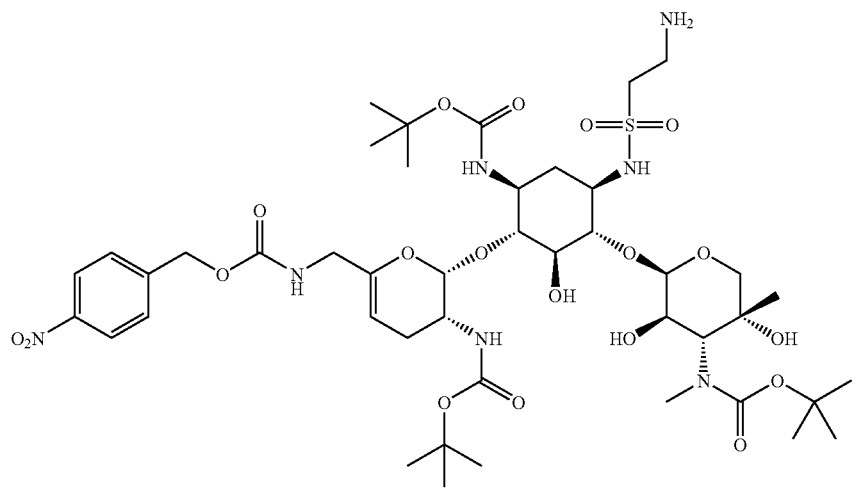 [SMILES: CN(C(=O)OC(C)(C)C)[C@@H]1[C@@H](O)[C@@H](O[C@@H]2[C@@H](O)[C@H](O[C@H]3OC(CNC(=O)OCc4ccc([N+](=O)[O-])cc4)=CC[C@H]3NC(=O)OC(C)(C)C)[C@@H](NC(=O)OC(C)(C)C)C[C@H]2NS(=O)(=O)CCN)OC[C@]1(C)O]

6'-PNZ-2',3,3''-triBoc-1-(2-amino-ethylsulfonamide)-sisomicin

6'-PNZ-2',3,3''-triBoc-1-(N-phthalimido-2-amino-ethylsulfonamide)-sisomicin (0.081 mmol) was submitted to Procedure 6 for phthalimido deprotection to yield 6'-PNZ-2',3,3''-triBoc-1-(2-amino-ethylsulfonamide)-sisomicin (MS m/e [M+H]$^+$ calcd 1034.5, found 1035.2), which was carried through to the next step without further purification.

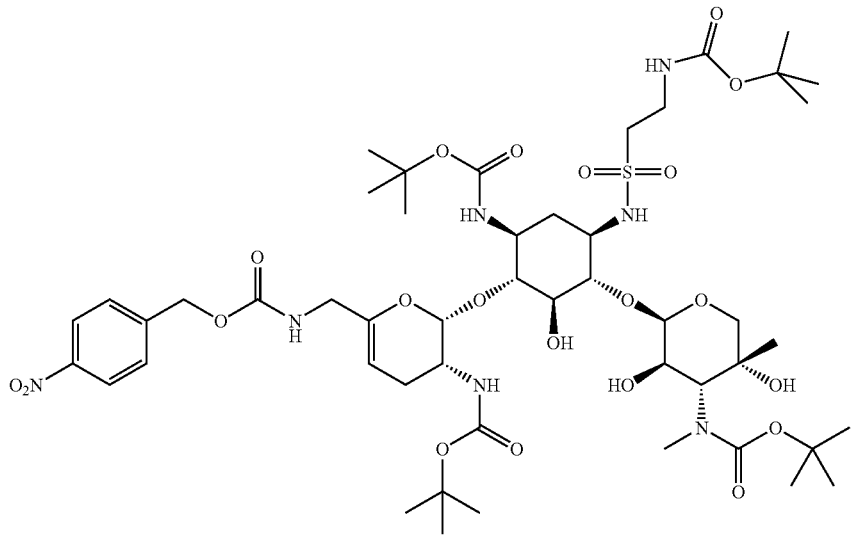 [SMILES: CN(C(=O)OC(C)(C)C)[C@@H]1[C@@H](O)[C@@H](O[C@@H]2[C@@H](O)[C@H](O[C@H]3OC(CNC(=O)OCc4ccc([N+](=O)[O-])cc4)=CC[C@H]3NC(=O)OC(C)(C)C)[C@@H](NC(=O)OC(C)(C)C)C[C@H]2NS(=O)(=O)CCNC(=O)OC(C)(C)C)OC[C@]1(C)O]

6'-PNZ-2',3,3''-triBoc-1-(N-Boc-2-amino-ethylsulfonamide)-sisomicin

6'-PNZ-2',3,3''-triBoc-1-(2-amino-ethylsulfonamide)-sisomicin (0.081 mmol) was submitted to Procedure 13 for N-Boc protection to yield 6'-PNZ-2',3,3''-triBoc-1-(N-Boc-2-amino-ethylsulfonamide)-sisomicin (MS m/e [M+H]$^+$ calcd 1134.5, found 1135.0), which was carried through to the next step without further purification.

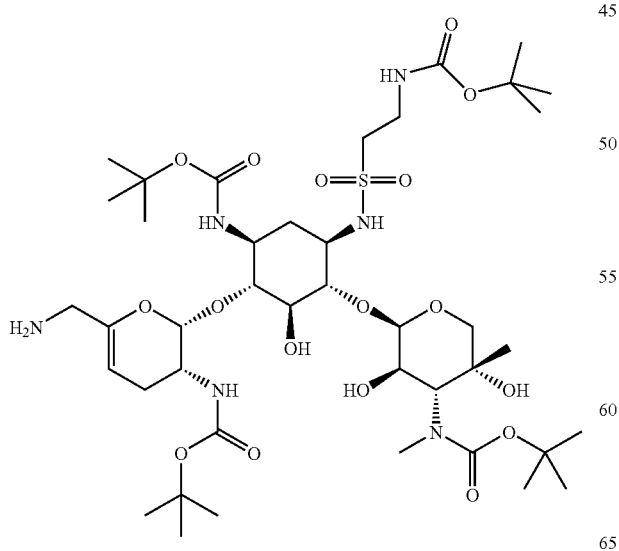

2',3"-triBoc-1-(N-Boc-2-amino-ethylsulfonamide)-sisomicin

6'-PNZ-2',3,3"-triBoc-1-(N-Boc-2-amino-ethylsulfonamide)-sisomicin (0.081 mmol) was submitted to Procedure 2 for PNZ removal to yield 2',3,3"-triBoc-1-(N-Boc-2-amino-ethylsulfonamide)-sisomicin (MS m/e [M+H]$^+$ calcd 955.5, found 956.2), which was carried through to the next step without further purification.

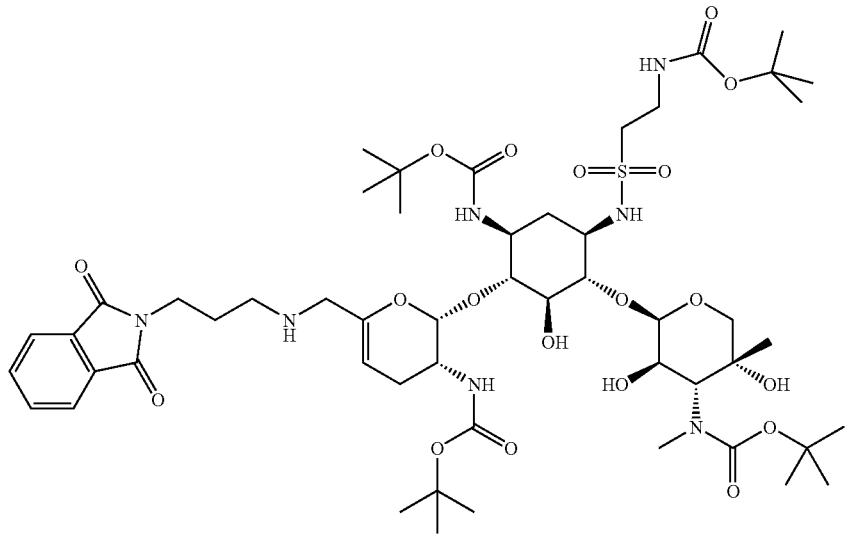 [SMILES: CN(C(=O)OC(C)(C)C)[C@@H]1[C@@H](O)[C@@H](O[C@@H]2[C@@H](O)[C@H](O[C@H]3OC(CNCCCN4C(=O)c5ccccc5C4=O)=CC[C@H]3NC(=O)OC(C)(C)C)[C@@H](NC(=O)OC(C)(C)C)C[C@H]2NS(=O)(=O)CCNC(=O)OC(C)(C)C)OC[C@]1(C)O]

6'-(N-Phthalimido-3-amino-propyl)-2',3,3"-triBoc-1-(N-Boc-2-amino-ethylsulfonamide)-sisomicin 2',3,3"-triBoc-1-(N-Boc-2-amino-ethylsulfonamide)-sisomicin (0.081 mmol) was treated with N-phthalimido-propionaldehyde following Procedure 1-Method A to yield the desired 6'-(N-phthalimido-3-amino-propyl)-2',3,3"-triBoc-1-(N-Boc-2-amino-ethylsulfonamide)-sisomicin (MS m/e [M+H]$^+$ calcd 1142.6, found 1143.5), which was carried through to the next step without further purification.

6'-(3-Amino-propyl)-2',3,3"-triBoc-1-(N-Boc-2-amino-ethylsulfonamide)-sisomicin 6'-(N-Phthalimido-3-amino-propyl)-2',3,3"-triBoc-1-(N-Boc-2-amino-ethylsulfonamide)-sisomicin (0.081 mmol) was submitted to Procedure 6 for phthalimido deprotection to yield 6'-(3-amino-propyl)-2',3,3"-triBoc-1-(N-Boc-2-amino-ethylsulfonamide)-sisomicin (MS m/e [M+H]$^+$ calcd 1012.5, found 1012.9), which was carried through to the next step without further purification.

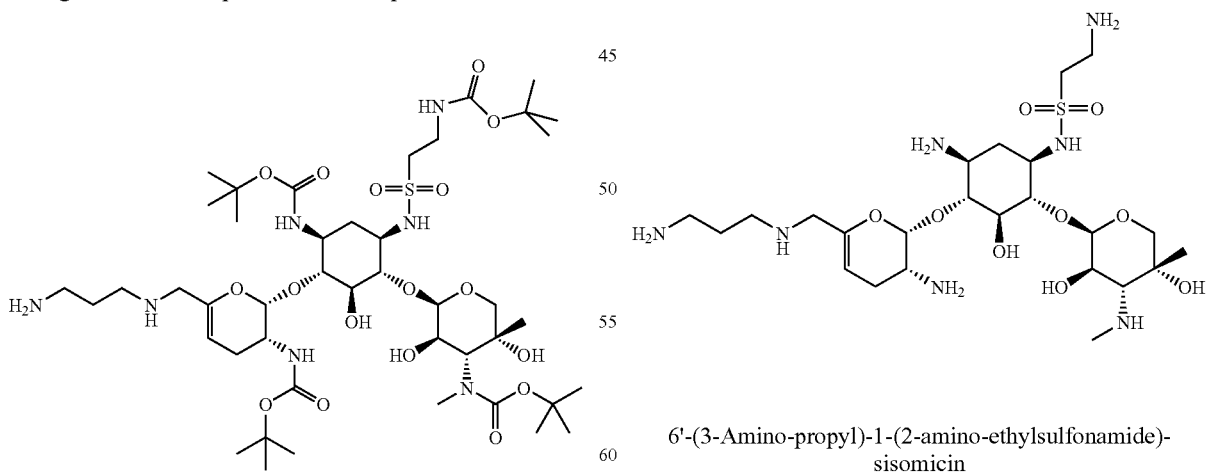

6'-(3-Amino-propyl)-1-(2-amino-ethylsulfonamide)-sisomicin

6'-(3-Amino-propyl)-2',3,3"-triBoc-1-(N-Boc-2-amino-ethylsulfonamide)-sisomicin (0.081 mmol) was submitted to Procedure 3-Method A for Boc removal to yield a crude, which was purified by RP HPLC Method 3 to yield 6'-(3-amino-propyl)-1-(2-amino-ethylsulfonamide)-sisomicin (0.0029 g, 0.0047 mmol, 5.8% yield): MS m/e [M+H]+ calcd 612.3, found 612.4; CLND 84.7% purity.

Example 27

6'-(2-Hydroxy-propanol)-1-(2-amino-ethylsulfonamide)-sisomicin

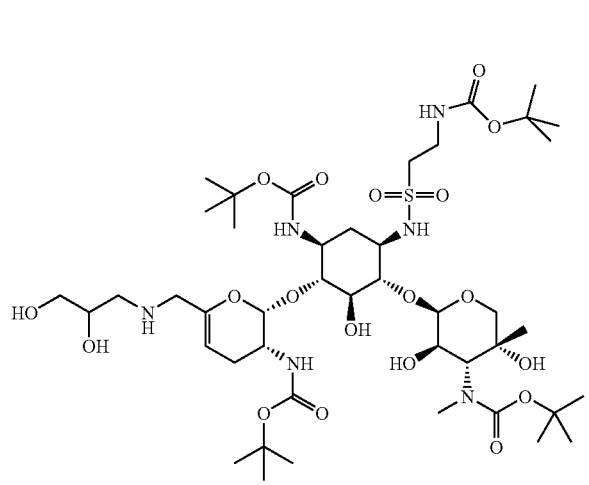 [SMILES: CN(C(=O)OC(C)(C)C)[C@@H]1[C@@H](O)[C@@H](O[C@@H]2[C@@H](O)[C@H](O[C@H]3OC(CNCC(O)CO)=CC[C@H]3NC(=O)OC(C)(C)C)[C@@H](NC(=O)OC(C)(C)C)C[C@H]2NS(=O)(=O)CCNC(=O)OC(C)(C)C)OC[C@]1(C)O]

6'-(2-Hydroxy-propanol)-2',3,3''-triBoc-1-(N-Boc-2-amino-ethylsulfonamide)-sisomicin 2',3,3''-triBoc-1-(N-Boc-2-amino-ethylsulfonamide)-sisomicin (0.081) was treated with DL-glyceraldehyde following Procedure 1-Method A to yield the desired 6'-(2-hydroxy-propanol)-2',3,3''-triBoc-1-(N-Boc-2-amino-ethylsulfonamide)-sisomicin (MS m/e [M+H]+ calcd 1029.5, found 1030.0), which was carried through to the next step without further purification.

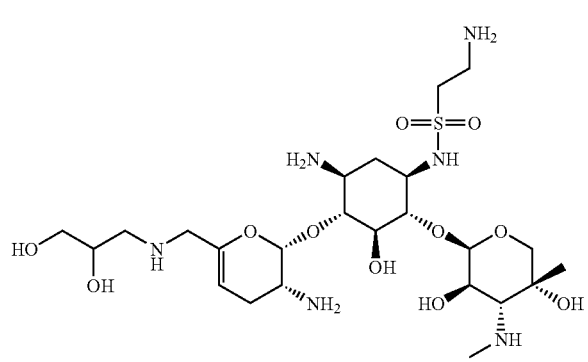 [SMILES: CN[C@@H]1[C@@H](O)[C@@H](O[C@@H]2[C@@H](O)[C@H](O[C@H]3OC(CNCC(O)CO)=CC[C@H]3N)[C@@H](N)C[C@H]2NS(=O)(=O)CCN)OC[C@]1(C)O]

6'-(2-Hydroxy-propanol)-1-(2-amino-ethylsulfonamide)-sisomicin

6'-(2-Hydroxy-propanol)-2',3,3''-triBoc-1-(N-Boc-2-amino-ethylsulfonamide)-sisomicin (0.081 mmol) was submitted to Procedure 3-Method A for Boc removal to yield a crude, which was purified by RP HPLC Method 3 to yield 6'-(2-hydroxy-propanol)-1-(2-amino-ethylsulfonamide)-sisomicin (0.0031 g, 0.0049 mmol, 6.0% yield): MS m/e [M+H]+ calcd 629.3, found 629.2; CLND 88.2% purity.

Example 28

6'-(2(S)-Hydroxy-propanol)-1-(4-amino-2(S)-hydroxy-butyryl)-sisomicin

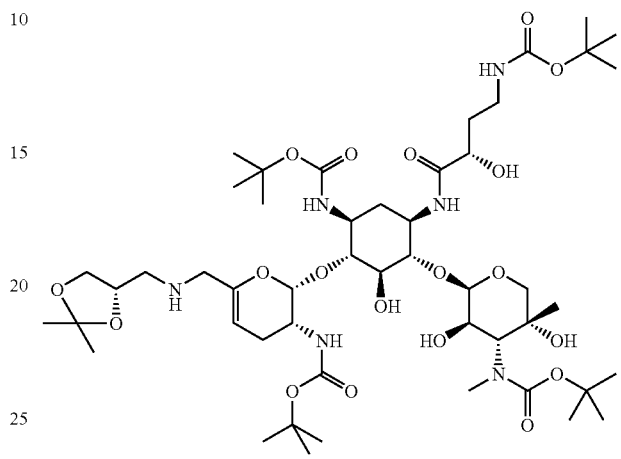

6'-(Methyl-(S)-1-(2,2-dimethyl-1,3-dioxolan-4-yl)-2',3,3''-triBoc-1-(N-Boc-4-amino-2(S)-hydroxy-butyryl)-sisomicin Treatment of 2',3,3''-triBoc-1-(N-Boc-4-amino-2(S)-hydroxy-butyryl)-sisomicin (0.078 mmol) with (R)-2,2-dimethyl-1,3-dioxolane-4-carboxaldehyde following Procedure 1-Method B gave the corresponding 6'-(methyl-(S)-1-(2,2-dimethyl-1,3-dioxolan-4-yl)-2',3,3''-triBoc-1-(N-Boc-4-amino-2(S)-hydroxy-butyryl)-sisomicin (MS m/e [M+H]+ calcd 1063.6, found 1063.4), which was carried through to the next step without further purification.

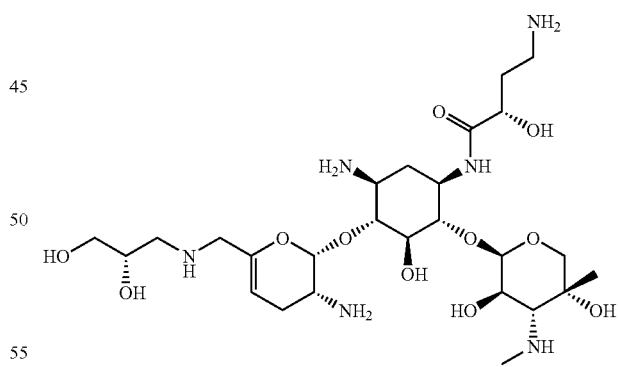

6'-(2(S)-Hydroxy-propanol)-1-(4-amino-2(S)-hydroxy-butyryl)-sisomicin

6'-(2(S)-Hydroxy-propanol)-2',3,3''-triBoc-1-(N-Boc-4-amino-2(S)-hydroxy-butyryl)-sisomicin (0.078 mmol) was submitted to Procedure 3-Method B to yield a crude, which was purified by RP HPLC Method 1-Column A to yield the desired 6'-(2(S)-hydroxy-propanol)-1-(4-amino-2(S)-hydroxy-butyryl)-sisomicin: MS m/e [M+H]+ calcd 623.3, found 623.4, [M+Na]+ 645.3; CLND 97.9% purity.

Example 29

6'-(2-Hydroxy-ethyl)-1-(2-amino-ethylsulfonamide)-sisomicin

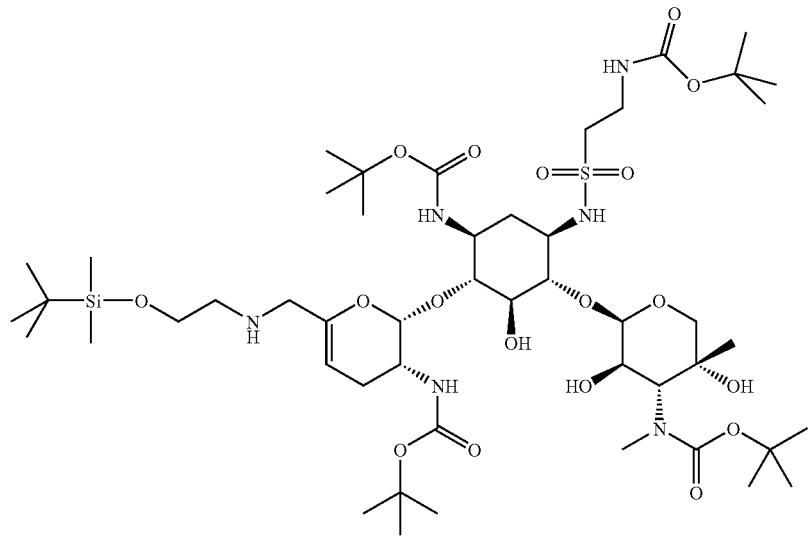 [SMILES: CN(C(=O)OC(C)(C)C)[C@@H]1[C@@H](O)[C@@H](O[C@@H]2[C@@H](O)[C@H](O[C@H]3OC(CNCCO[Si](C)(C)C(C)(C)C)=CC[C@H]3NC(=O)OC(C)(C)C)[C@@H](NC(=O)OC(C)(C)C)C[C@H]2NS(=O)(=O)CCNC(=O)OC(C)(C)C)OC[C@]1(C)O]

6'-(2-tert-Butyldimethylsilyloxy-ethyl)-2',3,3"-tri-Boc-1-(N-Boc-2-amino-ethylsulfonamide)-sisomicin 2',3,3"-triBoc-1-(N-Boc-2-amino-ethylsulfonamide)-sisomicin (0.081) was treated with tert-butyldimethylsilyloxy acetaldehyde following Procedure 1-Method A to yield the desired 6'-(2-tert-butyldimethylsilyloxy-ethyl)-2',3,3"-tri-Boc-1-(N-Boc-2-amino-ethylsulfonamide)-sisomicin (MS m/e [M+H]$^+$ calcd 1113.6, found 1114.2), which was carried through to the next step without further purification.

was submitted to Procedure 3-Method A for Boc and TBS removal to yield a crude, which was purified by RP HPLC Method 3 to yield 6'-(2-hydroxy-ethyl)-1-(2-amino-ethylsulfonamide)-sisomicin (0.0019 g, 0.0032 mmol, 3.9% yield): MS m/e [M+H]$^+$ calcd 599.3, found 599.2; CLND 90.5% purity.

Example 30

6'-(2-Amino-propanol)-1-(4-amino-2(S)-hydroxy-butyryl)-sisomicin

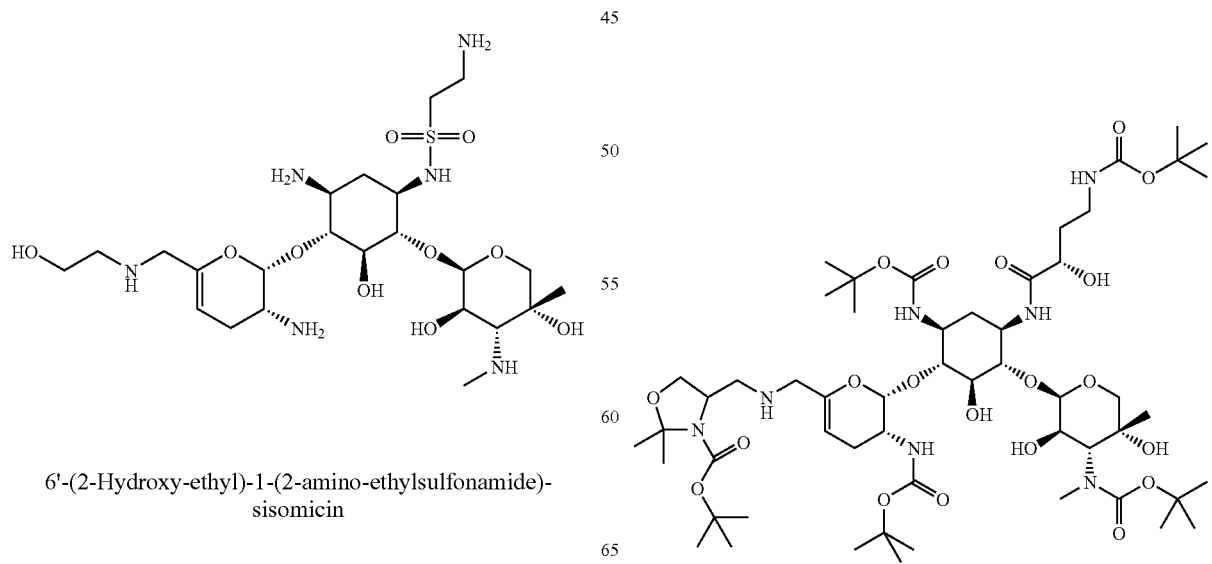

6'-(2-Hydroxy-ethyl)-1-(2-amino-ethylsulfonamide)-sisomicin

6'-(2-tert-Butyldimethylsilyloxy-ethyl)-2',3,3"-triBoc-1-(N-Boc-2-amino-ethylsulfonamide)-sisomicin (0.081 mmol)

6'-(N-Boc-2,2-dimethyl-1,3-oxazolidine-methyl)-2', 3,3"-triBoc-1-(N-Boc-4-amino-2(S)-hydroxy-butyryl)-sisomicin 2',3,3"-triBoc-1-(N-Boc-4-amino-2(S)-hydroxy-butyryl)-sisomicin (0.075 g, 0.079 mmol) was treated with N-Boc-4-formyl-2,2-dimethyl-1,3-oxazolidine following Procedure 1-Method A to yield the desired 6'-(N-Boc-2,2-dimethyl-1,3-oxazolidine-methyl)-2',3,3"-triBoc-1-(N-Boc-4-amino-2(S)-hydroxy-butyryl)-sisomicin (MS m/e [M+H]$^+$ calcd 1162.7, found 1163.1), which was carried through to the next step without further purification.

(0.079 mmol) was submitted to Procedure 3-Method A for Boc removal to yield a crude, which was purified by RP HPLC Method 3 to yield 6'-(2-amino-propanol)-1-(4-amino-2(S)-hydroxy-butyryl)-sisomicin (0.0082 g, 0.013 mmol, 16.4% yield): MS m/e [M+H]$^+$ calcd 622.4, found 622.6; CLND 75.5% purity.

Example 31

6'-(4-Hydroxy-piperidin-4-yl)-methyl)-1-(4-amino-2(S)-hydroxy-butyryl)-sisomicin

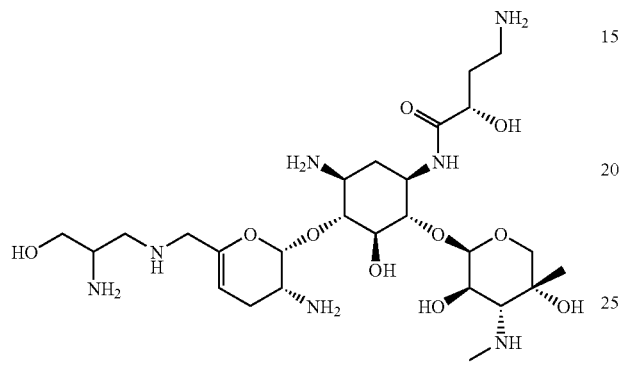

6'-(2-Amino-propanol)-1-(4-amino-2(S)-hydroxy-butyryl)-sisomicin

6'-(N-Boc-2,2-dimethyl-1,3-oxazolidine-methyl)-2',3,3"-triBoc-1-(N-Boc-4-amino-2(S)-hydroxy-butyryl)-sisomicin

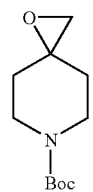

N-Boc-1-oxa-6-azaspiro[2.5]octane

4-Methylene-piperidine (0.222 g, 1.12 mmol) was submitted to Procedure 14 to form the desired N-Boc-1-oxa-6-azaspiro[2.5]octane (0.215 g, 1.01 mmol, 90.2% yield): $^1$H NMR (250 MHz, DMSO-d$_6$) δ 3.29-3.61 (m, 6 H), 1.56-1.70 (m, 2 H), 1.30-1.54 (m, 11 H).

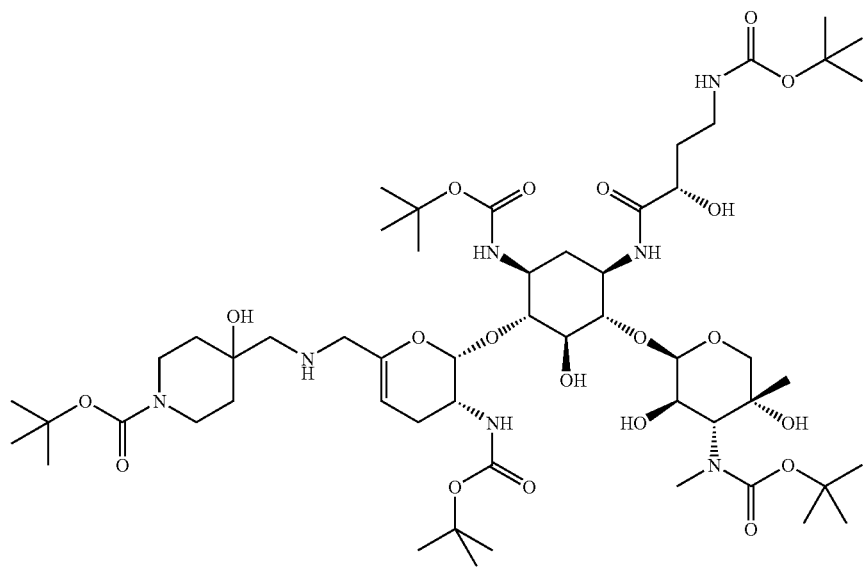 [SMILES: CN(C(=O)OC(C)(C)C)[C@@H]1[C@@H](O)[C@@H](O[C@@H]2[C@@H](O)[C@H](O[C@H]3OC(CNCC4(O)CCN(C(=O)OC(C)(C)C)CC4)=CC[C@H]3NC(=O)OC(C)(C)C)[C@@H](NC(=O)OC(C)(C)C)C[C@H]2NC(=O)[C@@H](O)CCNC(=O)OC(C)(C)C)OC[C@]1(C)O]

6'-(4-Hydroxy-N-Boc-piperidin-4-yl)-methyl)-2',3,3"-triBoc-1-(N-Boc-4-amino-2(S)-hydroxy-butyryl)-sisomicin 2',3,3"-triBoc-1-(N-Boc-4-amino-2(S)-hydroxy-butyryl)-sisomicin (0.075 g, 0.079 mmol) was treated with N-Boc-1-oxa-6-azaspiro[2.5]octane following Procedure 5 to yield the desired 6'-(4-hydroxy-N-Boc-piperidin-4-yl)-methyl)-2',3,3"-triBoc-1-(N-Boc-4-amino-2(S)-hydroxy-butyryl)-sisomicin (MS m/e [M+H]+ calcd 1162.7, found 1163.2), which was carried through to the next step without further purification.

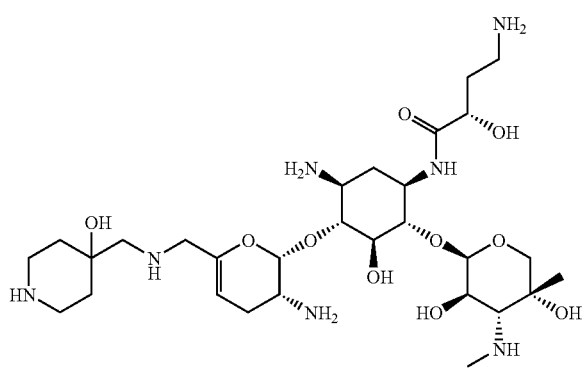 [SMILES: CN[C@@H]1[C@@H](O)[C@@H](O[C@@H]2[C@@H](O)[C@H](O[C@H]3OC(CNCC4(O)CCNCC4)=CC[C@H]3N)[C@@H](N)C[C@H]2NC(=O)[C@@H](O)CCN)OC[C@]1(C)O]

6'-(4-Hydroxy-piperidin-4-yl)-methyl)-1-(4-amino-2(S)-hydroxy-butyryl)-sisomicin 6'-(4-hydroxy-N-Boc-piperidin-4-yl)-methyl)-2',3,3"-triBoc-1-(N-Boc-4-amino-2(S)-hydroxy-butyryl)-sisomicin (0.079 mmol) was submitted to Procedure 3-Method A for Boc removal to yield a crude, which was purified by RP HPLC Method 3 to yield 6'-(4-hydroxy-piperidin-4-yl)-methyl)-1-(4-amino-2(S)-hydroxy-butyryl)-sisomicin (0.0023 g, 0.0035 mmol, 4.4% yield): MS m/e [M+H]+ calcd 662.4, found 662.8; CLND 94.5% purity.

Example 32

6'-(2-Hydroxy-5-amino-pentyl)-1-(4-amino-2(S)-hydroxy-butyryl)-sisomicin

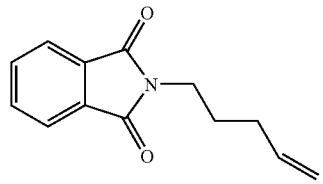 [SMILES: C=CCCCN1C(=O)c2ccccc2C1=O]

2-(Pent-4-enyl)-isoindoline-1,3-dione

To a stirring solution of 5-bromo-pentene (6.0 g, 0.040 mol) in DMF (30 mL) was added $K_2CO_3$ (4.7 g, 0.034 mol) and potassium phthalimide (6.21 g, 0.033 mmol) and the reaction mixture was heated at 100° C. for 1 hr. The reaction mixture was cooled to room temperature, and water (50 mL) was added. The aqueous layer was then extracted with ethyl acetate (2×50 mL), and the combined organic layers were washed with 5% aq. $NaHCO_3$ (2×20 mL), brine (30 mL) and dried over $Na_2SO_4$. Filtration and solvent evaporation gave an oil, which was purified by flash chromatography (silica gel/hexanes:ethyl acetate 0-35%) to yield the desired 2-(pent-4-enyl)-isoindoline-1,3-dione as a solid (6.36 g, 0.029 mmol, 72.5% yield): MS m/e [M+H]+ calcd 216.1, found 216.1; NMR (250 MHz, DMSO-$d_6$) δ 7.79-7.95 (m, 4 H), 5.70-5.91 (m, 1 H), 4.90-5.11 (m, 2 H), 3.58 (t, 2 H), 1.98-2.10 (m, 2H), 1.59-1.78 (m, 2 H).

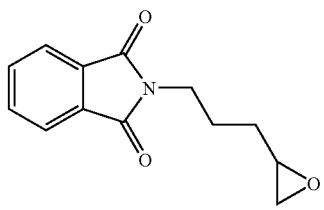 [SMILES: O=C1c2ccccc2C(=O)N1CCCC1CO1]

2-(3-(Oxiran-2-yl)-propyl)-isoindoline-1,3-dione 2-(Pent-4-enyl)-isoindoline-1,3-dione (6.36 g, 0.029 mmol) was submitted to Procedure 14 for epoxide formation to yield 2-(3-(oxiran-2-yl)-propyl-isoindoline-1,3-dione (5.8 g, 0.025 mmol, 86.2% yield): MS m/e [M+H]+ calcd 232.1, found 232.1; ¹H NMR (250 MHz, DMSO-$d_6$) δ 7.75-7.90 (m, 4 H, Ar), 3.52 (t, 2 H, $CH_2$), 2.87-2.96 (m, 1 H, CH), 2.70 (t, 1 H), 2.30-2.45 (m, 1 H), 1.36-1.80 (m, 4 H).

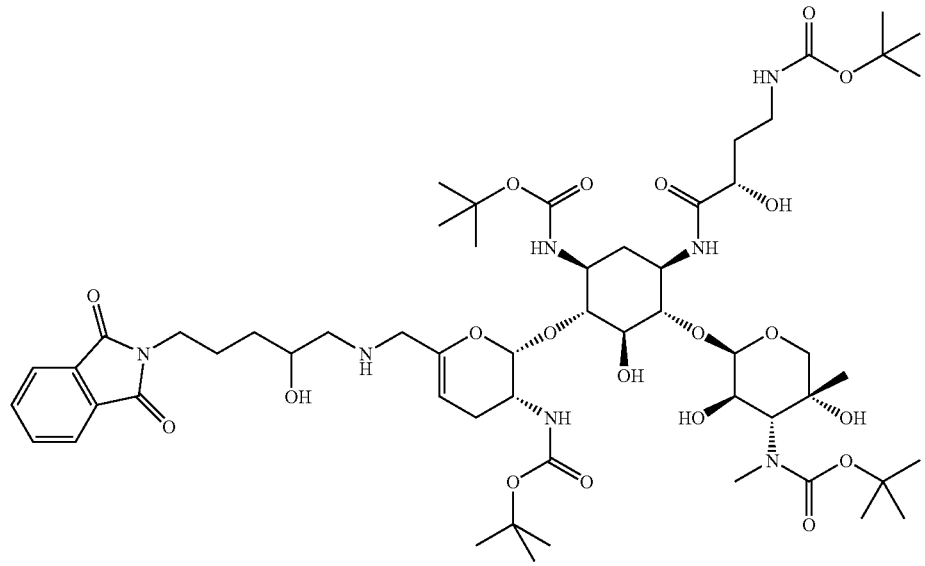 [SMILES: CN(C(=O)OC(C)(C)C)[C@@H]1[C@@H](O)[C@@H](O[C@@H]2[C@@H](O)[C@H](O[C@H]3OC(CNCC(O)CCCN4C(=O)c5ccccc5C4=O)=CC[C@H]3NC(=O)OC(C)(C)C)[C@@H](NC(=O)OC(C)(C)C)C[C@H]2NC(=O)[C@@H](O)CCNC(=O)OC(C)(C)C)OC[C@]1(C)O]

6'-(N-Phthalimido-2-hydroxy-5-amino-pentyl)-2',3,3"-triBoc-1-(N-Boc-4-amino-2(S)-hydroxy-butyryl)-sisomicin

2',3,3"-triBoc-1-(N-Boc-4-amino-2(S)-hydroxy-butyryl)-sisomicin (0.075 g, 0.079 mmol) was treated with 2-(3-(oxiran-2-yl)propyl)-isoindoline-1,3-dione following Procedure 5 to yield the desired 6'-(N-phthalimido-2-hydroxy-5-amino-pentyl)-2',3,3"-triBoc-1-(N-Boc-4-amino-2(S)-hydroxy-butyryl)-sisomicin (MS m/e [M+H]$^+$ calcd 1180.6, found 1181.1), which was carried through to the next step without further purification.

6'-(2-Hydroxy-5-amino-pentyl)-2',3,3"-triBoc-1-(N-Boc-4-amino-2(S)-hydroxy-butyryl)-sisomicin

6'-(N-Phthalimido-2-hydroxy-5-amino-pentyl)-2',3,3"-triBoc-1-(N-Boc-4-amino-2(S)-hydroxy-butyryl)-sisomicin (0.079 mmol) was submitted to Procedure 6 for phthalimido removal to yield 6'-(2-hydroxy-5-amino-pentyl)-2',3,3"-triBoc-1-(N-Boc-4-amino-2(S)-hydroxy-butyryl)-sisomicin (MS m/e [M+H]$^+$ calcd 1050.6, found 1051.3), which was carried through to the next step without further purification.

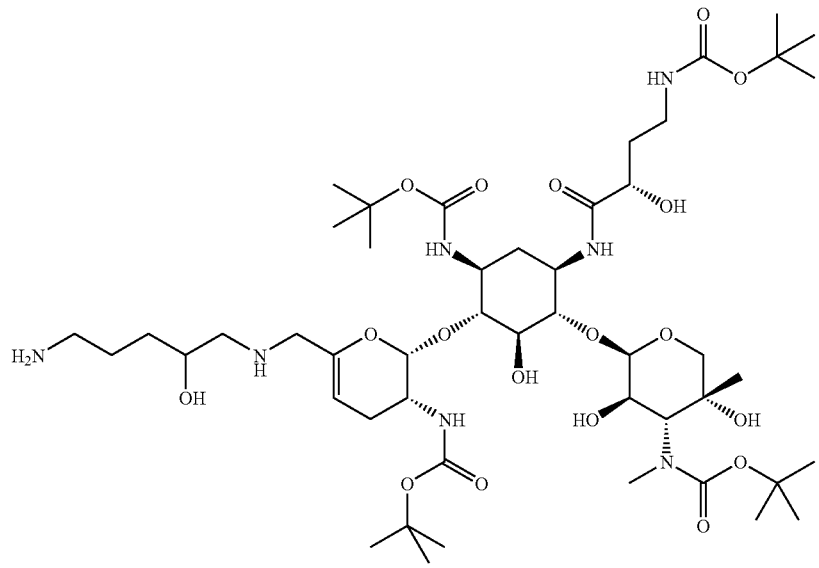 [SMILES: CN(C(=O)OC(C)(C)C)[C@@H]1[C@@H](O)[C@@H](O[C@@H]2[C@@H](O)[C@H](O[C@H]3OC(CNCC(O)CCCN)=CC[C@H]3NC(=O)OC(C)(C)C)[C@@H](NC(=O)OC(C)(C)C)C[C@H]2NC(=O)[C@@H](O)CCNC(=O)OC(C)(C)C)OC[C@]1(C)O]

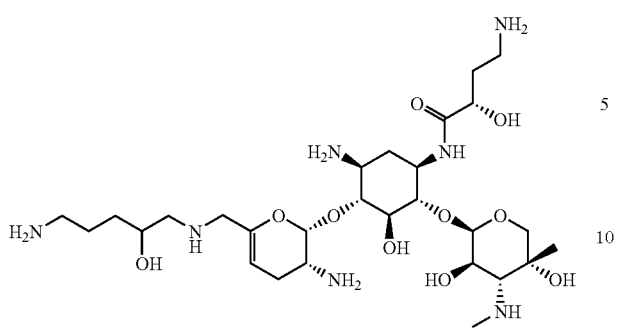

6'-(2-Hydroxy-5-amino-pentyl)-1-(4-amino-2(S)-hydroxy-butyryl)-sisomicin

6'-(2-Hydroxy-5-amino-pentyl)-2',3,3''-triBoc-1-(N-Boc-4-amino-2-(S)-hydroxy-butyryl)-sisomicin (0.079 mmol) was submitted to Procedure 3-Method A for Boc removal to yield a crude, which was purified by RP HPLC Method 3 to yield 6'-(2-hydroxy-5-amino-pentyl)-1-(4-amino-2(S)-hydroxy-butyryl)-sisomicin (0.0024 g, 0.0037 mmol, 4.7% yield): MS m/e [M+H]$^+$ calcd 650.4, found 650.8; CLND 95.3% purity.

Example 33

6'-(Methyl-trans-3-amino-cyclobutyl)-1-(4-amino-2(S)-hydroxy-butyryl)-sisomicin

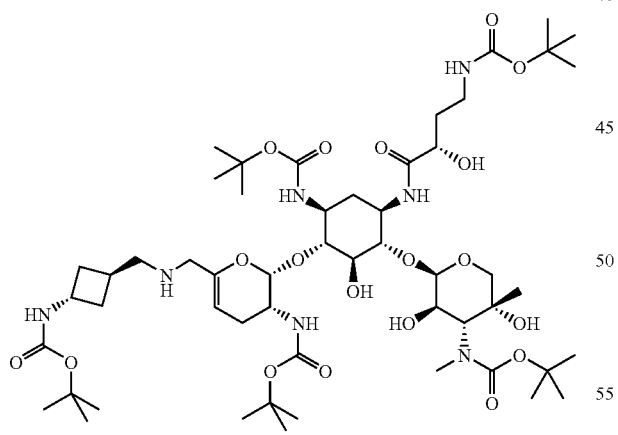

6'-(Methyl-trans-N-Boc-3-amino-cyclobutyl)-2',3,3''-triBoc-1-(N-Boc-4-amino-2(S)-hydroxy-butyryl)-sisomicin 2',3,3''-triBoc-1-(N-Boc-4-amino-2(S)-hydroxy-butyryl)-sisomicin (1.0 g, 1.05 mmol was treated with trans-N-Boc-3-amino-cyclobutyl-carboxaldehyde following Procedure 1-Method B to give the desired 6'-(methyl-trans-N-Boc-3-amino-cyclobutyl)-2',3,3''-triBoc-1-(N-Boc-4-amino-2(S)-hydroxy-butyryl)-sisomicin (MS m/e [M+H]$^+$ calcd 1132.6, found 1133.0), which was carried through to the next step without further purification.

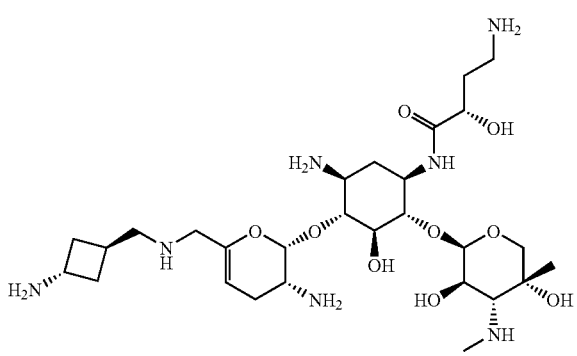 [SMILES: CN[C@@H]1[C@@H](O)[C@@H](O[C@@H]2[C@@H](O)[C@H](O[C@H]3OC(CNC[C@H]4C[C@H](N)C4)=CC[C@H]3N)[C@@H](N)C[C@H]2NC(=O)[C@@H](O)CCN)OC[C@]1(C)O]

6'-(Methyl-trans-3-amino-cyclobutyl)-1-(4-amino-2(S)-hydroxy-butyryl)-sisomicin

6'-(Methyl-trans-N-Boc-3-amino-cyclobutyl)-2',3,3''-triBoc-1-(N-Boc-4-amino-2(S)-hydroxy-butyryl)-sisomicin (1.05 mmol) was submitted to Procedure 3-Method B for Boc removal to yield a crude, which was purified by RP HPLC Method 1-Column B to yield 6'-(methyl-trans-3-amino-cyclobutyl)-1-(4-amino-2(S)-hydroxy-butyryl)-sisomicin (0.110 g, 0.174 mmol, 16.6% yield): MS m/e [M+H]$^+$ calcd 632.4, found 632.8; CLND 96.1% purity.

Example 34

6'-(2-Hydroxy-ethyl)-1-(3-hydroxy-pyrrolidin-3-yl-acetyl)-sisomicin

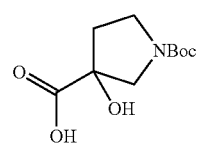 [SMILES: CC(C)(C)OC(=O)N1CCC(O)(C(=O)O)C1]

N-Boc-3-hydroxypyrrolidine-3-carboxylic acid

N-Boc-3-pyrrolidone (0.010 mmol) was submitted to Procedure 15 to yield the desired N-Boc-3-hydroxy-pyrrolidine-3-carboxylic acid.

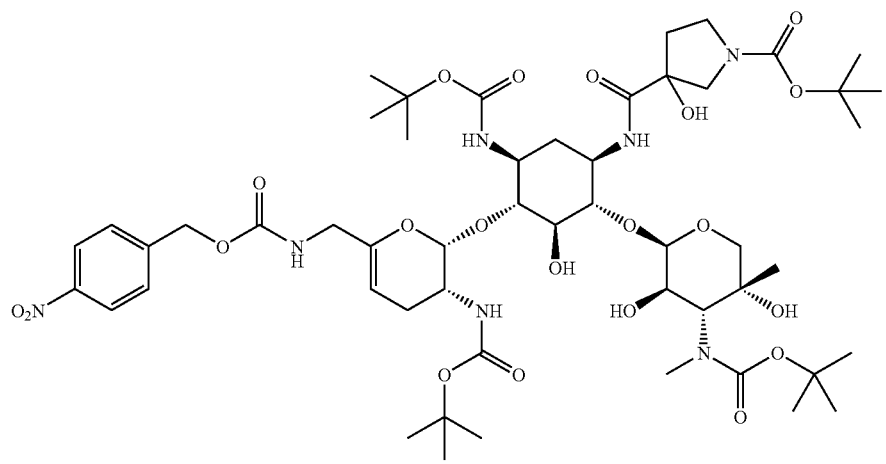 [SMILES: CN(C(=O)OC(C)(C)C)[C@@H]1[C@@H](O)[C@@H](O[C@@H]2[C@@H](O)[C@H](O[C@H]3OC(CNC(=O)OCc4ccc([N+](=O)[O-])cc4)=CC[C@H]3NC(=O)OC(C)(C)C)[C@@H](NC(=O)OC(C)(C)C)C[C@H]2NC(=O)C2(O)CCN(C(=O)OC(C)(C)C)C2)OC[C@]1(C)O]

6'-PNZ-2',3,3''-triBoc-1-(N-Boc-3-hydroxy-pyrrolidin-3-yl-acetyl)-sisomicin

Treatment of 6'-PNZ-2',3,3''-triBoc-sisomicin (0.075 g, 0.081 mmol) with N-Boc-3-hydroxy-pyrrolidine-3-carboxylic acid following Procedure 4-Method B gave the desired 6'-PNZ-2',3,3''-triBoc-1-(N-Boc-3-hydroxy-pyrrolidin-3-yl-acetyl)-sisomicin (MS m/e [M+H]$^+$ calcd 1140.6, found 1141.4), which was carried through to the next step without further purification.

2',3,3''-triBoc-1-(N-Boc-3-hydroxy-pyrrolidin-3-yl-acetyl)-sisomicin

6'-PNZ-2',3,3''-triBoc-1-(N-Boc-3-hydroxy-pyrrolidin-3-yl-acetyl)-sisomicin (0.081 mmol) was submitted to Procedure 2 for PNZ removal to yield 2',3,3''-triBoc-1-(N-Boc-3-hydroxy-pyrrolidin-3-yl-acetyl)-sisomicin (MS m/e [M+H]$^+$ calcd 961.5, found 961.8), which was carried through to the next step without further purification.

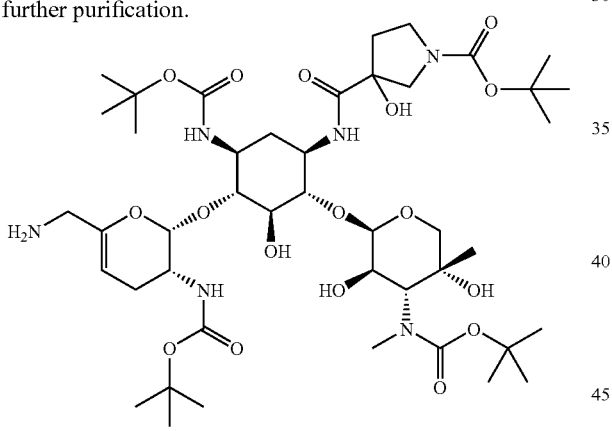

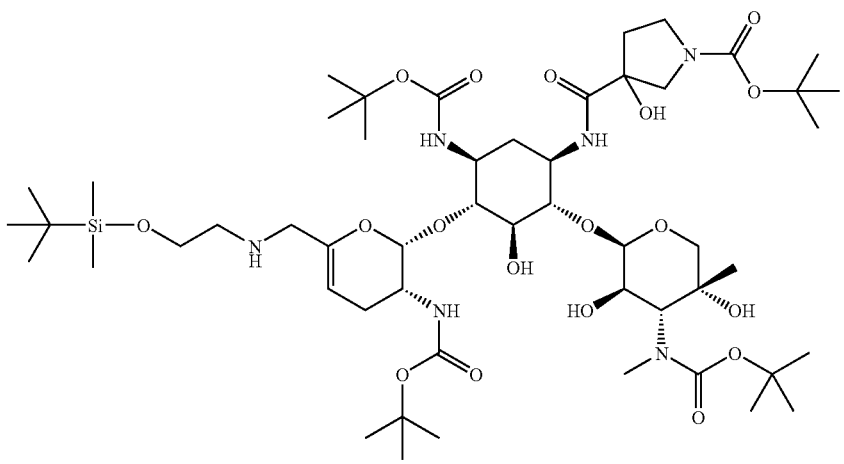 [SMILES: CN(C(=O)OC(C)(C)C)[C@@H]1[C@@H](O)[C@@H](O[C@@H]2[C@@H](O)[C@H](O[C@H]3OC(CNCCO[Si](C)(C)C(C)(C)C)=CC[C@H]3NC(=O)OC(C)(C)C)[C@@H](NC(=O)OC(C)(C)C)C[C@H]2NC(=O)C2(O)CCN(C(=O)OC(C)(C)C)C2)OC[C@]1(C)O]

6'-(2-tert-Butyldimethylsilyloxy-ethyl)-2',3,3''-tri-Boc-1-(N-Boc-3-hydroxy-pyrrolidin-3-yl-acetyl)-sisomicin 2',3,3''-triBoc-1-(N-Boc-3-hydroxy-pyrrolidin-3-yl-acetyl)-sisomicin (0.081 mmol) was treated with tert-butyldimethylsilyloxy acetaldehyde following Procedure 1-Method A to yield the desired 6'-(2-tert-butyldimethylsilyloxy-ethyl)-2',3,3''-triBoc-1-(N-Boc-3-hydroxy-pyrrolidin-3-yl-acetyl)-sisomicin (MS m/e [M+H]+ calcd 1119.6, found 1119.9), which was carried through to the next step without further purification.

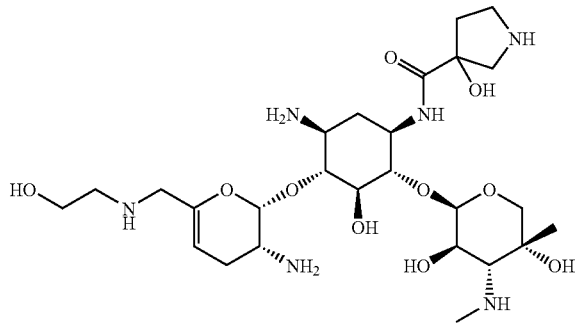 [SMILES: CN[C@@H]1[C@@H](O)[C@@H](O[C@@H]2[C@@H](O)[C@H](O[C@H]3OC(CNCCO)=CC[C@H]3N)[C@@H](N)C[C@H]2NC(=O)C2(O)CCNC2)OC[C@]1(C)O]

6'-(2-Hydroxy-ethyl)-1-(3-hydroxy-pyrrolidin-3-yl-acetyl)-sisomicin

6'-(2-tert-Butyldimethylsilyloxy-ethyl)-2',3,3''-triBoc-1-(N-Boc-3-hydroxy-pyrrolidin-3-yl-acetyl)-sisomicin (0.081 mmol) was submitted to Procedure 3-Method A for Boc and TBS removal to yield a crude, which was purified by RP HPLC Method 3 to yield 6'-(2-hydroxy-ethyl)-1-(3-hydroxy-pyrrolidin-3-yl-acetyl)-sisomicin (0.008 g, 0.013 mmol, 16.0% yield): MS m/e [M+H]+ calcd 605.3, found 605.8; CLND 92.2% purity.

Example 35

6'-(2-Hydroxy-4-amino-butyl)-1-(3-hydroxy-pyrrolidin-3-yl-acetyl)-sisomicin

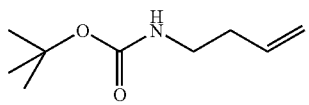

N-Boc-1-amino-but-3-ene

3-Buten-1-amine (4.93 g, 0.069 mol) was submitted to Procedure 13 for Boc protection to yield a crude, which was purified by flash chromatography (silica gel/hexanes: ethyl acetate 0-30%) to yield N-Boc-1-amino-but-3-ene (6.47 g, 0.038 mol, 55.1% yield).

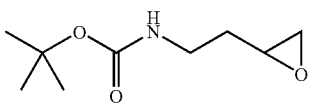

N-Boc-2-(oxiran-2-yl)-ethyl carbamate

N-Boc-1-amino-but-3-ene (6.47 g, 0.038 mol) was submitted to Procedure 14 for epoxide formation to yield a crude, which was purified by flash chromatography (silica gel/hexanes:ethyl acetate 0-45%) to yield N-Boc-2-(oxiran-2-yl)-ethyl carbamate (6.0 g, 0.032 mol, 84.2% yield): $^1$H NMR (250 MHz, DMSO-$d_6$) δ 2.98-3.09 (m, 2 H), 2.83-2.92 (m, 1 H), 2.65 (t, 1 H), 2.42 (dd, 1 H), 1.44-1.66 (m, 2 H), 1.36 (s, 9 H, (CH$_3$)$_3$).

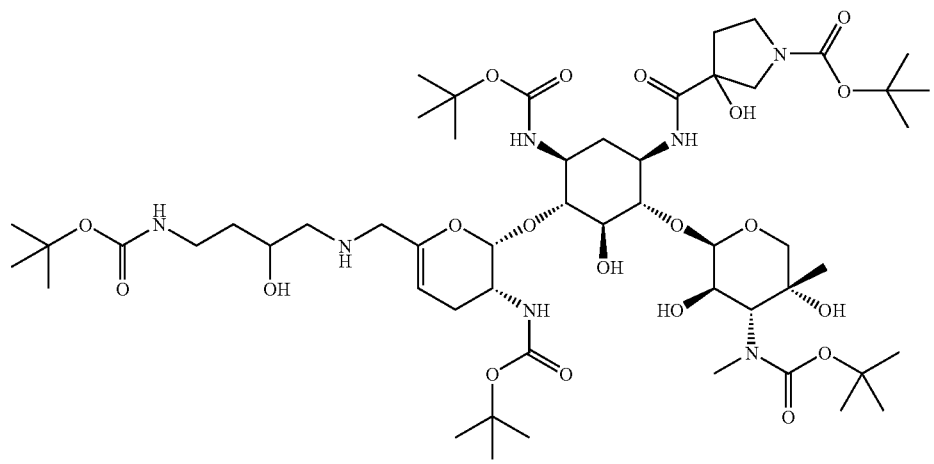 [SMILES: CN(C(=O)OC(C)(C)C)[C@@H]1[C@@H](O)[C@@H](O[C@@H]2[C@@H](O)[C@H](O[C@H]3OC(CNCC(O)CCNC(=O)OC(C)(C)C)=CC[C@H]3NC(=O)OC(C)(C)C)[C@@H](NC(=O)OC(C)(C)C)C[C@H]2NC(=O)C2(O)CCN(C(=O)OC(C)(C)C)C2)OC[C@]1(C)O]

6'-(N-Boc-2-hydroxy-4-amino-butyl)-2',3,3''-triBoc-1-(N-Boc-3-hydroxy-pyrrolidin-3-yl-acetyl)-sisomicin 2',3,3''-triBoc-1-(N-Boc-3-hydroxy-pyrrolidin-3-yl-acetyl)-sisomicin (0.081 mmol) was treated with N-Boc-2-(oxiran-2-yl)-ethyl carbamate following Procedure 5 to yield the desired 6'-(N-Boc-2-hydroxy-4-amino-butyl)-2',3,3''-triBoc-1-(N-Boc-3-hydroxy-pyrrolidin-3-yl-acetyl)-sisomicin (MS m/e [M+H]$^+$ calcd 1148.6, found 1149.1), which was carried through to the next step without further purification.

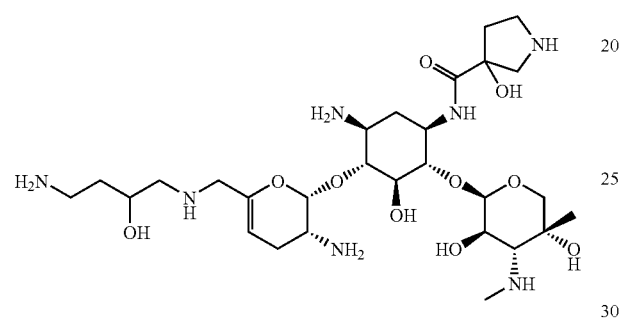

6'-(2-Hydroxy-4-amino-butyl)-1-(3-hydroxy-pyrrolidin-3-yl-acetyl)-sisomicin

6'-(N-Boc-2-hydroxy-4-amino-butyl)-2',3,3''-triBoc-1-(N-Boc-3-hydroxy-pyrrolidin-3-yl-acetyl)-sisomicin (0.081 mmol) was submitted to Procedure 3-Method A for Boc removal to yield a crude, which was purified by RP HPLC Method 3 to yield 6'-(2-hydroxy-4-amino-butyl)-1-(3-hydroxy-pyrrolidin-3-yl-acetyl)-sisomicin (0.0015 g, 0.0023 mmol, 2.8% yield): MS m/e [M+H]$^+$ calcd 648.4, found 648.4; CLND 87.1% purity.

Example 36

6'-(Methyl-cyclopropyl)-1-(3-hydroxy-azetidin-3-yl-acetyl)-sisomicin

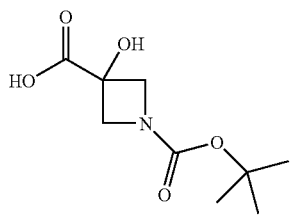

N-Boc-3-hydroxy-azetidin-3-carboxylic acid

N-Boc-3-azetidinone (21.9 g, 0.128 mol) was submitted to Procedure 15 to yield the desired N-Boc-3-hydroxy-azetidin-3-carboxylic acid (18.7 g, 0.086 mol, 67.0% yield): MS m/e [M+H]$^+$ calcd 218.1, found 218.2.

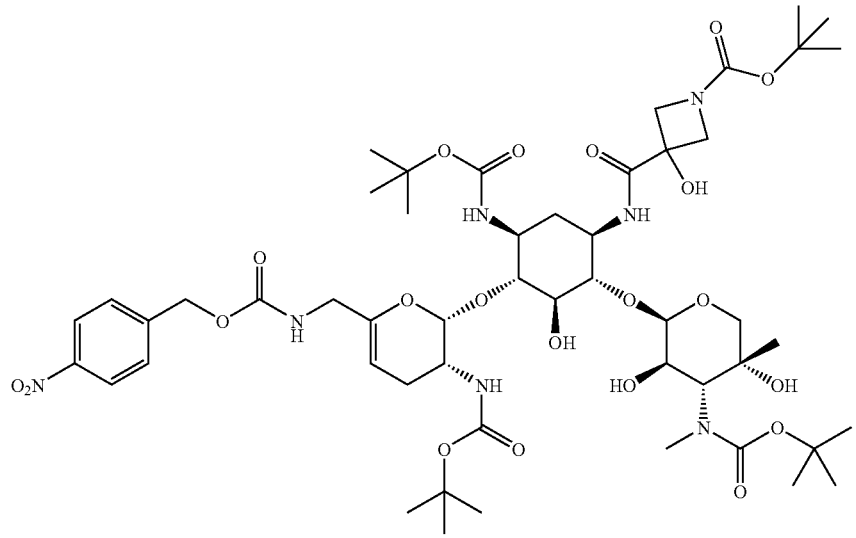 [SMILES: CN(C(=O)OC(C)(C)C)[C@@H]1[C@@H](O)[C@@H](O[C@@H]2[C@@H](O)[C@H](O[C@H]3OC(CNC(=O)OCc4ccc([N+](=O)[O-])cc4)=CC[C@H]3NC(=O)OC(C)(C)C)[C@@H](NC(=O)OC(C)(C)C)C[C@H]2NC(=O)C2(O)CN(C(=O)OC(C)(C)C)C2)OC[C@]1(C)O]

6'-PNZ-2',3,3''-triBoc-1-(N-Boc-3-hydroxy-azetidin-3-yl-acetyl)-sisomicin

Treatment of 6'-PNZ-2',3,3''-triBoc-sisomicin (0.075 g, 0.081 mmol) with N-Boc-3-hydroxy-azetidin-3-carboxylic acid following Procedure 4-Method B gave the desired 6'-PNZ-2',3,3''-triBoc-1-(N-Boc-3-hydroxy-azetidin-3-yl-acetyl)-sisomicin, which was carried through to the next step without further purification.

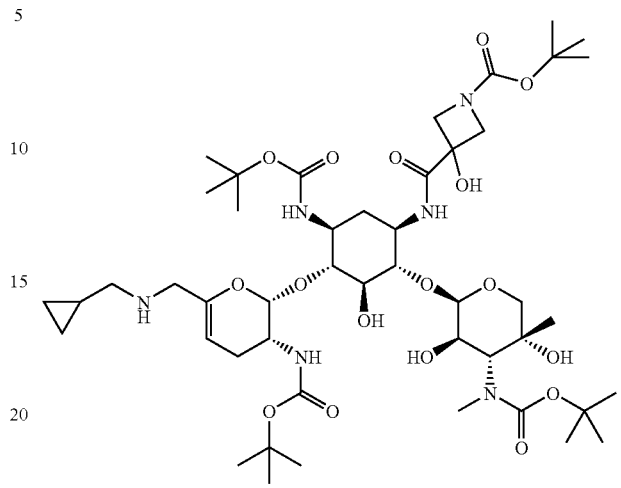

2',3,3''-triBoc-1-(N-Boc-3-hydroxy-azetidin-3-yl-acetyl)-sisomicin

6'-PNZ-2',3,3''-triBoc-1-(N-Boc-3-hydroxy-azetidin-3-yl-acetyl)-sisomicin (0.081 mmol) was submitted to Procedure 2 for PNZ removal to yield 2',3,3''-triBoc-1-(N-Boc-3-hydroxy-azetidin-3-yl-acetyl)-sisomicin (MS m/e [M+H]+ calcd 947.5, found 948.0), which was carried through to the next step without further purification.

6'-(Methyl-cyclopropyl)-2',3,3''-triBoc-1-(N-Boc-3-hydroxy-azetidin-3-yl-acetyl)-sisomicin 2',3,3''-triBoc-1-(N-Boc-3-hydroxy-azetidin-3-yl-acetyl)-sisomicin (0.081 mmol) was treated with cyclopropane carboxaldehyde following Procedure 1-Method A to yield the desired 6'-(methyl-cyclopropyl)-2',3,3''-triBoc-1-(N-Boc-3-hydroxy-azetidin-3-yl-acetyl)-sisomicin (MS m/e [M+H]+ calcd 1001.6, found 1101.9), which was carried through to the next step without further purification.

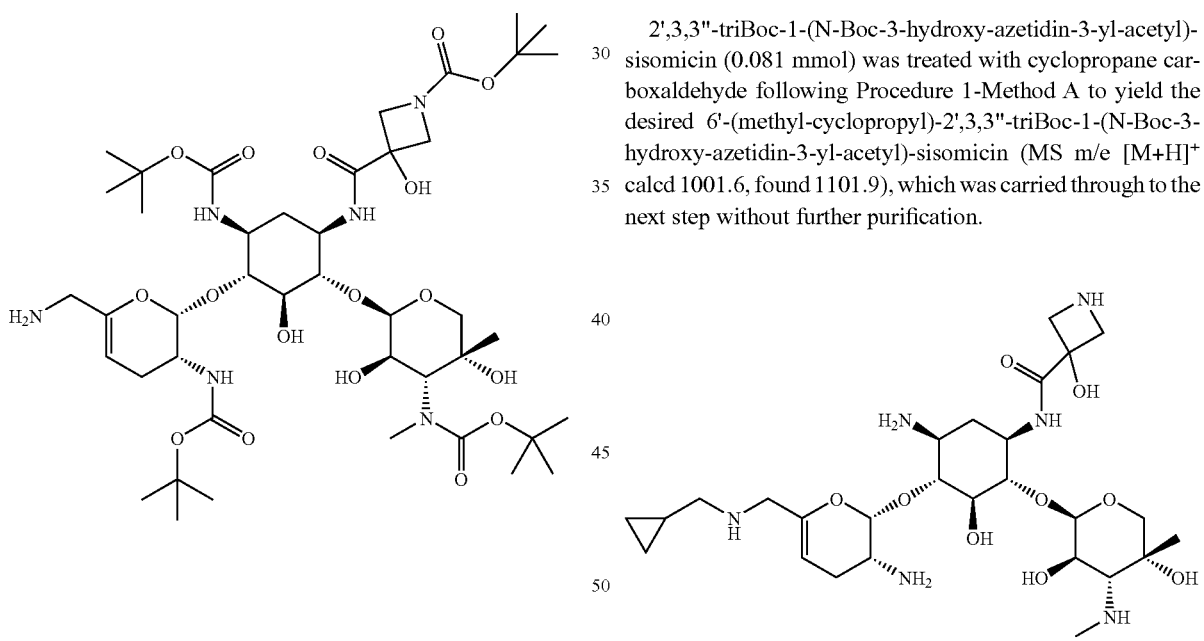

6'-(Methyl-cyclopropyl)-1-(3-hydroxy-azetidin-3-yl-acetyl)-sisomicin

6'-(Methyl-cyclopropyl)-2',3,3''-triBoc-1-(N-Boc-3-hydroxy-azetidin-3-yl-acetyl)-sisomicin (0.081 mmol) was submitted to Procedure 3-Method A for Boc removal to yield a crude, which was purified by RP HPLC Method 1-Column A to yield 6'-(methyl-cyclopropyl)-1-(3-hydroxy-azetidin-3-yl-acetyl)-sisomicin (0.0041 g 0.0068 mmol, 8.4% yield): MS m/e [M+H]+ calcd 601.3, found 601.6; CLND 88.2% purity.

Example 37

6'-(2-Hydroxy-ethyl)-1-(3-hydroxy-azetidin-3-yl-acetyl)-sisomicin

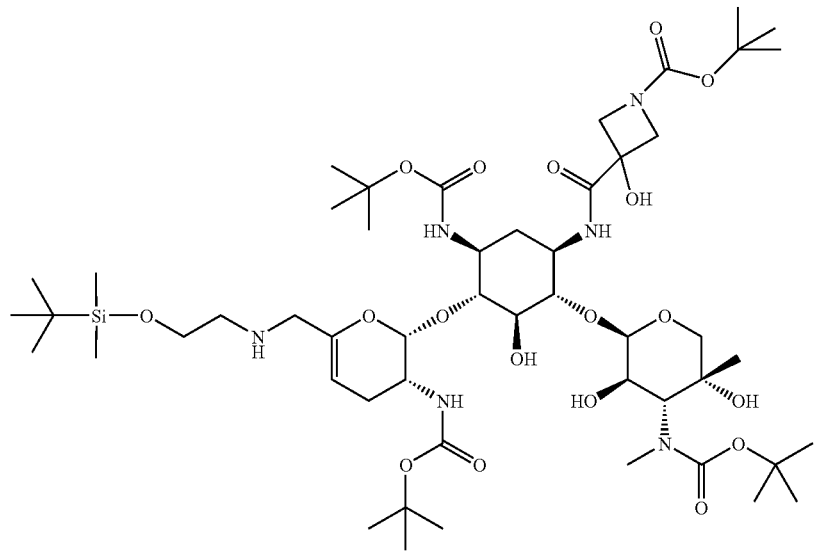 [SMILES: CN(C(=O)OC(C)(C)C)[C@@H]1[C@@H](O)[C@@H](O[C@@H]2[C@@H](O)[C@H](O[C@H]3OC(CNCCO[Si](C)(C)C(C)(C)C)=CC[C@H]3NC(=O)OC(C)(C)C)[C@@H](NC(=O)OC(C)(C)C)C[C@H]2NC(=O)C2(O)CN(C(=O)OC(C)(C)C)C2)OC[C@]1(C)O]

6'-(2-tert-Butyldimethylsilyloxy-ethyl)-2',3,3"-tri-Boc-1-(N-Boc-3-hydroxy-azetidin-3-yl-acetyl)-sisomicin 2',3,3"-triBoc-1-(N-Boc-3-hydroxy-azetidin-3-yl-acetyl)-sisomicin (0.081 mmol) was treated with tert-butyldimethylsilyloxy acetaldehyde following Procedure 1-Method A to yield the desired 6'-(2-tert-butyldimethylsilyloxy-ethyl)-2',3,3"-triBoc-1-(N-Boc-3-hydroxy-azetidin-3-yl-acetyl)-sisomicin (MS m/e [M+H]$^+$ calcd 1105.6, found 1106.0), which was carried through to the next step without further purification.

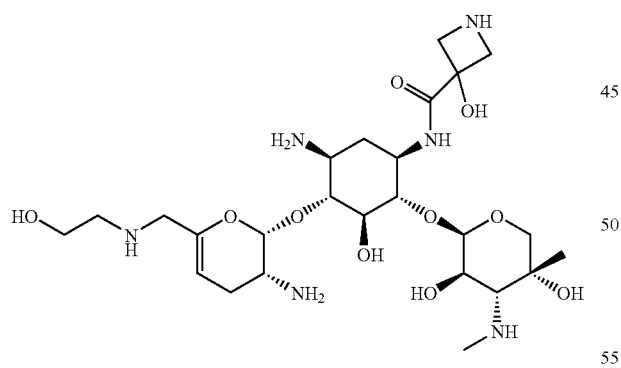

6'-(2-Hydroxy-ethyl)-1-(3-hydroxy-azetidin-3-yl-acetyl)-sisomicin

6'-(2-tert-Butyldimethylsilyloxy-ethyl)-2',3,3"-triBoc-1-(N-Boc-3-hydroxy-azetidin-3-yl-acetyl)-sisomicin (0.081 mmol) was submitted to Procedure 3-Method A for Boc and TBS removal to yield a crude, which was purified by RP HPLC Method 1-Column A to yield 6'-(2-hydroxy-ethyl)-1 (3-hydroxy-azetidin-3-yl-acetyl)-sisomicin (0.0039 g, 0.0066 mmol, 8.1% yield): MS m/e [M+H]$^+$ calcd 591.3, found 591.4; CLND 94.7% purity.

Example 38

6'-(2-Amino-ethyl)-1-(4-amino-2(S)-hydroxy-butyryl)-sisomicin

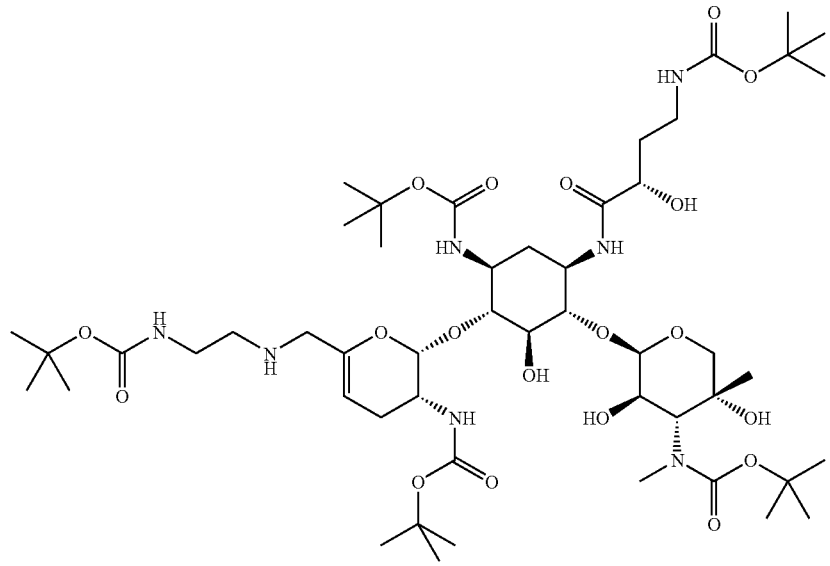 [SMILES: CN(C(=O)OC(C)(C)C)[C@@H]1[C@@H](O)[C@@H](O[C@@H]2[C@@H](O)[C@H](O[C@H]3OC(CNCCNC(=O)OC(C)(C)C)=CC[C@H]3NC(=O)OC(C)(C)C)[C@@H](NC(=O)OC(C)(C)C)C[C@H]2NC(=O)[C@@H](O)CCNC(=O)OC(C)(C)C)OC[C@]1(C)O]

6'-(N-Boc-2-amino-ethyl)-2',3,3''-triBoc-1-(N-Boc-4-amino-2(S)-hydroxy-butyryl)-sisomicin 2',3,3''-triBoc-1-(N-Boc-4-amino-2(S)-hydroxy-butyryl)-sisomicin (0.075 g, 0.079 mmol) was treated with N-Boc-2-amino acetaldehyde following Procedure 1-Method A to give the desired 6'-(N-Boc-2-amino-ethyl)-2',3,3''-triBoc-1-(N-Boc-4-amino-2(S)-hydroxy-butyryl)-sisomicin (MS m/e [M+H]$^+$ calcd 1092.6, found 1093.0), which was carried through to the next step without further purification.

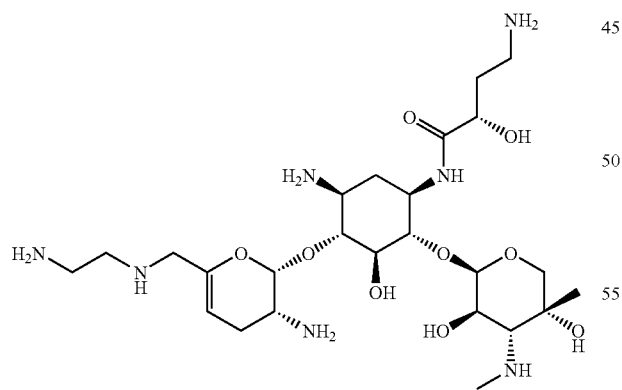

6'-(2-Amino-ethyl)-1-(4-amino-2(S)-hydroxy-butyryl)-sisomicin

6'-(N-Boc-2-amino-ethyl)-2',3,3''-triBoc-1-(N-Boc-4-amino-2(S)-hydroxy-butyryl)-sisomicin (0.079 mmol) was submitted to Procedure 3-Method A for Boc removal to yield a crude, which was purified by RP HPLC Method 3 to yield 6'-(2-amino-ethyl)-1-(4-amino-2(S)-hydroxy-butyryl)-sisomicin (0.0048 g, 0.0081 mmol, 10.2% yield): MS m/e [M+H]$^+$ calcd 592.4, found 592.6; CLND 77.1% purity.

Example 39

6'-(Methyl-(1-hydroxy-3-methylamino-cyclobutyl)-1-(4-amino-2(S)-hydroxy-butyryl)-sisomicin

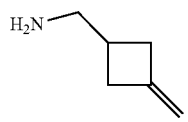

3-Methylene-1-methylamino-cyclobutane

To a stirring solution of 3-methylene-1-cyano-cyclobutane (2.5 g, 0.026 mol) in THF (35 ml) at 0° C. was slowly added 2M LiAlH$_4$ (22 mL, 0.044 mmol) and the reaction was allowed to warm to room temperature. The reaction was then quenched by the addition of sat. aq. NH$_4$Cl (10 mL), and THF (10 mL). The organic layer was separated and concentrated to dryness to yield a residue, which was dissolved in ethyl acetate (100 mL). The organic layer was washed with 5% NaHCO$_3$ (2×20 mL), brine (20 mL), dried over Na$_2$SO$_4$, filtered and concentrated to yield the desired 3-methylene-1-methylamino-cyclobutane as an oil, which was carried through to the next step without further purification.

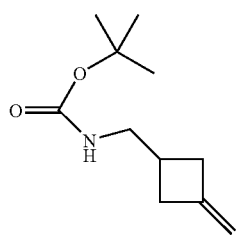

3-Methylene-1-N-Boc-methylamino-cyclobutane

To a stirring solution of 3-methylene-1-methylamino-cyclobutane (2.52 g, 0.026 mol) in 1N NaOH (15 ml) and THF (15 mL), was added Boc$_2$O (6.7 g, 0.030 mol) and the reaction mixture was stirred overnight. THF was evaporated and the aqueous layer was extracted with ethyl acetate (2×40 mL). The combined organic layers were washed with 5% NaHCO$_3$ (2×20 mL) brine (20 mL), dried over Na$_2$SO$_4$, filtered and concentrated to dryness to yield a crude, which was purified by flash chromatography (silica gel/hexanes:ethyl acetate 0%-60%) to yield the desired 3-methylene-1-N-Boc-methylamino-cyclobutane (1.9 g, 0.0096 mol, 36.9% yield): $^1$H NMR (250 MHz, DMSO-d$_6$) δ 6.88 (bs, 1 H), 4.72 (s, 2 H), 2.95-3.05 (m, 2 H), 2.56-2.71 (m, 2 H), 2.21-2.40 (m, 3 H), 1.20 (s, 9 H).

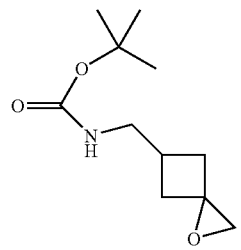

N-Boc-1-oxaspiro[2.3]hexan-5-yl-methanamine

3-Methylene-1-N-Boc-methylamino-cyclobutane (1.9 g, 0.0096 mol) was submitted to Procedure 14 for epoxide formation to yield N-Boc-1-oxaspiro[2.3]hexan-5-yl-methanamine (1.34 g, 6.27 mol, 65.3% yield): $^1$H NMR (250 MHz, DMSO-d$_6$) δ 2.99-3.10 (m, 2 H), 2.60-2.66 (m, 2 H), 1.99-2.47 (m, 5 H), 1.40 (s, 9 H).

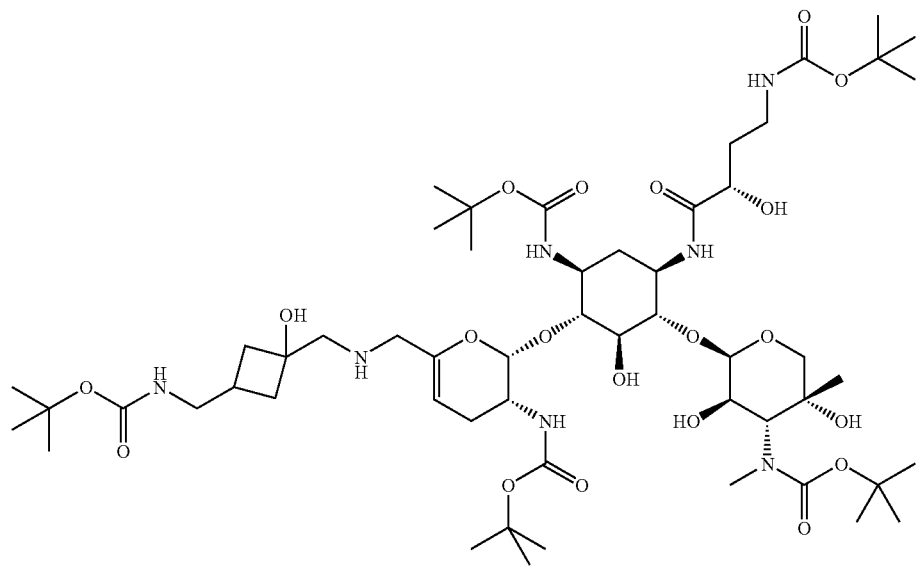 [SMILES: CN(C(=O)OC(C)(C)C)[C@@H]1[C@@H](O)[C@@H](O[C@@H]2[C@@H](O)[C@H](O[C@H]3OC(CNCC4(O)CC(CNC(=O)OC(C)(C)C)C4)=CC[C@H]3NC(=O)OC(C)(C)C)[C@@H](NC(=O)OC(C)(C)C)C[C@H]2NC(=O)[C@@H](O)CCNC(=O)OC(C)(C)C)OC[C@]1(C)O]

149

6'-(Methyl-(1-hydroxy-N-Boc-3-methylamino-cyclobutyl)-2',3,3''-triBoc-1-(N-Boc-4-amino-2(S)-hydroxy-butyryl)-sisomicin

2',3,3''-triBoc-1-(N-Boc-4-amino-2(S)-hydroxy-butyryl)-sisomicin (0.075 g, 0.079 mmol) was treated with N-Boc-1-oxaspiro[2.3]hexan-5-yl-methanamine following Procedure 5 to give the desired 6'-(methyl-(1-hydroxy-N-Boc-3-methylamino-cyclobutyl)-2',3,3''-triBoc-1-(N-Boc-4-amino-2(S)-hydroxy-butyryl)-sisomicin (MS m/e [M+H]$^+$ calcd 1162.7, found 1163.0), which was carried through to the next step without further purification.

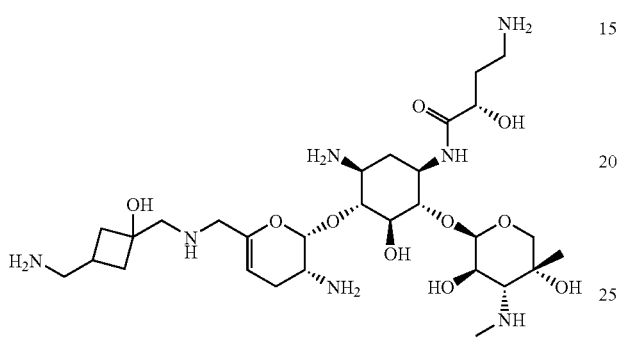

150

6'-(Methyl-(1-hydroxy-3-methylamino-cyclobutyl)-1-(4-amino-2(S)-hydroxy-butyryl)-sisomicin

6'-(Methyl-(1-hydroxy-N-Boc-3-methylamino-cyclobutyl)-2',3,3''-triBoc-1-(N-Boc-4-amino-2(S)-hydroxy-butyryl)-sisomicin (0.079 mmol) was submitted to Procedure 3-Method A for Boc removal to yield a crude, which was purified by RP HPLC Method 3 to yield 6'-(methyl-(1-hydroxy-3-methylamino-cyclobutyl)-1-(4-amino-2(S)-hydroxy-butyryl)-sisomicin (0.0037 g, 0.0056 mmol, 7.1% yield): MS m/e [M+H]$^+$ calcd 662.4, found 662.0; CLND 82.5% purity.

Example 40

6'-(3-Amino-propyl)-1-(3-hydroxy-pyrrolidin-3-yl-acetyl)-sisomicin

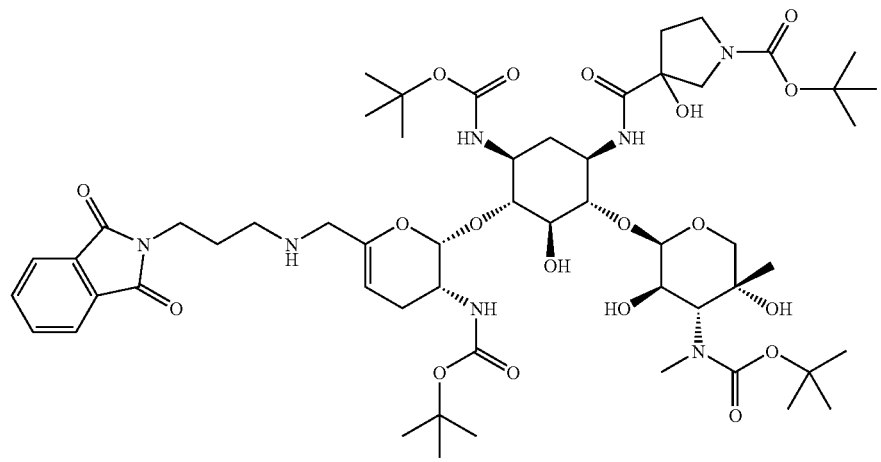 [SMILES: CN(C(=O)OC(C)(C)C)[C@@H]1[C@@H](O)[C@@H](O[C@@H]2[C@@H](O)[C@H](O[C@H]3OC(CNCCCN4C(=O)c5ccccc5C4=O)=CC[C@H]3NC(=O)OC(C)(C)C)[C@@H](NC(=O)OC(C)(C)C)C[C@H]2NC(=O)C2(O)CCN(C(=O)OC(C)(C)C)C2)OC[C@]1(C)O]

6'-(N-Phthalimido-3-amino-propyl)-2',3,3"-triBoc-1-(N-Boc-3-hydroxy-pyrrolidin-3-yl-acetyl)-sisomicin 2',3,3"-triBoc-1-(N-Boc-3-hydroxy-pyrrolidin-3-yl-acetyl)-sisomicin (0.081 mmol) was treated with N-phthalimido propionaldehyde following Procedure 1-Method A to yield the desired 6'-(N-phthalimido-3-amino-propyl)-2',3,3"-triBoc-1-(N-Boc-3-hydroxy-pyrrolidin-3-yl-acetyl)-sisomicin (MS m/e [M+H]+ calcd 1148.6, found 1148.8), which was carried through to the next step without further purification.

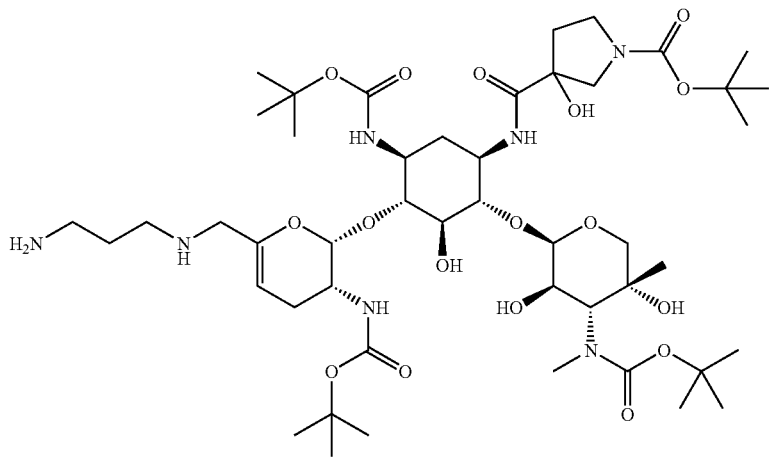 [SMILES: CN(C(=O)OC(C)(C)C)[C@@H]1[C@@H](O)[C@@H](O[C@@H]2[C@@H](O)[C@H](O[C@H]3OC(CNCCCN)=CC[C@H]3NC(=O)OC(C)(C)C)[C@@H](NC(=O)OC(C)(C)C)C[C@H]2NC(=O)C2(O)CCN(C(=O)OC(C)(C)C)C2)OC[C@]1(C)O]

6'-(3-Amino-propyl)-2',3,3"-triBoc-1-(N-Boc-3-hydroxy-pyrrolidin-3-yl-acetyl)-sisomicin 6'-(N-Phthalimido-3-amino-propyl)-2',3,3"-triBoc-1-(N-Boc-3-hydroxy-pyrrolidin-3-yl-acetyl)-sisomicin (0.081 mmol) was submitted to Procedure 6 for phthalimido deprotection to yield 6'-(3-amino-propyl)-2',3,3"-triBoc-1-(N-Boc-3-hydroxy-pyrrolidin-3-yl-acetyl)-sisomicin, which was carried through to the next step without further purification.

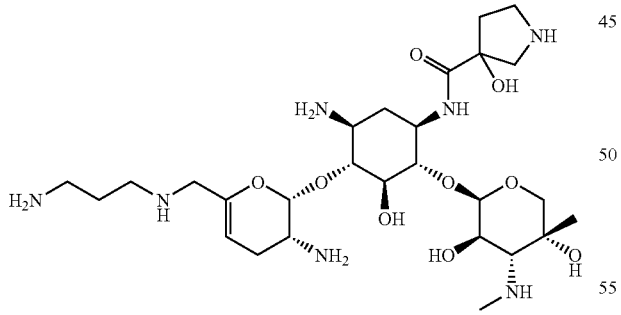

6'-(3-Amino-propyl)-1-(3-hydroxy-pyrrolidin-3-yl-acetyl)-sisomicin

6'-(3-Amino-propyl)-2',3,3"-triBoc-1-(N-Boc-3-hydroxy-pyrrolidin-3-yl-acetyl)-sisomicin (0.081 mmol) was submitted to Procedure 3-Method A for Boc removal to yield a crude, which was purified by RP HPLC Method 3 to yield 6'-(3-amino-propyl)-1-(3-hydroxy-pyrrolidin-3-yl-acetyl)-sisomicin (0.0023 g, 0.0037 mmol, 4.6% yield): MS m/e [M+H]+ calcd 618.4, found 618.8; CLND 93.1% purity.

Example 41

6'-(Methyl-cyclopropyl)-1-(3-hydroxy-pyrrolidin-3-yl-acetyl)-sisomicin

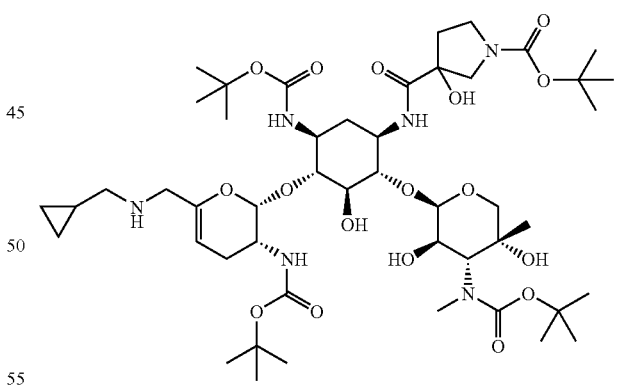

6'-(Methyl-cyclopropyl)-2',3,3"-triBoc-1-(N-Boc-3-hydroxy-pyrrolidin-3-yl-acetyl)-sisomicin 2',3,3"-triBoc-1-(N-Boc-3-hydroxy-pyrrolidin-3-yl-acetyl)-sisomicin (0.081 mmol) was treated with cyclopropane carboxaldehyde following Procedure 1-Method A to yield the desired 6'-(methyl-cyclopropyl)-2',3,3"-triBoc-1-(N-Boc-3-hydroxy-pyrrolidin-3-yl-acetyl)-sisomicin (MS m/e [M+H]+ calcd 1015.6, found 1015.6), which was carried through to the next step without further purification.

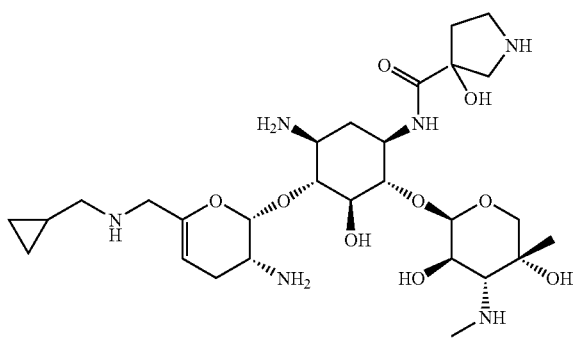 [SMILES: CN[C@@H]1[C@@H](O)[C@@H](O[C@@H]2[C@@H](O)[C@H](O[C@H]3OC(CNCC4CC4)=CC[C@H]3N)[C@@H](N)C[C@H]2NC(=O)C2(O)CCNC2)OC[C@]1(C)O]

6'-(Methyl-cyclopropyl)-1-(3-hydroxy-pyrrolidin-3-yl-acetyl)-sisomicin

6'-(methyl-cyclopropyl)-2',3,3"-triBoc-1-(N-Boc-3-hydroxy-pyrrolidin-3-yl-acetyl)-sisomicin (0.081 mmol) was submitted to Procedure 3-Method A for Boc removal to yield a crude, which was purified by RP HPLC Method 3 to yield 6'-(methyl-cyclopropyl)-1-(3-hydroxy-pyrrolidin-3-yl-acetyl)-sisomicin (0.0021 g, 0.0034 mmol, 4.2% yield): MS m/e [M+H]+ calcd 615.4, found 615.2; CLND 96.5% purity.

Example 42

6'-(2-Hydroxy-3-amino-propyl)-1-(3-hydroxy-pyrrolidin-3-yl-acetyl)-sisomicin

6'-(N-Boc-2-hydroxy-3-amino-propyl)-2',3,3"-tri-Boc-1-(N-Boc-3-hydroxy-pyrrolidin-3-yl-acetyl)-sisomicin 2',3,3"-triBoc-1-(N-Boc-3-hydroxy-pyrrolidin-3-yl-acetyl)-sisomicin (0.081 mmol) was treated with N-Boc-oxiran-2-yl-methanamine following Procedure 5 to yield the desired 6'-(N-Boc-2-hydroxy-3-amino-propyl)-2',3,3"-tri-Boc-1-(N-Boc-3-hydroxy-pyrrolidin-3-yl-acetyl)-sisomicin (MS m/e [M+H]+ calcd 1134.6, found 1134.9), which was carried through to the next step without further purification.

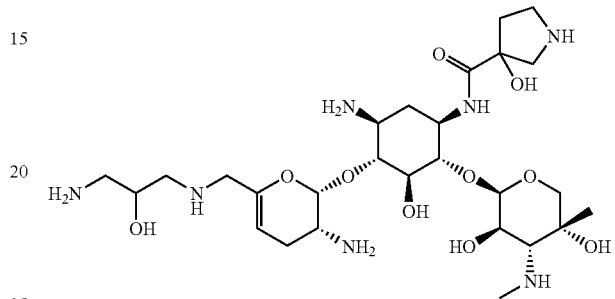

6'-(2-Hydroxy-3-amino-propyl)-1-(3-hydroxy-pyrrolidin-3-yl-acetyl)-sisomicin

6'-(N-Boc-2-hydroxy-3-amino-propyl)-2',3,3"-triBoc-1-(N-Boc-3-hydroxy-pyrrolidin-3-yl-acetyl)-sisomicin (0.081 mmol) was submitted to Procedure 3-Method A for Boc removal to yield a crude, which was purified by RP HPLC Method 3 to yield 6'-(2-hydroxy-3-amino-propyl)-1-(3-hy-

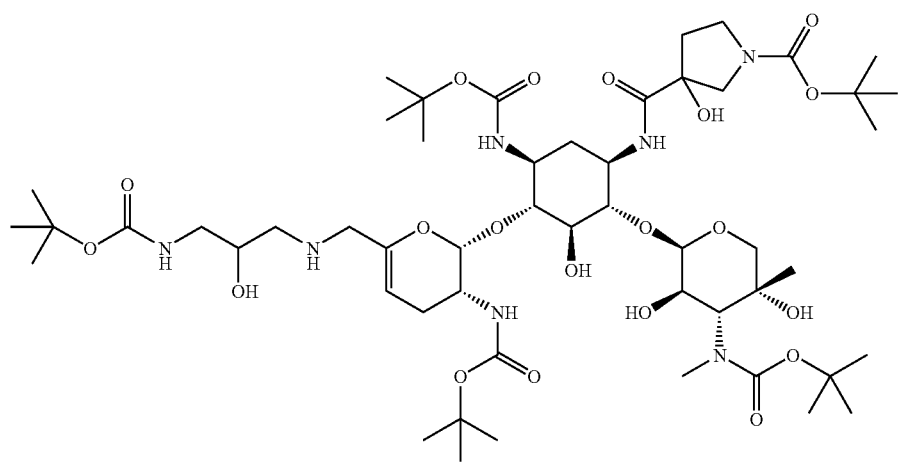 [SMILES: CN(C(=O)OC(C)(C)C)[C@@H]1[C@@H](O)[C@@H](O[C@@H]2[C@@H](O)[C@H](O[C@H]3OC(CNCC(O)CNC(=O)OC(C)(C)C)=CC[C@H]3NC(=O)OC(C)(C)C)[C@@H](NC(=O)OC(C)(C)C)C[C@H]2NC(=O)C2(O)CCN(C(=O)OC(C)(C)C)C2)OC[C@]1(C)O]

droxy-pyrrolidin-3-yl-acetyl)-sisomicin (0.003 g, 0.0047 mmol, 5.8% yield): MS m/e [M+H]$^+$ calcd 634.4, found 634.4; CLND 95.1% purity.

Example 43

6'-(4-Amino-butyl)-1-(4-amino-2(S)-hydroxy-butyryl)-sisomicin

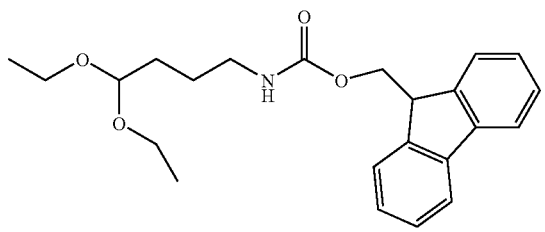 [SMILES: CCOC(CCCNC(=O)OCC1c2ccccc2-c2ccccc21)OCC]

N-Fmoc-4-amino-butyraldehyde diethyl acetal

4-Amino-butyraldehyde diethyl acetal (8.0 g, 0.050 mol) was Fmoc protected following Procedure 16 to give the desired N-Fmoc-4-amino-butyraldehyde diethyl acetal (22.08 g, MS m/e [M+Na]$^+$ calcd 406.2, found 406.1), which was carried through to the next step without further purification.

N-Fmoc-4-amino-butyraldehyde

To a stirring solution of N-Fmoc-4-amino-butyraldehyde diethyl acetal (0.050 mmol) in 1,4-dioxane (100 mL) was added aq. HCl (100 ml, 1:1 v/v, H$_2$O:conc. HCl) and the reaction progress was monitored by MS. Upon completion, the organic solvent was removed by rotary evaporation, and the aqueous layer was extracted with ethyl acetate (2×200 mL). The combined organic layers were washed with 5% NaHCO$_3$ (2×75 mL), brine (75 mL), dried over Na$_2$SO$_4$, filtered and concentrated to dryness to yield the desired N-Fmoc-4-amino-butyraldehyde (15.35 g, 0.049 mol, 90.0% yield), which was carried through to the next step without further purification: MS m/e [M+Na]$^+$ calcd 332.1, found 332.0.

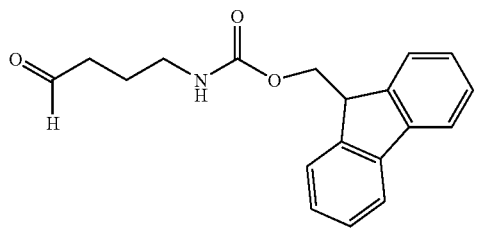 [SMILES: O=CCCCNC(=O)OCC1c2ccccc2-c2ccccc21]

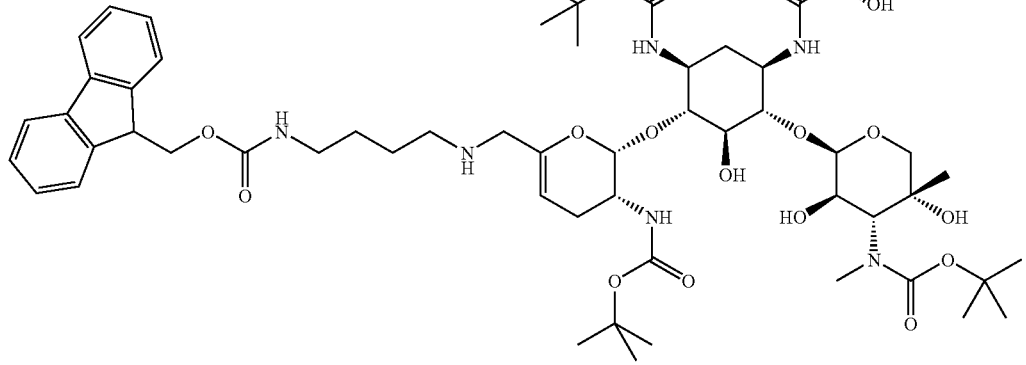

6'-(N-Fmoc-4-amino-butyl)-2',3,3"-triBoc-1-(N-Boc-4-amino-2(S)-hydroxy-butyryl)-sisomicin 2',3,3"-triBoc-1-(N-Boc-4-amino-2(S)-hydroxy-butyryl)-sisomicin (0.075 g, 0.079 mmol) was treated with N-Fmoc-4-amino-butyraldehyde following Procedure 1-Method A to give the desired 6'-(N-Fmoc-4-amino-butyl)-2',3,3"-triBoc-1-(N-Boc-4-amino-2(S)-hydroxy-butyryl)-sisomicin (MS m/e [M+H]$^+$ calcd 1242.7, found 1242.9), which was carried through to the next step without further purification.

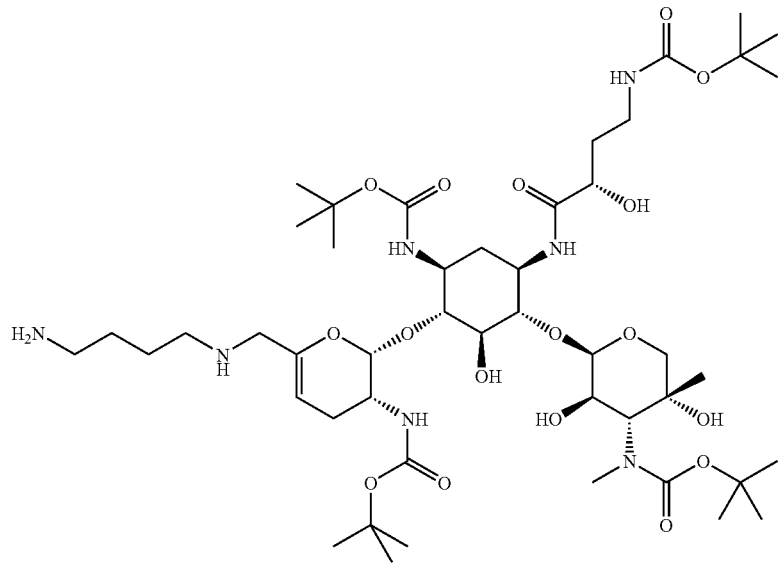 [SMILES: CN(C(=O)OC(C)(C)C)[C@@H]1[C@@H](O)[C@@H](O[C@@H]2[C@@H](O)[C@H](O[C@H]3OC(CNCCCCN)=CC[C@H]3NC(=O)OC(C)(C)C)[C@@H](NC(=O)OC(C)(C)C)C[C@H]2NC(=O)[C@@H](O)CCNC(=O)OC(C)(C)C)OC[C@]1(C)O]

6'-(4-Amino-butyl)-2',3,3''-triBoc-1-(N-Boc-4-amino-2(S)-hydroxy-butyryl)-sisomicin To a stirring solution of 6'-(N-Fmoc-4-amino-butyl)-2',3,3''-triBoc-1-(N-Boc-4-amino-2(S)-hydroxy-butyryl)-sisomicin (0.079 mmol) in DMF (1.5 mL) was added piperidine (0.3 mmol) and the reaction mixture was stirred for 2 hours. The reaction mixture was then diluted with water (5 mL) and extracted with ethyl acetate (2×10 mL). The combined organic layers were washed with water (2×5 mL), brine (5 mL), dried over $Na_2SO_4$, filtered and concentrated to dryness to yield 6'-(4-amino-butyl)-2',3,3''-triBoc-1-(N-Boc-4-amino-2(S)-hydroxy-butyryl)-sisomicin (MS m/e $[M+H]^+$ calcd 1020.6, found 1020.9), which was carried through to the next step without further purification.

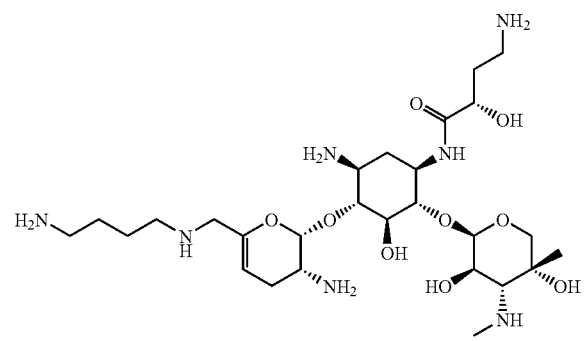 [SMILES: CN[C@@H]1[C@@H](O)[C@@H](O[C@@H]2[C@@H](O)[C@H](O[C@H]3OC(CNCCCCN)=CC[C@H]3N)[C@@H](N)C[C@H]2NC(=O)[C@@H](O)CCN)OC[C@]1(C)O]

6'-(4-Amino-butyl)-1-(4-amino-2(S)-hydroxy-butyryl)-sisomicin

6'-(4-amino-butyl)-2',3,3''-triBoc-1-(N-Boc-4-amino-2(S)-hydroxy-butyryl)-sisomicin (0.079 mmol) was submitted to Procedure 3-Method A for Boc removal to yield a crude, which was purified by RP HPLC Method 3 to yield 6'-(4-amino-butyl)-1-(4-amino-2(S)-hydroxy-butyryl)-sisomicin (0.010 g, 0.016 mmol, 20.2% yield): MS m/e $[M+H]^+$ calcd 620.4, found 620.8; CLND 93.4% purity.

Example 44

6'-(5-Amino-pentyl)-1-(4-amino-2(S)-hydroxy-butyryl)-sisomicin

6'-Nosyl-2',3,3''-triBoc-1-(N-Boc-4-amino-2(S)-hydroxy-butyryl)-sisomicin

2',3,3''-triBoc-1-(N-Boc-4-amino-2(S)-hydroxy-butyryl)-sisomicin (0.075 g, 0.079 mmol) was submitted to Procedure 8 for nosylation to give the desired 6'-nosyl-2',3,3''-triBoc-1-(N-Boc-4-amino-2(S)-hydroxy-butyryl)-sisomicin (MS m/e $[M+H]^+$ calcd 1134.5, found 1134.8), which was carried through to the next step without further purification.

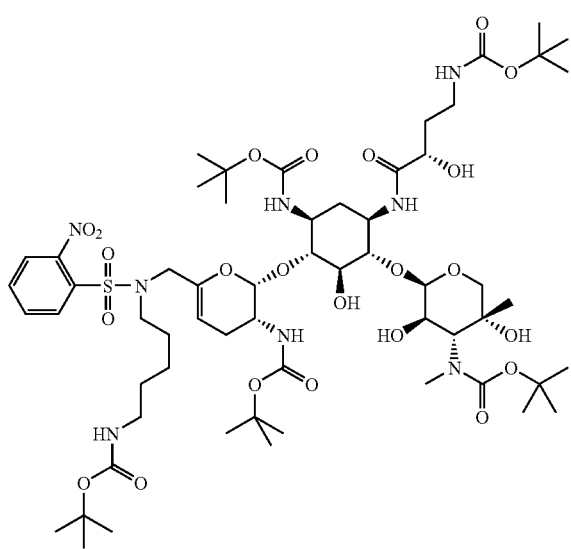 [SMILES: CN(C(=O)OC(C)(C)C)[C@@H]1[C@@H](O)[C@@H](O[C@@H]2[C@@H](O)[C@H](O[C@H]3OC(CN(CCCCCNC(=O)OC(C)(C)C)S(=O)(=O)c4ccccc4[N+](=O)[O-])=CC[C@H]3NC(=O)OC(C)(C)C)[C@@H](NC(=O)OC(C)(C)C)C[C@H]2NC(=O)[C@@H](O)CCNC(=O)OC(C)(C)C)OC[C@]1(C)O]

6α-Nosyl-6'-(N-Boc-5-amino-pentyl)-2',3,3''-triBoc-
1-(N-Boc-4-amino-2(S)-hydroxy-butyryl)-sisomicin 6'-Nosyl-2',3,3''-triBoc-1-(N-Boc-4-amino-2(S)-hydroxy-butyryl)-sisomicin (0.079 mmol) was treated with N-Boc-5-amino-pentanol following Procedure 17 to yield 6'-nosyl-6'-(N-Boc-5-amino-pentyl)-2',3,3''-triBoc-1-(N-Boc-4-amino-2(S)-hydroxy-butyryl)-sisomicin (MS m/e [M+H]$^+$ calcd 1319.6, found 1319.9), which was carried through to the next step without further purification.

6'-(N-Boc-5-amino-pentyl)-2',3,3''-triBoc-1-(N-Boc-4-amino-2(S)-hydroxy-butyryl)-sisomicin 6'-Nosyl-6'-(N-Boc-5-amino-pentyl)-2',3,3''-triBoc-1-(N-Boc-4-amino-2(S)-hydroxy-butyryl)-sisomicin (0.079 mmol) was submitted to Procedure 9 for nosyl removal to yield 6'-(N-Boc-5-amino-pentyl)-2',3,3''-triBoc-1-(N-Boc-4-amino-2(S)-hydroxy-butyryl)-sisomicin (MS m/e [M+H]$^+$ calcd 1134.7, found 1135.0), which was carried through to the next step without further purification.

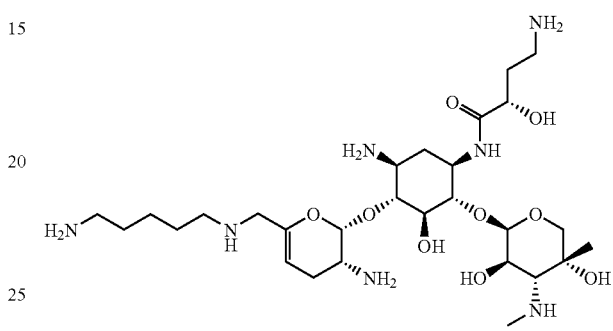

6'-(5-Amino-pentyl)-1-(4-amino-2(S)-hydroxy-butyryl)-sisomicin

6'-(N-Boc-5-amino-pentyl)-2',3,3''-triBoc-1-(N-Boc-4-amino-2(S)-hydroxy-butyryl)-sisomicin (0.079 mmol) was submitted to Procedure 3-Method A for Boc removal to yield a crude, which was purified by RP HPLC Method 3 to yield 6'-(5-amino-pentyl)-1-(4-amino-2(S)-hydroxy-butyryl)-si-

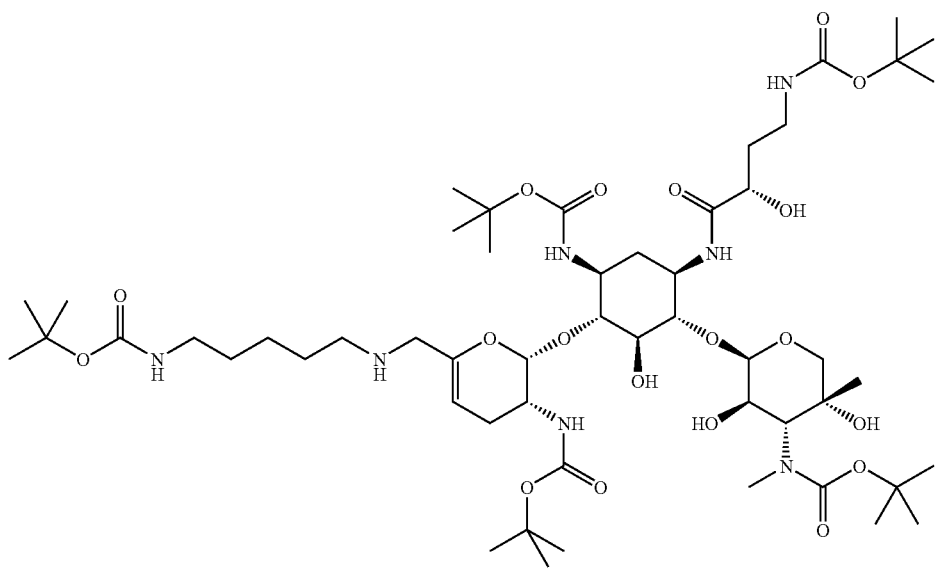 [SMILES: CN(C(=O)OC(C)(C)C)[C@@H]1[C@@H](O)[C@@H](O[C@@H]2[C@@H](O)[C@H](O[C@H]3OC(CNCCCCCNC(=O)OC(C)(C)C)=CC[C@H]3NC(=O)OC(C)(C)C)[C@@H](NC(=O)OC(C)(C)C)C[C@H]2NC(=O)[C@@H](O)CCNC(=O)OC(C)(C)C)OC[C@]1(C)O]

somicin (0.009 g, 0.014 mmol, 17.7% yield): MS m/e [M+H]+ calcd 634.4, found 634.6; CLND 82.6% purity.

Example 45

6'-(Ethyl-2-(1-methylpiperazin-2-yl)-1-(4-amino-2(S)-hydroxy-butyryl)-sisomicin

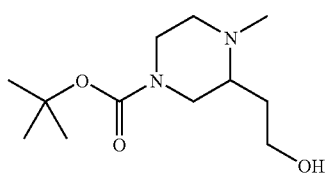 [SMILES: CN1CCN(C(=O)OC(C)(C)C)CC1CCO]

2-(4-Boc-1-methylpiperazin-2-yl)-ethanol 2-(1-Methylpiperazin-2-yl)-ethanol (0.5 g, 3.47 mmol) was Boc protected following Procedure 13 to yield 2-(4-Boc-1-methylpiperazin-2-yl)-ethanol (0.75 g, 3.08 mmol, 88.7% yield): MS m/e [M+H]+ calcd 245.2, found 245.1.

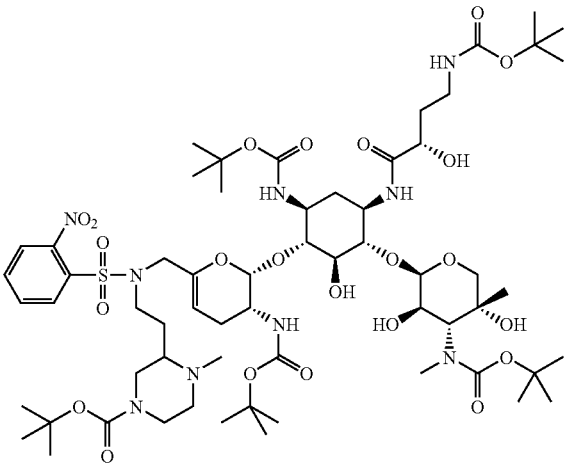 [SMILES: CN1CCN(C(=O)OC(C)(C)C)CC1CCN(CC1=CC[C@@H](NC(=O)OC(C)(C)C)[C@@H](O[C@H]2[C@H](O)[C@@H](O[C@H]3OC[C@](C)(O)[C@H](N(C)C(=O)OC(C)(C)C)[C@H]3O)[C@H](NC(=O)[C@@H](O)CCNC(=O)OC(C)(C)C)C[C@@H]2NC(=O)OC(C)(C)C)O1)S(=O)(=O)c1ccccc1[N+](=O)[O-]]

6'-(Ethyl-2-(4-Boc-1-methylpiperazin-2-yl)-1-(N-Boc-4-amino-2(S)-hydroxy-butyryl)-sisomicin 6'-Nosyl-2',3,3''-triBoc-1-(N-Boc-4-amino-2(S)-hydroxy-butyryl)-sisomicin (0.079 mmol) was treated with 2-(4-Boc-1-methylpiperazin-2-yl)-ethanol following Procedure 17 to yield 6'-nosyl-6'-(ethyl-2-(4-Boc-1-methylpiperazin-2-yl)-2',3,3''-triBoc-1-(N-Boc-4-amino-2(S)-hydroxy-butyryl)-sisomicin (MS m/e [M+H]+ calcd 1360.7, found 1360.8), which was carried through to the next step without further purification.

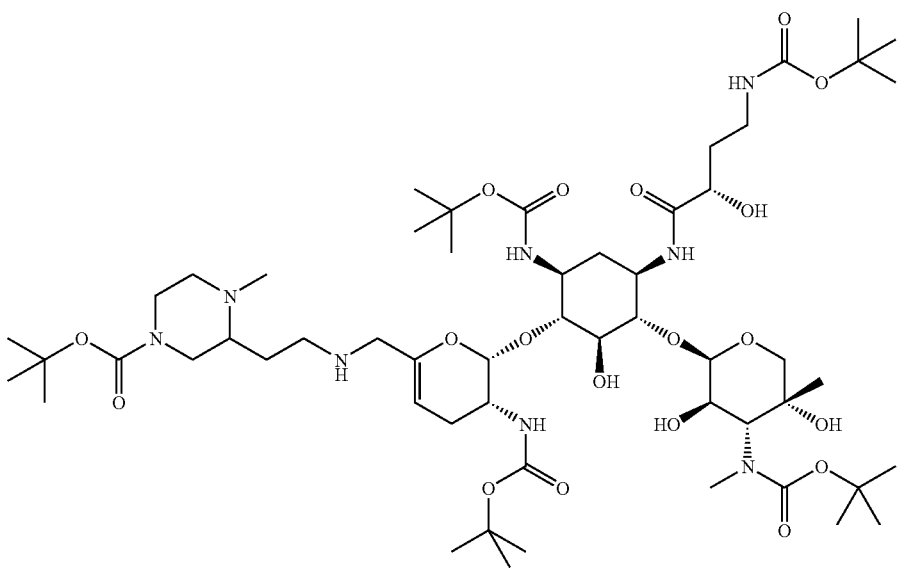 [SMILES: CN1CCN(C(=O)OC(C)(C)C)CC1CCNCC1=CC[C@@H](NC(=O)OC(C)(C)C)[C@@H](O[C@H]2[C@H](O)[C@@H](O[C@H]3OC[C@](C)(O)[C@H](N(C)C(=O)OC(C)(C)C)[C@H]3O)[C@H](NC(=O)[C@@H](O)CCNC(=O)OC(C)(C)C)C[C@@H]2NC(=O)OC(C)(C)C)O1]

6'-(Ethyl-2-(4-Boc-1-methylpiperazin-2-yl)-2',3,3"-triBoc-1-(N-Boc-4-amino-2-(S)-hydroxy-butyryl)-sisomicin 6'-Nosyl-6'-(ethyl-2-(4-Boc-1-methylpiperazin-2-yl)-2',3,3"-triBoc-1-(N-Boc-4-amino-2(S)-hydroxy-butyryl)-sisomicin (0.079 mmol) was submitted to Procedure 9 for nosyl removal to yield 6'-(ethyl-2-(4-Boc-1-methylpiperazin-2-yl)-2',3,3"-triBoc-1-(N-Boc-4-amino-2(S)-hydroxy-butyryl)-sisomicin (MS m/e [M+H]$^+$ calcd 1175.7, found 1176.0), which was carried through to the next step without further purification.

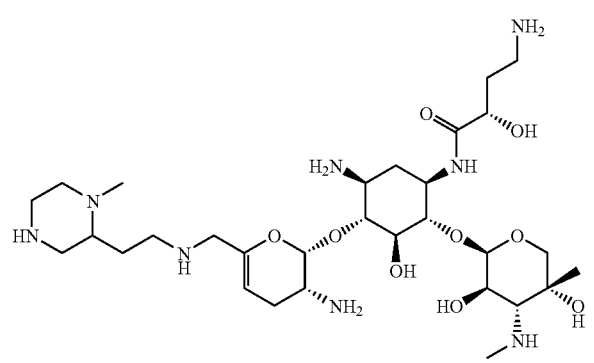 [SMILES: CN[C@@H]1[C@@H](O)[C@@H](O[C@@H]2[C@@H](O)[C@H](O[C@H]3OC(CNCCC4CNCCN4C)=CC[C@H]3N)[C@@H](N)C[C@H]2NC(=O)[C@@H](O)CCN)OC[C@]1(C)O]

6'-(Ethyl-2-(1-methylpiperazin-2-yl)-1-(4-amino-2(S)-hydroxy-butyryl)-sisomicin 6'-(Ethyl-2-(4-Boc-1-methylpiperazin-2-yl)-2',3,3"-triBoc-1-(N-Boc-4-amino-2(S)-hydroxy-butyryl)-sisomicin (0.079 mmol) was submitted to Procedure 3-Method A for Boc removal to yield a crude, which was purified by RP HPLC Method to yield 6'-(ethyl-2-(1-methylpiperazin-2-yl)-1-(4-amino-2(S)-hydroxy-butyryl)-sisomicin (0.010 g, 0.015 mmol, 18.9% yield): MS m/e [M+H]$^+$ calcd 675.4, found 675.4; CLND 93.0% purity.

Example 46

6'-(Methyl-(1-hydroxy-3-amino-cyclobutyl)-1-(4-amino-2(S)-hydroxy-butyryl)-sisomicin

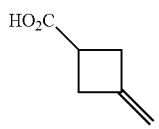

3-Methylene-cyclobutane carboxylic acid

To a stirring solution of KOH (70.0 g, 1.25 mol) in EtOH/H$_2$O (500 mL, 1:1 v/v) was added 3-methylenecyclobutane carbonitrile (25.0 g, 0.26 mol) and the reaction mixture was refluxed for 6 h. The reaction progress was monitored by TLC and, upon completion, the mixture was cooled and acidified to pH 3-4 with HCl. The ethanol was evaporated, and the remaining aqueous layer was extracted with Et$_2$O (200 mL). The organic layer was washed with water (2×20 mL), brine (30 ml), dried over Na$_2$SO$_4$, filtered and concentrated to dryness to yield 3-methylene-cyclobutane carboxylic acid, which was carried through to the next step without further purification: $^1$H NMR (250 MHz, CDCl$_3$) δ 10.75 (bs, 1 H), 4.80 (s, 2 H), 2.85-3.26 (m, 5 H).

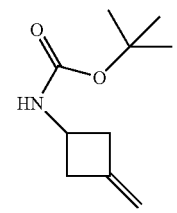

N-Boc-3-Methylene-cyclobutanamine

To a stirring solution of 3-methylene-cyclobutane carboxylic acid (1.0 g, 8.9 mmol) in THF (90 mL) was added NaN$_3$ (2.0 g, 31.1 mmol), followed by tetrabutyl ammonium bromide (0.48 g, 1.5 mmol) and Zn(OTf)$_2$ (0.1 g, 0.3 mmol), and the reaction mixture was heated to 40° C. Boc$_2$O (2.1 g, 9.8 mmol) was then added at once, and the reaction was heated at 45° C. overnight. The reaction was then cooled to 0° C. and was quenched with 10% aq. NaNO$_2$ (180 mL). The THF was evaporated and the aqueous layer was extracted with EtOAc (180 mL). The organic layer was washed with 5% aq. NaHCO$_3$ (2×20 mL), brine (30 ml), dried over Na$_2$SO$_4$, filtered and concentrated to dryness to yield a crude, which was purified by flash chromatography (silica gel/hexanes:ethyl acetate: 0-90%) to yield the desired N-Boc-3-methylene-cyclobutanamine (0.57 g, 3.1 mmol, 34.9% yield): $^1$H NMR (250 MHz, CDCl$_3$) δ 4.83 (s, 2 H), 4.79 (bs, 1 H), 4.05-4.23 (m, 1 H), 2.92-3.11 (m, 2 H), 2.50-2.65 (m, 2 H), 1.44 (s, 9 H).

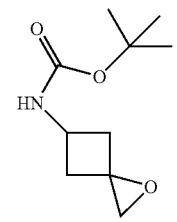

N-Boc-1-oxaspiro[2.3]hexan-5-amine

N-Boc-3-methylene-cyclobutanamine (1.65 g, 9.0 mmol) was submitted to Procedure 14 for epoxide formation to yield N-Boc-1-oxaspiro[2.3]hexan-5-amine (1.46 g, 7.33 mmol, 81.5% yield): $^1$H NMR (250 MHz, CDCl$_3$) δ 4.79 (bs, 1 H), 4.13-4.31 (m, 1 H), 2.66-2.83 (m, 4 H), 2.31-2.47 (m, 2 H), 1.45 (s, 9 H).

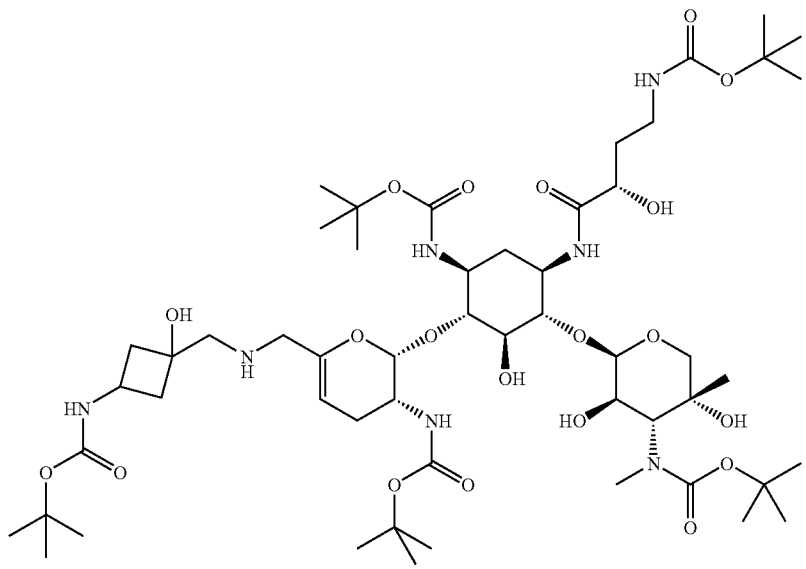 [SMILES: CN(C(=O)OC(C)(C)C)[C@@H]1[C@@H](O)[C@@H](O[C@@H]2[C@@H](O)[C@H](O[C@H]3OC(CNCC4(O)CC(NC(=O)OC(C)(C)C)C4)=CC[C@H]3NC(=O)OC(C)(C)C)[C@@H](NC(=O)OC(C)(C)C)C[C@H]2NC(=O)[C@@H](O)CCNC(=O)OC(C)(C)C)OC[C@]1(C)O]

6'-(Methyl-(1-hydroxy-N-Boc-3-amino-cyclobutyl)-1-(N-Boc-4-amino-2(S)-hydroxy-butyryl)-sisomicin 2',3,3''-triBoc-1-(N-Boc-4-amino-2(S)-hydroxy-butyryl)-sisomicin (0.079 mmol) was treated with N-Boc-1-oxaspiro[2.3]hexan-5-amine following Procedure 5 to yield 6'-(methyl-(1-hydroxy-N-Boc-3-amino-cyclobutyl)-2',3,3''-triBoc-1-(N-Boc-4-amino-2(S)-hydroxy-butyryl)-sisomicin (MS m/e [M+H]$^+$ calcd 1148.6, found 1148.6), which was carried through to the next step without further purification.

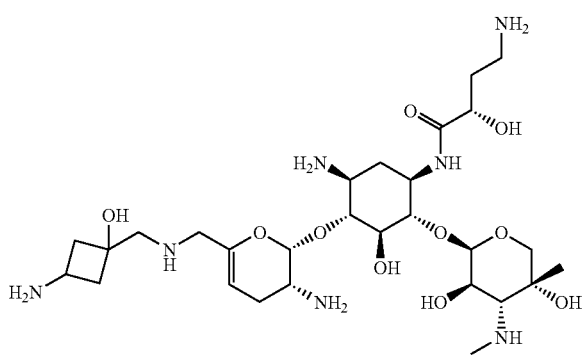 [SMILES: CN[C@@H]1[C@@H](O)[C@@H](O[C@@H]2[C@@H](O)[C@H](O[C@H]3OC(CNCC4(O)CC(N)C4)=CC[C@H]3N)[C@@H](N)C[C@H]2NC(=O)[C@@H](O)CCN)OC[C@]1(C)O]

6'-(Methyl-(1-hydroxy-3-amino-cyclobutyl)-1-(4-amino-2(S)-hydroxy-butyryl)-sisomicin 6'-(Methyl-(1-hydroxy-N-Boc-3-amino-cyclobutyl)-2',3,3''-triBoc-1-(N-Boc-4-amino-2(S)-hydroxy-butyryl)-sisomicin (0.079 mmol) was submitted to Procedure 3-Method A for Boc removal to yield a crude, which was purified by RP HPLC Method 3 to yield 6'-(methyl-(1-hydroxy-3-amino-cyclobutyl)-1-(4-amino-2(S)-hydroxy-butyryl)-sisomicin (0.0098 g, 0.015 mmol, 18.9% yield): MS m/e [M+H]$^+$ calcd 648.4, found 648.4; CLND 82.0% purity.

Example 47

6'-(Methyl-(1-hydroxy-3-amino-cyclobutyl)-1-(3-hydroxy-azetidin-3-yl-acetyl)-sisomicin

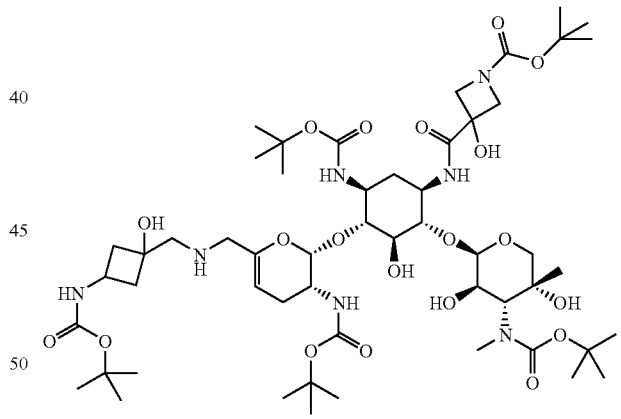

6'-(Methyl-(1-hydroxy-N-Boc-3-amino-cyclobutyl)-2',3,3''-triBoc-1-(N-Boc-3-hydroxy-azetidin-3-yl-acetyl)-sisomicin 2',3,3''-triBoc-1-(N-Boc-3-hydroxy-azetidin-3-yl-acetyl)-sisomicin (0.081 mmol) was treated with N-Boc-1-oxaspiro[2.3]hexan-5-amine following Procedure 5 to yield 6'-(methyl-(1-hydroxy-N-Boc-3-amino-cyclobutyl)-2',3,3''-triBoc-1-(N-Boc-3-hydroxy-azetidin-3-yl-acetyl)-sisomicin (MS m/e [M+H]$^+$ calcd 1146.6, found 1147.0), which was carried through to the next step without further purification.

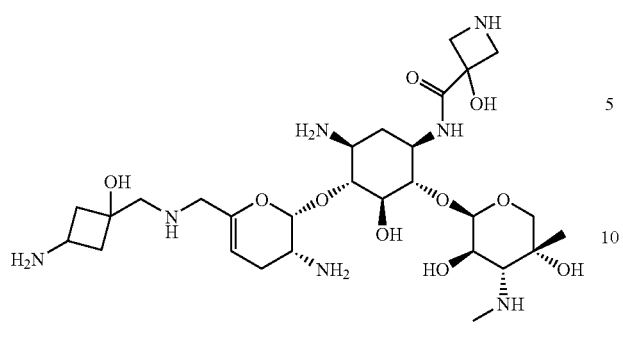

6'-(Methyl-(1-hydroxy-3-amino-cyclobutyl)-1-(3-hydroxy-azetidin-3-yl-acetyl)-sisomicin 6'-(Methyl-(1-hydroxy-N-Boc-3-amino-cyclobutyl)-2',3,3"-triBoc-1-(N-Boc-3-hydroxy-azetidin-3-yl-acetyl)-sisomicin (0.081 mmol) was submitted to Procedure 3-Method A for Boc removal to yield a crude, which was purified by RP HPLC Method 1-Column A to yield 6'-(methyl-(1-hydroxy-3-amino-cyclobutyl)-1-(3-hydroxy-azetidin-3-yl-acetyl)-sisomicin (0.0089 g, 0.014 mmol, 17.3% yield): MS m/e [M+H]$^+$ calcd 646.4, found 646.6; CLND 95.7% purity.

Example 48

6'-(3-Amino-propyl)-1-(4-amino-2(S)-hydroxy-butyryl)-sisomicin desired 6'-(N-phthalimido-3-amino-propyl)-2',3,3"-triBoc-1-(N-Boc-4-amino-2(S)-hydroxy-butyryl)-sisomicin (MS m/e [M+H]$^+$ calcd 1136.6, found 1136.7), which was carried through to the next step without further purification.

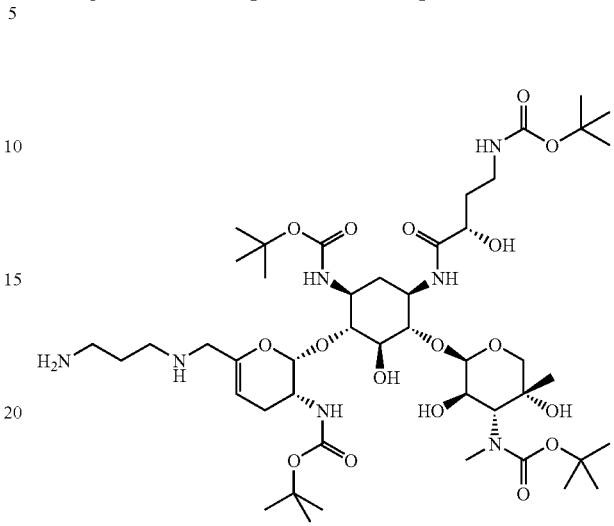

6'-(3-Amino-propyl)-2',3,3"-triBoc-1-(N-Boc-4-amino-2(S)-hydroxy-butyryl)-sisomicin 6'-(N-Phthalimido-3-amino-propyl)-2',3,3"-triBoc-1-(N-Boc-4-amino-2(S)-hydroxy-butyryl)-sisomicin (0.079

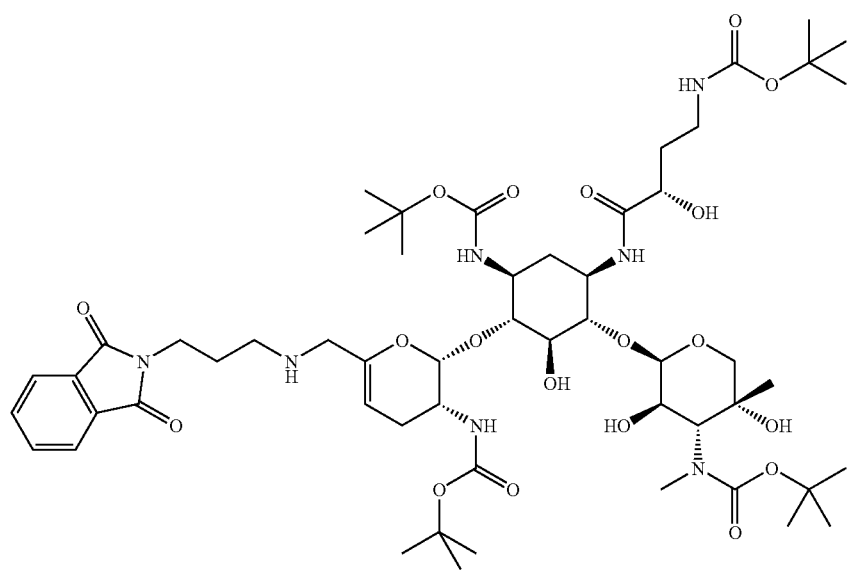 [SMILES: CN(C(=O)OC(C)(C)C)[C@@H]1[C@@H](O)[C@@H](O[C@@H]2[C@@H](O)[C@H](O[C@H]3OC(CNCCCN4C(=O)c5ccccc5C4=O)=CC[C@H]3NC(=O)OC(C)(C)C)[C@@H](NC(=O)OC(C)(C)C)C[C@H]2NC(=O)[C@@H](O)CCNC(=O)OC(C)(C)C)OC[C@]1(C)O]

6'-(N-Phthalimido-3-amino-propyl)-2',3,3"-triBoc-1-(N-Boc-4-amino-2(S)-hydroxy-butyryl)-sisomicin 2',3,3"-triBoc-1-(N-Boc-4-amino-2(S)-hydroxy-butyryl)-sisomicin (0.079 mmol) was treated with N-phthalimido propionaldehyde following Procedure 1-Method A to yield the mmol) was submitted to Procedure 6 for phthalimido deprotection to yield 6'-(3-amino-propyl)-2',3,3"-triBoc-1-(N-Boc-4-amino-2(S)-hydroxy-butyryl)-sisomicin (MS m/e [M+H]$^+$ calcd 1006.6, found 1007.1), which was carried through to the next step without further purification.

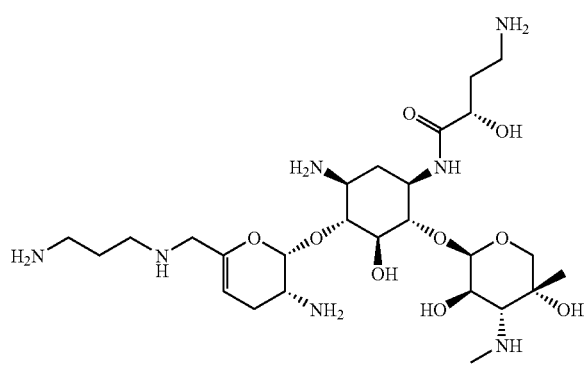 [SMILES: CN[C@@H]1[C@@H](O)[C@@H](O[C@@H]2[C@@H](O)[C@H](O[C@H]3OC(CNCCCN)=CC[C@H]3N)[C@@H](N)C[C@H]2NC(=O)[C@@H](O)CCN)OC[C@]1(C)O]

6'-(3-Amino-propyl)-1-(4-amino-2(S)-hydroxy-butyryl)-sisomicin

6'-(3-Amino-propyl)-2',3,3"-triBoc-1-(N-Boc-4-amino-2(S)-hydroxy-butyryl)-sisomicin (0.079 mmol) was submitted to Procedure 3-Method A for Boc removal to yield a crude, which was purified by RP HPLC Method 3 to yield 6'-(3-amino-propyl)-1-(4-amino-2(S)-hydroxy-butyryl)-sisomicin (0.010 g, 0.016 mmol, 20.2% yield): MS m/e [M+H]$^+$ calcd 606.4, found 606.4; CLND 95.8% purity.

Example 49

6'-(Methyl-pyrrolidin-2-yl)-1-(4-amino-2(S)-hydroxy-butyryl)-sisomicin

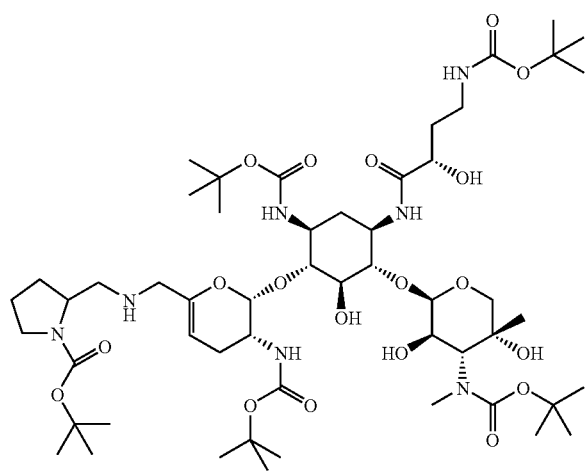 [SMILES: CN(C(=O)OC(C)(C)C)[C@@H]1[C@@H](O)[C@@H](O[C@@H]2[C@@H](O)[C@H](O[C@H]3OC(CNCC4CCCN4C(=O)OC(C)(C)C)=CC[C@H]3NC(=O)OC(C)(C)C)[C@@H](NC(=O)OC(C)(C)C)C[C@H]2NC(=O)[C@@H](O)CCNC(=O)OC(C)(C)C)OC[C@]1(C)O]

6'-(Methyl-N-Boc-pyrrolidin-2-yl)-2',3,3"-triBoc-1-(4-amino-2(S)-hydroxy-butyryl)-sisomicin 2',3,3"-triBoc-1-(N-Boc-4-amino-2(S)-hydroxy-butyryl)-sisomicin (0.079 mmol) was treated with N-Boc-DL-prolinal following Procedure 1-Method A to yield the desired 6'-(methyl-N-Boc-pyrrolidin-2-yl)-2',3,3"-triBoc-1-(N-Boc-4-amino-2(S)-hydroxy-butyryl)-sisomicin (MS m/e [M+H]$^+$ calcd 1132.6, found 1133.0), which was carried through to the next step without further purification.

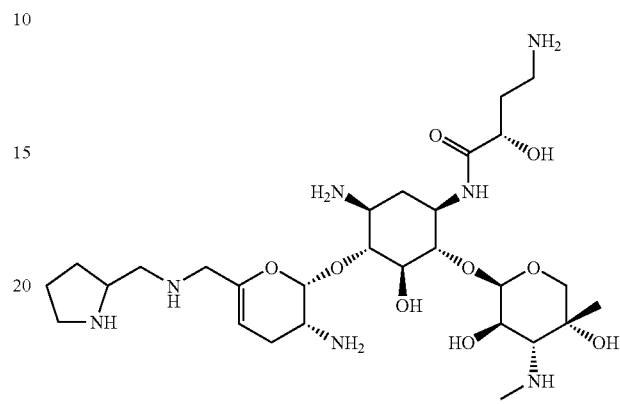

6'-(Methyl-pyrrolidin-2-yl)-1-(4-amino-2(S)-hydroxy-butyryl)-sisomicin

6'-(Methyl-N-Boc-pyrrolidin-2-yl)-2',3,3"-triBoc-1-(N-Boc-4-amino-2(S)-hydroxy-butyryl)-sisomicin (0.079 mmol) was submitted to Procedure 3-Method A for Boc removal to yield a crude, which was purified by RP HPLC Method 3 to yield 6'-(methyl-pyrrolidin-2-yl)-1-(4-amino-2(S)-hydroxy-butyryl)-sisomicin (0.010 g, 0.016 mmol, 20.2% yield): MS m/e [M+H]$^+$ calcd 632.4, found 632.8; CLND 90.9% purity.

Example 50

6'-(2(S)-Hydroxy-3-propanoic)-1-(4-amino-2(S)-hydroxy-butyryl)-sisomicin

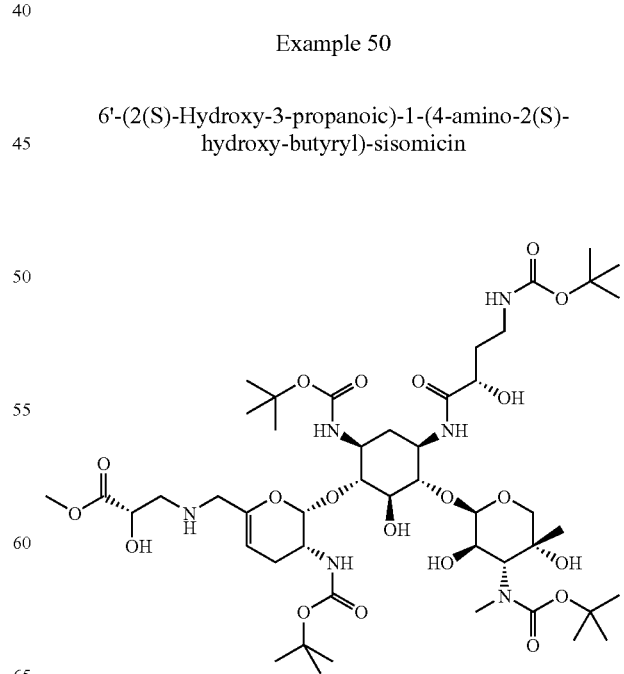

6'-(2(S)-Hydroxy-3-methyl-propanoate)-2',3,3"-tri-Boc-1-(N-Boc-4-amino-2-(S)-hydroxy-butyryl)-sisomicin 2',3,3"-triBoc-1-(N-Boc-4-amino-2(S)-hydroxy-butyryl)-sisomicin (0.079 mmol) was treated with methyl-2-(R)-glycidate following Procedure 5 to yield the desired 6'-(2(S)-hydroxy-3-methyl-propanoate)-2',3,3"-triBoc-1-(N-Boc-4-amino-2(S)-hydroxy-butyryl)-sisomicin (MS m/e [M+H]$^+$ calcd 1051.6, found 1052.2), which was carried through to the next step without further purification.

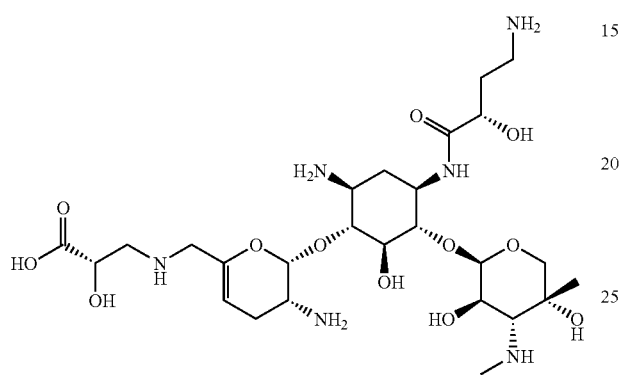

6'-(2(S)-Hydroxy-3-propanoic)-1-(4-amino-2(S)-hydroxy-butyryl)-sisomicin

6'-(2(S)-Hydroxy-3-methyl-propanoate)-2',3,3"-triBoc-1-(N-Boc-4-amino-2(S)-hydroxy-butyryl)-sisomicin (0.079 mmol) was submitted to Procedure 3-Method A for Boc removal and ester hydrolysis to yield a crude, which was purified by RP HPLC Method 3 to yield 6'-(2(S)-hydroxy-3-propanoic)-1-(4-amino-2(S)-hydroxy-butyryl)-sisomicin (0.0028 g, 0.0044 mmol, 5.6% yield): MS m/e [M+H]$^+$ calcd 637.3, found 637.6; CLND 89.8% purity.

Example 51

6'-(2,2-Dimethyl-3-amino-propyl)-1-(3-amino-2(S)-hydroxy-propionyl)-sisomicin

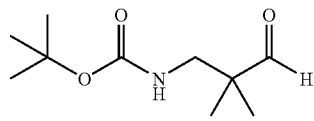

N-Boc-2,2-dimethyl-3-amino-propionaldehyde

N-Boc-2,2-dimethyl propanol (0.415 g, 2.04 mmol) was submitted to Procedure 18 to yield N-Boc-2,2-dimethyl-3-amino-propionaldehyde (0.39 g, 1.94 mmol, 95.1% yield): $^1$H NMR (250 MHz, CDCl3) δ 9.42 (s, 1 H), 4.80 (bs, 1 H), 3.11 (d, 2 H), 1.39 (s, 9 H), 1.06 (s, 6 H).

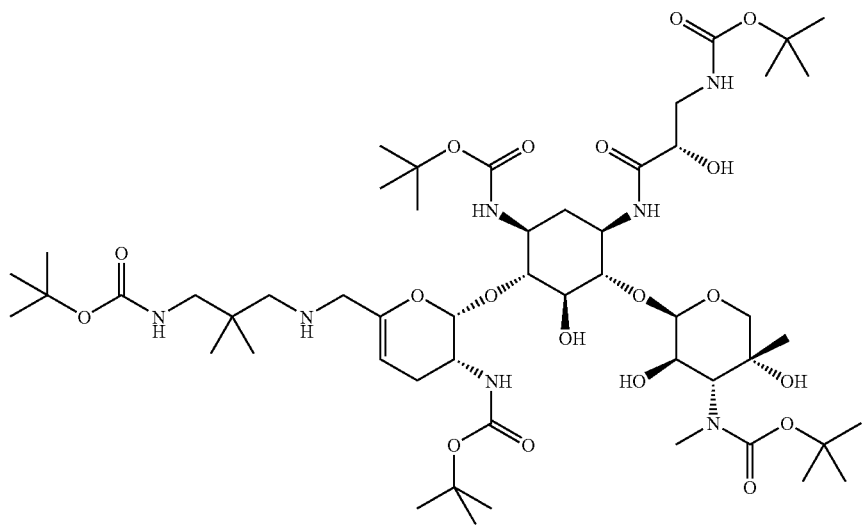

6'-(N-Boc-2,2-dimethyl-3-amino-propyl)-2',3,3"-triBoc-1-(N-Boc-3-amino-2(S)-hydroxy-propionyl)-sisomicin 2',3,3"-triBoc-1-(N-Boc-3-amino-2(S)-hydroxy-propionyl)-sisomicin (0.075 g, 0.080 mmol) was treated with N-Boc-2,2-dimethyl-3-amino-propionaldehyde following Procedure 1-Method A to yield the desired 6'-(N-Boc-2,2-dimethyl-3-amino-propyl)-2',3,3"-triBoc-1-(N-Boc-3-amino-2(S)-hydroxy-propionyl)-sisomicin, which was carried through to the next step without further purification.

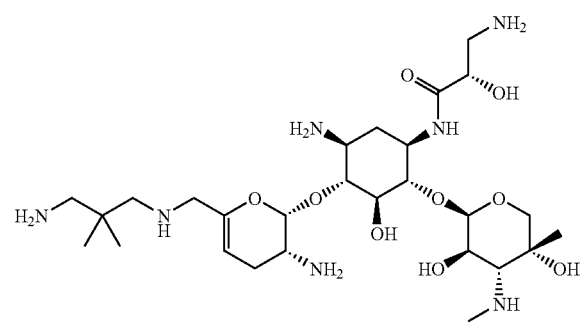 [SMILES: CN[C@@H]1[C@@H](O)[C@@H](O[C@@H]2[C@@H](O)[C@H](O[C@H]3OC(CNCC(C)(C)CN)=CC[C@H]3N)[C@@H](N)C[C@H]2NC(=O)[C@@H](O)CN)OC[C@]1(C)O]

6'-(2,2-Dimethyl-3-amino-propyl)-1-(3-amino-2(S)-hydroxy-propionyl)-sisomicin

6'-(N-Boc-2,2-dimethyl-3-amino-propyl)-2',3,3"-triBoc-1-(N-Boc-3-amino-2(S)-hydroxy-propionyl)-sisomicin (0.080 mmol) was submitted to Procedure 3-Method A for Boc removal to yield a crude, which was purified by RP HPLC Method 3 to yield 6'-(2,2-dimethyl-3-amino-propyl)-1-(3-amino-2(S)-hydroxy-propionyl)-sisomicin (0.0057 g, 0.0092 mmol, 11.5% yield): MS m/e [M+H]$^+$ calcd 620.4, found 620.8; CLND 97.4% purity.

Example 52

6'-(3-Amino-3-cyclopropyl-propyl)-1-(3-amino-2(S)-hydroxy-propionyl)-sisomicin

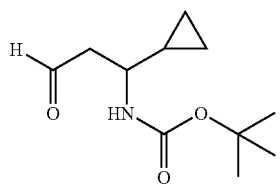

N-Boc-3-amino-3-cyclopropyl propionaldehyde

N-Boc-3-amino-propanol (0.130 g, 0.60 mmol) was submitted to Procedure 18 for oxidation to the corresponding N-Boc-3-amino-3-cyclopropyl propionaldehyde, which was carried through to the next step without further purification.

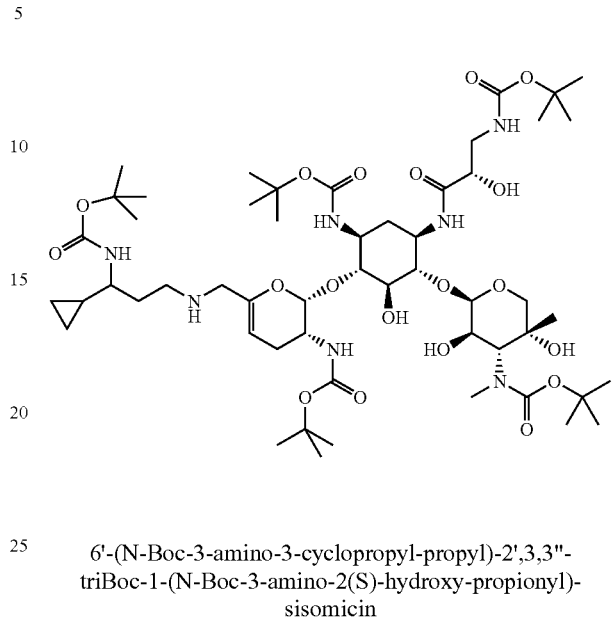

6'-(N-Boc-3-amino-3-cyclopropyl-propyl)-2',3,3"-triBoc-1-(N-Boc-3-amino-2(S)-hydroxy-propionyl)-sisomicin 2',3,3"-triBoc-1-(N-Boc-3-amino-2(S)-hydroxy-propionyl)-sisomicin (0.075 g, 0.080 mmol) was treated with N-Boc-3-amino-3-cyclopropyl propionaldehyde following Procedure 1-Method A to yield the desired 6'-(N-Boc-3-amino-3-cyclopropyl-propyl)-2',3,3"-triBoc-1-(N-Boc-3-amino-2(S)-hydroxy-propionyl)-sisomicin, which was carried through to the next step without further purification.

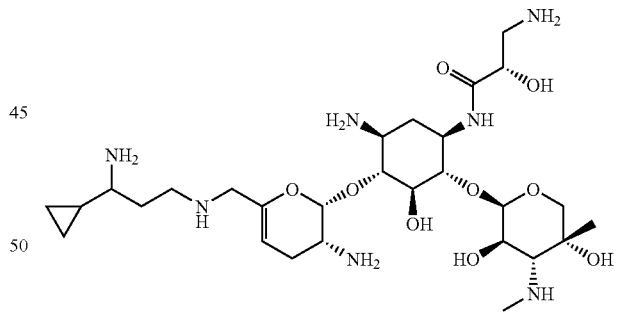

6'-(3-Amino-3-cyclopropyl-propyl)-1-(3-amino-2(S)-hydroxy-propionyl)-sisomicin

6'-(N-Boc-3-amino-3-cyclopropyl-propyl)-2',3,3"-triBoc-1-(N-Boc-3-amino-2(S)-hydroxy-propionyl)-sisomicin (0.080 mmol) was submitted to Procedure 3-Method A for Boc removal to yield a crude, which was purified by RP HPLC Method 3 to yield 6'-(3-amino-3-cyclopropyl-propyl)-1-(3-amino-2(S)-hydroxy-propionyl)-sisomicin (0.0067 g, 0.010 mmol, 12.5% yield): MS m/e [M+H]$^+$ calcd 632.4, found 632.8; CLND 96.7% purity.

Example 53

6'-(Methyl-4(S)-hydroxy-pyrrolidin-2(R)-yl)-1-(3-amino-2(S)-hydroxy-propionyl)-sisomicin

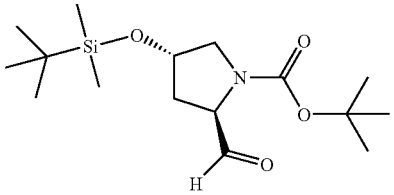 [SMILES: CC(C)(C)OC(=O)N1C[C@@H](O[Si](C)(C)C(C)(C)C)C[C@@H]1C=O]

4(S)-tert-Butyldimethylsilyloxy-N-Boc-pyrrolidin-2(R)-carboxaldehyde

4(S)-tert-Butyldimethylsilyloxy-N-Boc-pyrrolidin-2(R)-methanol (0.50 g, 1.50 mmol) was submitted to Procedure 18 for oxidation to the corresponding 4(S)-tert-butyldimethylsilyloxy-N-Boc-pyrrolidin-2(R)-carboxaldehyde, which was carried through to the next step without further purification.

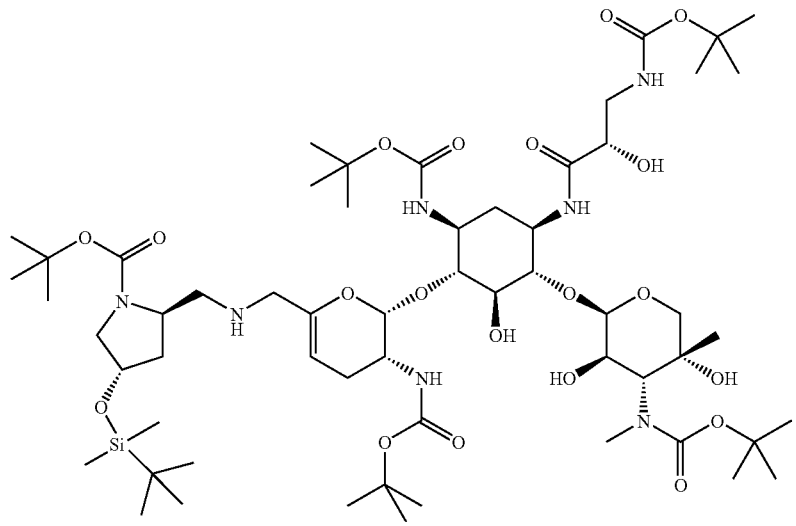 [SMILES: CN(C(=O)OC(C)(C)C)[C@@H]1[C@@H](O)[C@@H](O[C@@H]2[C@@H](O)[C@H](O[C@H]3OC(CNC[C@H]4C[C@H](O[Si](C)(C)C(C)(C)C)CN4C(=O)OC(C)(C)C)=CC[C@H]3NC(=O)OC(C)(C)C)[C@@H](NC(=O)OC(C)(C)C)C[C@H]2NC(=O)[C@@H](O)CNC(=O)OC(C)(C)C)OC[C@]1(C)O]

6'-(Methyl-N-Boc-4(S)-tert-butyldimethylsilyloxy-2(R)-pyrrolidin-2(R)-yl)-2',3,3''-triBoc-1-(N-Boc-3-amino-2(S)-hydroxy-propionyl)-sisomicin 2',3,3''-triBoc-1-(N-Boc-3-amino-2(S)-hydroxy-propionyl)-sisomicin (0.075 g, 0.080 mmol) was treated with 4(S)-tert-butyldimethylsilyloxy-N-Boc-pyrrolidin-2(R)-carboxaldehyde following Procedure 1-Method A to yield the desired 6'-(methyl-N-Boc-4(S)-tert-butyldimethylsilyloxy-pyrrolidin-2(R)-yl)-2',3,3''-triBoc-1-(N-Boc-3-amino-2(S)-hydroxy-propionyl)-sisomicin (MS m/e [M+H]$^+$ calcd 1248.7, found 1248.8), which was carried through to the next step without further purification.

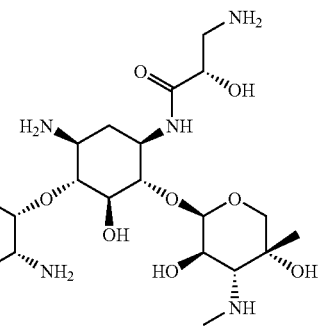

6'-(Methyl-4(S)-hydroxy-pyrrolidin-2(R)-yl)-1-(3-amino-2(S)-hydroxy-propionyl)-sisomicin 6'-(Methyl-N-Boc-4(S)-tert-butyldimethylsilyloxy-pyrrolidin-2(R)-yl)-2',3,3''-triBoc-1-(N-Boc-3-amino-2(S)-hydroxy-propionyl)-sisomicin (0.080 mmol) was submitted to Procedure 3-Method A for Boc and TBS removal to yield a crude, which was purified by RP HPLC Method 1-Column A to yield 6'-(methyl-4(S)-hydroxy-pyrrolidin-2(R)-yl-methyl)-1-(3-amino-2(S)-hydroxy-propionyl)-sisomicin (0.0022 g, 0.0035 mmol, 4.4% yield): MS m/e [M+H]$^+$ calcd 634.4, found 634.6; CLND 98.0% purity.

Example 54

6'-(3-Propanol)-1-(3-amino-2(S)-hydroxy-propionyl)-sisomicin

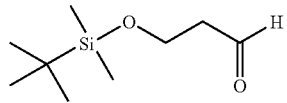

3-tert-Butyldimethylsilyloxy-propanal 3-tert-Butyldimethylsilyloxy-propanol (0.50 g, 2.62 mmol) was submitted to Procedure 18 for oxidation to the corresponding 3-tert-butyldimethylsilyloxy-propanal, which was carried through to the next step without further purification.

6'-(3-tert-Butyldimethylsilyloxy-propanol)-2',3,3''-triBoc-1-(N-Boc-3-amino-2-(S)-hydroxy-propionyl)-sisomicin

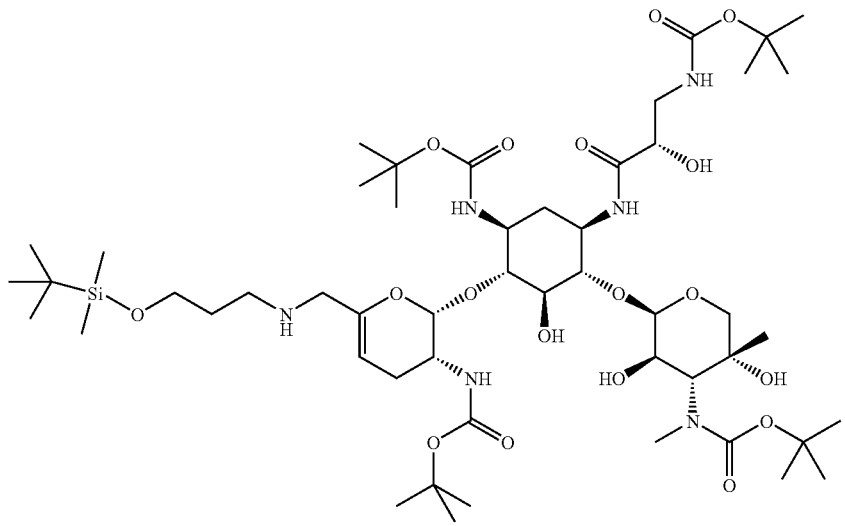 [SMILES: CN(C(=O)OC(C)(C)C)[C@@H]1[C@@H](O)[C@@H](O[C@@H]2[C@@H](O)[C@H](O[C@H]3OC(CNCCCO[Si](C)(C)C(C)(C)C)=CC[C@H]3NC(=O)OC(C)(C)C)[C@@H](NC(=O)OC(C)(C)C)C[C@H]2NC(=O)[C@@H](O)CNC(=O)OC(C)(C)C)OC[C@]1(C)O]

2',3,3''-triBoc-1-(N-Boc-3-amino-2(S)-hydroxy-propionyl)-sisomicin (0.075 g, 0.080 mmol) was treated with 3-tert-butyldimethylsilyloxy-propanal following Procedure 1-Method A to yield the desired 6'-(3-tert-butyldimethylsilyloxy-propanol)-2',3,3''-triBoc-1-(N-Boc-3-amino-2(S)-hydroxy-propionyl)-sisomicin (MS m/e [M+H]$^+$ calcd 1107.6, found 1107.9), which was carried through to the next step without further purification.

6'-(3-Propanol)-1-(3-amino-2(S)-hydroxy-propionyl)-sisomicin

6'-(3-tert-Butyldimethylsilyloxy-propanol)-2',3,3''-tri-Boc-1-(N-Boc-3-amino-2(S)-hydroxy-propionyl)-sisomicin (0.080 mmol) was submitted to Procedure 3-Method A for Boc and TBS removal to yield a crude, which was purified by RP HPLC Method 3 to yield 6'-(3-propanol)-1-(3-amino-2 (S)-hydroxy-propionyl)-sisomicin (0.011 g, 0.018 mmol, 22.5% yield): MS m/e [M+H]$^+$ calcd 593.3, found 593.8; CLND 98.4% purity.

Example 55

6'-(2-Methyl-2-amino-propyl)-1-(3-amino-2(S)-hydroxy-propionyl)-sisomicin

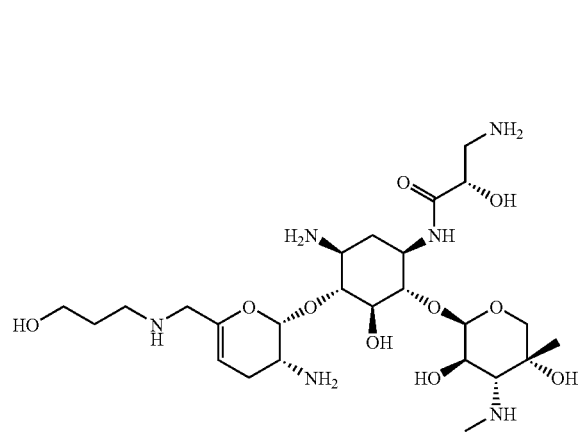 [SMILES: CN[C@@H]1[C@@H](O)[C@@H](O[C@@H]2[C@@H](O)[C@H](O[C@H]3OC(CNCCCO)=CC[C@H]3N)[C@@H](N)C[C@H]2NC(=O)[C@@H](O)CN)OC[C@]1(C)O]

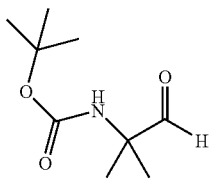

2-Methyl-N-Boc-2-amino-propanal

2-Methyl-N-Boc-2-amino-propanol (0.83 g, 4.38 mmol) was submitted to Procedure 18 for oxidation to the corresponding 2-methyl-N-Boc-2-amino-propanal (0.706 g, 3.77 mmol, 86.1% yield): $^1$H NMR (250 MHz, CDCl$_3$) δ 9.40 (s, 1 H), 1.57 (s, 1 H), 1.41 (s, 9 H), 1.30 (s, 6 H).

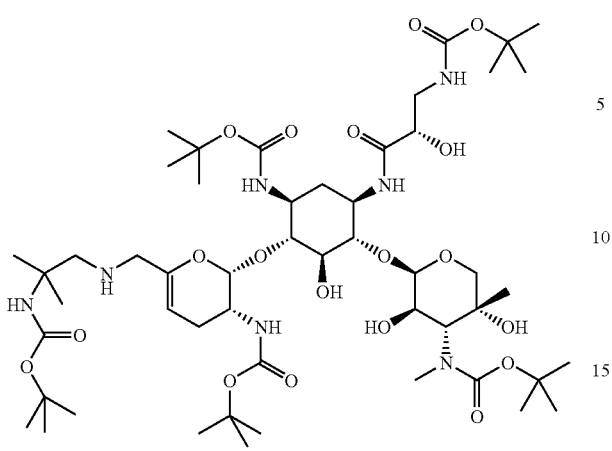

6'-(2-Methyl-N-Boc-2-amino-propyl)-2',3,3''-triBoc-1-(N-Boc-3-amino-2-(S)-hydroxy-propionyl)-sisomicin 2',3,3''-triBoc-1-(N-Boc-3-amino-2(S)-hydroxy-propionyl)-sisomicin (0.075 g, 0.080 mmol) was treated with 2-methyl-N-Boc-2-amino-propanal following Procedure 1-Method A to yield the desired 6'-(2-methyl-N-Boc-2-amino-propyl)-2',3,3''-triBoc-1-(N-Boc-3-amino-2(S)-hydroxy-propionyl)-sisomicin (MS m/e [M+H]⁺ calcd 1106.6, found 1107.0), which was carried through to the next step without further purification.

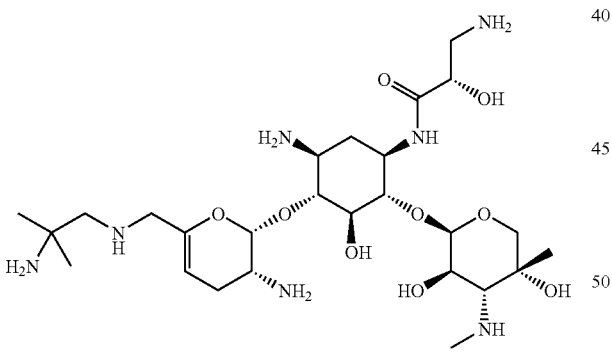

6'-(2-Methyl-2-amino-propyl)-1-(3-amino-2(S)-hydroxy-propionyl)-sisomicin

6'-(2-Methyl-N-Boc-2-amino-propyl)-2',3,3''-triBoc-1-(N-Boc-3-amino-2(S)-hydroxy-propionyl)-sisomicin (0.080 mmol) was submitted to Procedure 3-Method A for Boc removal to yield a crude, which was purified by RP HPLC Method 3 to yield 6'-(2-methyl-2-amino-propyl)-1-(3-amino-2(S)-hydroxy-propionyl)-sisomicin (0.010 g, 0.016 mmol, 20.0% yield): MS m/e [M+H]⁺ calcd 606.4, found 606.4; CLND 99.2% purity.

Example 56

6'-(Methyl-1-amino-cyclobutyl)-1-(3-amino-2(S)-hydroxy-propionyl)-sisomicin

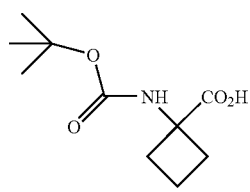

N-Boc-1-amino-cyclobutane carboxylic acid

1-Amino-cyclobutane carboxylic acid ethyl ester (1.0 g, 6.28 mmol) was dissolved in 1N HCl (10 mL) and the reaction was heated to a reflux for 2 hours. The reaction mixture was then concentrated to dryness to yield a crude which was submitted to Procedure 13 for Boc protection to yield the desired N-Boc-1-Amino-cyclobutane carboxylic acid.

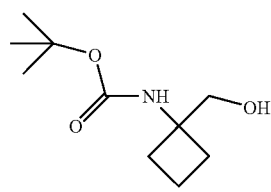

N-Boc-1-amino-cyclobutyl-methanol

N-Boc-1-amino-cyclobutane carboxylic acid (6.28 mmol) was submitted to Procedure 19 for reduction to the corresponding N-Boc-1-Amino-cyclobutyl-methanol.

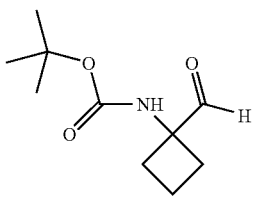

N-Boc-1-amino-cyclobutane carboxaldehyde

N-Boc-1-amino-cyclobutyl-methanol (0.25 g, 1.24 mmol) was submitted to Procedure 18 to yield the corresponding N-Boc-1-amino-cyclobutane carboxaldehyde (0.24 g, 1.20 mmol, 96.8% yield): ¹H NMR (250 MHz, CDCl3) δ 9.0 (s, 1 H), 4.91 (bs, 1 H), 3.74 (bs, 2 H), 1.71-2.20 (m, 4 H), 1.42 (s, 9 H).

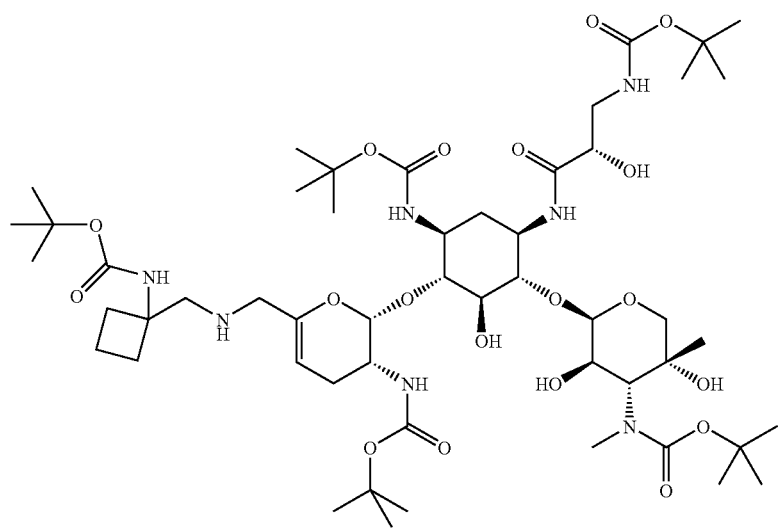 [SMILES: CN(C(=O)OC(C)(C)C)[C@@H]1[C@@H](O)[C@@H](O[C@@H]2[C@@H](O)[C@H](O[C@H]3OC(CNCC4(NC(=O)OC(C)(C)C)CCC4)=CC[C@H]3NC(=O)OC(C)(C)C)[C@@H](NC(=O)OC(C)(C)C)C[C@H]2NC(=O)[C@@H](O)CNC(=O)OC(C)(C)C)OC[C@]1(C)O]

6'-(N-Boc-methyl-1-amino-cyclobutyl)-2',3,3"-tri-Boc-1-(N-Boc-3-amino-2-(S)-hydroxy-propionyl)-sisomicin 2',3,3"-triBoc-1-(N-Boc-3-amino-2(S)-hydroxy-propionyl)-sisomicin (0.075 g, 0.080 mmol) was treated with N-Boc-1-amino-cyclobutane carboxaldehyde following Procedure 1-Method A to yield the desired 6'-(N-Boc-methyl-1-amino-cyclobutyl)-2',3,3"-triBoc-1-(N-Boc-3-amino-2(S)-hydroxy-propionyl)-sisomicin (MS m/e [M+H]$^+$ calcd 1118.6, found 1118.9), which was carried through to the next step without further purification.

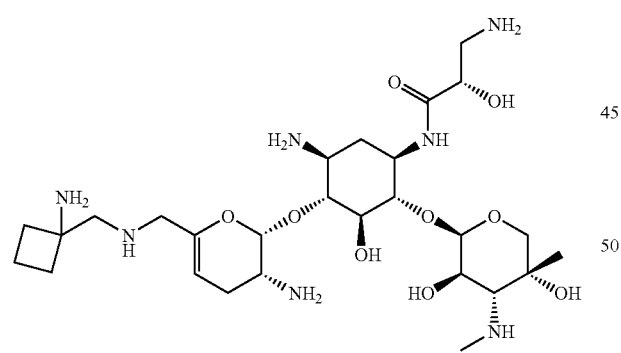

6'-(Methyl-1-amino-cyclobutyl)-1-(3-amino-2(S)-hydroxy-propionyl)-sisomicin

6'-(N-Boc-methyl-1-amino-cyclobutyl)-2',3,3"-triBoc-1-(N-Boc-3-amino-2(S)-hydroxy-propionyl)-sisomicin (0.080 mmol) was submitted to Procedure 3-Method A for Boc removal to yield a crude, which was purified by RP HPLC Method 1-Column A to yield 6'-(methyl-1-amino-cyclobutyl)-1-(3-amino-2(S)-hydroxy-propionyl)-sisomicin (0.002 g, 0.0032 mmol, 4.0% yield): MS m/e [M+H]$^+$ calcd 618.4, found 619.0; CLND 69.4% purity.

Example 57

6'-(3-Amino-propyl)-1-(3-hydroxy-azetidin-3-yl-acetyl)-sisomicin

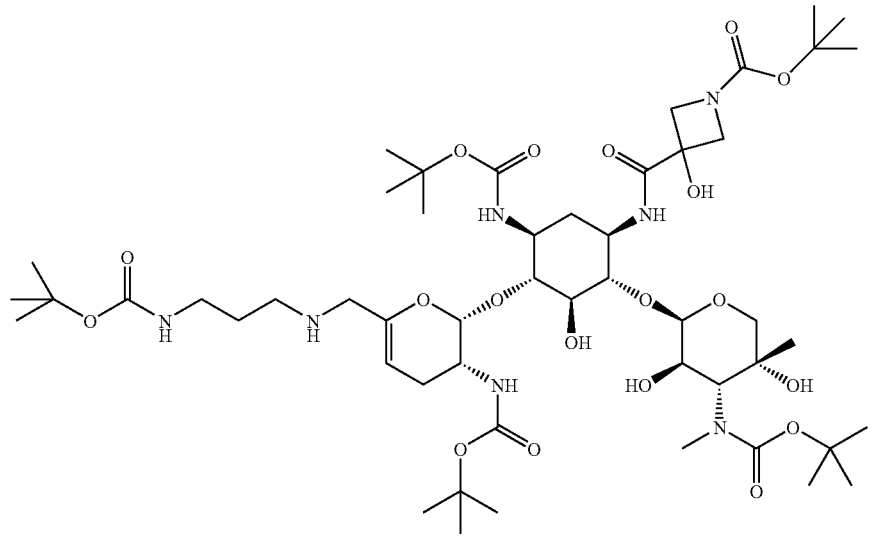 [SMILES: CN(C(=O)OC(C)(C)C)[C@@H]1[C@@H](O)[C@@H](O[C@@H]2[C@@H](O)[C@H](O[C@H]3OC(CNCCCNC(=O)OC(C)(C)C)=CC[C@H]3NC(=O)OC(C)(C)C)[C@@H](NC(=O)OC(C)(C)C)C[C@H]2NC(=O)C2(O)CN(C(=O)OC(C)(C)C)C2)OC[C@]1(C)O]

6'-(N-Boc-3-amino-propyl)-2',3,3''-triBoc-1-(N-Boc-3-hydroxy-azetidin-3-yl-acetyl)-sisomicin 2',3,3''-triBoc-1-(N-Boc-3-hydroxy-azetidin-3-yl-acetyl)-sisomicin (0.49 g, 0.46 mmol) was treated with N-Boc-3-amino-propionaldehyde following Procedure 1-Method B to yield the desired 6'-(N-Boc-3-amino-propyl)-2',3,3''-triBoc-1-(N-Boc-3-hydroxy-azetidin-3-yl-acetyl)-sisomicin (MS m/e [M+H]$^+$ calcd 1104.6, found 1104.6), which was carried through to the next step without further purification.

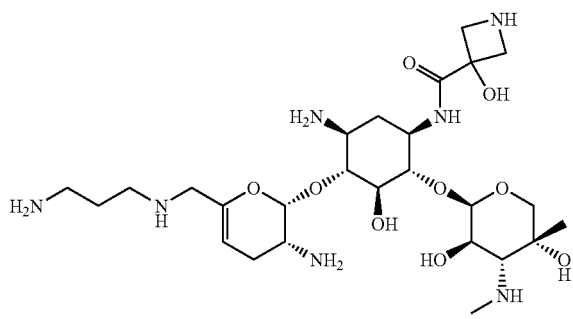 [SMILES: CN[C@@H]1[C@@H](O)[C@@H](O[C@@H]2[C@@H](O)[C@H](O[C@H]3OC(CNCCCN)=CC[C@H]3N)[C@@H](N)C[C@H]2NC(=O)C2(O)CNC2)OC[C@]1(C)O]

6'-(3-Amino-propyl)-1-(3-hydroxy-azetidin-3-yl-acetyl)-sisomicin

6'-(N-Boc-3-amino-propyl)-2',3,3''-triBoc-1-(N-Boc-3-hydroxy-azetidin-3-yl-acetyl)-sisomicin (0.46 mmol) was submitted to Procedure 3-Method B for Boc removal to yield a crude, which was purified by RP HPLC Method 1-Column B to yield 6'-(3-amino-propyl)-1-(3-hydroxy-azetidin-3-yl-acetyl)-sisomicin: MS m/e [M+H]$^+$ calcd 604.4, found 604.2; CLND 92.4% purity.

Example 58

6'-(3-Amino-propyl)-1-(1-hydroxy-3-amino-cyclobutyl-acetyl)-sisomicin

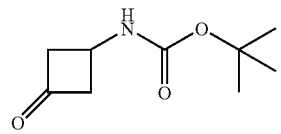

N-Boc-3-amino-cyclobutanone

To a vigorously stirring solution of N-Boc-3-methylene-cyclobutanamine (9.8 g, 53.5 mmol) in DCM (160 mL) and H$_2$O (160 mL) was added K$_2$CO$_3$ (3 g, 21.7 mmol), followed by NaClO$_4$ (35 g, 163.5 mmol), tetrabutylammonium chloride (0.2 g, 0.72 mmol) and RuCl$_3$ (0.6 g, 7.6 mmol). During the course of the reaction, the organic solution turned dark brown, the catalyst turned black, while the upper aqueous layer turned white. The reaction was monitored by TLC, and upon completion, the reaction mixture was filtered through a pad of celite. The filtrates were transferred to a separatory funnel, and the aqueous layer was extracted with DCM (2×50 mL). The combined organic layers were washed with 5% NaHCO$_3$ (2×30 mL), brine (30 mL), dried over Na$_2$SO$_4$, filtered and evaporated to dryness to yield a crude, which was purified by flash chromatography (silica gel/hexanes:ethyl acetate 0-60%) to yield the desired N-Boc-3-amino-cyclobutanone (7.13 g, 38.53 mmol, 72% yield): NMR (250 MHz, CDCl$_3$) δ 4.88 (bs, 1 H), 4.13-4.29 (m, 1 H), 3.23-3.41 (m, 2 H), 2.9-3.05 (m, 2 H), 1.39 (s, 9 H).

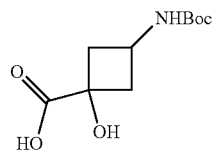 [SMILES: CC(C)(C)OC(=O)NC1CC(O)(C(=O)O)C1]

N-Boc-1-hydroxy-3-amino-cyclobutyl-carboxylic acid

N-Boc-3-amino-cyclobutanone (7.13 g, 38.53 mmol) was submitted to Procedure 15 to yield the desired N-Boc-1-hydroxy-3-amino-cyclobutyl-carboxylic acid (MS m/e [M+H]$^+$ calcd 232.1, found 232.2.

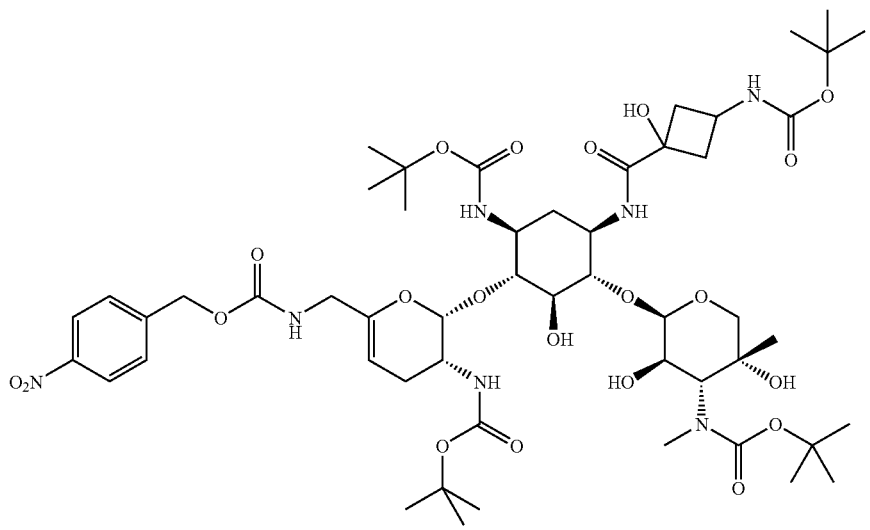 [SMILES: CN(C(=O)OC(C)(C)C)[C@@H]1[C@@H](O)[C@@H](O[C@@H]2[C@@H](O)[C@H](O[C@H]3OC(CNC(=O)OCc4ccc([N+](=O)[O-])cc4)=CC[C@H]3NC(=O)OC(C)(C)C)[C@@H](NC(=O)OC(C)(C)C)C[C@H]2NC(=O)C2(O)CC(NC(=O)OC(C)(C)C)C2)OC[C@]1(C)O]

6'-PNZ-2',3,3''-triBoc-1-(N-Boc-1-hydroxy-3-amino-cyclobutyl-acetyl)-sisomicin

Treatment of 6'-PNZ-2',3,3''-triBoc-sisomicin (0.87 mmol) with N-Boc-1-hydroxy-3-amino-cyclobutyl-carboxylic acid following Procedure 4-Method A gave the desired 6'-PNZ-2',3,3''-triBoc-1-(N-Boc-1-hydroxy-3-amino-cyclobutyl-acetyl)-sisomicin, which was carried through to the next step without further purification.

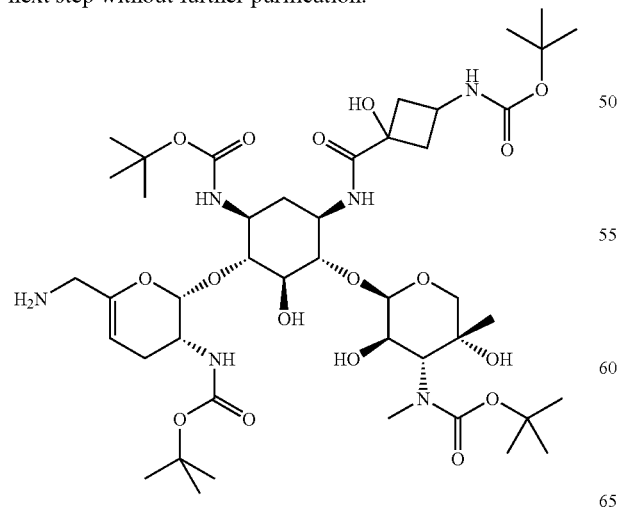

2',3,3''-triBoc-1-(N-Boc-1-hydroxy-3-amino-cyclobutyl-acetyl)-sisomicin

6'-PNZ-2',3,3''-triBoc-1-(N-Boc-1-hydroxy-3-amino-cyclobutyl-acetyl)-sisomicin (0.87 mmol) was submitted to Procedure 2 for PNZ removal to yield 2',3,3''-triBoc-1-(N-Boc-1-hydroxy-3-amino-cyclobutyl-acetyl)-sisomicin (MS m/e [M+H]+ calcd 961.5, found 961.3), which was carried through to the next step without further purification.

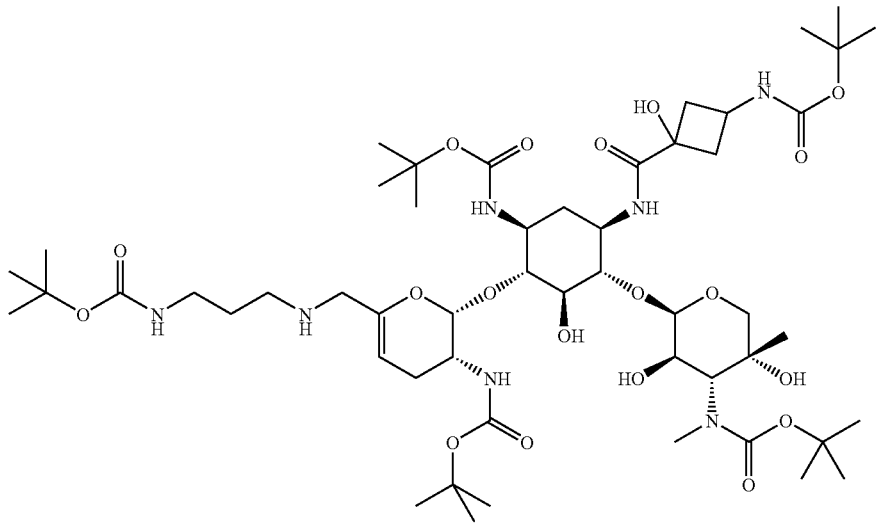 [SMILES: CN(C(=O)OC(C)(C)C)[C@@H]1[C@@H](O)[C@@H](O[C@@H]2[C@@H](O)[C@H](O[C@H]3OC(CNCCCNC(=O)OC(C)(C)C)=CC[C@H]3NC(=O)OC(C)(C)C)[C@@H](NC(=O)OC(C)(C)C)C[C@H]2NC(=O)C2(O)CC(NC(=O)OC(C)(C)C)C2)OC[C@]1(C)O]

6'-(N-Boc-3-amino-propyl)-2',3,3''-triBoc-1-(N-Boc-1-hydroxy-3-amino-cyclobutyl-acetyl)-sisomicin 2',3,3''-triBoc-1-(N-Boc-1-hydroxy-3-amino-cyclobutyl-acetyl)-sisomicin (0.87 mmol) was treated with N-Boc-3-amino-propionaldehyde following Procedure 1-Method B to yield the desired 6'-(N-Boc-3-amino-propyl)-2',3,3''-triBoc-1-(N-Boc-1-hydroxy-3-amino-cyclobutyl-acetyl)-sisomicin (MS m/e [M+H]+ calcd 1118.6, found 1118.6), which was carried through to the next step without further purification.

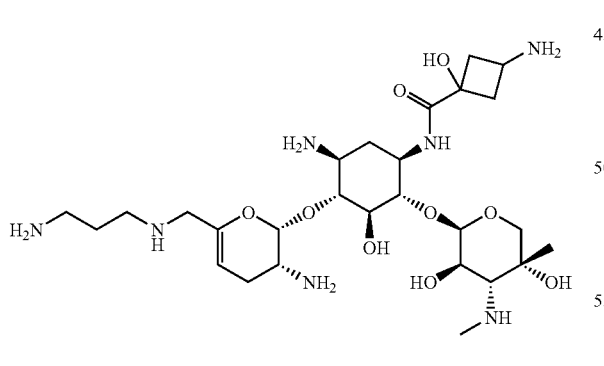

6'-(3-Amino-propyl)-1-(1-hydroxy-3-amino-cyclobutyl-acetyl)-sisomicin

6'-(N-Boc-3-amino-propyl)-2',3,3''-triBoc-1-(N-Boc-1-hydroxy-3-amino-cyclobutyl-acetyl)-sisomicin (0.87 mmol) was submitted to Procedure 3-Method B for Boc removal to yield a crude, which was purified by RP HPLC Method 1-Column B to yield 6'-(3-amino-propyl)-1-(1-hydroxy-3-amino-cyclobutyl-acetyl)-sisomicin: MS m/e [M+H]+ calcd 618.4, found 618.2; CLND 84.2% purity.

Example 59

6'-(Methyl-trans-3-amino-cyclobutyl)-1-(3-amino-2(S)-hydroxy-propionyl)-sisomicin

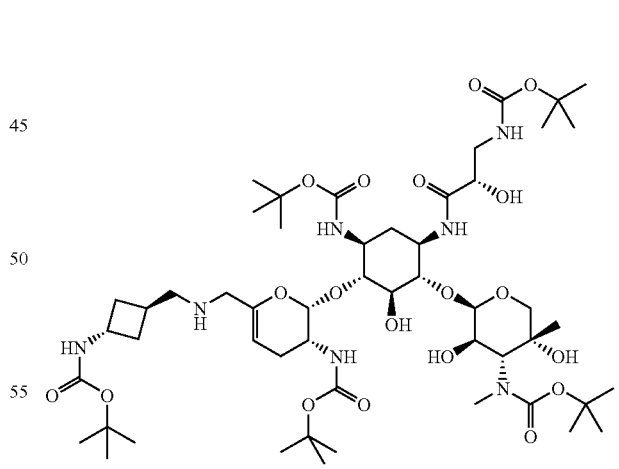

6'-(N-Boc-methyl-trans-3-amino-cyclobutyl)-2',3,3''-triBoc-1-(N-Boc-3-amino-2(S)-hydroxy-propionyl)-sisomicin 2',3,3''-triBoc-1-(N-Boc-3-amino-2(S)-hydroxy-propionyl)-sisomicin (1.0 g, 1.07 mmol) was treated with N-Boc-3-trans-amino-cyclobutyl-carboxaldehyde following Procedure 1-Method B to yield the desired 6'-(N-Boc-methyl-trans-3-amino-cyclobutyl)-2',3,3''-triBoc-1-(N-Boc-3-amino-2(S)-hydroxy-propionyl)-sisomicin (MS m/e [M+H]+ calcd 1118.6, found 1118.5), which was carried through to the next step without further purification.

6'-(N-Boc-methyl-trans-3-amino-cyclobutyl)-2',3,3''-triBoc-1-(N-Boc-1-hydroxy-3-amino-cyclobutyl-acetyl)-sisomicin 2',3,3''-triBoc-1-(N-Boc-1-hydroxy-3-amino-cyclobutyl-acetyl)-sisomicin (1.0 g, 1.042 mmol) was treated with N-Boc-3-trans-amino-cyclobutyl-carboxaldehyde following Procedure 1-Method B to yield the desired 6'-(N-Boc-methyl-trans-3-amino-cyclobutyl)-2',3,3''-triBoc-1-(N-Boc-1-hydroxy-3-amino-cyclobutyl-acetyl)-sisomicin (MS m/e [M+H]+ calcd 1144.6, found 1144.5), which was carried through to the next step without further purification.

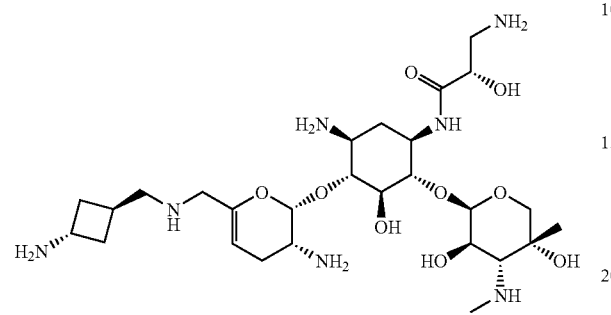

6'-(Methyl-trans-3-amino-cyclobutyl)-1-(3-amino-2(S)-hydroxy-propionyl)-sisomicin 6'-(N-Boc-methyl-trans-3-amino-cyclobutyl)-2',3,3''-triBoc-1-(N-Boc-3-amino-2(S)-hydroxy-propionyl)-sisomicin (1.07 mmol) was submitted to Procedure 3-Method B for Boc removal to yield a crude, which was purified by RP HPLC Method 1-Column B to yield 6'-(methyl-trans-3-amino-cyclobutyl)-1-(3-amino-2-(S)-hydroxy-propionyl)-sisomicin (0.033 g, 0.053 mmol, 4.9% yield): MS m/e [M+H]+ calcd 618.4, found 618.3, [M+Na]+ 640.3; CLND 96.5% purity.

Example 60

6'-(Methyl-trans-3-amino-cyclobutyl)-1-(1-hydroxy-3-amino-cyclobutyl-acetyl)-sisomicin

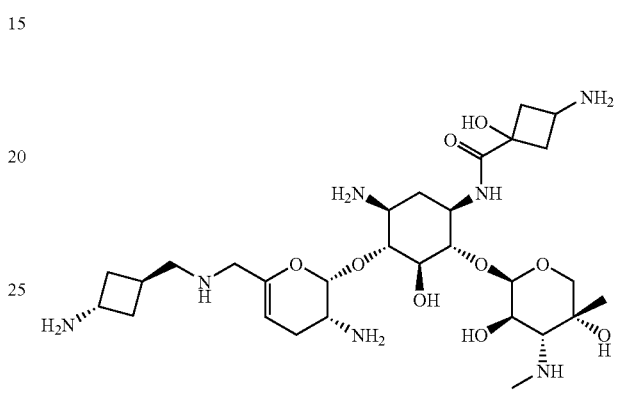

6'-(Methyl-trans-3-amino-cyclobutyl)-1-(1-hydroxy-3-amino-cyclobutyl-acetyl)-sisomicin 6'-(N-Boc-methyl-trans-3-amino-cyclobutyl)-2',3,3''-triBoc-1-(N-Boc-1-hydroxy-3-amino-cyclobutyl-acetyl)-sisomicin (1.042 mmol) was submitted to Procedure 3-Method B for Boc removal to yield a crude, which was purified by RP HPLC Method 1-Column B to yield 6'-(methyl-trans-3-amino-cyclobutyl)-1-(1-hydroxy-3-amino-cyclobutyl-

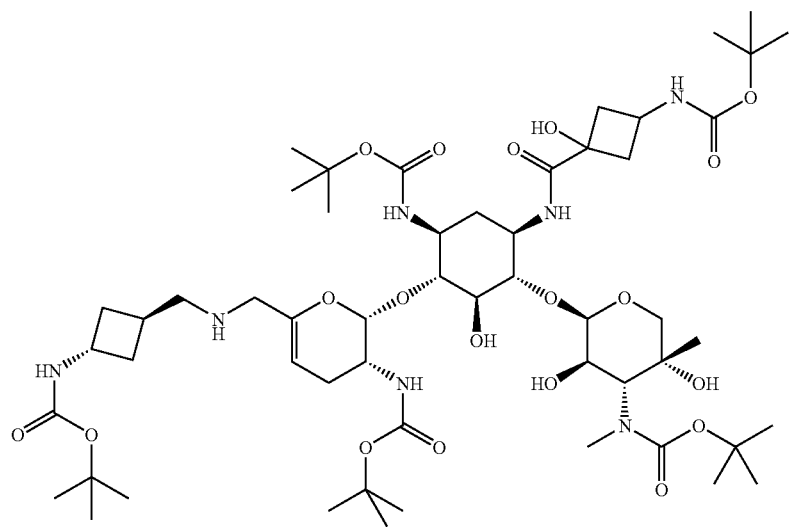 [SMILES: CN(C(=O)OC(C)(C)C)[C@@H]1[C@@H](O)[C@@H](O[C@@H]2[C@@H](O)[C@H](O[C@H]3OC(CNC[C@H]4C[C@H](NC(=O)OC(C)(C)C)C4)=CC[C@H]3NC(=O)OC(C)(C)C)[C@@H](NC(=O)OC(C)(C)C)C[C@H]2NC(=O)C2(O)CC(NC(=O)OC(C)(C)C)C2)OC[C@]1(C)O]

acetyl)-sisomicin (0.033 g, 0.051 mmol, 4.9% yield): MS m/e [M+H]+ calcd 644.4, found 644.3; CLND 94.5% purity.

Example 61

6'-Methyl-1-(3-hydroxy-azetidin-3-yl-acetyl)-sisomicin

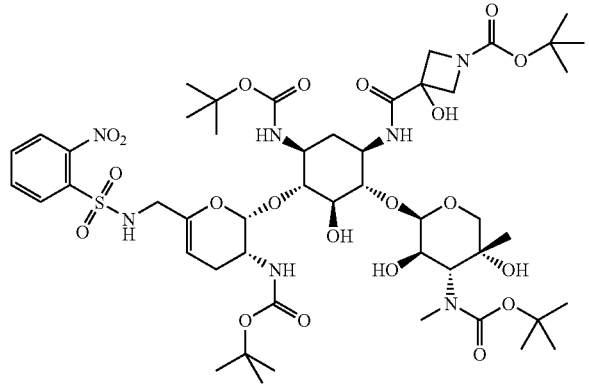 [SMILES: CN(C(=O)OC(C)(C)C)[C@@H]1[C@@H](O)[C@@H](O[C@@H]2[C@@H](O)[C@H](O[C@H]3OC(CNS(=O)(=O)c4ccccc4[N+](=O)[O-])=CC[C@H]3NC(=O)OC(C)(C)C)[C@@H](NC(=O)OC(C)(C)C)C[C@H]2NC(=O)C2(O)CN(C(=O)OC(C)(C)C)C2)OC[C@]1(C)O]

6'-Nosyl-2',3,3''-triBoc-1-(N-Boc-3-hydroxy-azetidin-3-yl-acetyl)-sisomicin

2',3,3''-triBoc-1-(N-Boc-3-hydroxy-azetidin-3-yl-acetyl)-sisomicin (1.0 g, 1.06 mmol) was submitted to Procedure 8 for nosylation to yield 6'-nosyl-2',3,3''-triBoc-1-(N-Boc-3-hydroxy-azetidin-3-yl-acetyl)-sisomicin (MS m/e [M+H]+ calcd 1132.5, found 1132.8), which was carried through to the next step without further purification.

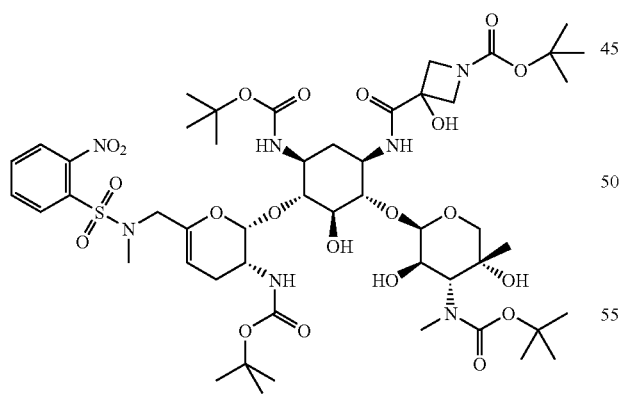

6'-Methyl-6'-nosyl-2',3,3''-triBoc-1-(N-Boc-3-hydroxy-azetidin-3-yl-acetyl)-sisomicin 6'-Nosyl-2',3,3''-triBoc-1-(N-Boc-3-hydroxy-azetidin-3-yl-acetyl)-sisomicin (1.06 mmol) was treated with MeI following Procedure 11 to yield 6'-methyl-6'-nosyl-2',3,3''-triBoc-1-(N-Boc-3-hydroxy-azetidin-3-yl-acetyl)-sisomicin (MS m/e [M+H]+ calcd 1146.5, found 1147.0), which was carried through to the next step without further purification.

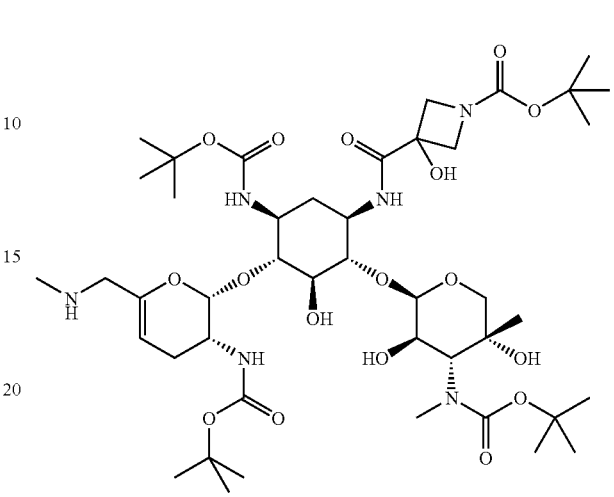

6'-Methyl-2',3,3''-triBoc-1-(N-Boc-3-hydroxy-azetidin-3-yl-acetyl)-sisomicin

6'-Methyl-6'-nosyl-2',3,3''-triBoc-1-(N-Boc-3-hydroxy-azetidin-3-yl-acetyl)-sisomicin (1.06 mmol) was submitted to Procedure 9 for nosyl deprotection to yield 6'-methyl-2',3,3''-triBoc-1-(N-Boc-3-hydroxy-azetidin-3-yl-acetyl)-sisomicin (MS m/e [M+H]+ calcd 961.5, found 961.8), which was carried through to the next step without further purification.

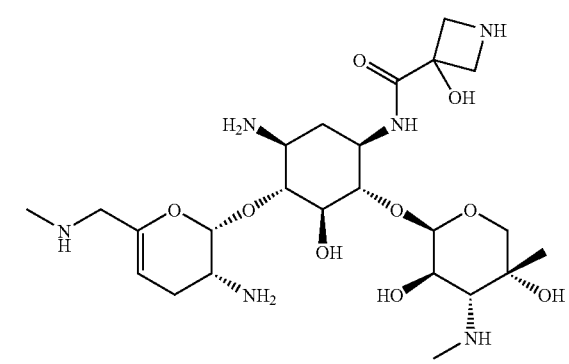 [SMILES: CNCC1=CC[C@@H](N)[C@@H](O[C@H]2[C@H](O)[C@@H](O[C@H]3OC[C@](C)(O)[C@H](NC)[C@H]3O)[C@H](NC(=O)C3(O)CNC3)C[C@@H]2N)O1]

6'-Methyl-1-(3-hydroxy-azetidin-3-yl-acetyl)-sisomicin

6'-Methyl-2',3,3''-triBoc-1-(N-Boc-3-hydroxy-azetidin-3-yl-acetyl)-sisomicin (1.06 mmol) was submitted to Procedure 3-Method A for Boc removal to yield a crude, which was purified by RP HPLC Method 1-Column B to yield 6'-methyl-1-(3-hydroxy-azetidin-3-yl-acetyl)-sisomicin (0.247 g, 0.441 mmol, 41.6% yield): MS m/e [M+H]+ calcd 561.3, found 561.2; CLND 96.7% purity.

Example 62

6'-(2-Hydroxy-ethyl)-1-(1-hydroxy-3-amino-cyclobutyl-acetyl)-sisomicin

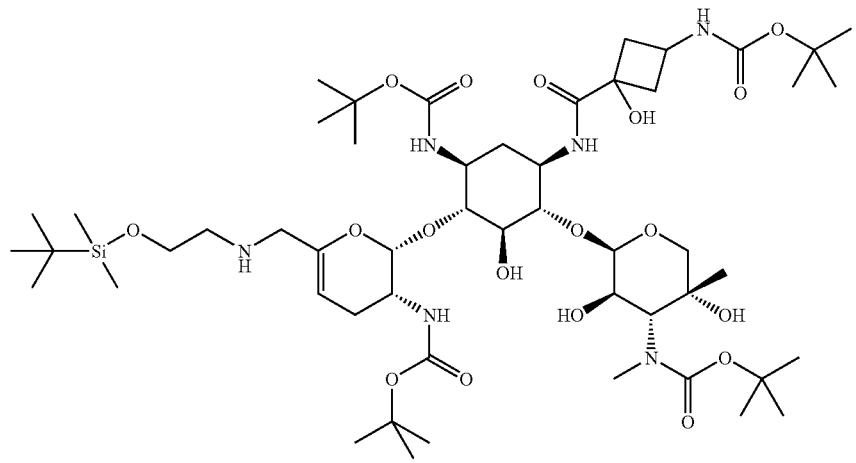 [SMILES: CN(C(=O)OC(C)(C)C)[C@@H]1[C@@H](O)[C@@H](O[C@@H]2[C@@H](O)[C@H](O[C@H]3OC(CNCCO[Si](C)(C)C(C)(C)C)=CC[C@H]3NC(=O)OC(C)(C)C)[C@@H](NC(=O)OC(C)(C)C)C[C@H]2NC(=O)C2(O)CC(NC(=O)OC(C)(C)C)C2)OC[C@]1(C)O]

6'-(2-tert-Butyldimethylsilyloxy-ethyl)-2',3,3"-tri-Boc-1-(N-Boc-1-hydroxy-3-amino-cyclobutyl-acetyl)-sisomicin 2',3,3"-triBoc-1-(N-Boc-1-hydroxy-3-amino-cyclobutyl-acetyl)-sisomicin (0.65 g, 0.67 mmol) was treated with tert-butyldimethylsilyloxy acetaldehyde following Procedure 1-Method A to yield the desired 6'-(2-tert-butyldimethylsilyloxy-ethyl)-2',3,3"-triBoc-1-(N-Boc-1-hydroxy-3-amino-cyclobutyl-acetyl)-sisomicin (MS m/e [M+H]$^+$ calcd 1119.6, found 1119.9), which was carried through to the next step without further purification.

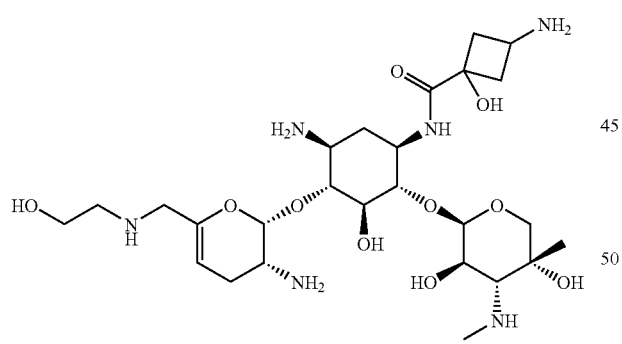

6'-(2-Hydroxy-ethyl)-1-(1-hydroxy-3-amino-cyclobutyl-acetyl)-sisomicin

6'-(2-tert-Butyldimethylsilyloxy-ethyl)-2',3,3"-triBoc-1-(N-Boc-1-hydroxy-3-amino-cyclobutyl-acetyl)-sisomicin (0.67 mmol) was submitted to Procedure 3-Method A for Boc and TBS removal to yield a crude, which was purified by RP HPLC Method 1-Column B to yield 6'-(2-hydroxy-ethyl)-1-(1-hydroxy-3-amino-cyclobutyl-acetyl)-sisomicin (0.067 g, 0.111 mmol, 16.6% yield): MS m/e [M+H]$^+$ calcd 605.3, found 605.6; CLND 97.5% purity.

Example 63

6'-(Methyl-trans-3-amino-cyclobutyl)-1-(3-hydroxy-azetidin-3-yl-acetyl)-sisomicin

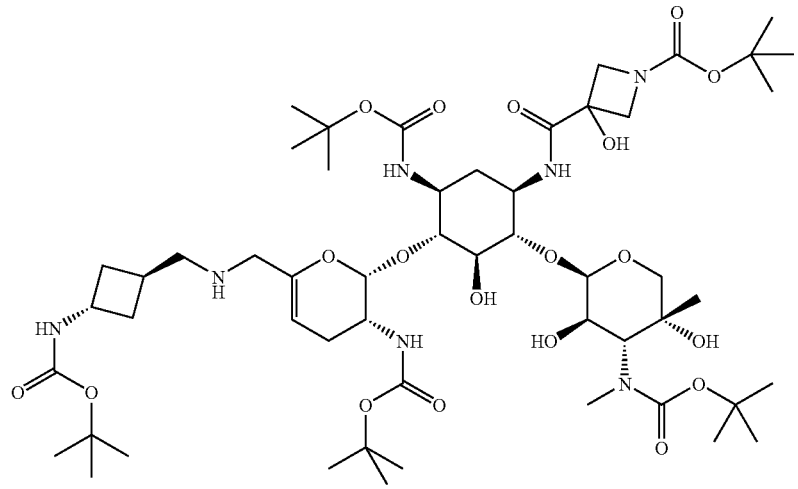 [SMILES: CN(C(=O)OC(C)(C)C)[C@@H]1[C@@H](O)[C@@H](O[C@@H]2[C@@H](O)[C@H](O[C@H]3OC(CNC[C@H]4C[C@H](NC(=O)OC(C)(C)C)C4)=CC[C@H]3NC(=O)OC(C)(C)C)[C@@H](NC(=O)OC(C)(C)C)C[C@H]2NC(=O)C2(O)CN(C(=O)OC(C)(C)C)C2)OC[C@]1(C)O]

6'-(N-Boc-methyl-trans-3-amino-cyclobutyl)-2',3,3''-triBoc-1-(N-Boc-3-hydroxy-azetidin-3-yl-acetyl)-sisomicin 2',3,3''-triBoc-1-(N-Boc-1-hydroxy-azetidin-3-yl-acetyl)-sisomicin (1.0 g, 1.06 mmol) was treated with N-Boc-3-trans-amino-cyclobutyl-carboxaldehyde following Procedure 1-Method B to yield the desired 6'-(N-Boc-methyl-trans-3-amino-cyclobutyl)-2',3,3''-triBoc-1-(N-Boc-3-hydroxy-azetidin-3-yl-acetyl)-sisomicin (MS m/e [M+H]+ calcd 1130.6, found 1130.5), which was carried through to the next step without further purification.

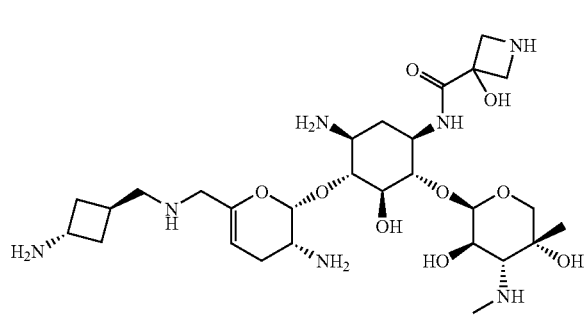 [SMILES: CN[C@@H]1[C@@H](O)[C@@H](O[C@@H]2[C@@H](O)[C@H](O[C@H]3OC(CNC[C@H]4C[C@H](N)C4)=CC[C@H]3N)[C@@H](N)C[C@H]2NC(=O)C2(O)CNC2)OC[C@]1(C)O]

6'-(Methyl-trans-3-amino-cyclobutyl)-1-(3-hydroxy-azetidin-3-yl-acetyl)-sisomicin 6'-(N-Boc-methyl-trans-3-amino-cyclobutyl)-2',3,3''-triBoc-1-(N-Boc-3-hydroxy-azetidin-3-yl-acetyl)-sisomicin (1.06 mmol) was submitted to Procedure 3-Method B for Boc removal to yield a crude, which was purified by RP HPLC Method 1-Column B to yield 6'-(methyl-trans-3-amino-cyclobutyl)-1-(3-hydroxy-azetidin-3-yl-acetyl)-sisomicin (0.018 g, 0.029 mmol, 2.7% yield): MS m/e [M+H]+ calcd 630.4, found 630.3; CLND 75.6% purity.

Example 64

6'-Methyl-1-(1-hydroxy-3-amino-cyclobutyl-acetyl)-sisomicin

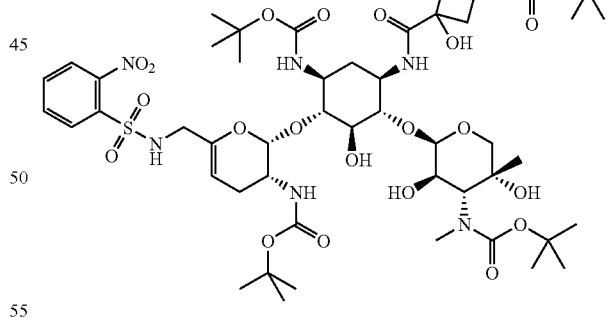

6'-Nosyl-2',3,3''-triBoc-1-(N-Boc-1-hydroxy-3-amino-cyclobutyl-acetyl)-sisomicin 2',3,3''-triBoc-1-(N-Boc-1-hydroxy-3-amino-cyclobutyl-acetyl)-sisomicin (1.0 g, 1.04 mmol) was submitted to Procedure 8 for nosylation to yield 6'-nosyl-2',3,3''-triBoc-1-(N-Boc-1-hydroxy-3-amino-cyclobutyl-acetyl)-sisomicin (MS m/e [M+H]+ calcd 1146.5, found 1147.0), which was carried through to the next step without further purification.

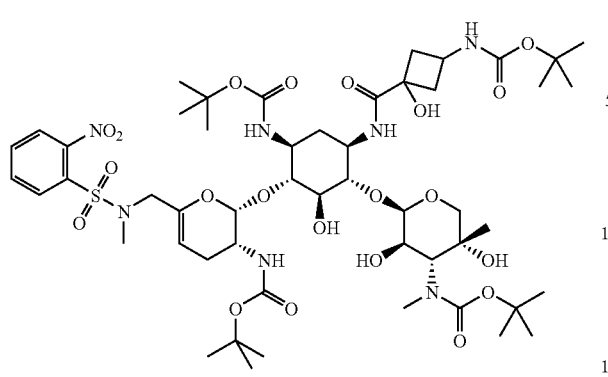

6'-Methyl-6'-nosyl-2',3,3''-triBoc-1-(N-Boc-1-hydroxy-3-amino-cyclobutyl-sisomicin 6'-Nosyl-2',3,3''-triBoc-1-(N-Boc-1-hydroxy-3-amino-cyclobutyl-acetyl)-sisomicin (1.04 mmol) was treated with MeI following Procedure 11 to yield 6'-methyl-6'-nosyl-2',3,3''-triBoc-1-(N-Boc-1-hydroxy-3-amino-cyclobutyl-acetyl)-sisomicin (MS m/e [M+H]+ calcd 1160.5, found 1161.1), which was carried through to the next step without further purification.

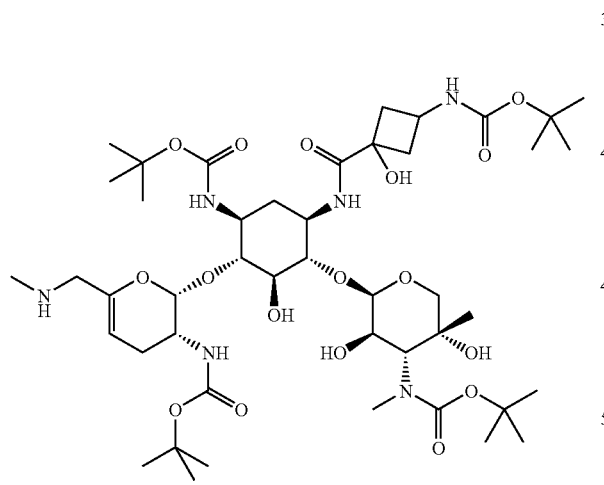

6'-Methyl-2',3,3''-triBoc-1-(N-Boc-1-hydroxy-3-amino-cyclobutyl-acetyl)-sisomicin 6'-Methyl-6'-nosyl-2',3,3''-triBoc-1-(N-Boc-1-hydroxy-3-amino-cyclobutyl-acetyl)-sisomicin (1.04 mmol) was submitted to Procedure 9 for nosyl deprotection to yield 6'-methyl-2',3,3''-triBoc-1-(N-Boc-1-hydroxy-3-amino-cyclobutyl-acetyl)-sisomicin (MS m/e [M+H]+ calcd 975.5, found 975.9), which was carried through to the next step without further purification.

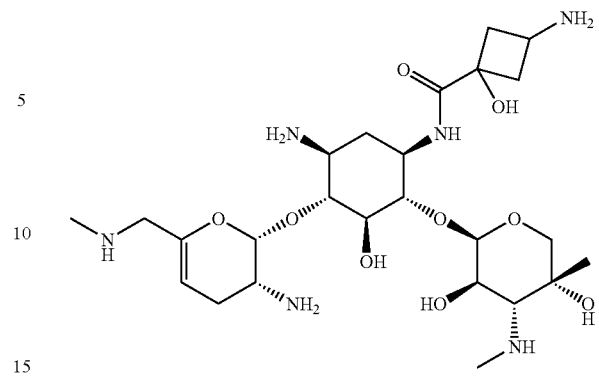

6'-Methyl-1-(1-hydroxy-3-amino-cyclobutyl-acetyl)-sisomicin

6'-Methyl-2',3,3''-triBoc-1-(N-Boc-1-hydroxy-3-amino-cyclobutyl-acetyl)-sisomicin (1.04 mmol) was submitted to Procedure 3-Method A for Boc removal to yield a crude, which was purified by RP HPLC Method 1-Column B to yield 6'-methyl-1-(1-hydroxy-3-amino-cyclobutyl-acetyl)-sisomicin (0.098 g, 0.170 mmol, 16.3% yield): MS m/e [M+H]+ calcd 575.3, found 575.3; CLND 98.5% purity.

Example 65

6'-(Methyl-4(S)-amino-pyrrolidin-2(S)-yl)-1-(3-amino-2(S)-hydroxy-propionyl)-sisomicin

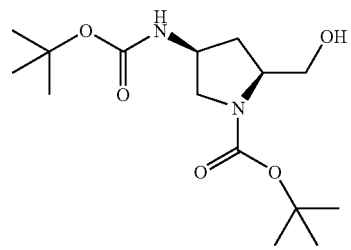 [SMILES: CC(C)(C)OC(=O)N[C@H]1C[C@@H](CO)N(C(=O)OC(C)(C)C)C1]

N,N-diBoc-4(S)-amino-2(S)-methanol-pyrrolidine

N,N-diBoc-4(S)-amino-pyrrolidine-2(S)-carboxylic acid (1.03 g, 3.12 mmol) was submitted to Procedure 19 to yield the corresponding N,N-diBoc-4(S)-amino-2(S)-methanol pyrrolidine (0.605 g, 1.91 mmol, 61.2% yield), which was carried through to the next step without further purification.

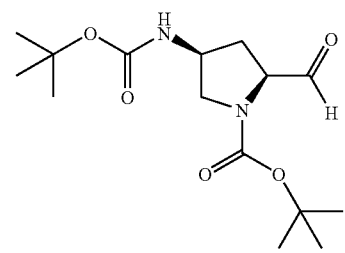 [SMILES: CC(C)(C)OC(=O)N[C@H]1C[C@@H](C=O)N(C(=O)OC(C)(C)C)C1]

N,N-diBoc-4(S)-amino-pyrrolidine-2(S)-carbaldehyde

N,N-diBoc-4(S)-amino-2(S)-methanol pyrrolidine (0.486 g, 1.53 mmol) was submitted to Procedure 18 for oxidation to the corresponding N,N-diBoc-4(S)-amino-pyrrolidine-2(S)-carbaldehyde, which was carried through to the next step without further purification.

6'-(Methyl-4(S)-amino-pyrrolidin-2(S)-yl)-1-(3-amino-2(S)-hydroxy-propionyl)-sisomicin 6'-(Methyl-N,N-diBoc-4(S)-amino-pyrrolidin-2(S)-yl)-2',3,3''-triBoc-1-(N-Boc-3-amino-2(S)-hydroxy-propionyl)-sisomicin (0.080 mmol) was submitted to Procedure 3-Method A for Boc removal to yield a crude, which was purified by RP

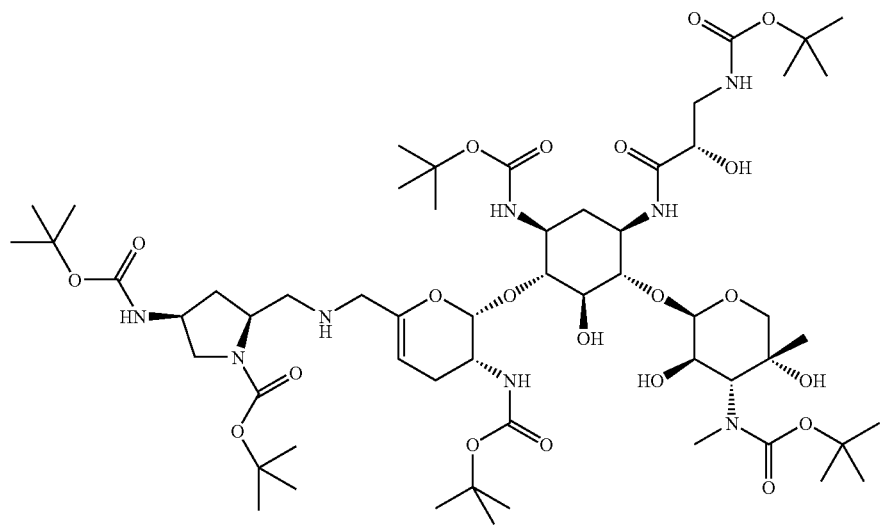 [SMILES: CN(C(=O)OC(C)(C)C)[C@@H]1[C@@H](O)[C@@H](O[C@@H]2[C@@H](O)[C@H](O[C@H]3OC(CNC[C@@H]4C[C@H](NC(=O)OC(C)(C)C)CN4C(=O)OC(C)(C)C)=CC[C@H]3NC(=O)OC(C)(C)C)[C@@H](NC(=O)OC(C)(C)C)C[C@H]2NC(=O)[C@@H](O)CNC(=O)OC(C)(C)C)OC[C@]1(C)O]

6'-(Methyl-N,N-diBoc-4(S)-amino-pyrrolidin-2(S)-yl)-2',3,3''-triBoc-1-(N-Boc-3-amino-2(S)-hydroxy-propionyl)-sisomicin 2',3,3''-triBoc-1-(N-Boc-3-amino-2(S)-hydroxy-propionyl)-sisomicin (0.075 g, 0.080 mmol) was treated with N,N-diBoc-4(S)-amino-pyrrolidine-2(S)-carbaldehyde following Procedure 1-Method A to yield the desired 6'-(methyl-N,N-diBoc-4(S)-amino-pyrrolidin-2(S)-yl)-2',3,3''-triBoc-1-(N-Boc-3-amino-2(S)-hydroxy-propionyl)-sisomicin (MS m/e [M+H]$^+$ calcd 1233.7, found 1234.0), which was carried through to the next step without further purification.

HPLC Method 3 to yield 6'-(methyl-4(S)-amino-pyrrolidin-2(S)-yl)-1-(3-amino-2(S)-hydroxy-propionyl)-sisomicin (0.0006 g, 0.0009 mmol, 1.1% yield): MS m/e [M+H]$^+$ calcd 633.4, found 633.4; CLND 81.7% purity.

Example 66

6'-(Methyl-1-aminomethyl-cyclopropyl)-1-(3-amino-2(S)-hydroxy-propionyl)-sisomicin

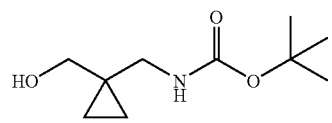

N-Boc-1-aminomethyl-cyclopropyl-methanol

N-Boc-1-aminomethyl-cyclopropane carboxylic acid (1.0 g, 4.64 mmol) was submitted to Procedure 19 to yield the corresponding N-Boc-1-aminomethyl-cyclopropyl-methanol (0.99 g, MS m/e [M+H]$^+$ calcd 202.1, found 202.1), which was carried through to the next step without further purification.

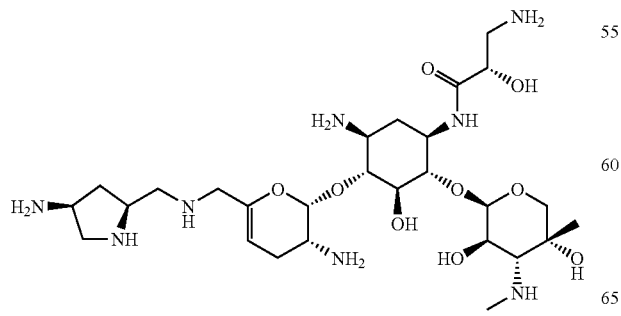

N-Boc-1-aminomethyl-cyclopropane carboxaldehyde

N-Boc-1-aminomethyl-cyclopropyl-methanol (0.87 g, 4.32 mmol) was submitted to Procedure 18 for oxidation to the corresponding N-Boc-1-aminomethyl-cyclopropane carboxaldehyde, which was carried through to the next step without further purification.

Boc removal to yield a crude, which was purified by RP HPLC Method 3 to yield 6'-(methyl-1-aminomethyl-cyclopropyl)-1-(3-amino-2(S)-hydroxy-propionyl)-sisomicin

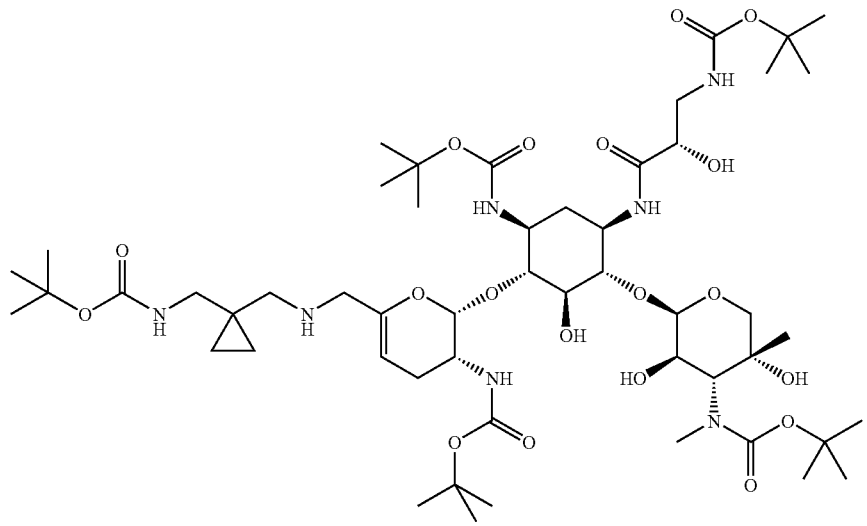 [SMILES: CN(C(=O)OC(C)(C)C)[C@@H]1[C@@H](O)[C@@H](O[C@@H]2[C@@H](O)[C@H](O[C@H]3OC(CNCC4(CNC(=O)OC(C)(C)C)CC4)=CC[C@H]3NC(=O)OC(C)(C)C)[C@@H](NC(=O)OC(C)(C)C)C[C@H]2NC(=O)[C@@H](O)CNC(=O)OC(C)(C)C)OC[C@]1(C)O]

6'-(Methyl-N-Boc-1-aminomethyl-cyclopropyl)-2',3,3''-triBoc-1-(N-Boc-3-amino-2(S)-hydroxy-propionyl)-sisomicin 2',3,3''-triBoc-1-(N-Boc-3-amino-2(S)-hydroxy-propionyl)-sisomicin (0.075 g, 0.080 mmol) was treated with N-Boc-1-aminomethyl-cyclopropane carboxaldehyde following Procedure 1-Method A to yield the desired 6'-(methyl-N-Boc-1-aminomethyl-cyclopropyl)-2',3,3''-triBoc-1-(N-Boc-3-amino-2(S)-hydroxy-propionyl)-sisomicin (MS m/e [M+H]$^+$ calcd 1118.6, found 1118.8), which was carried through to the next step without further purification.

(0.0033 g, 0.0053 mmol, 6.6% yield): MS m/e [M+H]$^+$ calcd 618.4, found 618.4; CLND 94.5% purity.

Example 67

6'-(Methyl-1-Amino-cyclopropyl)-1-(3-amino-2(S)-hydroxy-propionyl)-sisomicin

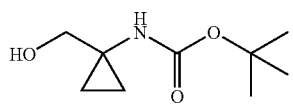

N-Boc-1-amino-cyclopropyl-methanol

N-Boc-1-amino-cyclopropane carboxylic acid (0.25 g, 1.24 mmol) was submitted to Procedure 19 to yield the corresponding N-Boc-1-amino-cyclopropyl-methanol (0.051 g, 0.27 mmol, 21.8% yield), which was carried through to the next step without further purification.

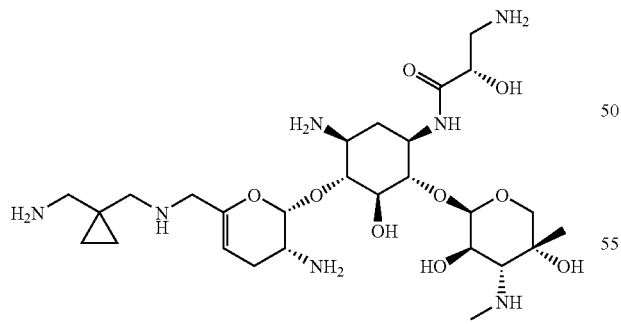

6'-(Methyl-1-aminomethyl-cyclopropyl)-1-(3-amino-2(S)-hydroxy-propionyl)-sisomicin 6'-(Methyl-N-Boc-1-aminomethyl-cyclopropyl)-2',3,3''-triBoc-1-(N-Boc-3-amino-2(S)-hydroxy-propionyl)-sisomicin (0.080 mmol) was submitted to Procedure 3-Method A for

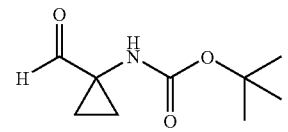

N-Boc-1-amino-cyclopropane carboxaldehyde

N-Boc-1-amino-cyclopropyl-methanol (0.051 g, 0.27 mmol) was submitted to Procedure 18 for oxidation to the corresponding N-Boc-1-amino-cyclopropane carboxaldehyde, which was carried through to the next step without further purification.

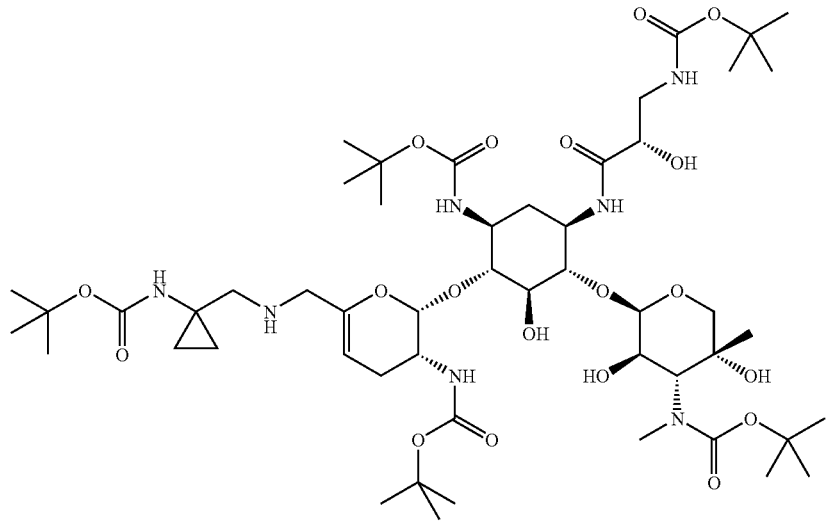 [SMILES: CN(C(=O)OC(C)(C)C)[C@@H]1[C@@H](O)[C@@H](O[C@@H]2[C@@H](O)[C@H](O[C@H]3OC(CNCC4(NC(=O)OC(C)(C)C)CC4)=CC[C@H]3NC(=O)OC(C)(C)C)[C@@H](NC(=O)OC(C)(C)C)C[C@H]2NC(=O)[C@@H](O)CNC(=O)OC(C)(C)C)OC[C@]1(C)O]

6'-(Methyl-N-Boc-1-amino-cyclopropyl)-2',3,3''-triBoc-1-(N-Boc-3-amino-2(S)-hydroxy-propionyl)-sisomicin 2',3,3''-triBoc-1-(N-Boc-3-amino-2(S)-hydroxy-propionyl)-sisomicin (0.075 g, 0.080 mmol) was treated with N-Boc-1-amino-cyclopropane carboxaldehyde following Procedure 1-Method A to yield the desired 6'-(methyl-N-Boc-1-amino-cyclopropyl)-2',3,3''-triBoc-1-(N-Boc-3-amino-2(S)-hydroxy-propionyl)-sisomicin (MS m/e [M+H]$^+$ calcd 1104.6, found 1105.2), which was carried through to the next step without further purification.

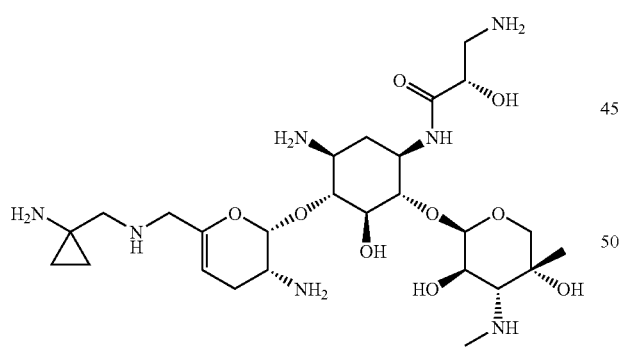

6'-(Methyl-1-amino-cyclopropyl)-1-(3-amino-2(S)-hydroxy-propionyl)-sisomicin

6'-(Methyl-N-Boc-1-amino-cyclopropyl)-2',3,3''-triBoc-1-(N-Boc-3-amino-2(S)-hydroxy-propionyl)-sisomicin (0.080 mmol) was submitted to Procedure 3-Method A for Boc removal to yield a crude, which was purified by RP HPLC Method 3 to yield 6'-(methyl-1-amino-cyclopropyl)-1-(3-amino-2(S)-hydroxy-propionyl)-sisomicin (0.0042 g, 0.0069 mmol, 8.6% yield): MS m/e [M+H]$^+$ calcd 604.4, found 604.6; CLND 95.4% purity.

Example 68

6'-(2-Hydroxy-4-amino-butyl)-1-(3-amino-2(S)-hydroxy-propionyl)-sisomicin

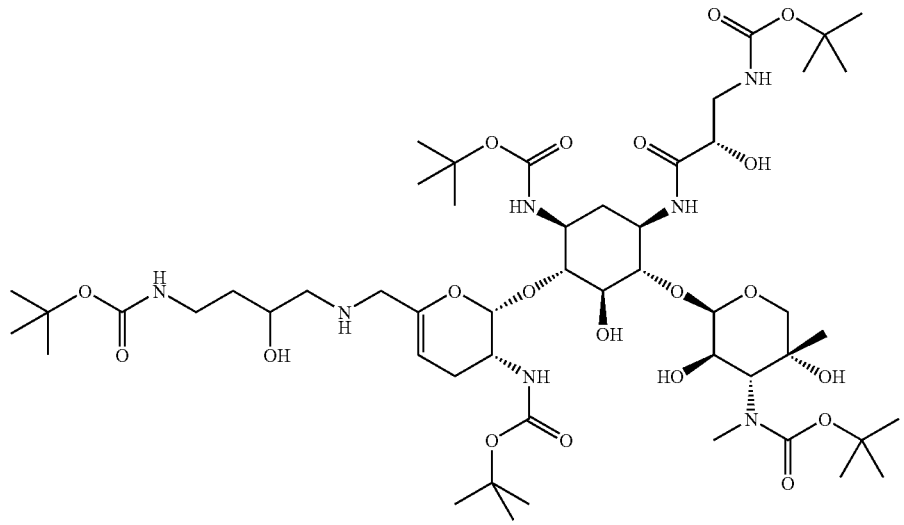 [SMILES: CN(C(=O)OC(C)(C)C)[C@@H]1[C@@H](O)[C@@H](O[C@@H]2[C@@H](O)[C@H](O[C@H]3OC(CNCC(O)CCNC(=O)OC(C)(C)C)=CC[C@H]3NC(=O)OC(C)(C)C)[C@@H](NC(=O)OC(C)(C)C)C[C@H]2NC(=O)[C@@H](O)CNC(=O)OC(C)(C)C)OC[C@]1(C)O]

6'-(N-Boc-2-hydroxy-4-amino-butyl)-2',3,3''-triBoc-1-(N-Boc-3-amino-2(S)-hydroxy-propionyl)-sisomicin 2',3,3''-triBoc-1-(N-Boc-3-amino-2(S)-hydroxy-propionyl)-sisomicin (0.075 g, 0.080 mmol) was treated with N-Boc-2-(oxiran-2-yl)-ethyl carbamate following Procedure 5 to yield the desired 6'-(N-Boc-2-hydroxy-4-amino-butyl)-2',3,3''-triBoc-1-(N-Boc-3-amino-2(S)-hydroxy-propionyl)-sisomicin (MS m/e [M+H]$^+$ calcd 1122.6, found 1122.9), which was carried through to the next step without further purification.

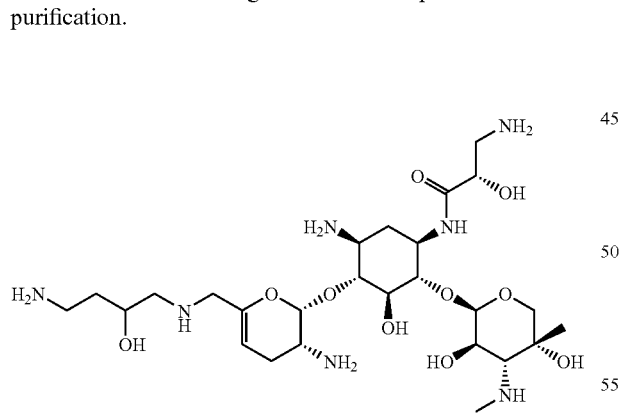

6'-(2-Hydroxy-4-amino-butyl)-1-(3-amino-2(S)-hydroxy-propionyl)-sisomicin

6'-(N-Boc-2-hydroxy-4-amino-butyl)-2',3,3''-triBoc-1-(N-Boc-3-amino-2(S)-hydroxy-propionyl)-sisomicin (0.080 mmol) was submitted to Procedure 3-Method A for Boc removal to yield a crude, which was purified by RP HPLC Method 3 to yield 6'-(2-hydroxy-4-amino-butyl)-1-(3-amino-2(S)-hydroxy-propionyl)-sisomicin (0.0024 g, 0.0038 mmol, 4.7% yield): MS m/e [M+H]$^+$ calcd 622.4, found 622.6; CLND 93.2% purity.

Example 69

6'-(Methyl-1(R)-amino-2(S)-hydroxy-cyclopent-4(S)-yl)-1-(3-amino-2(S)-hydroxy-propionyl)-sisomicin

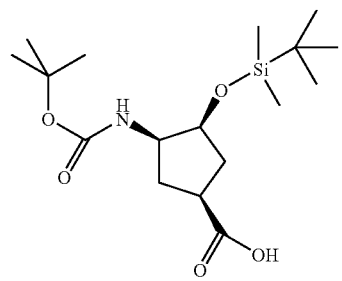 [SMILES: CC(C)(C)OC(=O)N[C@@H]1C[C@H](C(=O)O)C[C@@H]1O[Si](C)(C)C(C)(C)C]

N-Boc-1(R)-amino-2(S)-tert-butyldimethylsilyloxy-cyclopentane-4(S)-carboxylic acid To a stirring solution of N-Boc-1(R)-amino-2(S)-hydroxy-cyclopentane-4(S)-carboxylic acid methyl ester (0.622 g, 2.40 mmol) in DCM (1.9 mL) was added imidazole (0.164 g, 2.41 mmol), DMAP (0.047 g, 0.35 mmmol) and TBSCl (0.363 g, 2.40 mmol) and the reaction was stirred at room temperature for 18 hours, followed by heating at 40° C. for 1 hour. The reaction mixture was cooled to room temperature, and was quenched with H$_2$O (3 mL). The organic layer was separated and was concentrated to dryness to yield a residue, which was dissolved in isopropanol (6 mL) and 1M NaOH (2.9 mL), and the reaction was heated at 60° C. for 1 hour. The reaction was cooled to 0° C. and slowly acidified to pH 3 with 1M HCl (3 mL). After adding chloroform (18 mL), the organic layer was separated, dried over Na₂SO₄, and concentrated to dryness to yield the desired acid (0.75 g, 2.09 mmol, 87.1% yield).

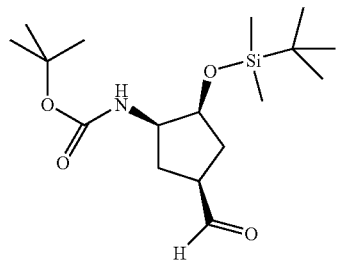

N-Boc-1(R)-amino-2(S)-tert-butyldimethylsilyloxy-cyclopentane-4(S)-carboxaldehyde N-Boc-1(R)-amino-2(S)-tert-butyldimethylsilyloxy-4(S)-hydroxymethyl-cyclopentane (0.44 g, 1.27 mmol) was submitted to Procedure 18 for oxidation to the corresponding N-Boc-1(R)-amino-2(S)-tert-butyldimethylsilyloxy-cyclopentane-4(S)-carboxaldehyde (0.42 g, 1.22 mmol, 96.1% yield).

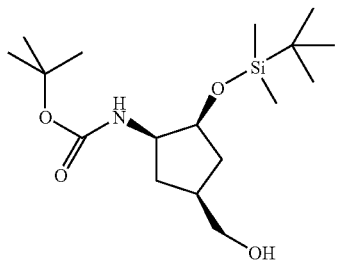 [SMILES: CC(C)(C)OC(=O)N[C@@H]1C[C@H](CO)C[C@@H]1O[Si](C)(C)C(C)(C)C]

N-Boc-1(R)-amino-2(S)-tert-butyldimethylsilyloxy-4(S)-hydroxymethyl-cyclopentane

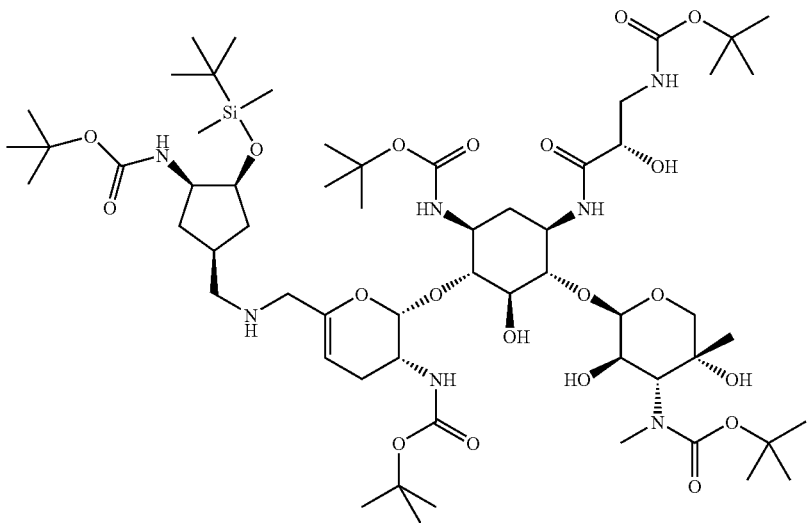 [SMILES: CN(C(=O)OC(C)(C)C)[C@@H]1[C@@H](O)[C@@H](O[C@@H]2[C@@H](O)[C@H](O[C@H]3OC(CNC[C@@H]4C[C@H](O[Si](C)(C)C(C)(C)C)[C@H](NC(=O)OC(C)(C)C)C4)=CC[C@H]3NC(=O)OC(C)(C)C)[C@@H](NC(=O)OC(C)(C)C)C[C@H]2NC(=O)[C@@H](O)CNC(=O)OC(C)(C)C)OC[C@]1(C)O]

6'-(Methyl-N-Boc-1(R)-amino-2(S)-tert-butyldimethylsilyloxy-cyclopent-4(S)-yl)-2',3,3''-triBoc-1-(N-Boc-3-amino-2(S)-hydroxy-propionyl)-sisomicin N-Boc-1(R)-amino-2(S)-tert-butyldimethylsilyloxy-cyclopentane-4(S)-carboxylic acid (0.53 g, 1.47 mmol) was submitted to Procedure 19 for reduction to the corresponding N-Boc-1(R)-amino-2(S)-tert-butyldimethylsilyloxy-4(S)-hydroxymethyl-cyclopentane (0.44 g, 1.27 mmol, 86.4% yield): ¹H NMR (250 MHz, CDCl₃) δ 4.69-4.79 (m, 1 H), 4.08-4.13 (m, 1 H), 3.88 (bs, 1 H), 3.52-3.61 (m, 2 H), 2.16-2.30 (m, 2 H), 1.96-2.14 (m, 2 H), 1.48-1.53 (m, 2 H), 1.47 (s, 9 H), 0.91 (s, 9 H), 0.09 (s, 6 H).

2',3,3''-triBoc-1-(N-Boc-3-amino-2(S)-hydroxy-propionyl)-sisomicin (0.075 g, 0.080 mmol) was treated with N-Boc-1(R)-amino-2(S)-tert-butyldimethylsilyloxy-cyclopentane-4(S)-carboxaldehyde following Procedure 1-Method A to yield the desired 6'-(methyl-N-Boc-1(R)-amino-2(S)-tert-butyldimethylsilyloxy-cyclopent-4(S)-yl)-2',3,3''-triBoc-1-(N-Boc-3-amino-2(S)-hydroxy-propionyl)-sisomicin (MS m/e [M+H]⁺ calcd 1262.7, found 1263.2), which was carried through to the next step without further purification.

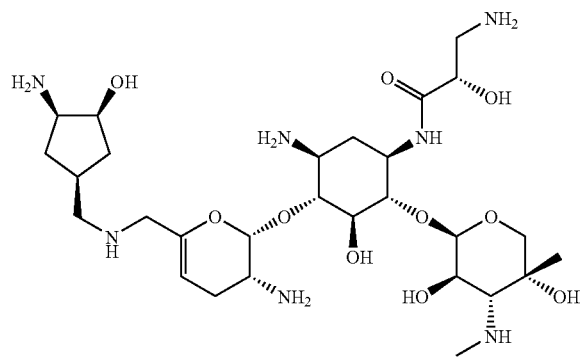 [SMILES: CN[C@@H]1[C@@H](O)[C@@H](O[C@@H]2[C@@H](O)[C@H](O[C@H]3OC(CNC[C@H]4C[C@@H](N)[C@@H](O)C4)=CC[C@H]3N)[C@@H](N)C[C@H]2NC(=O)[C@@H](O)CN)OC[C@]1(C)O]

6'-(Methyl-1(R)-amino-2(S)-hydroxy-cyclopent-4(S)-yl)-1-(3-amino-2(S)-hydroxy-propionyl)-sisomicin 6'-(Methyl-N-Boc-1(R)-amino-2(S)-tert-butyldimethylsilyloxy-cyclopent-4(S)-yl)-2',3,3''-triBoc-1-(N-Boc-3-amino-2(S)-hydroxy-propionyl)-sisomicin (0.080 mmol) was submitted to Procedure 3-Method A for Boc and TBS removal to yield a crude, which was purified by RP HPLC Method 3 to yield 6'-(methyl-1(R)-amino-2(S)-hydroxy-cyclopent-4(S)-yl)-1-(3-amino-2(S)-hydroxy-propionyl)-sisomicin (0.0039 g, 0.0060 mmol, 7.5% yield): MS m/e [M+H]$^{30}$ calcd 648.4, found 648.4; CLND 91.6% purity.

Example 70

6'-(Ethyl-2-(3-hydroxy-azetidin-3-yl))-1-(3-amino-2(S)-hydroxy-propionyl)-sisomicin

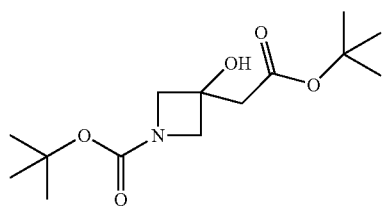 [SMILES: CC(C)(C)OC(=O)CC1(O)CN(C(=O)OC(C)(C)C)C1]

tent-Butyl-2-(N-Boc-3-hydroxy-azetidin-3-yl)acetate

To a stirring solution of N-Boc-3-azetidinone (0.45 g, 2.64 mmol) in THF (5 mL) was slowly added a 0.5 M solution of 2-tert-butoxy-2-oxoethyl-zinc chloride in Et$_2$O (10 mL, 5.0 mmol), and the reaction mixture was stirred for 5 h. The reaction was then quenched with sat. aq. NH$_4$Cl (10 mL), and the aqueous layer was separated and extracted with ethyl acetate (2×30 mL). The combined organic layers were washed with 5% aq. NaHCO$_3$ (2×10 mL), brine (15 mL), dried over Na$_2$SO$_4$, filtered and concentrated to dryness to yield tert-butyl-2-(N-Boc-3-hydroxy-azetidin-3-yl)-acetate (MS m/e [M+H]$^+$ calcd 288.2, found 287.7).

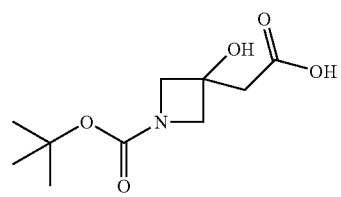 [SMILES: CC(C)(C)OC(=O)N1CC(O)(CC(=O)O)C1]

2-(N-Boc-3-hydroxy-azetidin-3-yl)-acetic acid

To a stirring solution of tert-butyl-2-(N-Boc-3-hydroxy-azetidin-3-yl)-acetate (0.86 g, 2.99 mmol) in dioxane (18 mL) was added 3M HCl (5 mL), and the mixture was heated at 70° C. for 1 h. The reaction mixture was then cooled to 0° C. and it was basified with 2 M NaOH (8 mL), followed by addition of BOC$_2$O (1.0 g, 4.6 mmol). The reaction mixture was allowed to warm to room temperature for 2 h, and was then concentrated to half its total volume on the rotary evaporator. Isopropanol (3 mL) and chloroform (12 mL) were then added and the mixture was cooled to 0° C. and slowly acidified to pH 3 with 1M HCl. The organic layer was then separated, dried over Na$_2$SO$_4$, and concentrated to dryness to yield 2-(N-Boc-3-hydroxy-azetidin-3-yl)-acetic acid (0.65 g, 2.81 mmol, 94.0% yield).

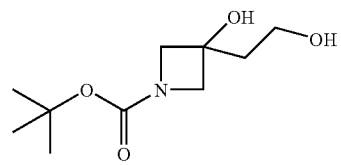

N-Boc-3-(2-hydroxy-ethyl)-azetidin-3-ol 2-(N-Boc-3-hydroxy-azetidin-3-yl)-acetic acid (0.44 g, 1.90 mmol) was submitted to Procedure 19 for reduction to yield the corresponding N-Boc-3-(2-hydroxy-ethyl)-azetidin-3-ol (0.29 g, 1.33 mmol, 70.0% yield).

2-(N-Boc-3-hydroxy-azetidin-3-yl)-acetaldehyde

N-Boc-3-(2-hydroxy-ethyl)-azetidin-3-ol (0.29 g, 1.33 mmol) was submitted to Procedure 18 for oxidation to the corresponding 2-(N-Boc-3-hydroxy-azetidin-3-yl)-acetaldehyde, which was carried through to the next step without further purification.

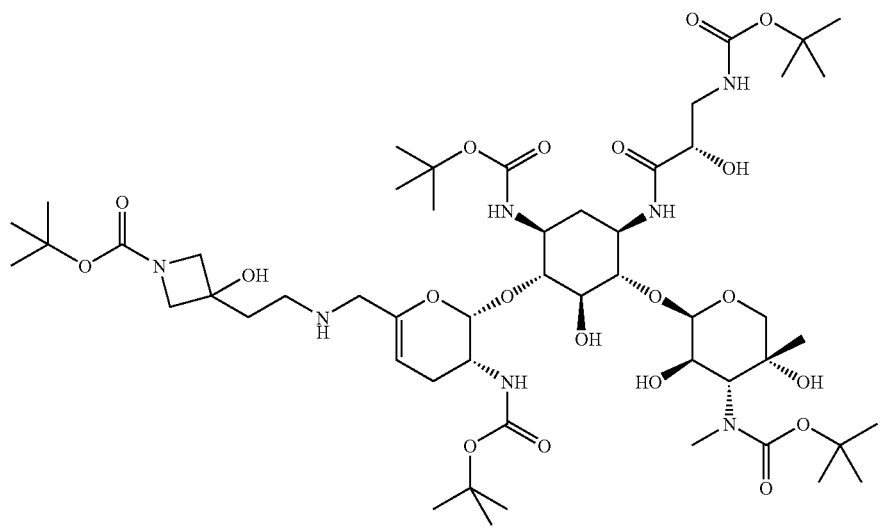 [SMILES: CN(C(=O)OC(C)(C)C)[C@@H]1[C@@H](O)[C@@H](O[C@@H]2[C@@H](O)[C@H](O[C@H]3OC(CNCCC4(O)CN(C(=O)OC(C)(C)C)C4)=CC[C@H]3NC(=O)OC(C)(C)C)[C@@H](NC(=O)OC(C)(C)C)C[C@H]2NC(=O)[C@@H](O)CNC(=O)OC(C)(C)C)OC[C@]1(C)O]

6'-(Ethyl-2-(N-Boc-3-hydroxy-azetidin-3-yl))-2',3,3''-triBoc-1-(N-Boc-3-amino-2(S)-hydroxy-propionyl)-sisomicin 2',3,3''-triBoc-1-(N-Boc-3-amino-2(S)-hydroxy-propionyl)-sisomicin (0.075 g, 0.080 mmol) was treated with 2-(N-Boc-3-hydroxy-azetidin-3-yl)-acetaldehyde following Procedure 1-Method A to yield the desired 6'-(ethyl-2-(N-Boc-3-hydroxy-azetidin-3-yl))-2',3,3''-triBoc-1-(N-Boc-3-amino-2(S)-hydroxy-propionyl)-sisomicin (MS m/e [M+H]+ calcd 1134.6, found 1135.1), which was carried through to the next step without further purification.

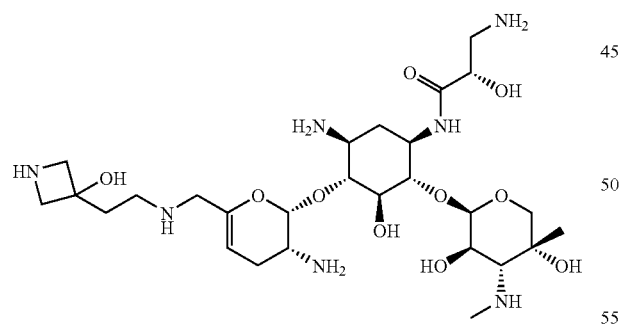

6'-(Ethyl-2-(3-hydroxy-azetidin-3-yl))-1-(3-amino-2(S)-hydroxy-propionyl)-sisomicin 6'-(Ethyl-2-(N-Boc-3-hydroxy-azetidin-3-yl))-2',3,3''-triBoc-1-(N-Boc-3-amino-2(S)-hydroxy-propionyl)-sisomicin (0.080 mmol) was submitted to Procedure 3-Method A for Boc removal to yield a crude, which was purified by RP HPLC Method 1-Column A to yield 6'-(ethyl-2-(3-hydroxy-azetidin-3-yl))-1-(3-amino-2(S)-hydroxy-propionyl)-sisomicin (0.0098 g, 0.015 mmol, 18.7% yield): MS m/e [M+H]+ calcd 634.4, found 634.8; CLND 92.4% purity.

Example 71

6'-Methylcyclopropyl-1-(2-(azetidin-3-yl)-2-hydroxy-acetyl)-sisomicin

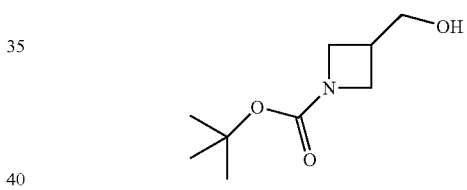

N-Boc-3-hydroxymethyl-azetidine

N-Boc-azetidine-3-carboxylic acid (1.94 g, 9.64 mmol) was submitted to Procedure 19 for reduction to the corresponding N-Boc-3-hydroxymethyl-azetidine, which was carried through to the next step without further purification.

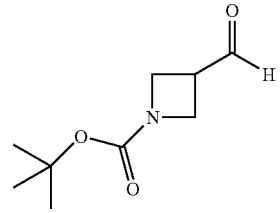

N-Boc-azetidine-3-carboxaldehyde

N-Boc-3-hydroxymethyl-azetidine (9.64 mmol) was submitted to Procedure 18 for oxidation to the desired N-Boc-azetidine-3-carboxaldehyde, which was carried through to the next step without further purification.

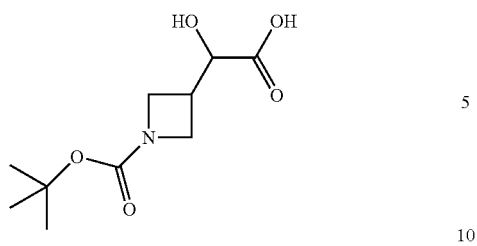

2-(N-Boc-azetidin-3-yl)-2-hydroxy-acetic acid

N-Boc-azetidine-3-carboxaldehyde (1.60 g, 8.64 mmol) was submitted to Procedure 15 to yield the desired 2-(N-Boc-azetidin-3-yl)-2-hydroxy-acetic acid (MS m/e [M+H]+ calcd 232.1, found 231.8).

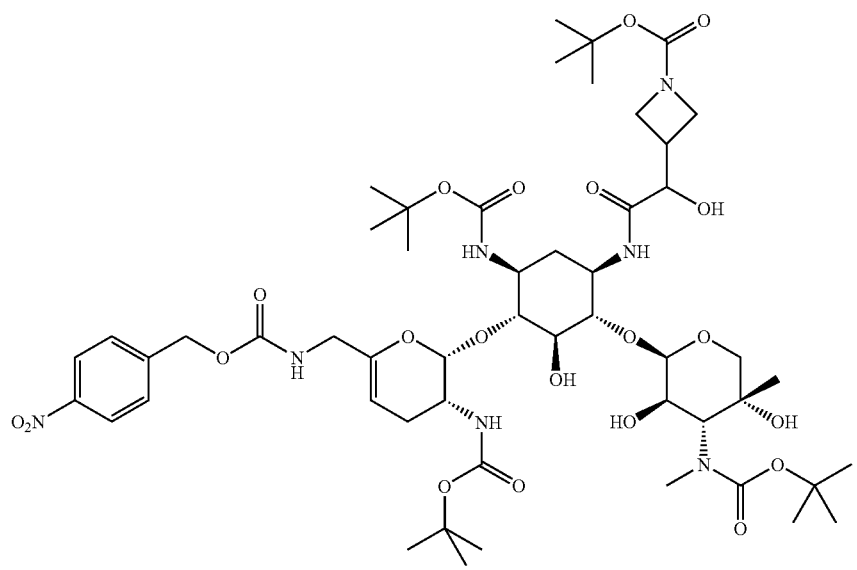 [SMILES: CN(C(=O)OC(C)(C)C)[C@@H]1[C@@H](O)[C@@H](O[C@@H]2[C@@H](O)[C@H](O[C@H]3OC(CNC(=O)OCc4ccc([N+](=O)[O-])cc4)=CC[C@H]3NC(=O)OC(C)(C)C)[C@@H](NC(=O)OC(C)(C)C)C[C@H]2NC(=O)C(O)C2CN(C(=O)OC(C)(C)C)C2)OC[C@]1(C)O]

6'-PNZ-2',3,3''-triBoc-1-(2-(N-Boc-azetidin-3-yl)-2-hydroxy-acetyl)-sisomicin

Treatment of 6'-PNZ-2',3,3''-triBoc-sisomicin (0.075 g, 0.081 mmol) with 2-(N-Boc-azetidin-3-yl)-2-hydroxy-acetic acid following Procedure 4-Method B gave the desired 6'-PNZ-2',3,3''-triBoc-1-(2-(N-Boc-azetidin-3-yl)-2-hydroxy-acetyl)-sisomicin (MS m/e [M+H]+ calcd 1140.5, found 1140.8), which was carried through to the next step without further purification.

6'-Methylcyclopropyl-2',3,3''-triBoc-1-(N-Boc-2-azetidin-3-yl-2-hydroxy-acetyl)-sisomicin 2',3,3''-triBoc-1-(2-(N-Boc-azetidin-3-yl)-2-hydroxy-acetyl)-sisomicin (0.081 mmol) was treated with cyclopropane carboxaldehye following Procedure 1-Method A to yield the desired 6'-methylcyclopropyl-2',3,3''-triBoc-1-(2-(N-Boc-azetidin-3-yl)-2-hydroxy-acetyl)-sisomicin (MS m/e [M+H]$^+$ calcd 1015.6, found 1015.8), which was carried through to the next step without further purification.

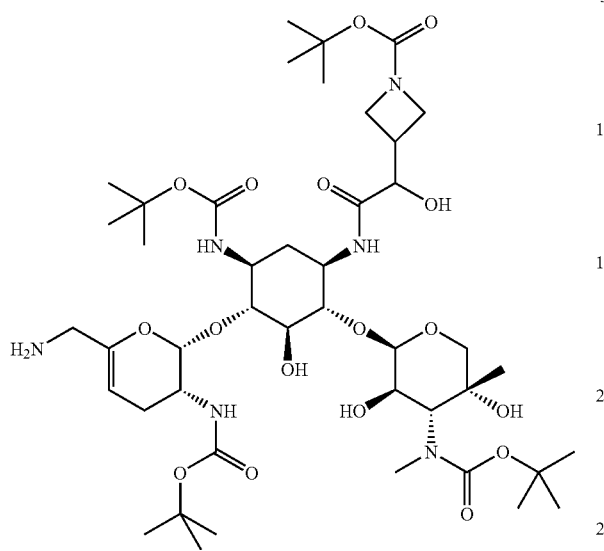

2',3,3''-triBoc-1-(2-(N-Boc-azetidin-3-yl)-2-hydroxy-acetyl)-sisomicin

6'-PNZ-2',3,3''-triBoc-1-(2-(N-Boc-azetidin-3-yl)-2-hydroxy-acetyl)-sisomicin (0.081 mmol) was submitted to Procedure 2 for PNZ removal to yield 2',3,3''-triBoc-1-(2-(N-Boc-azetidin-3-yl)-2-hydroxy-acetyl)-sisomicin (MS m/e [M+H]$^+$ calcd 961.5, found 962.0), which was carried through to the next step without further purification.

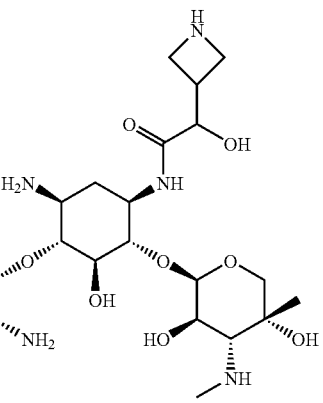

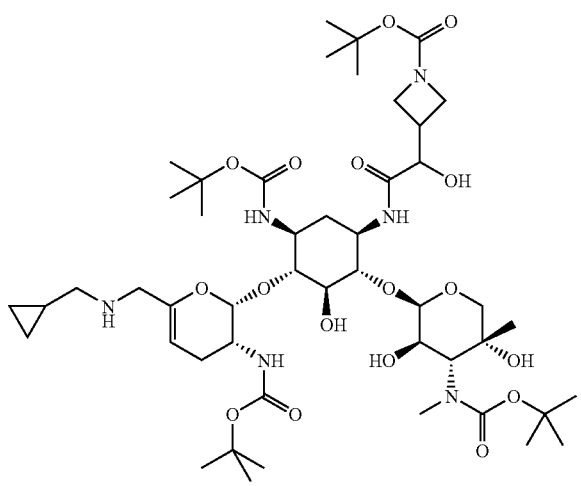 [SMILES: CN(C(=O)OC(C)(C)C)[C@@H]1[C@@H](O)[C@@H](O[C@@H]2[C@@H](O)[C@H](O[C@H]3OC(CNCC4CC4)=CC[C@H]3NC(=O)OC(C)(C)C)[C@@H](NC(=O)OC(C)(C)C)C[C@H]2NC(=O)C(O)C2CN(C(=O)OC(C)(C)C)C2)OC[C@]1(C)O]

6'-Methylcyclopropyl-1-(2-(azetidin-3-yl)-2-hydroxy-acetyl)-sisomicin

6'-Methylcyclopropyl-2',3,3''-triBoc-1-(2-(N-Boc-azetidin-3-yl)-2-hydroxy-acetyl)-sisomicin (0.081 mmol) was submitted to Procedure 3-Method A for Boc removal to yield a crude, which was purified by RP HPLC Method 1-Column A to yield 6'-methylcyclopropyl-1-(2-(azetidin-3-yl)-2-hydroxy-acetyl)-sisomicin (0.0033 g, 0.0054 mmol, 6.7% yield): MS m/e [M+H]$^+$ calcd 615.4, found 615.5; CLND 77.4% purity.

Example 72

6'-(Methyl-trans-3-amino-cyclobutyl)-1-(2-(azetidin-3-yl)-2-hydroxy-acetyl)-sisomicin

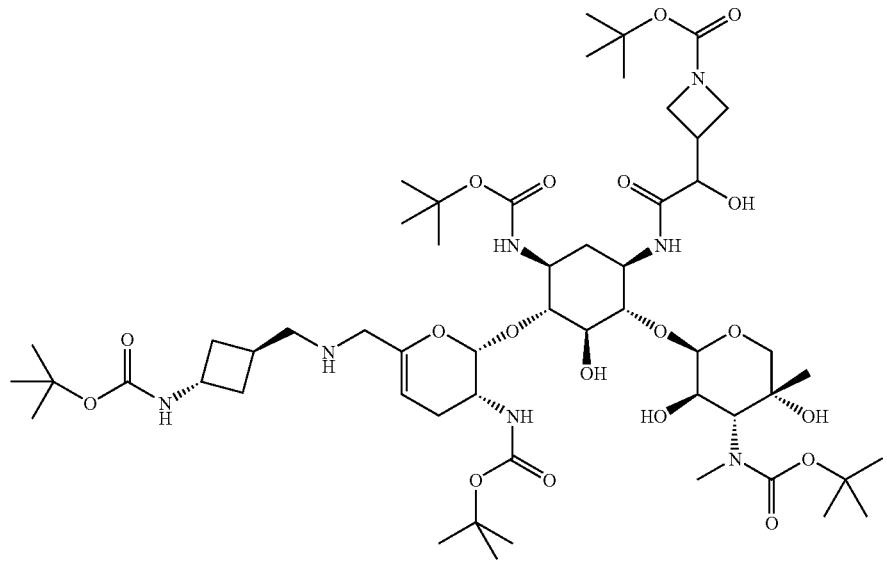 [SMILES: CN(C(=O)OC(C)(C)C)[C@@H]1[C@@H](O)[C@@H](O[C@@H]2[C@@H](O)[C@H](O[C@H]3OC(CNC[C@H]4C[C@H](NC(=O)OC(C)(C)C)C4)=CC[C@H]3NC(=O)OC(C)(C)C)[C@@H](NC(=O)OC(C)(C)C)C[C@H]2NC(=O)C(O)C2CN(C(=O)OC(C)(C)C)C2)OC[C@]1(C)O]

6'-(N-Boc-methyl-trans-3-amino-cyclobutyl)-2',3,3''-triBoc-1-(2-(N-Boc-azetidin-3-yl)-2-hydroxy-acetyl)-sisomicin 2',3,3''-triBoc-1-(2-(N-Boc-azetidin-3-yl)-2-hydroxy-acetyl)-sisomicin (0.081 mmol) was treated with N-Boc-trans-3-amino-cyclobutyl-carboxaldehyde following Procedure 1-Method B to give the desired 6'-(N-Boc-methyl-trans-3-amino-cyclobutyl)-2',3,3''-triBoc-1-(2-(N-Boc-azetidin-3-yl)-2-hydroxy-acetyl)-sisomicin (MS m/e [M+H]$^+$ calcd 1144.6, found 1145.0), which was carried through to the next step without further purification.

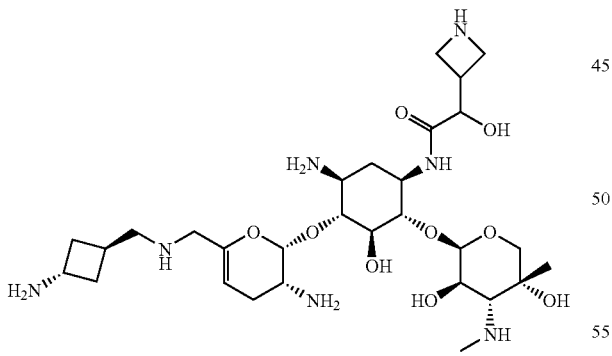

6'-(Methyl-trans-3-amino-cyclobutyl)-1-(2-(azetidin-3-yl)-2-hydroxy-acetyl)-sisomicin 6'-(N-Boc-methyl-trans-3-amino-cyclobutyl)-2',3,3''-triBoc-1-(2-(N-Boc-azetidin-3-yl)-2-hydroxy-acetyl)-sisomicin (0.081 mmol) was submitted to Procedure 3-Method A for Boc removal to yield a crude, which was purified by RP HPLC Method 1-Column A to yield 6'-(methyl-trans-3-amino-cyclobutyl)-1-(2-(azetidin-3-yl)-2-hydroxy-acetyl)-sisomicin (0.0053 g, 0.0082 mmol, 10.1% yield): MS m/e [M+H]$^+$ calcd 644.4, found 644.4; CLND 86.0% purity.

Example 73

6'-(Methyl-azetidin-3-yl)-1-(3-amino-2(S)-hydroxy-propionyl)-sisomicin

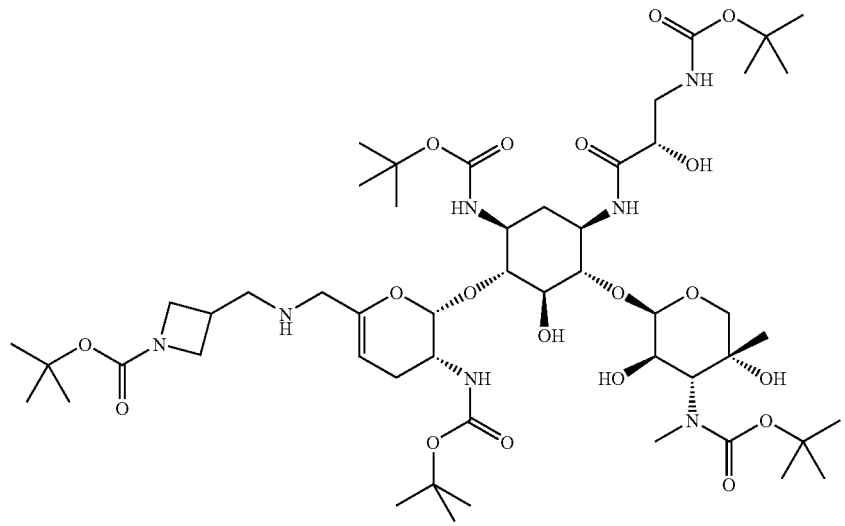 [SMILES: CN(C(=O)OC(C)(C)C)[C@@H]1[C@@H](O)[C@@H](O[C@@H]2[C@@H](O)[C@H](O[C@H]3OC(CNCC4CN(C(=O)OC(C)(C)C)C4)=CC[C@H]3NC(=O)OC(C)(C)C)[C@@H](NC(=O)OC(C)(C)C)C[C@H]2NC(=O)[C@@H](O)CNC(=O)OC(C)(C)C)OC[C@]1(C)O]

6'-(Methyl-N-Boc-azetidin-3-yl)-2',3,3"-triBoc-1-(N-Boc-3-amino-2(S)-hydroxy-propionyl)-sisomicin 2',3,3"-triBoc-1-(N-Boc-3-amino-2(S)-hydroxy-propionyl)-sisomicin (0.9 g, 0.96 mmol) was treated with N-Boc-azetidine-3-carboxaldehyde following Procedure 1-Method A to yield the desired 6'-(methyl-N-Boc-azetidin-3-yl)-2',3, 3"-triBoc-1-(N-Boc-3-amino-2(S)-hydroxy-propionyl)-sisomicin (MS m/e [M+H]$^+$ calcd 1104.6, found 1105.1), which was carried through to the next step without further purification.

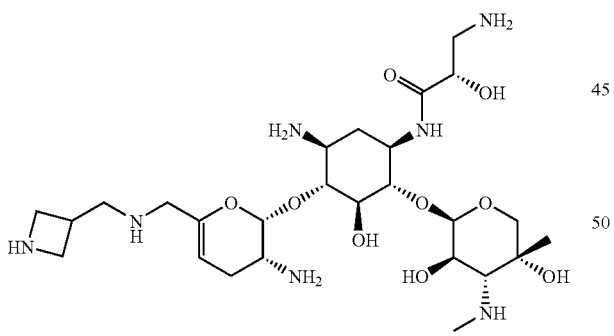

6'-(Methyl-azetidin-3-yl)-1-(3-amino-2(S)-hydroxy-propionyl)-sisomicin

6'-(Methyl-N-Boc-azetidin-3-yl)-2',3,3"-triBoc-1-(N-Boc-3-amino-2(S)-hydroxy-propionyl)-sisomicin (0.96 mmol) was submitted to Procedure 3-Method A for Boc removal to yield a crude, which was purified by RP HPLC Method 1-Column B to yield 6'-(methyl-azetidin-3-yl)-1-(3-amino-2(S)-hydroxy-propionyl)-sisomicin (0.0082 g, 0.014 mmol, 1.46% yield): MS m/e [M+H]$^+$ calcd 604.4, found 604.6; CLND 86.3% purity.

Example 74

6'-(Methyl-1-aminomethyl-cyclopropyl)-1-(2-(azetidin-3-yl)-2-hydroxy-acetyl)-sisomicin

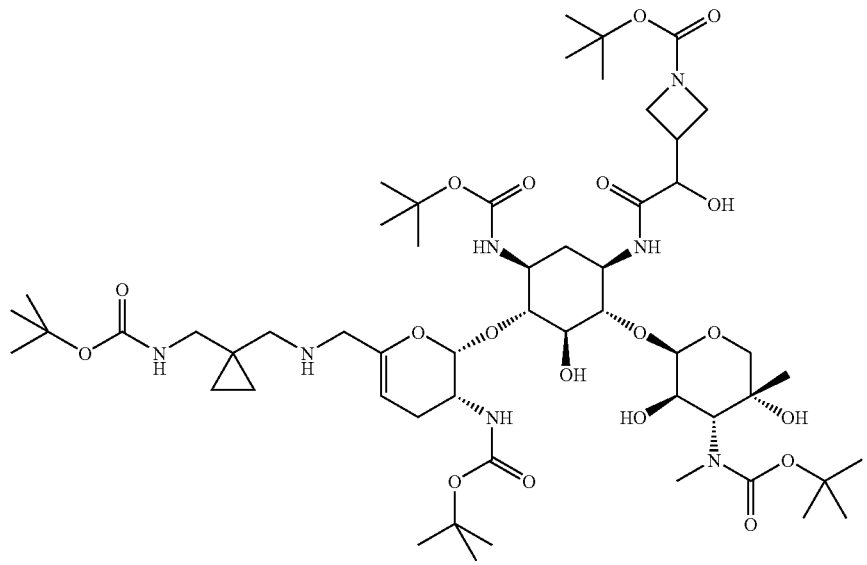 [SMILES: CN(C(=O)OC(C)(C)C)[C@@H]1[C@@H](O)[C@@H](O[C@@H]2[C@@H](O)[C@H](O[C@H]3OC(CNCC4(CNC(=O)OC(C)(C)C)CC4)=CC[C@H]3NC(=O)OC(C)(C)C)[C@@H](NC(=O)OC(C)(C)C)C[C@H]2NC(=O)C(O)C2CN(C(=O)OC(C)(C)C)C2)OC[C@]1(C)O]

6'-(Methyl-N-Boc-1-aminomethyl-cyclopropyl)-2',3,3''-triBoc-1-(2-(N-Boc-azetidin-3-yl)-2-hydroxy-acetyl)-sisomicin 2',3,3''-triBoc-1-(2-(N-Boc-azetidin-3-yl)-2-hydroxy-acetyl)-sisomicin (0.081 mmol) was treated with N-Boc-1-aminomethyl-cyclopropane carboxaldehyde following Procedure 1-Method A to yield the desired 6'-(methyl-N-Boc-1-aminomethyl-cyclopropyl)-2',3,3''-triBoc-1-(2-(N-Boc-azetidin-3-yl)-2-hydroxy-acetyl)-sisomicin (MS m/e [M+H]$^+$ calcd 1144.6, found 1144.8), which was carried through to the next step without further purification.

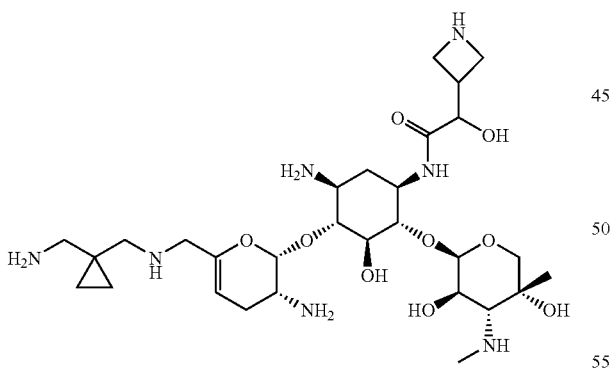

6'-(Methyl-1-aminomethyl-cyclopropyl)-1-(2-(azetidin-3-yl)-2-hydroxy-acetyl)-sisomicin 6'-(Methyl-N-Boc-1-aminomethyl-cyclopropyl)-2',3,3''-triBoc-1-(2-(N-Boc-azetidin-3-yl)-2-hydroxy-acetyl)-sisomicin (0.081 mmol) was submitted to Procedure 3-Method A for Boc removal to yield a crude, which was purified by RP HPLC Method 1-Column A to yield 6'-(methyl-1-aminomethyl-cyclopropyl)-1-(2-(azetidin-3-yl)-2-hydroxy-acetyl)-sisomicin (0.0005 g, 0.0008 mmol, 0.9% yield): MS m/e [M+H]$^+$ calcd 644.4, found 644.6; CLND 79.8% purity.

Example 75

6'-(2-Hydroxy-ethyl)-1-(2-(azetidin-3-yl)-2-hydroxy-acetyl)-sisomicin

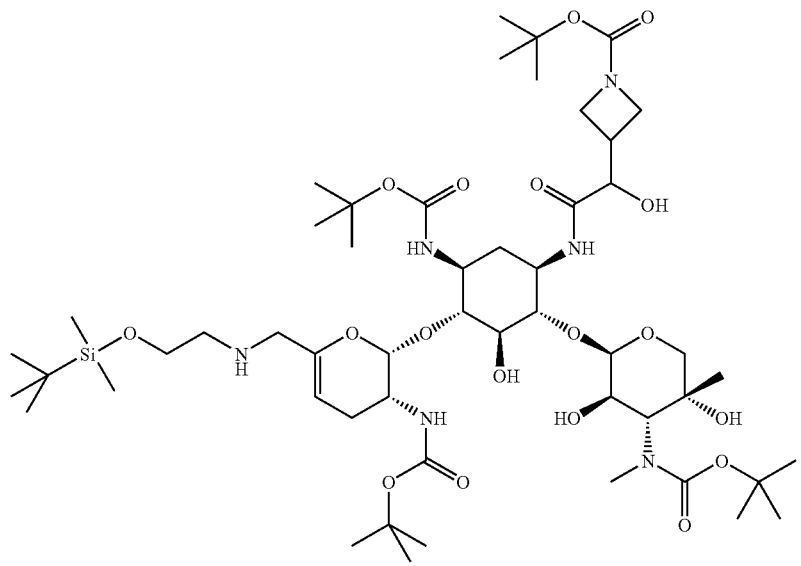 [SMILES: CN(C(=O)OC(C)(C)C)[C@@H]1[C@@H](O)[C@@H](O[C@@H]2[C@@H](O)[C@H](O[C@H]3OC(CNCCO[Si](C)(C)C(C)(C)C)=CC[C@H]3NC(=O)OC(C)(C)C)[C@@H](NC(=O)OC(C)(C)C)C[C@H]2NC(=O)C(O)C2CN(C(=O)OC(C)(C)C)C2)OC[C@]1(C)O]

6'-(2-tert-Butyldimethylsilyloxy-ethyl)-2',3,3"-tri-Boc-1-(2-(N-Boc-azetidin-3-yl)-2-hydroxy-acetyl)-sisomicin 2',3,3"-triBoc-1-(2-(N-Boc-azetidin-3-yl)-2-hydroxy-acetyl)-sisomicin (0.081 mmol) was treated with tert-butyldimethylsilyloxy acetaldehyde following Procedure 1-Method A to yield the desired 6'-(2-tert-butyldimethylsilyloxy-ethyl)-2',3,3"-triBoc-1-(2-(N-Boc-azetidin-3-yl)-2-hydroxy-acetyl)-sisomicin (MS m/e [M+H]$^+$ calcd 1119.6, found 1119.8), which was carried through to the next step without further purification.

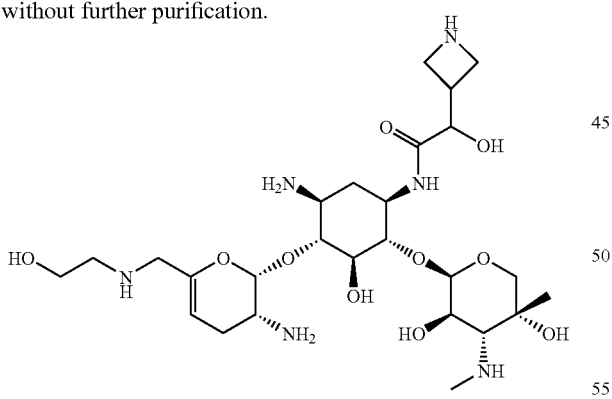

6'-(2-Hydroxy-ethyl)-1-(2-(azetidin-3-yl)-2-hydroxy-acetyl)-sisomicin

6'-(2-tert-Butyldimethylsilyloxy-ethyl)-2',3,3"-triBoc-1-(2-(N-Boc-azetidin-3-yl)-2-hydroxy-acetyl)-sisomicin (0.081 mmol) was submitted to Procedure 3-Method A for Boc and TBS removal to yield a crude, which was purified by RP HPLC Method 1-Column A to yield 6'-(2-hydroxy-ethyl)-1-(2-(azetidin-3-yl)-2-hydroxy-acetyl)-sisomicin (0.0037 g, 0.0061 mmol, 7.5% yield): MS m/e [M+H]$^+$ calcd 605.3, found 605.7; CLND 82.4% purity.

Example 76

6'-(3-Amino-propyl)-1-(2-(azetidin-3-yl)-2-hydroxy-acetyl)-sisomicin

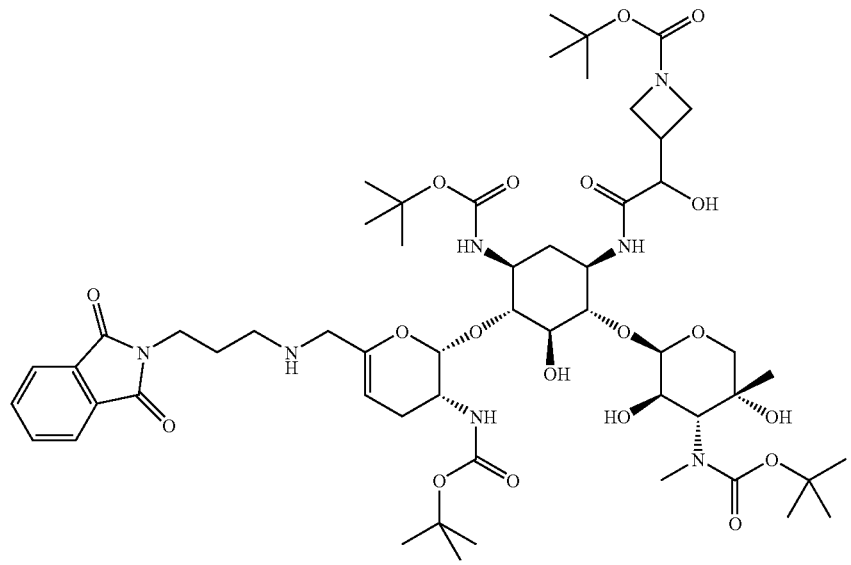 [SMILES: CN(C(=O)OC(C)(C)C)[C@@H]1[C@@H](O)[C@@H](O[C@@H]2[C@@H](O)[C@H](O[C@H]3OC(CNCCCN4C(=O)c5ccccc5C4=O)=CC[C@H]3NC(=O)OC(C)(C)C)[C@@H](NC(=O)OC(C)(C)C)C[C@H]2NC(=O)C(O)C2CN(C(=O)OC(C)(C)C)C2)OC[C@]1(C)O]

6'-(N-Phthalimido-3-amino-propyl)-2',3,3''-triBoc-1-(2-(N-Boc-azetidin-3-yl)-2-hydroxy-acetyl)-sisomicin 2',3,3''-triBoc-1-(2-(N-Boc-azetidin-3-yl)-2-hydroxy-acetyl)-sisomicin (0.081 mmol) was treated with N-phthalimido propionaldehyde following Procedure 1-Method A to yield the desired 6'-(N-phthalimido-3-amino-propyl)-2',3,3''-triBoc-1-(2-(N-Boc-azetidin-3-yl)-2-hydroxy-acetyl)-sisomicin (MS m/e [M+H]$^+$ calcd 1148.6, found 1148.8), which was carried through to the next step without further purification.

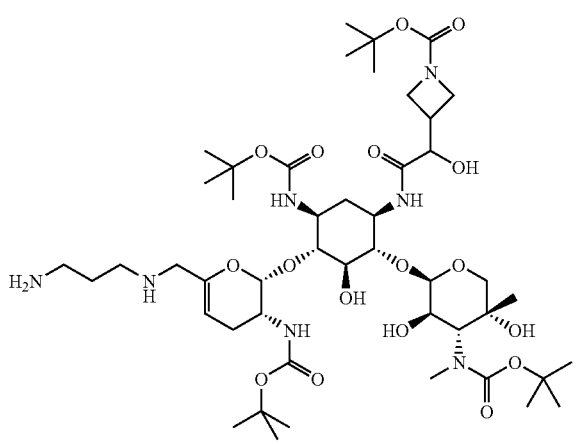 [SMILES: CN(C(=O)OC(C)(C)C)[C@@H]1[C@@H](O)[C@@H](O[C@@H]2[C@@H](O)[C@H](O[C@H]3OC(CNCCCN)=CC[C@H]3NC(=O)OC(C)(C)C)[C@@H](NC(=O)OC(C)(C)C)C[C@H]2NC(=O)C(O)C2CN(C(=O)OC(C)(C)C)C2)OC[C@]1(C)O]

6'-(3-Amino-propyl)-2',3,3''-triBoc-1-(2-(N-Boc-azetidin-3-yl)-2-hydroxy-acetyl-sisomicin 6'-(N-Phthalimido-3-amino-propyl)-2',3,3''-triBoc-1-(2-(N-Boc-azetidin-3-yl)-2-hydroxy-acetyl)-sisomicin (0.081 mmol) was submitted to Procedure 6 for phthalimido deprotection to yield 6'-(3-amino-propyl)-2',3,3''-triBoc-1-(2-(N-Boc-azetidin-3-yl)-2-hydroxy-acetyl)-sisomicin (MS m/e [M+H]$^+$ calcd 1018.6, found 1018.9), which was carried through to the next step without further purification.

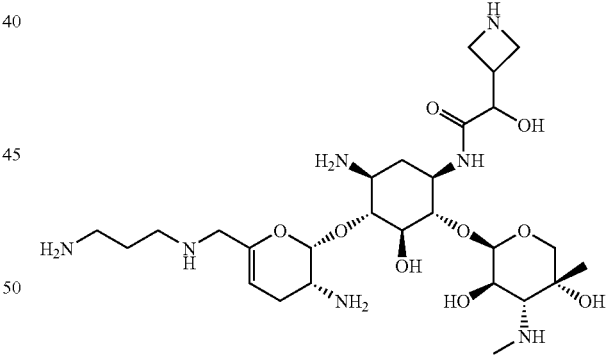

6'-(3-Amino-propyl)-1-(2-(azetidin-3-yl)-2-hydroxy-acetyl)-sisomicin

6'-(3-Amino-propyl)-2',3,3''-triBoc-1-(2-(N-Boc-azetidin-3-yl)-2-hydroxy-acetyl)-sisomicin (0.081 mmol) was submitted to Procedure 3-Method A for Boc removal to yield a crude, which was purified by RP HPLC Method 1-Column A to yield 6'-(3-amino-propyl)-1-(2-(azetidin-3-yl)-2-hydroxy-acetyl)-sisomicin (0.003 g, 0.0048 mmol, 5.9% yield): MS m/e [M+H]$^+$ calcd 618.4, found 618.8; CLND 87.5% purity.

Example 77

6'(2-Hydroxy-4-amino-butyl)-1-(2-(azetidin-3-yl)-2-hydroxy-acetyl)-sisomicin

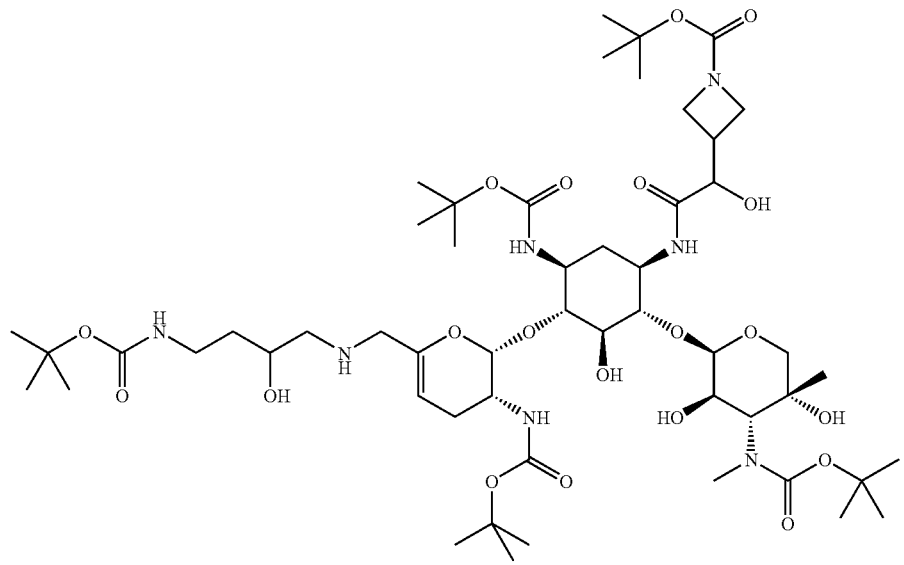 [SMILES: CN(C(=O)OC(C)(C)C)[C@@H]1[C@@H](O)[C@@H](O[C@@H]2[C@@H](O)[C@H](O[C@H]3OC(CNCC(O)CCNC(=O)OC(C)(C)C)=CC[C@H]3NC(=O)OC(C)(C)C)[C@@H](NC(=O)OC(C)(C)C)C[C@H]2NC(=O)C(O)C2CN(C(=O)OC(C)(C)C)C2)OC[C@]1(C)O]

6'-(N-Boc-2-hydroxy-4-amino-butyl)-2',3,3''-triBoc-1-(2-(N-Boc-azetidin-3-yl)-2-hydroxy-acetyl)-sisomicin 2',3,3''-triBoc-1-(2-(N-Boc-azetidin-3-yl)-2-hydroxy-acetyl)-sisomicin (0.081 mmol) was treated with N-Boc-2-(oxiran-2-yl)-ethyl carbamate following Procedure 5 to yield the desired 6'-(N-Boc-2-hydroxy-4-amino-butyl)-2',3,3''-triBoc-1-(2-(N-Boc-azetidin-3-yl)-2-hydroxy-acetyl)-sisomicin (MS m/e [M+H]$^+$ calcd 1148.6, found 1148.9), which was carried through to the next step without further purification.

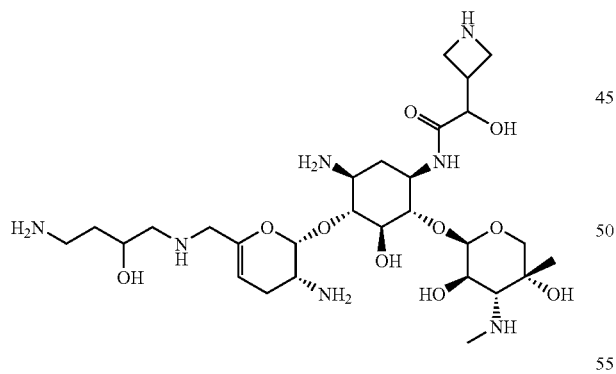

6'-(2-Hydroxy-4-amino-butyl)-1-(2-(azetidin-3-yl)-2-hydroxy-acetyl)-sisomicin

6'-(N-Boc-2-hydroxy-4-amino-butyl)-2',3,3''-triBoc-1-(2-(N-Boc-azetidin-3-yl)-2-hydroxy-acetyl)-sisomicin (0.081 mmol) was submitted to Procedure 3-Method A for Boc removal to yield a crude, which was purified by RP HPLC Method 1-Column A to yield 6'-(2-hydroxy-4-amino-butyl)-1-(2-(azetidin-3-yl)-2-hydroxy-acetyl)-sisomicin (0.0013 g, 0.002 mmol, 2.5% yield): MS m/e [M+H]$^+$ calcd 648.4, found 648.4; CLND 80.8% purity.

Example 78

6'-(Methyl-trans-3-amino-cyclobutyl)-1-(3-hydroxy-pyrrolidin-3-yl-acetyl)-sisomicin

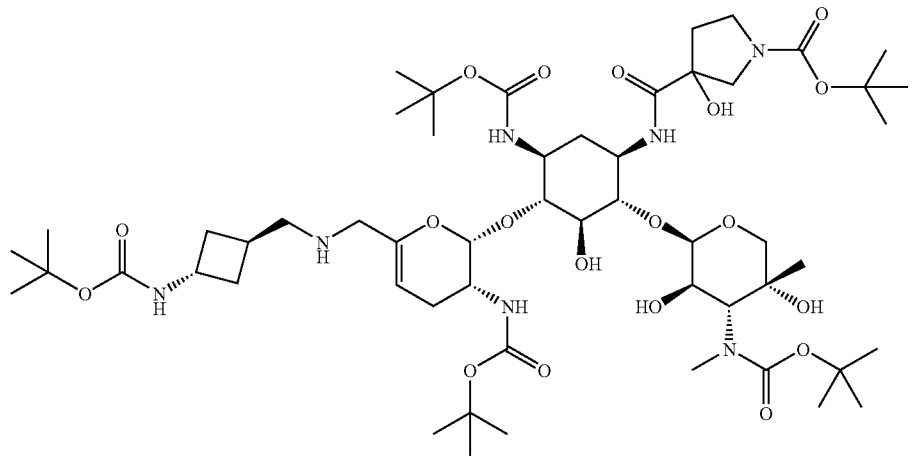 [SMILES: CN(C(=O)OC(C)(C)C)[C@@H]1[C@@H](O)[C@@H](O[C@@H]2[C@@H](O)[C@H](O[C@H]3OC(CNC[C@H]4C[C@H](NC(=O)OC(C)(C)C)C4)=CC[C@H]3NC(=O)OC(C)(C)C)[C@@H](NC(=O)OC(C)(C)C)C[C@H]2NC(=O)C2(O)CCN(C(=O)OC(C)(C)C)C2)OC[C@]1(C)O]

6'-(N-Boc-methyl-trans-3-amino-cyclobutyl)-2',3,3"-triBoc-1-(N-Boc-3-hydroxy-pyrrolidin-3-yl-acetyl)-sisomicin 2',3,3"-triBoc-1-(N-Boc-3-hydroxy-pyrrolidin-3-yl-acetyl)-sisomicin (0.081 mmol) was treated with N-Boc-trans-3-amino-cyclobutyl-carboxaldeyhde following Procedure 1-Method A to yield the desired 6'-(N-Boc-methyl-trans-3-amino-cyclobutyl)-2',3,3"-triBoc-1-(N-Boc-3-hydroxy-pyrrolidin-3-yl-acetyl)-sisomicin (MS m/e [M+H]$^+$ calcd 1144.6, found 1145.1), which was carried through to the next step without further purification.

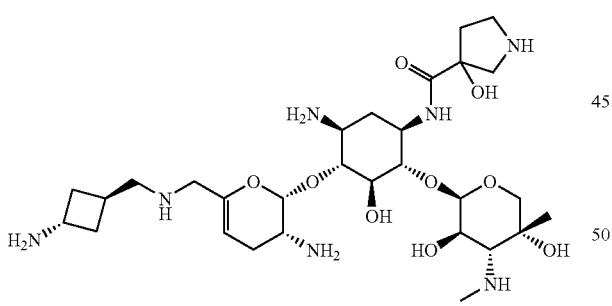

6'-(Methyl-trans-3-amino-cyclobutyl)-1-(3-hydroxy-pyrrolidin-3-yl-acetyl)-sisomicin 6'-(N-Boc-methyl-trans-3-amino-cyclobutyl)-2',3,3"-triBoc-1-(N-Boc-3-hydroxy-pyrrolidin-3-yl-acetyl)-sisomicin (0.081 mmol) was submitted to Procedure 3-Method A for Boc removal to yield a crude, which was purified by RP HPLC Method 1-Column A to yield 6'-(methyl-trans-3-amino-cyclobutyl)-1-(3-hydroxy-pyrrolidin-3-yl-acetyl)-sisomicin (0.0025 g, 0.0039 mmol, 4.8% yield): MS m/e [M+H]$^+$ calcd 644.4, found 644.4; CLND 93.9% purity

Example 79

6'-(Methyl-1-aminomethyl-cyclopropyl)-1-(3-hydroxy-pyrrolidin-3-yl-acetyl)-sisomicin

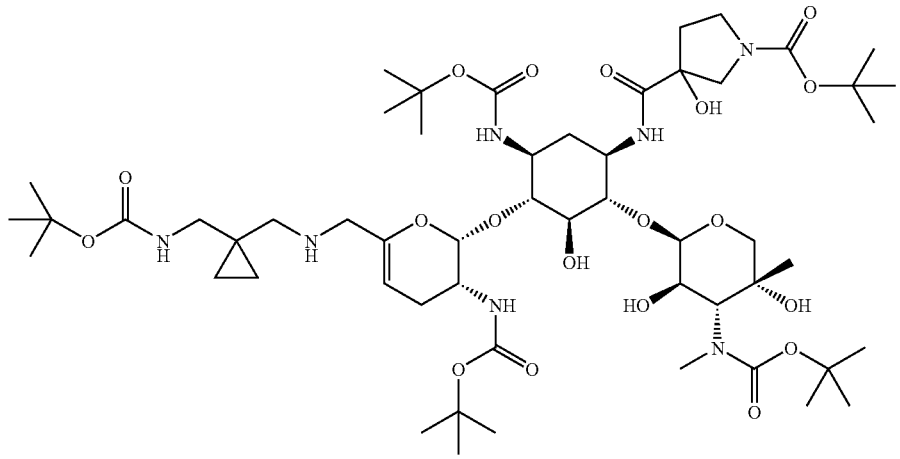 [SMILES: CN(C(=O)OC(C)(C)C)[C@@H]1[C@@H](O)[C@@H](O[C@@H]2[C@@H](O)[C@H](O[C@H]3OC(CNCC4(CNC(=O)OC(C)(C)C)CC4)=CC[C@H]3NC(=O)OC(C)(C)C)[C@@H](NC(=O)OC(C)(C)C)C[C@H]2NC(=O)C2(O)CCN(C(=O)OC(C)(C)C)C2)OC[C@]1(C)O]

6'-(Methyl-N-Boc-1-aminomethyl-cyclopropyl)-2',3,3''-triBoc-1-(N-Boc-3-hydroxy-pyrrolidin-3-yl-acetyl)-sisomicin 2',3,3''-triBoc-1-(N-Boc-3-hydroxy-pyrrolidin-3-yl-acetyl)-sisomicin (0.081 mmol) was treated with N-Boc-1-aminomethyl-cyclopropane carboxaldehyde following Procedure 1-Method A to yield the desired 6'-(methyl-N-Boc-1-aminomethyl-cyclopropyl)-2',3,3''-triBoc-1-(N-Boc-3-hydroxy-pyrrolidin-3-yl-acetyl)-sisomicin (MS m/e [M+H]$^+$ calcd 1144.6, found 1145.0), which was carried through to the next step without further purification.

6'-(Methyl-1-aminomethyl-cyclopropyl)-1-(3-hydroxy-pyrrolidin-3-yl-acetyl)-sisomicin 6'-(Methyl-N-Boc-1-aminomethyl-cyclopropyl)-2',3,3''-triBoc-1-(N-Boc-3-hydroxy-pyrrolidin-3-yl-acetyl)-sisomicin (0.081 mmol) was submitted to Procedure 3-Method A for Boc removal to yield a crude, which was purified by RP HPLC Method 1-Column A to yield 6'-(methyl-1-aminomethyl-cyclopropyl)-1-(3-hydroxy-pyrrolidin-3-yl-acetyl)-sisomicin (0.0018 g, 0.0028 mmol, 3.5% yield): MS m/e [M+H]$^+$ calcd 644.4, found 644.6; CLND 80.2% purity

Example 80

6'-(4-Hydroxy-5-amino-pentyl)-1-(3-amino-2(S)-hydroxy-propionyl)-sisomicin

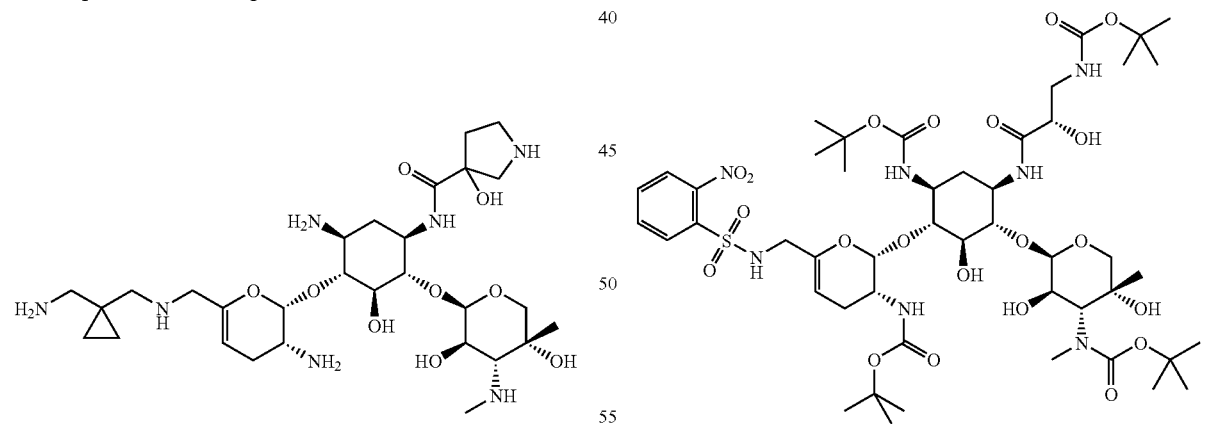

6'-Nosyl-2',3,3''-triBoc-1-(N-Boc-3-amino-2(S)-hydroxy-propionyl)-sisomicin

2',3,3''-triBoc-1-(N-Boc-3-amino-2(S)-hydroxy-propionyl)-sisomicin (0.075 g, 0.080 mmol) was submitted to Procedure 8 for nosylation to yield 6'-nosyl-2',3,3''-triBoc-1-(N-Boc-3-amino-2(S)-hydroxy-propionyl)-sisomicin (MS m/e [M+H]$^+$ calcd 1120.5, found 1120.9), which was carried through to the next step without further purification.

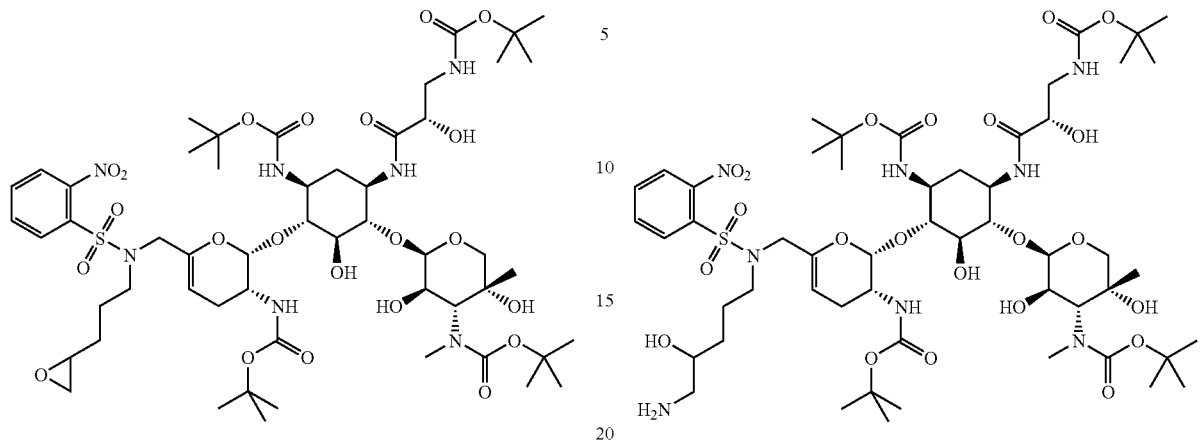

6'-(4,5-Epoxy-pentyl)-6'-nosyl-2',3,3''-triBoc-1-(N-Boc-3-amino-2(S)-hydroxy-propionyl)-sisomicin 6'-(4-Hydroxy-5-amino-pentyl)-6'-nosyl-2',3,3''-tri-Boc-1-(N-Boc-3-amino-2(S)-hydroxy-propionyl)-sisomicin 6'-Nosyl-2',3,3''-triBoc-1-(N-Boc-3-amino-2(S)-hydroxy-propionyl)-sisomicin (0.080 mmol) was treated with 5-bromo-1,2-epoxypentane following Procedure 11 to yield 6'-(4,5-epoxy-pentyl)-6'-nosyl-2',3,3''-triBoc-1-(N-Boc-3-amino-2(S)-hydroxy-propionyl)-sisomicin (MS m/e [M+H]$^+$ calcd 1204.5, found 1204.6), which was carried through to the next step without further purification.

6'-(4,5-Epoxy-pentyl)-6'-nosyl-2',3,3''-triBoc-1-(N-Boc-3-amino-2(S)-hydroxy-propionyl)-sisomicin (0.080 mmol) was treated with 27% aq. NH$_3$ following Procedure 5 to yield 6'-(4-hydroxy-5-amino-pentyl)-6'-nosyl-2',3,3''-triBoc-1-(N-Boc-3-amino-2(S)-hydroxy-propionyl)-sisomicin (MS m/e [M+H]$^+$ calcd 1221.6, found 1222.2), which was carried through to the next step without further purification.

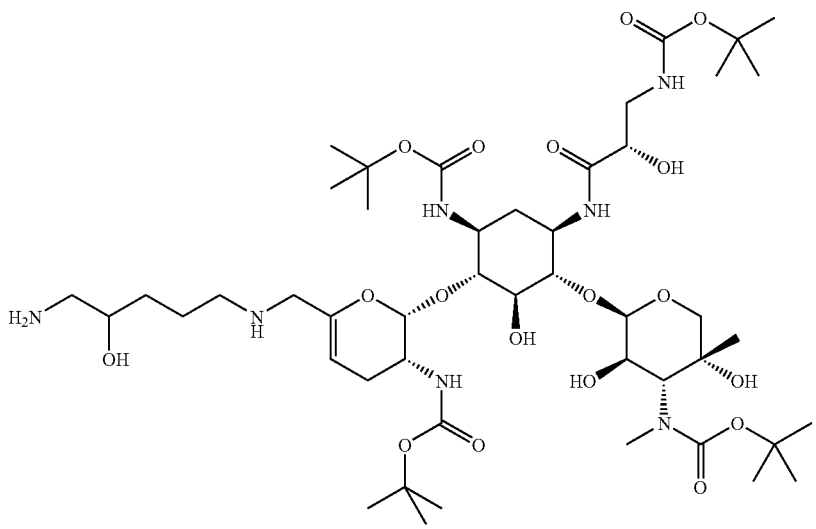 [SMILES: CN(C(=O)OC(C)(C)C)[C@@H]1[C@@H](O)[C@@H](O[C@@H]2[C@@H](O)[C@H](O[C@H]3OC(CNCCCC(O)CN)=CC[C@H]3NC(=O)OC(C)(C)C)[C@@H](NC(=O)OC(C)(C)C)C[C@H]2NC(=O)[C@@H](O)CNC(=O)OC(C)(C)C)OC[C@]1(C)O]

6'-(4-Hydroxy-5-amino-pentyl)-2',3,3''-triBoc-1-(N-Boc-3-amino-2(S)-hydroxy-propionyl)-sisomicin 6'-(4-Hydroxy-5-amino-pentyl)-6'-nosyl-2',3,3''-triBoc-1-(N-Boc-3-amino-2(S)-hydroxy-propionyl)-sisomicin (0.080 mmol) was submitted to Procedure 9 for nosyl deprotection to yield 6'-(4-hydroxy-5-amino-pentyl)-2',3,3''-triBoc-1-(N-Boc-3-amino-2(S)-hydroxy-propionyl)-sisomicin (MS m/e [M+H]$^+$ calcd 1036.6, found 1037.1), which was carried through to the next step without further purification.

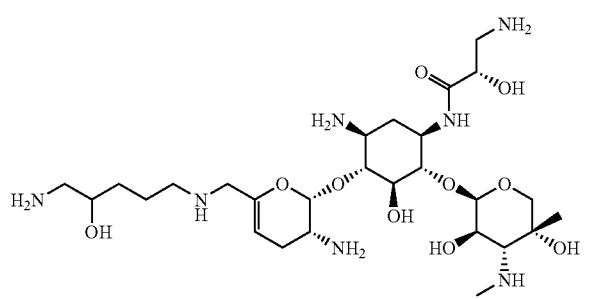 [SMILES: CN[C@@H]1[C@@H](O)[C@@H](O[C@@H]2[C@@H](O)[C@H](O[C@H]3OC(CNCCCC(O)CN)=CC[C@H]3N)[C@@H](N)C[C@H]2NC(=O)[C@@H](O)CN)OC[C@]1(C)O]

6'-(4-Hydroxy-5-amino-pentyl)-1-(3-amino-2(S)-hydroxy-propionyl)-sisomicin

6'-(4-Hydroxy-5-amino-pentyl)-2',3,3''-triBoc-1-(N-Boc-3-amino-2(S)-hydroxy-propionyl)-sisomicin (0.080 mmol) was submitted to Procedure 3-Method A for Boc removal to yield a crude, which was purified by RP HPLC Method 1-Column A to yield 6'-(4-hydroxy-5-amino-pentyl)-1-(3-amino-2(S)-hydroxy-propionyl)-sisomicin (0.0020 g, 0.0031 mmol, 3.9% yield): MS m/e [M+H]$^+$ calcd 636.4, found 636.4; CLND 94.5% purity.

Example 81

6'-(N-(Azetidin-3-yl)-2-amino-ethyl)-1-(3-amino-2(S)-hydroxy-propionyl)-sisomicin

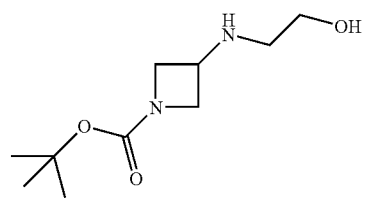

N-(N-Boc-azetidin-3-yl)-2-amino-ethanol

N-Boc-3-azetidinone (1.0 g, 5.84 mmol) was treated with ethanolamine following Procedure 1-Method A to yield N-(N-Boc-azetidin-3-yl)-2-amino-ethanol (0.75 g, 3.46 mmol, 62.3% yield): MS m/e [M+H]$^+$ calcd 217.1, found 217.2.

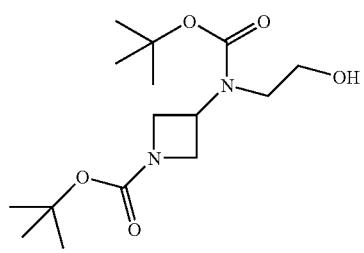 [SMILES: CC(C)(C)OC(=O)N1CC(N(CCO)C(=O)OC(C)(C)C)C1]

N-Boc-N-(N-Boc-azetidin-3-yl)-2-amino-ethanol

N-(N-Boc-azetidin-3-yl)-2-amino-ethanol (0.75 g, 3.46 mmol) was submitted to Procedure 13 for Boc protection to yield a crude, which was purified by flash chromatography (silica gel/hexanes: ethyl acetate 0-100%) to yield N-Boc-N-(N-Boc-azetidin-3-yl)-2-amino-ethanol (MS m/e [M+H]$^+$ calcd 317.2, found 317.4).

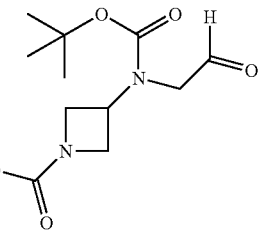

N-Boc-N-(N-Boc-azetidin-3-yl)-2-amino-acetaldehyde

N-Boc-N-(N-Boc-azetidin-3-yl)-2-amino-ethanol was submitted to Procedure 18 for oxidation to N-Boc-N-(N-Boc-azetidin-3-yl)-2-amino-acetaldehyde, which was carried through to the next step without further purification.

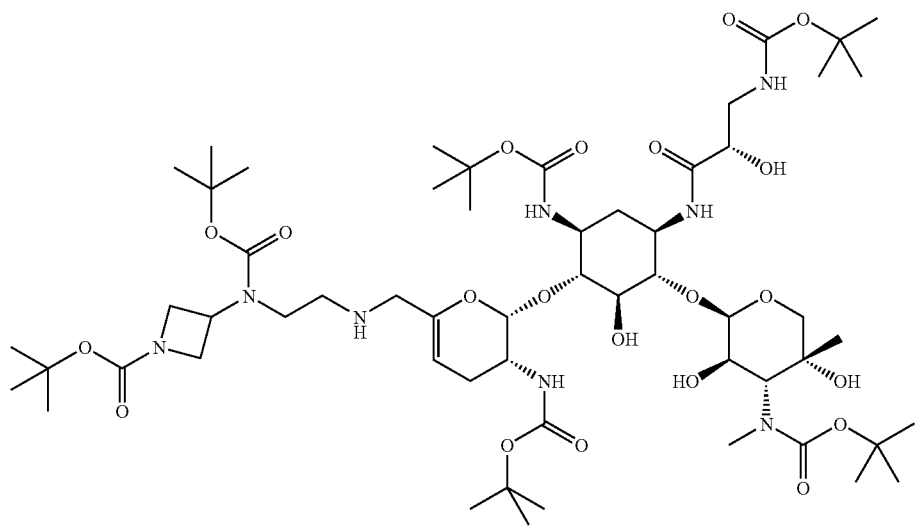 [SMILES: CN(C(=O)OC(C)(C)C)[C@@H]1[C@@H](O)[C@@H](O[C@@H]2[C@@H](O)[C@H](O[C@H]3OC(CNCCN(C(=O)OC(C)(C)C)C4CN(C(=O)OC(C)(C)C)C4)=CC[C@H]3NC(=O)OC(C)(C)C)[C@@H](NC(=O)OC(C)(C)C)C[C@H]2NC(=O)[C@@H](O)CNC(=O)OC(C)(C)C)OC[C@]1(C)O]

6'-(N-Boc-N-(N-Boc-azetidin-3-yl)-2-amino-ethyl)-2',3,3"-triBoc-1-(N-Boc-3-amino-2(S)-hydroxy-propionyl)-sisomicin 2',3,3"-triBoc-1-(N-Boc-3-amino-2(S)-hydroxy-propionyl)-sisomicin (0.075 g, 0.080 mmol) was treated with N-Boc-N-(N-Boc-azetidin-3-yl)-2-amino-acetaldehyde following Procedure 1-Method A to yield the corresponding 6'-(N-Boc-N-(N-Boc-azetidin-3-yl)-2-amino-ethyl)-2',3,3"-triBoc-1-(N-Boc-3-amino-2(S)-hydroxy-propionyl)-sisomicin (MS m/e [M+H]$^+$ calcd 1233.7, found 1233.9), which was carried through to the next step without further purification.

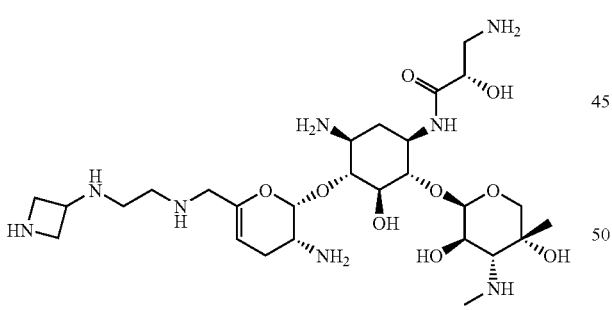

6'-(N-(Azetidin-3-yl)-2-amino-ethyl)-1-(3-amino-2(S)-hydroxy-propionyl)-sisomicin 6'-(N-Boc-N-(N-Boc-azetidin-3-yl)-2-amino-ethyl)-2',3,3"-triBoc-1-(N-Boc-3-amino-2(S)-hydroxy-propionyl)-sisomicin (0.080 mmol) was submitted to Procedure 3-Method A for Boc removal to yield a crude, which was purified by RP HPLC Method 1-Column A to yield 6'-(N-(azetidin-3-yl)-2-amino-ethyl)-1-(3-amino-2(S)-hydroxy-propionyl)-sisomicin (0.0069 g, 0.011 mmol, 13.7% yield): MS m/e [M+H]$^+$ calcd 633.4, found 633.4; CLND 85.5% purity.

Example 82

6'-(2-Hydroxy-3-amino-propyl)-1-(2-(azetidin-3-yl)-2-hydroxy-acetyl)-sisomicin

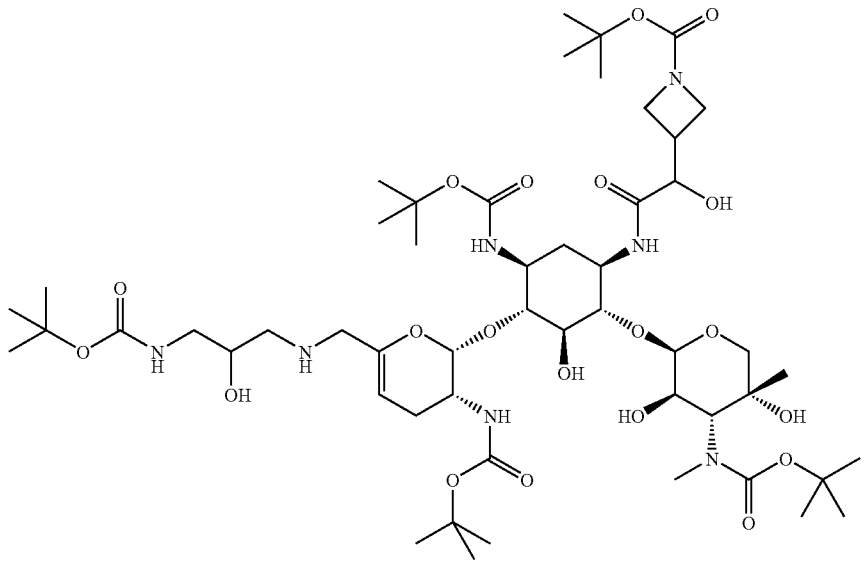 [SMILES: CN(C(=O)OC(C)(C)C)[C@@H]1[C@@H](O)[C@@H](O[C@@H]2[C@@H](O)[C@H](O[C@H]3OC(CNCC(O)CNC(=O)OC(C)(C)C)=CC[C@H]3NC(=O)OC(C)(C)C)[C@@H](NC(=O)OC(C)(C)C)C[C@H]2NC(=O)C(O)C2CN(C(=O)OC(C)(C)C)C2)OC[C@]1(C)O]

6'-(N-Boc-2-hydroxy-3-amino-propyl)-2',3,3"-tri-Boc-1-(2-(N-Boc-azetidin-3-yl)-2-hydroxy-acetyl)-sisomicin 2',3,3"-triBoc-1-(2-(N-Boc-azetidin-3-yl)-2-hydroxy-acetyl)-sisomicin (0.081 mmol) was treated with N-tert-butyl-(2-oxiranyl-methyl) carbamate following Procedure 5 to give the desired 6'-(N-Boc-2-hydroxy-3-amino-propyl)-2',3,3"-triBoc-1-(2-(N-Boc-azetidin-3-yl)-2-hydroxy-acetyl)-sisomicin (MS m/e [M+H]$^+$ calcd 1134.6, found 1135.1), which was carried through to the next step without further purification.

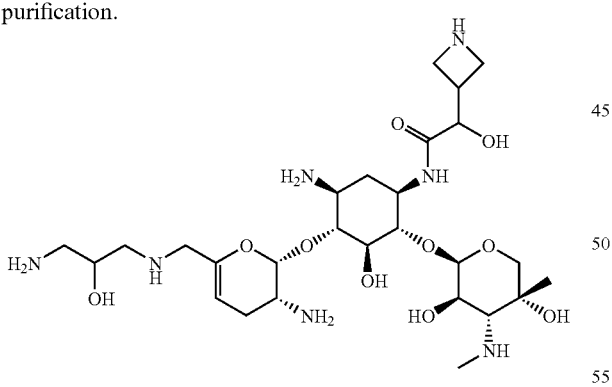

6'(2-Hydroxy-3-amino-propyl)-1-(2-(azetidin-3-yl)-2-hydroxy-acetyl)-sisomicin

6'-(N-Boc-2-hydroxy-3-amino-propyl)-2',3,3"-triBoc-1-(2-(N-Boc-azetidin-3-yl)-2-hydroxy-acetyl)-sisomicin (0.081 mmol) was submitted to Procedure 3-Method A for Boc removal to yield a crude, which was purified by RP HPLC Method 1-Column A to yield 6'-(2-hydroxy-3-amino-propyl)-1-(2-(azetidin-3-yl)-2-hydroxy-acetyl)-sisomicin (0.0012 g, 0.0018 mmol, 2.3% yield): MS m/e [M+H]$^+$ calcd 634.4, found 634.6; CLND 82.5% purity.

Example 83

6'-(Methyl-3-amino-1-hydroxy-cyclobutyl)-1-(2-(azetidin-3-yl)-2-hydroxy-acetyl)-sisomicin

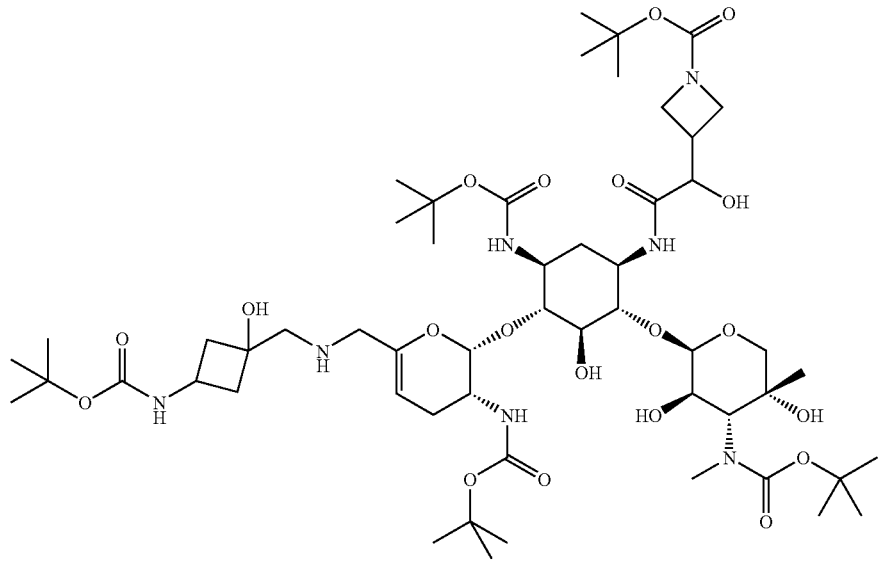 [SMILES: CN(C(=O)OC(C)(C)C)[C@@H]1[C@@H](O)[C@@H](O[C@@H]2[C@@H](O)[C@H](O[C@H]3OC(CNCC4(O)CC(NC(=O)OC(C)(C)C)C4)=CC[C@H]3NC(=O)OC(C)(C)C)[C@@H](NC(=O)OC(C)(C)C)C[C@H]2NC(=O)C(O)C2CN(C(=O)OC(C)(C)C)C2)OC[C@]1(C)O]

6'-(Methyl-N-Boc-3-amino-1-hydroxy-cyclobutyl)-2',3,3"-triBoc-1-(2-(N-Boc-azetidin-3-yl)-2-hydroxy-acetyl)-sisomicin 2',3,3"-triBoc-1-(2-(N-Boc-azetidin-3-yl)-2-hydroxy-acetyl)-sisomicin (0.081 mmol) was treated with N-Boc-1-oxaspiro[2.3]hexan-5-amine following Procedure 5 to give the desired 6'-(methyl-N-Boc-3-amino-1-hydroxy-cyclobutyl)-2',3,3"-triBoc-1-(2-(N-Boc-azetidin-3-yl)-2-hydroxy-acetyl)-sisomicin (MS m/e [M+H]$^+$ calcd 1160.6, found 1161.0), which was carried through to the next step without further purification.

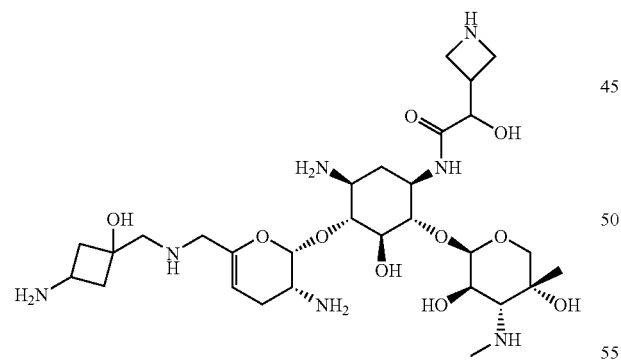

6'-(Methyl-3-amino-1-hydroxy-cyclobutyl)-1-(2-(azetidin-3-yl)-2-hydroxy-acetyl)-sisomicin 6'-(Methyl-N-Boc-3-amino-1-hydroxy-cyclobutyl)-2',3,3"-triBoc-1-(2-(N-Boc-azetidin-3-yl)-2-hydroxy-acetyl)-sisomicin (0.081 mmol) was submitted to Procedure 3-Method A for Boc removal to yield a crude, which was purified by RP HPLC Method 1-Column A to yield 6'-(methyl-3-amino-1-hydroxy-cyclobutyl)-1-(2-(azetidin-3-yl)-2-hydroxy-acetyl)-sisomicin (0.0013 g, 0.0019 mmol, 2.3% yield): MS m/e [M+H]$^+$ calcd 660.4, found 660.4; CLND 94.3% purity.

Example 84

2'-(Methyl-pyrrolidin-3-yl)-1-(4-amino-2(S)-hydroxy-butyryl)-sisomicin

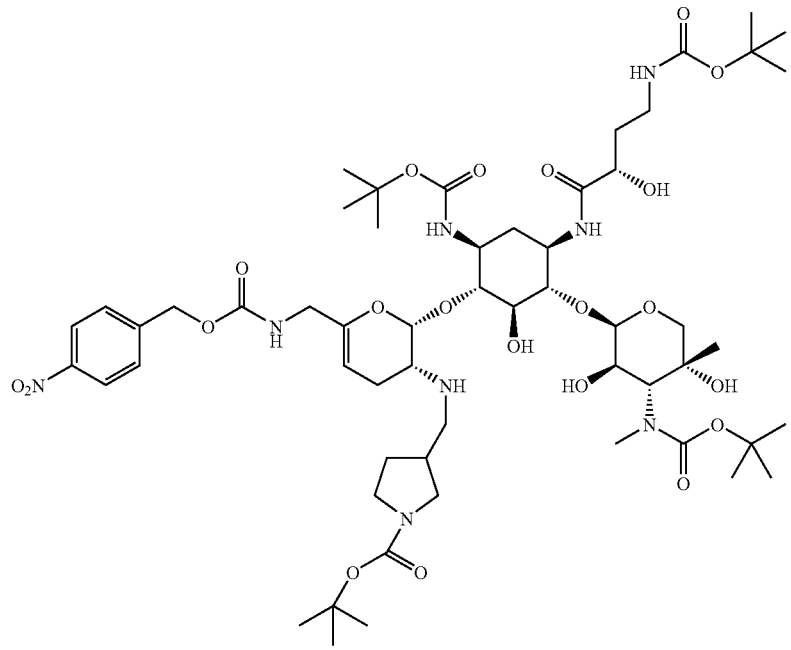 [SMILES: CN(C(=O)OC(C)(C)C)[C@@H]1[C@@H](O)[C@@H](O[C@@H]2[C@@H](O)[C@H](O[C@H]3OC(CNC(=O)OCc4ccc([N+](=O)[O-])cc4)=CC[C@H]3NCC3CCN(C(=O)OC(C)(C)C)C3)[C@@H](NC(=O)OC(C)(C)C)C[C@H]2NC(=O)[C@@H](O)CCNC(=O)OC(C)(C)C)OC[C@]1(C)O]

6'-PNZ-2'-(methyl-N-Boc-pyrrolidin-3-yl)-3,3''-di-Boc-1-(N-Boc-4-amino-2(S)-hydroxy-butyryl)-sisomicin Treatment of 6'-PNZ-3,3''-diBoc-1-(N-Boc-4-amino-2(S)-hydroxy-butyryl)-sisomicin (0.075 g, 0.073 mmol) with N-Boc-3-pyrrolidine carbaldehyde following Procedure 1-Method B gave the desired 6'-PNZ-2'-(methyl-N-Boc-pyrrolidin-3-yl)-3,3''-diBoc-1-(N-Boc-4-amino-2(S)-hydroxy-butyryl)-sisomicin, which was carried through to the next step without further purification.

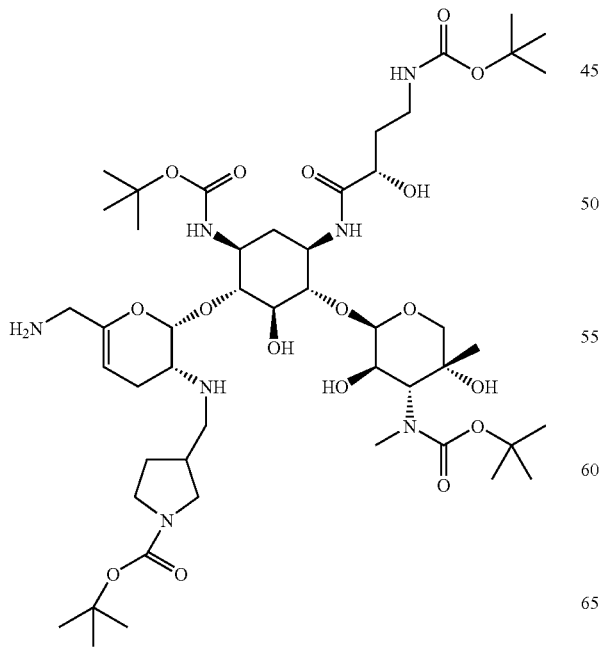

245

2'-(Methyl-N-Boc-pyrrolidin-3-yl)-3,3''-diBoc-1-(N-Boc-4-amino-2(S)-hydroxy-butyryl)-sisomicin

6'-PNZ-2'-(methyl-N-Boc-pyrrolidin-3-yl)-3,3''-diBoc-1-(N-Boc-4-amino-2(S)-hydroxy-butyryl)-sisomicin (0.073 mmol) was submitted to Procedure 2 for PNZ removal to yield 2'-(methyl-N-Boc-pyrrolidin-3-yl)-3,3''-diBoc-1-(N-Boc-4-amino-2(S)-hydroxy-butyryl)-sisomicin, which was carried through to the next step without further purification.

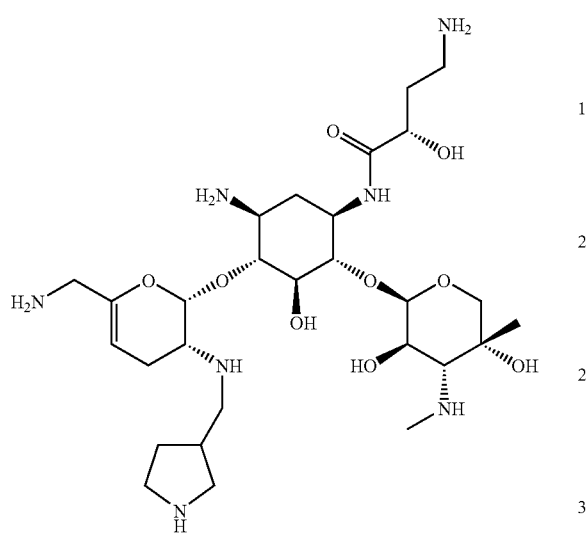

246

2'-(Methyl-pyrrolidin-3-yl)-1-(4-amino-2(S)-hydroxy-butyryl)-sisomicin

2'-(Methyl-N-Boc-pyrrolidin-3-yl)-3,3''-diBoc-1-(N-Boc-4-amino-2(S)-hydroxy-butyryl)-sisomicin (0.073 mmol) was submitted to Procedure 3-Method B for Boc removal to yield a crude, which was purified by RP HPLC Method 1-Column A) to yield 2'-(methyl-pyrrolidin-3-yl)-1-(4-amino-2(S)-hydroxy-butyryl)-sisomicin: MS m/e [M+H]$^+$ calcd 632.4, found 632.3, [M+Na]$^+$ 654.4; CLND 93.7% purity.

Example 85

2'-(Methyl-pyrrolidin-2-yl)-1-(4-amino-2(S)-hydroxy-butyryl)-sisomicin

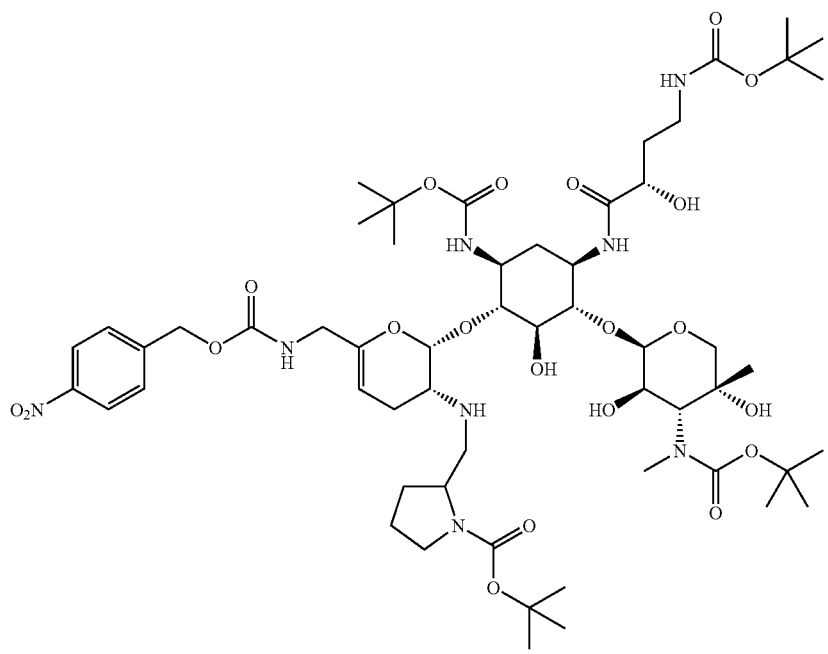 [SMILES: CN(C(=O)OC(C)(C)C)[C@@H]1[C@@H](O)[C@@H](O[C@@H]2[C@@H](O)[C@H](O[C@H]3OC(CNC(=O)OCc4ccc([N+](=O)[O-])cc4)=CC[C@H]3NCC3CCCN3C(=O)OC(C)(C)C)[C@@H](NC(=O)OC(C)(C)C)C[C@H]2NC(=O)[C@@H](O)CCNC(=O)OC(C)(C)C)OC[C@]1(C)O]

6'-PNZ-2'-(methyl-N-Boc-pyrrolidin-2-yl)-3,3''-di-Boc-1-(N-Boc-4-amino-2(S)-hydroxy-butyryl)-sisomicin Treatment of 6'-PNZ-3,3''-diBoc-1-(N-Boc-4-amino-2(S)-hydroxy-butyryl)-sisomicin (0.075 g, 0.073 mmol) with N-Boc-prolinal following Procedure 1-Method B gave the desired 6'-PNZ-2'-(methyl-N-Boc-pyrrolidin-2-yl)-3,3''-di-Boc-1-(N-Boc-4-amino-2(S)-hydroxy-butyryl)-sisomicin, which was carried through to the next step without further purification.

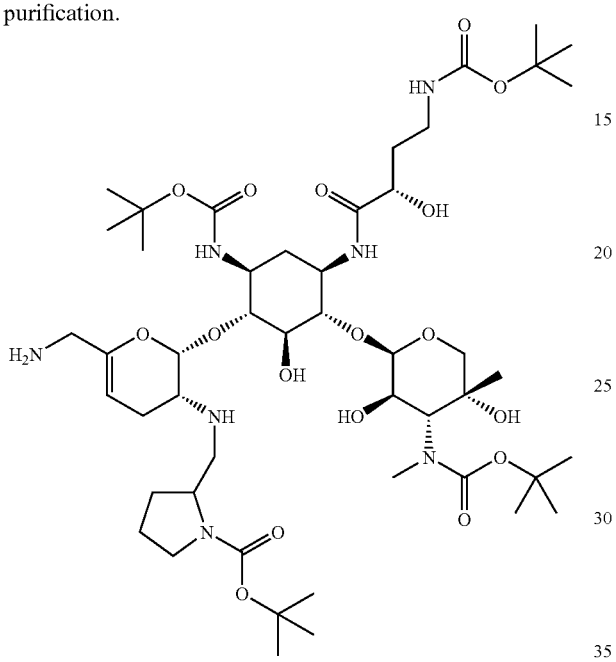

2'-(Methyl-N-Boc-pyrrolidin-2-yl)-3,3''-diBoc-1-(N-Boc-4-amino-2(S)-hydroxy-butyryl)-sisomicin 6'-PNZ-2'-(methyl-N-Boc-pyrrolidin-2-yl)-3,3''-diBoc-1-(N-Boc-4-amino-2(S)-hydroxy-butyryl)-sisomicin (0.073 mmol) was submitted to Procedure 2 for PNZ removal to yield 2'-(methyl-N-Boc-pyrrolidin-2-yl)-3,3''-diBoc-1-(N-Boc-4-amino-2(S)-hydroxy-butyryl)-sisomicin (MS m/e [M+H]$^+$ calcd 1032.6, found 1032.5), which was carried through to the next step without further purification.

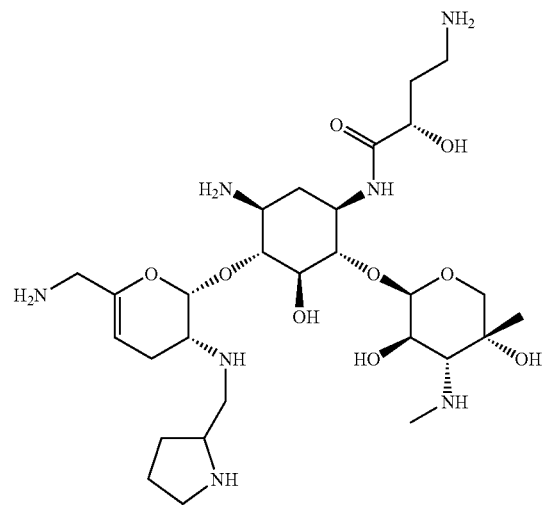 [SMILES: CN[C@@H]1[C@@H](O)[C@@H](O[C@@H]2[C@@H](O)[C@H](O[C@H]3OC(CN)=CC[C@H]3NCC3CCCN3)[C@@H](N)C[C@H]2NC(=O)[C@@H](O)CCN)OC[C@]1(C)O]

2'-(Methyl-pyrrolidin-2-yl)-1-(4-amino-2(S)-hydroxy-butyryl)-sisomicin

2'-(Methyl-N-Boc-pyrrolidin-2-yl)-3,3''-diBoc-1-(N-Boc-4-amino-2(S)-hydroxy-butyryl)-sisomicin (0.073 mmol) was submitted to Procedure 3-Method B for Boc removal to yield a crude, which was purified by RP HPLC Method 1-Column A to yield 2'-(methyl-pyrrolidin-2-yl)-1-(4-amino-2(S)-hydroxy-butyryl)-sisomicin: MS m/e [M+H]$^+$ calcd 632.4, found 632.3, [M+Na]$^+$ 654.4; CLND 97.6% purity.

Example 86

2'-(N-Methyl-amino-acetyl)-1-(4-amino-2(S)-hydroxy-butyryl)-sisomicin

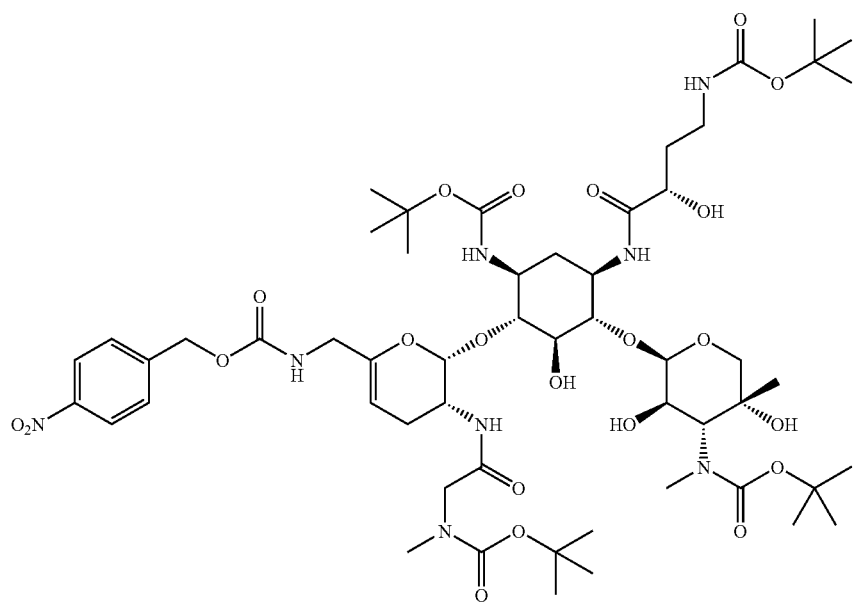 [SMILES: CN(CC(=O)N[C@@H]1CC=C(CNC(=O)OCc2ccc([N+](=O)[O-])cc2)O[C@@H]1O[C@H]1[C@H](O)[C@@H](O[C@H]2OC[C@](C)(O)[C@H](N(C)C(=O)OC(C)(C)C)[C@H]2O)[C@H](NC(=O)[C@@H](O)CCNC(=O)OC(C)(C)C)C[C@@H]1NC(=O)OC(C)(C)C)C(=O)OC(C)(C)C]

6'-PNZ-2'-(N-Boc-N-methyl-amino-acetyl)-3,3''-diBoc-1-(N-Boc-4-amino-2(S)-hydroxy-butyryl)-sisomicin Treatment of 6'-PNZ-3,3''-diBoc-1-(N-Boc-4-amino-2(S)-hydroxy-butyryl)-sisomicin (0.060 g, 0.06 mmol) with N-Boc-sarcosine following Procedure 20 gave the desired 6'-PNZ-2'-(N-Boc-N-methyl-amino-acetyl)-3,3''-diBoc-1-(N-Boc-4-amino-2(S)-hydroxy-butyryl)-sisomicin, which was carried through to the next step without further purification.

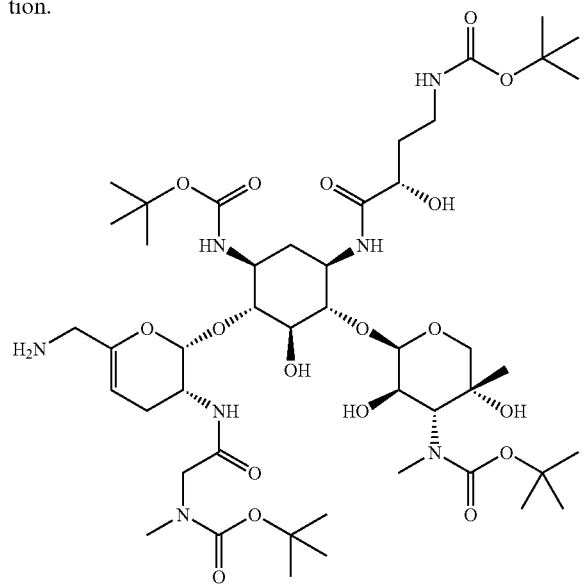

2'-(N-Boc-N-methyl-amino-acetyl)-3,3''-diBoc-1-(N-Boc-4-amino-2(S)-hydroxy-butyryl)-sisomicin 6'-PNZ-2'-(N-Boc-N-methyl-amino-acetyl)-3,3''-diBoc-1-(N-Boc-4-amino-2(S)-hydroxy-butyryl)-sisomicin (0.06 mmol) was submitted to Procedure 2 for PNZ removal to yield 2'-(N-Boc-N-methyl-amino-acetyl)-3,3''-diBoc-1-(N-Boc-4-amino-2(S)-hydroxy-butyryl)-sisomicin (MS m/e [M+H]$^+$ calcd 1020.6, found 1020.4), which was carried through to the next step without further purification.

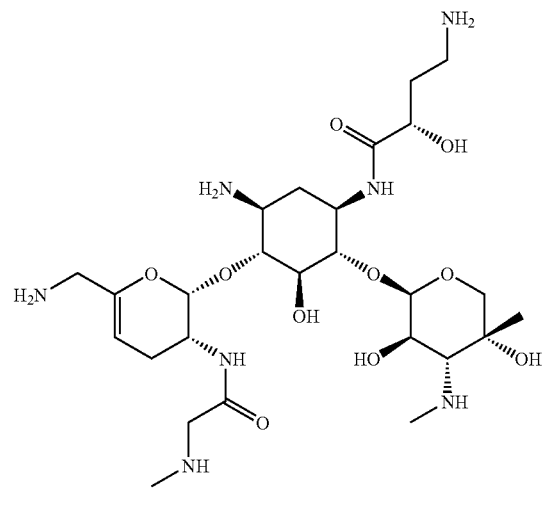 [SMILES: CNCC(=O)N[C@@H]1CC=C(CN)O[C@@H]1O[C@H]1[C@H](O)[C@@H](O[C@H]2OC[C@](C)(O)[C@H](NC)[C@H]2O)[C@H](NC(=O)[C@@H](O)CCN)C[C@@H]1N]

2'-(N-Methyl-amino-acetyl)-1-(4-amino-2(S)-hydroxy-butyryl)-sisomicin

2'-(N-Boc-N-methyl-amino-acetyl)-3,3''-diBoc-1-(N-Boc-4-amino-2(S)-hydroxy-butyryl)-sisomicin (0.06 mmol) was submitted to Procedure 3-Method B for Boc removal to yield a crude, which was purified by RP HPLC Method 1-Column A to yield 2'-(N-methyl-amino-acetyl)-1-(4-amino-2(S)-hydroxy-butyryl)-sisomicin: MS m/e [M+H]$^+$ calcd 620.3, found 620.3, [M+Na]$^+$ 642.3; CLND 97.6% purity.

Example 87

2'-(2-Amino-acetyl)-1-(4-amino-2(S)-hydroxy-butyryl)-sisomicin

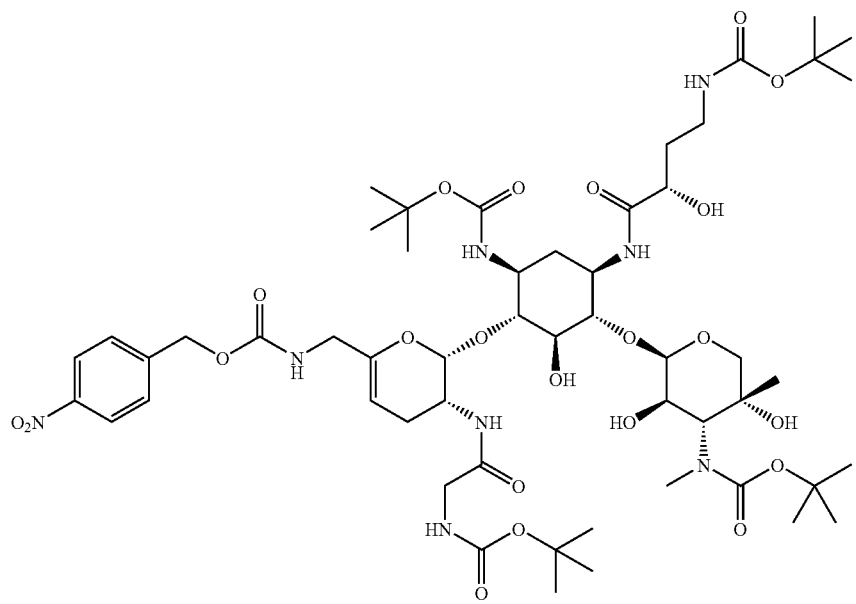 [SMILES: CN(C(=O)OC(C)(C)C)[C@@H]1[C@@H](O)[C@@H](O[C@@H]2[C@@H](O)[C@H](O[C@H]3OC(CNC(=O)OCc4ccc([N+](=O)[O-])cc4)=CC[C@H]3NC(=O)CNC(=O)OC(C)(C)C)[C@@H](NC(=O)OC(C)(C)C)C[C@H]2NC(=O)[C@@H](O)CCNC(=O)OC(C)(C)C)OC[C@]1(C)O]

6'-PNZ-2'-(N-Boc-2-amino-acetyl)-3,3''-diBoc-1-(N-Boc-4-amino-2(S)-hydroxy-butyryl)-sisomicin Treatment of 6'-PNZ-3,3''-diBoc-1-(N-Boc-4-amino-2(S)-hydroxy-butyryl)-sisomicin (0.060 g, 0.06 mmol) with N-Boc-glycine following Procedure 20 gave the desired 6'-PNZ-2'-(N-Boc-2-amino-acetyl)-3,3''-diBoc-1-(N-Boc-4-amino-2(S)-hydroxy-butyryl)-sisomicin, which was carried through to the next step without further purification.

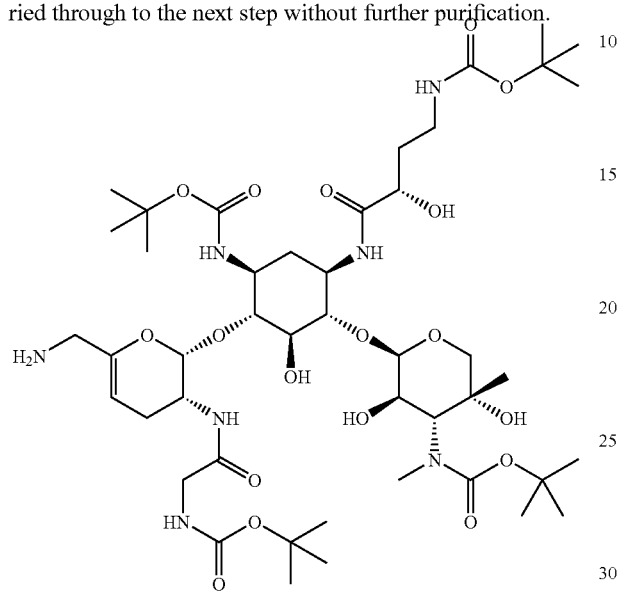

2'-(N-Boc-2-amino-acetyl)-3,3''-diBoc-1-(N-Boc-4-amino-2(S)-hydroxy-butyryl)-sisomicin 6'-PNZ-2'-(N-Boc-2-amino-acetyl)-3,3''-diBoc-1-(N-Boc-4-amino-2(S)-hydroxy-butyryl)-sisomicin (0.06 mmol) was submitted to Procedure 2 for PNZ removal to yield 2'-(N-Boc-2-amino-acetyl)-3,3''-diBoc-1-(N-Boc-4-amino-2(S)-hydroxy-butyryl)-sisomicin, which was carried through to the next step without further purification.

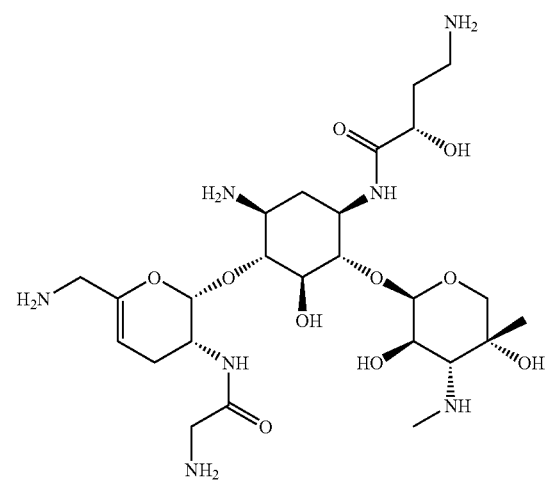 [SMILES: CN[C@@H]1[C@@H](O)[C@@H](O[C@@H]2[C@@H](O)[C@H](O[C@H]3OC(CN)=CC[C@H]3NC(=O)CN)[C@@H](N)C[C@H]2NC(=O)[C@@H](O)CCN)OC[C@]1(C)O]

2'-(2-Amino-acetyl)-1-(4-amino-2(S)-hydroxy-butyryl)-sisomicin

2'-(N-Boc-2-amino-acetyl)-3,3''-diBoc-1-(N-Boc-4-amino-2(S)-hydroxy-butyryl)-sisomicin (0.06 mmol) was submitted to Procedure 3-Method B for Boc removal to yield a crude, which was purified by RP HPLC Method 1-Column A to yield 2'-(2-amino-acetyl)-1-(4-amino-2(S)-hydroxy-butyryl)-sisomicin: MS m/e [M+H]+ calcd 606.3, found 606.3, [M+Na]+ 628.2; CLND 97.4% purity.

Example 88

2'-(2-Amino-propionyl)-1-(4-amino-2(S)-hydroxy-butyryl)-sisomicin

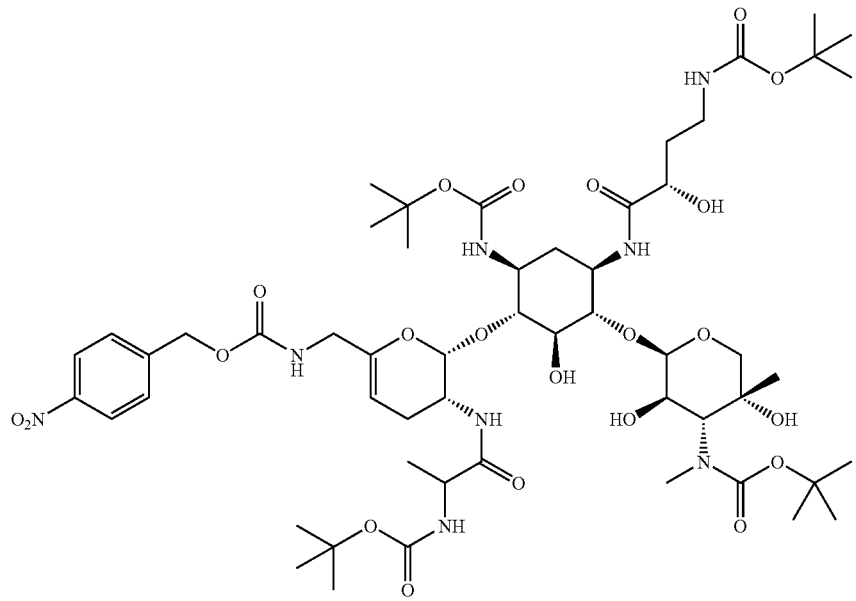 [SMILES: CC(NC(=O)OC(C)(C)C)C(=O)N[C@@H]1CC=C(CNC(=O)OCc2ccc([N+](=O)[O-])cc2)O[C@@H]1O[C@H]1[C@H](O)[C@@H](O[C@H]2OC[C@](C)(O)[C@H](N(C)C(=O)OC(C)(C)C)[C@H]2O)[C@H](NC(=O)[C@@H](O)CCNC(=O)OC(C)(C)C)C[C@@H]1NC(=O)OC(C)(C)C]

253

6'-PNZ-2'-(N-Boc-2-amino-propionyl)-3,3''-diBoc-1-(N-Boc-4-amino-2(S)-hydroxy-butyryl)-sisomicin Treatment of 6'-PNZ-3,3''-diBoc-1-(N-Boc-4-amino-2(S)-hydroxy-butyryl)-sisomicin (0.060 g, 0.06 mmol) with N-Boc-alanine following Procedure 4-Method A gave the desired 6'-PNZ-2'-(N-Boc-2-amino-propionyl)-3,3''-diBoc-1-(N-Boc-4-amino-2(S)-hydroxy-butyryl)-sisomicin (MS m/e [M+H]$^+$ calcd 1199.6, found 1199.2, [M+Na]$^+$ 1221.4), which was carried through to the next step without further purification.

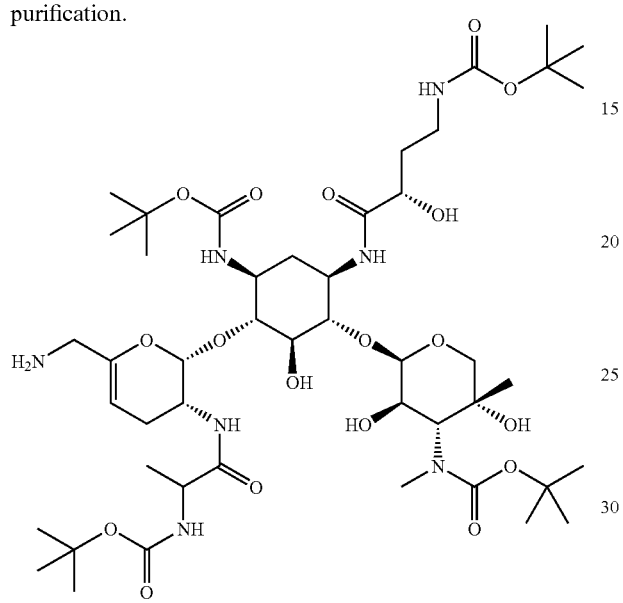

2'-(N-Boc-2-amino-propionyl)-3,3''-diBoc-1-(N-Boc-4-amino-2(S)-hydroxy-butyryl)-sisomicin 6'-PNZ-2'-(N-Boc-2-amino-propionyl)-3,3''-diBoc-1-(N-Boc-4-amino-2(S)-hydroxy-butyryl)-sisomicin (0.06 mmol) was submitted to Procedure 2 for PNZ removal to yield 2'-(N-Boc-2-amino-propionyl)-3,3''-diBoc-1-(N-Boc-4-amino-2(S)-hydroxy-butyryl)-sisomicin (MS m/e [M+H]$^+$ calcd 1020.6, found 1020.4, [M+Na]$^+$ 1042.4), which was carried through to the next step without further purification.

254

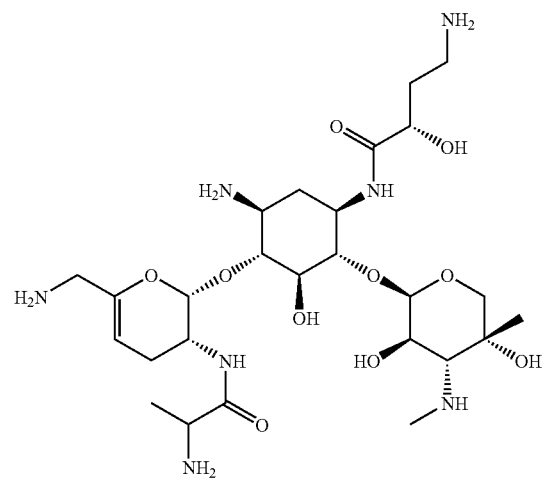 [SMILES: CN[C@@H]1[C@@H](O)[C@@H](O[C@@H]2[C@@H](O)[C@H](O[C@H]3OC(CN)=CC[C@H]3NC(=O)C(C)N)[C@@H](N)C[C@H]2NC(=O)[C@@H](O)CCN)OC[C@]1(C)O]

2'-(2-Amino-propionyl)-1-(4-amino-2(S)-hydroxy-butyryl)-sisomicin

2'-(N-Boc-2-amino-propionyl)-3,3''-diBoc-1-(N-Boc-4-amino-2(S)-hydroxy-butyryl)-sisomicin (0.06 mmol) was submitted to Procedure 3-Method B for Boc removal to yield a crude, which was purified by RP HPLC Method 1-Column A to yield 2'-(2-amino-propionyl)-1-(4-amino-2(S)-hydroxy-butyryl)-sisomicin (0.0092 g, 0.0148 mmol, 24.7% yield): MS m/e [M+H]$^+$ calcd 620.3, found 620.2, [M+Na]$^+$ 642.4; CLND 97.5% purity.

Example 89

2'-(3-Amino-2-hydroxy-propionyl)-1-(4-amino-2(S)-hydroxy-butyryl)-sisomicin

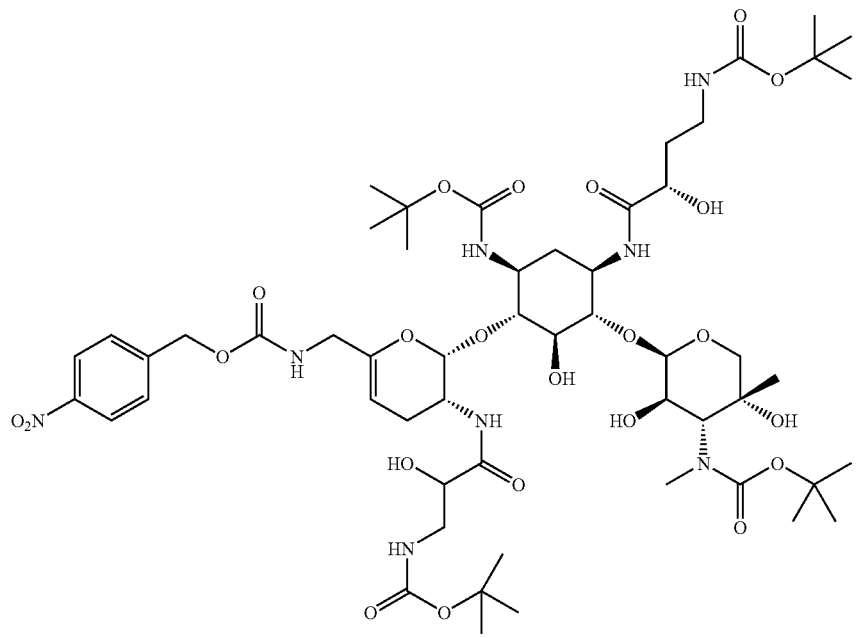 [SMILES: CN(C(=O)OC(C)(C)C)[C@@H]1[C@@H](O)[C@@H](O[C@@H]2[C@@H](O)[C@H](O[C@H]3OC(CNC(=O)OCc4ccc([N+](=O)[O-])cc4)=CC[C@H]3NC(=O)C(O)CNC(=O)OC(C)(C)C)[C@@H](NC(=O)OC(C)(C)C)C[C@H]2NC(=O)[C@@H](O)CCNC(=O)OC(C)(C)C)OC[C@]1(C)O]

6'-PNZ-2'-(N-Boc-3-amino-2-hydroxy-propionyl)-3,3"-diBoc-1-(N-Boc-4-amino-2(S)-hydroxy-butyryl)-sisomicin Treatment of 6'-PNZ-3,3"-diBoc-1-(N-Boc-4-amino-2(S)-hydroxy-butyryl)-sisomicin (0.065 g, 0.06 mmol) with N-Boc-isoserine following Procedure 4-Method A gave the desired 6'-PNZ-2'-(N-Boc-3-amino-2-hydroxy-propionyl)-3,3"-diBoc-1-(N-Boc-4-amino-2(S)-hydroxy-butyryl)-sisomicin (MS m/e [M+H]$^+$ calcd 1215.6, found 1215.0, [M+Na]$^+$ 1237.3), which was carried through to the next step without further purification.

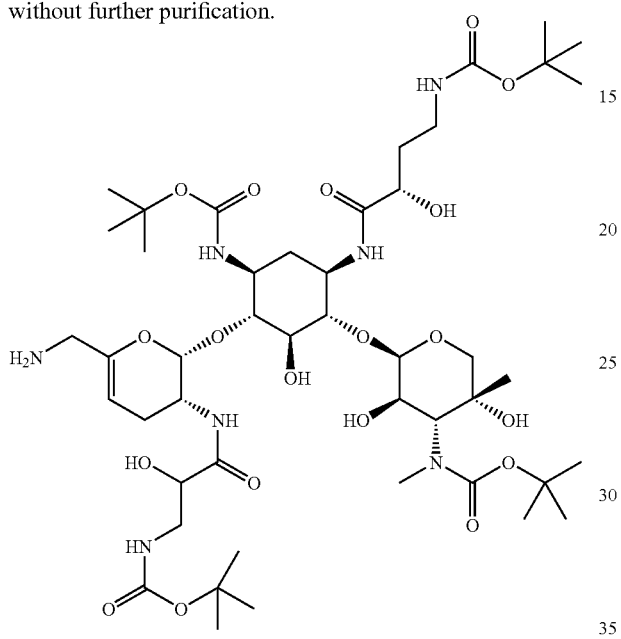

2'-(N-Boc-3-amino-2-hydroxy-propionyl)-3,3"-diBoc-1-(N-Boc-4-amino-2(S)-hydroxy-butyryl)-sisomicin 6'-PNZ-2'-(N-Boc-3-amino-2-hydroxy-propionyl)-3,3"-diBoc-1-(N-Boc-4-amino-2(S)-hydroxy-butyryl)-sisomicin (0.06 mmol) was submitted to Procedure 2 for PNZ removal to yield 2'-(N-Boc-3-amino-2-hydroxy-propionyl)-3,3"-diBoc-1-(N-Boc-4-amino-2(S)-hydroxy-butyryl)-sisomicin (MS m/e [M+H]$^+$ calcd 1036.6, found 1036.3, [M+Na]$^+$ 1058.4), which was carried through to the next step without further purification.

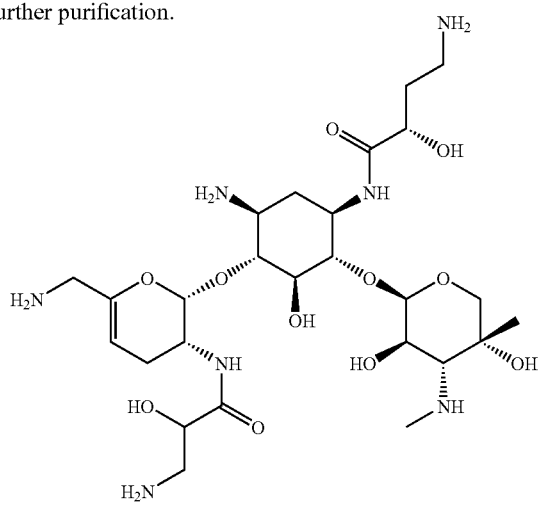

2'-(3-Amino-2-hydroxy-propionyl)-1-(4-amino-2(S)-hydroxy-butyryl)-sisomicin

2'-(N-Boc-3-amino-2-hydroxy-propionyl)-3,3"-diBoc-1-(N-Boc-4-amino-2(S)-hydroxy-butyryl)-sisomicin (0.06 mmol) was submitted to Procedure 3-Method B for Boc removal to yield a crude, which was purified by RP HPLC Method 1-Column A to yield 2'-(3-amino2-hydroxy-propionyl)-1-(4-amino-2(S)-hydroxy-butyryl)-sisomicin (0.005 g, 0.008 mmol, 13.3% yield): MS m/e [M+H]$^+$ calcd 636.3, found 636.2, [M+Na]$^+$ 658.3; CLND 97.5% purity.

Example 90

2'-(Pyrrolidin-2-yl-acetyl)-1-(4-amino-2(S)-hydroxy-butyryl)-sisomicin

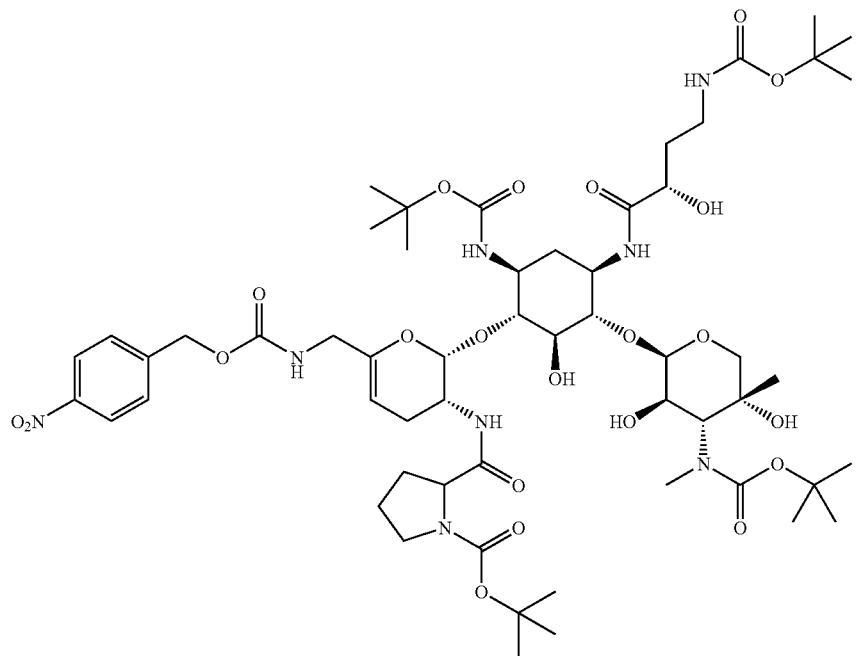 [SMILES: CN(C(=O)OC(C)(C)C)[C@@H]1[C@@H](O)[C@@H](O[C@@H]2[C@@H](O)[C@H](O[C@H]3OC(CNC(=O)OCc4ccc([N+](=O)[O-])cc4)=CC[C@H]3NC(=O)C3CCCN3C(=O)OC(C)(C)C)[C@@H](NC(=O)OC(C)(C)C)C[C@H]2NC(=O)[C@@H](O)CCNC(=O)OC(C)(C)C)OC[C@]1(C)O]

6'-PNZ-2'-(N-Boc-pyrrolidin-2-yl-acetyl)-3,3"-di-Boc-1-(N-Boc-4-amino-2(S)-hydroxy-butyryl)-sisomicin Treatment of 6'-PNZ-3,3"-diBoc-1-(N-Boc-4-amino-2(S)-hydroxy-butyryl)-sisomicin (0.060 g, 0.06 mmol) with N-Boc-proline following Procedure 20 gave the desired 6'-PNZ-2'-(N-Boc-pyrrolidin-2-yl-acetyl)-3,3"-diBoc-1-(N-Boc-4-amino-2(S)-hydroxy-butyryl)-sisomicin, which was carried through to the next step without further purification.

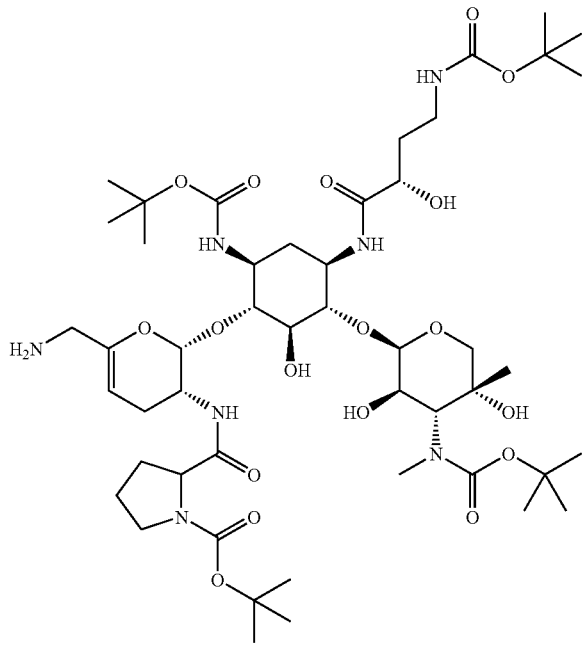 [SMILES: CN(C(=O)OC(C)(C)C)[C@@H]1[C@@H](O)[C@@H](O[C@@H]2[C@@H](O)[C@H](O[C@H]3OC(CN)=CC[C@H]3NC(=O)C3CCCN3C(=O)OC(C)(C)C)[C@@H](NC(=O)OC(C)(C)C)C[C@H]2NC(=O)[C@@H](O)CCNC(=O)OC(C)(C)C)OC[C@]1(C)O]

2'-(N-Boc-pyrrolidin-2-yl-acetyl)-3,3"-diBoc-1-(N-Boc-4-amino-2(S)-hydroxy-butyryl)-sisomicin 6'-PNZ-2'-(N-Boc-pyrrolidin-2-yl-acetyl)-3,3"-diBoc-1-(N-Boc-4-amino-2(S)-hydroxy-butyryl)-sisomicin (0.06 mmol) was submitted to Procedure 2 for PNZ removal to yield 2'-(N-Boc-pyrrolidin-2-yl-acetyl)-3,3"-diBoc-1-(N-Boc-4-amino-2(S)-hydroxy-butyryl)-sisomicin, which was carried through to the next step without further purification.

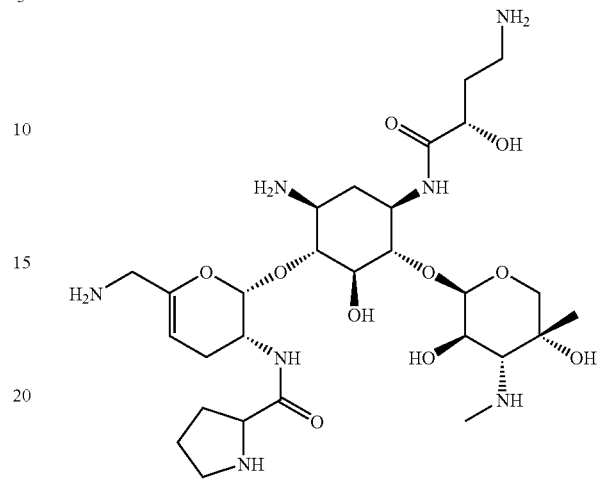

2'-(Pyrrolidin-2-yl-acetyl)-1-(4-amino-2(S)-hydroxy-butyryl)-sisomicin

2'-(N-Boc-pyrrolidin-2-yl-acetyl)-3,3"-diBoc-1-(N-Boc-4-amino-2(S)-hydroxy-butyryl)-sisomicin (0.06 mmol) was submitted to Procedure 3-Method B for Boc removal to yield a crude, which was purified by RP HPLC Method 1-Column A to yield 2'-(pyrrolidin-2-yl-acetyl)-1-(4-amino-2(S)-hydroxy-butyryl)-sisomicin: MS m/e [M+H]$^+$ calcd 646.4, found 646.3, [M+Na]$^+$ 668.2; CLND 78.0% purity.

Example 91

2'-(3-Amino-propyl)-1-(4-amino-2(S)-hydroxy-butyryl)-sisomicin

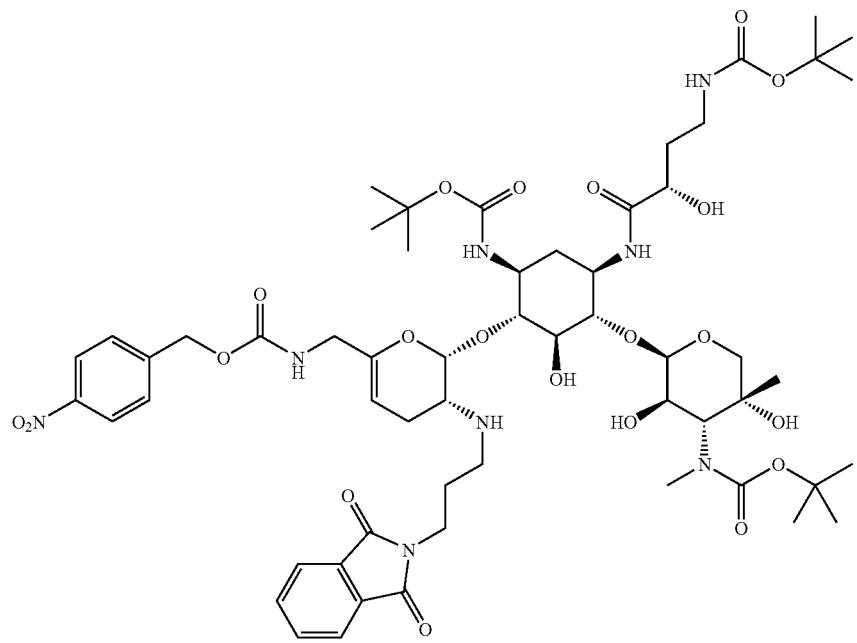 [SMILES: CN(C(=O)OC(C)(C)C)[C@@H]1[C@@H](O)[C@@H](O[C@@H]2[C@@H](O)[C@H](O[C@H]3OC(CNC(=O)OCc4ccc([N+](=O)[O-])cc4)=CC[C@H]3NCCCN3C(=O)c4ccccc4C3=O)[C@@H](NC(=O)OC(C)(C)C)C[C@H]2NC(=O)[C@@H](O)CCNC(=O)OC(C)(C)C)OC[C@]1(C)O]

6'-PNZ-2'-(N-phthalimido-3-amino-propyl)-3,3''-diBoc-1-(N-Boc-4-amino-2(S)-hydroxy-butyryl)-sisomicin To a solution of 6'-PNZ-3,3''-diBoc-1-(N-Boc-4-amino-2(S)-hydroxy-butyryl)-sisomicin (0.105 g, 0.102 mmol) in DMF (1 mL) was added 3-phthalimido-propionaldehyde (0.041 g, 0.204 mmol) and 3 Å Molecular Sieves (10-15), and the reaction was shaken for 2 hours. A solution of NaCNBH$_3$ (0.013 g, 0.204 mmol) in MeOH (3 mL) was then added and the reaction was stirred overnight. The reaction was diluted with EtOAc (5 mL) and the organic layer was washed with sat. aq. NH$_4$Cl, sat. aq. NaHCO$_3$ (3 mL), brine (3 mL), dried over Na$_2$SO$_4$, filtered and concentrated to dryness to yield 6'-PNZ-2'-(N-phthalimido-3-amino-propyl)-3,3''-diBoc-1-(N-Boc-4-amino-2(S)-hydroxy-butyryl)-sisomicin (MS m/e [M+H]$^+$ calcd 1215.6, found 1215.3, [M+Na]$^+$ 1237.3), which was carried through to the next step without further purification.

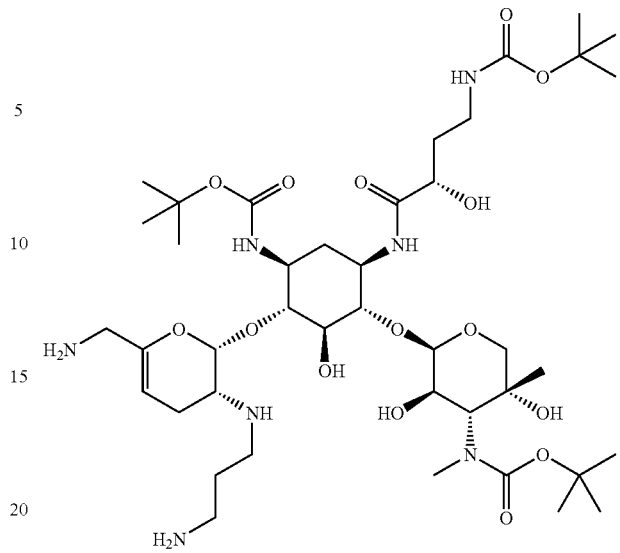

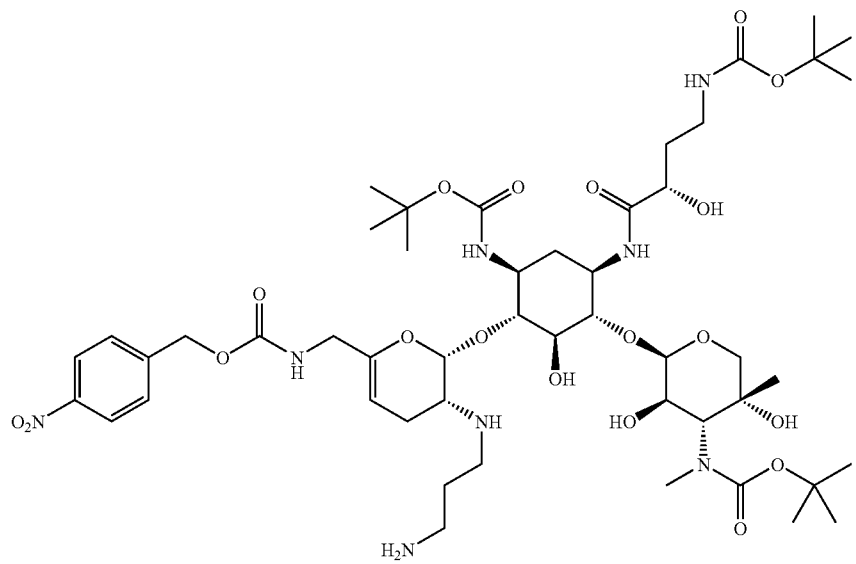 [SMILES: CN(C(=O)OC(C)(C)C)[C@@H]1[C@@H](O)[C@@H](O[C@@H]2[C@@H](O)[C@H](O[C@H]3OC(CNC(=O)OCc4ccc([N+](=O)[O-])cc4)=CC[C@H]3NCCCN)[C@@H](NC(=O)OC(C)(C)C)C[C@H]2NC(=O)[C@@H](O)CCNC(=O)OC(C)(C)C)OC[C@]1(C)O]

6'-PNZ-2'-(3-amino-propyl)-3,3''-diBoc-1-(N-Boc-4-amino-2(S)-hydroxy-butyryl)-sisomicin 6'-PNZ-2'-(N-phthalimido-3-amino-propyl)-3,3''-diBoc-1-(N-Boc-4-amino-2(S)-hydroxy-butyryl)-sisomicin (0.102 mmol) was submitted to Procedure 6 for phthalimido removal to yield 6'-PNZ-2'-(3-amino-propyl)-3,3''-diBoc-1-(N-Boc-4-amino-2(S)-hydroxy-butyryl)-sisomicin (MS m/e [M+H]$^+$ calcd 1085.5, found 1085.4, [M+Na]$^+$ 1107.4), which was carried through to the next step without further purification.

2'-(3-Amino-propyl)-3,3''-diBoc-1-(N-Boc-4-amino-2(S)-hydroxy-butyryl)-sisomicin 6'-PNZ-2'-(3-amino-propyl)-3,3''-diBoc-1-(N-Boc-4-amino-2(S)-hydroxy-butyryl)-sisomicin (0.102 mmol) was submitted to Procedure 2 for PNZ removal to yield 2'-(3-amino-propyl)-3,3''-diBoc-1-(N-Boc-4-amino-2(S)-hydroxy-butyryl)-sisomicin (MS m/e [M+H]$^+$ calcd 906.5, found 906.2), which was carried through to the next step without further purification.

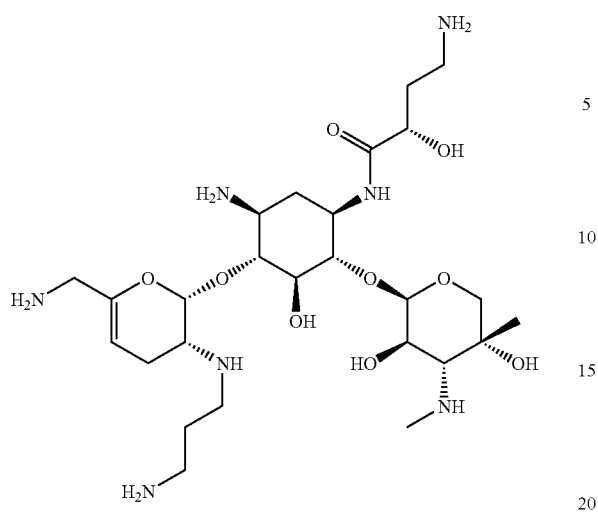

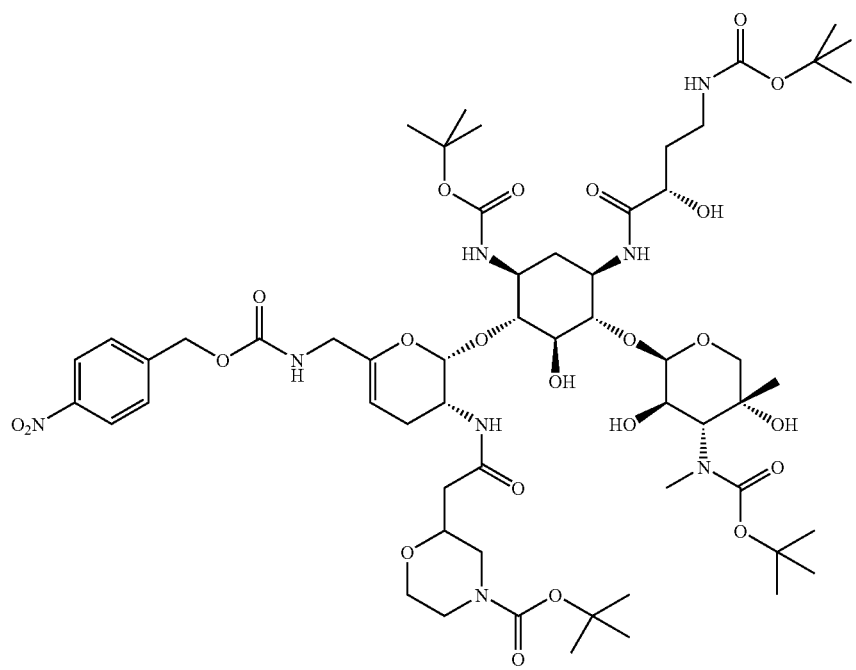 [SMILES: CN(C(=O)OC(C)(C)C)[C@@H]1[C@@H](O)[C@@H](O[C@@H]2[C@@H](O)[C@H](O[C@H]3OC(CNC(=O)OCc4ccc([N+](=O)[O-])cc4)=CC[C@H]3NC(=O)CC3CN(C(=O)OC(C)(C)C)CCO3)[C@@H](NC(=O)OC(C)(C)C)C[C@H]2NC(=O)[C@@H](O)CCNC(=O)OC(C)(C)C)OC[C@]1(C)O]

6'-PNZ-2'-(N-Boc-morpholin-2-yl-acetyl)-3,3''-di-Boc-1-(N-Boc-4-amino-2(S)-hydroxy-butyryl)-sisomicin Treatment of 6'-PNZ-3,3''-diBoc-1-(N-Boc-4-amino-2(S)-hydroxy-butyryl)-sisomicin (0.075 g, 0.073 mmol) with N-Boc-morpholine-2-acetic acid following Procedure 4-Method A gave the desired 6'-PNZ-2'-(N-Boc-morpholin-2-yl-acetyl)-3,3''-diBoc-1-(N-Boc-4-amino-2(S)-hydroxy-butyryl)-sisomicin (MS m/e [M+H]$^+$ calcd 1255.6, found 1255.8), which was carried through to the next step without further purification.

2'-(3-Amino-propyl)-1-(4-amino-2(S)-hydroxy-butyryl)-sisomicin

2'-(3-Amino-propyl)-3,3''-diBoc-1-(N-Boc-4-amino-2(S)-hydroxy-butyryl)-sisomicin (0.102 mmol) was submitted to Procedure 3-Method B for Boc removal to yield a crude, which was purified by RP HPLC Method 1-Column A to yield 2'-(3-amino-propyl)-1-(4-amino-2(S)-hydroxy-butyryl)-sisomicin (0.0021 g, 0.0035 mmol, 3.4% yield): MS m/e [M+H]$^+$ calcd 606.4, found 606.2, [M+Na]$^+$ 628.3; CLND 94.0% purity.

Example 92

2'-(Morpholin-2-yl-acetyl)-1-(4-amino-2(S)-hydroxy-butyryl)-sisomicin

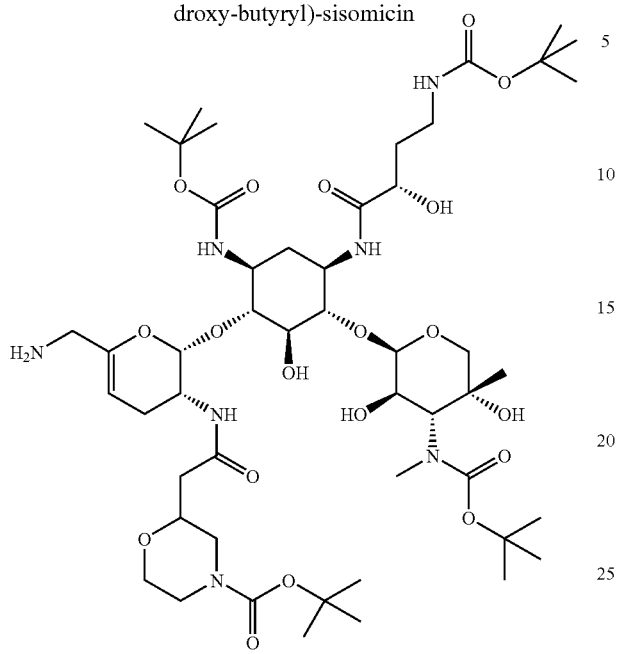

2'-(N-Boc-morpholin-2-yl-acetyl)-3,3''-diBoc-1-(N-Boc-4-amino-2(S)-hydroxy-butyryl)-sisomicin 6'-PNZ-2'-(N-Boc-morpholin-2-yl-acetyl)-3,3''-diBoc-1-(N-Boc-4-amino-2(S)-hydroxy-butyryl)-sisomicin (0.073 mmol) was submitted to Procedure 2 for PNZ removal to yield 2'-(N-Boc-morpholin-2-yl-acetyl)-3,3''-diBoc-1-(N-Boc-4-amino-2(S)-hydroxy-butyryl)-sisomicin (MS m/e [M+H]$^+$ calcd 1076.6, found 1076.3, [M+Na]$^+$ 1098.4), which was carried through to the next step without further purification.

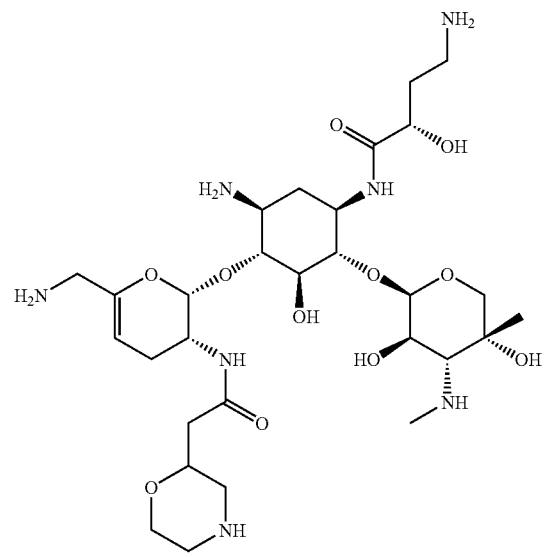 [SMILES: CN[C@@H]1[C@@H](O)[C@@H](O[C@@H]2[C@@H](O)[C@H](O[C@H]3OC(CN)=CC[C@H]3NC(=O)CC3CNCCO3)[C@@H](N)C[C@H]2NC(=O)[C@@H](O)CCN)OC[C@]1(C)O]

2'-(Morpholin-2-yl-acetyl)-1-(4-amino-2(S)-hydroxy-butyryl)-sisomicin

2'-(N-Boc-morpholin-2-yl-acetyl)-3,3''-diBoc-1-(N-Boc-4-amino-2(S)-hydroxy-butyryl)-sisomicin (0.073 mmol) was submitted to Procedure 3-Method B for Boc removal to yield a crude, which was purified by RP HPLC Method 1-Column A to yield 2'-(morpholin-2-yl-acetyl)-1-(4-amino-2(S)-hydroxy-butyryl)-sisomicin (0.0051 g, 0.0075 mmol, 10.3% yield): MS m/e [M+H]$^+$ calcd 676.4, found 676.2, [M+Na]$^+$ 698.4; CLND 96.2% purity.

Example 93

2'-(2-Amino-ethyl-sulfonamide)-1-(4-amino-2(S)-hydroxy-butyryl)-sisomicin

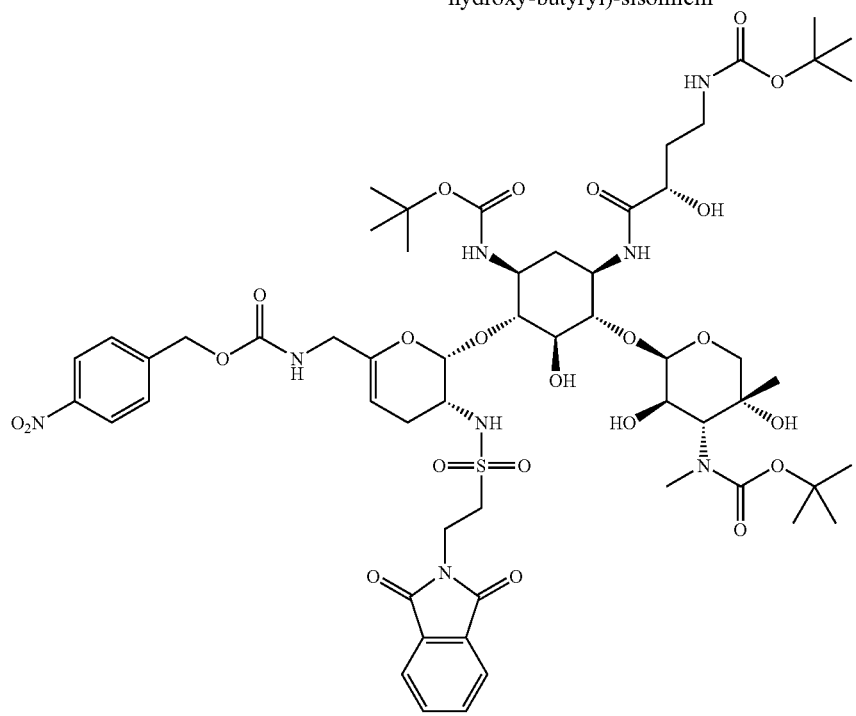

6'-PNZ-2'-(N-phthalimido-2-amino-ethylsulfonamide)-3,3"-diBoc-1-(N-Boc-4-amino-2(S)-hydroxy-butyryl)-sisomicin To a stirring solution of 6'-PNZ-3,3"-diBoc-1-(N-Boc-4-amino-2(S)-hydroxy-butyryl)-sisomicin (0.108 g, 0.105 mmol) in DMF (1 mL) at 0° C. was added DIPEA (0.054 mL, 0.31 mmol) followed by N-phthalimido-2-amino-ethanesulfonyl chloride (0.048 g, 0.175 mmol) and the reaction was allowed to warm to room temperature. The reaction was diluted with EtOAc (4 mL) and washed with $H_2O$ (3×4 mL). The combined organic layers were dried over $Na_2SO_4$, filtered and concentrated to yield 6'-PNZ-2'-(N-phthalimido-2-amino-ethylsulfonamide)-3,3"-diBoc-1-(N-Boc-4-amino-2(S)-hydroxy-butyryl)-sisomicin (MS m/e $[M+H]^+$ calcd 1265.5, found 1265.3, $[M+Na]^+$ 1287.2), which was carried through to the next step without further purification.

6'-PNZ-2'-(2-amino-ethylsulfonamide)-3,3"-diBoc-1-(N-Boc-4-amino-2(S)-hydroxy-butyryl)-sisomicin 6'-PNZ-2'-(N-Phthalimido-2-amino-ethylsulfonamide)-3,3"-diBoc-1-(N-Boc-4-amino-2(S)-hydroxy-butyryl)-sisomicin (0.105 mmol) was submitted to Procedure 6 for phthalimido removal to yield 6'-PNZ-2'-(2-amino-ethylsulfonamide)-3,3"-diBoc-1-(N-Boc-4-amino-2(S)-hydroxy-butyryl)-sisomicin (MS m/e $[M+H]^+$ calcd 1135.5, found 1134.9), which was carried through to the next step without further purification.

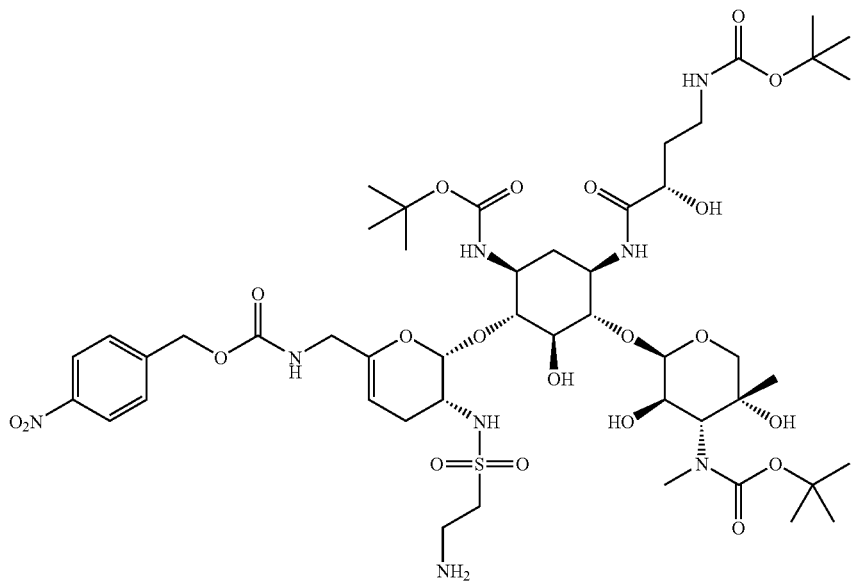 [SMILES: CN(C(=O)OC(C)(C)C)[C@@H]1[C@@H](O)[C@@H](O[C@@H]2[C@@H](O)[C@H](O[C@H]3OC(CNC(=O)OCc4ccc([N+](=O)[O-])cc4)=CC[C@H]3NS(=O)(=O)CCN)[C@@H](NC(=O)OC(C)(C)C)C[C@H]2NC(=O)[C@@H](O)CCNC(=O)OC(C)(C)C)OC[C@]1(C)O]

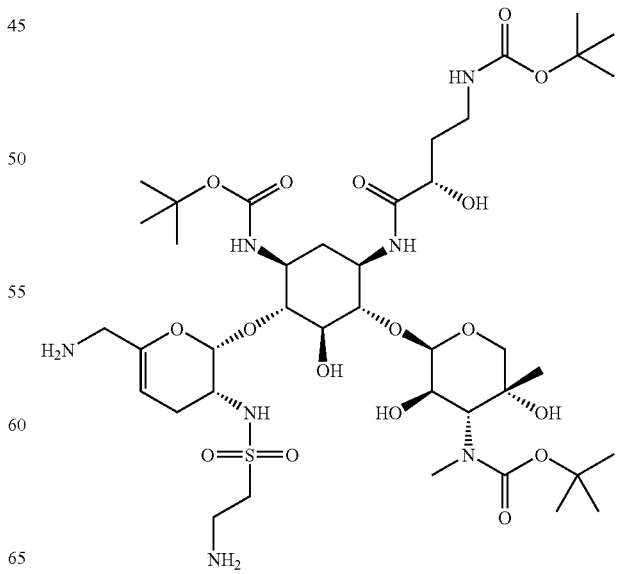

2'-(2-Amino-ethylsulfonamide)-3,3''-diBoc-1-(N-Boc-4-amino-2(S)-hydroxy-butyryl)-sisomicin 6'-PNZ-2'-(2-amino-ethylsulfonamide)-3,3''-diBoc-1-(N-Boc-4-amino-2(S)-hydroxy-butyryl)-sisomicin (0.105 mmol) was submitted to Procedure 2 for PNZ removal to yield 2'-(2-amino-ethylsulfonamide)-3,3''-diBoc-1-(N-Boc-4-amino-2(S)-hydroxy-butyryl)-sisomicin (MS m/e [M+H]$^+$ calcd 956.5, found 956.2, [M+Na]$^+$ 978.3), which was carried through to the next step without further purification.

2'-(2-Amino-ethylsulfonamide)-1-(4-amino-2(S)-hydroxy-butyryl)-sisomicin

2'-(2-Amino-ethylsulfonamide)-3,3''-diBoc-1-(N-Boc-4-amino-2(S)-hydroxy-butyryl)-sisomicin (0.105 mmol) was submitted to Procedure 3-Method B for Boc removal to yield a crude, which was purified by RP HPLC Method 1-Column A to yield 2'-(2-amino-ethylsulfonamide)-1-(4-amino-2(S)-hydroxy-butyryl)-sisomicin (0.016 g, 0.0244 mmol, 23.2% yield): MS m/e [M+H]$^+$ calcd 656.3, found 656.1, [M+Na]$^+$ 678.3; CLND 92.3% purity.

Example 94

2'-(N,N-Dimethyl-2,2-dimethyl-3-amino-propyl)-1-(4-amino-2(S)-hydroxy-butyryl)-sisomicin

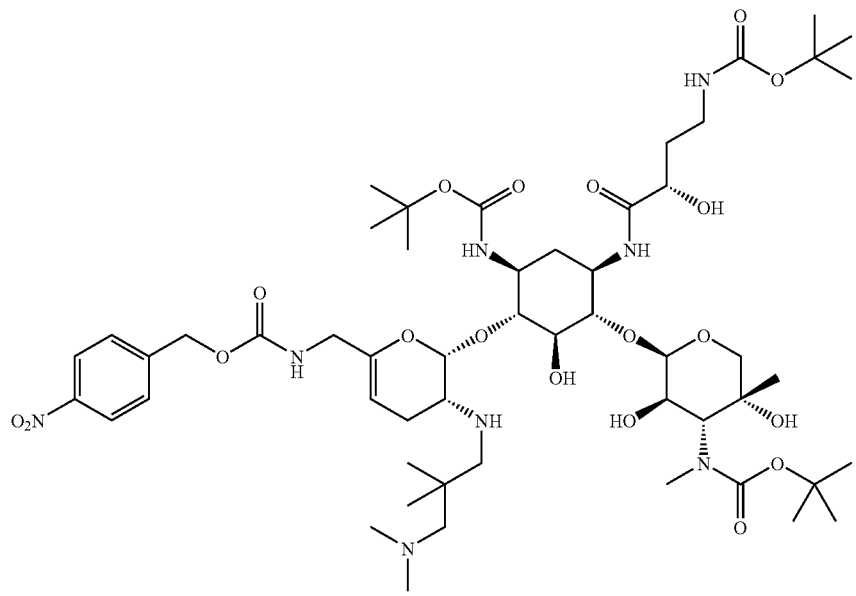

6'-PNZ-2'-(N,N-dimethyl-2,2-dimethyl-3-amino-propyl)-3,3''-diBoc-1-(N-Boc-4-amino-2(S)-hydroxy-butyryl)-sisomicin

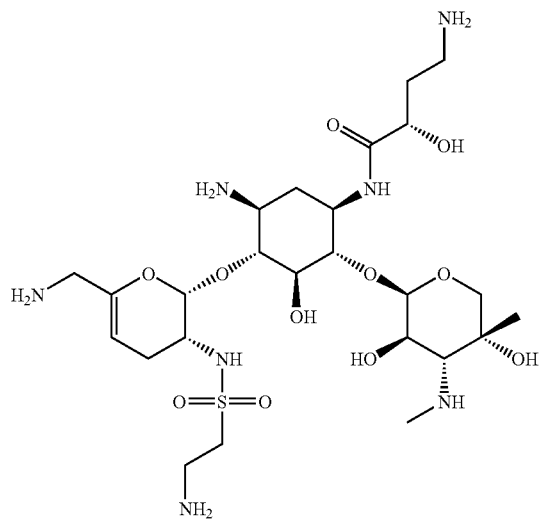 [SMILES: CN[C@@H]1[C@@H](O)[C@@H](O[C@@H]2[C@@H](O)[C@H](O[C@H]3OC(CN)=CC[C@H]3NS(=O)(=O)CCN)[C@@H](N)C[C@H]2NC(=O)[C@@H](O)CCN)OC[C@]1(C)O]

Treatment of 6'-PNZ-3,3''-diBoc-1-(N-Boc-4-amino-2(S)-hydroxy-butyryl)-sisomicin (0.200 g, 0.195 mmol) with N,N-dimethyl-2,2-dimethyl-3-amino-propionaldehyde (0.033 g, 0.25 mmol) following Procedure 1-Method A gave the desired 6'-PNZ-2'-(N,N-dimethyl-2,2-dimethyl-3-amino-propyl)-3,3''-diBoc-1-(N-Boc-4-amino-2(S)-hydroxy-butyryl)-sisomicin (MS m/e [M+H]$^+$ calcd 1141.6, found 1141.5), which was carried through to the next step without further purification.

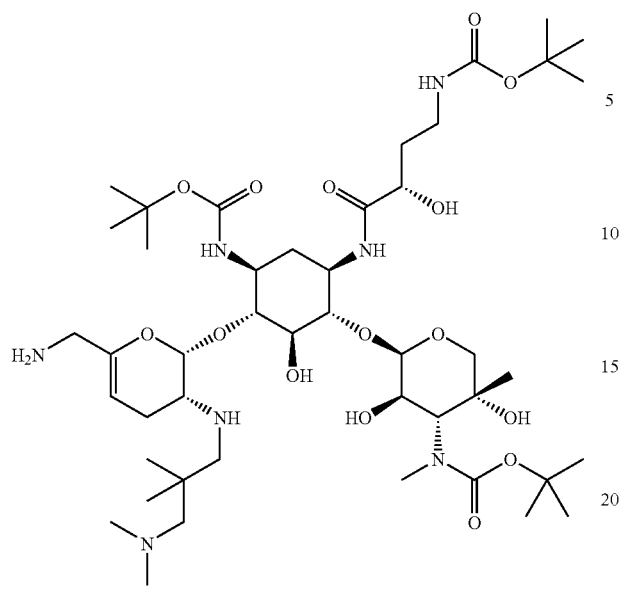

2'-(N,N-Dimethyl-2,2-dimethyl-3-amino-propyl)-3,3''-diBoc-1-(N-Boc-4-amino-2(S)-hydroxy-butyryl)-sisomicin 6'-PNZ-2'-(N,N-dimethyl-2,2-dimethyl-3-amino-propyl)-3,3''-diBoc-1-(N-Boc-4-amino-2(S)-hydroxy-butyryl)-sisomicin (0.195 mmol) was submitted to Procedure 2 for PNZ removal to yield 2'-(N,N-dimethyl-2,2-dimethyl-3-amino-propyl)-3,3''-diBoc-1-(N-Boc-4-amino-2(S)-hydroxy-butyryl)-sisomicin (MS m/e [M+H]$^+$ calcd 962.6, found 962.4, [M+Na]$^+$ 984.4), which was carried through to the next step without further purification.

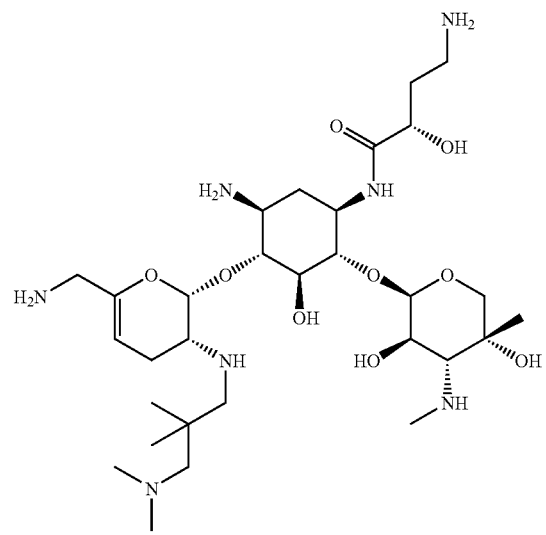 [SMILES: CN[C@@H]1[C@@H](O)[C@@H](O[C@@H]2[C@@H](O)[C@H](O[C@H]3OC(CN)=CC[C@H]3NCC(C)(C)CN(C)C)[C@@H](N)C[C@H]2NC(=O)[C@@H](O)CCN)OC[C@]1(C)O]

2'-(N,N-Dimethyl-2,2-dimethyl-3-amino-propyl)-1-(4-amino-2(S)-hydroxy-butyryl)-sisomicin 2'-(N,N-Dimethyl-2,2-dimethyl-3-amino-propyl)-3,3''-di-Boc-1-(N-Boc-4-amino-2(S)-hydroxy-butyryl)-sisomicin (0.195 mmol) was submitted to Procedure 3-Method B for Boc removal to yield a crude, which was purified by RP HPLC Method 1-Column A to yield 2'-(N,N-dimethyl-2,2-dimethyl-3-amino-propyl)-1-(4-amino-2(S)-hydroxy-butyryl)-sisomicin (0.00069 g, 0.001 mmol, 0.5% yield): MS m/e [M+H]$^+$ calcd 662.4, found 662.3, [M+Na]$^+$ 684.3; CLND 86.2% purity.

Example 95

2'-(2(S)-Amino-propyl)-1-(4-amino-2(S)-hydroxy-butyryl)-sisomicin

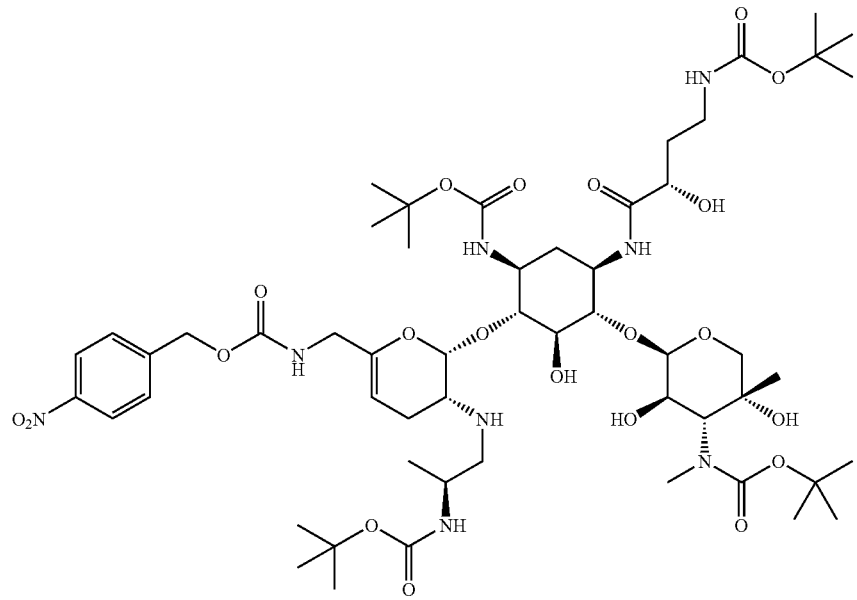 [SMILES: C[C@@H](CN[C@@H]1CC=C(CNC(=O)OCc2ccc([N+](=O)[O-])cc2)O[C@@H]1O[C@H]1[C@H](O)[C@@H](O[C@H]2OC[C@](C)(O)[C@H](N(C)C(=O)OC(C)(C)C)[C@H]2O)[C@H](NC(=O)[C@@H](O)CCNC(=O)OC(C)(C)C)C[C@@H]1NC(=O)OC(C)(C)C)NC(=O)OC(C)(C)C]

6'-PNZ-2'-(N-Boc-2(S)-amino-propyl)-3,3''-diBoc-1-(N-Boc-4-amino-2(S)-hydroxy-butyryl)-sisomicin Treatment of 6'-PNZ-3,3''-diBoc-1-(N-Boc-4-amino-2(S)-hydroxy-butyryl)-sisomicin (0.200 g, 0.195 mmol) with N-Boc-2(S)-amino-propanal following Procedure 1-Method A gave the desired 6'-PNZ-2'-(N-Boc-2(S)-amino-propyl)-3,3''-diBoc-1-(N-Boc-4-amino-2(S)-hydroxy-butyryl)-sisomicin, which was carried through to the next step without further purification.

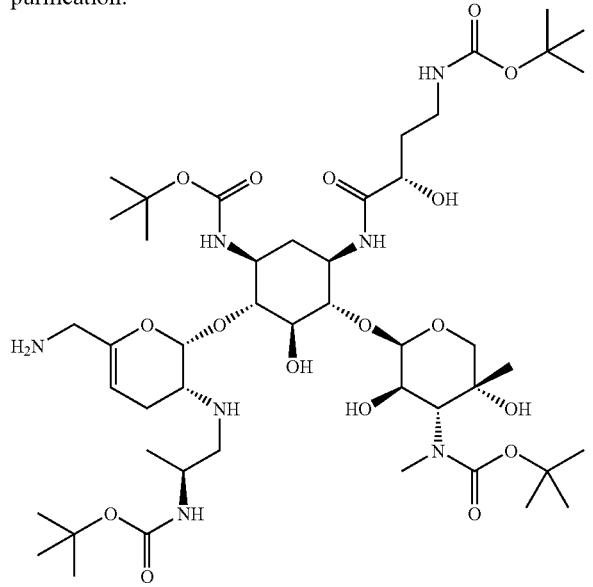 [SMILES: C[C@@H](CN[C@@H]1CC=C(CN)O[C@@H]1O[C@H]1[C@H](O)[C@@H](O[C@H]2OC[C@](C)(O)[C@H](N(C)C(=O)OC(C)(C)C)[C@H]2O)[C@H](NC(=O)[C@@H](O)CCNC(=O)OC(C)(C)C)C[C@@H]1NC(=O)OC(C)(C)C)NC(=O)OC(C)(C)C]

2'-(N-Boc-2(S)-amino-propyl)-3,3''-diBoc-1-(N-Boc-4-amino-2(S)-hydroxy-butyryl)-sisomicin 6'-PNZ-2'-(N-Boc-2(S)-amino-propyl)-3,3''-diBoc-1-(N-Boc-4-amino-2(S)-hydroxy-butyryl)-sisomicin (0.195 mol) was submitted to Procedure 2 for PNZ removal to yield 2'-(N-Boc-2(S)-amino-propyl)-3,3''-diBoc-1-(N-Boc-4-amino-2(S)-hydroxy-butyryl)-sisomicin (MS m/e [M+H]$^+$ calcd 1006.6, found 1007.1), which was carried through to the next step without further purification.

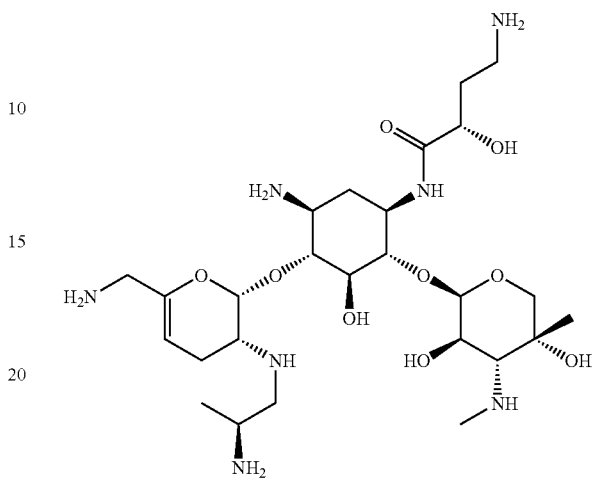

2'-(2(S)-Amino-propyl)-1-(4-amino-2(S)-hydroxy-butyryl)-sisomicin

2'-(N-Boc-2(S)-amino-propyl)-3,3''-diBoc-1-(N-Boc-4-amino-2(S)-hydroxy-butyryl)-sisomicin (0.195 mmol) was submitted to Procedure 3-Method B for Boc removal to yield a crude, which was purified by RP HPLC Method 1-Column A to yield 2'-(2(S)-amino-propyl)-1-(4-amino-2(S)-hydroxy-butyryl)-sisomicin (0.0035 g, 0.0058 mmol, 3.0% yield): MS m/e [M+H]$^+$ calcd 606.4, found 606.3; CLND 89.4% purity.

Example 96

2'-(Azetidin-3-yl)-1-(4-amino-2(S)-hydroxy-butyryl)-sisomicin

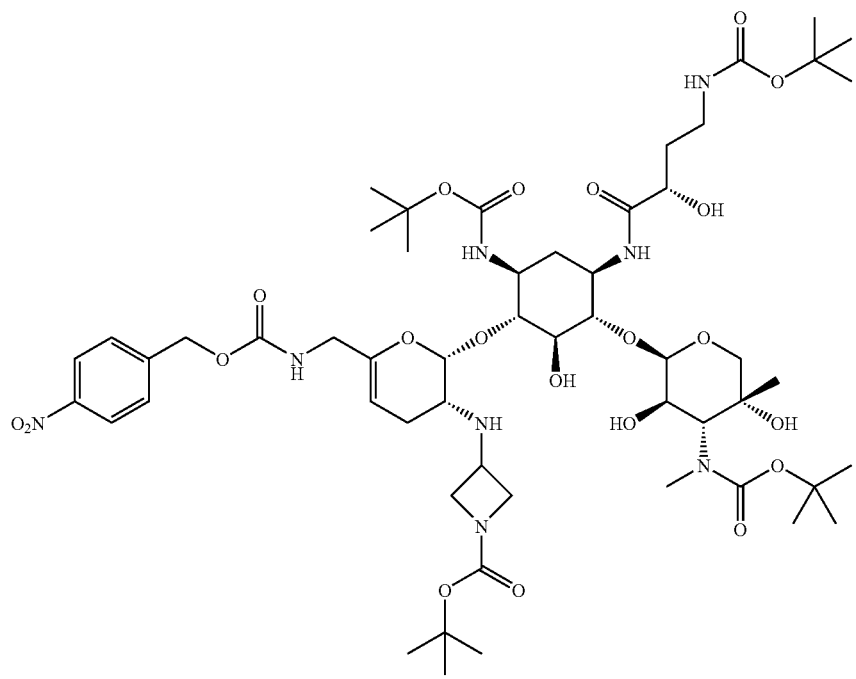 [SMILES: CN(C(=O)OC(C)(C)C)[C@@H]1[C@@H](O)[C@@H](O[C@@H]2[C@@H](O)[C@H](O[C@H]3OC(CNC(=O)OCc4ccc([N+](=O)[O-])cc4)=CC[C@H]3NC3CN(C(=O)OC(C)(C)C)C3)[C@@H](NC(=O)OC(C)(C)C)C[C@H]2NC(=O)[C@@H](O)CCNC(=O)OC(C)(C)C)OC[C@]1(C)O]

6'-PNZ-2'-(N-Boc-azetidin-3-yl)-3,3''-diBoc-1-(N-Boc-4-amino-2(S)-hydroxy-butyryl)-sisomicin Treatment of 6'-PNZ-3,3''-diBoc-1-(N-Boc-4-amino-2 (S)-hydroxy-butyryl)-sisomicin (0.200 g, 0.195 mmol) with N-Boc-3-azetidinone (0.043 g, 0.253 mmol) following Procedure 1-Method A gave the desired 6'-PNZ-2'-(N-Boc-azetidin-3-yl)-3,3''-diBoc-1-(N-Boc-4-amino-2(S)-hydroxy-butyryl)-sisomicin (MS m/e [M+H]$^+$ calcd 1183.6, found 1184.3), which was carried through to the next step without further purification.

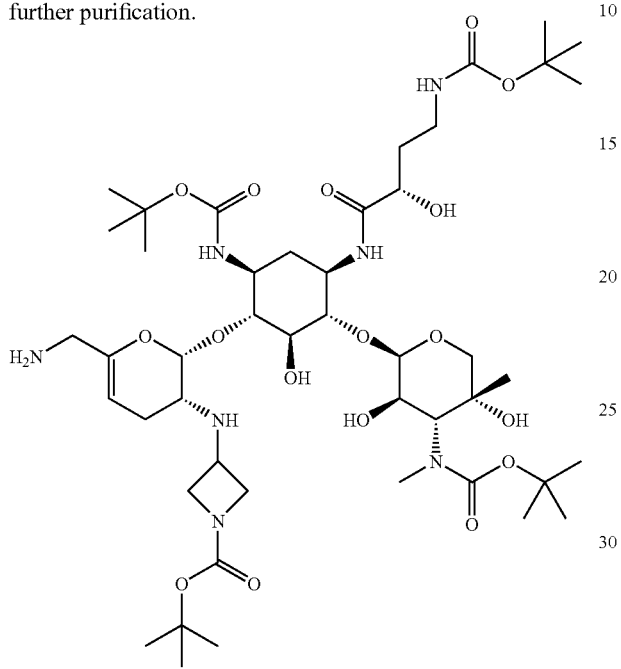

2'-(N-Boc-azetidin-3-yl)-3,3''-diBoc-1-(N-Boc-4-amino-2(S)-hydroxy-butyryl)-sisomicin 6'-PNZ-2'-(N-Boc-azetidin-3-yl)-3,3''-diBoc-1-(N-Boc-4-amino-2(S)-hydroxy-butyryl)-sisomicin (0.195 mmol) was submitted to Procedure 2 for PNZ removal to yield 2'-(N-Boc-azetidin-3-yl)-3,3''-diBoc-1-(N-Boc-4-amino-2(S)-hydroxy-butyryl)-sisomicin (MS m/e [M+H]$^+$ calcd 1004.6, found 1005.1), which was carried through to the next step without further purification.

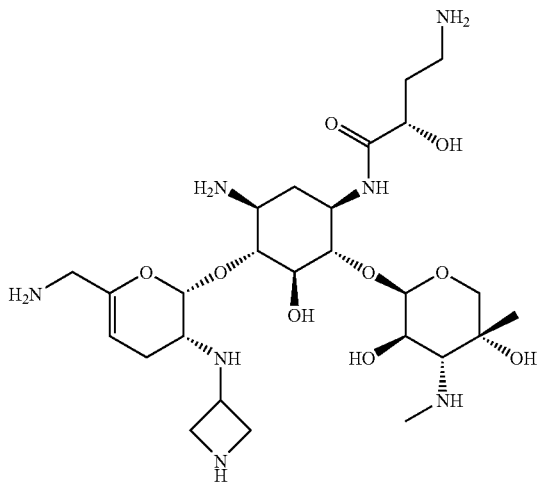 [SMILES: CN[C@@H]1[C@@H](O)[C@@H](O[C@@H]2[C@@H](O)[C@H](O[C@H]3OC(CN)=CC[C@H]3NC3CNC3)[C@@H](N)C[C@H]2NC(=O)[C@@H](O)CCN)OC[C@]1(C)O]

2'-(Azetidin-3-yl)-1-(4-amino-2(S)-hydroxy-butyryl)-sisomicin

2'-(N-Boc-azetidin-3-yl)-3,3''-diBoc-1-(N-Boc-4-amino-2(S)-hydroxy-butyryl)-sisomicin (0.195 mmol) was submitted to Procedure 3-Method B for Boc removal to yield a crude, which was purified by RP HPLC Method 1-Column A to yield 2'-(azetidin-3-yl)-1-(4-amino-2(S)-hydroxy-butyryl)-sisomicin (0.0144 g, 0.024 mmol, 12.3% yield): MS m/e [M+H]$^+$ calcd 604.4, found 604.2, [M+Na]$^+$ 626.3; CLND 99.2% purity.

Example 97

2'-(2-Amino-propanol)-1-(4-amino-2(S)-hydroxy-butyryl)-sisomicin

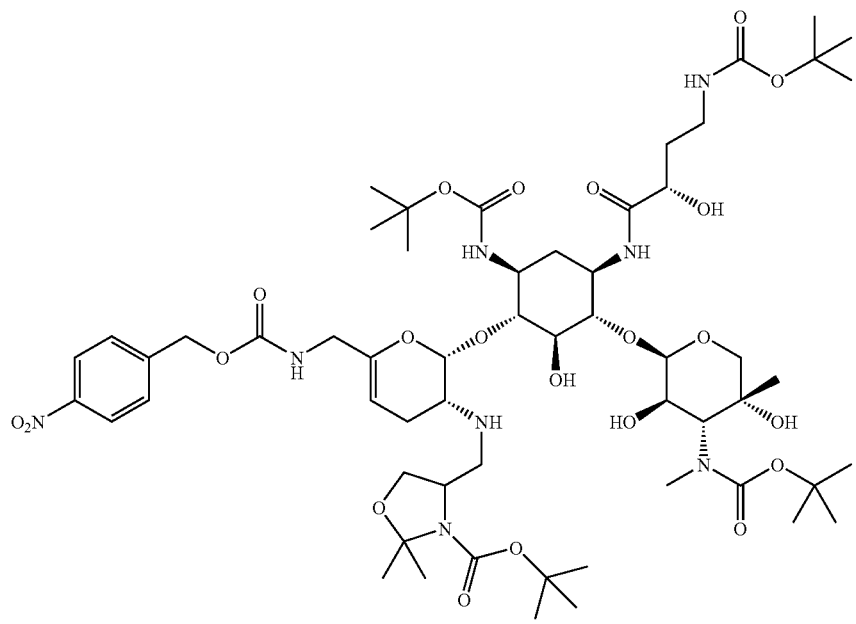 [SMILES: CN(C(=O)OC(C)(C)C)[C@@H]1[C@@H](O)[C@@H](O[C@@H]2[C@@H](O)[C@H](O[C@H]3OC(CNC(=O)OCc4ccc([N+](=O)[O-])cc4)=CC[C@H]3NCC3COC(C)(C)N3C(=O)OC(C)(C)C)[C@@H](NC(=O)OC(C)(C)C)C[C@H]2NC(=O)[C@@H](O)CCNC(=O)OC(C)(C)C)OC[C@]1(C)O]

6'-PNZ-2'-(Methyl-N-Boc-2,2-dimethyl-1,3-oxazolidin-4-yl)-3,3''-diBoc-1-(N-Boc-4-amino-2(S)-hydroxy-butyryl)-sisomicin Treatment of 6'-PNZ-3,3''-diBoc-1-(N-Boc-4-amino-2(S)-hydroxy-butyryl)-sisomicin (0.100 g, 0.097 mmol) with N-Boc-2,2-dimethyl-1,3-oxazolidine-4-carboxaldehyde (0.026 g, 0.12 mmol) following Procedure 1-Method A gave the desired 6'-PNZ-2'-(methyl-N-Boc-2,2-dimethyl-1,3-oxazolidin-4-yl)-3,3''-diBoc-1-(N-Boc-4-amino-2(S)-hydroxy-butyryl)-sisomicin (MS m/e [M+H]$^+$ calcd 1241.6, found 1242.1), which was carried through to the next step without further purification.

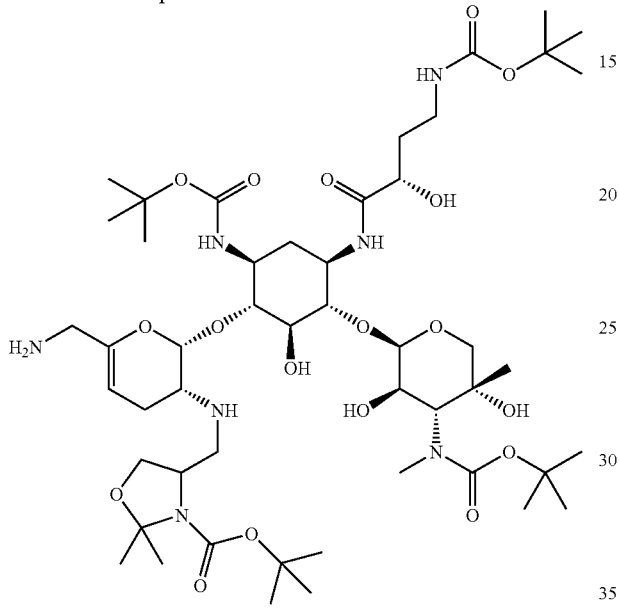

2'-(Methyl-N-Boc-2,2-dimethyl-1,3-oxazolidin-4-yl)-3,3''-diBoc-1-(N-Boc-4-amino-2(S)-hydroxy-butyryl)-sisomicin 6'-PNZ-2'-(methyl-N-Boc-2,2-dimethyl-1,3-oxazolidin-4-yl)-3,3''-diBoc-1-(N-Boc-4-amino-2(S)-hydroxy-butyryl)-sisomicin (0.097 mmol) was submitted to Procedure 2 for PNZ removal to yield 2'-(methyl-N-Boc-2,2-dimethyl-1,3-oxazolidin-4-yl)-3,3''-diBoc-1-(N-Boc-4-amino-2(S)-hydroxy-butyryl)-sisomicin (MS m/e [M+H]$^+$ calcd 1062.6, found 1063.3), which was carried through to the next step without further purification.

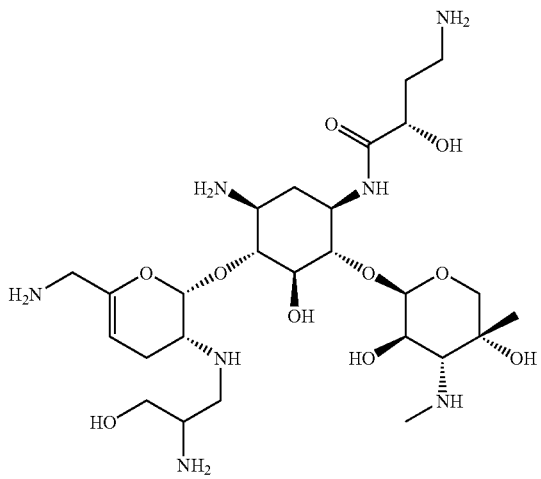 [SMILES: CN[C@@H]1[C@@H](O)[C@@H](O[C@@H]2[C@@H](O)[C@H](O[C@H]3OC(CN)=CC[C@H]3NCC(N)CO)[C@@H](N)C[C@H]2NC(=O)[C@@H](O)CCN)OC[C@]1(C)O]

2'-(2-Amino-propanol)-1-(4-amino-2(S)-hydroxy-butyryl)-sisomicin

2'-(Methyl-N-Boc-2,2-dimethyl-1,3-oxazolidin-4-yl)-3,3''-diBoc-1-(N-Boc-4-amino-2(S)-hydroxy-butyryl)-sisomicin (0.097 mmol) was submitted to Procedure 3-Method B for Boc removal to yield a crude, which was purified by RP HPLC Method 1-Column A to yield 2'-(2-amino-propanol)-1-(4-amino-2(S)-hydroxy-butyryl)-sisomicin (0.0042 g, 0.0067 mmol, 6.9% yield): MS m/e [M+H]$^+$ calcd 622.4, found 622.3, [M+Na]$^+$ 644.4; CLND 93.9% purity.

Example 98

2'-(2-Hydroxy-ethyl)-1-(4-amino-2(S)-hydroxy-butyryl)-sisomicin

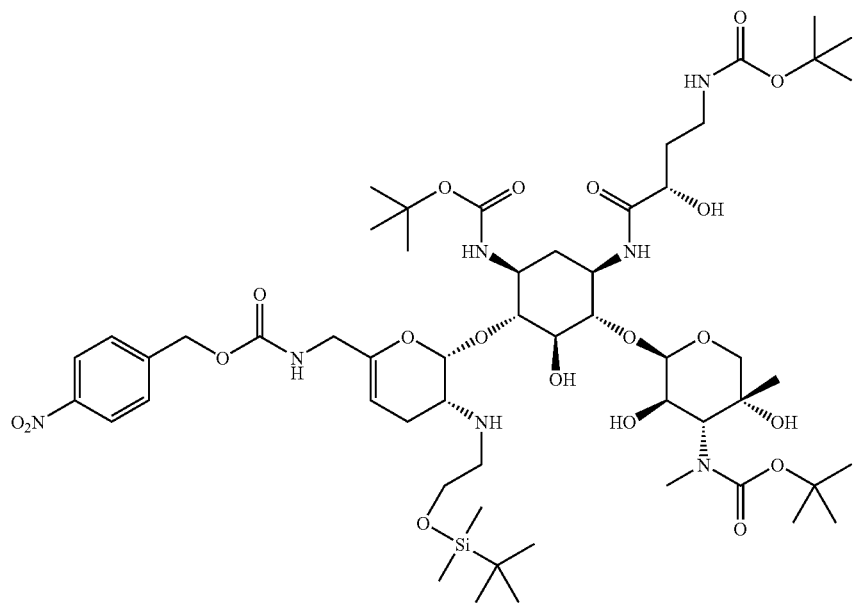 [SMILES: CN(C(=O)OC(C)(C)C)[C@@H]1[C@@H](O)[C@@H](O[C@@H]2[C@@H](O)[C@H](O[C@H]3OC(CNC(=O)OCc4ccc([N+](=O)[O-])cc4)=CC[C@H]3NCCO[Si](C)(C)C(C)(C)C)[C@@H](NC(=O)OC(C)(C)C)C[C@H]2NC(=O)[C@@H](O)CCNC(=O)OC(C)(C)C)OC[C@]1(C)O]

6'-PNZ-2'-(2-tert-butyldimethylsilyloxy-ethyl)-3,3''-diBoc-1-(N-Boc-4-amino-2(S)-hydroxy-butyryl)-sisomicin Treatment of 6'-PNZ-3,3''-diBoc-1-(N-Boc-4-amino-2(S)-hydroxy-butyryl)-sisomicin (0.075 g, 0.073 mmol) with tert-butyldimethylsilyloxy acetaldehyde following Procedure 1-Method A gave the desired 6'-PNZ-2'-(2-tert-butyldimethylsilyloxy-ethyl)-3,3''-diBoc-1-(N-Boc-4-amino-2(S)-hydroxy-butyryl)-sisomicin (MS m/e [M+H]+ calcd 1186.6, found 1187.1), which was carried through to the next step without further purification.

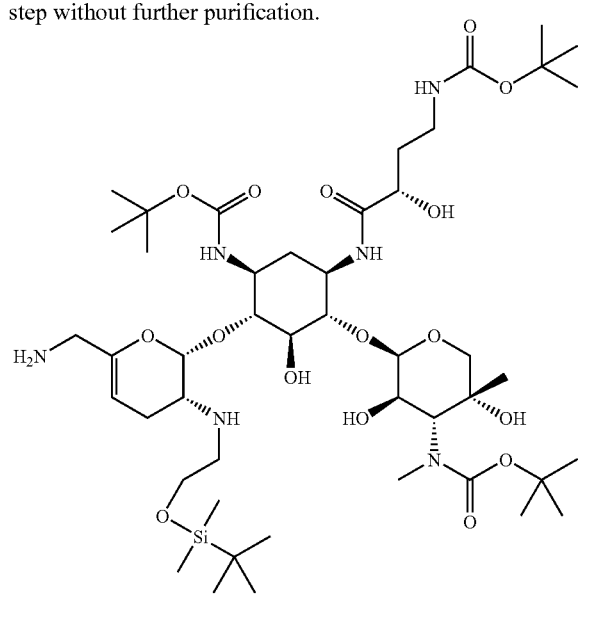

2'-(2-tert-Butyldimethylsilyloxy-ethyl)-3,3''-diBoc-1-(N-Boc-4-amino-2(S)-hydroxy-butyryl)-sisomicin 6'-PNZ-2'-(2-tert-butyldimethylsilyloxy-ethyl)-3,3''-diBoc-1-(N-Boc-4-amino-2(S)-hydroxy-butyryl)-sisomicin (0.073 mmol) was submitted to Procedure 2 for PNZ removal to yield 2'-(2-tert-butyldimethylsilyloxy-ethyl)-3,3''-diBoc-1-(N-Boc-4-amino-2(S)-hydroxy-butyryl)-sisomicin, which was carried through to the next step without further purification.

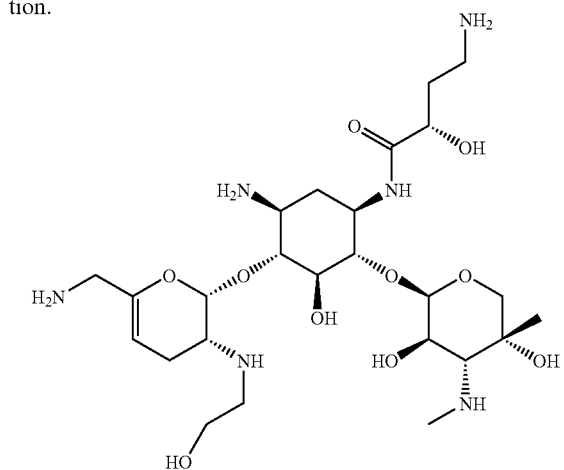

2'-(2-Hydroxy-ethyl)-1-(4-amino-2(S)-hydroxy-butyryl)-sisomicin

2'-(2-tert-Butyldimethylsilyloxy-ethyl)-3,3''-diBoc-1-(N-Boc-4-amino-2(S)-hydroxy-butyryl)-sisomicin (0.073 mmol) was submitted to Procedure 3-Method A for Boc removal to yield a crude, which was purified by Method 3 to yield 2'-(2-hydroxy-ethyl)-1-(4-amino-2(S)-hydroxy-butyryl)-sisomicin (0.0107 g, 0.018 mmol, 24.6% yield): MS m/e [M+H]+ calcd 593.3, found 593.8; CLND 95.9% purity.

Example 99

2'-(2,5-Diamino-pentoyl)-1-(4-amino-2(S)-hydroxy-butyryl)-sisomicin

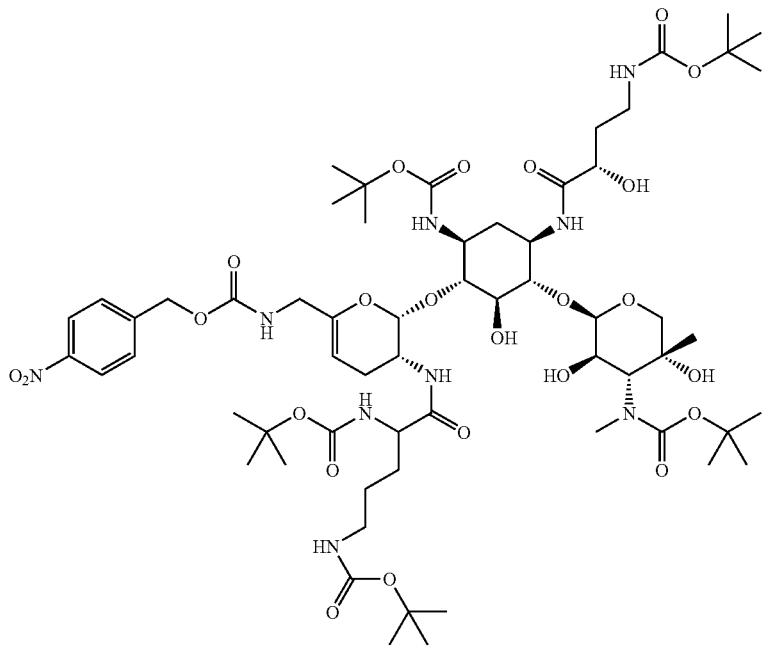 [SMILES: CN(C(=O)OC(C)(C)C)[C@@H]1[C@@H](O)[C@@H](O[C@@H]2[C@@H](O)[C@H](O[C@H]3OC(CNC(=O)OCc4ccc([N+](=O)[O-])cc4)=CC[C@H]3NC(=O)C(CCCNC(=O)OC(C)(C)C)NC(=O)OC(C)(C)C)[C@@H](NC(=O)OC(C)(C)C)C[C@H]2NC(=O)[C@@H](O)CCNC(=O)OC(C)(C)C)OC[C@]1(C)O]

6'-PNZ-2'-(N-Boc, N-Boc-2,5-diamino-pentoyl)-3,3"-diBoc-1-(N-Boc-4-amino-2(S)-hydroxy-butyryl)-sisomicin Treatment of 6'-PNZ-3,3"-diBoc-1-(N-Boc-4-amino-2(S)-hydroxy-butyryl)-sisomicin (0.075 g, 0.073 mmol) with Boc-DL-ORN(Boc)-OH following Procedure 4-Method B gave the desired 6'-PNZ-2'-(N-Boc, N-Boc-2,5-diamino-pentoyl)-3,3"-diBoc-1-(N-Boc-4-amino-2(S)-hydroxy-butyryl)-sisomicin (MS m/e [M+H]$^+$ calcd 1342.7, found 1342.7), which was carried through to the next step without further purification.

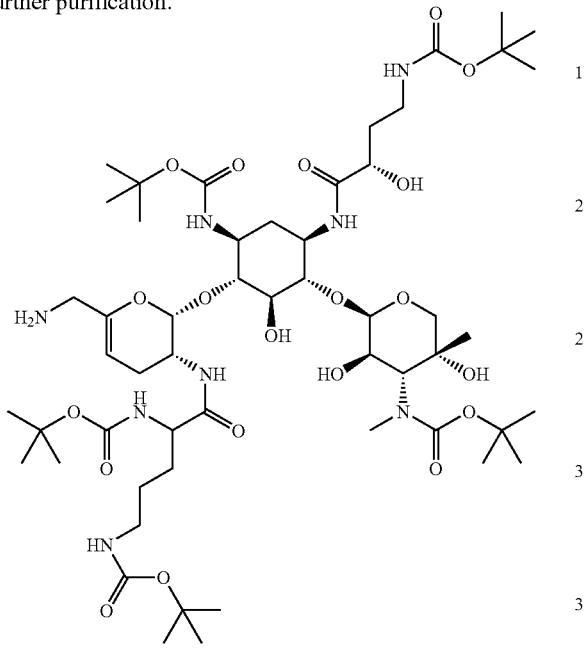

2'-(N-Boc, N-Boc-2,5-diamino-pentoyl)-3,3"-diBoc-1-(N-Boc-4-amino-2(S)-hydroxy-butyryl)-sisomicin 6'-PNZ-2'-(N-Boc, N-Boc-2,5-diamino-pentoyl)-3,3"-diBoc-1-(N-Boc-4-amino-2(S)-hydroxy-butyryl)-sisomicin (0.073 mmol) was submitted to Procedure 2 for PNZ removal to yield 2'-(N-Boc, N-Boc-2,5-diamino-pentoyl)-3,3"-diBoc-1-(N-Boc-4-amino-2(S)-hydroxy-butyryl)-sisomicin, which was carried through to the next step without further purification.

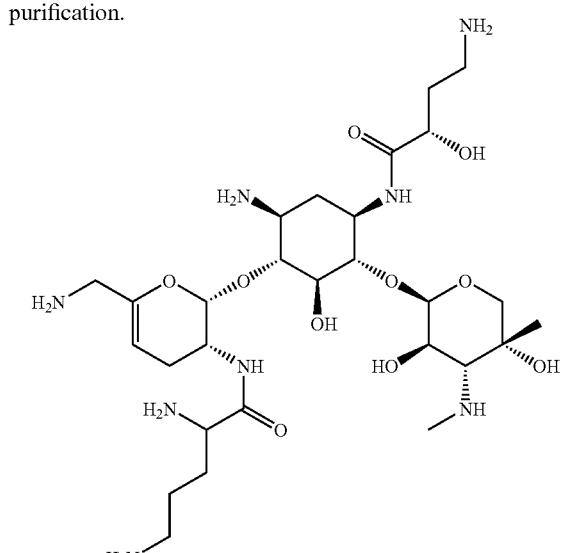

2'-(2,5-Diamino-pentoyl)-1-(4-amino-2(S)-hydroxy-butyryl)-sisomicin

2'-(N-Boc, N-Boc-2,5-diamino-pentoyl)-3,3"-diBoc-1-(N-Boc-4-amino-2(S)-hydroxy-butyryl)-sisomicin (0.073 mmol) was submitted to Procedure 3-Method A for Boc removal to yield a crude, which was purified by Method 3 to yield 2'-(2,5-diamino-pentoyl)-1-(4-amino-2(S)-hydroxy-butyryl)-sisomicin (0.0075 g, 0.0113 mmol, 15.5% yield): MS m/e [M+H]$^+$ calcd 663.4, found 663.4; CLND 94.8% purity.

Example 100

2'-(2-Hydroxy-propanol)-1-(4-amino-2(S)-hydroxy-butyryl)-sisomicin

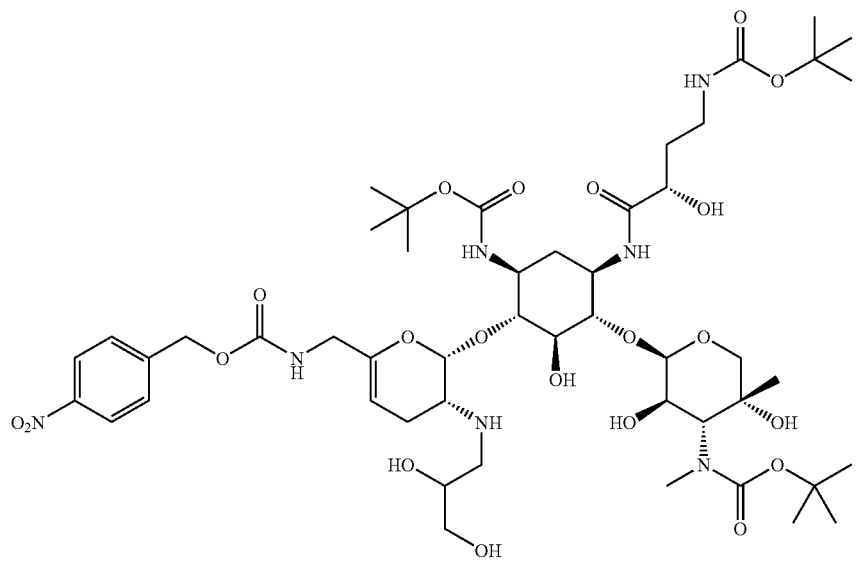 [SMILES: CN(C(=O)OC(C)(C)C)[C@@H]1[C@@H](O)[C@@H](O[C@@H]2[C@@H](O)[C@H](O[C@H]3OC(CNC(=O)OCc4ccc([N+](=O)[O-])cc4)=CC[C@H]3NCC(O)CO)[C@@H](NC(=O)OC(C)(C)C)C[C@H]2NC(=O)[C@@H](O)CCNC(=O)OC(C)(C)C)OC[C@]1(C)O]

6'-PNZ-2'-(2-hydroxy-propanol)-3,3''-diBoc-1-(N-Boc-4-amino-2(S)-hydroxy-butyryl)-sisomicin Treatment of 6'-PNZ-3,3''-diBoc-1-(N-Boc-4-amino-2(S)-hydroxy-butyryl)-sisomicin (0.075 g, 0.073 mmol) with DL-glyceraldehyde dimer following Procedure 1-Method A gave the desired 6'-PNZ-2'-(2-hydroxy-propanol)-3,3''-diBoc-1-(N-Boc-4-amino-2(S)-hydroxy-butyryl)-sisomicin (MS m/e [M+H]$^+$ calcd 1102.5, found 1103.2), which was carried through to the next step without further purification.

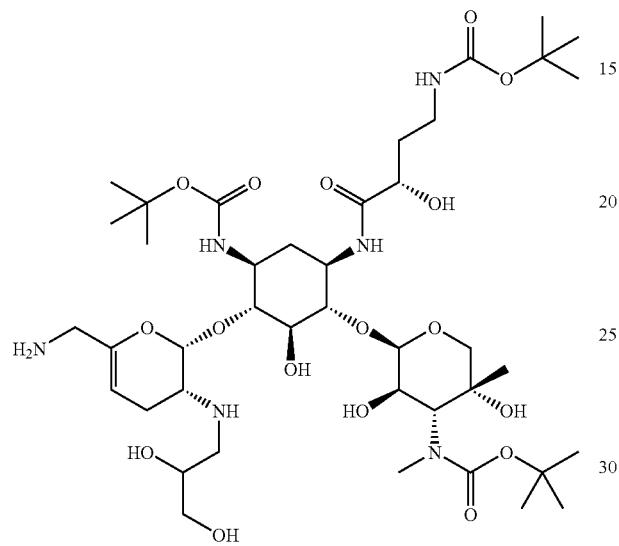

2'-(2-Hydroxy-propanol)-3,3''-diBoc-1-(N-Boc-4-amino-2(S)-hydroxy-butyryl)-sisomicin 6'-PNZ-2'-(2-hydroxy-propanol)-3,3''-diBoc-1-(N-Boc-4-amino-2(S)-hydroxy-butyryl)-sisomicin (0.073 mmol) was submitted to Procedure 2 for PNZ removal to yield 2'-(2-hydroxy-propanol)-3,3''-diBoc-1-(N-Boc-4-amino-2(S)-hydroxy-butyryl)-sisomicin, which was carried through to the next step without further purification.

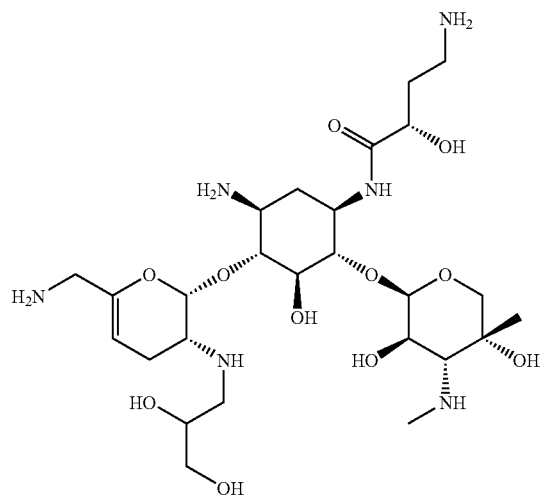 [SMILES: CN[C@@H]1[C@@H](O)[C@@H](O[C@@H]2[C@@H](O)[C@H](O[C@H]3OC(CN)=CC[C@H]3NCC(O)CO)[C@@H](N)C[C@H]2NC(=O)[C@@H](O)CCN)OC[C@]1(C)O]

2'-(2-Hydroxy-propanol)-1-(4-amino-2(S)-hydroxy-butyryl)-sisomicin

2'-(2-Hydroxy-propanol)-3,3''-diBoc-1-(N-Boc-4-amino-2(S)-hydroxy-butyryl)-sisomicin (0.073 mmol) was submitted to Procedure 3-Method A for Boc removal to yield a crude, which was purified by Method 3 to yield 2'-(2-hydroxy-propanol)-1-(4-amino-2(S)-hydroxy-butyryl)-sisomicin (0.0008 g, 0.00128 mmol, 1.75% yield): MS m/e [M+H]$^+$ calcd 623.3, found 623.8; CLND 94.7% purity.

Example 101

2'-(2-Hydroxy-3-amino-propyl)-1-(4-amino-2(S)-hydroxy-butyryl)-sisomicin

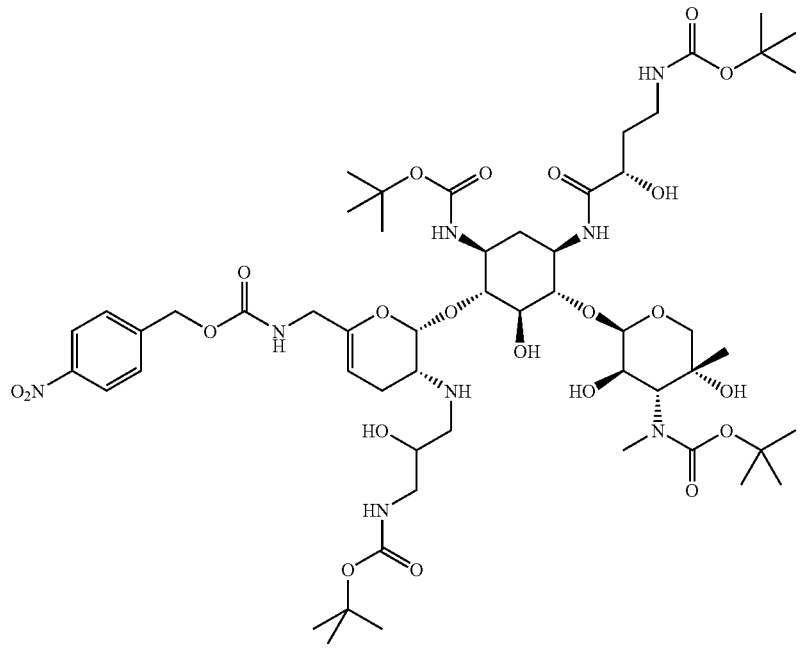 [SMILES: CN(C(=O)OC(C)(C)C)[C@@H]1[C@@H](O)[C@@H](O[C@@H]2[C@@H](O)[C@H](O[C@H]3OC(CNC(=O)OCc4ccc([N+](=O)[O-])cc4)=CC[C@H]3NCC(O)CNC(=O)OC(C)(C)C)[C@@H](NC(=O)OC(C)(C)C)C[C@H]2NC(=O)[C@@H](O)CCNC(=O)OC(C)(C)C)OC[C@]1(C)O]

6'-PNZ-2'-(2-hydroxy-N-Boc-3-amino-propyl)-3,3"-diBoc-1-(N-Boc-4-amino-2(S)-hydroxy-butyryl)-sisomicin Treatment of 6'-PNZ-3,3"-diBoc-1-(N-Boc-4-amino-2(S)-hydroxy-butyryl)-sisomicin (0.075 g, 0.073 mmol) with N-tert-butyl-(2-oxiranyl-methyl) carbamate following Procedure 5 gave the desired 6'-PNZ-2'-(2-hydroxy-N-Boc-3-amino-propyl)-3,3"-diBoc-1-(N-Boc-4-amino-2(S)-hydroxy-butyryl)-sisomicin (MS m/e [M+H]$^+$ calcd 1201.6, found 1201.6), which was carried through to the next step without further purification.

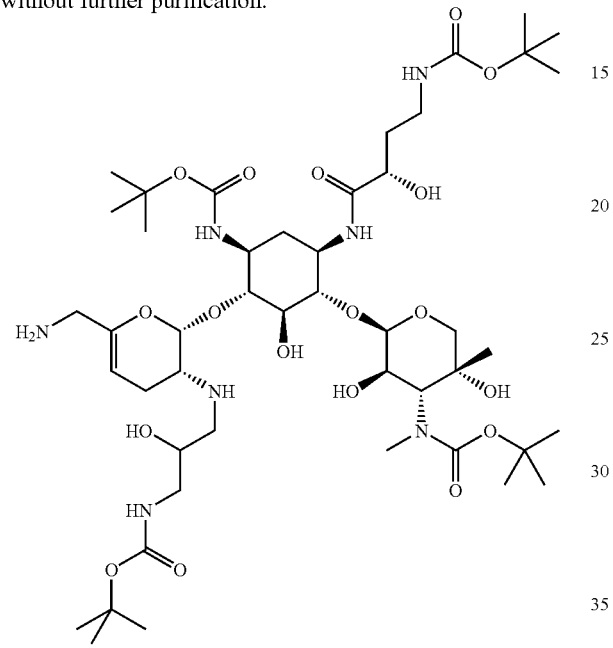

2'-(2-Hydroxy-N-Boc-3-amino-propyl)-3,3"-diBoc-1-(N-Boc-4-amino-2(S)-hydroxy-butyryl)-sisomicin

6'-PNZ-2'-(2-hydroxy-N-Boc-3-amino-propyl)-3,3"-diBoc-1-(N-Boc-4-amino-2(S)-hydroxy-butyryl)-sisomicin (0.073 mmol) was submitted to Procedure 2 for PNZ removal to yield 2'-(2-hydroxy-N-Boc-3-amino-propyl)-3,3"-diBoc-1-(N-Boc-4-amino-2(S)-hydroxy-butyryl)-sisomicin (MS m/e [M+H]$^+$ calcd 1022.6, found 1023.1), which was carried through to the next step without further purification.

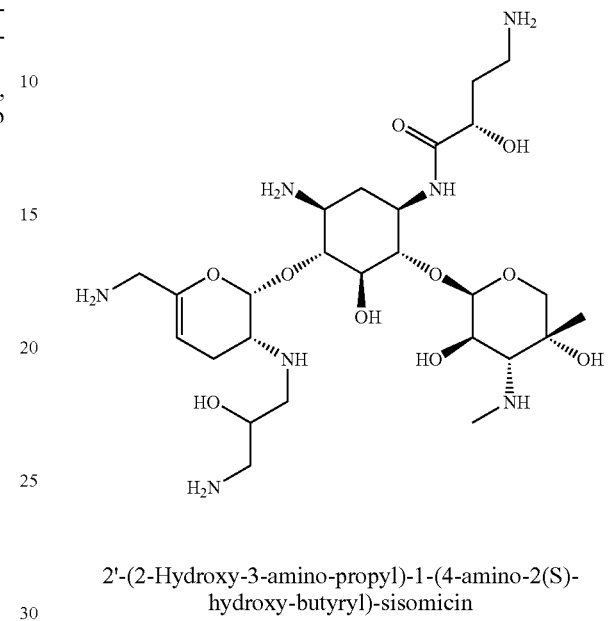

2'-(2-Hydroxy-3-amino-propyl)-1-(4-amino-2(S)-hydroxy-butyryl)-sisomicin

2'-(2-Hydroxy-N-Boc-3-amino-propyl)-3,3"-diBoc-1-(N-Boc-4-amino-2(S)-hydroxy-butyryl)-sisomicin (0.073 mmol) was submitted to Procedure 3-Method A for Boc removal to yield a crude, which was purified by Method 3 to yield 2'-(2-hydroxy-3-amino-propyl)-1-(4-amino-2(S)-hydroxy-butyryl)-sisomicin (0.0112 g, 0.018 mmol, 24.6% yield): MS m/e [M+H]$^+$ calcd 622.4, found 622.6; CLND 88.3% purity.

Example 102

2'-(4-Amino-butyl)-1-(4-amino-2(S)-hydroxy-butyryl)-sisomicin

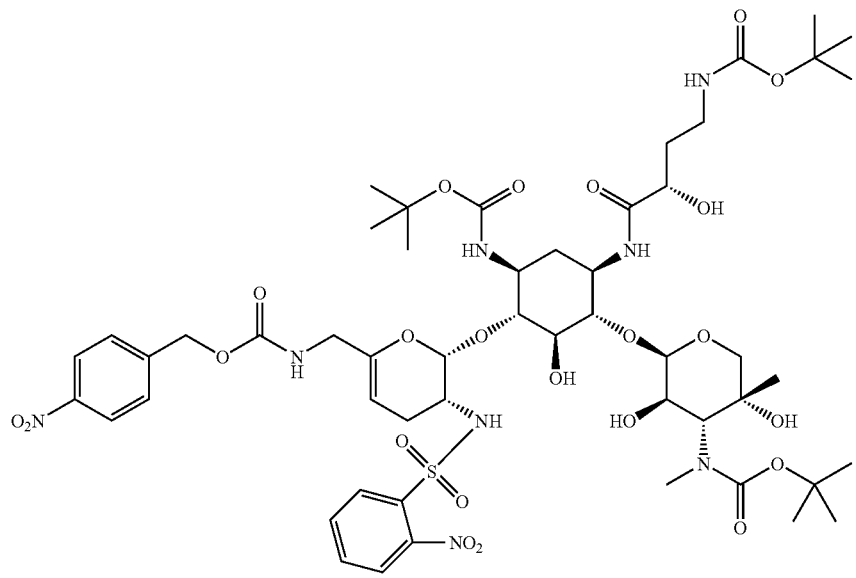 [SMILES: CN(C(=O)OC(C)(C)C)[C@@H]1[C@@H](O)[C@@H](O[C@@H]2[C@@H](O)[C@H](O[C@H]3OC(CNC(=O)OCc4ccc([N+](=O)[O-])cc4)=CC[C@H]3NS(=O)(=O)c3ccccc3[N+](=O)[O-])[C@@H](NC(=O)OC(C)(C)C)C[C@H]2NC(=O)[C@@H](O)CCNC(=O)OC(C)(C)C)OC[C@]1(C)O]

6'-PNZ-2'-nosyl-3,3''-diBoc-1-(N-Boc-4-amino-2
(S)-hydroxy-butyryl)-sisomicin

Treatment of 6'-PNZ-3,3''-diBoc-1-(N-Boc-4-amino-2
(S)-hydroxy-butyryl)-sisomicin (0.075 g, 0.073 mmol) with
2-nitrobenzenesulfonyl chloride following Procedure 8 gave
the desired 6'-PNZ-2'-nosyl-3,3''-diBoc-1-(N-Boc-4-amino-
2(S)-hydroxy-butyryl)-sisomicin, which was carried through
to the next step without further purification.

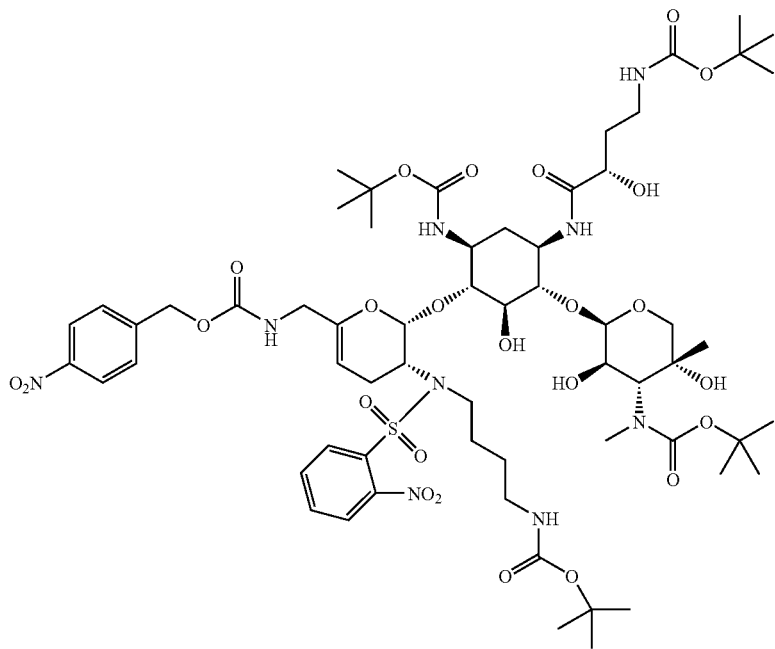 [SMILES: CN(C(=O)OC(C)(C)C)[C@@H]1[C@@H](O)[C@@H](O[C@@H]2[C@@H](O)[C@H](O[C@H]3OC(CNC(=O)OCc4ccc([N+](=O)[O-])cc4)=CC[C@H]3N(CCCCNC(=O)OC(C)(C)C)S(=O)(=O)c3ccccc3[N+](=O)[O-])[C@@H](NC(=O)OC(C)(C)C)C[C@H]2NC(=O)[C@@H](O)CCNC(=O)OC(C)(C)C)OC[C@]1(C)O]

6'-PNZ-2'-nosyl-2'-(N-Boc-4-amino-butyl)-3,3''-
diBoc-1-(N-Boc-4-amino-2(S)-hydroxy-butyryl)-
sisomicin 6'-PNZ-2'-nosyl-3,3''-diBoc-1-(N-Boc-4-amino-2(S)-hy-
droxy-butyryl)-sisomicin (0.073 mmol) was treated with
N-Boc-4-amino-1-butanol following Procedure 17 to yield
the desired 6'-PNZ-2'-nosyl-2'-(N-Boc-4-amino-butyl)-3,3''-
diBoc-1-(N-Boc-4-amino-2(S)-hydroxy-butyryl)-sisomicin
(MS m/e [M+H]$^+$ calcd 1384.6, found 1384.2), which was
carried through to the next step without further purification.

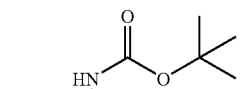
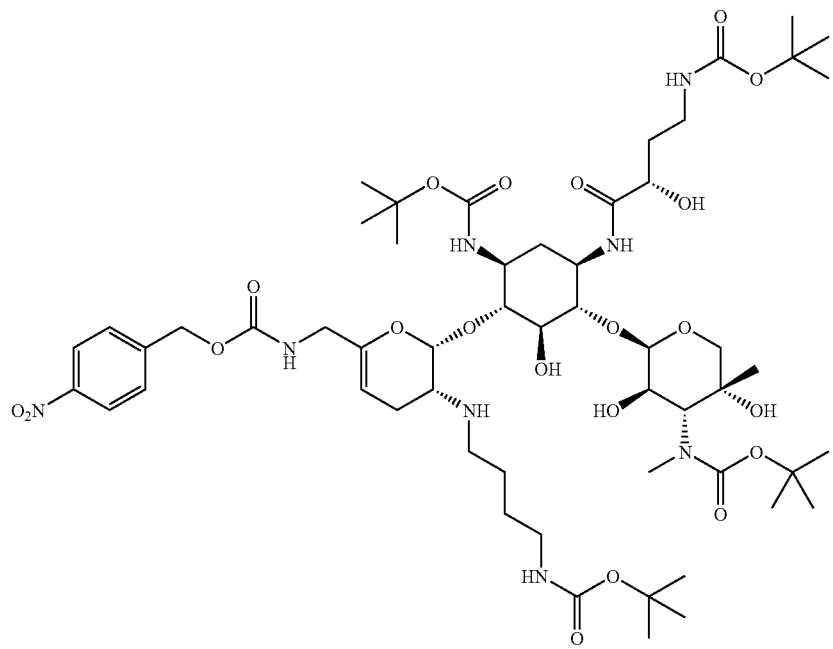 [SMILES: CN(C(=O)OC(C)(C)C)[C@@H]1[C@@H](O)[C@@H](O[C@@H]2[C@@H](O)[C@H](O[C@H]3OC(CNC(=O)OCc4ccc([N+](=O)[O-])cc4)=CC[C@H]3NCCCCNC(=O)OC(C)(C)C)[C@@H](NC(=O)OC(C)(C)C)C[C@H]2NC(=O)[C@@H](O)CCNC(=O)OC(C)(C)C)OC[C@]1(C)O]

6'-PNZ-2'-(N-Boc-4-amino-butyl)-3,3''-diBoc-1-(N-Boc-4-amino-2(S)-hydroxy-butyryl)-sisomicin 6'-PNZ-2'-nosyl-2'-(N-Boc-4-amino-butyl)-3,3''-diBoc-1-(N-Boc-4-amino-2(S)-hydroxy-butyryl)-sisomicin (0.073 mmol) was submitted to Procedure 9 for nosyl deprotection to yield the desired 6'-PNZ-2'-(N-Boc-4-amino-butyl)-3,3''-diBoc-1-(N-Boc-4-amino-2(S)-hydroxy-butyryl)-sisomicin (MS m/e [M+H]+ calcd 1199.6, found 1200.1), which was carried through to the next step without further purification.

2'-(N-Boc-4-amino-butyl)-3,3''-diBoc-1-(N-Boc-4-amino-2(S)-hydroxy-butyryl)-sisomicin 6'-PNZ-2'-(N-Boc-4-amino-butyl)-3,3''-diBoc-1-(N-Boc-4-amino-2(S)-hydroxy-butyryl)-sisomicin (0.073 mmol) was submitted to Procedure 2 for PNZ removal to yield the desired 2'-(N-Boc-4-amino-butyl)-3,3''-diBoc-1-(N-Boc-4-amino-2(S)-hydroxy-butyryl)-sisomicin, which was carried through to the next step without further purification.

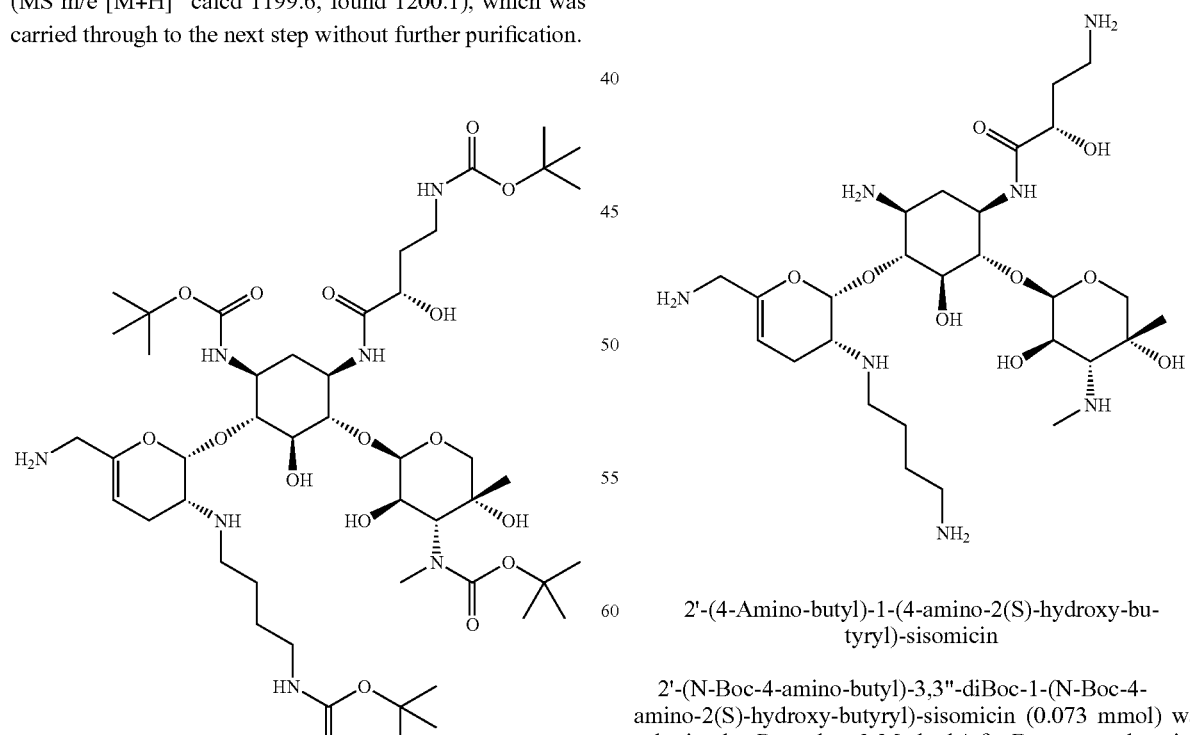

2'-(4-Amino-butyl)-1-(4-amino-2(S)-hydroxy-butyryl)-sisomicin

2'-(N-Boc-4-amino-butyl)-3,3''-diBoc-1-(N-Boc-4-amino-2(S)-hydroxy-butyryl)-sisomicin (0.073 mmol) was submitted to Procedure 3-Method A for Boc removal to yield a crude, which was purified by Method 3 to yield 2'-(4-amino-butyl)-1-(4-amino-2(S)-hydroxy-butyryl)-sisomicin (0.00065 g, 0.001 mmol, 1.37% yield): MS m/e [M+H]+ calcd 620.4, found 620.8; CLND 85.6% purity.

Example 103

2'-Guanidinium-1-(4-amino-2(S)-hydroxy-butyryl)-sisomicin

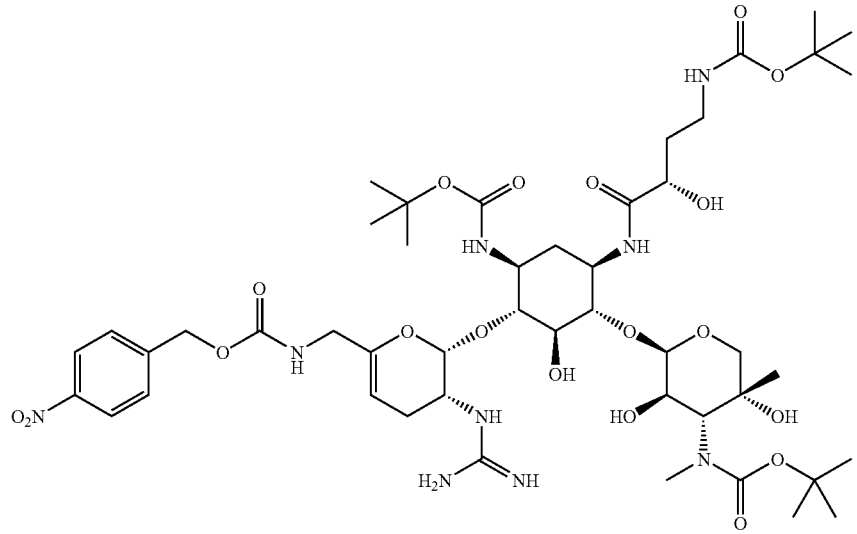 [SMILES: CN(C(=O)OC(C)(C)C)[C@@H]1[C@@H](O)[C@@H](O[C@@H]2[C@@H](O)[C@H](O[C@H]3OC(CNC(=O)OCc4ccc([N+](=O)[O-])cc4)=CC[C@H]3NC(=N)N)[C@@H](NC(=O)OC(C)(C)C)C[C@H]2NC(=O)[C@@H](O)CCNC(=O)OC(C)(C)C)OC[C@]1(C)O]

6'-PNZ-2'-guanidinium-3,3"-diBoc-1-(N-Boc-4-amino-2(S)-hydroxy-butyryl)-sisomicin Treatment of 6'-PNZ-3,3"-diBoc-1-(N-Boc-4-amino-2(S)-hydroxy-butyryl)-sisomicin (0.7 g, 0.68 mmol) with 1H-pyrazole-1-carboxamidine hydrochloride (0.142 g, 0.96 mmol) following Procedure 7 gave the desired 6'-PNZ-2'-guanidinium-3,3"-diBoc-1-(N-Boc-4-amino-2(S)-hydroxy-butyryl)-sisomicin (MS m/e [M+H]+ calcd 1070.5, found 1070.8), which was carried through to the next step without further purification.

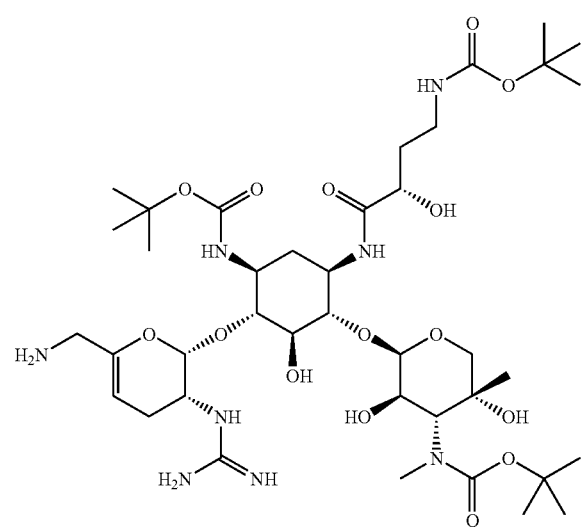 [SMILES: CN(C(=O)OC(C)(C)C)[C@@H]1[C@@H](O)[C@@H](O[C@@H]2[C@@H](O)[C@H](O[C@H]3OC(CN)=CC[C@H]3NC(=N)N)[C@@H](NC(=O)OC(C)(C)C)C[C@H]2NC(=O)[C@@H](O)CCNC(=O)OC(C)(C)C)OC[C@]1(C)O]

2'-Guanidinium-3,3"-diBoc-1-(N-Boc-4-amino-2(S)-hydroxy-butyryl)-sisomicin

6'-PNZ-2'-guanidinium-3,3"-diBoc-1-(N-Boc-4-amino-2(S)-hydroxy-butyryl)-sisomicin (0.68 mmol) was submitted to Procedure 2 for PNZ removal to yield 2'-guanidinium-3,3"-diBoc-1-(N-Boc-4-amino-2(S)-hydroxy-butyryl)-sisomicin (MS m/e [M+H]+ calcd 891.5, found 891.9), which was carried through to the next step without further purification.

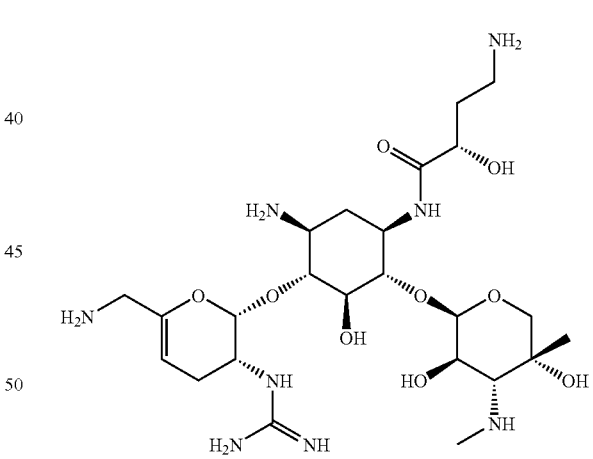

2'-Guanidinium-1-(4-amino-2(S)-hydroxy-butyryl)-sisomicin

2'-Guanidinium-3,3"-diBoc-1-(N-Boc-4-amino-2(S)-hydroxy-butyryl)-sisomicin (0.68 mmol) was submitted to Procedure 3-Method B for Boc removal to yield a crude, which was purified by RP HPLC Method 1-Column B to yield 2'-guanidinium-1-(4-amino-2(S)-hydroxy-butyryl)-sisomicin (0.110 g, 0.186 mmol, 27.4% yield): MS m/e [M+H]+ calcd 591.3, found 591.6; CLND 97.5% purity.

Example 104

2'-(Methyl-trans-3-amino-cyclobutyl)-1-(4-amino-2(S)-hydroxy-butyryl)-sisomicin

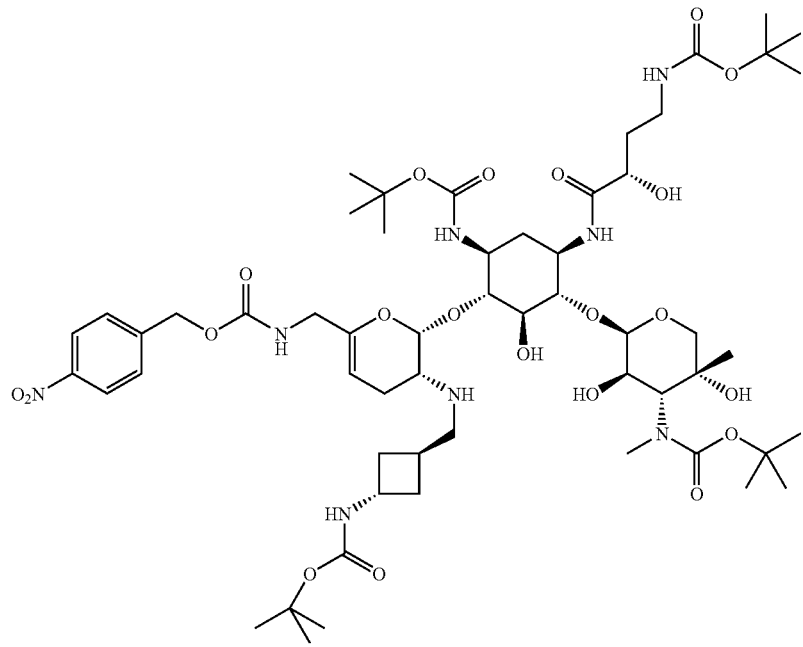 [SMILES: CN(C(=O)OC(C)(C)C)[C@@H]1[C@@H](O)[C@@H](O[C@@H]2[C@@H](O)[C@H](O[C@H]3OC(CNC(=O)OCc4ccc([N+](=O)[O-])cc4)=CC[C@H]3NC[C@H]3C[C@H](NC(=O)OC(C)(C)C)C3)[C@@H](NC(=O)OC(C)(C)C)C[C@H]2NC(=O)[C@@H](O)CCNC(=O)OC(C)(C)C)OC[C@]1(C)O]

6'-PNZ-2'-(methyl-trans-N-Boc-3-amino-cyclobutyl)-3,3"-diBoc-1-(N-Boc-4-amino-2(S)-hydroxy-butyryl)-sisomicin Treatment of 6'-PNZ-3,3"-diBoc-1-(N-Boc-3-amino-2(S)-hydroxy-butyryl)-sisomicin (0.075 g, 0.073 mmol) with N-Boc-trans-3-amino-cyclobutyl-carboxaldehyde following Procedure 1-Method A gave the desired 6'-PNZ-2'-(methyl-trans-N-Boc-3-amino-cyclobutyl)-3,3"-diBoc-1-(N-Boc-4-amino-2(S)-hydroxy-butyryl)-sisomicin (MS m/e [M+H]+ calcd 1211.6, found 1212.0), which was carried through to the next step without further purification.

2'-(Methyl-trans-N-Boc-3-amino-cyclobutyl)-3,3"-diBoc-1-(N-Boc-4-amino-2(S)-hydroxy-butyryl)-sisomicin 6'-PNZ-2'-(methyl-trans-N-Boc-3-amino-cyclobutyl)-3,3"-diBoc-1-(N-Boc-4-amino-2(S)-hydroxy-butyryl)-sisomicin (0.073 mmol) was submitted to Procedure 2 for PNZ removal to yield 2'-(methyl-trans-N-Boc-3-amino-cyclobutyl)-3,3"-diBoc-1-(N-Boc-4-amino-2(S)-hydroxy-butyryl)-sisomicin, which was carried through to the next step without further purification.

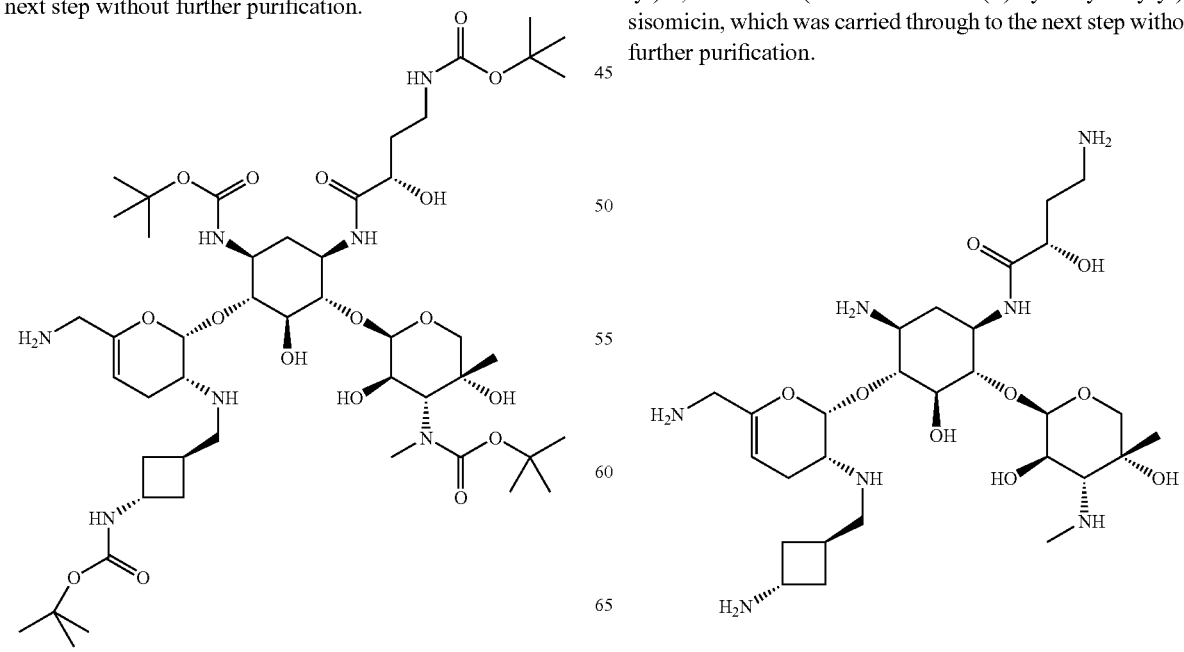

2'-(Methyl-trans-3-amino-cyclobutyl)-1-(4-amino-2(S)-hydroxy-butyryl)-sisomicin

2'-(Methyl-trans-N-Boc-3-amino-cyclobutyl)-3,3''-di-Boc-1-(N-Boc-4-amino-2(S)-hydroxy-butyryl)-sisomicin (0.073 mmol) was submitted to Procedure 3-Method A for Boc removal to yield a crude, which was purified by Method 3 to yield 2'-(methyl-trans-3-amino-cyclobutyl)-1-(4-amino-2(S)-hydroxy-butyryl)-sisomicin (0.0103 g, 0.016 mmol, 21.9% yield): MS m/e [M+H]$^+$ calcd 632.4, found 632.8; CLND 90.4% purity.

Example 105

6',2'-bis-Guanidinium-sisomicin

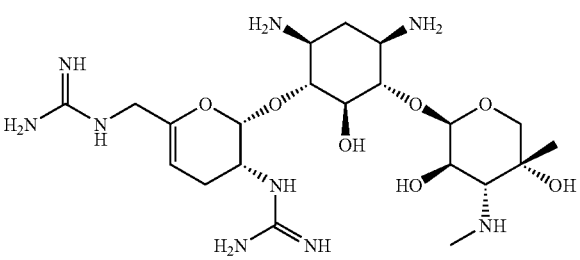

6',2'-bis-Guanidinium-sisomicin

6',2'-bis-Guanidinium-1,3,3''-triBoc-sisomicin (0.100 mmol) was submitted to Procedure 3-Method A for Boc removal to yield a crude, which was purified by Method 3 to yield 6',2'-bisguanidinium-sisomicin (0.0017 g, 0.0032 mmol, 3.2% yield): MS m/e [M+H]$^+$ calcd 532.3, found 532.6; CLND 92.2% purity.

Example 106

6'-(2-Hydroxy-ethyl)-2'-guanidinium-sisomicin

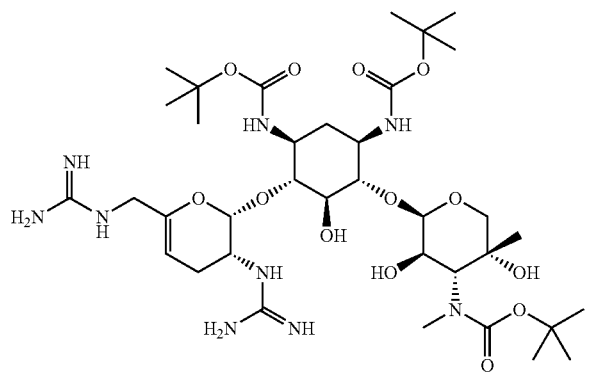 [SMILES: CN(C(=O)OC(C)(C)C)[C@@H]1[C@@H](O)[C@@H](O[C@@H]2[C@@H](O)[C@H](O[C@H]3OC(CNC(=N)N)=CC[C@H]3NC(=N)N)[C@@H](NC(=O)OC(C)(C)C)C[C@H]2NC(=O)OC(C)(C)C)OC[C@]1(C)O]

6',2'-bis-Guanidinium-1,3,3''-triBoc-sisomicin

Treatment of 1,3,3'-tri-Boc-sisomicin (0.075 g, 0.100 mmol) with 1H-pyrazole-1-carboxamidine hydrochloride (0.037 g, 0.25 mmol) following Procedure 7 gave the desired 6',2'-bisguanidinium-1,3,3''-triBoc-sisomicin (MS m/e [M+H]$^+$ calcd 832.5, found 832.8), which was carried through to the next step without further purification.

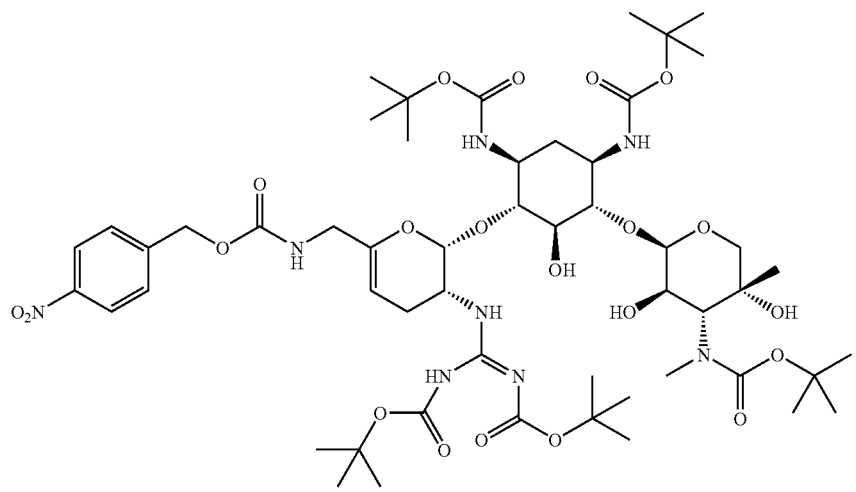 [SMILES: CN(C(=O)OC(C)(C)C)[C@@H]1[C@@H](O)[C@@H](O[C@@H]2[C@@H](O)[C@H](O[C@H]3OC(CNC(=O)OCc4ccc([N+](=O)[O-])cc4)=CC[C@H]3N/C(=N/C(=O)OC(C)(C)C)NC(=O)OC(C)(C)C)[C@@H](NC(=O)OC(C)(C)C)C[C@H]2NC(=O)OC(C)(C)C)OC[C@]1(C)O]

6'-PNZ-2'-N,N-diBoc-guanidinium-1,3,3''-triBoc-sisomicin

Treatment of 6'-PNZ-1,3,3''-triBoc-sisomicin (0.075 g, 0.081 mmol) with N,N-bisBoc-1H-pyrazole-1-carboxamidine following Procedure 7 gave the desired 6'-PNZ,2'-N,N-diBoc-guanidinium-1,3,3''-triBoc-sisomicin (MS m/e [M+H]$^+$ calcd 1169.6, found 1170.1), which was carried through to the next step without further purification.

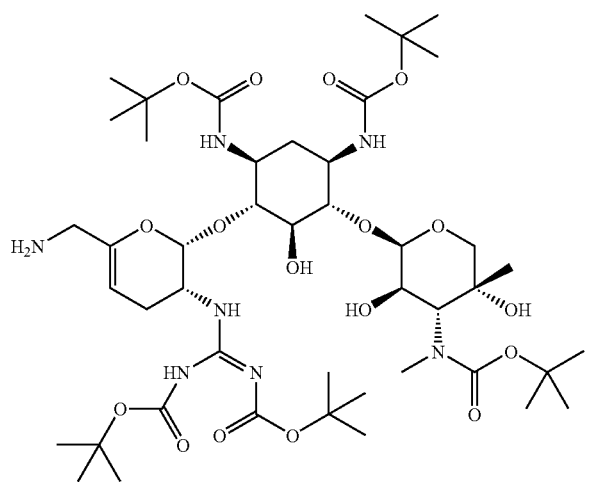 [SMILES: CN(C(=O)OC(C)(C)C)[C@@H]1[C@@H](O)[C@@H](O[C@@H]2[C@@H](O)[C@H](O[C@H]3OC(CN)=CC[C@H]3N/C(=N/C(=O)OC(C)(C)C)NC(=O)OC(C)(C)C)[C@@H](NC(=O)OC(C)(C)C)C[C@H]2NC(=O)OC(C)(C)C)OC[C@]1(C)O]

2'-N,N-diBoc-guanidinium-1,3,3''-triBoc-sisomicin

6'-PNZ,2'-N,N-diBoc-guanidinium-1,3,3''-triBoc-sisomicin (0.081 mmol) was submitted to Procedure 10 for PNZ removal to yield the desired 2'-N,N-diBoc-guanidinium-1,3,3''-triBoc-sisomicin (MS m/e [M+H]$^+$ calcd 990.5, found 990.9), which was carried through to the next step without further purification.

6'-(2-tert-Butyldimethylsilyloxy-ethyl)-2'-N,N-di-Boc-guanidinium-1,3,3''-triBoc-sisomicin Treatment of 2'-N,N-diBoc-guanidinium-1,3,3''-triBoc-sisomicin (0.081 mmol) with tert-butyldimethylsilyloxy acetaldehyde following Procedure 1-Method A gave the desired 6'-(2-tert-butyldimethylsilyloxy-ethyl)-2'-N,N-di-Boc-guanidinium-1,3,3''-triBoc-sisomicin (MS m/e [M+H]$^+$ calcd 1148.7, found 1149.1), which was carried through to the next step without further purification.

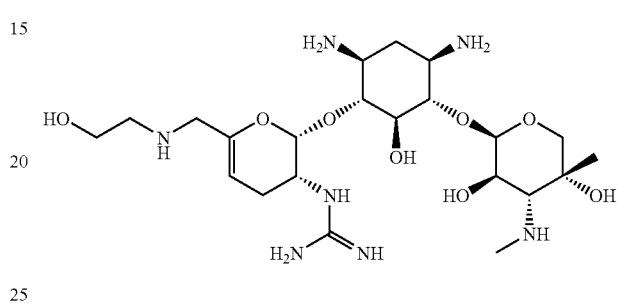

6'-(2-Hydroxy-ethyl)-2'-guanidinium-sisomicin

6'-(2-tert-Butyldimethylsilyloxy-ethyl)-2'-N,N-diBoc-guanidinium-1,3,3''-triBoc-sisomicin (0.081 mmol) was submitted to Procedure 3-Method A for Boc and TBS removal to yield a crude, which was purified by Method 1-Column A to yield 6'-(2-hydroxy-ethyl)-2'-guanidinium-sisomicin (0.00096 g, 0.0018 mmol, 2.2% yield): MS m/e [M+H]$^+$ calcd 534.3, found 534.2; CLND 84.4% purity.

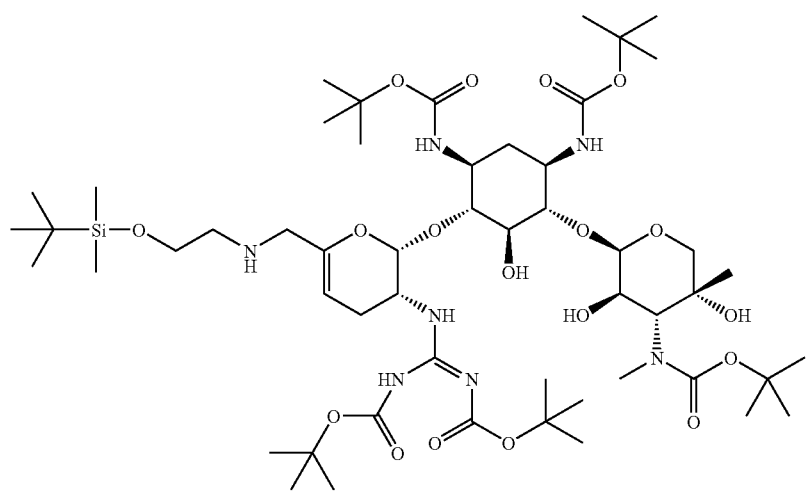 [SMILES: CN(C(=O)OC(C)(C)C)[C@@H]1[C@@H](O)[C@@H](O[C@@H]2[C@@H](O)[C@H](O[C@H]3OC(CNCCO[Si](C)(C)C(C)(C)C)=CC[C@H]3N/C(=N/C(=O)OC(C)(C)C)NC(=O)OC(C)(C)C)[C@@H](NC(=O)OC(C)(C)C)C[C@H]2NC(=O)OC(C)(C)C)OC[C@]1(C)O]

Example 107

6'-(Methyl-trans-3-amino-cyclobutyl)-2'-guanidinium-sisomicin

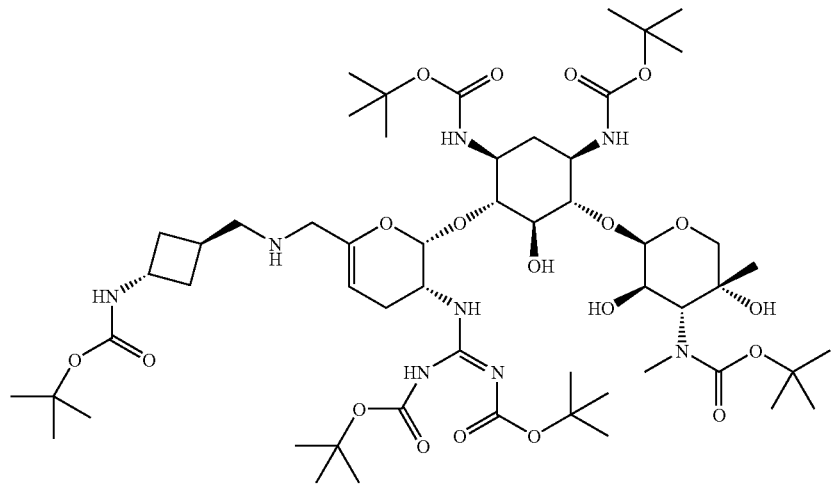 [SMILES: CN(C(=O)OC(C)(C)C)[C@@H]1[C@@H](O)[C@@H](O[C@@H]2[C@@H](O)[C@H](O[C@H]3OC(CNC[C@H]4C[C@H](NC(=O)OC(C)(C)C)C4)=CC[C@H]3N/C(=N/C(=O)OC(C)(C)C)NC(=O)OC(C)(C)C)[C@@H](NC(=O)OC(C)(C)C)C[C@H]2NC(=O)OC(C)(C)C)OC[C@]1(C)O]

6'-(Methyl-trans-N-Boc-3-amino-cyclobutyl)-2'-N,N-diBoc-guanidinium-1,3,3"-triBoc-sisomicin Treatment of 2'-N,N-diBoc-guanidinium-1,3,3"-triBoc-sisomicin (0.081 mmol) with N-Boc-trans-3-amino-cyclobutyl-carboxaldeyhde following Procedure 1-Method A gave the desired 6'-(methyl-trans-N-Boc-3-amino-cyclobutyl)-2'-N,N-diBoc-guanidinium-1,3,3"-triBoc-sisomicin (MS m/e [M+H]$^+$ calcd 1173.7, found 1174.1), which was carried through to the next step without further purification.

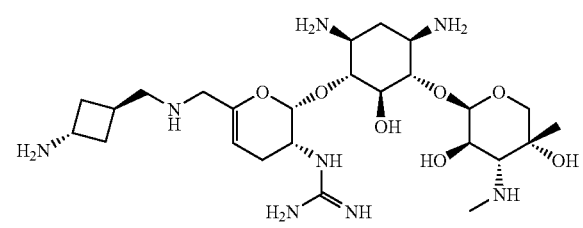 [SMILES: CN[C@@H]1[C@@H](O)[C@@H](O[C@@H]2[C@@H](O)[C@H](O[C@H]3OC(CNC[C@H]4C[C@H](N)C4)=CC[C@H]3NC(=N)N)[C@@H](N)C[C@H]2N)OC[C@]1(C)O]

6'-(Methyl-trans-3-amino-cyclobutyl)-2'-guanidinium-sisomicin

6'-(Methyl-trans-N-Boc-3-amino-cyclobutyl)-2'-N,N-diBoc-guanidinium-1,3,3"-triBoc-sisomicin (0.081 mmol) was submitted to Procedure 3-Method A for Boc removal to yield a crude, which was purified by Method 1-Column A to yield 6'-(methyl-trans-3-amino-cyclobutyl)-2'-guanidinium-sisomicin (0.001 g, 0.0017 mmol, 2.1% yield): MS m/e [M+H]$^+$ calcd 573.4, found 573.1; CLND 86.8% purity.

Example 108

6'-Methyl-2'-guanidinium-sisomicin

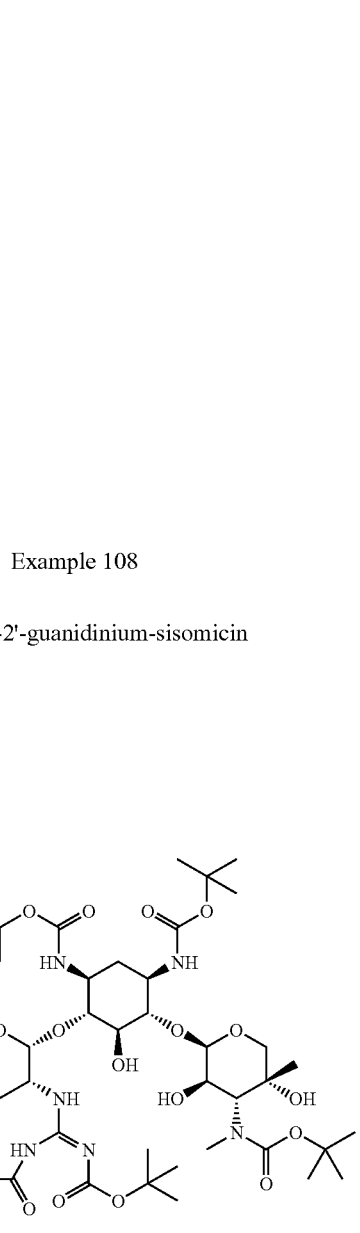

6'-Nosyl-2'-N,N-diBoc-guanidinium-1,3,3"-triBoc-sisomicin

Treatment of 2'-N,N-diBoc-guanidinium-1,3,3"-triBoc-sisomicin (0.081 mmol) with 2-nitrobenzene sulfonyl chloride following Procedure 8 gave the desired 6'-nosyl-2'-N,N-diBoc-guanidinium-1,3,3"-triBoc-sisomicin, which was carried through to the next step without further purification.

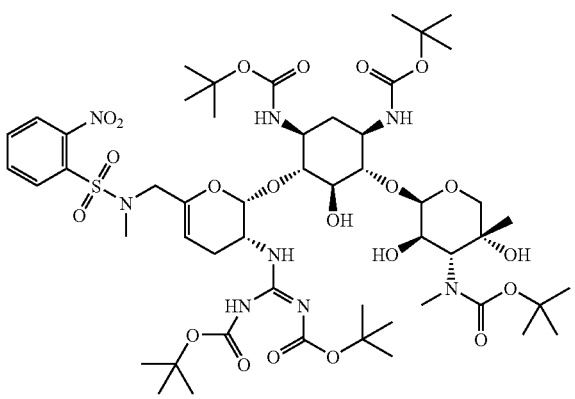 [SMILES: CN(C(=O)OC(C)(C)C)[C@@H]1[C@@H](O)[C@@H](O[C@@H]2[C@@H](O)[C@H](O[C@H]3OC(CN(C)S(=O)(=O)c4ccccc4[N+](=O)[O-])=CC[C@H]3N/C(=N/C(=O)OC(C)(C)C)NC(=O)OC(C)(C)C)[C@@H](NC(=O)OC(C)(C)C)C[C@H]2NC(=O)OC(C)(C)C)OC[C@]1(C)O]

6'-Nosyl-6'-methyl-2'-N,N-diBoc-guanidinium-1,3,
3"-triBoc-sisomicin

6'-Nosyl-2'-N,N-diBoc-guanidinium-1,3,3"-triBoc-sisomicin (0.081 mmol) was treated with methyl iodide following Procedure 11 to yield the desired 6'-nosyl-6'-methyl-2'-N,N-diBoc-guanidinium-1,3,3"-triBoc-sisomicin (MS m/e [M+H]$^+$ calcd 1189.5, found 1190.0), which was carried through to the next step without further purification.

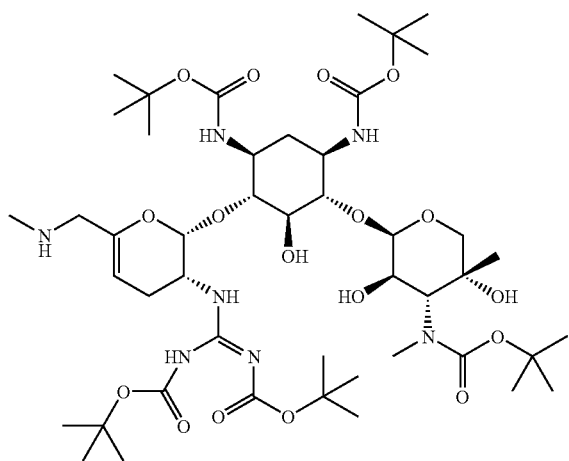 [SMILES: CNCC1=CC[C@@H](N/C(=N/C(=O)OC(C)(C)C)NC(=O)OC(C)(C)C)[C@@H](O[C@H]2[C@H](O)[C@@H](O[C@H]3OC[C@](C)(O)[C@H](N(C)C(=O)OC(C)(C)C)[C@H]3O)[C@H](NC(=O)OC(C)(C)C)C[C@@H]2NC(=O)OC(C)(C)C)O1]

6'-Methyl-2'-N,N-diBoc-guanidinium-1,3,3"-triBoc-sisomicin

6'-Nosyl-6'-methyl-2'-N,N-diBoc-guanidinium-1,3,3"-triBoc-sisomicin (0.081 mmol) was submitted to Procedure 9 for nosyl deprotection to yield the desired 6'-methyl-2'-N,N-diBoc-guanidinium-1,3,3"-triBoc-sisomicin (MS m/e [M+H]$^+$ calcd 1004.6, found 1005.1), which was carried through to the next step without further purification.

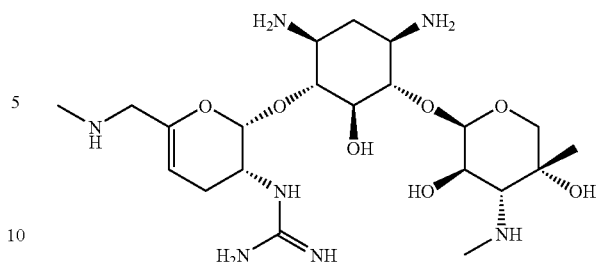

6'-Methyl-2'-guanidinium-sisomicin

6'-Methyl-2'-N,N-diBoc-guanidinium-1,3,3"-triBoc-sisomicin (0.081 mmol) was submitted to Procedure 3-Method A for Boc removal to yield a crude, which was purified by Method 1-Column A to yield 6'-methyl-2'-guanidinium-sisomicin (0.0029 g, 0.0058 mmol, 7.1% yield): MS m/e [M+H]$^+$ calcd 504.3, found 504.4; CLND 94.3% purity.

Example 109

Compounds of structure (I):

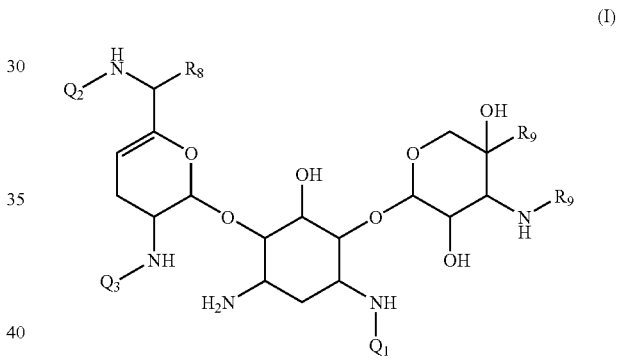

(I)

wherein at least one $R_9$ group is hydrogen may be made according to the general synthetic and purification procedures set forth above. For example, during the synthesis of Examples 1-108, the corresponding 3" and 4" des-methyl compounds are made and may be purified from the crude products using Method 1 or Method 3 of the general purification procedures set forth above.

Example 110

MIC Assay Protocol

Minimum inhibitory concentrations (MIC) were determined by reference Clinical and Laboratory Standards Institute (CLSI) broth microdilution methods per M7-A7 [2006]. Quality control ranges utilizing *E. coli* ATCC 25922, *P. aeruginosa* ATCC 27853 and *S. aureus* ATCC 29213, and interpretive criteria for comparator agents were as published in CLSI M100-S17 [2007]. Briefly, serial two-fold dilutions of the test compounds were prepared at 2× concentration in Mueller Hinton Broth. The compound dilutions were mixed in 96-well assay plates in a 1:1 ratio with bacterial inoculum. The inoculum was prepared by suspension of a colony from an agar plate that was prepared the previous day. Bacteria were suspended in sterile saline and added to each assay plate to obtain a final concentration of 5×10⁵ CFU/mL. The plates were incubated at 35° C. for 20 hours in ambient air. The MIC was determined to be the lowest concentration of the test compound that resulted in no visible bacterial growth as compared to untreated control. Data for certain representative compounds is shown in Table 1 below.

TABLE 1

| Example # | AECO001 | APAE001 |
|---|---|---|
| 1 | A | B |
| 2 | B | B |
| 3 | B | C |
| 4 | B | B |
| 5 | A | B |
| 6 | B | B |
| 7 | A | B |
| 8 | A | B |
| 9 | B | C |
| 10 | B | B |
| 11 | A | B |
| 12 | B | B |
| 13 | B | C |
| 14 | B | B |
| 15 | A | B |
| 16 | A | B |
| 17 | A | B |
| 18 | A | B |
| 19 | A | B |
| 20 | C | C |
| 21 | B | B |
| 22 | B | B |
| 23 | C | C |
| 24 | B | B |
| 25 | B | B |
| 26 | B | B |
| 27 | B | C |
| 28 | B | B |
| 29 | B | C |
| 30 | A | B |
| 31 | B | B |
| 32 | A | B |
| 33 | A | B |
| 34 | A | B |
| 35 | A | B |
| 36 | A | B |
| 37 | A | B |
| 38 | A | B |
| 39 | A | B |
| 40 | B | B |
| 41 | A | B |
| 42 | B | B |
| 43 | A | A |
| 44 | A | B |
| 45 | A | B |
| 46 | A | B |
| 47 | B | B |
| 48 | A | B |
| 49 | A | B |
| 50 | C | C |
| 51 | A | C |
| 52 | A | B |
| 53 | B | C |
| 54 | A | B |
| 55 | B | C |
| 56 | A | C |
| 57 | A | A |
| 58 | A | B |
| 59 | A | B |
| 60 | A | B |
| 61 | A | B |
| 62 | A | B |
| 63 | A | B |
| 64 | A | B |
| 65 | B | B |
| 66 | A | B |
| 67 | B | B |
| 68 | B | B |
| 69 | A | B |
| 70 | B | C |
| 71 | B | C |
| 72 | B | B |
| 73 | B | B |
| 74 | B | C |
| 75 | B | C |
| 76 | B | B |
| 77 | B | B |
| 78 | A | B |
| 79 | B | C |
| 80 | A | A |
| 81 | B | C |
| 82 | B | C |
| 83 | B | C |
| 84 | A | B |
| 85 | A | B |
| 86 | B | B |
| 87 | B | B |
| 88 | B | B |
| 89 | A | B |
| 90 | A | B |
| 91 | A | A |
| 92 | A | C |
| 93 | A | B |
| 94 | B | C |
| 95 | A | C |
| 96 | A | B |
| 97 | A | B |
| 98 | B | B |
| 99 | B | B |
| 100 | B | C |
| 101 | A | B |
| 102 | A | B |
| 103 | A | A |
| 104 | A | B |
| 105 | C | C |
| 106 | A | B |
| 107 | B | A |
| 108 | A | B |

* AECO001 is ATCC25922 and APAE001 is ATCC27853.
** MIC Key:
MIC's of 1.0 µg/mL or less = A
MIC's of greater than 1.0 µg/mL to 16.0 µg/mL = B
MIC's of greater than 16.0 µg/mL = C Example 111

In Vivo Efficacy Models

As shown in Table 2 below, certain representative compounds and certain known aminoglycosides (i.e., gentamicin and amikacin) were tested for in vivo efficacy in a murine septicemia model of infection. Two models were run on each compound, using *E. coli* and *P. aeruginosa* QC bacterial strains. Both studies employed the same design. Male CD-1 (CRL)-derived mice (individual body weight, 24±2 grams) were inoculated IP with the 2×LD90-100 dose of *E. coli* ATCC 25922 (4.5×105 CFU/mouse) in 0.5 mL of BHI broth containing 5% mucin, or the 2×LD90-100 dose of *P. aeruginosa* ATCC 27853 (5.8×104 CFU/0.5 mL/mouse) in BHI broth containing 5% mucin. At 1 hour after bacterial challenge, the mice received a single SC or IV dose of vehicle or test substance to assess in vivo anti-infective activity. Mortality was recorded once daily for 7 days after bacterial inoculation. In both studies, a single IV or SC dose of all test compounds improved the survival rate in a dose-dependent manner, as seen in Table 2.

TABLE 2

| Test Compound | MIC E. coli | MIC P. aeruginosa | ED50/MIC E. Coli | ED50/MIC P. aeruginosa |
|---|---|---|---|---|
| Gentamicin | A | A | 2.4 | 12 |
| Amikacin | B | B | 1.5 | 13 |
| Example 1 | A | B | <2 | 4 |
| Example 15 | A | B | <1 | 1 |
| Example 16 | A | B | 1 | 3 |
| Example 17 | A | B | 1 | 5 |
| Example 22 | B | B | 1 | 8 |
| Example 57 | A | A | 2 | 14 |
| Example 96 | A | B | <1 | 3 |
| Example 103 | A | A | 2 | 6 |

* MIC Key:
MIC's of 1.0 μg/mL or less = A
MIC's of greater than 1.0 μg/mL to 16.0 μg/mL = B
MIC's of greater than 16.0 μg/mL = C
** ED50 values are mg/kg Example 112

As shown in Table 3 below, certain di-substituted sisomicin derivatives, certain mono-substituted sisomicin derivatives and sisomicin were tested against QC and aminoglycoside resistant bacterial strains containing confirmed resistance mechanisms that covalently modify the 6'-amino group in many aminoglycosides. These MIC assays were conducted following the same protocol as set forth in Example 110. As shown, substituted sisomicin derivatives with groups other than methyl at the 6'-position have improved activity against strains expressing the AAC6'-modifying enzymes. Furthermore, di-substituted sisomicin derivatives show superior activity relative to the mono-substituted derivatives with respect to those strains expressing the AAC6'-modifying enzymes.

TABLE 3

| Test Compound | AECO001 | AECO040 | ASMA003 | AACA005 |
|---|---|---|---|---|
| Sisomicin | 0.5 | 32 | 8 | 32 |
| Mono-substituted Compound 1 | 1 | >64 | 1 | 2 |
| Mono-substituted Compound 2 | 1 | 1 | 0.5 | 4 |
| Mono-substituted Compound 3 | 0.5 | 0.25 | 1 | 0.5 |
| Mono-substituted Compound 4 | 2 | 16 | 1 | 1 |
| Mono-substituted Compound 5 | 0.5 | 8 | 2 | 32 |
| Mono-substituted Compound 6 | 0.5 | 4 | 4 | 16 |
| Mono-substituted Compound 7 | 1 | 4 | 16 | 32 |
| Example 1 | 0.5 | 0.5 | 2 | 2 |
| Example 12 | 1 | 0.5 | 4 | 2 |
| Example 13 | 1 | 0.125 | 2 | 2 |
| Example 16 | 1 | 1 | 2 | 2 |
| Example 17 | 1 | 0.5 | 2 | 2 |
| Example 18 | 1 | 0.25 | 4 | 2 |
| Example 48 | 1 | 0.5 | 2 | 2 |
| Example 61 | 1 | 16 | 4 | 2 |

* Key:

| Strain | ACH Code | Phenotype |
|---|---|---|
| E. coli | AECO001 | ATCC25922 |
|  | AECO040 | AAC(6')-I |
| S. marcescens | ASMA003 | ANT(2") + AAC(6') |
| A. calcoaceticus | AACA005 | AAC(6')-I |

** Comparative Compounds:

| Mono-Substituted Compound # | Structure |
|---|---|
| 1 | 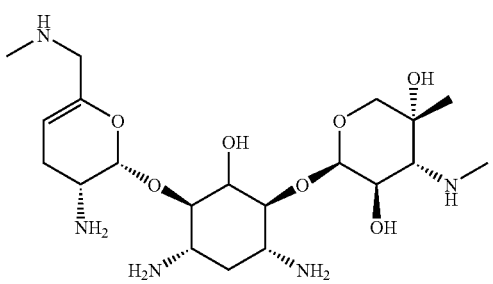 |
| 2 | 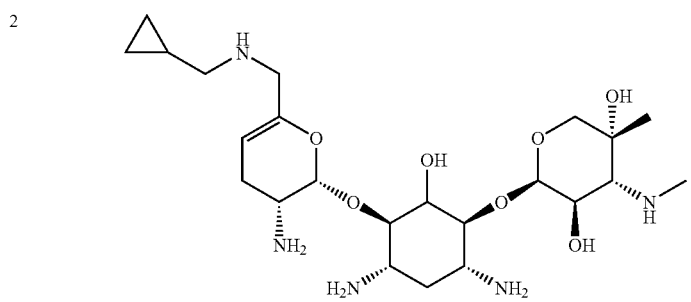 |

| Mono-Substituted Compound # | Structure |
|---|---|
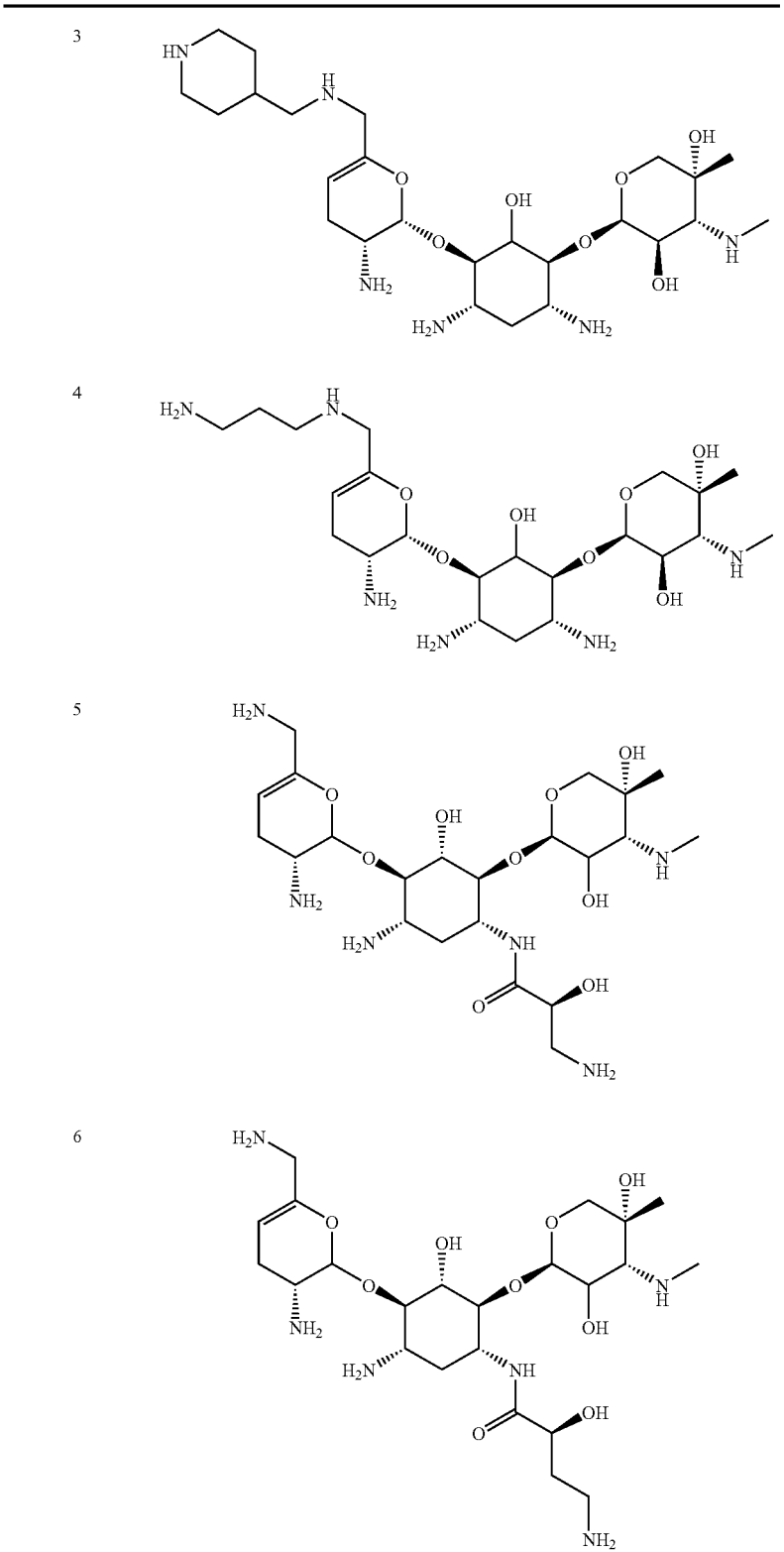

| Mono-Substituted Compound # | Structure |
|---|---|
| 7 | 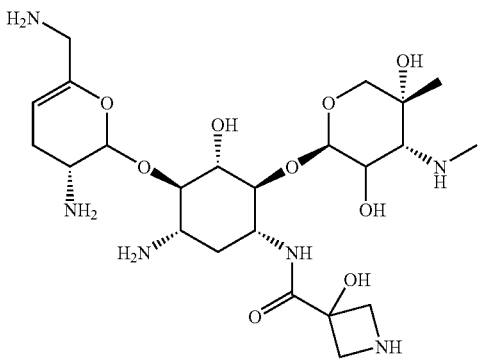 [SMILES: CN[C@@H]1C(O)[C@@H](O[C@@H]2[C@@H](O)[C@H](OC3OC(CN)=CC[C@H]3N)[C@@H](N)C[C@H]2NC(=O)C2(O)CNC2)OC[C@]1(C)O] |

All of the U.S. patents, U.S. patent application publications, U.S. patent applications, foreign patents, foreign patent applications and non-patent publications referred to in this specification are incorporated herein by reference, in their entirety to the extent not inconsistent with the present description.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A compound having the following structure (I):

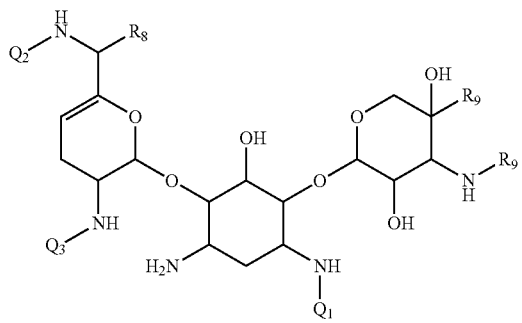

(I)

or a stereoisomer or pharmaceutically acceptable salt thereof, wherein:

$Q_1$ is hydrogen,

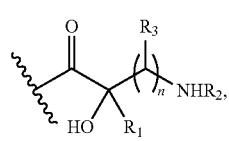

$Q_2$ is hydrogen, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —C(=NH)NR$_4$R$_5$, —(CR$_{10}$R$_{11}$)$_p$R$_{12}$,

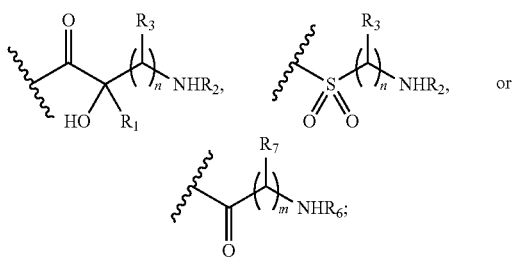

$Q_3$ is hydrogen, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —C(=NH)NR$_4$R$_5$, —(CR$_{10}$R$_{11}$)$_p$R$_{12}$,

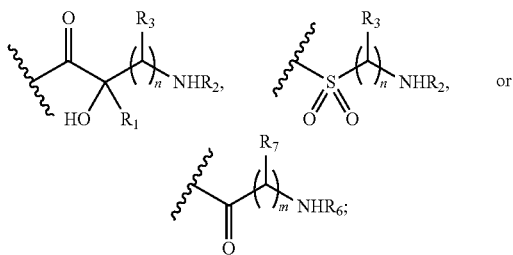

each $R_1$, $R_2$, $R_3$, $R_4$, $R_5$, $R_8$ and $R_{10}$ is, independently, hydrogen or $C_1$-$C_6$ alkyl, or $R_1$ and $R_2$ together with the atoms to which they are attached can form a heterocyclic ring having from 4 to 6 ring atoms, or $R_2$ and $R_3$ together with the atoms to which they are attached can form a heterocyclic ring having from 4 to 6 ring atoms, or $R_1$ and $R_3$ together with the atoms to which they are attached can form a carbocyclic ring having from 4 to 6 ring atoms, or $R_4$ and $R_5$ together with the atom to which they are attached can form a heterocyclic ring having from 4 to 6 ring atoms;

each $R_6$ and $R_7$ is, independently, hydrogen, hydroxyl, amino or $C_1$-$C_6$ alkyl, or $R_6$ and $R_7$ together with the atoms to which they are attached can form a heterocyclic ring having from 4 to 6 ring atoms;
each $R_9$ is, independently, hydrogen or methyl;
each $R_{11}$ is, independently, hydrogen, hydroxyl, amino or $C_1$-$C_6$ alkyl;
each $R_{12}$ is, independently, hydroxyl or amino;
each n is, independently, an integer from 0 to 4;
each m is, independently, an integer from 0 to 4; and
each p is, independently, an integer from 1 to 5, and
wherein (i) at least two of $Q_1$, $Q_2$ and $Q_3$ are other than hydrogen, and (ii) if $Q_1$ is hydrogen, then at least one of $Q_2$ and $Q_3$ is —C(=NH)NR$_4$R$_5$.

2. A compound of claim 1 wherein $R_8$ is hydrogen.
3. A compound of claim 1 wherein each $R_9$ is methyl.
4. A compound of claim 1 wherein $Q_1$ and $Q_2$ are other than hydrogen.
5. A compound of claim 4 wherein $Q_3$ is hydrogen.
6. A compound of claim 4 wherein $Q_1$ is:

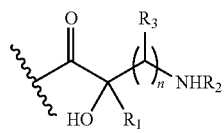

wherein:
  $R_1$ is hydrogen;
  $R_2$ is hydrogen; and
  each $R_3$ is hydrogen.
7. A compound of claim 6 wherein $Q_1$ is:

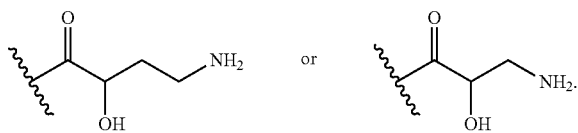 [SMILES: *C(=O)C(O)CCN ; "or" ; *C(=O)C(O)CN]

8. A compound claim 4 wherein $Q_2$ is —(CR$_{10}$R$_{11}$)$_p$R$_{12}$.
9. A compound of claim 8 wherein each $R_{10}$ is hydrogen.
10. A compound of claim 9 wherein each $R_{11}$ is hydrogen.
11. A compound of claim 4 wherein the compound is:
6'-(2-Hydroxy-ethyl)-1-(4-amino-2(S)-hydroxy-butyryl) -sisomicin;
6'-(2-Hydroxy-ethyl)-1-(4-amino-2(R)-hydroxy-butyryl) -sisomicin;
6'-(2-Hydroxy-propanol)-1-(4-amino-2(R)-hydroxy-butyryl) -sisomicin;
6'-(Methyl-piperidin-4-yl)-1-(4-amino-2(R)-hydroxy-butyryl) -sisomicin;
6'-(Methyl-cyclopropyl)-1-(4-amino-2(R)-hydroxy-butyryl) -sisomicin;
6'-(3-Amino-propyl)-1-(4-amino-2(R)-hydroxy-butyryl) -sisomicin;
6'-Methyl-cyclopropyl-1-(3-amino-2(R)-hydroxy-propionyl) -sisomicin;
6'-Methyl-piperidinyl-1-(3-amino-2(R)-hydroxy-propionyl) -sisomicin;
6'-(2-Hydroxy-ethyl)-1-(3-amino-2(R)-hydroxy-propionyl) -sisomicin;
6'-(2-Hydroxy-propanol)-1-(3-amino-2(R)-hydroxy-propionyl) -sisomicin;
6'-(3-Amino-propyl)-1-(3-amino-2(R)-hydroxy-propionyl) -sisomicin;
6'-(Methyl-piperidin-4-yl)-1-(4-amino-2(S)-hydroxy-butyryl) -sisomicin;
6'-(Methyl-cyclopropyl)-1-(3-amino-2(S)-hydroxy-propionyl) -sisomicin;
6'-(2-Hydroxy-propanol)-1-(3-amino-2(S)-hydroxy-propionyl) -sisomicin;
6'-(Methyl-piperidin-4-yl)-1-(3-amino-2(S)-hydroxy -propionyl)-sisomicin;
6'-(2-Hydroxy-ethyl)-1-(3-amino-2(S)-hydroxy-propionyl) -sisomicin;
6'-(3-Amino-propyl)-1-(3-amino-2(S)-hydroxy-propionyl) -sisomicin;
6'-(Methyl-cyclopropyl)-1-(4-amino-2(S)-hydroxy-butyryl) -sisomicin;
6'-(2-Hydroxy-propanol)-1-(4-amino-2(S)-hydroxy-butyryl) -sisomicin;
6'-(3-Amino-2-hydroxy-propyl)-1-(3-amino-2(S)-hydroxy -propionyl)-sisomicin;
6'-(2-Hydroxy-ethyl)-1-(2-hydroxy-acetyl)-sisomicin;
6'-(3-Amino-propyl)-1-(2-amino-ethylsulfonamide)-sisomicin;
6'-(2-Hydroxy-propanol)-1-(2-amino-ethylsulfonamide)-sisomicin;
6'-(2(S)-Hydroxy-propanol)-1-(4-amino-2(S)-hydroxy-butyryl) -sisomicin;
6'-(2-Hydroxy-ethyl)-1-(2-amino-ethylsulfonamide)-sisomicin;
6'-(Methyl-trans-3-amino-cyclobutyl)-1-(4-amino-2(S) -hydroxy-butyryl)-sisomicin;
6'-(2-Hydroxy-ethyl)-1-(3-hydroxy-pyrrolidin-3-yl-acetyl) -sisomicin;
6'-(2-Hydroxy-4-amino-butyl)-1-(3-hydroxy-pyrrolidin-3-yl-acetyl)-sisomicin;
6'-(Methyl-cyclopropyl)-1-(3-hydroxy-azetidin-3-yl-acetyl) -sisomicin;
6'-(2-Hydroxy-ethyl)-1-(3-hydroxy-azetidin-3-yl-acetyl) -sisomicin;
6'-(Methyl-(1-hydroxy-3-methylamino-cyclobutyl)-1-(4-amino -2(S)-hydroxy-butyryl) -sisomicin;
6'-(3-Amino-propyl)-1-(3-hydroxy-pyrrolidin-3-yl-acetyl) -sisomicin;
6'-(Methyl-cyclopropyl)-1-(3-hydroxy-pyrrolidin-3-yl-acetyl) -sisomicin;
6'-(2-Hydroxy-3-amino-propyl)-1-(3-hydroxy-pyrrolidin-3-yl-acetyl)-sisomicin;
6'-(3-Amino-propyl)-1-(4-amino-2(S)-hydroxy-butyryl) -sisomicin;
6'-(Methyl-pyrrolidin-2-yl)-1-(4-amino-2(S)-hydroxy -butyryl)-sisomicin;
6'-(3-Amino-propyl)-1-(3-hydroxy-azetidin-3-yl-acetyl) -sisomicin;
6'-(3-Amino-propyl)-1-(1-hydroxy-3-amino-cyclobutyl-acetyl) -sisomicin;
6'-(Methyl-trans-3-amino-cyclobutyl)-1-(3-amino-2(S) -hydroxy-propionyl)-sisomicin;
6'-(Methyl-trans-3-amino-cyclobutyl)-1-(1-hydroxy-3-amino -cyclobutyl-acetyl)-sisomicin;
6'-(2-Hydroxy-ethyl)-1-(1-hydroxy-3-amino -cyclobutyl -acetyl)-sisomicin;
6'-Methylcyclopropyl-1-(2-(azetidin-3-yl)-2-hydroxy-acetyl) -sisomicin;
6'-(Methyl-trans-3-amino-cyclobutyl)-1-(2-(azetidin-3-yl)-2-hydroxy-acetyl)-sisomicin;
6'-(2-Hydroxy-ethyl)-1-(2-(azetidin-3-yl)-2-hydroxy -acetyl)-sisomicin;
6'-(3-Amino-propyl)-1-(2-(azetidin-3-yl)-2-hydroxy -acetyl)-sisomicin;

6'-(Methyl-trans-3-amino-cyclobutyl)-1-(3-hydroxy-pyrrolidin-3-yl-acetyl)-sisomicin;

6'-(2-Hydroxy-3-amino-propyl)-1-(2-(azetidin-3-yl)-2-hydroxy-acetyl)-sisomicin; or 6'-(Methyl-3-amino-1-hydroxy-cyclobutyl)-1-(2-(azetidin-3-yl)-2-hydroxy-acetyl)-sisomicin.

12. A pharmaceutical composition comprising a compound of claim 1, or a stereoisomer or pharmaceutically acceptable salt thereof, and a pharmaceutically acceptable carrier, diluent or excipient.

13. A method of treating a bacterial infection in a mammal in need thereof, comprising administering to the mammal an effective amount of a compound of claim 1 or a composition of claim 12.

14. A compound of claim 4 wherein the compound is 6'-(2-Hydroxy-ethyl)-1-(4-amino-2(S)-hydroxy-butyryl)-sisomicin.

15. A compound of claim 2, wherein each $R_9$ is methyl.

16. A compound of claim 15, wherein $Q_3$ is hydrogen.

17. A compound of claim 16, wherein $Q_1$ is:

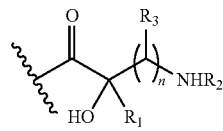

wherein:
$R_1$ is hydrogen;
$R_2$ is hydrogen; and
each $R_3$ is hydrogen.

18. A compound of claim 17, wherein $Q_1$ is:

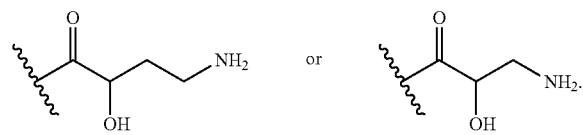 [SMILES: *C(=O)C(O)CCN ; "or" ; *C(=O)C(O)CN]

19. A compound of claim 18, wherein $Q_1$ is:

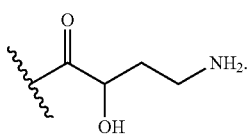 [SMILES: *C(=O)C(O)CCN]

20. A compound of claim 19, wherein $Q_2$ is —$(CR_{10}R_{11})_pR_{12}$.

21. A compound of claim 20, wherein each $R_{10}$ is hydrogen.

22. A compound of claim 21, wherein each $R_{11}$ is hydrogen.

23. A compound of claim 22, wherein p is 2.

24. A compound of claim 23, wherein $R_{12}$ is hydroxyl.

25. A pharmaceutical composition comprising a compound of claim 24, or a pharmaceutically acceptable salt thereof, and a pharmaceutically acceptable carrier, diluent or excipient.

26. A method for treating a bacterial infection in a mammal in need thereof, comprising administering to the mammal an effective amount of a compound of claim 24 or a composition of claim 25.

27. A pharmaceutical composition comprising 6'-(2-Hydroxy-ethyl)-1-(4-amino-2(S)-hydroxy-butyryl)-sisomicin, or a pharmaceutically acceptable salt thereof, and a pharmaceutically acceptable carrier, diluent or excipient.

28. A method for treating a bacterial infection in a mammal in need thereof, comprising administering to the mammal an effective amount of a composition of claim 27.

29. A compound of claim 1, wherein $Q_1$ is

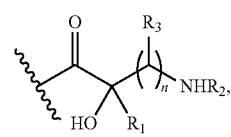

and
$Q_2$ is —$(CR_{10}R_{11})_pR_{12}$.

30. A compound of claim 29 wherein $R_8$ is hydrogen.

31. A compound of claim 29 wherein each $R_9$ is methyl.

32. A compound of claim 29 wherein $Q_3$ is hydrogen.

33. A compound of claim 29 wherein $R_1$ is hydrogen, $R_2$ is hydrogen and each $R_3$ is hydrogen.

34. A compound of claim 29, wherein n is 1 or 2.

35. A compound of claim 33, wherein n is 1 or 2.

36. A compound of claim 29, wherein each $R_{10}$ is hydrogen, each $R_{11}$ is hydrogen and $R_{12}$ is hydroxyl.

37. A compound of claim 29, wherein p is 2.

38. A compound of claim 36, wherein p is 2.

39. A compound of claim 29, wherein $R_1$ is hydrogen, $R_2$ is hydrogen, each $R_3$ is hydrogen, each $R_{10}$ is hydrogen, each $R_{11}$ is hydrogen and $R_{12}$ is hydroxyl.

40. A compound of claim 29, wherein n is 1 or 2, and p is 2.

41. A compound of claim 39, wherein n is 1 or 2, and p is 2.

42. A compound of claim 29, wherein $Q_1$ is:

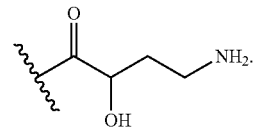 [SMILES: *C(=O)C(O)CCN]

43. A pharmaceutical composition comprising a compound of claim 29, or a pharmaceutically acceptable salt thereof, and a pharmaceutically acceptable carrier, diluent or excipient.

44. A method for treating a bacterial infection in a mammal in need thereof, comprising administering to the mammal an effective amount of a compound of claim 29 or a composition of claim 43.

* * * * *